United States Patent
Beutler et al.

(10) Patent No.: US 11,040,959 B2
(45) Date of Patent: Jun. 22, 2021

(54) DIPROVOCIMS: A NEW AND POTENT CLASS OF TLR AGONISTS

(71) Applicants: The Scripps Research Institute, La Jolla, CA (US); The Board of Regents of the University of Texas System, Austin, TX (US); Bruce Beutler, Dallas, TX (US); Dale L. Boger, La Jolla, CA (US)

(72) Inventors: Bruce Beutler, Dallas, TX (US); Dale L. Boger, La Jolla, CA (US)

(73) Assignees: The Board of Regents of the University of Texas System, Austin, TX (US); The Scripps Research Institute, La Jolla, CA (US)

(*) Notice: Subject to any disclaimer, the term of this patent is extended or adjusted under 35 U.S.C. 154(b) by 166 days.

(21) Appl. No.: 16/303,043

(22) PCT Filed: Jun. 29, 2017

(86) PCT No.: PCT/US2017/040028
§ 371 (c)(1),
(2) Date: Nov. 19, 2018

(87) PCT Pub. No.: WO2018/005812
PCT Pub. Date: Jan. 4, 2018

(65) Prior Publication Data
US 2020/0207742 A1   Jul. 2, 2020

Related U.S. Application Data

(60) Provisional application No. 62/356,314, filed on Jun. 29, 2016.

(51) Int. Cl.
C07D 403/10 (2006.01)
A61P 37/04 (2006.01)

(52) U.S. Cl.
CPC ............ C07D 403/10 (2013.01); A61P 37/04 (2018.01)

(58) Field of Classification Search
CPC .................................................. C07D 403/10
See application file for complete search history.

(56) References Cited

U.S. PATENT DOCUMENTS 9,649,373 B2   5/2017 Beutler et al.
9,918,959 B2   3/2018 Boger et al.

2005/0004144 A1   1/2005 Carson et al.
2007/0161674 A1   7/2007 Collibee et al.
2010/0173969 A1   7/2010 Pepys
2014/0323390 A1   10/2014 Wu et al.

OTHER PUBLICATIONS

WO2018005812 International Search Report.
WO2018005812 Written Opinion.
May 13, 2017 AAI Meeting Slide Presentation.
AAI Meeting; Abstract—Wang et al., *J Immunol* May 1, 2017, 198 [1Supplement] 129.3.
A-10-AAI Meeting—Wang Poster—2017.
Wang et al., *Proc Natl Acad Sci, Usa*, 115(37):E8698-E8706 (Aug. 27, 2018).
Morin et al., *J Am Chem Soc* 140:14440-14454 (Oct. 1, 2018).
Jin et al., *Curr. Opin. Immunol.* 20:414-419 (2008).
Cheng et al., *Sci. Adv.* 1:e1400139 (2015).
Wang et al., *Chem. Soc. Rev.* 42:4859-4866 (2013).
Extended EPO Search Report and associated pages.
Wang et al., *Chem. Soc. Rev.* 42:4859-4866 (2013); Supplemental Information.

*Primary Examiner* — Shawquia Jackson
(74) *Attorney, Agent, or Firm* — Husch Blackwell LLP

(57) ABSTRACT

A diprovocim compound that corresponds in structure to structural Formula V is disclosed, wherein A, W, Z, $R^1$, $R^2$, $R^3$ and $R^4$ (when present) are defined within. A diprovocim compound has immune-adjuvant properties on human and mouse cells in culture and on in vivo immunization of mice. A composition containing a diprovocim and a method of using a compound are also disclosed. The immunostimulatory activity of a diprovocim compound is similar to that of LPS, to which there is no apparent structural similarity. A contemplated compound bears no structural similarity to either the TLR1/TLR2 lipoprotein agonists nor to any other synthetic TLR agonist, and is remarkably easy to prepare and synthetically modify.

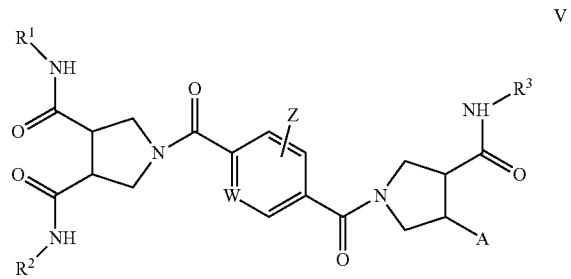

16 Claims, 7 Drawing Sheets
Specification includes a Sequence Listing.

DIPROVOCIMS: A NEW AND POTENT CLASS OF TLR AGONISTS

CROSS-REFERENCE TO RELATED APPLICATION

This application claims priority to U.S. application Ser. No. 62/356,314, filed on Jun. 29, 2016, whose disclosures are incorporated herein by reference.

GOVERNMENTAL SUPPORT

This invention was made with governmental support under AI082657 and CA042056 awarded by the National Institutes of Health. The government has certain rights in the invention.

SEQUENCE LISTING

The instant application contains a Sequence Listing which has been submitted electronically in ASCII format and is hereby incorporated by reference in its entirety. The Sequence Listing: is named "TSRI1761.1US_ST25.txt"; was created on Aug. 20, 2019; and is 4 kilobytes in size.

BACKGROUND ART

The human immune system is composed of two components, the innate and adaptive immune systems. The innate immune system is encoded into the germline of an organism and constitutes the first line of defense in mammals, responding to pathogens and abnormal cells through initiation of intracellular signaling cascades that lead to the activation of transcription factors that trigger the production of cytokines and chemokines with participation of multiple cell types including dendritic cells, macrophages, neutrophils, and natural killer cells [Beutler, Mol. Immunol. 2004, 40:845-859].

The subsequent adaptive immune system is acquired and involves antigen-specific T cell and B cell responses mediated by antigen-presenting dendritic cells, and serves to provide protection to the host longer term through the action of T cell receptors and antibodies to neutralize the pathogens and abnormal cells [Beutler, Mol. Immunol. 2004, 40:845-859; and Hoebe et al., Nat. Immunol. 2004, 5:971-974].

The Toll-like receptors (TLRs) [(a) Moresco et al., Curr. Biol. 2011, 21:R488-R493; (b) Blasius et al., Immunity 2010, 32:305-315; (c) Kawai et al., Nat. Immunol. 2010, 13:373-384; (d) Beutler, Blood 2009, 113:1399-1407; (e) Hashimoto et al., Cell 1988, 52:269-279; (f) Lemaitre et al., Cell 1996, 86:973; (g) Poltorak et al., Science 1998, 282: 2085-2088; (h) Beutler et al., J. Endotoxin Res. 2001, 7:277-280; (i) Beutler et al., Nat. Rev. Immunol. 2003, 3:169-176; and Medzhitov et al., Nature 1997, 388:394-397] are the most widely recognized set of the pathogen-associated or damage-associated molecular pattern (PAMPs and DAMPs) receptors that recognize molecular components of pathogens or abnormal cells and marshal the initial innate immune response.[3,5] [(a) Moresco et al., Curr. Biol. 2011, 21:R488-R493; (b) Blasius et al., Immunity 2010, 32:305-315; (c) Kawai et al., Nat. Immunol. 2010, 13:373-384; (d) Beutler, Blood 2009, 113:1399-1407; (e) Poltorak et al., Science 1998, 282:2085-2088; (f) Beutler et al., J. Endotoxin Res. 2001, 7:277-280; (g) Beutler et al., Nat. Rev. Immunol. 2003, 3:169-176]. They also induce the adaptive immune response [Medzhitov et al., Nature 1997, 388:394-397], and the action of vaccines is due in part to the activation of the TLR system [(a) Vogel, Clin. Infect. Dis. 2000, 30 (Suppl 3):S266-S270; (b) Guy, Nat. Rev. Microbiol. 2007, 5:505-517; and (c) Coffman et al., Immunity 2010, 33:492-503].

TLR agonists are useful in the treatment of not only infectious diseases but also cancer, representing a complementary small molecule approach in the emerging area of immunotherapy. [(a) Vogel, Clin. Infect. Dis. 2000, 30 (Suppl 3):S266-S270; (b) Guy, Nat. Rev. Microbiol. 2007, 5:505-517; (c) Coffman et al., Immunity 2010, 33:492-503; (d) Czarniecki, J. Med. Chem. 2008, 51:6621-6626; (e) Peri et al., J. Med. Chem. 2014, 57:3612-3622; (f) Wang et al., Chem. Soc. Rev. 2013, 42:4859-4866; (g) Hennessy et al., Nat. Rev. Drug Discovery 2010, 9:293-301; (h) Meyer et al., Expert Opin. Invest. Drugs 2008, 17:1051-1065; (i) Hoebe et al., Curr. Pharmaceut. Des. 2006, 12:4123-4134; and (j) Kanzler et al., Nat. Med. 2007, 13:552-559]. As such, they are attractive as new vaccine adjuvants for both infectious diseases and oncology that act by well-defined mechanisms, as prophylactics against pathogen exposure (e.g.; biodefense) [(a) Amlie-Lefond et asl., J. Allergy Clin. Immunol. 2005, 116:1334; and (b) O'Neill et al., Pharmacol. Rev. 2009, 61:177], or as immunostimulators alone or in combination with other drugs. However, a limited number of small molecule classes have been found to behave as TLR agonists [(a) Amlie-Lefond et al., J. Allergy Clin. Immunol. 2005, 116:1334; and (b) O'Neill et al., Pharmacol. Rev. 2009, 61:177], particularly in oncology [(a) Czarniecki, J. Med. Chem. 2008, 51:6621-6626; (b) Peri et al., J. Med. Chem. 2014, 57:3612-3622; (c) Wang et al., Chem. Soc. Rev. 2013, 42:4859-4866; (d) Hennessy et al., Nat. Rev. Drug Discovery 2010, 9:293-301; (e) Meyer et al., Expert Opin. Invest. Drugs 2008, 17:1051-1065; (f) Hoebe et al., Curr. Pharmaceut. Des. 2006, 12:4123-4134; and (g) Kanzler et al., Nat. Med. 2007, 13:552-559].

Notable examples include the TLR7 agonists imiquimod [Prins et al., J. Immunol. 2005, 176:157-164], isotoribine [Lee et al., Proc. Natl. Acad. Sci. USA 2003, 100:6646-6651], and 8-oxo-9-benzyladenine [Lee et al., Proc. Natl. Acad. Sci. U.S.A. 2006, 103:1828-1833], as well as the TLR7/8 agonist resiquimod [Smits et al., Cancer Immunol. Immunother. 2010, 59:35-46] that today still serve as the inspiration for nearly all such work [Beesu et al., J. Med. Chem. 2014, 57:7325-7341; and Wu et al., Sci. Transl. Med. 2014, 6(263):263ra160].

Recently, in unbiased studies designed to discover small molecule stimulators of the immune system or new signaling receptors, the present inventors and co-workers disclosed the identification, characterization, [Wang et al., Proc. Natl. Acad. Sci. USA 2016, 113:E884-E893] and systematic structure-activity relationship study [Morin et al., J. Med. Chem. 2016, 59:4812-4830] of the neoseptins, a new class of TLR4 agonists [Johnson, Curr. Top. Med. Chem. 2008, 8:64-79; (b) Casella et el., Cell Mol. Life Sci. 2008, 65:3231-3240; (c) Persing et al., Trends Microbiol. 2002, 10:S32-S37; (d) Neve et al., J. Med. Chem. 2014, 57:1252-1275; (e) Chan et al., J. Med. Chem. 2013, 56:4206-4223; and (f) Zimmer et al., J. Biol. Chem. 2008, 283:27916-27926] that bear no structural similarity to bacterial lipopolysaccharide (LPS) or its active core Lipid A (LPA) [Johnson, Curr. Top. Med. Chem. 2008, 8:64-79; (b) Casella et el., Cell Mol. Life Sci. 2008, 65:3231-3240; (c) Persing et al., Trends Microbiol. 2002, 10:S32-S37].

Relevant to the studies disclosed herein, studies decades ago defined and systematically examined a series of TLR agonists that are derived from the activating N-terminal segments of bacterial triacylated lipoproteins and lipopeptides (e.g; PAM3CSK4 [(a) Metzger et al., Int. J. Peptide Protein Res. 1991, 37:46; (b) Bessler et al., *J. Immunol.* 1985, 135:1900; and (c) Deres et al., *Nature* 1989, 342:561], which were shown later to act by heterodimerization of TLR1/TLR2 at the cell surface [(a) Alexopoulou et al., *Nat. Med.* 2002, 8:878; (b) Takeuchi et al., *J. Immunol.* 2002, 169:10; (c) Jin et al., *Cell* 2007, 130:1071; and Review: (d) Jin et al., *Curr. Opin. Immunol.* 2008, 20:414-419]. Such agonists based on and mimicking the lipoproteins and lipopeptides are effective vaccine adjuvants (admixed or covalently-linked with antigens) [(a) Metzger et al., *Int. J. Peptide Protein Res.* 1991, 37:46; (b) Bessler et al., *J. Immunol.* 1985, 135:1900; and (c) Deres et al., *Nature* 1989, 342:561], and continue to be used and further optimized today [(a) Salunke et al., *J. Med. Chem.* 2013, 56:5885-5900; (b) Salunke et al., *J. Med. Chem.* 2012, 55:3353-3363; and (c) Agnihotri et al., *J. Med. Chem.* 2011, 54:8148].

Among the TLRs, TLR2 requires heterodimerization with either TLR1 or TLR6 for activation with bacterial triacylated lipoproteins. A widely-recognized agonist activating TLR1/TLR2 is PAM3CSK4, and bacterial diacylated lipopolypeptides such as MALP-2 stimulate TLR2/TLR6, [Muhlradt et al., *J. Exp. Med.* 1997, 185:1951]). Structural formulas those agonists are shown below [Buwitt-Beckmann

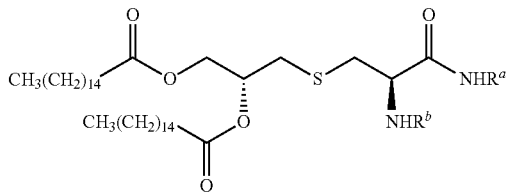

1, Pam3CSK4, $R^a$ = SKKKK (SEQ ID NO: 1), $R^b$ = CO(CH$_2$)$_{14}$CH$_3$
2, MALP-2, $R^a$ = GNNDESNISFKEK (SEQ ID NO: 2), $R^b$ = H et al., *J. Biol. Chem.* 2006, 281:9049] from left to right, and from amino- to carboxy-terminus.

Complementary to recent studies describing the discovery of the first, albeit less potent, class of small molecule TLR2/TLR1 agonists [(a) Guan et al., *J. Biol. Chem.* 2010, 285:23755-23762; and (b) Cheng et al., *Sci. Adv.* 2015, 1:e1400139], herein is disclosed the discovery of compounds named diprovocims. This exceptionally potent class of TLR2/TLR1 agonists emerged from screening a unique chemical library designed to promote cell surface receptor dimerization [Goldberg et al., *J. Am. Chem. Soc.* 2002, 124:544-555]. The disclosure that follows provides more details about this new class of synthetic TLR agonists.

BRIEF SUMMARY OF THE INVENTION

A contemplated diprovocim compound corresponds in structure to structural Formula V,

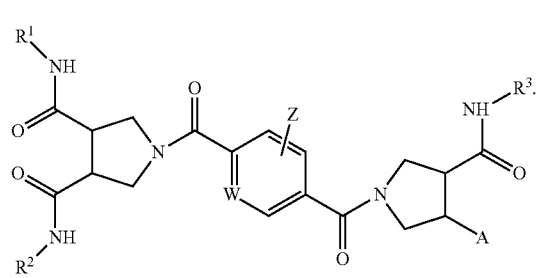

V

In Formula V,

—A is hydrogen (hydrido) or —C(O)NH—$R^4$. $R^1$, $R^2$, $R^3$ and $R^4$ are the same or different and are a 2-(4-fluorophenyl) ethyl, trans-2-phenylcyclopropyl, trans-2-(4-fluorophenyl) cyclopropyl group or a $C_3$-$C_{18}$ hydrocarbyl group, with the provisos that 1) at least two of $R^1$, $R^2$, $R^3$ and $R^4$ ($R^{1-4}$) or at least two of $R^1$, $R^2$, and $R^3$ ($R^{1-3}$), when -A is hydrido, are a trans-2-phenylcyclopropyl group, or a trans-2-(4-fluorophenyl)cyclopropyl group or a mixture thereof, or each of $R^1$, $R^2$, $R^3$ and $R^4$ is a 2-(4-fluorophenyl)-ethyl group, and 2) at least one depicted 3,4-pyrrolidinyldicarboxyl (or pyrrolidinyldicarboxyl) group has the (S,S) configuration, and each depicted R substituent other than a $C_3$-$C_{18}$ hydrocarbyl group is a trans-2-phenylcyclopropyl, a trans-2-(4-fluorophenyl)cyclopropyl group or a mixture thereof when each of $R^{1-4}$ is other than 2-(4-fluorophenyl)ethyl, 3) no more than two of $R^{1-4}$ are $C_3$-$C_{18}$ hydrocarbyl groups, and 4) when A is hydrido, only one of $R^{1-3}$ is a $C_8$-$C_{18}$ hydrocarbyl group and the depicted $R^3$-containing pyrrolidinylcarboxamido group has either the R or S configurations, or a mixture of both configurations. More preferably, both pyrrolidinyldicarboxyl groups, when present, have the (S,S) configuration.

W is nitrogen (N), making the depicted central aromatic ring a substituted pyridyl group, or W is CH, making that aromatic ring a substituted phenyl group.

In Formula V, —Z is one or more of halogen (fluoro, chloro, or bromo), —H, —NH$_2$, —OH, —OCH$_3$, —NO$_2$, —OCH$_2$CO$_2$H, —O(CH$_2$CH$_2$O)$_n$CH$_2$CH$_2$CO$_2$H, —OCH$_2$CONH(CH$_2$CH$_2$O)$_n$CH$_2$CH$_2$CO$_2$H, —NHCOCH$_2$O—(CH$_2$CH$_2$O)$_n$CH$_2$CO$_2$H, —OCH$_2$CONHCH$_2$CONHCH(CHOH)CO$_2$H, —OCH$_2$CONHCH$_2$CONHCHCO$_2$H(CH$_2$CO$_2$H), —OCH$_2$CONHCH$_2$CONHCH(CHOH) (CH$_2$CH$_2$O)$_n$CH$_2$CH$_2$CO$_2$H, —OCH$_2$CONHCH$_2$CONHCH[(CH$_2$)$_4$NH$_2$]CO$_2$H, —OCH$_2$CONHCH$_2$CONHCH(CH$_2$OH)CO{NHCH[(CH$_2$)$_4$NH$_2$]CO}$_m$NHCH—[(CH$_2$)$_4$NH$_2$]CO$_2$H (SEQ ID NOs: 3-8), —OCH$_2$CONHCH$_2$CO{NHCH[(CH$_2$)$_4$NH$_2$]CO}$_p$NHCH[(CH$_2$)$_4$NH$_2$]CO$_2$H (SEQ ID NOs: 9-13), and —OCH$_2$CONHCH$_2$CO{NHCH(CH$_2$OH)CO}$_q$NHCH(CH$_2$OH)CO$_2$H (SEQ ID NOs: 14-18). The data hereinafter illustrate the activity in inducing the release of TNF-α from cultured human THP-1 cells and/or mouse monocytes using a compound of Formula V whose —Z group is among those recited above.

"n" is a number whose average value is one to about eight, and preferably 2 to about 5. Thus, oligo polyoxyethelene groups having one to about five linked oxyethylene groups are contemplated as being bonded within a Z substituent group. The oligo oxyethylenes are typically mixtures with varying numbers of repeating oxyethylene units so that "n" is referred to as a number with an average value.

"m" is a number whose value is 1 to about 6, and preferably is 2 to about 5.

"p" is a number whose value is 1 to about 6, and preferably is 2 to about 5.

"q" is a number whose value is 1 to about 6, and preferably is 2 to about 5.

In some preferred aspects, substituent —Z is preferably —H (hydrido), —OH (hydroxyl) or —NH$_2$ (amino) when a compound of Formula V is used as an active ingredient that is free in a pharmaceutical or other composition (not coupled to a larger molecule) or as an intermediate as prior to being coupled to a linking group or to a larger molecule.

One particularly preferred aspect of the invention contemplates a compound of Formula I, below, that is also a compound of Formula V in which

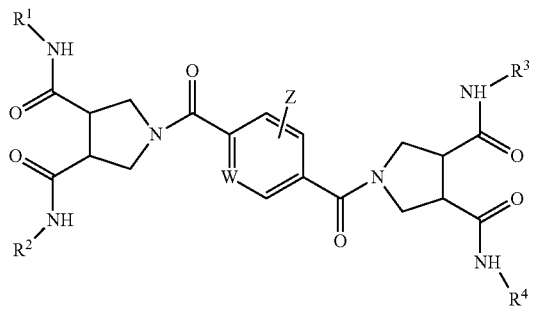

-A is —C(O)NH—R⁴. Thus, the depicted $R^{1-4}$, W and Z moieties are as described above.

Preferably, at least one of substituent pair $R^1$ and $R^3$ or $R^1$ and $R^2$ is a trans-2-phenyl-cyclopropyl or a trans-2-(4-fluorophenyl)cyclopropyl group. It is also preferred that at least one of $R^1$ and $R^3$ or $R^1$ and $R^2$ has the (1S,2R) configuration of a trans-2-phenylcyclopropyl or trans-2-(4-fluorophenyl)cyclopropyl group. More preferably, at least three of $R^1$, $R^2$, $R^3$ and $R^4$ are the (1S,2R) enantiomer of a trans-2-phenylcyclopropyl or a trans-2-(4-fluorophenyl)cyclopropyl group. In another preference, each of $R^1$, $R^2$, $R^3$ and $R^4$ is a 2-(phenyl)ethyl group.

In another preferred aspect of the invention, W of a compound of Formula V is CH so that a contemplated compound has a central aromatic ring that is a substituted phenyl group. In a further preference, each of the two 3,4-pyrrolidinyl-dicarboxyl groups present (depicted) in Formulas V and Ia (below) has the same configuration. That same

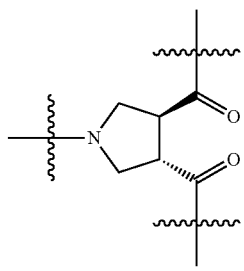 [SMILES: *C(=O)[C@@H]1CN(*)C[C@H]1C(*)=O]

configuration is preferably the (S,S) configuration as shown above, where the wavy lines indicate that additional portions of the molecule are not shown for added clarity. Structural Formula Ia that illustrates these preferences is shown below where $R^1$, $R^2$, $R^3$ and $R^4$ and Z are as previously described.

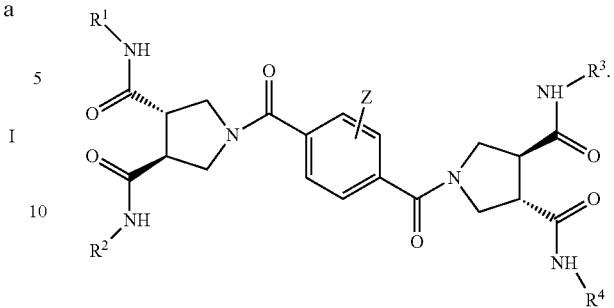

A contemplated compound is useful as is as a small molecule, as well as tethered to another molecule such as an antibody or protein or peptidal antigen. As such, —Z is preferably —H, —NH₂, or —OH when used as a small molecule, or —Z is —NH₂ or —OH when used as an intermediate for coupling to a larger molecule. It is also preferred that a contemplated compound be present as a single enantiomer.

A still further preferred aspect of a compound of Formula V is a compound of Formula Va,

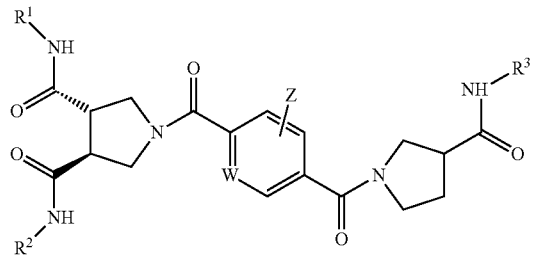

that is present when -A of Formula V is hydrido and one of $R^{1-3}$ is a $C_8$-$C_{18}$ hydrocarbyl group, while the other two of $R^{1-3}$ is. Each of $R^{1-3}$ can also be a trans-2-phenylcyclopropyl, a trans-2-(4-fluoro-phenyl)cyclopropyl group, or a mixture thereof. Thus, at least two of the depicted $R^{1-3}$ substituents are a trans-2-phenylcyclopropyl group, a trans-2-(4-fluorophenyl)cyclopropyl group, or a mixture thereof, and W and Z are as previously defined.

In one particularly preferred illustrative compound, $R^1$ and $R^2$ are a trans-2-phenylcyclopropyl group, a trans-2-(4-fluorophenyl)cyclopropyl group, or a mixture of both substituents, and $R^3$ is a $C_8$-$C_{18}$ hydrocarbyl group. The depicted —C(O)—$R^3$ group can be in either the R configuration, the S configuration or present as a mixture of both configurations.

The present invention also contemplates a pharmaceutical composition that comprises an amount of a compound of Formula V, or a compound of sub-generic Formulas I, Ia or Va, effective to induce release of TNF-α from in vitro cultured human PMA differentiated THP-1 cells. That compound is present in the composition dissolved or dispersed in a physiologically tolerable diluent.

Another aspect of this invention contemplates a method of enhancing an immunogen-specific humoral immune response. In that method, immune cells are contacted with an adjuvant-effective amount of a compound of claim 1 and an immunogen to which the immune response is to be enhanced.

The word "hydrocarbyl" is used herein as a short hand term for a non-aromatic group that includes straight and branched chain aliphatic as well as cyclic groups or radicals that contain only carbon and hydrogen. Inasmuch as alicyclic groups are cyclic aliphatic groups, such substituents are deemed to be subsumed within the aliphatic groups. Thus, alkyl, alkenyl and alkynyl groups are contemplated.

Usual chemical suffix nomenclature is followed when using the word "hydrocarbyl" except that the usual practice of removing the terminal "yl" and adding an appropriate suffix is not always followed because of the possible similarity of a resulting name to that of one or more substituents.

Where a specific aliphatic hydrocarbyl substituent group is intended, that group is recited; i.e., $C_1$-$C_4$ alkyl, methyl or tert-butyl. Exemplary hydrocarbyl groups contain a chain of 3 to 16 carbon atoms, and preferably 3 to about 10 carbon atoms, and more preferably still, about 5 to about 10 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein. Where a specific aliphatic hydrocarbyl substituent group is intended, that group is recited; i.e., $C_1$-$C_4$ alkyl, methyl or 2-propyl.

Examples of straight and branched chain alkyl radicals include methyl, ethyl, n-propyl, isopropyl, n-butyl, isobutyl, sec-butyl, tert-butyl, pentyl, hexyl, heptyl, octyl, nonyl, decyl, undecyl, lauryl, myristyl, and stearyl. The branched chain $C_5$-$C_{18}$ are also contemplated, but are too numerous to name specifically. Illustrative cyclic alkyl groups include cyclopropyl, cyclopentyl, 3-methylcyclopentyl and cyclohexyl. Examples of suitable alkenyl radicals include ethenyl (vinyl), 2-propenyl, 3-propenyl, 1,4-butadienyl, 1-butenyl, 2-butenyl, and 3-butenyl, 2-pentenyl and 3-hexenyl. Examples of alkynyl radicals include ethynyl, 2-propynyl, 1-propynyl, 1-butynyl, 2-butynyl, 3-butynyl, and 1-methyl-2-propynyl, 3-methyl-1-butynyl and 2-methyl-1-pentynyl. Illustrative mono-, di- and tri-enes, as well as the mono-, di- and tri-ynes of the $C_7$-$C_{18}$ hydrocarbyl substituents are also contemplated and are too numerous to name specifically. Cyclic alkynes are analogous to the cyclic alkenes.

As a skilled worker will understand, a substituent that cannot exist such as a $C_1$ alkenyl or alkynyl group or a $C_1$-$C_2$ cyclic group is not intended to be encompassed by the word "hydrocarbyl", although such substituents with two or more carbon atoms are intended for other than cyclic substituents.

BRIEF DESCRIPTION OF THE DRAWINGS

In the drawings forming a portion of this disclosure.

DETAILED DESCRIPTION OF PREFERRED EMBODIMENTS

Figure 1A:
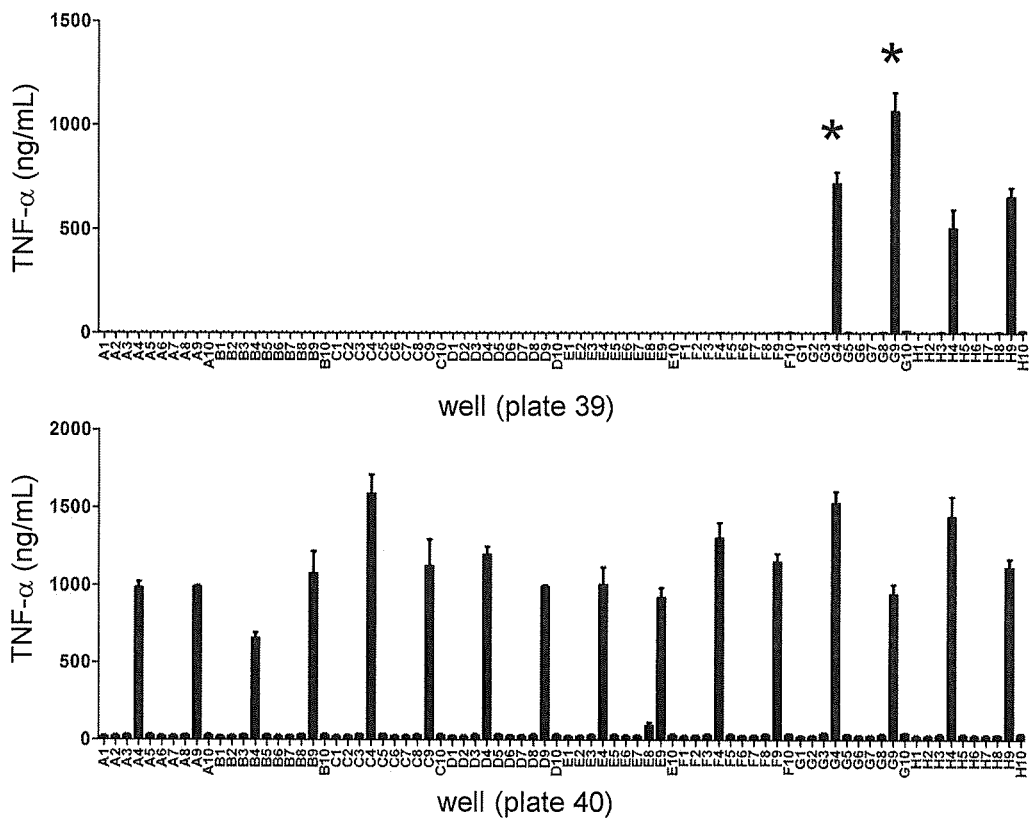
FIG. 1A is a schematic showing screening results for the receptor dimerization library (plate 39 G-H wells and plate 40 all wells) obtained by measuring stimulated TNF-α release from differentiated human THP-1 cells (10 compound mixtures tested at 50 μM). The compound mixtures in the starred wells were prepared as individual compounds.

The present invention contemplates a compound of Formula V that is often referred to herein as a diprovocim. The most active of the diprovocims elicits full agonist activity at extraordinarily low concentrations ($EC_{50}$=100 pM) in cultured human cells, being more potent than Pam3CSK4 or any other known TLR agonist. The compound class exhibits exquisite structure-activity relationships, acts by a well-defined mechanism (TLR1/TLR2 agonist), and selected members are active in human and murine systems. The observed efficacy matches that of natural potent agonists such as LPS or the lipopeptides, but is observed with an even greater potency, and a diprovocim is active in vivo as an adjuvant. This compound class bears no structural similarity to either the TLR1/TLR2 lipoprotein agonists nor to any other synthetic TLR agonist, and they are remarkably easy to prepare and synthetically modify.

Thus, a preferred diprovocim compound corresponds in structure to structural Formula V,

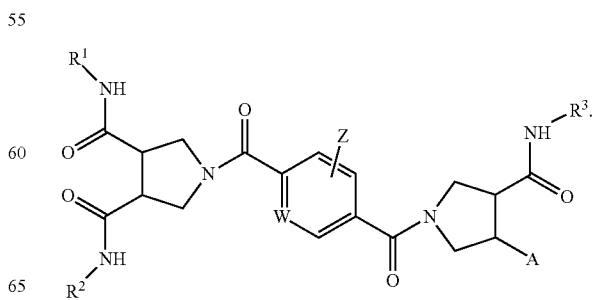

In Formula V, -A is hydrogen (hydrido) or —C(O)NH—$R^4$. $R^1$, $R^2$, $R^3$ and $R^4$ are the same or different and are a 2-(4-fluorophenyl)ethyl, a trans-2-phenylcyclopropyl, a trans-2-(4-fluorophenyl)cyclopropyl or a $C_3$-$C_{18}$ hydrocarbyl group, with the provisos that: 1) at least two of $R^1$, $R^2$, $R^3$ and $R^4$ ($R^{1-4}$) or at least two of $R^1$, $R^2$, and $R^3$ ($R^{1-3}$) are a trans-2-phenyl-cyclopropyl, a trans-2-(4-fluorophenyl)cyclopropyl group or a mixture thereof, or each of $R^{1-4}$ is a 2-(4-fluorophenyl)ethyl group, 2) at least one depicted pyrrolidinyldicarboxamido group has the (S,S) configuration, and each depicted R substituent other than a $C_3$-$C_{18}$ hydrocarbyl group is a trans-2-phenylcyclopropyl, a trans-2-(4-fluorophenyl)-cyclopropyl group or a mixture thereof when each of $R^{1-4}$ is other than 2-(4-fluorophenyl)ethyl, 3) no more than two of $R^{1-4}$ are $C_3$-$C_{18}$ hydrocarbyl groups when -A is —C(O)NH—$R^4$, and 4) when A is hydrido, one of $R^{1-3}$ can be a $C_8$-$C_{18}$ hydrocarbyl group and the depicted $R^3$-containing pyrrolidinylcarboxamido group can have either the R or S configurations, or a mixture of both configurations.

In Formula V, —Z is one or more of halogen (fluoro, chloro or bromo), —H, —$NH_2$, —OH, —$OCH_3$, —$NO_2$, —$OCH_2CO_2H$, —$O(CH_2CH_2O)_nCH_2CH_2CO_2H$, —$OCH_2CONH(CH_2CH_2O)_nCH_2CH_2CO_2H$, —$NHCOCH_2O$—$(CH_2CH_2O)_nCH_2CO_2H$, —$OCH_2CONHCH_2CONHCH(CHOH)CO_2H$, —$OCH_2CONHCH_2CONHCHCO_2H(CH_2CO_2H)$, —$OCH_2CONHCH_2CONHCH(CHOH)$ ($CH_2CH_2O)_nCH_2CH_2CO_2H$, —$OCH_2CONHCH_2CONHCH[(CH_2)_4NH_2]CO_2H$, —$OCH_2CONHCH_2CONHCH(CH_2OH)CO\{NHCH[(CH_2)_4NH_2]CO\}_mNHCH$—
[$(CH_2)_4NH_2$]$CO_2H$ (SEQ ID NOs: 3-8), —$OCH_2CONHCH_2CO\{NHCH[(CH_2)_4NH_2]CO\}_pNHCH[(CH_2)_4NH_2]CO_2H$ (SEQ ID NOs: 9-13) and —$OCH_2CONHCH_2CO\{NHCH(CH_2OH)CO\}_qNHCH(CH_2OH)CO_2H$ (SEQ ID NOs: 14-18).

When amino acid residues are present in a —Z group as shown above, it is preferred that each residue be in the L-configuration, except for glycine that has no L configuration.

Substituent —Z is preferably —H (hydrido), —OH (hydroxyl) or —$NH_2$ (amino) when a compound of Formula V is used as an active ingredient that is free in a pharmaceutical or other composition (not coupled to a larger molecule) or as an intermediate as prior to being coupled to a linking group or to a larger molecule.

W is nitrogen (N) or CH. Thus, when W is N, the compound has a central substituted pyridyl moiety, whereas when W is CH, the central moiety is a substituted phenyl group.

"n" is a number whose average value is one to about eight, and preferably 2 to about 5. Thus, oligo polyoxyethelene groups having one to about five linked oxyethylene groups are contemplated as being bonded within a Z substituent group. The oligo oxyethylenes are typically mixtures with varying numbers of repeating oxyethylene units so that "n" is referred to as a number with an average value.

"m" is a number whose value is 1 to about 6, and preferably is 2 to about 5.

"p" is a number whose value is 1 to about 6, and preferably is 2 to about 5.

"q" is a number whose value is 1 to about 6, and preferably is 2 to about 5.

In regard to "m", "p" and "q" the numbers involved are shown by the data to be active with differing numbers of repeating elements related to those numbers. As a consequence, the presence of a few repeated elements more or less than the recited upper number provide some activity to the recited compound.

A particularly preferred aspect of the invention contemplates a compound of Formula I, below, that is a sub-generic compound of Formula V in

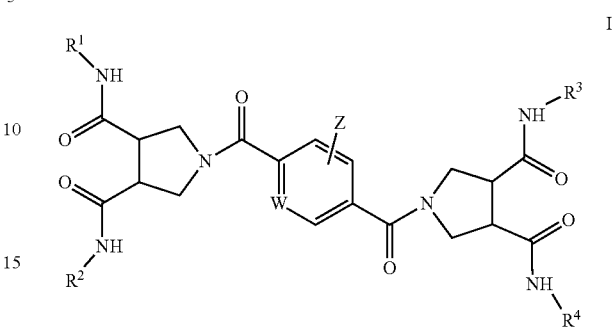

which -A —C(O)NH—$R^4$. Thus, the depicted $R^{1-4}$, W and Z moieties are as described above.

In one preferred compound of Formula I, at least one member of substituent pair $R^1$ and $R^3$ (either $R^1$ or $R^3$) or pair $R^1$ and $R^2$ (either $R^1$ or $R^2$) is a trans-2-phenylcyclopropyl or trans-2-(4-fluorophenyl)cyclopropyl group. It is also preferred that at least one member of substituent pair $R^1$ and $R^3$ or pair $R^1$ and $R^2$ has the (1S,2R) configuration of a trans-2-phenylcyclopropyl or trans-2-(4-fluoro-phenyl)cyclopropyl group.

More preferably, at least three substituents of $R^1$, $R^2$, $R^3$ and $R^4$ have the (1S,2R) configuration of a trans-2-phenylcyclopropyl or trans-2-(4-fluorophenyl)cyclo-propyl group. More preferably still, each of $R^1$, $R^2$, $R^3$ and $R^4$ has the (1S,2R) configuration of a trans-2-phenylcyclopropyl or a trans-2-(4-fluorophenyl)cyclopropyl group.

In another preference, each depicted pyrrolidinyldicarboxamido group has the (S,S) configuration and each depicted $R^{1-4}$ substituent is a trans-2-phenylcyclopropyl, a trans-2-(4-fluoro-phenyl)cyclopropyl group or a mixture thereof, and bonds to the cyclopropyl moiety have a (1S,2R) configuration.

In another aspect, up to two of $R^{1-4}$ in a compound of Formula V or one of its sub-generic formulas can be a $C_3$-$C_{16}$ hydrocarbyl group. It is preferable that the hydrocarbyl group be an alkyl group and have a length of 3 to about 10 carbon atoms, and more preferably still, about 5 to about 10 carbon atoms. Straight chained hydrocarbyl groups are also preferred, although up to two methyl and ethyl group substituents or both can be present as can an carbocyclic ring, and also one or two double or triple bonds. Specific $C_3$-$C_{16}$ hydrocarbyl groups are discussed previously in the discussion of the use of the word "hydrocarbyl" group.

As is seen from Formula V, each molecule contains at least one, and preferably two, 3,4-pyrrolidinyldicarboxyl groups. The carboxyl groups are bonded to amine-terminated $R^1$, $R^2$, $R^3$ and $R^4$ substituents, forming four (or three) amido linkages. The two pyrrolidinyldicarboxyl groups can also therefore also be referred to as two pyrrolidinyldicarboxamido groups.

Substituents bonded to the carboxyl groups of a pyrrolidinyldicarboxyl group can be in a cis or trans conformation, that is the two substituents can both project above or below the plane of the depicted ring (cis), or one can project above that plane and the other substituent project below (trans). A cis-disubstituted pyrrolidinyl-dicarboxyl group with two identical substituents has a symmetric configuration and does not have enantiomeric forms. A trans-disubstituted pyrrolidinyldicarboxyl group with those same two identical substituents has an asymmetric (chiral) configuration and has enantiomeric forms. The two chiral configurations are referred to as (S,S) and (R,R), and are shown below.

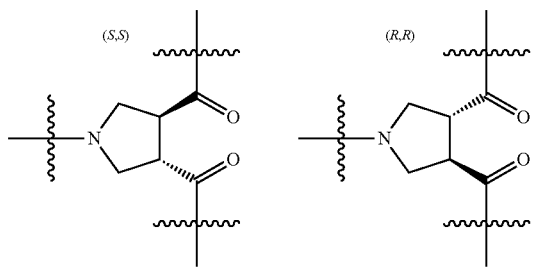 [SMILES: *C(=O)[C@@H]1CN(*)C[C@H]1C(*)=O ; *C(=O)[C@H]1CN(*)C[C@@H]1C(*)=O]

It is preferred that at least one, and more preferably both 3,4-pyrrolidinyldicarboxyl groups have the (S,S) configuration.

On the other hand, when -A of Formula V is hydrido and one of $R^{1-3}$ is a $C_8$-$C_{18}$ hydrocarbyl group, a preferred compound corresponds in structure to Formula Va, below, in which the depicted $R^{1-3}$, W Va

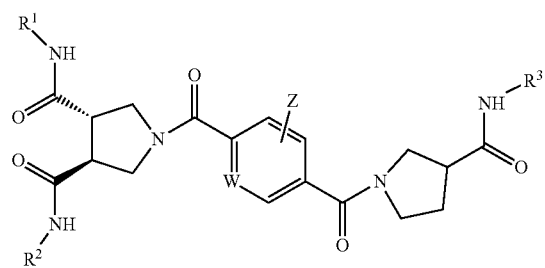

and Z moieties are as described above. The depicted —C(O)—$R^3$ group can be in either the R configuration, the S configuration or present as a mixture of both configurations.

In a compound of Formula Va, the number of carbon atoms of a $R^3$ group here is preferably 8 to 18, and more preferably 10 to 16 carbon atoms. This hydrocarbyl group is also more preferably an alkyl group that is a straight chained substituent although methyl and ethyl branches can be tolerated as can double and/or triple bonds in the chain. Cyclic hydrocarbyl substituent compounds and carbocyclic ring-containing substituents can also be utilized.

It is also preferred that W be CH. Structural Formula Ia, shown below, incorporates several of the above preferences.

Ia

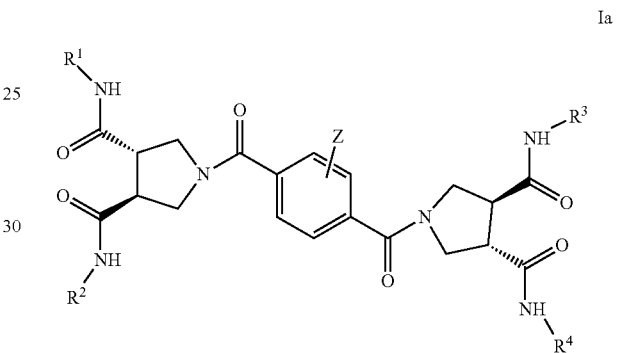

Structural formulas of preferred compounds of Formula Ia in which —Z is hydrido (—H) are shown below as compounds of Formulas A, B, C, D, E, F, G and H, and are also shown with their synthetic compound number and as a diprovocim-numbered compound.

A

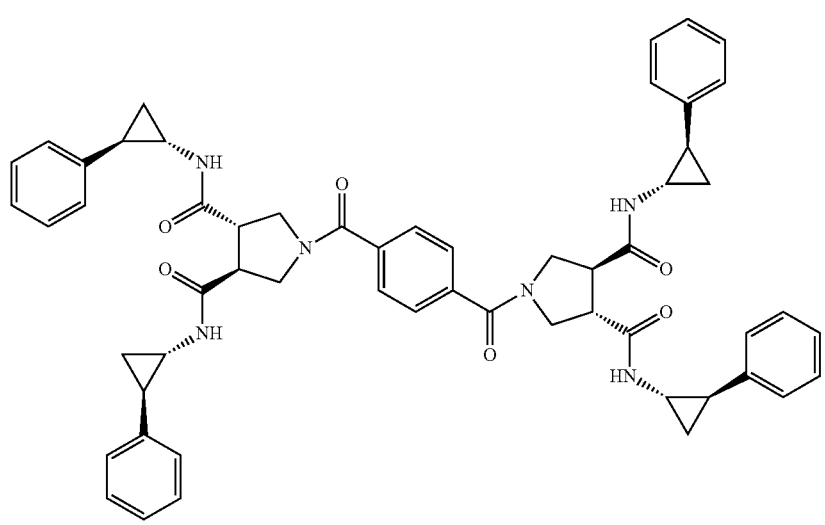

3 (diprovocim-1)

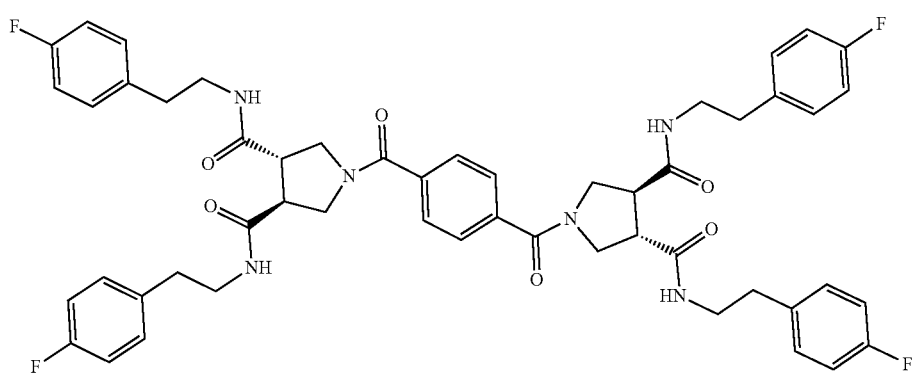
4 (diprovocim-2)
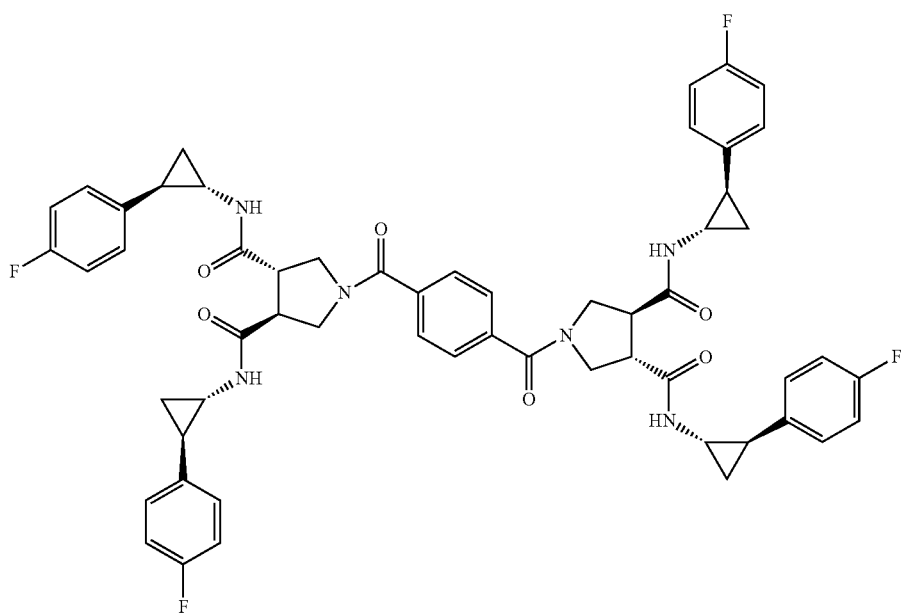
118 (diprovocim-3)
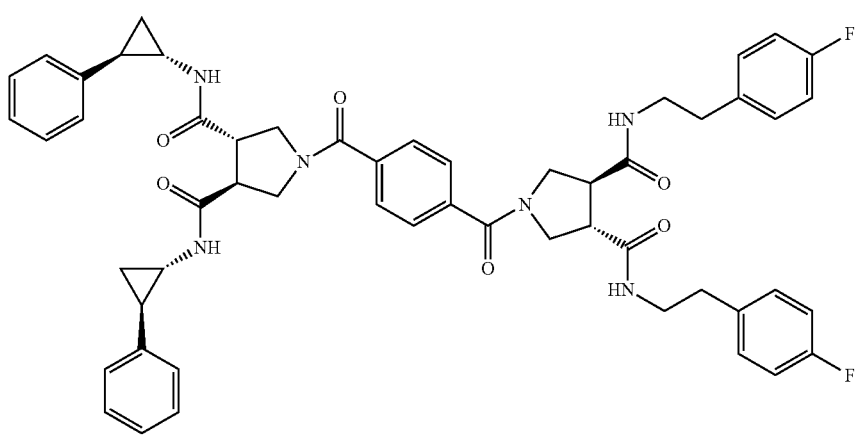
114 (diprovocim-4)

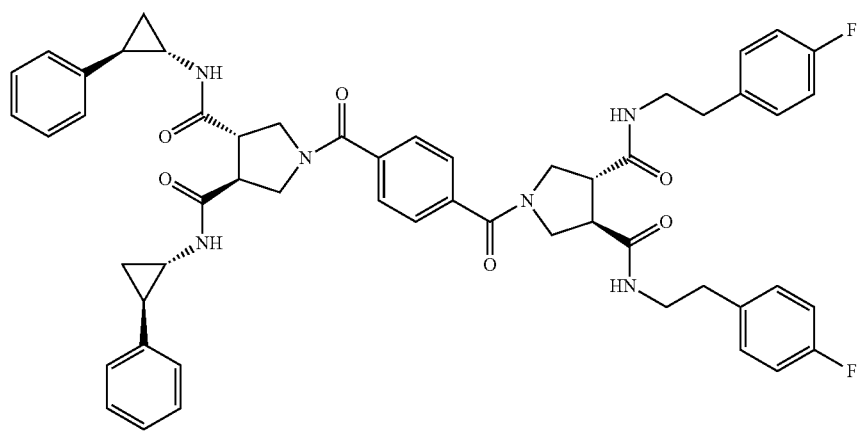

115 (diprovocim-5)

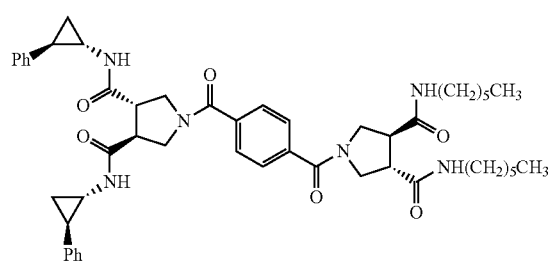

138 (diprovosim-6)

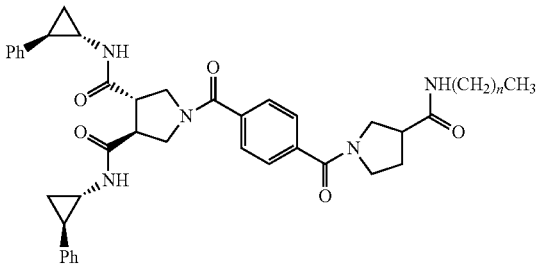

n = 9-15

Pharmaceutical Composition and Methods

A contemplated Compound of Formula V, a diprovocim, and of the sub-generic formulas thereof, can also be used in the manufacture of a medicament (pharmaceutical composition). When so used, a contemplated compound of Formula V is present dissolved or dispersed in a pharmaceutically acceptable diluent (or carrier) in an amount (or at a concentration) effective to induce release of TNF-α from in vitro cultured human PMA differentiated THP-1 cells.

One use for such a composition is as an adjuvant for a vaccine or inducing an immune response in cultured cells. As such, an improved method of enhancing an immunogen-specific humoral immune response is contemplated that comprises contacting immune cells with an adjuvant-effective amount of a compound of Formula V and an immunogen to which that response is to be enhanced. In a live mammal, this method is a method of vaccinating in which a mammal in need of vaccination is administered an effective amount of an immunogen and an effective amount of a compound of Formula V as an adjuvant. Here, the improvement comprises using a Compound of Formula V or its pharmaceutically acceptable salt as the adjuvant.

For example, studies illustrated elsewhere herein, diprovocim-1 acts as a robust in vivo adjuvant or TLR1/TLR2 agonist that evoked a potent TLR2-dependent adjuvant activity in vivo in mice at 0.25-5 mg/kg (i.m.) when co-injected with ovalbumin as immunogen by an intramuscular route. In addition, diprovocim-1 did not display the overt toxicity that is characteristic of LPS administration when used as an adjuvant.

A contemplated composition also typically contains pharmaceutically acceptable salts, buffers and the like excipients that collectively are referred to as pharmaceutically (or physiologically) acceptable diluents or carriers as compared to those that can be present in a composition that is not intended for pharmaceutical use, as in an in vitro assay.

A compound of the invention can be provided for use by itself, or as a pharmaceutically acceptable salt. A contemplated Compound of Formula I, an aniline, is a weak base. Parental anilinium ion has a reported pKa value of 4.6. A carboxyl group is also present in the molecule that is preferably esterified, but can be present as a salt.

Exemplary salts useful for a contemplated compound include but are not limited to the following: sulfate, hydrochloride, hydro bromides, acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenyl-propionate, picrate, pivalate, propionate, succinate, tartrate, thiocyanate, tosylate, mesylate and undecanoate. Salts of the carboxylate group include sodium, potassium, magnesium, calcium, aluminum, ammonium, and the many substituted ammonium salts.

The reader is directed to Berge, *J. Pharm. Sci.* 1977 68(1):1-19 for lists of commonly used pharmaceutically acceptable acids and bases that form pharmaceutically acceptable salts with pharmaceutical compounds.

In some cases, the salts can also be used as an aid in the isolation, purification or resolution of the compounds of this invention. In such uses, the acid used and the salt prepared need not be pharmaceutically acceptable.

As is seen from the data that follow, a contemplated compound is active in in vivo and in in vitro assay studies at micromolar amounts. When used in an assay such as an in vitro assay, a contemplated compound is present in the composition in an amount that is sufficient to provide a concentration of about 10 µM to about 100 µM to contact cells to be assayed.

A contemplated pharmaceutical composition contains an effective amount of a Compound of Formula V or a pharmaceutically acceptable salt thereof dissolved or dispersed in a physiologically (pharmaceutically) acceptable carrier. In some embodiments, an adjuvant effective (TLR2 agonist effective) amount is utilized. Such a composition can be administered to mammalian cells in vitro as in a cell culture to contact those cells, or the cells can be contacted in vivo as in a living, host mammal in need.

When used as a vaccine adjuvant, a Compound of Formula V is preferably administered together with the selected immunogen. Both components are preferably present together in a single composition. However, the two ingredients can be present in separately administered compositions, and those separate compositions can be administered up to about one to about two hours apart. It is preferred when two separate compositions are administered, that they be administered as close together in time as possible.

A compound of Formula V was illustratively administered in vivo in a weight of adjuvant per kilogram of subject animal at about 0.25 to about 10, and preferably at about 0.5 to about 5 mg/kg. Usually, a Compound of Formula V contemplated here is administered parenterally in vivo in a weight amount per square meter of the recipient's body surface area (bsa). For adults, this amount is typically about 1 to about 20 mg/m$^2$ bsa, and about one-half those amounts for children A contemplated composition is typically administered in vivo to a subject in need thereof a plurality of times within one month, such as daily or weekly, and can be administered over a period of several months to several years. More usually, a contemplated composition is administered a plurality of times over a course of treatment.

A contemplated pharmaceutical composition can be administered orally (perorally) or parenterally, which is preferred, in a formulation containing conventional nontoxic pharmaceutically acceptable carriers, adjuvants, and vehicles as desired. The term parenteral as used herein includes subcutaneous injections, intravenous, intramuscular (which is most preferred), intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

A contemplated pharmaceutical composition is preferably adapted for parenteral administration. Thus, a pharmaceutical composition is preferably in liquid form when administered, and most preferably, the liquid is an aqueous liquid, although other liquids are contemplated as discussed below, and a presently most preferred composition is an injectable preparation.

Thus, injectable preparations, for example, sterile injectable aqueous or oleaginous solutions or suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline.

Other liquid pharmaceutical compositions include, for example, solutions suitable for parenteral administration. Sterile water solutions of a Compound of Formula V or sterile solution of a Compound of Formula V in solvents comprising water, ethanol, or propylene glycol are examples of liquid compositions suitable for parenteral administration. In some aspects, a contemplated Compound of Formula V is provided as a dry powder that is to be dissolved in an appropriate liquid medium such as sodium chloride for injection prior to use.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of an injectable composition. Dimethyl acetamide, surfactants including ionic and nonionic detergents, polyethylene glycols can be used. Mixtures of solvents and wetting agents such as those discussed above are also useful. Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Solid dosage forms for oral administration can include capsules, tablets, pills, powders, and granules. The amount of a contemplated Compound of Formula V (a diprovocim) in a solid dosage form is as discussed previously, an amount sufficient to provide a concentration of about 10 mM to about 100 mM, preferably about 1 nM to about 50 nM, in the serum or blood plasma. A solid dosage form can also be administered a plurality of times during a one week time period.

In such solid dosage forms, a compound of this invention is ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

A mammal in need of treatment (a subject) and to which a pharmaceutical composition containing a Compound of Formula V is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where an in vitro assay is contemplated, a sample to be assayed such as cells and tissue can be used. These in vitro compositions typically contain water, sodium or potassium chloride, and one or more buffer salts such as and acetate and phosphate salts, Hepes or the like, a metal ion chelator such as EDTA that are buffered to a desired pH value such as pH 4.0-8.5, preferably about pH 7.2-7.4, depending on the assay to be performed, as is well known. Preferably, the pharmaceutical composition is in unit dosage form. In such form, the composition is divided into unit doses containing appropriate quantities of the active compound. The unit dosage form can be a packaged preparation, the package containing discrete quantities of the preparation, for example, in vials or ampules.

In another preferred embodiment, a contemplated Compound of Formula V is administered as an adjuvant along with one or more immunogenic materials as a vaccine. One such composition is illustrated herein in which olvalbumin was used as the immunogen in the vaccination of C57BL/6J mice.

Results and Discussion

Screen and Results

The discovery of the role of the TLRs emerged in genetic studies in whole organisms that used random nucleic acid mutations to identify phenotypic changes derived from altered genes impacting the immune system (lack of sensitivity to LPS due to a mutated and disabled TLR4). [(a) Poltorak et al., *Science* 1998, 282:2085-2088; (b) Beutler et al., *J. Endotoxin Res.* 2001, 7:277-280; (c) Beutler et al., *Nat. Rev. Immunol.* 2003, 3:169-176.] Complementary to such efforts, the use of an alternative unbiased chemical genetics approach was explored [O' Connor et al., *Chem. Soc. Rev.* 2011, 40:4332-4345] screening libraries of compounds in cell-based functional assays for stimulated signaling of an immune response.

A screening campaign was conducted with nearly 100,000 compounds [(a) Whitby et al., *Acc. Chem. Res.* 2012, 45:1698-1709; and (b) Boger et al., *Angew. Chem. Int. Ed.* 2003, 42:4138-4176], using a newly developed functional assay that measured the stimulated release of TNF-α from treated human THP-1 cells partially differentiated along the macrophage line [unpublished results of the inventors and co-workers]. The functional activity measured by this assay is both a rare activation event (activator/agonist vs inhibitor/antagonist) and is extraordinarily sensitive, such that even weak and rare stimulation of TNF-α release proved detectable. The libraries screened in the efforts represent a unique compound collection populated by nontraditional compounds [(a) Whitby et al., *Acc. Chem. Res.* 2012, 45:1698-1709; and (b) Boger et al., *Angew. Chem. Int. Ed.* 2003, 42:4138-4176] designed to target protein-protein [(a) Shaginian et al., *J. Am. Chem. Soc.* 2009, 131:5564-5572; and (b) Whitby et al., *J. Am. Chem. Soc.* 2011, 133:10184-10194] or protein-DNA interactions [Stover et al., *J. Am. Chem. Soc.* 2009, 131:3342-3348] as well as the major enzyme classes [Otrubova et al., *Bioorg. Med. Chem. Lett.* 2014, 24:3807-3813].

The library screening for TNF-α production in partially differentiated human THP-1 cells resulted in the discovery of several classes of compounds, the most potent of which is reported herein. The lead compounds described here emerged from a 1,000-membered subset of a compound library (about 6,000 compounds) designed to promote cell surface receptor dimerization, with each half monomer of the C2-symmetrical compounds designed to bind each protein receptor monomer [Goldberg et al., *J. Am. Chem. Soc.* 2002, 124:544-555].

Figure 1B:
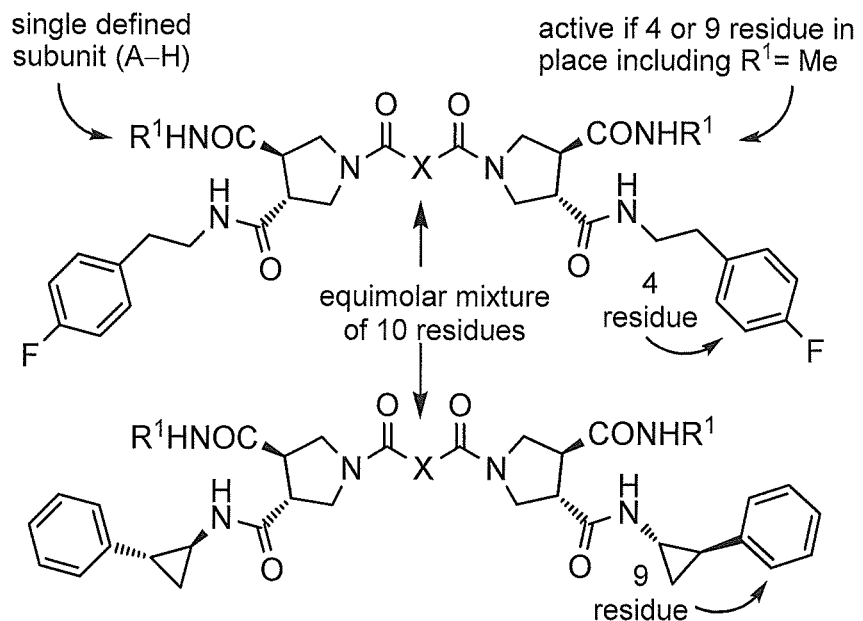
FIG. 1B shows structural formulas of active mixtures containing $R^2$ residues 4 and 9 of the library where $R^1$ is a single defined substituent and X is a mixture of ten linkers.

The sublibrary from which the leads emerged was prepared as 100 mixtures of 10 compounds on the trans-pyrrolidine-3,4-dicarboxylate core template [Whitby et al., *J. Am. Chem. Soc.* 2011, 133:10184-10194], and was composed of all individual combinations of ten defined $R^1$ and another ten defined $R^2$ substituents, and a mixture of ten linkers (denoted by X, FIGS. 1A and 1B) [Goldberg et al., *J. Am. Chem. Soc.* 2002, 124:544-555]. The compounds were assessed as a mixture of diastereomers, having been prepared using racemic trans-pyrrolidine-3,4-dicarboxylic acid and racemic trans-2-phenylcyclopropylamine as found in the original library. A general structural formula for the compounds of this sublibrary is shown below as Formula X.

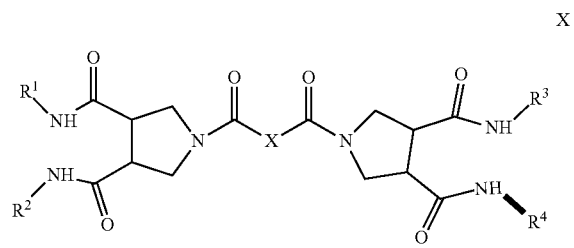

X

The screening results for stimulated TNF-α release from differentiated human THP-1 cells were remarkable, providing pools of 10 compounds that displayed activity each and every time the $R^2$ subunit was either 4-fluorophenethylamine (residue 4, plate well X4) or trans-2-phenylcyclopropylamine (residue 9, plate well X9) in the tested pools independent of the structure of $R^1$. Analogous libraries with different cores (e.g.; iminodiacetic acid, isoindoline-4,5-dicarboxylic acid), additional $R^1$ and $R^2$ substituents, alternative linker groupings, and even higher order displays (e.g.; trimer, tetramer) as described in Goldberg et al., *J. Am. Chem. Soc.* 2002, 124:544-555 failed to provide activity in the screen.

Even more remarkable is the fact that there are a large number of closely related $R^1$ and $R^2$ substituents within the sublibrary from which the leads emerged that were inactive, including phenethylamine, (4-methoxyphen)ethylamine, (4-hydroxyphen)ethylamine, (3-methoxyphen)ethylamine, benzylamine and a series of substituted derivatives. These combinations of set of ten X, $R^1$ and $R^2$ substituents are shown in the table below.

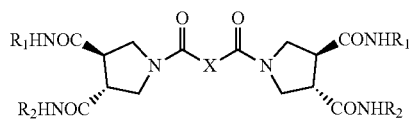
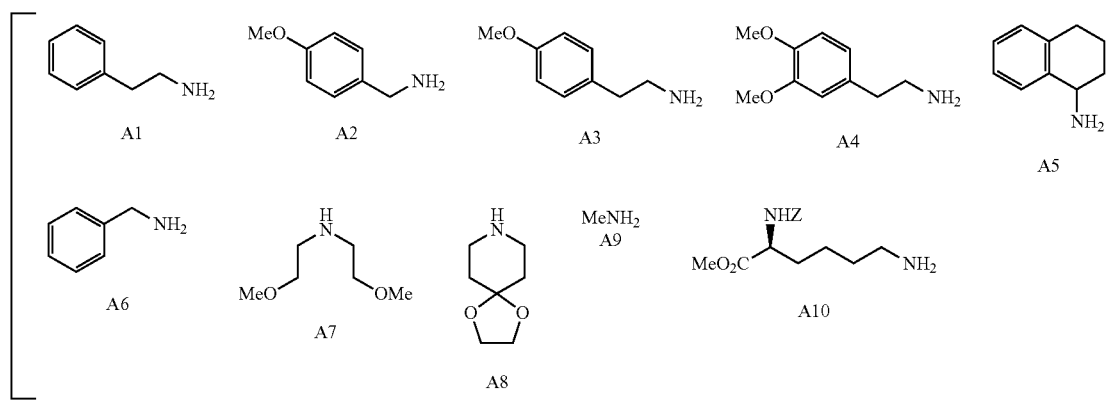
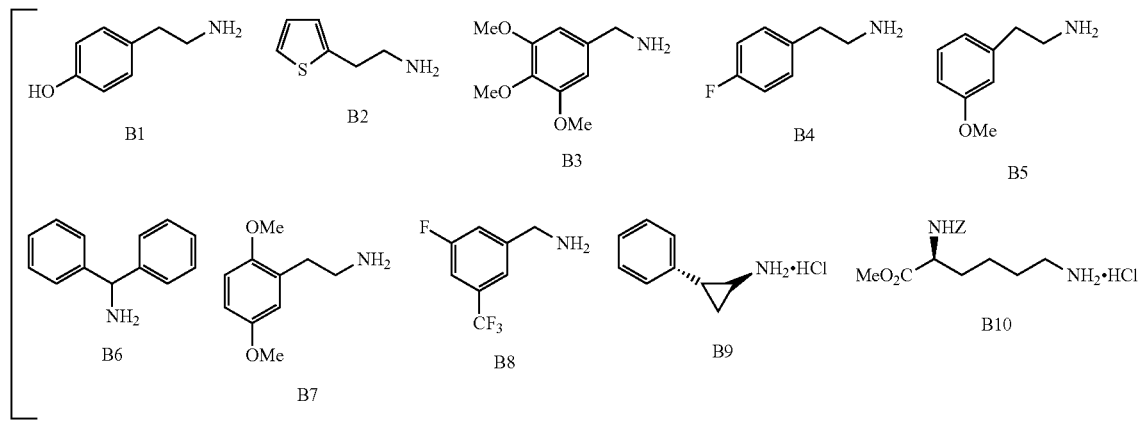
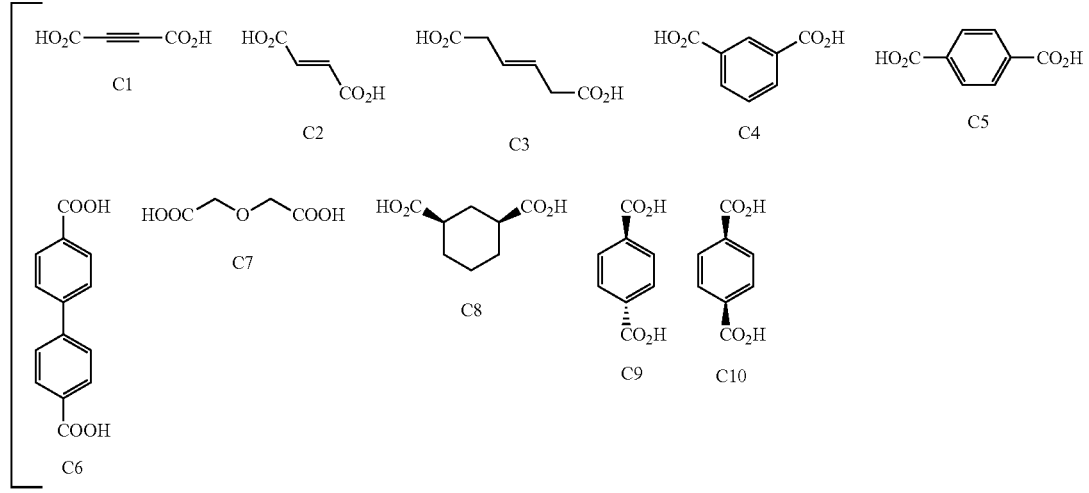

Thus, from the initial screening results, it was also determined that even small deviations from the structure resulted in no detection of activity, providing a first level structure-activity relationship (SAR) study directly from screen. Not only was the detected activity robust and structurally specific, but the remarkable repetitive observation of activity with each appearance of residue 4 or residue 9 $R^2$ substituents in the compound regardless of the identity of $R^1$ further indicated that the activity was not the result of an unrecognized artefact.

Diprovocim-1

Figure 2A:
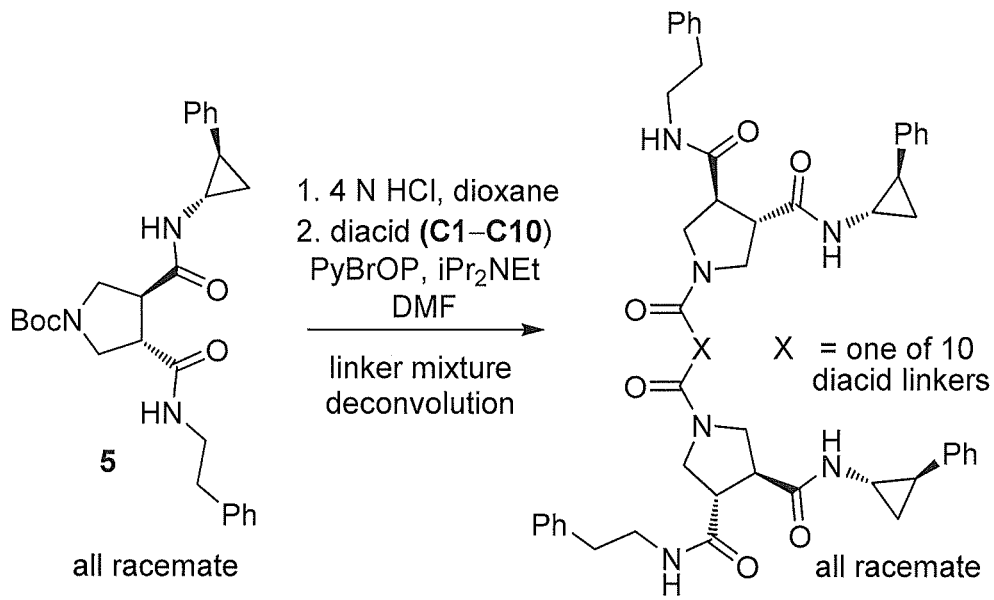
FIG. 2A illustrates the steps for the synthesis of the individual compounds in plate 39G9 used to identify linker of active compounds.
Figure 2B:
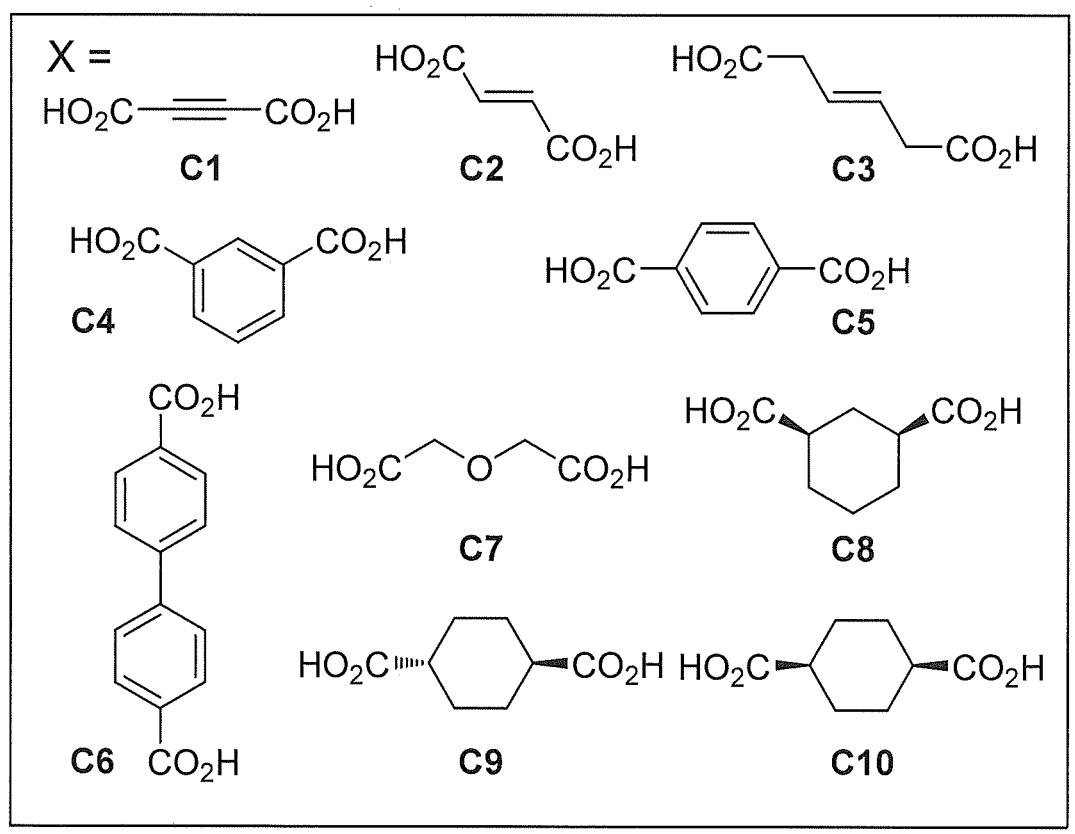
FIG. 2B illustrates the structural formulas of the ten linking groups X (C1 through C10) used in the reaction illustrated in FIG. 2A.
Figure 2C:
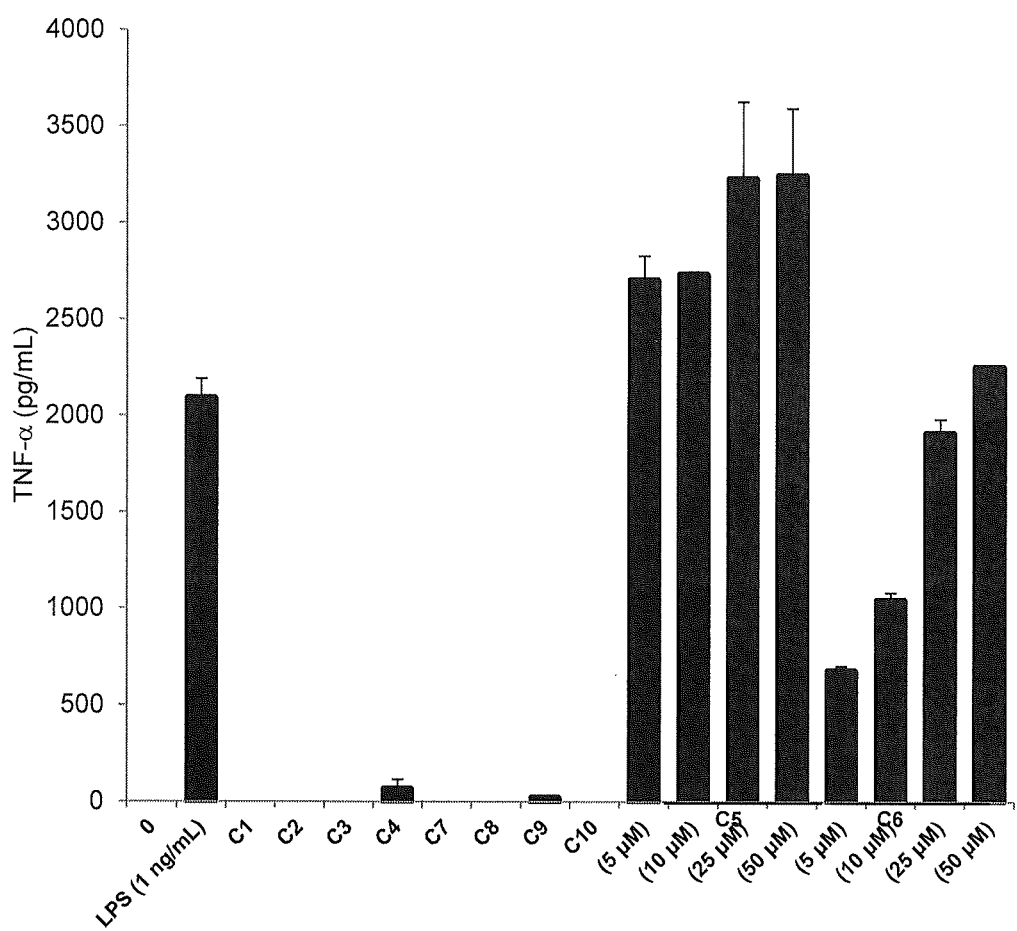
FIG. 2C is a graph of relative activities of individual compounds in the plate 39G9 mixture of the receptor dimerization library measuring stimulated TNF-α release from differentiated human THP-1 cells (tested at 50 μM unless indicated otherwise).

Two of the active wells observed in the screen (plate 39G4 and plate 39G9), containing either the residue 4 or residue 9 $R^2$ substituent, were prepared and retested as their individual compounds, identifying only two active linkers with the benzene-1,4-dicarboxylic acid linker being by far the most potent. This is illustrated in FIGS. 2A through 2C, with the results from the testing of the individual compounds found in plate 39G9.

Structurally-specific activity was observed and even dicarboxylic acid linkers spatially or structurally related to benzene-1,4-dicarboxylic acid were inactive (e.g.; C5 vs C4 or C9 and C10). For simplicity, the analogous studies conducted concurrently with plate 39G4, containing the $R^2$ residue 4 [(4-fluorophen)ethylamine] substituent, that entail identification of the active compound in the well and its optimization are detailed separately following the discussion of chronological work conducted on plate 39G9.

Figure 3:
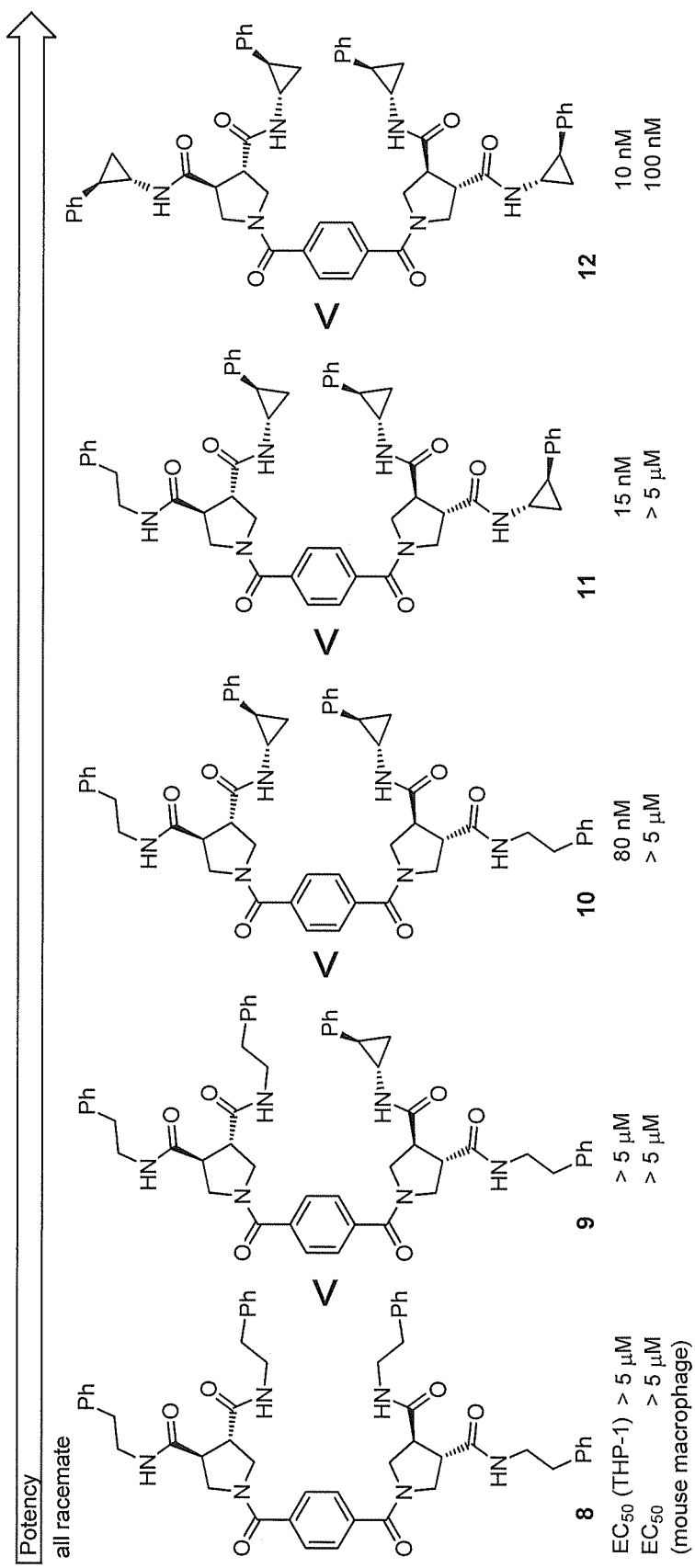
FIG. 3 shows structural formulas of compounds establishing the importance of the presence and number of 2-phenylcyclopropylamine residues derived from active lead (10) in plate 39G9. $EC_{50}$ values are derived from dose-response curves for the stimulated release of TNF-α from differentiated THP-1 cells or mouse macrophages are shown beneath each appropriate structural formula of Compounds 8-12. Half maximal effective concentration ($EC_{50}$) refers to the concentration of a drug, antibody or toxicant that induces a response halfway between the baseline and maximum after a specified exposure time. It is commonly used as a measure of a drug's potency.

Because the $R^2$ side chain was key to the activity, a set of five compounds was prepared containing the identified linker (benzene-1,4-dicarboxylic acid), to systematically establish the importance of the presence and number of 2-phenylcyclopropylamine ($R^2$) versus phenethylamine ($R^1$) side chains present in the compounds in plate 39G9 (FIG. 3). The compounds were prepared from the three pyrrolidine-3,4-dicarboxamides 5-7 and

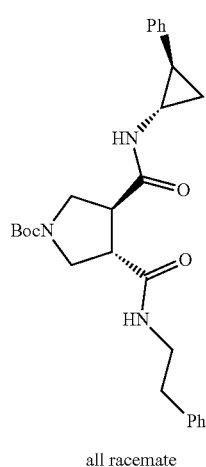

all racemate

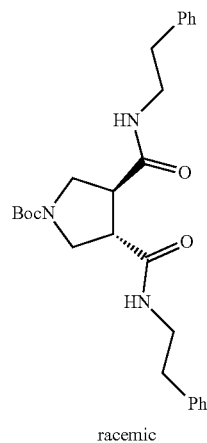

racemic

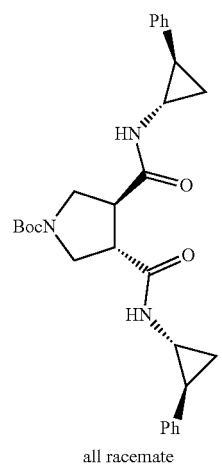

all racemate simultaneous (8, 10 and 12) coupling with benzene—

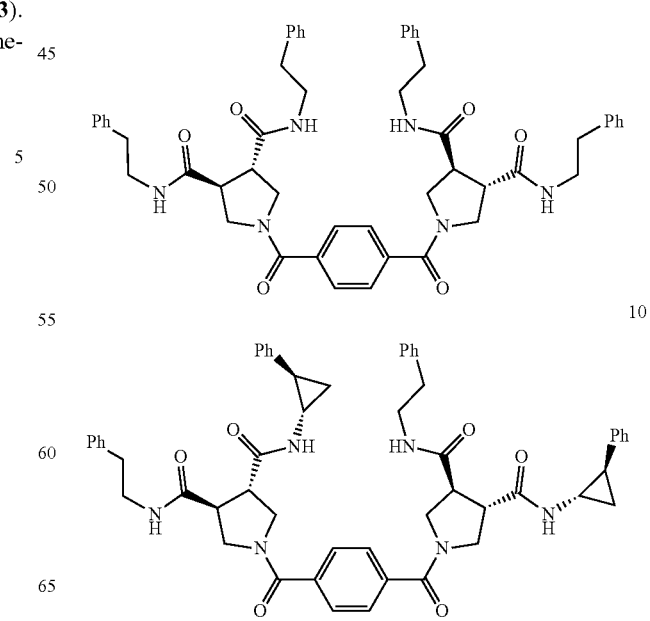

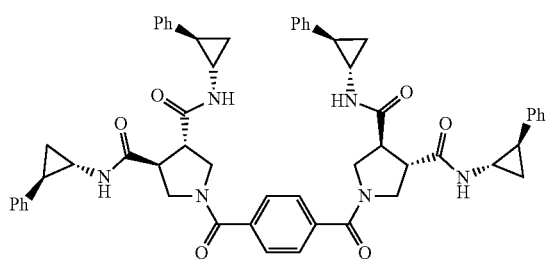

12

1,4-dicarboxylic acid (2 equiv PyBrOP, i-Pr$_2$NEt, DMF, 23° C.) or sequential (9 and 11) couplings starting

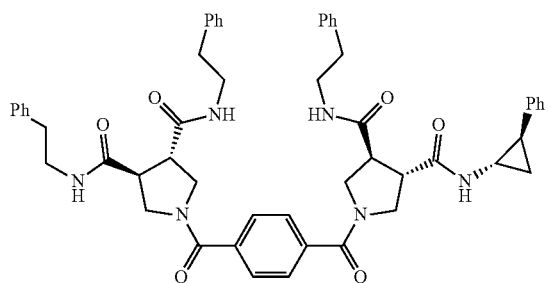

9

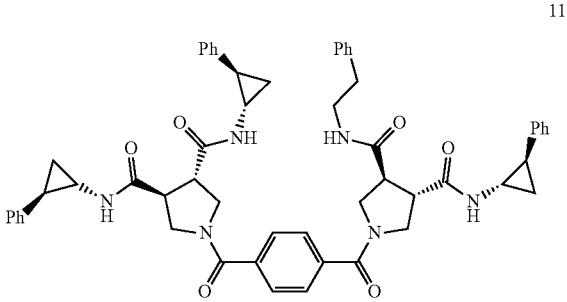

11 with the mono methyl ester of benzene-1,4-dicarboxylic acid with an intermediate hydrolysis of the methyl ester (4 equiv LiOH, THF:MeOH:H$_2$O 4:1:1, 23° C.).

The results of their assessment were stunning. Although the compounds that contained no or one 2-phenylcyclopropylamine substituents were inactive (8 and 9), each added 2-phenylcyclopropylamine substituent (two as found in the library, three, and four) incrementally (3-5-fold each) increased the potency (potency with number of residue 9 side chains: 0 and 1<2<3<4). The compounds containing three and four 2-phenylcyclopropylamine substituents (11 and 12) were more potent than the original lead 10 (EC$_{50}$=80 nM) that emerged from the library and compound 12, containing four such substituents, was exceptionally potent (EC$_{50}$=10 nM) and equally efficacious with LPS.

Just as significantly and although the leads that emerged from the screening library were inactive in stimulating the release of TNF-α from mouse macrophages, indicating species-selective activity, compound 12 was active at doing so, albeit at a lower potency (EC$_{50}$=100 nM). Although a lack of activity in a murine system would not be detrimental to their advancement for human studies, the observation of activity in mouse macrophages with 12 and subsequent related analogues is especially useful in conducting pharmacological in vivo studies in mouse models.

This activity of 12 is even more impressive because it was prepared with racemic trans-pyrrolidine-3,4-dicarboxylic acid and racemic trans-2-phenylcyclopropylamine as found in the original library. As a consequence and although each trans stereochemical relationship in the pyrrolidine cores and the side chain substituents is fixed, 12 was still a mixture of all possible 21 diastereomers and enantiomers arising from the use of racemic materials.

As daunting as this may seem, the unraveling of the activity within this complex diastereomeric mixture proved surprisingly straightforward. Each enantiomer of 2-phenylcyclopropylamine (1S,2R and 1R,2S) is commercially available [Bridgewater, N.J. 08807], and a reported resolution [Bao et al., U.S. Pat. No. 6,489,354 B1] was used to obtain the two enantiomers (S,S and R,R) of N-Boc-pyrrolidine-3,4-dicaboxylic acid. These were used to prepare four pyrrolidine/side chain subunits 15-18, representing

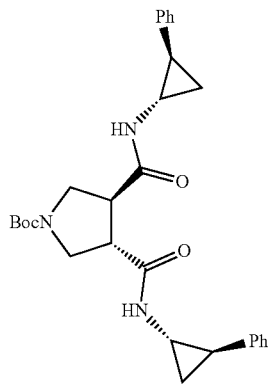

15

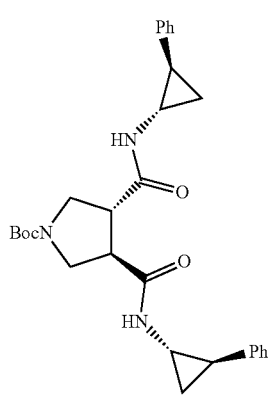

16

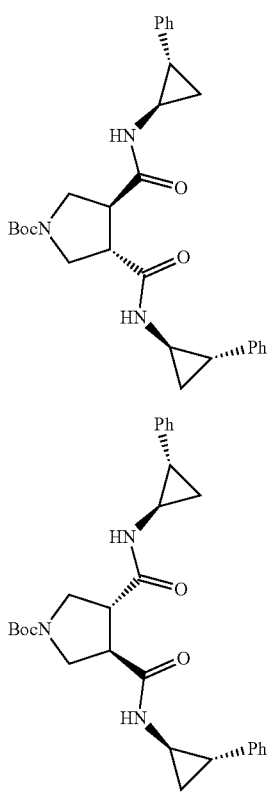

all combinations of each enantiomer of N-Boc-pyrrolidine-3,4-dicaboxylic acid independently substituted with each enantiomer of 2-phenylcyclopropylamine (same enantiomer at each of two sites) (Scheme 1, hereinafter).

Initially and for simplicity, combinations were not examined where the two substitution sites on the pyrrolidine core contained the two different enantiomers (1S,2R and 1R,2S) of 2-phenylcyclopropylamine. The four substituted pyrrolidine core monomers 15-18 were then N-Boc deprotected (4 N HCl, dioxane, 23° C., 2 hours) and simultaneously or sequentially coupled to benzene-1,4-dicarboxylic acid to provide the linked dimers containing each and all combinations of the individual enantiomerically defined monomers (10 compounds). Consistent with a specific receptor interaction, the results of their assessment conducted with full dose-response curves were remarkable and crystal clear.

Activity was observed only in compounds that contained the (S,S)-pyrrolidine-3,4-dicarboxylic acid core and only when the (1S,2R)-2-phenyl-cyclopropylamine side chain was present. In fact, the activity increased as the number of (1S,2R)- vs (1R,2S)-2-phenylcyclopropylamine substituents increased in much the same manner as was observed in the side chain series 8-12. This further indicated that the incorporation of the inactive (1R,2S)-2-phenylcyclopropylamine enantiomer in pyrrolidine monomers also containing the active 1S,2R enantiomer would be unproductive (remaining 11 compounds). Moreover, this activity spanned a huge range, all but one of the compounds being less potent than the all racemate or inactive altogether (Scheme 1, hereinafter).

As used herein, the phrase "all racemate" means all possible diastereomers and enanatiomers within the trans stereoisomers. The side chains can therefore have combinations of enantiomer relationships.

Compound 3 (diprovocim-1), composed of a single enantiomer of the pyrrolidine core

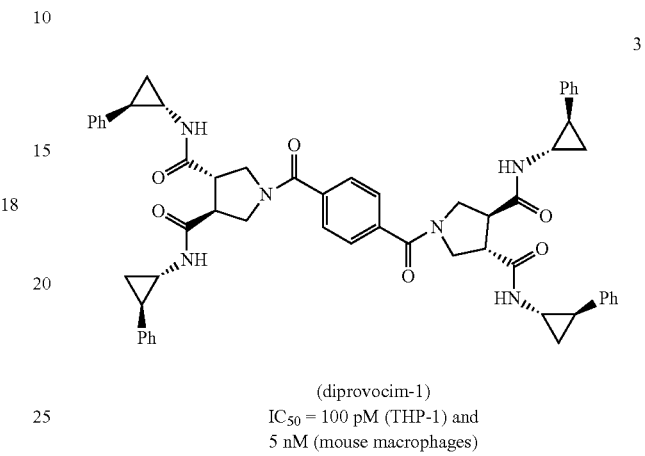

(diprovocim-1)
$IC_{50}$ = 100 pM (THP-1) and
5 nM (mouse macrophages)

dicarboxylic acid (S,S) and a single enantiomer of the 2-phenylcyclopropylamine (1S,2R) proved to be by far the most active diastereomer, exhibiting a stunning potency ($EC_{50}$=100 pM) in stimulating the release of TNF-α from human differentiated THP-1 cells. This activity proved to be 100-fold more potent than the all racemate 12 ($EC_{50}$=10 nM), quantitatively consistent with it being responsible for essentially all of the activity observed in the original all racemate mixture composed of 21 diasteromers. It, (3), was also found to be roughly ≥30-fold more potent than any other diastereomer; and no other diastereomer in this set exceeded the potency of the all racemate mixture. In addition, diprovocim-1 (3) was potent ($EC_{50}$=1 nM) and effective at stimulating the release of TNF-α from mouse macrophages.

Moreover, (3) proved to be more potent than the all racemate 12, whereas all other diastereomers were much less active, and no others approached or matched the activity of the all racemate (Scheme 1). In a direct side-by-side comparison in the assay for the stimulated release of TNF-α from differentiated human THP-1 cells, diprovocim-1 (3) proved to be equally efficacious but more potent than Pam3CSK4 (1, $EC_{50}$=0.91 nM).

Thus, ten diastereomers were prepared of the all racemate 12, identifying the active component. $EC_{50}$ values derived from dose-response curves for the stimulated release of TNF-α from differentiated human THP-1 cells and mouse macrophages by 3 (diprovocim-1) and 19-27 are shown in Scheme 1, below, along with the various pairs of compounds used.

Scheme 1
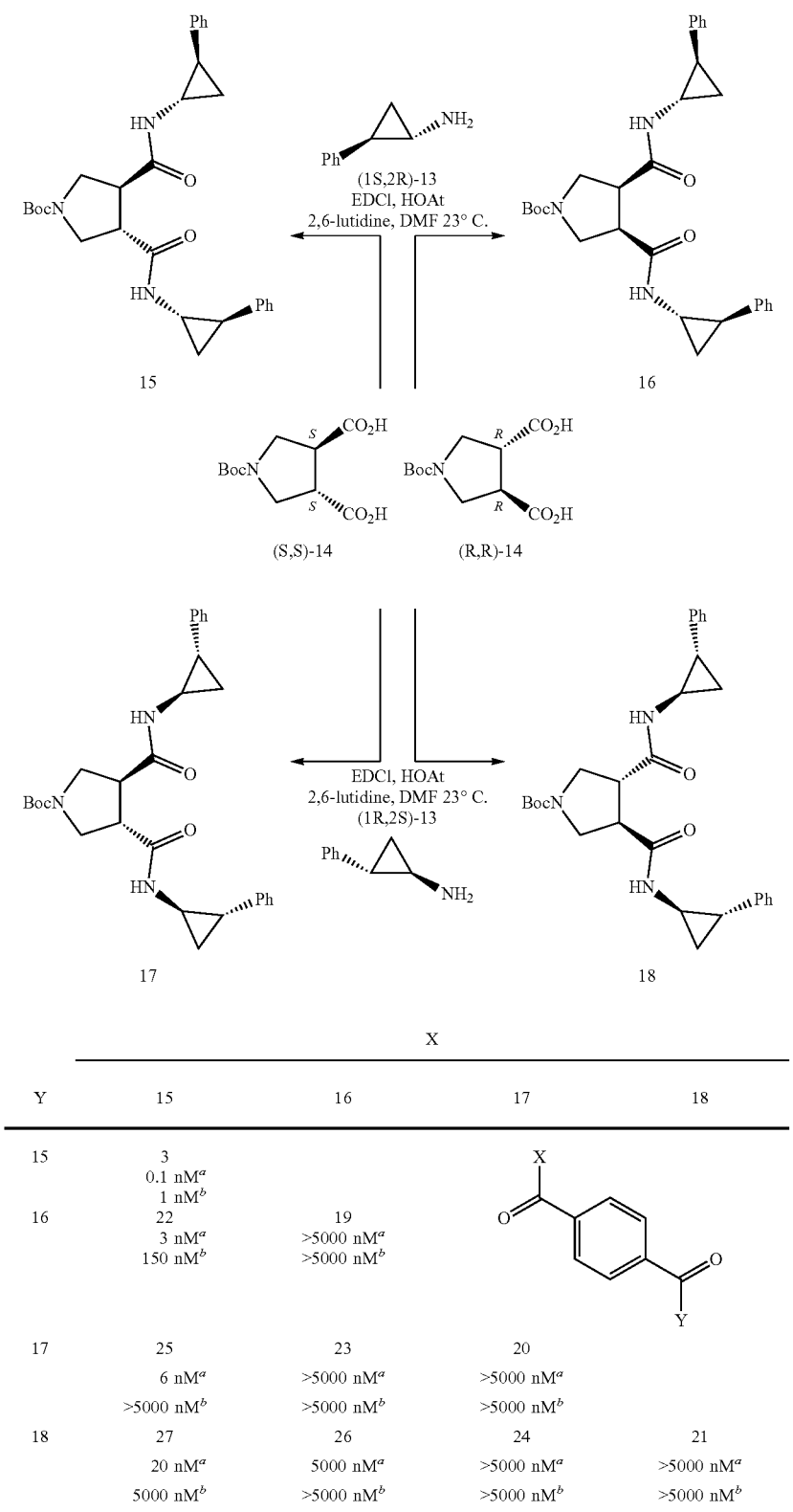
| Y | 15 | 16 | 17 | 18 |
|---|---|---|---|---|
| 15 | 3<br>0.1 nM[a]<br>1 nM[b] | | | |
| 16 | 22<br>3 nM[a]<br>150 nM[b] | 19<br>>5000 nM[a]<br>>5000 nM[b] | | |
| 17 | 25<br>6 nM[a]<br>>5000 nM[b] | 23<br>>5000 nM[a]<br>>5000 nM[b] | 20<br>>5000 nM[a]<br>>5000 nM[b] | |
| 18 | 27<br>20 nM[a]<br>5000 nM[b] | 26<br>5000 nM[a]<br>>5000 nM[b] | 24<br>>5000 nM[a]<br>>5000 nM[b] | 21<br>>5000 nM[a]<br>>5000 nM[b] |
[a]EC$_{50}$ TNF-α release from human THP-1 cells.
[b]EC$_{50}$ TNF-α release from mouse macrophages.

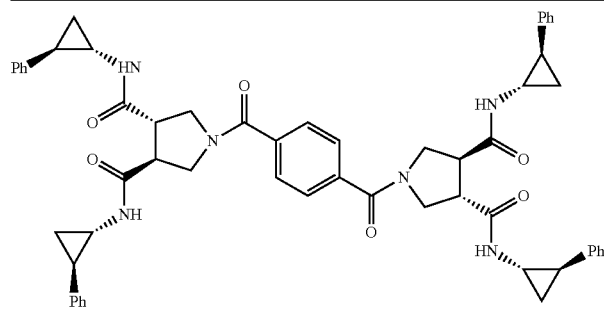

3 (diprovocim-1)
EC$_{50}$ = 100 pM (THP-1) and
1 nM (mouse macrophages)

Compound 8 was also prepared as the single all (S)-enantiomer from 15 and was found to be inactive (EC$_{50}$>5 µM) like the all racemate mixture, failing to stimulate the release of TNF-α from either partially differentiated THP-1 cells or mouse macrophages. Just as significantly, it was found to be incapable of acting as an antagonist, inhibiting the activity of diprovocim-1 (3), when co-administered at 5 µM. This indicates that the lack of agonist activity with 8, and presumably related compounds, is due to ineffective binding to the target TLRs and is not due to effective binding but failure to induce the active dimer receptor conformation.

To unambiguously establish the importance of the presence of each (1S,2R)-2-phenylcyclopropylamine amide substituent and to rule out an inhibitory effect of the presence an alternative substituent, a complete series of deletion analogues of diprovocim-1 (3) was prepared with sequential removal of each side chain. Using the (3S,4S)-pyrrolidine-3,4-dicarboxamide 15, (3S)-pyrrolidine-3-carboxamide 28 [prepared in three steps from commercially available (3S)-pyrrolidine-3-carboxylic acid (S)-β-proline], proline, and dimethylamine (not shown), sequential amide couplings starting with the mono methyl ester of benzene-1,4-dicarboxylic acid with an intermediate hydrolysis of the methyl ester provided each deletion analogue 29-33 in three steps or less.

28

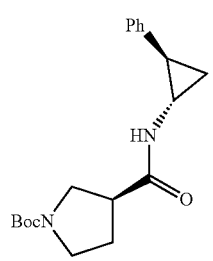

29

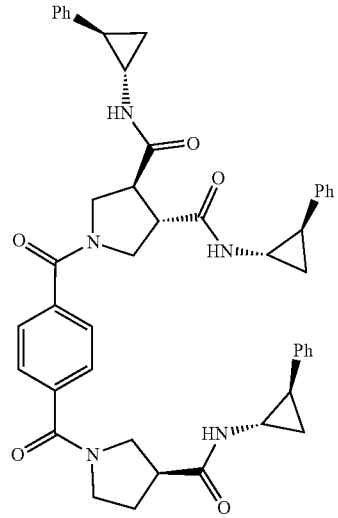

EC$_{50}$
200 nM (THP-1)
>5 µM (mm)

30

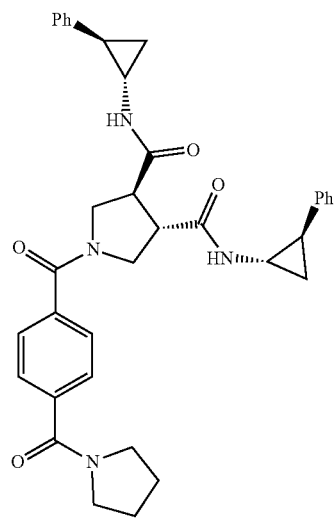

EC$_{50}$
2 µM (THP-1)
>5 µM (mm)

31

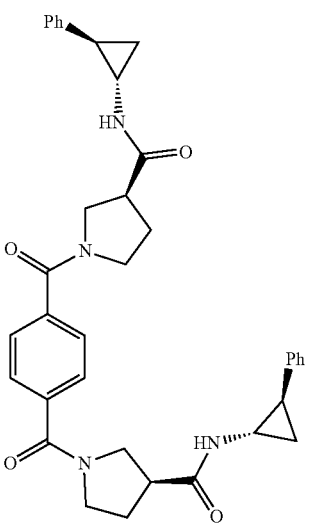

32

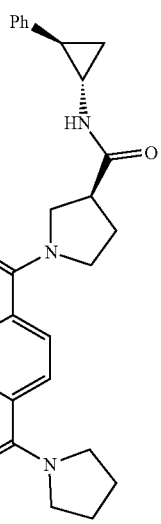

33

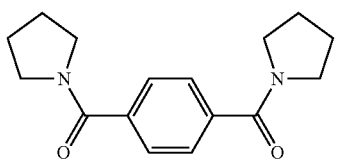

34

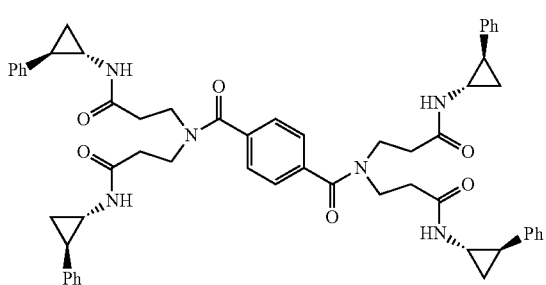

Of these compounds, only 29, which contains three of the four (1S,2R)-2-phenylcyclopropylamine carboxamide substituents, displayed significant activity in the mouse macrophage assay ($EC_{50}$=200 nM, THP-1), and it was found to be 2000-fold less active than diprovocim-1 (3). Compound 30, containing one of the two intact monomers with two side chains, exhibited a small amount of activity ($EC_{50}$=2 µM, THP-1), being 10-fold less active in mouse macrophages than even 29 and 20,000-fold less active than diprovocim-1. All others, 31-33, were inactive even assayed at 5 µM.

Similarly, compound 34, constituting an acyclic analogue of the pyrrolidine, lacking only the pyrrolidine C3-C4 carbon-carbon bond and removing four chiral centers, was prepared in three steps from commercially available N-Boc-iminodipropionic acid and benzene-1,4-dicarboxylic acid. It also was found be inactive in mouse macrophages when tested up to a concentration of 5 µM.

Thus, the presence and stereochemistry of each and every (1S,2R)-2-phenylcyclopropylamine amide substituent, the presence and stereochemistry of the two intact (S,S)-pyrrolidine-3,4-dicarboxylate cores, and the benzene-1,4-dicarboxylate linker are all integral and specific to the expressed activity of diprovocim-1 (3).

The compound linkers found in the original library were reexamined, but now enlisting only the active enantiomer of the substituted pyrrolidine-3,4-dicarboxamide (15), thereby producing compounds bearing four (1S,2R)-2-phenylcyclopropylamine amide substituents in place of the all racemate containing only two such racemic substituents. Each was prepared in a single coupling step from 15 and the linker dicarboxylic acid (2 equiv PyBrOP, i-$Pr_2$NEt, DMF, 23° C., 18 hours).

Not surprisingly, benzene-1,4-dicarboxylic acid remained the most potent linker in the series. Table 1, below, shows the reaction sequence and the $EC_{50}$ values derived from dose-response curves for the stimulated release of TNF-α from differentiated human THP-1 cells or mouse macrophages by 3 (diprovocim-1) and Compounds 35-43.

TABLE 1

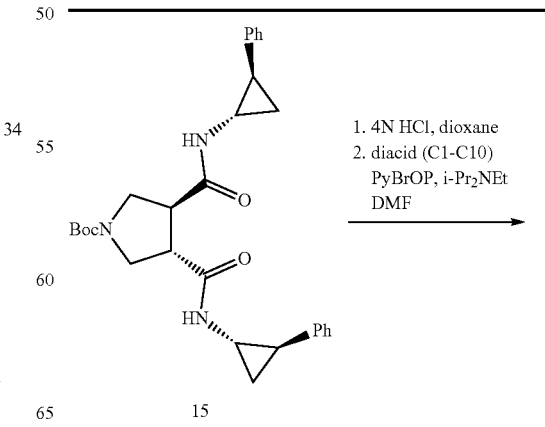

15

TABLE 1-continued

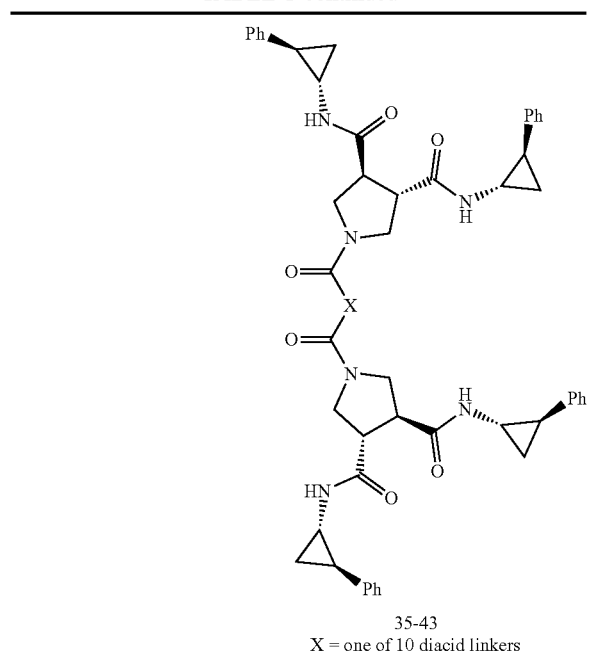

35-43
X = one of 10 diacid linkers

| Entry | Linker | EC$_{50}$ (nM) (THP-1)$^a$ | EC$_{50}$ (nM) (mouse)$^b$ |
|---|---|---|---|
| 35 | HO$_2$C—≡—CO$_2$H  C1 | >5000 | >5000 |
| 36 | HO$_2$C–CH=CH–CO$_2$H  C2 | >5000 | >5000 |
| 37 | HO$_2$C–CH$_2$–CH=CH–CH$_2$–CO$_2$H  C3 | >5000 | >5000 |
| 38 | 1,3-benzene(CO$_2$H)$_2$  C4 | >5000 | >5000 |
| 3 | 1,4-benzene(CO$_2$H)$_2$  C5 | 0.1 | 1 |
| 39 | biphenyl-4,4'-(CO$_2$H)$_2$  C6 | 90 | 2300 |
| 40 | HO$_2$C–CH$_2$–O–CH$_2$–CO$_2$H  C7 | >5000 | >5000 |
| 41 | 1,3-cyclohexane(CO$_2$H)$_2$  C8 | >5000 | >5000 |
| 42 | cis-1,4-cyclohexane(CO$_2$H)$_2$  C9 | >5000 | >5000 |
| 43 | trans-1,4-cyclohexane(CO$_2$H)$_2$  C10 | >5000 | >5000 |

$^a$EC$_{50}$ TNF-α release from human THP-1 cells
$^b$EC$_{50}$ TNF-α release from mouse macrophages What is remarkable in these comparisons is how specific the activity remained for this one linker with all other, even closely related, linkers being ≥1000-fold less active, with most displaying no activity even at concentrations >50,000-fold higher. Clearly, the linker contribution to the activity of 3 is just as specific and integral as that of the substituted pyrrolidine-3,4-dicarboxamide monomers.

In a continuation of these studies, an expanded group of dicarboxylic acid linkers was examined that are close in structure to the active benzene-1,4-dicarboxlic acid in efforts to more carefully define its structural requirements and perhaps further improve on the stunning activity of diprovocim-1. This was inspired in part by the weak activity observed with the biphenyl-4,4'-dicarboxylic acid linker (EC$_{50}$=90 nM) in the original linker set.

The initial series examined placed the two carboxylic acids on phenyl or naphthyl aromatic rings, but located spatially in positions slightly altered from that found in diprovocim-1 (Table 2). Each was prepared in a single coupling step from 15 and the linker dicarboxylic acid (2 equiv PyBrOP, i-Pr$_2$NEt, DMF, 23° C., 18 hours). No compound in this small series displayed activity for the stimulated release of TNF-α from differentiated human THP-1 cells and mouse macrophages by 44-48 that was close to that of diprovocim-1. All except 44 were inactive, and 44 was >10-fold less active than diprovocim-1 although its potency was substantially better than that of the compound with the biphenyl-4,4'-dicarboxylic acid linker.

TABLE 2

44-48

| Entry | Linker | EC$_{50}$ (nM) (THP-1)$^a$ | EC$_{50}$ (nM) (mouse)$^b$ |
|---|---|---|---|

TABLE 2-continued

| # | Structure | | |
|---|---|---|---|
| 44 | 2,6-naphthalene dicarboxylic acid (HO₂C-naphthyl-CO₂H) | 2 | 380 |
| 45 | 1,4-naphthalene dicarboxylic acid | >5000 | >5000 |
| 46 | 1,3-phenylenediacetic acid (HO₂C-CH₂-C₆H₄-CH₂-CO₂H) | >5000 | >5000 |
| 47 | 1,5-naphthalene dicarboxylic acid | >5000 | >5000 |
| 48 | 1,4-phenylenediacetic acid | >5000 | >5000 |

[a]EC$_{50}$ TNF-α release from human THP-1 cells
[b]EC$_{50}$ TNF-α release from mouse macrophages With the further appreciation of the importance of the precise spacing of the dicarboxylic acid in the structure of the linker, a more targeted examination of alternative linkers was conducted. Thus, linkers examined included isosteric replacements of the benzene ring (49), six-membered heterocyclic dicarboxylic acids (50, 51) that might alter the physical properties (e.g.; solubility) or define an orientation of the adjacent pyrrolidine-3,4-dicarboxamide, an acyclic unsaturated dicarboxylic acid linker that might flexibly substitute for benzene (52), a series of further substituted benzene-1,4-dicaboxylic acids introducing functionality for use in conjugation to candidate antigens (53-58), and those used to explore disubstitution (59-63). The latter series was especially interesting because of the substituents' marked influence for adoption of preferred conformational orientations of the adjacent pyrrolidine-3,4-dicarboxamides through destabilizing steric interactions or stabilizing hydrogen bonding. Each was prepared by acid-catalyzed N-Boc deprotection of 15 (4 N HCl, dioxane, 23° C.) and a single coupling step with the linker dicarboxylic acid (2 equiv PyBrOP, i-Pr$_2$NEt, DMF, 23° C., 18 hours)

Remarkably and as benign as many of the changes are, all such compounds examined were less potent than diprovocim-1, highlighting again the unique role the linker contributes to the expression of the biological activity. Although the number of compounds on which to base the conclusions is small, potency seems to smoothly decrease as the size of the (adjacent) substituents increase (e.g.; potency: 3>53= 55>58>54>57 and 3>60>61>62>63). Although not required for their applications, compounds (53 and 55) within this series still exhibit excellent potency sufficient to confidently establish that functionalization sites on the linker core are available for conjugation with candidate antigens when warranted. These results are shown in Table 3.

TABLE 3

Compounds 49-63 with structure containing two pyrrolidine-3,4-dicarboxamide units bearing phenylcyclopropyl amide groups, connected by linker X.

| Entry | Linker | EC$_{50}$ (nM) (THP-1)[a] | EC$_{50}$ (nM) (mouse)[b] |
|---|---|---|---|
| 49 | 2,5-thiophene dicarboxylic acid | 350 | >5000 |
| 50 | pyrazine-2,5-dicarboxylic acid | 130 | >5000 |
| 51 | pyridine-2,5-dicarboxylic acid | 4 | 270 |
| 52 | maleic/fumaric acid (HO₂C-CH=CH-CO₂H) | >5000 | >5000 |
| 53 | 2-hydroxy-1,4-benzenedicarboxylic acid | 0.2 | 130 |
| 54 | 2-nitro-1,4-benzenedicarboxylic acid | 20 | >5000 |
| 55 | 2-amino-1,4-benzenedicarboxylic acid | 1 | 140 |
| 56 | 2-(prop-2-yn-1-yloxy)-1,4-benzenedicarboxylic acid | 15 | 750 |
| 57 | 2-methoxy-1,4-benzenedicarboxylic acid | 30 | 250 |

TABLE 3-continued

| # | Structure | IC50a | IC50b |
|---|---|---|---|
| 58 | 3-Br-benzene-1,4-dicarboxylic acid | 5 | 10 |
| 59 | 4,6-(OH)2-benzene-1,3-dicarboxylic acid | 20 | >5000 |
| 60 | tetrafluoro-benzene-1,4-dicarboxylic acid | 110 | >5000 |
| 61 | 2,5-Cl2-benzene-1,4-dicarboxylic acid | 360 | >5000 |
| 62 | 2,5-Br2-benzene-1,4-dicarboxylic acid | 860 | >5000 |
| 63 | 2,5-(CH3)2-benzene-1,4-dicarboxylic acid | >5000 | >5000 |

[a] IC$_{50}$ TNF-α release from human THP-1 cells
[b] IC$_{50}$ TNF-α release from mouse macrophages

Diprovocim-2

An analogous, but more straightforward series of studies was conducted with the active plate 39G4 well. Similar to the results leading to diprovocim-1, examination of the 10 individual compounds in the well mixture identified the active linker (benzene-1,4-dicarboxylic acid, not shown). Because the $R^2$ side chain was key to the observation of the repetitive activity seen in the original screen independent of the structure of $R^1$, a set of five compounds was prepared with the active benzene-1,4-dicarboxylic acid linker to establish the importance of the presence and number of 4-fluorophenethylamine ($R^2$) versus phenethylamine ($R^1$) side chains present in the compounds in the plate 39G9 well (Table 4)

TABLE 4

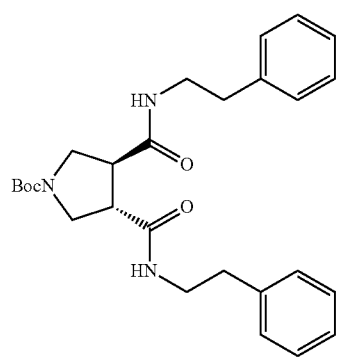

6

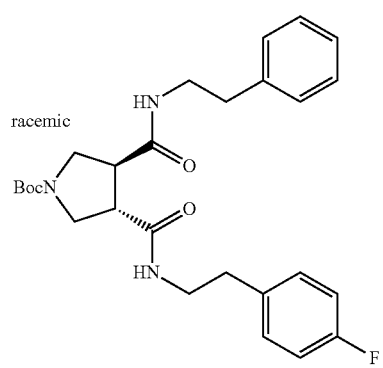 [SMILES: CC(C)(C)OC(=O)N1C[C@@H](C(=O)NCCc2ccccc2)[C@H](C(=O)NCCc2ccc(F)cc2)C1]

64

TABLE 4-continued
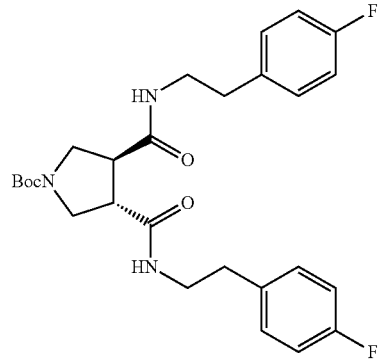 [SMILES: CC(C)(C)OC(=O)N1C[C@@H](C(=O)NCCc2ccc(F)cc2)[C@H](C(=O)NCCc2ccc(F)cc2)C1]
65
6, 64 or 65
1. 4N HCl, dioxane
2. HO$_2$C—Ph—CO$_2$H
   PyBrOP, i-Pr$_2$NEt
↓
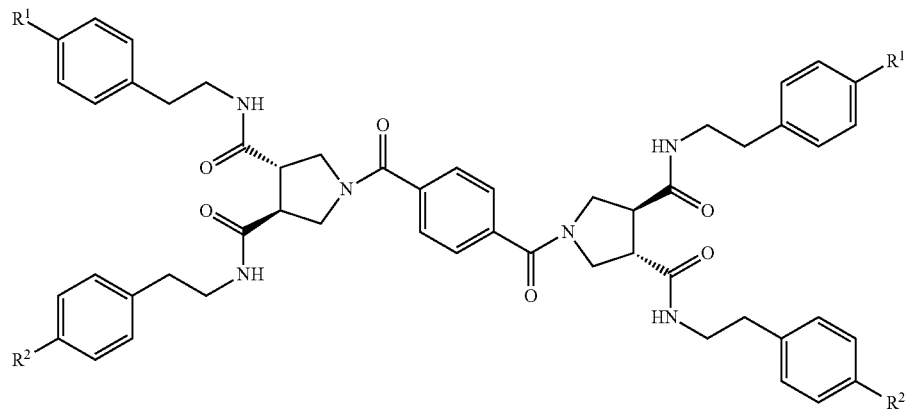
8, R$^1$ = R$^2$ = H
67, R$^1$ = H, R$^2$ = F
69, R$^1$ = R$^2$ = F
6 or 65
| 1. 4N HCl, dioxane | 3. LiOH, solvent |
| 2. HO$_2$C—Ph—CO$_2$Me | 4. 64, 4N HCl, then |
| PyBrOP, i-Pr$_2$NEt | PyBrOP, i-Pr$_2$NEt |
↓

TABLE 4-continued

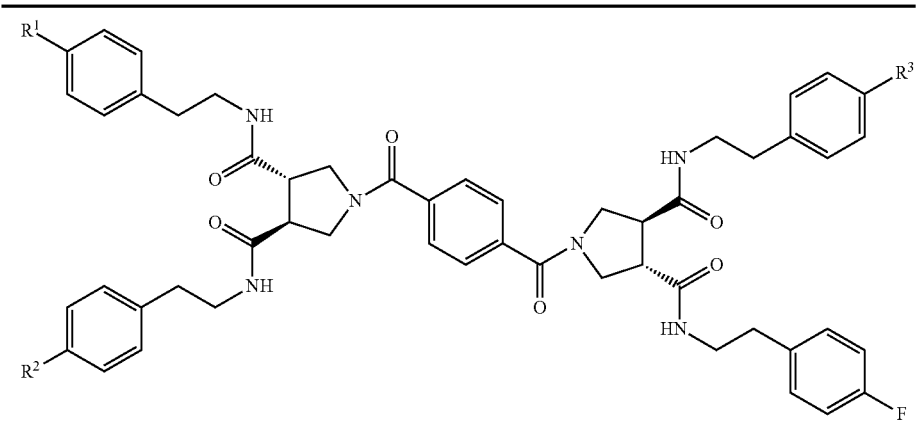

66, $R^1 = R^2 = R^3 = H$
68, $R^1 = H, R^2 = R^3 = F$ 69 ($EC_{50}$ 100 nM) > 68 (280 nM) > 67 (>5 μM) > 66 (>5 μM) > 8 (>5 μM)
(all racemate)
substituents: 4F > 3F > 2F > 1F > 0F The five compounds were prepared from the three pyrrolidine-3,4-dicarboxamides 6, 64 and 65 and simultaneous (8, 67 and 69) or sequential (66 and 68) coupling with benzene-1,4-dicarboxylic acid or its mono methyl ester, respectively. The results of their assessment were clear. Activity was enhanced with the addition of each and every 4-fluorophenethylamine side chain (about 3-5-fold) and 69, containing four, was the most potent ($EC_{50}$=100 nM, racemate) compound in the set.

Because the 4-fluoro substituent on the 4-fluorophenethylamide uniquely conveyed activity to the compounds (phenethylamide inactive), a series of alternative substituents was examined in which the 4-fluoro group was moved to the 3- and 2-positions, conservatively replaced with other halogens (Cl and Br), replaced with a series of small and benign electron-donating or electron-withdrawing groups including some capable of serving as hydrogen bond donors or acceptors, replaced with a large phenyl group, or with incorporation of a 2-naphthyl aromatic ring (Table 5).

TABLE 5

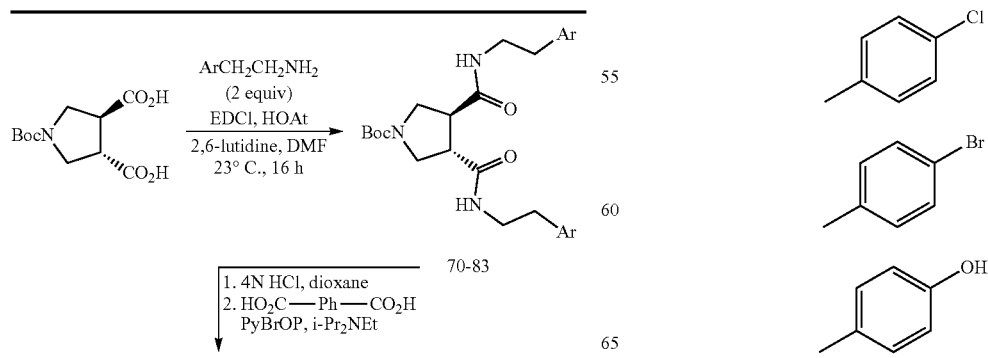

TABLE 5-continued

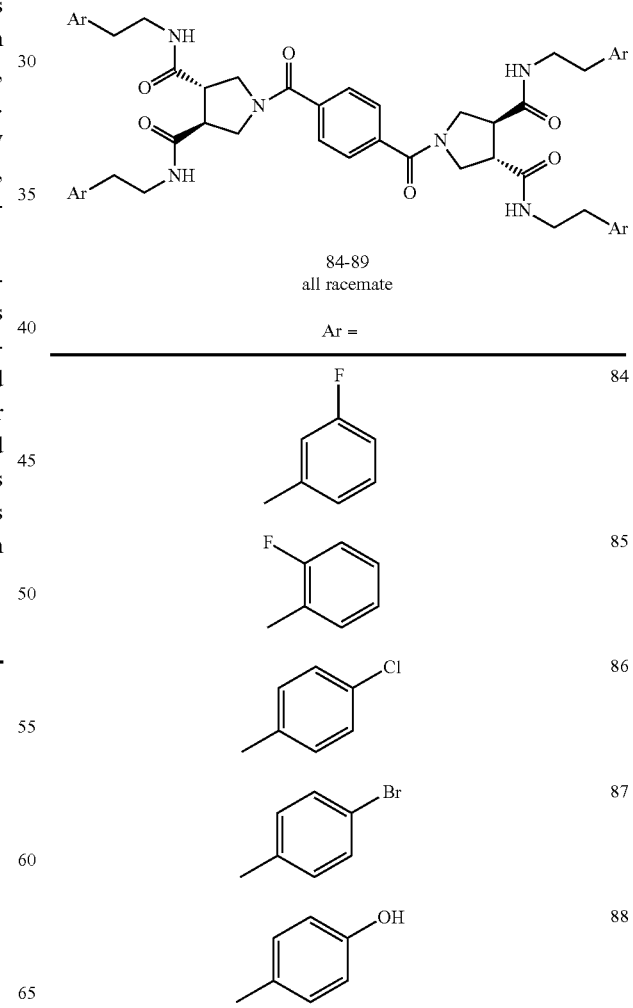

84-89
all racemate

Ar =

| | | |
|---|---|---|
| F (3-position) | | 84 |
| F (2-position) | | 85 |
| Cl (4-position) | | 86 |
| Br (4-position) | | 87 |
| OH (4-position) | | 88 |

TABLE 5-continued

| Structure | # |
|---|---|
|  4-OMe-phenyl | 89 |
|  4-NH2-phenyl | 90 |
|  4-NO2-phenyl | 91 |
|  4-Me-phenyl | 92 |
|  4-CF3-phenyl | 93 |
|  4-CO2Me-phenyl | 94 |
|  4-CN-phenyl | 95 |
|  4-Ph-phenyl | 96 |
| naphthyl | 97 |

84, $EC_{50}$ = 1 µM, all other compounds inactive ($EC_{50}$ > 5 µM)

Each compound was prepared as a racemate by coupling racemic N-Boc trans-pyrrolidine-3,4-dicarboxylic acid with the arylethylamine (2 equiv, EDCI, 1-hydroxy-7-azabenzotriazole (HOAt), 2,6-lutidine, DMF, 23° C., 16 hours) followed by N-Boc deprotection (4 N HCl, dioxane 23° C., 3 hours) and subsequent coupling with benzene-1,4-dicarboxylic acid (2 equiv PyBrOP, i-Pr$_2$NEt, DMF, 23° C., 18-24 hours).

Remarkably and stunningly, all were inactive at stimulating the release of TNF-α from human differentiated THP-1 cells at concentrations up to 5 µM with the exception of 84 ($EC_{50}$=1 µM, >10-fold less active), which incorporated the most conservative change of moving the fluorine substituent from the p- to m-position (3-vs 4-fluorophenethylamide). Clearly the fluorine substituent and the 4-fluorophenethylamide side chains are essential and remarkably specific to the expression of the biological properties of the compounds.

Compound 69 was a mixture of three compounds (two enantiomers and one meso compound), making the establishment of the active enantiomer in the mixture straightforward. Each of the two enantiomers (S,S and R,R) of N-Boc-pyrrolidine-3,4-dicaboxylic acid [Bao et al., U.S. Pat. No. 6,489,354 B1] was coupled with 4-fluorophenethylamine (EDCI, HOAt, 2,6-lutidine, 23° C., 16 hours) to prepare the two possible enantiomeric pyrrolidine-3,4-dicarboxamides (S,S)- and (R,R)-65 (Table 6). These were independently but simultaneously coupled with benzene-1,4-dicarboxylic acid (2 equiv PyBrOP, i-Pr$_2$NEt, DMF, 23° C., 18-24 hours) to provide the two enantiomers 4 and 98, bearing the all S or all R configurations, respectively. Similarly, sequential coupling (PyBrOP, i-Pr$_2$NEt, DMF, 23° C.) of (S,S)- and (R,R)-65 with the mono methyl ester of benzene-1,4-dicarboxylic acid with an intermediate hydrolysis of the methyl ester (LiOH, THF/MeOH/H$_2$O, 23° C.) provided the meso isomer 99.

The all S enantiomer 4 ($EC_{50}$=50 nM, diprovocim-2) proved to be 3-fold more potent than the all racemate ($EC_{50}$=150 nM), whereas its all R enantiomer 98 was inactive by comparison ($EC_{50}$=>5 M, >100-fold less potent). Interestingly, the third meso isomer 99 ($EC_{50}$=70 nM), containing both a S,S- and R,R-pyrrolidine-3,4-dicarboxamide, was also active and nearly matched the potency of the all S enantiomer. Despite this potent activity in human THP-1 cells, no compound in this series stimulated the release of TNF-α from mouse macrophages.

TABLE 6

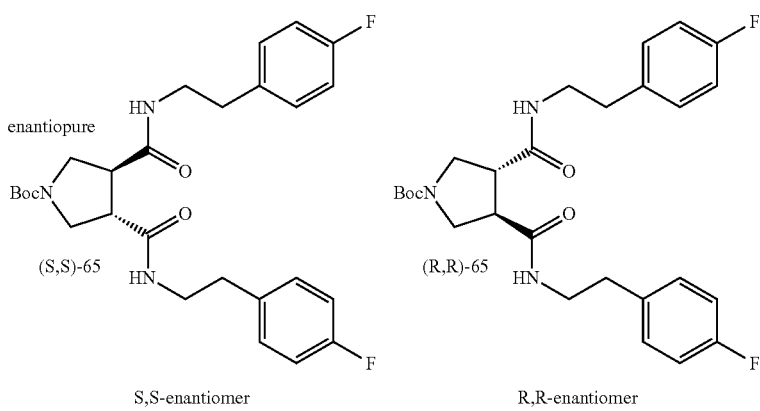 [SMILES: CC(C)(C)OC(=O)N1C[C@@H](C(=O)NCCc2ccc(F)cc2)[C@H](C(=O)NCCc2ccc(F)cc2)C1 ; CC(C)(C)OC(=O)N1C[C@H](C(=O)NCCc2ccc(F)cc2)[C@@H](C(=O)NCCc2ccc(F)cc2)C1]

S,S-enantiomer     R,R-enantiomer

TABLE 6-continued
(S,S)-65
1. 4N HCl, dioxane
2. HO₂C—Ph—CO₂H
   PyBrOP, i-Pr₂NEt
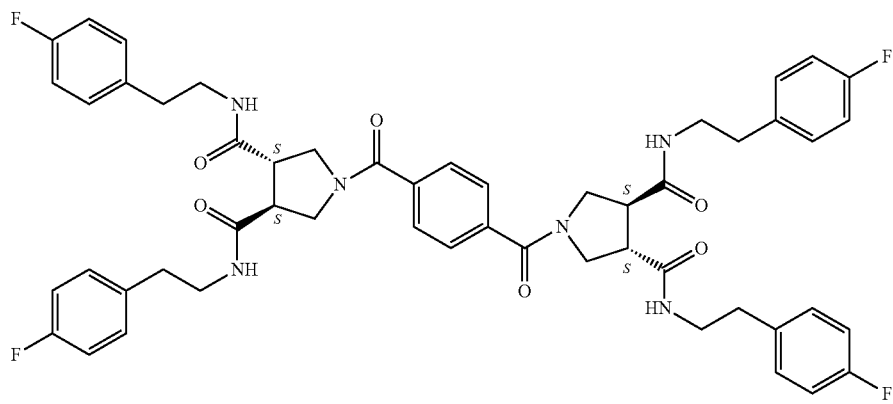
4, diprovocim-2
EC$_{50}$ = 50 nM
(R,R)-65
1. 4N HCl, dioxane
2. HO₂C—Ph—CO₂H
   PyBrOP, i-Pr₂NEt
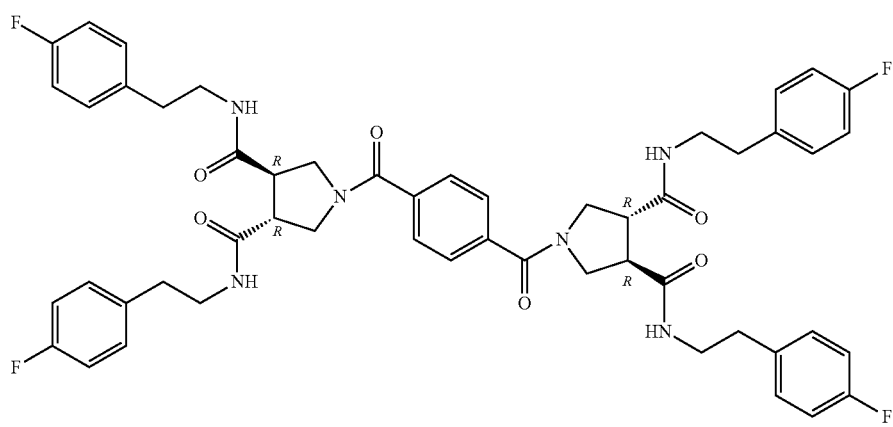
98
EC$_{50}$ = >5 μM TABLE 6-continued

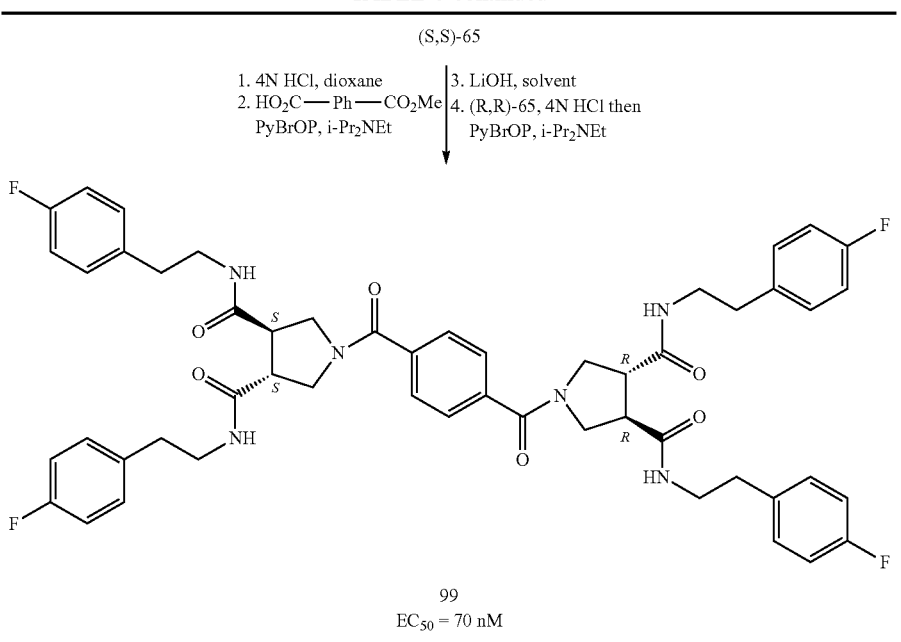

99
$EC_{50} = 70$ nM

With use of the enantiopure (S,S)-pyrrolidine-3,4-dicarboxamide 65, the dicarboxylic linkers in the original library as well as a subset of those that proved most interesting with diprovocim-1 were re-examined now with compounds that bear all four 4-fluorophenethylamide side chains, as shown below in Table 7. Each was prepared in a single coupling step (2 equiv PyBrOP, i-Pr$_2$NEt, DMF, 23° C., 18-24 hours) of the linker dicarboxylic acid following acid-catalyzed deprotection of enantiopure (S,S)-65. In this series, none of the alternative linkers provided compounds that were active in either human THP-1 cells or mouse macrophages and only the phenol 110, like the behavior of 53 versus diprovocim-1, nearly matched the activity diprovocim-2. The activities of these compounds (100-110) are shown in Table 7, below.

TABLE 7

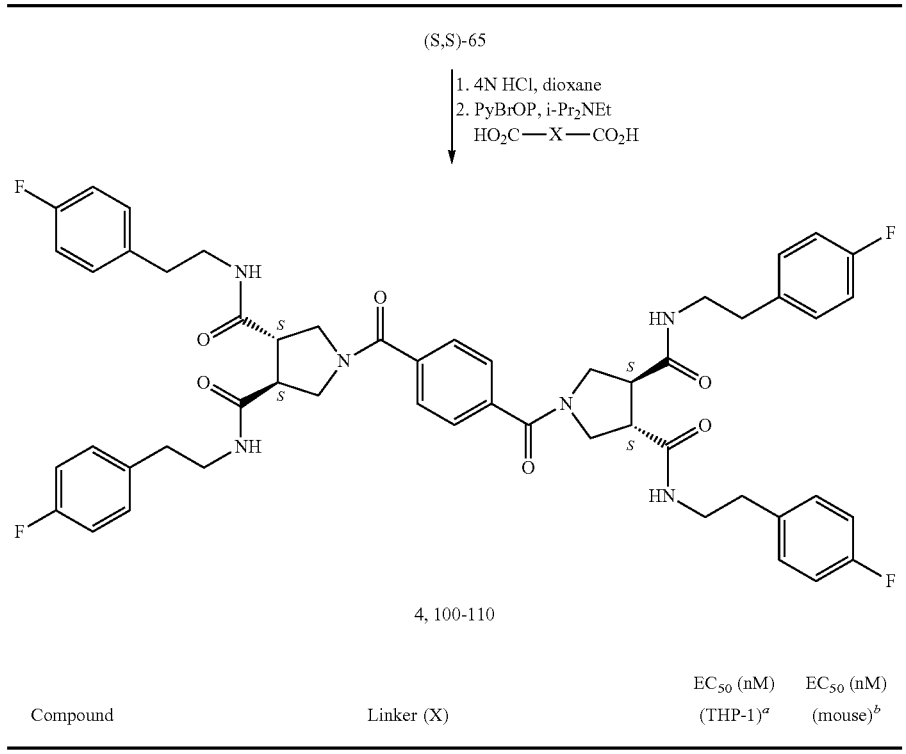

4, 100-110

| Compound | Linker (X) | EC$_{50}$ (nM) (THP-1)$^a$ | EC$_{50}$ (nM) (mouse)$^b$ |
| --- | --- | --- | --- |

TABLE 7-continued

| | | | | |
|---|---|---|---|---|
| 100 |  HO₂C———CO₂H | | >5000 | >5000 |
| 101 |  | | >5000 | >5000 |
| 102 |  | | >5000 | >5000 |
| 103 | 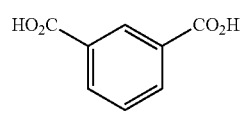 | | >5000 | >5000 |
| 4 |  | | 50 | >5000 |
| 104 | 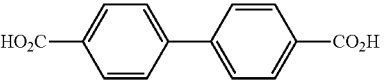 | | >5000 | >5000 |
| 105 | 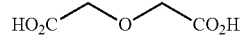 | | >5000 | >5000 |
| 106 | 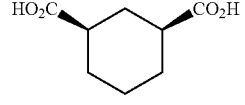 [SMILES: O=C(O)[C@@H]1CCC[C@H](C(=O)O)C1] | | >5000 | >5000 |
| 107 |  | | >5000 | >5000 |
| 108 |  | | >5000 | >5000 |
| 109 | 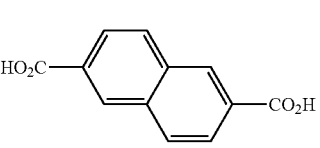 [SMILES: O=C(O)c1ccc2cc(C(=O)O)ccc2c1] | | >5000 | >5000 |
| 110 | 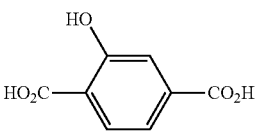 | | 130 | >5000 |

Figure 4:
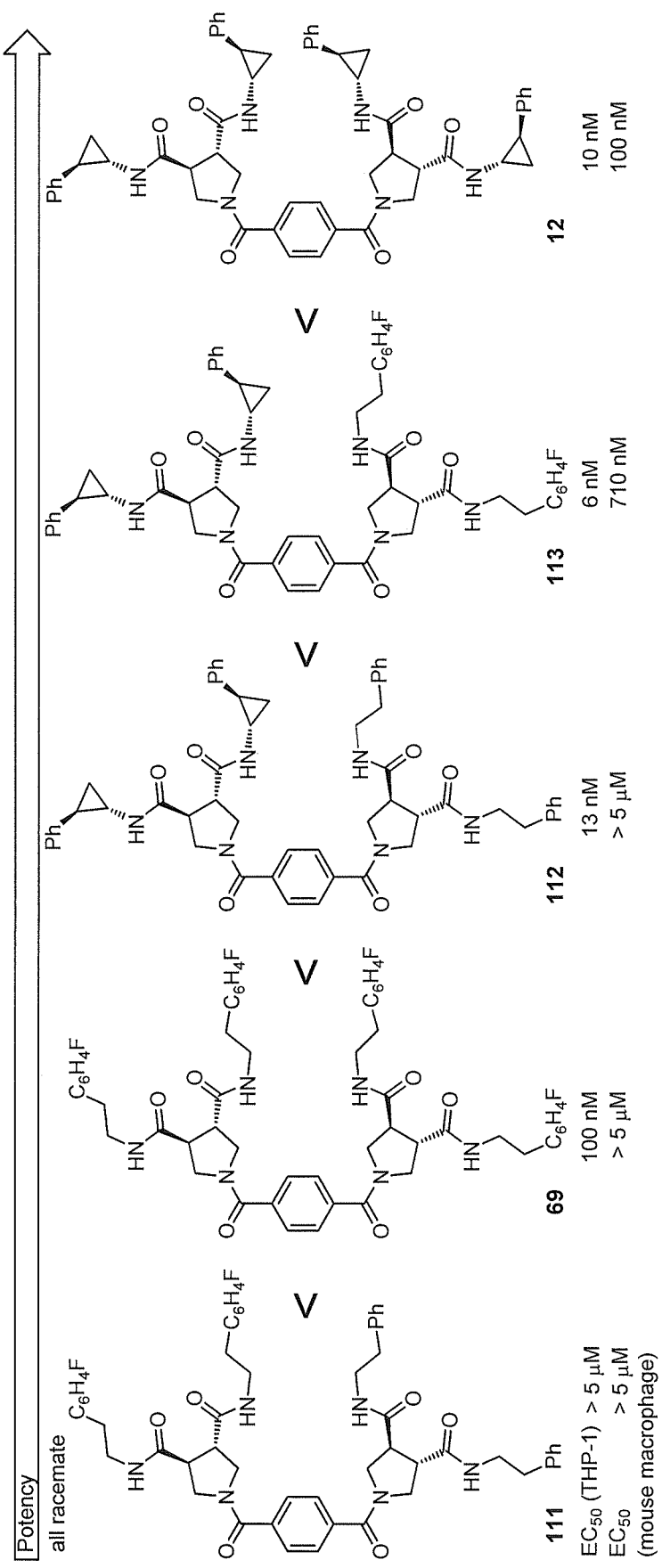
FIG. 4 shows structural formulas and activity data for all racemate hybrid structures of diprovocim-1 and diprovocim-2 and additional key analogues. $EC_{50}$ values are derived from dose-response curves for the stimulated release of TNF-α from differentiated human THP-1 cells or mouse macrophages.

[a] $EC_{50}$ TNF-α release from human THP-1 cells
[b] $EC_{50}$ TNF-α release from mouse macrophages Hybrid Structures of Diprovocim-1 and Diprovocim-2 and Additional Key Analogues Given the unique and apparently specific interactions only two of the examined side chains displayed and their importance to the expressed biological properties of 3 and 4, compounds containing a combination of the two side chains was explored (113) (FIG. 4). In the conduct of these studies, an additional small series of key diprovocim-1 and diprovocim-2 analogues were also prepared and examined (111 and 112).

These studies were first conducted with racemic 6 and 65 and the all racemate diastereomeric mixture 7 to assemble 111-113. These compounds were prepared by N-Boc deprotection of 65 or 7 and their coupling with the mono methyl ester of benzene-1,4-dicarboxylic acid followed by methyl ester hydrolysis and coupling with the free amine hydrochloride salt derived from 6 and, in the case of 7 also with the amine derived from 65.

Figure 5:
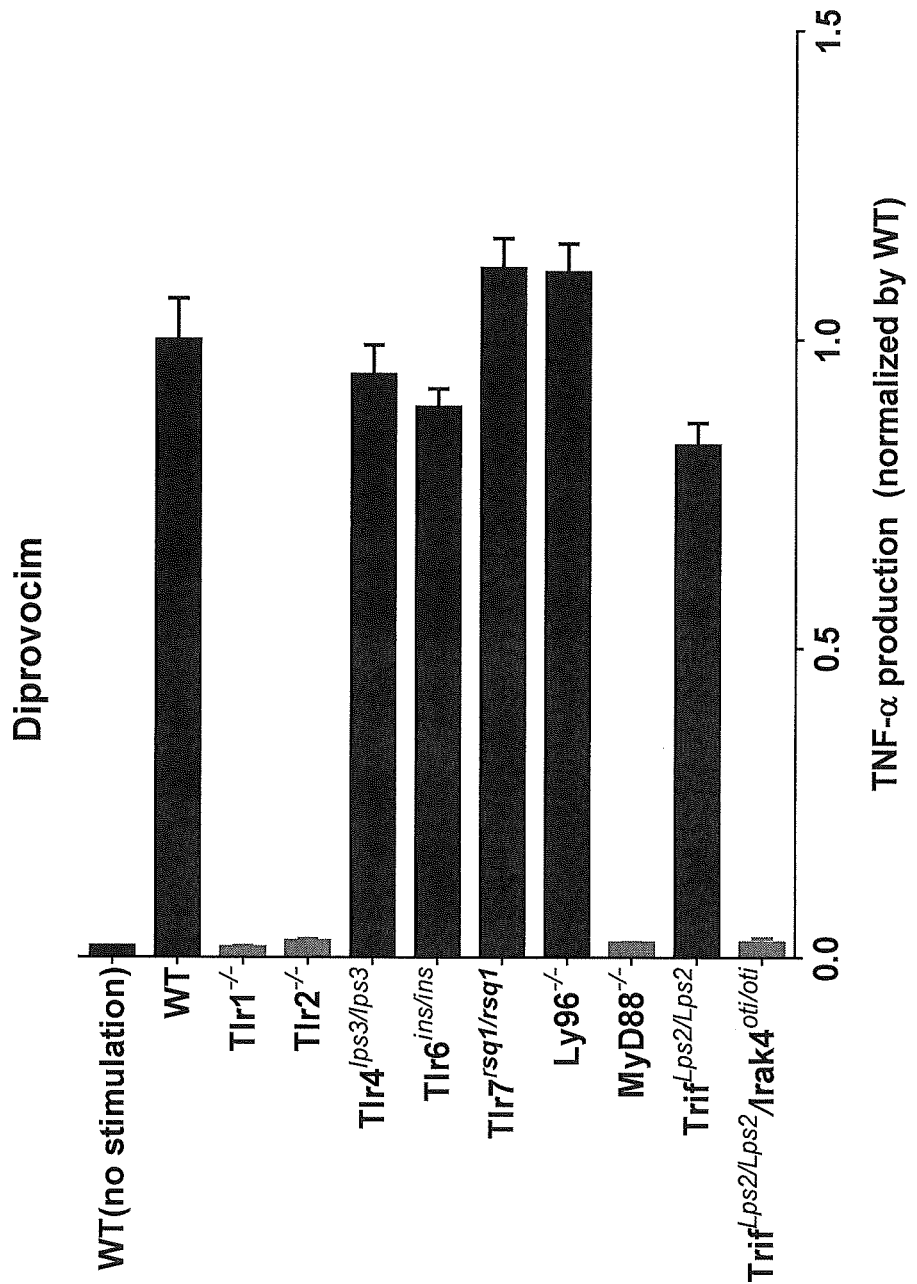
FIG. 5 is a graph that shows results of an assay for TNF-α release upon treatment with 3 using macrophages from mice containing disabling germline mutations or knockouts of genes encoding mTLRs and downstream signaling proteins. All results are representative of two independent experiments. Error bars represent SEM.
Figure 6:
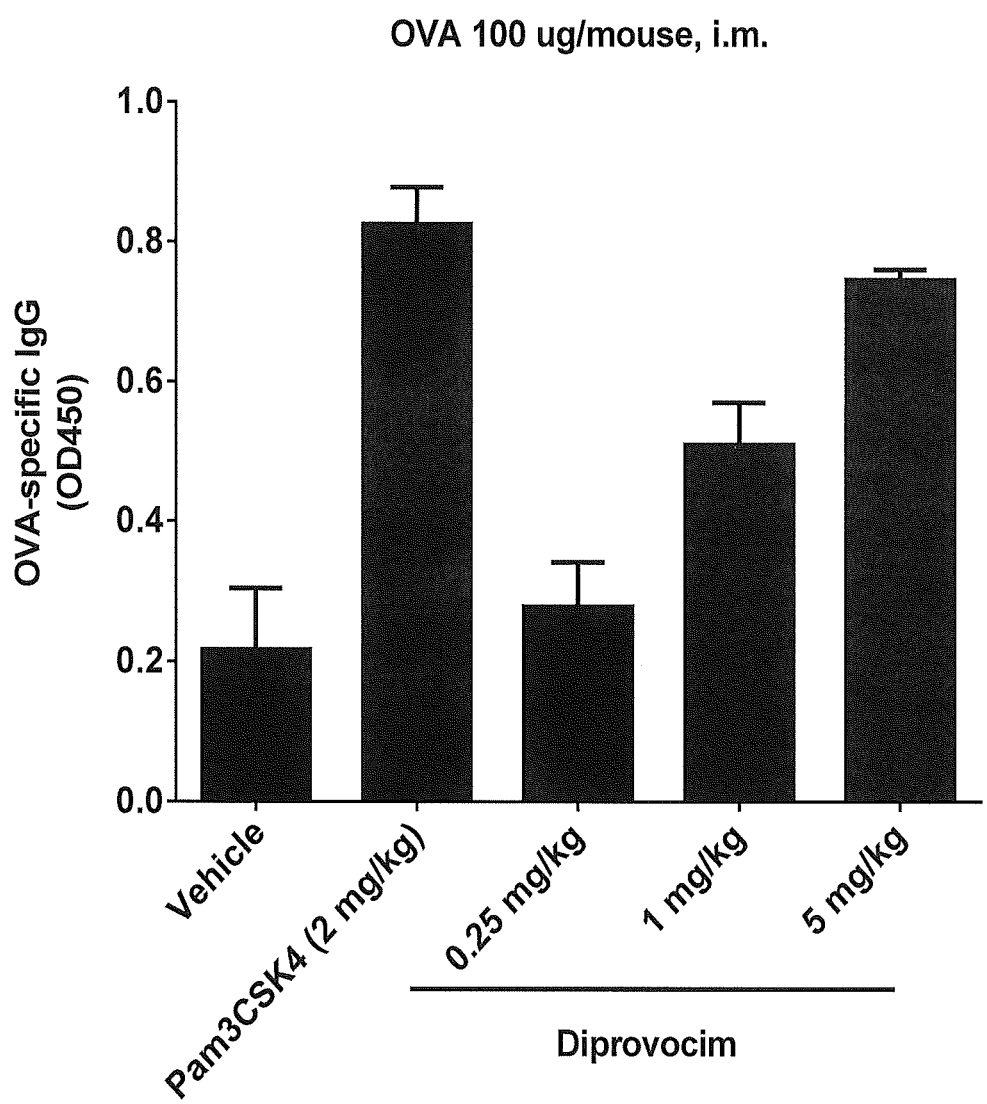
FIG. 6 is a graph that shows dose-dependent adjuvant activity of 3. C57BL/6 mice (4 per group) were immunized i.m. by 100 μg OVA with vehicle or 3 in vehicle at indicated doses. After 21 days, serum titers of OVA-specific IgG were measured by ELISA. Error bars represent SEM.

The resulting compounds (FIG. 5) displayed a consistent trend where replacement of the phenethylamine side chains with 4-fluorophenethylamine sided chains improved activity and where a 2-phenylcyclopropylamine replacement of the 4-fluorophenethylamine side chains further improved activity. Thus, the side chains can be used interchangeably with predictable influences on the biological potency (trans-2-phenylcyclopropylamine>4-fluorophenethylamine) suggesting they are binding at the same site influencing activity in a similar manner at its target. Interestingly, the activity of the structures 111 and 112, where the two 2-phenylcyclopropylamine or 4-fluorophenethylamine side chains are on the same pyrrolidine core, proved to be more potent than the compounds 10 and 67, where the two side chains are on opposite pyrrolidine cores.

The most potent of these hybrids (113) was prepared as single enantiomers, bearing the identified active enantiomer derived from 15 and either (S,S)- and (R,R)-65 (Table 8). They were assessed for the stimulated release of TNF-α from differentiated human THP-1 cells and mouse macrophages establishing the potent activity of both 114 (diprovocim-4) and 115 (diprovocim-5).

(diprovocim-5), containing one subunit derived from (R,R)-65, was 5-fold less active in human THP-1 cells and inactive in mouse macrophages, reflecting both a lower potency and greater species difference.

Diprovocim-3

Additionally, the incorporation of the fluorine group found in diprovocim-2 into the side chain substituent of diprovocim-1 was examined. Thus, coupling of (1S,2R)-2-(4-fluorophenyl)-cyclopropylamine [Benelkebir et al., *Bioorg. Med. Chem.* 2011, 19:3709 prepared (1R,2S)-116

TABLE 8

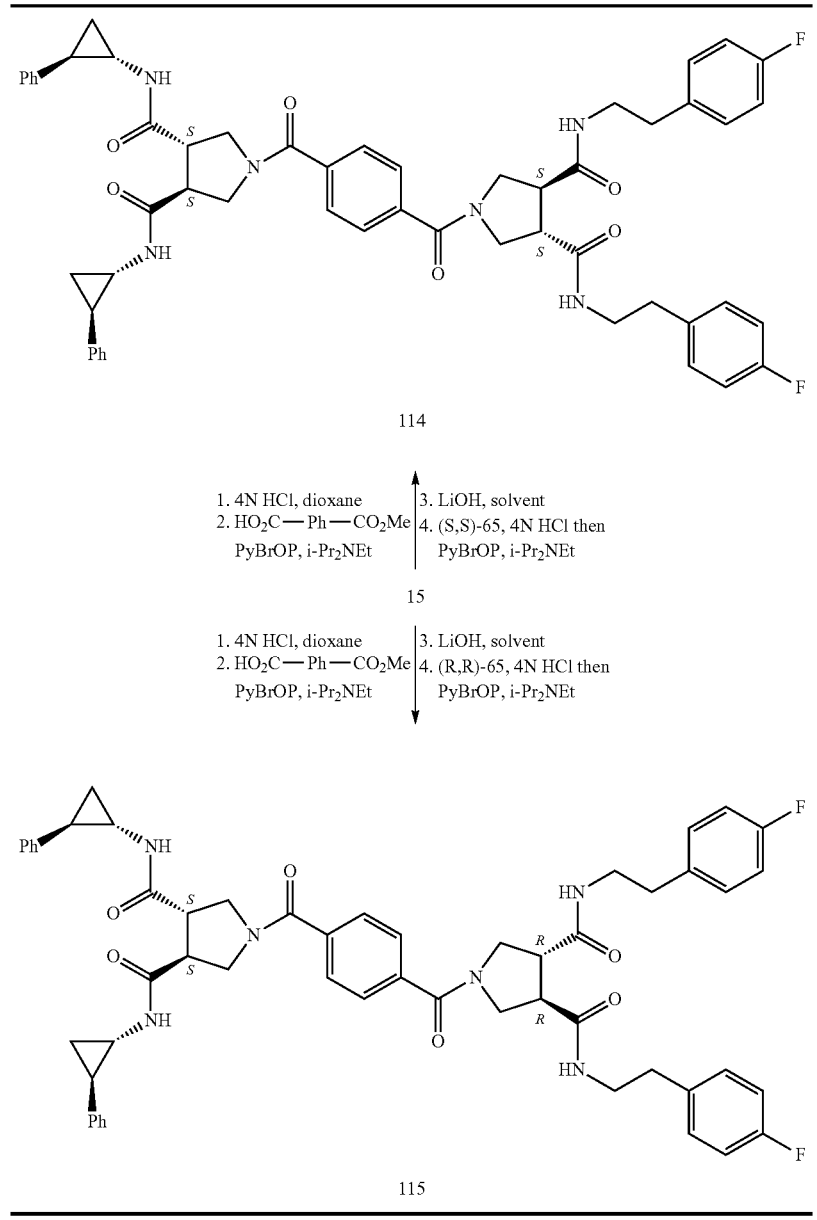

These studies established that the hybrid structure 114 (diprovocim-4), possessing the two (S,S)-pyrrolidine cores, is an effective TLR1/TLR2 agonist active in both human THP-1 cells and mouse macrophages. Thus, 114 displays properties like those of diprovocim-1. However, it is less potent than diprovocim-1 and more potent than diprovocim-2, displaying a potency between that of the compounds from which it is derived. The analogous hybrid structure 115 enantiomer, whereas the opposite enantiomer (1S,2R)-116 was used here) (116, 2 equiv) with (S,S)-14 (EDCI, HOAt, 2,6-lutidine, DMF, 23° C., 16 hours) followed by Boc deprotection of 117 (4 N HCl, dioxane, 23° C., 3 hours) and coupling of the resulting amine with benzene-1,4-dicarboxylic acid (PyBrOP, i-Pr$_2$NEt, DMF, 23° C., 18-24 hours) provided 118 (diprovocim-3), Scheme 2, below.

Scheme 2

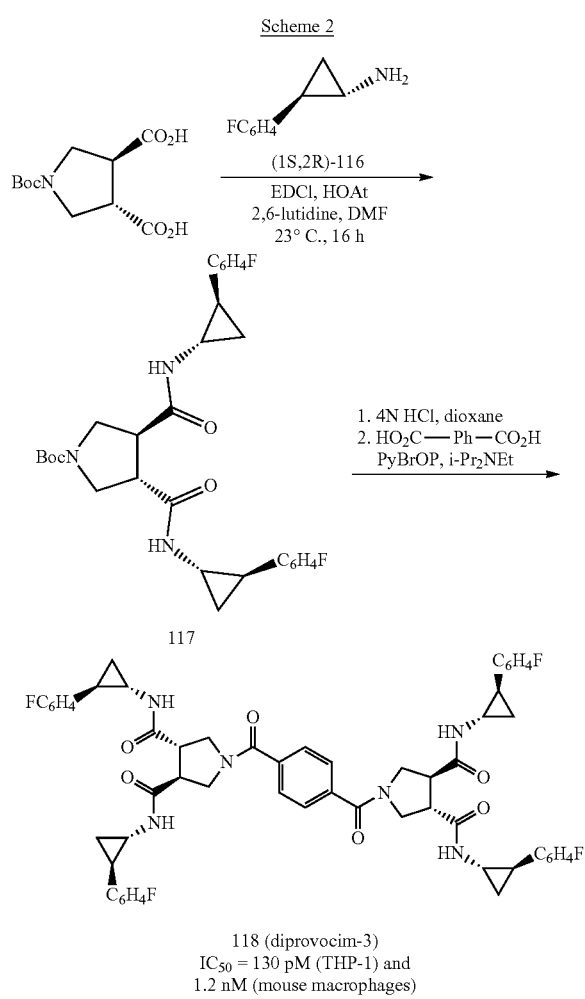

118 (diprovocim-3)
IC$_{50}$ = 130 pM (THP-1) and
1.2 nM (mouse macrophages)

Assessment for the stimulated release of TNF-α from differentiated human THP-1 cells (EC$_{50}$=130 pM) and mouse macrophages (EC$_{50}$=1.2 nM) revealed that the activity of 118 was indistinguishable from that of diprovocim-1 (3), displaying exceptionally potent activity. Thus, the addition of the p-fluoro group did not further enhance the potency of 3, but its presence also did not disrupt the activity of 3.

Another way of viewing this result is that introduction of the four rigidifying cyclopropanes into diprovocim-2 (4) improved the activity 400-fold. Moreover, the activity in mouse macrophages indicates that the fluorine atom is well tolerated in the murine system.

Hybrid Structures with Incorporation of the Lipid Side Chains Found in Endogenous TLR2/TLR1 and TLR2/TLR6 Ligands Among the TLRs, TLR2 requires heterodimerization with either TLR1 or TLR6 for activation with bacterial triacylated lipoproteins being the most widely-recognized agonists activating TLR1/TLR2 [e.g.; Pam3CSK4; see, Metzger et al., Int. J. Peptide Protein Res. 1991, 37, 46; Bessler et al., J. Immunol. 1985, 135, 1900; Deres et al., Nature 1989, 342, 561; Alexopoulou et al., J. Immunol. 2002, 169, 10; Jin et al., Cell 2007, 130, 1071; Review: Jin et al., Curr. Opin. Immunol. 2008, 20, 414-419; Salunke et al., J. Med. Chem. 2013, 56, 5885-5900; Salunke et al., J. Med. Chem. 2012, 55, 3353-3363; Agnihotri et al., J. Med. Chem. 2011, 54, 8148] and bacterial diacylated lipopolypeptides stimulating TLR2/TLR6 [e.g.; MALP-2; see, Muhlradt et al., J. Exp. Med. 1997, 185, 1951; Buwitt-Beckmann et al., J. Biol. Chem. 2006, 281, 9049].

TLR1/TLR2 preferentially binds triacyl lipopeptides and binds diacyl lipopeptides only weakly, whereas TLR2/TLR6 only binds diacyl lipopeptides. Crystallographic structures of Pam3CSK4 (three lipid chains) bound to hTLR1/TLR2 and Pam2CSK4 (two lipid chains) bound to mTRL2/TLR6 have been solved. [Jin et al., Cell 2007, 130, 1071-1082; Kang et al., Immunity 2009, 31, 873-884].

These studies revealed that the amide lipid chain of Pam3CSK4 inserts into a hydrophobic channel in TLR1, while the remaining two ester lipid chains bind in a hydrophobic channel in TLR2, forming and filling a long continuous hydrophobic pocket spanning both proteins at the TLR1/TLR2 heterodimer interface. In contrast, Pam2CSK4 binds with both ester lipid chains similarly bound to TLR2, but does not contain or require the amide lipid binding to TLR6 in order to promote and stabilize active TLR2/TLR6 dimer formation. In fact, TLR6 lacks the lipid binding pocket needed to accommodate the third amide lipid chain of the triacyl lipopeptides and proteins.

Within the diprovocims, the amide side chains are likely serving the role of the lipid chains, extending into the hydrophobic pockets spanning TLR1/TLR2. The distinction being that the symmetrical diprovocims contain four, not three, such groups. As a result and in order to explore alternative hydrophobic substituents, we examined a range of lipid amide replacements for the trans-2-phenyl-cyclopropylamine and 4-fluorophenethylamine derived amides explored hybrid structures containing three as well as four side chains. The first series examined were those that contain three side chains, linking one half of diprovocim-1 with a single lipid side chain amide attached either directly to the benzene-1,4-dicarboxylic acid linker (121-124) or as the amide substituent on (R)- or (S)-pyrrolidine-3-carboxylic acid (125-132). These were prepared effectively by coupling 120 with the corresponding amine and (R)- or (S)-pyrrolidine-3-carboxamide (EDCI, HOAt, 2,6-lutidine, DMF-CH$_2$Cl$_2$, 25° C., 3-4 hours). Their assessment for the stimulated release of TNF-α from differentiated human THP-1 cells and mouse macrophages revealed that no compound in the simplest series 121-124 exhibited agonist activity.

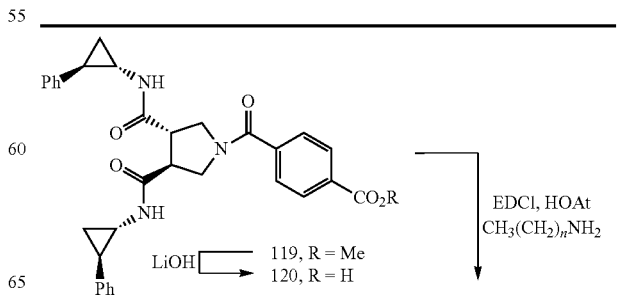

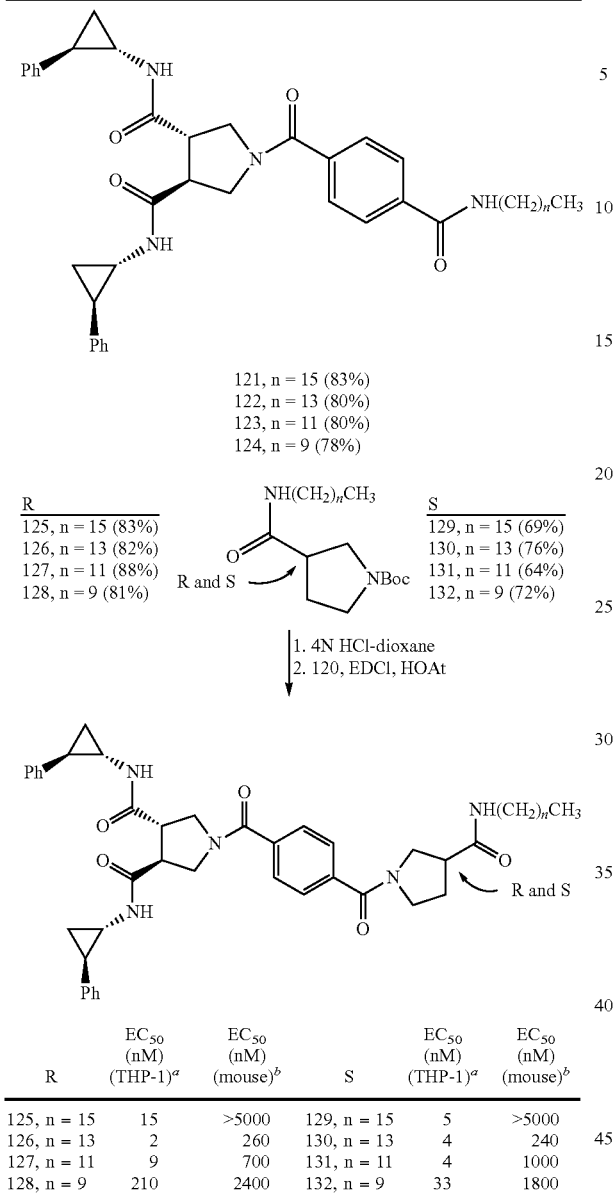

121, n = 15 (83%)
122, n = 13 (80%)
123, n = 11 (80%)
124, n = 9 (78%)

| R | | S |
|---|---|---|
| 125, n = 15 (83%) | | 129, n = 15 (69%) |
| 126, n = 13 (82%) | | 130, n = 13 (76%) |
| 127, n = 11 (88%) | R and S | 131, n = 11 (64%) |
| 128, n = 9 (81%) | | 132, n = 9 (72%) |

1. 4N HCl-dioxane
2. 120, EDCI, HOAt

| R | $EC_{50}$ (nM) (THP-1)[a] | $EC_{50}$ (nM) (mouse)[b] | S | $EC_{50}$ (nM) (THP-1)[a] | $EC_{50}$ (nM) (mouse)[b] |
|---|---|---|---|---|---|
| 125, n = 15 | 15 | >5000 | 129, n = 15 | 5 | >5000 |
| 126, n = 13 | 2 | 260 | 130, n = 13 | 4 | 240 |
| 127, n = 11 | 9 | 700 | 131, n = 11 | 4 | 1000 |
| 128, n = 9 | 210 | 2400 | 132, n = 9 | 33 | 1800 |

[a]$EC_{50}$ TNF-α release from human THP-1 cells.
[b]$EC_{50}$ TNF-α release from mouse macrophages.

In contrast, the series in which the lipid amide substituent was attached via a pyrrolidine-3-carboxamide stimulated the release of TNF-α from both human THP-1 cells and mouse macrophages. Like diprovocim-1, each was more effective in the human THP-1 cells than mouse macrophages (>10-fold, typically about 100-fold).

Little distinction was observed whether the lipid chain was attached via the (R)- or (S)-pyrrolidine-3-carboxamide. A preference for the lipid chain length was observed with the intermediate lengths displaying the greatest potency (126/130>127/131), and the longest chain examined (125/129) seemed to display a uniquely detrimental effect in mouse versus human cells likely representing species distinctions in the signaling receptors. The best in the series were ≥20-fold less potent than diprovocim-1 in human THP-1 cells and >200-fold less effective in mouse macrophages, comparable in their properties with diprovocim-3, and more effective than diprovocim-2.

An even more significant set of observations was made with hybrid structures that contained two such lipid side chains. The series examined were those that contain four side chains, linking one half of diprovocim-1 with symmetrical diamides derived from (S,S)-pyrrolidine-3,4-dicarboxylic acid, bearing two lipid side chain amides. Single step preparation of the (S,S)-pyrrolidine-3,4-dicarboxamides, obtained by coupling (S,S)-14 with the corresponding alkylamines (EDCI, HOAt, 2,6-lutidine, DMF-CH₂Cl₂, 25° C.), followed by N-Boc removal (4 N HCl, dioxane, 25° C.) and coupling of the resultant amine with 120 (EDCI, HOAt, 2,6-lutidine, DMF-CH₂Cl₂, 25° C., 3-4 hours) provided a series of hybrid structures 133-139 containing two lipid side chains.

Because of the activity observed in the initial smaller set, a comprehensive set of lipid side chain lengths was prepared and examined. Three compounds in this series (136-138), containing the intermediate lipid chain lengths (6-10 carbons), exhibited remarkably potent and robust activity ($EC_{50}$=280-170 pM, THP-1 cells), being more potent than Pam3CSK4 and approaching the activity of diprovocim-1.

The compounds with the longer lipid chain lengths, though still very potent, displayed progressively less potent activity (135>134>133) and the compound with a shorter chain length (139) was notably even less potent. The potency difference between stimulation of human versus mouse cell release of TNF-α smoothly and progressively diminished as the chain length was shortened with 138 exhibiting the most potent activity in both cell lines and a 20-fold differential. The behavior of 138, containing two C6 lipid side chains that closely approximate the length and number of carbon atoms found the diprovocim-1 and diprovocim-2 side chains, nearly matches that of diprovocim-1 in both the human THP-1 cells and mouse macrophages ($EC_{50}$=180 pM and 4 nM, respectively), being only 2-fold and 4-fold less potent than diprovocim-1. Because of this lipid chain length of 6 carbons, its activity that approaches that of diprovocim-1, and its incidental chronological discovery, it is a compound we have elected to refer to as diprovocim-6 (138).

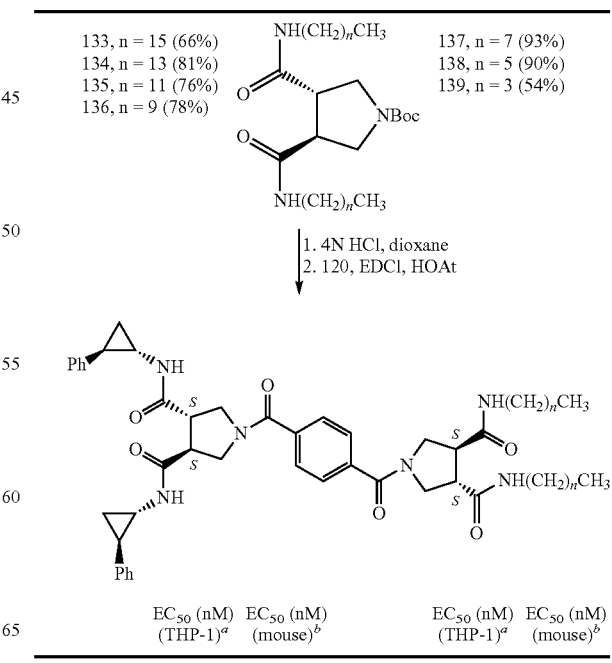

133, n = 15 (66%)
134, n = 13 (81%)
135, n = 11 (76%)
136, n = 9 (78%)
137, n = 7 (93%)
138, n = 5 (90%)
139, n = 3 (54%)

1. 4N HCl, dioxane
2. 120, EDCI, HOAt

| $EC_{50}$ (nM) (THP-1)[a] | $EC_{50}$ (nM) (mouse)[b] | $EC_{50}$ (nM) (THP-1)[a] | $EC_{50}$ (nM) (mouse)[b] |
|---|---|---|---|

-continued

| | | | | | |
|---|---|---|---|---|---|
| 133, n = 15 | 2.5 | 1000 | 137, n = 7 | 0.17 | 10 |
| 134, n = 13 | 1.3 | 620 | 138, n = 5 | 0.18 | 4 |
| 135, n = 11 | 1.0 | 1000 | 139, n = 3 | 50 | 360 |
| 136, n = 9 | 0.28 | 60 | | | |

[a] $EC_{50}$ TNF-α release from human THP-1 cells.
[b] $EC_{50}$ TNF-α release from mouse macrophages.

A series of analogues of the diprovocims in which all four side chains were replaced with a comprehensive set of lipid side chain amides was prepared and examined. The same (S,S)-pyrrolidine-3,4-dicarboxamides that contained the two amide lipid side chains (16-4 carbons) were coupled in a single step with benzene-1,4-dicarboxylic acid (C5) (EDCI, HOAt, 2,6-lutidine, DMF-CH$_2$Cl$_2$, 25° C., 4-5 hours) to provide 140-146.

However, no compound in this series proved capable of stimulating the release of TNF-α from either in the human THP-1 cells or mouse macrophages ($EC_{50}$>5 μM). Notably, this series of compounds also displayed especially poor solubility properties and it cannot be ruled out that this contributes to the lack of activity observed in the cell-based functional assays.

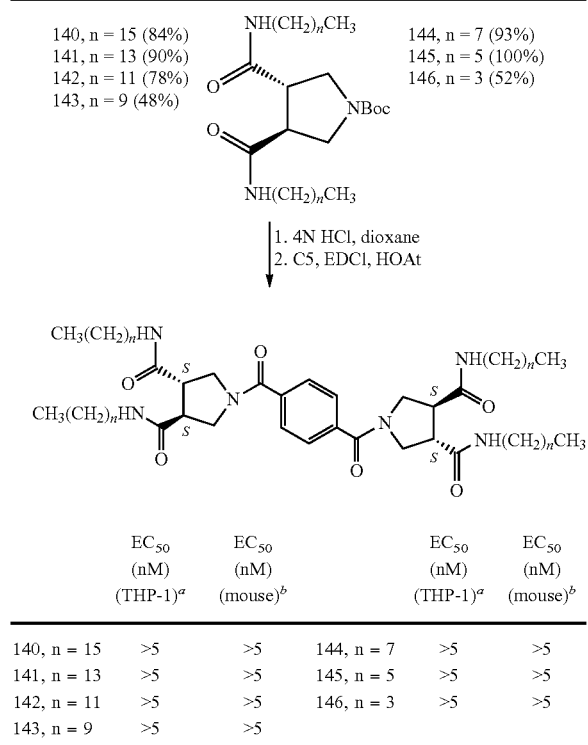

| | $EC_{50}$ (nM) (THP-1)[a] | $EC_{50}$ (nM) (mouse)[b] | | $EC_{50}$ (nM) (THP-1)[a] | $EC_{50}$ (nM) (mouse)[b] |
|---|---|---|---|---|---|
| 140, n = 15 | >5 | >5 | 144, n = 7 | >5 | >5 |
| 141, n = 13 | >5 | >5 | 145, n = 5 | >5 | >5 |
| 142, n = 11 | >5 | >5 | 146, n = 3 | >5 | >5 |
| 143, n = 9 | >5 | >5 | | | |

[a] $EC_{50}$ TNF-α release from human THP-1 cells.
[b] $EC_{50}$ TNF-α release from mouse macrophages.

Functionalized Derivatives

In anticipation of covalent linkage of antigenic peptides and with a recognition of the likely manner of diprovocim binding to TLR1/TLR2 with its side chain aryl substituents extending into the lipid binding pockets on adjacent dimerized TLR1 and TLR2 in a manner analogous to Pam3CSK4 [(a) Jin et al., *Cell* 2007, 130:1071; and Review: (b) Jin et al., *Curr. Opin. Immunol.* 2008, 20:414-419], a small series of further functionalized derivatives of diprovocim-1 was examined, below. These were prepared from either 53 or 55 through acylation or alkylation of the phenol or amine bound to the benzene ring of the central linker as in the compounds shown below. Earlier screening in mouse macrophages failed to detect this class of compounds, indicating that initial members in this class found in the compound libraries were insufficiently active against mTLRs to be detected. Optimized members are active in mouse as well as human cells, but still significantly more potent on the human targets and in functional assays in human cells.

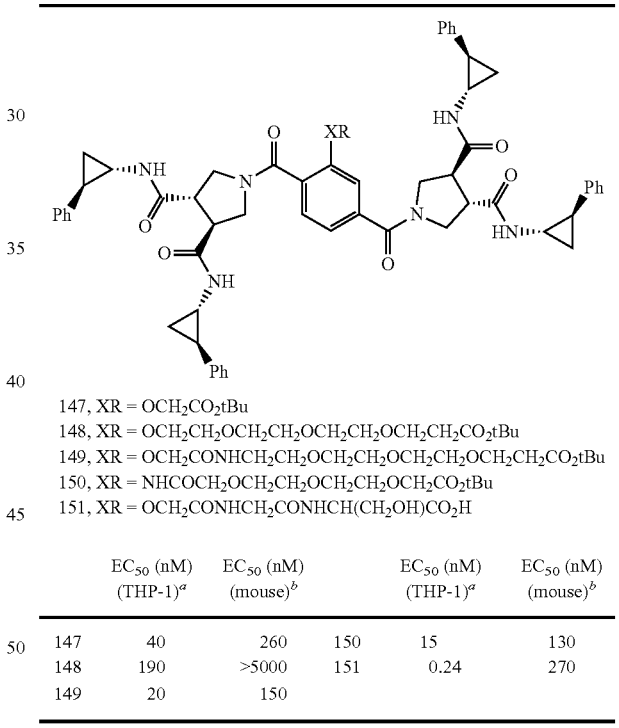

147, XR = OCH$_2$CO$_2$tBu
148, XR = OCH$_2$CH$_2$OCH$_2$CH$_2$OCH$_2$CH$_2$OCH$_2$CH$_2$CO$_2$tBu
149, XR = OCH$_2$CONHCH$_2$CH$_2$OCH$_2$CH$_2$OCH$_2$CH$_2$OCH$_2$CH$_2$CO$_2$tBu
150, XR = NHCOCH$_2$OCH$_2$CH$_2$OCH$_2$CH$_2$OCH$_2$CO$_2$tBu
151, XR = OCH$_2$CONHCH$_2$CONHCH(CH$_2$OH)CO$_2$H

| | $EC_{50}$ (nM) (THP-1)[a] | $EC_{50}$ (nM) (mouse)[b] | | $EC_{50}$ (nM) (THP-1)[a] | $EC_{50}$ (nM) (mouse)[b] |
|---|---|---|---|---|---|
| 147 | 40 | 260 | 150 | 15 | 130 |
| 148 | 190 | >5000 | 151 | 0.24 | 270 |
| 149 | 20 | 150 | | | |

[a] $EC_{50}$ TNF-α release from human THP-1 cells.
[b] $EC_{50}$ TNF-α release from mouse macrophages.

Hits were confirmed in an ELISA assay for stimulated TNF-α release from human PMA differentiated THP-1 cells and this assay was used for establishing dose-response curves and measured $EC_{50}$ values.

Further results using a Z-functionalized diprovocim-1 are shown below. Illustrative compounds are shown in the Table below as Z group portions of compounds of Formula V. The wavy lines indicate the place of bonding of the Z— group to the residuum of the diprovocim molecule.

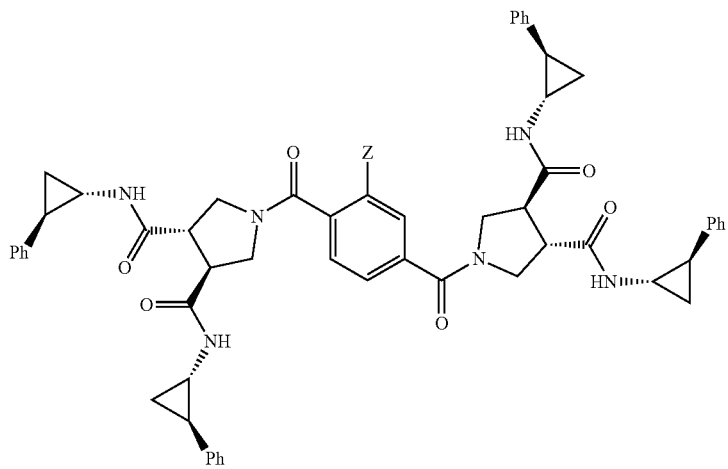
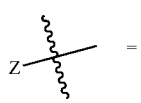 =
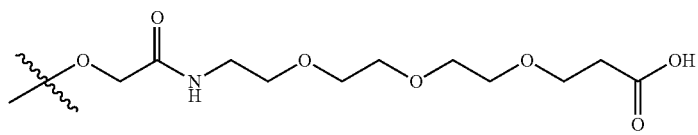
152
EC$_{50}$ (THP-1) = 71 nM
EC$_{50}$ (mouse) > 5000 nM
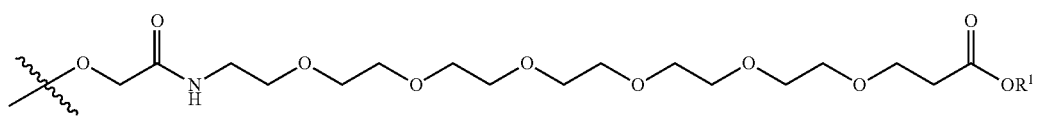
153 (R$^1$ = tBu)
EC$_{50}$ (THP-1) = 71 nM
EC$_{50}$ (mouse) > 5000 nM
154 (R$^1$ = H)
EC$_{50}$ (THP-1) = 620 nM
EC$_{50}$ (mouse) > 5000 nM
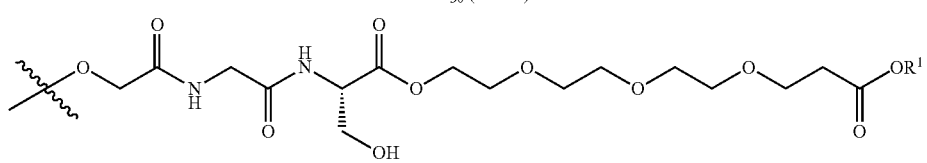
155 (GS, R$^1$ = tBu)
EC$_{50}$ (THP-1) = 46 nM
EC$_{50}$ (mouse) > 5000 nM
156 (GS, R$^1$ = H)
EC$_{50}$ (THP-1) = 7.4 nM
EC$_{50}$ (mouse) > 5000 nM

157 (GS, $R^1$ = tBu)
$EC_{50}$ (THP-1) = 240 nM
$EC_{50}$ (mouse) > 5000 nM
158 (GS, $R^1$ = H)
$EC_{50}$ (THP-1) = 230 nM
$EC_{50}$ (mouse) NA

159 (GG)
$EC_{50}$ (THP-1) = 0.79 nM
$EC_{50}$ (mouse) > 5000 nM

160 (GD, $R^1$ = tBu)
$EC_{50}$ (THP-1) = 86 nM
$EC_{50}$ (mouse) > 5000 nM
161 (GD, $R^1$ = H)
$EC_{50}$ (THP-1) = 1.9 nM
$EC_{50}$ (mouse) > 5000 nM

162 (GK, $R^1$ = tBu, $R^2$ = $CO_2$tBu)
$EC_{50}$ (THP-1) = 380 nM
$EC_{50}$ (mouse) > 5000 nM
163 (GK, $R^1$ = H, $R^2$ = H)
$EC_{50}$ (THP-1) = 1.2 nM
$EC_{50}$ (mouse) > 340 nM

164 (GSK, $R^1$ = tBu, $R^2$ = $CO_2$tBu)
$EC_{50}$ (THP-1) = 5000 nM
$EC_{50}$ (mouse) > 5000 nM
165 (GSK, $R^1$ = H, $R^2$ = H)
$EC_{50}$ (THP-1) = 2.3 nM
$EC_{50}$ (mouse) > 1200 nM

166 (GSKK)
$EC_{50}$ (THP-1) = 1.5 nM
$EC_{50}$ (mouse) > 5000 nM
SEQ ID NO: 3

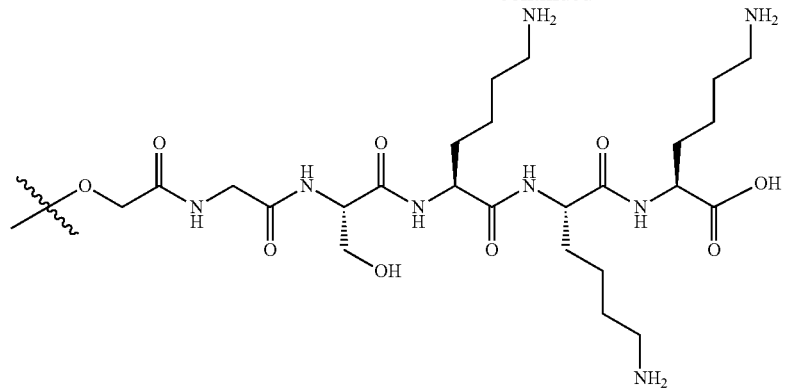
167 (GSKKK)
EC$_{50}$ (THP-1) = 4.5 nM
EC$_{50}$ (mouse) > 5000 nM
SEQ ID NO: 4
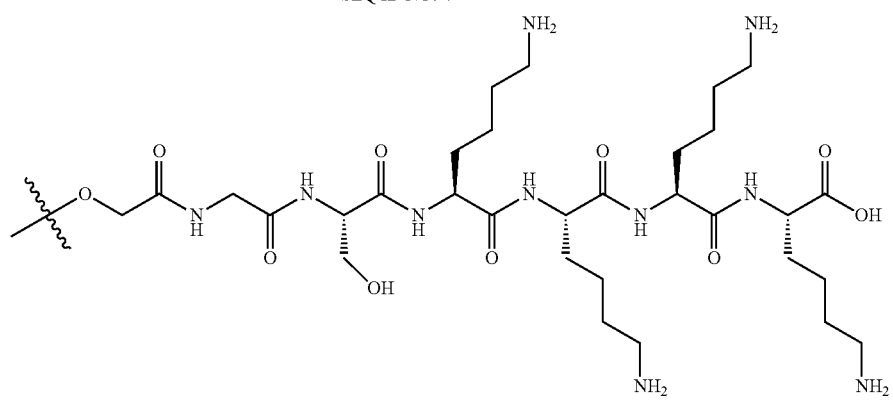
168 (GSKKKK)
EC$_{50}$ (THP-1) = 3.5 nM
EC$_{50}$ (mouse) > 270 nM
SEQ ID NO: 5
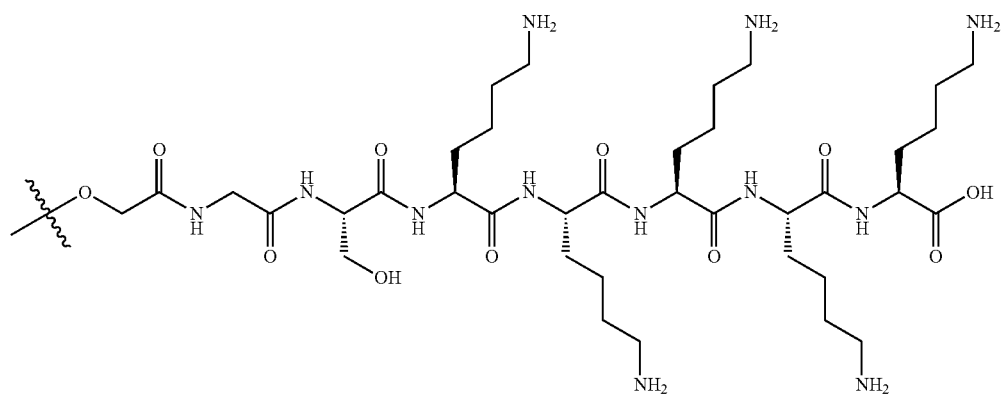
169 (GSKKKKK)
EC$_{50}$ (THP-1) = 9.0 nM
EC$_{50}$ (mouse) > 5000 nM
SEQ ID NO: 6

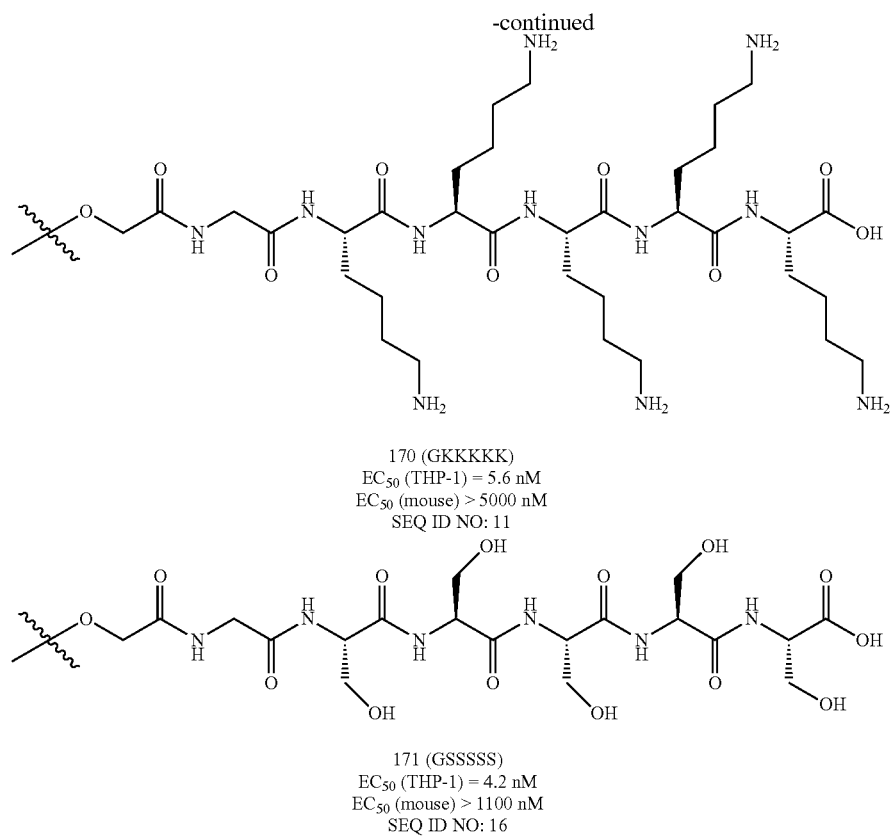

170 (GKKKKK)
EC$_{50}$ (THP-1) = 5.6 nM
EC$_{50}$ (mouse) > 5000 nM
SEQ ID NO: 11

171 (GSSSSS)
EC$_{50}$ (THP-1) = 4.2 nM
EC$_{50}$ (mouse) > 1100 nM
SEQ ID NO: 16

Diprovocim-1 was shown to be dependent on TLR1/TLR2, promoting activation by heterodimerization and its downstream signaling. It was found to be independent of TLR6, indicating it does not act by promoting TLR2/TLR6 heterodimerization, and it was found to be independent of all other TLRs. In these studies, it was also shown to be dependent on the TLR1/TLR2 signaling molecules MyD88 and IRAK4/TRIF. Like Pam3CSK4 and MALP-2, it activates NF-κβ, JNK, and p38 signaling pathway in THP-1 cells and in mouse macrophages, and it can induce IL-6 production in B16-F10 cells in vitro. It exhibits potent adjuvant activity in vivo in mice at 0.25-5 mg/kg (i.m.) that is dependent on TLR2, being ineffective in TLR2 KO mice.

General Procedures

All commercial reagents were used without further purification unless otherwise noted. All reactions were performed in oven-dried (200° C.) glassware and under an inert atmosphere of anhydrous Ar unless otherwise noted. Column chromatography was performed with silica gel 60. TLC was performed on EMD Millipore silica gel (250 μm) F254 glass plates and spots visualized by UV. PTLC was performed on EMD Millipore silica gel (250 and 500 μm) F254 glass plates.

Optical rotations were determined on a Rudolph Research Analytical Autopol III automatic polarimeter using the sodium D line (λ=589 nm) at room temperature (23° C.) and are reported as follows: $[\alpha]_D^{23}$, concentration (c=g/100 mL), and solvent.

$^1$H NMR was recorded on a Bruker 500 MHz and 600 MHz spectrometers. Chemical shifts are reported in ppm from an internal standard of residual CHCl$_3$ (δ 7.26 for 1H). Proton chemical data are reported as follows: chemical shift (δ), multiplicity (ovlp=overlapping, br=broad, s=singlet, d=doublet, t=triplet, q=quartet, m=multiplet), coupling constant, and integration.

High resolution mass spectra were obtained on an Agilent ESI-TOF/MS using Agilent ESI-L low concentration tuning mix as internal high resolution calibration standards. The purity of each tested compound (>95%) was determined on an Agilent 1100 LC/MS instrument using a ZORBAX® SB-C8 column (3.5 mm, 4.6 mm×50 mm, with a flow rate of 0.75 mL/minute and detection at 220 and 254 nm) with a 10-98% acetonitrile/water/0.1% formic acid gradient.

General Procedure for Coupling of Amines with N-Boc-Pyrrolidine-3,4-Dicarboxylic Acid N-Boc-Pyrrolidine-3,4-dicarboxylic acid (0.19 or 3.00 mmol), primary amine (0.42 or 6.15 mmol, 2.05-2.2 equiv), and 1-hydroxy-7-azabenzo-triazole (HOAt; 0.48 or 6.60 mmol, 2.20-2.50 equiv) were dissolved in anhydrous DMF (2 or 15 mL) under a N$_2$ atmosphere. 2,6-Lutidine (0.96 or 15.0 mmol, 5.00 equiv) was added slowly. Upon dissolution of the reagents (about 15 minutes), EDCI.HCl (7.50 mmol, 2.50 equiv) was added in one portion, and the reaction mixture was stirred for 18 hours, after which it was poured into aqueous 1 N HCl (150 mL) and EtOAc (100 mL). The aqueous phase was extracted with EtOAc (2×75 mL), and the combined organic phases were washed with aqueous 1 N HCl (75 mL), saturated aqueous NaHCO$_3$ (75 mL), and saturated aqueous NaCl (50 mL), sequentially. The organic phase was dried over Na$_2$SO$_4$, filtered and concentrated. Many compounds were advanced without purification but, where noted, were purified by flash column chromatography (SiO$_2$, 50% EtOAc/hexanes) gave the diamide product (67-75%).

General Procedure for N-Boc-Pyrrolidine Deprotection

The tert-butyl pyrrolidine-1-carboxylate derivative (2.00 mmol) was suspended in anhydrous THF (2 mL) at room temperature. 4 N HCl (8 mL, 4.0 M solution in dioxane) was added dropwise to a vigorously stirred reaction solution. After stirring 3 hours at room temperature, during which some product typically precipitated from the reaction mixture, the solvents were removed by $N_2$ stream over 16 hours. The residual solids were suspended in anhydrous THF and reconcentrated in vacuo (3×5 mL) to ensure complete removal of the dioxane. This process was repeated with anhydrous $Et_2O$ (3×5 mL) to provide the hydrochloride salt (87-99%) as an amorphous white solid.

General Procedure for Linking Diacid Coupling

Pyrrolidine-3,4-dicarboxamide hydrochloride (0.1 or 1.10 mmol, 2.20 equiv) and linking diacid (0.045 or 0.50 mmol, 1.00 equiv) were dissolved in anhydrous DMF (0.5 or 6 mL) at 23° C. i-$Pr_2NEt$ (0.23 or 1.50 mmol, 3.00-5.00 equiv) was added, followed by bromotripyrrolidinophosphonium hexafluorophosphate (PyBrOP; 0.10 or 1.00 mmol, 2.00-2.20 equiv) after 5 minutes. After 18-24 hours, the reaction mixture was diluted with EtOAc (10 or 150 mL) and washed with aqueous 0.5 N HCl (2×10 or 100 mL). The aqueous phase was extracted with EtOAc (1×10 or 75 mL). The combined organic phases were washed with aqueous 0.5 N HCl (2×10 mL), saturated aqueous $NaHCO_3$ (25 or 75 mL) and saturated aqueous NaCl (25 or 50 mL). The organic phase was dried over $Na_2SO_4$, decanted and concentrated to provide the coupled product contaminated with a small amount (about 10%) of tri(pyrrolidin-1-yl)phosphine oxide. The contaminant was removed by trituration with cold (0° C.) 1:1 $Et_2O$/EtOAc (3×5 mL), decanting the liquid phase to give the desired bis-pyrrolidine diamide (65-97%). Where necessary, flash column chromatography ($SiO_2$, 5-8% MeOH/$CH_2Cl_2$) was employed to purify the product.

Diprovocim-1 Synthesis

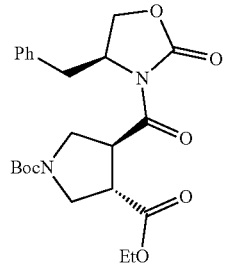 [SMILES: CCOC(=O)[C@@H]1CN(C(=O)OC(C)(C)C)C[C@H]1C(=O)N1C(=O)OC[C@@H]1Cc1ccccc1]

S-1: (3S,4S)-1-tert-Butyl 3-Ethyl 4-((S)-4-Benzyl-2-oxooxazolidine-3-carbonyl)pyrrolidine-1,3-dicarboxylate (3S,4S)-Ethyl 1-benzyl-4-((S)-4-benzyl-2-oxooxazolidine-3-carbonyl)pyrrolidine-3-carboxylate [prepared as a single stereoisomer according to: U.S. Pat. No. 6,489,354 B1] (3.43 g, 7.86 mmol) and $Boc_2O$ (1.80 g, 8.25 mmol, 1.05 equiv) were dissolved in EtOH (50 mL) at room temperature. $Pd(OH)_2$/C (500 mg) was added and the reaction mixture was sparged with $N_2$ for 15 minutes. A 3-way flushing adapter, equipped with $H_2$ balloon and vacuum source, was attached. The headspace above the reaction mixture was evacuated until the solvent began to boil, then backfilled with $H_2$. This vacuum/fill process was repeated 10-15 times to maximize $H_2$ in the headspace. The reaction mixture was stirred for 18 hours at 23° C. After 18 hours, the reaction mixture was filtered through a 6 cm Celite® plug, rinsing with EtOH (3×15 mL), and concentrated. Flash column chromatography ($SiO_2$, 25% EtOAc/hexanes) provided 2.93 g (84%) of the N-Boc pyrrolidine product as a clear, viscous oil. The identical procedure was employed with the (3R,4R)-diastereomer: (3R,4R)-ethyl 1-benzyl-4-((S)-4-benzyl-2-oxooxazolidine-3-carbonyl)pyrrolidine-3-carboxylate[1] (3.06 g, 7.01 mmol), $Boc_2O$ (1.60 g, 7.36 mmol), $Pd(OH)_2$/C (500 mg) and EtOH (50 mL) to afford 2.73 g (87%) of (3R,4R)—S-1 as a clear, viscous oil. Data for the (3S,4S)-diastereomer: $^1H$ NMR (400 MHz, $CDCl_3$) δ 7.40-7.19 (m, 5H), 4.69 (dd, J=9.0, 4.5 Hz, 1H), 4.52 (q, J=7.7 Hz, 1H), 4.29-4.14 (m, 4H), 3.95-3.75 (m, 2H), 3.60 (m, 2H), 3.52-3.27 (m, 2H), 2.86-2.71 (m, 1H), 1.46 (s, 9H), 1.28 (t, J=7.5 Hz, 3H). HRMS (ESI-TOF) m/z calcd for $C_{23}H_{31}N_2O_7$ $[M+H]^+$447.2126, found 447.2126. Data for the (3R,4R)-diastereomer: $^1H$ NMR (400 MHz, $CDCl_3$) δ 7.39-7.28 (m, 3H), 7.19 (d, J=7.3 Hz, 2H), 4.72 (ddd, J=11.3, 6.7, 3.4 Hz, 1H), 4.33-4.20 (m, 2H), 4.17 (q, J=8.0, 7.6 Hz, 2H), 3.97 (d, J=9.6 Hz, 1H), 3.92-3.79 (m, 1H), 3.65 (d, J=9.8 Hz, 1H), 3.59-3.33 (m, 2H), 3.24 (d, J=13.0 Hz, 1H), 2.84 (dd, J=13.4, 9.2 Hz, 1H), 1.48 (s, 9H), 1.26 (td, J=7.1, 1.6 Hz, 3H).

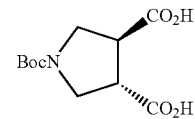

(S,S)-14 and (R,R)-14: (3S,4S)-1-(tert-Butoxycarbonyl)pyrrolidine-3,4-dicarboxylic Acid

[modified procedure from: Ma et al., *Tetrahedron Asymm.* 1997, 8; 883-887.]

(3S,4S)-1-tert-Butyl 3-ethyl 4-((S)-4-benzyl-2-oxooxazolidine-3-carbonyl)pyrrolidine-1,3-dicarboxylate ((3S,4S)—S-1; 2.06 g, 4.63 mmol) was dissolved in anhydrous THF (20 mL) and cooled to 0° C. Hydrogen peroxide (2.10 mL, ca. 18.5 mmol, 4.0 equiv, 30% w/v) was added dropwise to the stirred reaction solution. After 3-5 minutes, LiOH.$H_2O$ (500 mg, 11.9 mmol) was added. After 2 hours, additional LiOH (470 mg, 11.2 mmol) was added, along with $H_2O$ (10 mL) and THF (15 mL). The reaction mixture was stirred for 3 hours, warming to room temperature. Saturated aqueous $Na_2SO_3$ (10 mL) was added, and the THF was removed under a $N_2$ stream. The resulting mixture was poured into $H_2O$ (200 mL) and extracted with $CH_2Cl_2$ (2×100 mL) to remove the oxazolidinone. The aqueous phase was acidified with aqueous 1 N HCl to pH 2 (about 75 mL). The aqueous phase was extracted with EtOAc (3×125 mL), and the organic extracts were dried over $Na_2SO_4$, filtered and concentrated to provide 1.13 g (94%) of (3S,4S)-14 as a white solid that was not further purified. The identical procedure was employed with the (3R,4R)—S-1 diastereomer: (3R,4R)-1-tert-butyl 3-ethyl 4-((S)-4-benzyl-2-oxooxazolidine-3-carbonyl)pyrrolidine-1,3-dicarboxylate (1.88 g, 4.22 mmol), hydrogen peroxide (1.90 mL, 16.9 mmol), LiOH.$H_2O$ (885 mg, 21.1 mmol) and THF (20 mL) afforded 927 mg (85%) of (3R,4R)-14 as a white solid. For the (S,S)-14: $^1H$ NMR (500 MHz, DMSO-$d_6$) δ 3.59-3.48 (m, 2H), 3.41-3.31 (m, 2H), 3.30-3.18 (m, 2H), 1.39 (s, 9H).

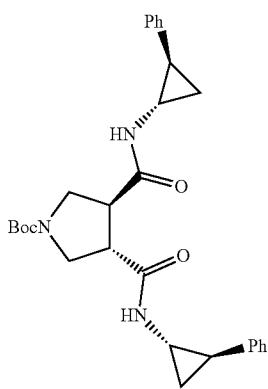 [SMILES: CC(C)(C)OC(=O)N1C[C@@H](C(=O)N[C@H]2C[C@@H]2c2ccccc2)[C@H](C(=O)N[C@H]2C[C@@H]2c2ccccc2)C1]

15: (3S,4S)-tert-Butyl 3,4-Bis(((1S,2R)-2-phenyl-cyclopropyl)carbamoyl)-pyrrolidine-1-carboxylate (3S,4S)-1-(tert-Butoxycarbonyl) pyrrolidine-3,4-dicarboxylic acid (14; 775 mg, 2.99 mmol), (1S,2R)-trans-2-phenylcyclopropylamine ((1S,2R)-13; 816 mg, 6.13 mmol, 2.05 equiv), and HOAt (895 mg, 6.58 mmol, 2.20 equiv) were dissolved in anhydrous DMF (15 mL) under $N_2$ atmosphere. 2,6-Lutidine (1.75 mL, 14.9 mmol, 5.00 equiv) was added slowly. Upon dissolution of the reagents (15 minutes), EDCI.HCl (1.43 g, 7.47 mmol, 2.50 equiv) was added in one portion, and the reaction mixture was stirred for 18 hours, after which it was poured into aqueous 1 N HCl (150 mL) and EtOAc (100 mL). The aqueous phase was extracted with EtOAc (2×75 mL), and the combined organic phases were washed with aqueous 1 N HCl (75 mL), saturated aqueous $NaHCO_3$ (75 mL), and saturated aqueous NaCl (50 mL), sequentially. The organic phase was dried over $Na_2SO_4$, filtered and concentrated. Flash column chromatography ($SiO_2$, 50% EtOAc/hexanes) gave 1.02 g (70%) of 15. $^1$H NMR (400 MHz, $CDCl_3$) δ 7.33-7.24 (m, 5H), 7.23-7.09 (m, 5H), 6.61 (s, 1H), 6.43 (s, 1H), 3.85 (t, J=9.7 Hz, 1H), 3.68 (m, 1H), 3.60 (t, J=10.5 Hz, 1H), 3.42 (t, J=10.4 Hz, 1H), 3.27 (q, J=10.0, 9.3 Hz, 1H), 3.12 (t, J=9.7 Hz, 1H), 2.88 (m, 2H), 2.05 (ddt, J=9.8, 6.4, 3.4 Hz, 2H), 1.46 (s, 9H), 1.24 (q, J=6.6 Hz, 2H), 1.13 (dt, J=10.1, 5.3 Hz, 2H). HRMS (ESI-TOF) m/z calcd for $C_{29}H_{36}N_3O_4$ $[M+H]^+$ 490.2700, found 490.2705.

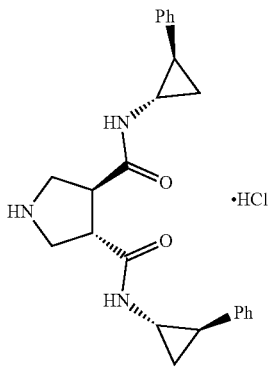 [SMILES: O=C(N[C@H]1C[C@@H]1c1ccccc1)[C@@H]1CNC[C@H]1C(=O)N[C@H]1C[C@@H]1c1ccccc1 ; Cl]

S-2: (3S,4S)—$N^3,N^4$-Bis((1S,2R)-2-phenylcyclopropyl)-pyrrolidine-3,4-dicarboxamide Hydrochloride (3S,4S)-tert-Butyl 3,4-bis(((1S,2R)-2-phenylcyclopropyl)carbamoyl)pyrrolidine-1-carboxylate (15; 998 mg, 2.04 mmol) was suspended in anhydrous THF (2 mL) at room temperature. 4 N HCl (8 mL, 4.0 M solution in dioxane) was added dropwise to a vigorously stirred reaction solution. After stirring 3 hours at room temperature, during which some product had precipitated from the reaction mixture, the solvents were removed by $N_2$ stream over 16 hours. The residual solids were suspended in anhydrous THF and reconcentrated in vacuo (3×5 mL) to ensure complete removal of the dioxane. This process was repeated with anhydrous $Et_2O$ (3×5 mL) to provide 870 mg (99%) of S-2 as an amorphous white solid. 1H NMR (500 μMHz, DMSO-$d_6$) δ 9.35 (s, 2H), 8.76 (d, J=4.4 Hz, 2H), 7.26 (t, J=7.6 Hz, 4H), 7.20-7.06 (m, 6H), 3.76-3.62 (m, 1H), 3.55-3.42 (m, 1H), 3.26 (t, J=8.2 Hz, 2H), 3.21-3.11 (m, 2H), 2.90-2.78 (m, 2H), 1.99 (ddd, J=9.6, 6.3, 3.4 Hz, 2H), 1.26-1.13 (m, 4H). HRMS (ESI-TOF) m/z calcd for $C_{24}H_{28}N_3O_2$ $[M+H]^+$ 390.2176, found 390.2178.

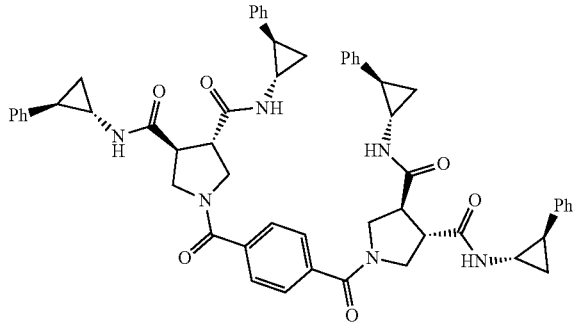 [SMILES: O=C(N[C@H]1C[C@@H]1c1ccccc1)[C@@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C[C@H]1C(=O)N[C@H]1C[C@@H]1c1ccccc1]

3 (Diprovocim-1): (3S,3'S,4S,4'S)-1,1'-Terephthaloylbis($N^3,N^4$-bis((1S,2R)-2-phenylcyclopropyl) pyrrolidine-3,4-dicarboxamide)

(3S,4S)—$N^3,N^4$-Bis((1S,2R)-2-phenyl-cyclopropyl)pyrrolidine-3,4-dicarboxamide hydrochloride (S-2; 500 mg, 1.17 mmol, 2.20 equiv) and terephthalic acid (benzene-1,4-dicarboxylic acid, 89 mg, 0.53 mmol, 1.00 equiv) were dissolved in anhydrous DMF (6 mL) at room temperature. i-$Pr_2$NEt (0.280 mL, 1.60 mmol, 3.00 equiv) was added, followed by PyBrOP (497 mg, 1.07 mmol, 2.00 equiv) after 5 minutes and the mixture was stirred at 23° C. for 18 hours. After 18 hours, the reaction mixture was diluted with EtOAc (300 mL) and washed with aqueous 0.5 N HCl (2×150 mL). The aqueous phase was extracted with EtOAc (1×50 mL). The combined organic phases were washed with saturated aqueous $NaHCO_3$ (100 mL) and saturated aqueous NaCl (75 mL). The organic phase was dried over $Na_2SO_4$, decanted and concentrated. Flash column chromatography ($SiO_2$, 5-8% MeOH/$CH_2Cl_2$) provided 3 contaminated with a small amount (about 10%) of tri(pyrrolidin-1-yl)phosphine oxide. The contaminant was removed by trituration with cold (0° C.) 1:1 $Et_2$O/EtOAc (3×5 mL), decanting off the liquid phase to provide 421 mg (86%) of 3. $[\alpha]_D^{26}$+57 (c 0.33, EtOH). IR (neat) $v_{max}$ 3259, 1633, 1539, 1426, 1386, 1073, 695 cm$^{-1}$. $^1$H NMR (600 MHz, DMSO-$d_6$) δ 8.42 (d, J=4.3 Hz, 2H), 8.29 (d, J=4.3 Hz, 2H), 7.56 (s, 4H), 7.27-7.21 (m, 8H), 7.19-7.09 (m, 8H), 7.09-7.03 (m, 4H), 3.80 (dd, J=12.0, 8.6 Hz, 2H), 3.71-3.58 (m, 2H), 3.51 (ddd, J=15.6, 11.2, 8.2 Hz, 4H), 3.19 (q, J=8.4 Hz, 2H), 3.10 (q, J=8.1 Hz, 2H), 2.90-2.80 (m, 2H), 2.80-2.73 (m, 2H), 1.97 (ddd, J=9.6, 6.4, 3.4 Hz, 2H), 1.86 (ddd, J=9.5, 6.3, 3.4 Hz, 2H), 1.21-1.13 (m, 4H), 1.13-1.05 (m, 4H). $^{13}$C NMR (151 μMHz, DMSO-$d_6$) δ 171.65, 170.93, 167.46, 141.28, 141.19, 137.71, 128.17, 128.14, 127.09, 125.83, 125.79, 125.60, 51.48, 48.74, 46.95, 45.83, 45.07, 32.54, 32.45, 25.87, 23.90, 23.81, 15.33, 15.24. HRMS (ESI-TOF) m/z calcd for $C_{56}H_{57}N_6O_6$ [M+H]$^+$ 909.4334, found 909.4334.

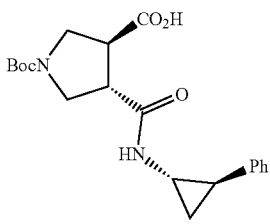 [SMILES: CC(C)(C)OC(=O)N1C[C@@H](C(=O)O)[C@H](C(=O)N[C@H]2C[C@@H]2c2ccccc2)C1]

S-3: trans-1-(tert-Butoxycarbonyl)-4-((trans-2-phenylcyclopropyl)carbamoyl)pyrrolidine-3-carboxylic Acid Racemic trans-1-(tert-butoxycarbonyl)-pyrrolidine-3,4-dicarboxylic acid [Padwa et al., *J. Org. Chem.* 1987, 52:235-244; and Sarmiento et al., *Tetrahedron: Asymmetry,* 2003, 14:1547-1551] (250 mg, 0.964 mmol), EDCI.HCl (185 mg, 0.964 mmol, 1.00 equiv), HOAt (144 mg, 1.06 mmol, 1.10 equiv) and 2,6-lutidine (0.56 mL, 4.82 mmol, 5.00 equiv) were dissolved in anhydrous DMF (5 mL) at room temperature. After stirring for 1 hour, racemic trans-2-phenylcyclopropylamine hydrochloride (164 mg, 0.964 mmol, 1.00 equiv) was added, and the mixture was stirred at 23° C. for 18 hours. The mixture was poured into aqueous 1 N HCl (50 mL) and EtOAc (50 mL). The aqueous phase was extracted with EtOAc (2×50 mL), and the combined organic phases were washed with aqueous 1 N HCl (50 mL), and saturated aqueous NaCl (50 mL), sequentially. The organic phase was dried over $Na_2SO_4$, decanted and concentrated. Flash column chromatography (SiO$_2$, 60:40:0.1 EtOAc/hexanes/AcOH) gave 157 mg (43%) of S-3. $^1$H NMR (500 μMHz, CDCl$_3$) δ 7.24 (t, J=7.1 Hz, 2H), 7.20-7.03 (m, 3H), 6.64 (s, 1H), 3.86-3.77 (m, 1H), 3.69-3.58 (m, 2H), 3.54 (t, J=9.7 Hz, 1H), 3.42-3.32 (m, 1H), 3.27-3.19 (m, 1H), 3.14 (d, J=7.9 Hz, 1H), 2.89-2.83 (m, 1H), 2.06-2.00 (m, 1H), 1.46 (s, 9H), 1.18 (dd, J=10.5, 7.2 Hz, 2H).

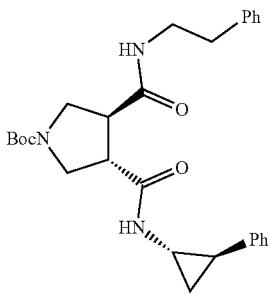 [SMILES: CC(C)(C)OC(=O)N1C[C@@H](C(=O)NCCc2ccccc2)[C@H](C(=O)N[C@H]2C[C@@H]2c2ccccc2)C1]

5: tert-Butyl trans-3-(Phenethyl-carbamoyl)-4-((trans-2-phenylcyclopropyl)carbamoyl)pyrrolidine-1-carboxylate trans-1-(tert-Butoxycarbonyl)-4-((trans-2-phenylcyclopropyl)carbamoyl)pyrrolidine-3-carboxylic acid (S-3; 100 mg, 0.267 mmol), phenethylamine (32 mg, 0.267 mmol, 1 equiv) and i-Pr$_2$NEt (140 μL, 0.801 mmol, 3.00 equiv) were dissolved in anhydrous DMF (1.5 mL) at room temperature. (Benzotriazol-1-yl-oxy)tripyrrolidino-phosphonium hexafluorophosphate (PyBOP; 153 mg, 0.294 mmol, 1.10 equiv) was added, and the mixture was stirred 16 hours. The mixture was diluted with EtOAc (50 mL) and washed with aqueous 1 N HCl (40 mL), saturated aqueous NaHCO$_3$ (30 mL) and saturated aqueous NaCl (30 mL), sequentially. The organic phase was dried over Na$_2$SO$_4$, decanted and concentrated. Flash column chromatography (SiO$_2$, 50% EtOAc/hexanes) provided 44 mg (34%) of 5. $^1$H NMR (500 MHz, acetone-$d_6$) δ 7.68 (d, J=4.4 Hz, 1H), 7.45 (s, 1H), 7.39-7.19 (m, 10H), 3.84-3.69 (m, 3H), 3.58-3.48 (m, 3H), 3.42 (dt, J=13.3, 9.7 Hz, 2H), 3.36-3.23 (m, 1H), 2.88 (qd, J=7.5, 6.6 Hz, 2H), 2.16-2.08 (m, 1H), 1.52 (s, 9H), 1.31-1.23 (m, 2H).

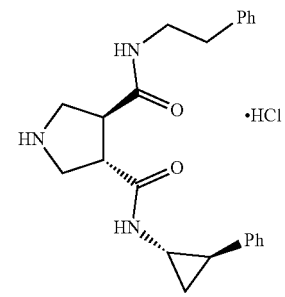 [SMILES: O=C(NCCc1ccccc1)[C@@H]1CNC[C@H]1C(=O)N[C@H]1C[C@@H]1c1ccccc1 ; Cl]

S-4: trans-N$^3$-Phenethyl-N$^4$-(trans-2-phenyl-cyclopropyl)pyrrolidine-3,4-dicarboxamide hydrochloride trans-tert-Butyl 3-(phenethylcarbamoyl)-4-((trans-2-phenylcyclopropyl)carbamoyl)pyrrolidine-1-carboxylate (5; 40 mg, 0.0819 mmol) was dissolved in 4 N HCl/dioxane solution (1.00 mL, 4.00 mmol, 49 equiv) at room temperature. After 2.5 hours, the mixture was concentrated under a stream of N$_2$ to provide 35 mg (99) of S-4.

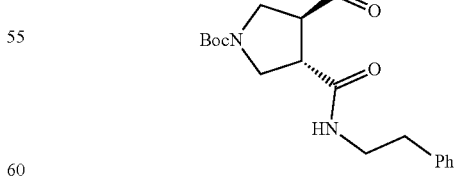

6: trans-tert-Butyl 3,4-Bis(phenethylcarbamoyl)-pyrrolidine-1-carboxylate

The general procedure for the coupling of amines with pyrrolidine-3,4-diacids was followed: racemic trans-1-(tertbutyloxycarbonyl)pyrrolidine-3,4-dicarboxylic acid (500 mg, 1.93 mmol), phenethylamine (468 mg, 3.86 mmol), 2,6-lutidine (1.12 mL, 9.64 mmol), EDCI.HCl (924 mg, 4.82 mmol), HOAt (580 mg, 4.24 mmol) and DMF (10 mL) were employed. Flash column chromatography (SiO$_2$, 50% EtOAc/hexanes) provided 563 mg (63) of 6. $^1$H NMR (500 MHz, CDCl$_3$) δ 7.35-7.26 (m, 4H), 7.25-7.20 (m, 2H), 7.19-7.13 (m, 4H), 6.20 (s, 1H), 5.94 (s, 1H), 3.75 (t, J=9.3 Hz, 1H), 3.64-3.40 (m, 6H), 3.36 (t, J=10.2 Hz, 1H), 3.17 (q, J=9.9 Hz, 1H), 2.99 (q, J=9.4 Hz, 1H), 2.79 (t, J=6.8 Hz, 4H), 1.45 (s, 9H).

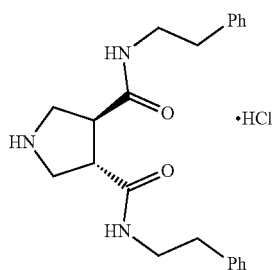 [SMILES: O=C(NCCc1ccccc1)[C@@H]1CNC[C@H]1C(=O)NCCc1ccccc1 ; Cl]

S-5: trans-N$^3$,N$^4$-Diphenethylpyrrolidine-3,4-dicarboxamide Hydrochloride

The general procedure for N-Boc-pyrrolidine deprotection was employed: N-Boc pyrrolidine 6 (202 mg, 0.434 mmol), anhydrous THF (2 mL), and 4 N HCl in dioxane (4 mL) were employed. Reconcentration from Et$_2$O (3×3 mL) gave 174 mg (99%) of S-5.

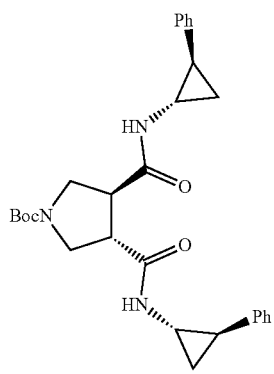 [SMILES: CC(C)(C)OC(=O)N1C[C@@H](C(=O)N[C@H]2C[C@@H]2c2ccccc2)[C@H](C(=O)N[C@H]2C[C@@H]2c2ccccc2)C1]

7: trans-tert-Butyl 3,4-Bis((trans-2-phenyl-cyclopropyl)carbamoyl)pyrrolidine-1-carboxylate Racemic trans-1-(tert-butoxycarbonyl)-pyrrolidine-3,4-dicarboxylic acid (250 mg, 0.964 mmol) and racemic trans-2-phenylcyclopropylamine hydrochloride (327 mg, 1.93 mmol, 2.00 equiv) were dissolved in anhydrous DMF (5 mL) under N$_2$ atmosphere. i-Pr$_2$NEt (250 μL, 1.93 mmol, 2.00 equiv) was added slowly. Upon dissolution of the reagents, EDCI.HCl (407 mg, 2.12 mmol, 2.20 equiv) was added in one portion, and the reaction mixture was stirred for 18 hours, after which it was poured into aqueous 0.5 N HCl (75 mL) and EtOAc (100 mL). The aqueous phase was extracted with EtOAc (2×75 mL), and the combined organic phases were washed again with aqueous 0.5 N HCl (50 mL), saturated aqueous NaHCO$_3$ (50 mL), and saturated aqueous NaCl (25 mL), sequentially. The organic phase was dried over Na$_2$SO$_4$, filtered and concentrated. Flash column chromatography (SiO$_2$, 25-50% EtOAc/hexanes gradient) gave 115 mg (24%) of 7. $^1$H NMR (500 MHz, CDCl$_3$) δ 7.30-7.24 (m, 5H), 7.23-7.07 (m, 5H), 6.59 (s, 1H), 6.34 (s, 1H), 3.84 (t, J=9.8 Hz, 1H), 3.69 (t, J=9.6 Hz, 1H), 3.59 (t, J=10.6 Hz, 1H), 3.45 (t, J=10.8 Hz, 1H), 3.24 (q, J=10.2 Hz, 1H), 3.13-3.07 (m, 1H), 2.90 (ddt, J=16.8, 7.6, 3.6 Hz, 2H), 2.09-1.96 (m, 2H), 1.46 (s, 9H), 1.30-1.21 (m, 2H), 1.20-1.09 (m, 2H).

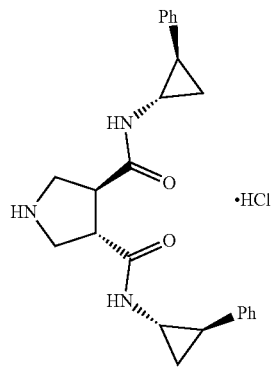 [SMILES: O=C(N[C@H]1C[C@@H]1c1ccccc1)[C@@H]1CNC[C@H]1C(=O)N[C@H]1C[C@@H]1c1ccccc1 ; Cl]

S-6: trans-N$^3$,N$^4$-Bis(trans-2-phenylcyclopropyl)-pyrrolidine-3,4-dicarboxamide Hydrochloride trans-tert-Butyl 3,4-bis((trans-2-phenyl-cyclopropyl)carbamoyl)pyrrolidine-1-carboxylate (7; 67 mg, 0.137 mmol) was dissolved in 4 N HCl/dioxane (5 mL, 145 equiv HCl) at room temperature. After stirring 2 hours, the solvent was removed under a N$_2$ stream for 12 hours. The residual solids were suspended in anhydrous THF (1 mL) and reconcentrated in vacuo (3×1 mL) to ensure complete removal of the dioxane. This process was repeated with anhydrous Et$_2$O (3×5 mL) to provide 58 mg (99%) of S-6.

8: trans,trans-1,1'-Terephthaloylbis-(N³, N⁴-diphenethylpyrrolidine-3,4-dicarboxamide)

The general procedure for linking diacid coupling was employed: Pyrrolidine-3,4-dicarboxamide hydrochloride S-5 (30 mg, 0.0746 mmol), terephthalic acid (5.6 mg, 0.0339 mmol), i-Pr$_2$NEt (18 µL, 0.102 mmol), PyBrOP (32 mg, 0.0679 mmol) and anhydrous DMF (375 µL) were employed. Mild heating (about 50° C.) was required for dissolution of reagents. The product precipitates as a white solid. After trituration with cold (0° C.) 1:1 Et$_2$O/EtOAc, 21.2 mg (73%) of 8 was isolated. $^1$H NMR (500 MHz, DMSO-d$_6$) δ 8.22 (t, J=5.5 Hz, 2H), 8.11-8.01 (m, 2H), 7.56 (d, J=1.2 Hz, 4H), 7.28 (t, J=7.5 Hz, 4H), 7.19 (dd, J=8.5, 6.7 Hz, 10H), 7.17-7.07 (m, 6H), 3.75 (dd, J=11.8, 8.7 Hz, 2H), 3.59 (t, J=9.1 Hz, 2H), 3.46 (t, J=9.6 Hz, 2H), 3.39 (td, J=9.3, 4.7 Hz, 2H), 3.31-3.15 (m, 10H), 3.12 (t, J=8.0 Hz, 2H), 2.72 (t, J=7.6 Hz, 4H), 2.64 (dt, J=8.9, 6.6 Hz, 4H). HRMS (ESI-TOF) m/z calcd for C$_{52}$H$_{57}$N$_6$O$_6$ [M+H]$^+$ 861.4334, found 861.4334.

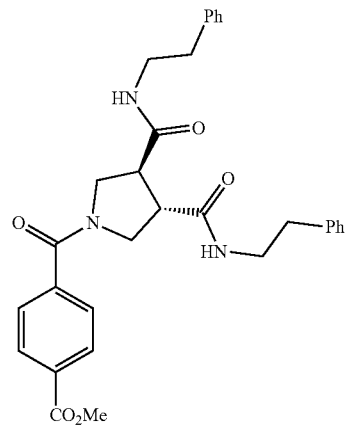 [SMILES: COC(=O)c1ccc(C(=O)N2C[C@@H](C(=O)NCCc3ccccc3)[C@H](C(=O)NCCc3ccccc3)C2)cc1]

S-7: Methyl 4-(trans-3,4-Bis-(phenethylcarbamoyl)-pyrrolidine-1-carbonyl)benzoate trans-N³,N⁴-Diphenethylpyrrolidine-3,4-dicarboxamide hydrochloride (S-5; 20 mg, 0.0498 mmol) monomethyl terephthalate (9.0 mg, 0.0498 mmol, 1.00 equiv) and i-Pr$_2$NEt (26 µL, 0.149 mmol, 3.00 equiv) were dissolved in anhydrous DMF (0.25 mL) at room temperature. PyBrOP (23 mg, 0.0498 mmol, 1.00 equiv) was added, and the mixture was stirred for 18 hours. The mixture was diluted with EtOAc (20 mL) and washed with aqueous 1 N HCl (10 mL). The aqueous phase was extracted with EtOAc (10 mL), and the combined organic layers were washed with saturated aqueous NaHCO$_3$ (10 mL) and saturated aqueous NaCl (10 mL) The organic phase was dried over Na$_2$SO$_4$, filtered and concentrated. Flash column chromatography (SiO$_2$, 75% EtOAc/hexanes) provided 17.1 mg (66%) of S-7. $^1$H NMR (500 MHz, CDCl$_3$) δ 8.07 (d, J=8.6 Hz, 2H), 7.54 (d, J=8.4 Hz, 2H), 7.35-7.07 (m, 10H), 6.43 (t, J=5.5 Hz, 1H), 6.32-6.22 (m, 1H), 4.09 (dd, J=12.1, 8.7 Hz, 1H), 3.94 (s, 3H), 3.75 (t, J=10.3 Hz, 1H), 3.65 (t, J=11.2 Hz, 1H), 3.59 (dd, J=10.9, 8.2 Hz, 1H), 3.53 (dd, J=13.4, 6.6 Hz, 1H), 3.47-3.39 (m, 3H), 3.23 (q, J=9.4 Hz, 1H), 3.10 (q, J=9.6 Hz, 1H), 2.80-2.71 (m, 4H).

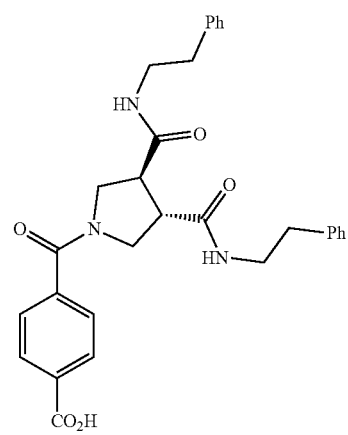 [SMILES: O=C(O)c1ccc(C(=O)N2C[C@@H](C(=O)NCCc3ccccc3)[C@H](C(=O)NCCc3ccccc3)C2)cc1]

S-8: 4-(trans-3,4-Bis(phenethylcarbamoyl)-pyrrolidine-1-carbonyl)benzoic Acid

Methyl 4-(trans-3,4-bis(phenethyl-carbamoyl)-pyrrolidine-1-carbonyl)benzoate (S-7; 14.7 mg, 0.0279 mmol) was dissolved in THF/MeOH/H$_2$O (100 µL, 20 µL, 20 µL, respectively) at room temperature. LiOH.H$_2$O (5 mg, 0.111 mmol, 4.00 equiv) was added in one portion. After 3 hours, the mixture was diluted with EtOAc (10 mL) and washed with aqueous 1 N HCl (10 mL). The aqueous phase was extracted once with EtOAc (5 mL), and the combined organic layers were dried over Na$_2$SO$_4$, decanted and concentrated to provide 13.5 mg (94%) of S-8.

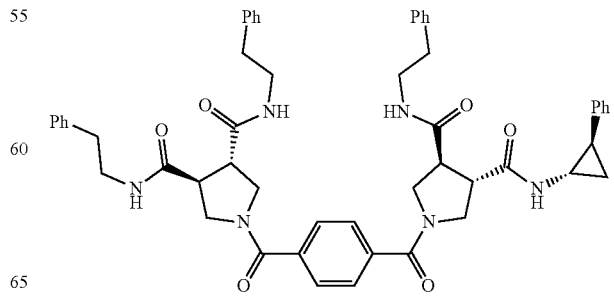

9: trans-1-(4-(trans-3,4-Bis(phenethylcarbamoyl)-pyrrolidine-1-carbonyl)benzoyl)-$N^3$-phenethyl-$N^4$-(trans-2-phenylcyclopropyl)pyrrolidine-3,4-dicarboxamide 4-(trans-3,4-Bis(phenethylcarbamoyl)-pyrrolidine-1-carbonyl)benzoic acid (S-8; 9.6 mg, 0.0186 mmol), trans-$N^3$-phenethyl-$N^4$-(trans-2-phenylcyclopropyl)-pyrrolidine-3,4-dicarboxamide hydrochloride (S-4; 7.7 mg, 0.0186 mmol, 1.00 equiv) and i-Pr$_2$NEt (10 µL, 0.0558 mmol, 3.00 equiv) were dissolved in anhydrous DMF (100 µL) at room temperature. PyBrOP (8.8 mg, 0.0186 mmol, 1.00 equiv) was added, and the mixture was stirred for 16 hours. The mixture was diluted with EtOAc (5 mL) and washed with aqueous 1 N HCl (2 mL). The aqueous phase was extracted with EtOAc (2 mL), and the combined organic layers were washed with saturated aqueous NaHCO$_3$ (2 mL) and saturated aqueous NaCl (2 mL). The organic phase was dried over Na$_2$SO$_4$, filtered and concentrated to give 16 mg (98%) of 9. $^1$H NMR (500 MHz, DMSO-d$_6$) δ 8.15 (d, J=5.6 Hz, 2H), 7.99 (t, J=5.6 Hz, 2H), 7.57 (s, 4H), 7.28 (dd, J=8.7, 8.3 Hz, 4H), 7.24-7.07 (m, 16H), 3.83-3.72 (m, 2H), 3.64-3.55 (m, 2H), 3.52-3.35 (m, 4H), 3.29-3.15 (m, 6H), 3.12 (q, J=7.8, 7.1 Hz, 2H), 2.72 (t, J=7.2 Hz, 4H), 2.64 (p, J=7.7 Hz, 4H), 1.99-1.91 (m, 2H), 1.28-1.04 (m, 2H). HRMS (ESI-TOF) m/z calcd for C$_{53}$H$_{57}$N$_6$O$_6$ [M+H]$^+$ 873.4334, found 873.4333.

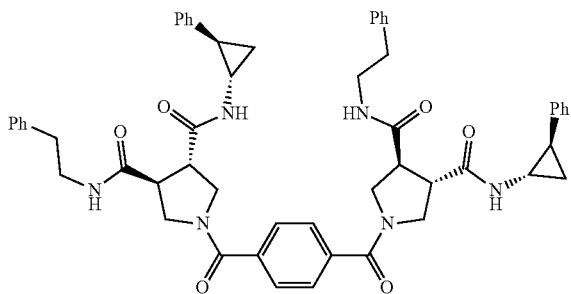 [SMILES: O=C(NCCc1ccccc1)[C@@H]1CN(C(=O)c2ccc(C(=O)N3C[C@@H](C(=O)NCCc4ccccc4)[C@H](C(=O)N[C@H]4C[C@@H]4c4ccccc4)C3)cc2)C[C@H]1C(=O)N[C@H]1C[C@@H]1c1ccccc1]

10: trans,trans-1, 1'-Terephthaloylbis($N^3$-phenethyl-$N^4$-(trans-2-phenylcyclopropyl)pyrrolidine-3,4-dicarboxamide)

trans-$N^3$-Phenethyl-$N^4$-(trans-2-phenylcyclopropyl)-pyrrolidine-3,4-dicarboxamide hydrochloride (S-4; 15.0 mg, 0.0362 mmol, 2.2 equiv), terephthalic acid (2.7 mg, 0.0165 mmol, 1.0 equiv), and i-Pr$_2$NEt (8.6 µL, 0.0494 mmol, 3.0 equiv) were dissolved in anhydrous DMF (200 µL) at room temperature. PyBrOP (15.4 mg, 0.0329 mmol, 2.0 equiv) was added in one portion, and the mixture was stirred for 18 hours. The mixture was diluted with EtOAc (5 mL) and washed with aqueous 1 N HCl (2 mL). The aqueous phase was extracted with EtOAc (2 mL), and the combined organic layers were washed with saturated aqueous NaHCO$_3$ (2 mL) and saturated aqueous NaCl (2 mL). The organic phase was dried over Na$_2$SO$_4$, filtered and concentrated to give 13.2 mg (92%) of 10. $^1$H NMR (600 MHz, DMSO-d$_6$) δ 8.47-8.24 (m, 1H), 8.24-8.12 (m, 1H), 8.01 (q, J=6.0, 5.2 Hz, 2H), 7.57 (s, 4H), 7.32-7.02 (m, 20H), 3.85-3.72 (m, 2H), 3.72-3.55 (m, 2H), 3.55-3.35 (m, 4H), 3.31-3.24 (m, 2H), 3.24-3.16 (m, 4H), 3.14-3.06 (m, 4H), 2.71 (t, J=7.7 Hz, 4H), 2.68-2.59 (m, 2H), 1.97-1.80 (m, 2H), 1.20-1.03 (m, 4H). HRMS (ESI-TOF) m/z calcd for C$_{54}$H$_{57}$N$_6$O$_6$ [M+H]$^+$ 885.4334, found 885.4335.

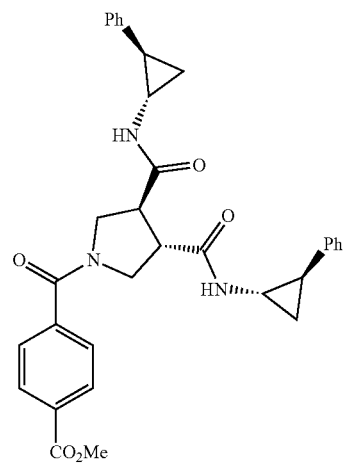 [SMILES: COC(=O)c1ccc(C(=O)N2C[C@@H](C(=O)N[C@H]3C[C@@H]3c3ccccc3)[C@H](C(=O)N[C@H]3C[C@@H]3c3ccccc3)C2)cc1]

S-9: Methyl 4-(trans-3,4-Bis((trans-2-phenylcyclopropyl)carbamoyl)pyrrolidine-1-carbonyl)benzoate trans-$N^3$,$N^4$-Bis(trans-2-phenylcyclopropyl)-pyrrolidine-3,4-dicarboxamide hydrochloride (S-6; 11.5 mg, 0.0270 mmol), monomethyl terephthalate (4.9 mg, 0.0270 mmol, 1.00 equiv) and i-Pr$_2$NEt (14 µL, 0.0810 mmol, 3.00 equiv) were dissolved in anhydrous DMF (0.15 mL) at room temperature. PyBrOP (12.6 mg, 0.0270 mmol, 1.00 equiv) was added, and the mixture was stirred for 18 hours. The mixture was diluted with EtOAc (5 mL) and washed with aqueous 1 N HCl (5 mL). The aqueous phase was extracted with EtOAc (5 mL), and the combined organic layers were washed with saturated aqueous NaHCO$_3$ (6 mL) and saturated aqueous NaCl (4 mL). The organic phase was dried over Na$_2$SO$_4$, filtered and concentrated. Flash column chromatography (SiO$_2$, 75% EtOAc/hexanes) produced 7.6 mg (51%) of S-9. $^1$H NMR (500 MHz, acetone-d$_6$) δ 8.08-8.03 (m, 2H), 7.70-7.62 (m, 3H), 7.56 (s, 1H), 7.25 (p, J=7.0 Hz, 5H), 7.20-7.09 (m, 5H), 3.95 (t, J=8.2 Hz, 1H), 3.91 (s, 3H), 3.79-3.61 (m, 3H), 3.33-3.20 (m, 2H), 2.98-2.90 (m, 1H), 2.88-2.84 (m, 1H), 1.98 (q, J=9.4 Hz, 1H), 1.25-1.10 (m, 4H).

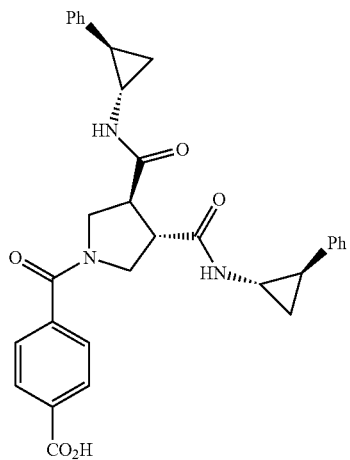 [SMILES: O=C(O)c1ccc(C(=O)N2C[C@@H](C(=O)N[C@H]3C[C@@H]3c3ccccc3)[C@H](C(=O)N[C@H]3C[C@@H]3c3ccccc3)C2)cc1]

S-10: 4-(trans-3,4-Bis((trans-2-phenylcyclopropyl)-carbamoyl)pyrrolidine-1-carbonyl)-benzoic Acid Methyl 4-(trans-3,4-Bis((trans-2-phenyl-cyclopropyl)carbamoyl)pyrrolidine-1-carbonyl)-benzoate (S-9; 7.6 mg, 0.0138 mmol) was dissolved in THF/MeOH/H$_2$O (100 μL, 20 μL, 20 μL, respectively) at room temperature. LiOH.H$_2$O (2.3 mg, 0.0551 mmol, 4.00 equiv) was added in one portion. After 1.5 hours, the mixture was diluted with EtOAc (5 mL) and washed with aqueous 2 N HCl (4 mL). The aqueous phase was extracted once with EtOAc (5 mL), and the combined organic layers were dried over Na$_2$SO$_4$, decanted and concentrated to afford 6.8 mg (92%) of S-10.

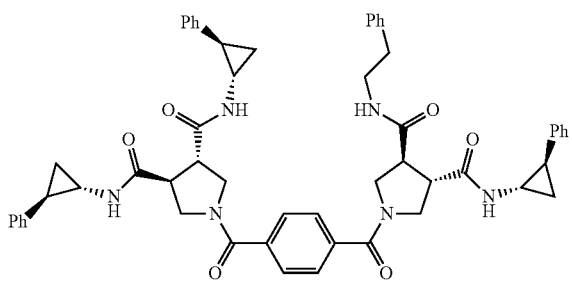 [SMILES: O=C(NCCc1ccccc1)[C@@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C[C@H]1C(=O)N[C@H]1C[C@@H]1c1ccccc1]

11: trans-1-(4-(trans-3,4-Bis((trans-2-phenylcyclopropyl)carbamoyl)pyrrolidine-1-carbonyl)benzoyl)-N$^3$-phenethyl-N$^4$-(trans-2-phenylcyclopropyl)pyrrolidine-3,4-dicarboxamide 4-(trans-3,4-Bis((trans-2-phenylcyclo-propyl)-carbamoyl)pyrrolidine-1-carbonyl)benzoic acid (S-10; 6.8 mg, 0.0126 mmol), trans-N$^3$-phenethyl-N$^4$-(trans-2-phenylcyclopropyl)-pyrrolidine-3,4-dicarboxamide hydrochloride (S-4; 5.2 mg, 0.0126 mmol, 1.00 equiv) and i-Pr$_2$NEt (5 μL, 0.0380 mmol, 3.00 equiv) were dissolved in anhydrous DMF (200 μL) at room temperature. PyBrOP (6.5 mg, 0.0139 mmol, 1.10 equiv) was added, and the reaction mixture was stirred for 16 hours. The mixture was diluted with EtOAc (5 mL) and washed with aqueous 1 N HCl (5 mL). The aqueous phase was extracted with EtOAc (4 mL), and the combined organic layers were washed with saturated aqueous NaHCO$_3$ (5 mL) and saturated aqueous NaCl (4 mL). The organic phase was dried over Na$_2$SO$_4$, filtered and concentrated to give 11 mg (97%) of 11. $^1$H NMR (600 MHz, DMSO-d$_6$) δ 8.45-8.40 (m, 2H), 8.30 (d, J=9.7 Hz, 2H), 7.62-7.52 (m, 4H), 7.33-7.00 (m, 20H), 3.86-3.72 (m, 2H), 3.72-3.58 (m, 2H), 3.59-3.42 (m, 4H), 3.24-3.14 (m, 2H), 3.10 (p, J=6.8 Hz, 2H), 2.92-2.81 (m, 2H), 2.80-2.75 (m, 2H), 2.75-2.59 (m, 2H), 2.00-1.89 (m, 2H), 1.86 (q, J=6.8, 5.7 Hz, 2H), 1.17 (ddd, J=17.1, 6.8, 5.8 Hz, 3H), 1.09 (q, J=6.7, 5.6 Hz, 3H). HRMS (ESI-TOF) m/z calcd for C$_{55}$H$_{57}$N$_6$O$_6$ [M+H]$^+$ 897.4334, found 897.4333.

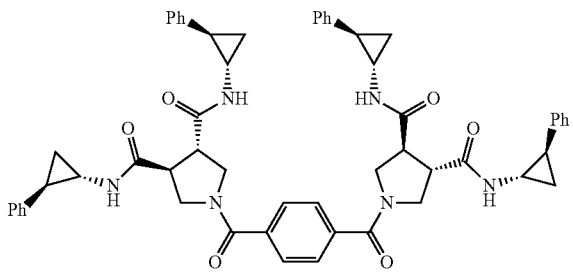 [SMILES: O=C(N[C@H]1C[C@@H]1c1ccccc1)[C@@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C[C@H]1C(=O)N[C@H]1C[C@@H]1c1ccccc1]

12: trans, trans-1,1'-Terephthaloylbis-(N$^3$,N$^4$-bis-(trans-2-phenylcyclopropyl)pyrrolidine-3,4-dicarboxamide)

trans-N$^3$,N$^4$-Bis(trans-2-phenylcyclopropyl)-pyrrolidine-3,4-dicarboxamide hydrochloride (S-6, 1.87 g, 4.40 mmol, 2.05 equiv) and terephthalic acid (benzene-1,4-dicarboxylic acid, 356 mg, 2.15 mmol, 1.00 equiv) were dissolved in anhydrous DMF (20 mL) at room temperature. i-Pr$_2$NEt (1.12 mL, 6.44 mmol, 3.00 equiv) was added, followed by PyBrOP (2.00, 4.29 mmol, 2.00 equiv) after 5 minutes. After 24 hours, the reaction mixture was diluted with EtOAc (400 mL) and washed with aqueous 0.5 N HCl (2×200 mL). The aqueous phase was extracted with EtOAc (1×100 mL). The combined organic phases were washed with saturated aqueous NaHCO$_3$ (100 mL) and saturated aqueous NaCl (75 mL). The organic phase was dried over Na$_2$SO$_4$, decanted and concentrated to reveal coupled product contaminated with a small amount (about 10%) of tri(pyrrolidin-1-yl) phosphine oxide. The contaminant was removed by trituration with cold (0° C.) 1:1 Et$_2$O/EtOAc (3×10 mL), decanting the liquid phase to provide 1.93 g (98%) of 12.

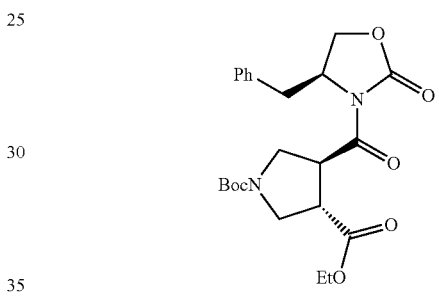

S-1: (3S,4S)-1-tert-Butyl 3-Ethyl 4-((S)-4-Benzyl-2-oxooxazolidine-3-carbonyl)pyrrolidine-1,3-dicarboxylate (3S,4S)-Ethyl 1-benzyl-4-((S)-4-benzyl-2-oxooxazolidine-3-carbonyl)pyrrolidine-3-carboxylate [prepared as a single stereoisomer according to: U.S. Pat. No. 6,489,354 B1] (3.43 g, 7.86 mmol) and Boc$_2$O (1.80 g, 8.25 mmol, 1.05 equiv) were dissolved in EtOH (50 mL) at room temperature. Pd(OH)$_2$/C (500 mg) was added and the reaction mixture was sparged with N$_2$ for 15 minutes. A 3-way flushing adapter, equipped with H$_2$ balloon and vacuum source, was attached. The headspace above the reaction mixture was evacuated until the solvent began to boil, then backfilled with H$_2$. This vacuum/fill process was repeated 10-15 times to maximize H$_2$ in the headspace. After 18 hours, the reaction mixture was filtered through a 6 cm Celite® plug, rinsing with EtOH aliquots (3×15 mL), and concentrated thoroughly. Flash column chromatography (SiO$_2$, 25% EtOAc/hexanes) provided 2.93 g (84%) S-1 as a clear, viscous oil. The identical procedure was employed with the (3R,4R)-diastereomer: pyrrolidine-3-carboxylate (3.06 g, 7.01 mmol), Boc$_2$O (1.60 g, 7.36 mmol), Pd(OH)$_2$/C (500 mg) and EtOH (50 mL) to afford 2.73 g (87%) of the N-Boc pyrrolidine, also as a clear, viscous oil. Data for the (3S,4S)-diastereomer: 1H NMR (400 MHz, CDCl$_3$) δ 7.40-7.19 (m, 5H), 4.69 (dd, J=9.0, 4.5 Hz, 1H), 4.52 (q, J=7.7 Hz, 1H), 4.29-4.14 (m, 4H), 3.95-3.75 (m, 2H), 3.60 (m, 2H), 3.52-3.27 (m, 2H), 2.86-2.71 (m, 1H), 1.46 (s, 9H), 1.28 (t, J=7.5 Hz, 3H). HRMS (ESI-TOF) m/z calcd for $C_{23}H_{31}N_2O_7$ [M+H]$^+$ 447.2126, found 447.2126. Data for the (3R,4R)-diastereomer: 1H NMR (400 MHz, CDCl$_3$) δ 7.39-7.28 (m, 3H), 7.19 (d, J=7.3 Hz, 2H), 4.72 (ddd, J=11.3, 6.7, 3.4 Hz, 1H), 4.33-4.20 (m, 2H), 4.17 (q, J=8.0, 7.6 Hz, 2H), 3.97 (d, J=9.6 Hz, 1H), 3.92-3.79 (m, 1H), 3.65 (d, J=9.8 Hz, 1H), 3.59-3.33 (m, 2H), 3.24 (d, J=13.0 Hz, 1H), 2.84 (dd, J=13.4, 9.2 Hz, 1H), 1.48 (s, 9H), 1.26 (td, J=7.1, 1.6 Hz, 3H).

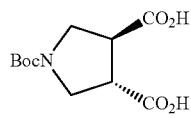

(S,S)-14 and (R,R)-14: (3S,4S)-1-(tert-Butoxycarbonyl) pyrrolidine-3,4-dicarboxylic Acid

[Modified procedure from: Ma et al., *Tetrahedron Asymm.* 1997, 8:883-887.]

3S,4S)-1-tert-Butyl 3-ethyl 4-((S)-4-benzyl-2-oxooxazolidine-3-carbonyl)pyrrolidine-1,3-dicarboxylate (2.06 g, 4.63 mmol) was dissolved in anhydrous THF (20 mL) and cooled to 0° C. Hydrogen peroxide (2.10 mL, ca. 18.5 mmol, 4.0 equiv, 30% w/v) was added dropwise to the stirred reaction solution. After 3-5 minutes, LiOH.H$_2$O (500 mg, 11.9 mmol) was added. After 2 hours, additional LiOH (470 mg, 11.2 mmol) was added, along with H$_2$O (10 mL) and THF (15 mL). The reaction mixture was stirred 3 hours, warming to room temperature. Saturated aqueous Na$_2$SO$_3$ (10 mL) was added, and the THF was removed under a N$_2$ stream. The resulting mixture was poured into H$_2$O (200 mL) and extracted with CH$_2$Cl$_2$ (2×100 mL) to remove the oxazolidinone. The aqueous phase was acidified with aqueous 1 N HCl to pH 2 (about 75 mL). The aqueous phase was extracted with EtOAc (3×125 mL), and the organic extracts were dried over Na$_2$SO$_4$, filtered and concentrated to provide 1.13 g (94%) of (S,S)-14 as a white solid. The identical procedure was employed with the (3R,4R)-diastereomer: pyrrolidine-3-carboxylate (1.88 g, 4.22 mmol), hydrogen peroxide (1.90 mL, 16.9 mmol), LiOH.H$_2$O (885 mg, 21.1 mmol) and THF (20 mL) to afford 927 mg (85%) of (3R,4R)-14 as a white solid. Data for (S,S)-14: $^1$H NMR (500 MHz, DMSO-d$_6$) δ 3.59-3.48 (m, 2H), 3.41-3.31 (m, 2H), 3.30-3.18 (m, 2H), 1.39 (s, 9H).

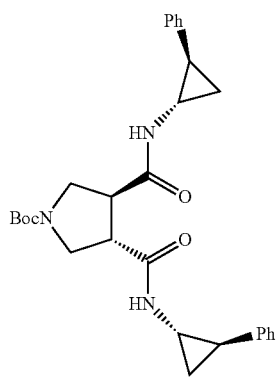 [SMILES: CC(C)(C)OC(=O)N1C[C@@H](C(=O)N[C@H]2C[C@@H]2c2ccccc2)[C@H](C(=O)N[C@H]2C[C@@H]2c2ccccc2)C1]

15: (3S,4S)-tert-Butyl 3,4-Bis-(((1S,2R)-2-phenyl-cyclopropyl)carbamoyl)pyrrolidine-1-carboxylate (3S,4S)-1-(tert-Butoxycarbonyl) pyrrolidine-3,4-dicarboxylic acid ((3S,4S)-14, 775 mg, 2.99 mmol), (1S,2R)-trans-2-phenylcyclopropylamine ((1S,2R)-13, 816 mg, 6.13 mmol, 2.05 equiv), and HOAt (895 mg, 6.58 mmol, 2.20 equiv) were dissolved in anhydrous DMF (15 mL) under N$_2$ atmosphere. 2,6-Lutidine (1.75 mL, 14.9 mmol, 5.00 equiv) was added slowly. Upon dissolution of the reagents (about 15 minutes), EDCI.HCl (1.43 g, 7.47 mmol, 2.50 equiv) was added in one portion, and the reaction mixture was stirred for 18 hours, after which it was poured into aqueous 1 N HCl (150 mL) and EtOAc (100 mL). The aqueous phase was extracted with EtOAc (2×75 mL), and the combined organic phases were washed with aqueous 1 N HCl (75 mL), saturated aqueous NaHCO$_3$ (75 mL), and saturated aqueous NaCl (50 mL), sequentially. The organic phase was dried over Na$_2$SO$_4$, filtered and concentrated. Flash column chromatography (SiO$_2$, 50% EtOAc/hexanes) gave 1.02 g (70%) of 15. $^1$H NMR (400 MHz, CDCl$_3$) δ 7.33-7.24 (m, 5H), 7.23-7.09 (m, 5H), 6.61 (s, 1H), 6.43 (s, 1H), 3.85 (t, J=9.7 Hz, 1H), 3.68 (m, 1H), 3.60 (t, J=10.5 Hz, 1H), 3.42 (t, J=10.4 Hz, 1H), 3.27 (q, J=10.0, 9.3 Hz, 1H), 3.12 (t, J=9.7 Hz, 1H), 2.88 (m, 2H), 2.05 (ddt, J=9.8, 6.4, 3.4 Hz, 2H), 1.46 (s, 9H), 1.24 (q, J=6.6 Hz, 2H), 1.13 (dt, J=10.1, 5.3 Hz, 2H). HRMS (ESI-TOF) m/z calcd for $C_{29}H_{36}N_3O_4$ [M+H]$^+$ 490.2700, found 490.2705.

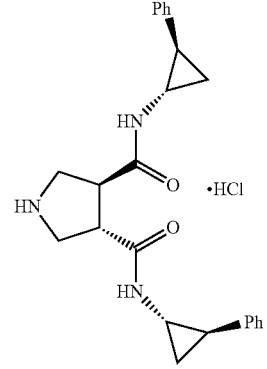 [SMILES: O=C(N[C@H]1C[C@@H]1c1ccccc1)[C@@H]1CNC[C@H]1C(=O)N[C@H]1C[C@@H]1c1ccccc1 ; Cl]

S-2: (3S,4S)—N$^3$,N$^4$-Bis(1S,2R)-2-phenylcyclopropyl)-pyrrolidine-3,4-dicarboxamide Hydrochloride (3S,4S)-tert-Butyl 3,4-bis(((1S,2R)-2-phenyl-cyclopropyl)carbamoyl)pyrrolidine-1-carboxylate (15, 998 mg, 2.04 mmol) was suspended in anhydrous THF (2 mL) at room temperature. 4 N HCl (8 mL, 4.0 M solution in dioxane) was added dropwise to the vigorously stirred reaction solution. After stirring 3 hours at room temperature, during which some product had precipitated from the reaction mixture, the solvents were removed by N$_2$ stream over 16 hours. The residual solids were suspended in anhydrous THF and reconcentrated in vacuo (3×5 mL) to ensure complete removal of the dioxane. This process was repeated with anhydrous Et$_2$O (3×5 mL) to reveal 870 mg (99%) of S-2 as an amorphous white solid. $^1$H NMR (500 MHz, DMSO-d$_6$) δ 9.35 (s, 2H), 8.76 (d, J=4.4 Hz, 2H), 7.26 (t, J=7.6 Hz, 4H), 7.20-7.06 (m, 6H), 3.76-3.62 (m, 1H), 3.55-3.42 (m, 1H), 3.26 (t, J=8.2 Hz, 2H), 3.21-3.11 (m, 2H), 2.90-2.78 (m, 2H), 1.99 (ddd, J=9.6, 6.3, 3.4 Hz, 2H), 1.26-1.13 (m, 4H). HRMS (ESI-TOF) m/z calcd for $C_{24}H_{28}N_3O_2$ $[M+H]^+$ 390.2176, found 390.2178.

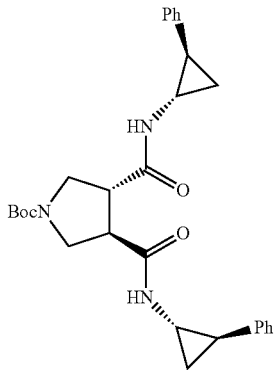 [SMILES: CC(C)(C)OC(=O)N1C[C@H](C(=O)N[C@H]2C[C@@H]2c2ccccc2)[C@@H](C(=O)N[C@H]2C[C@@H]2c2ccccc2)C1]

16: (3R,4R)-tert-Butyl 3,4-Bis(((1S,2R)-2-phenyl-cyclopropyl)carbamoyl)pyrrolidine-1-carboxylate The general procedure for the coupling of amines with pyrrolidine diacids was followed: (3R,4R)-1-(tert-butoxycarbonyl)pyrrolidine-3,4-dicarboxylic acid ((R,R)-14, 40 mg, 0.154 mmol), (1S,2R)-trans-2-phenylcyclopropylamine ((1S,2R)-13, 42 mg, 0.316 mmol), 2,6-lutidine (90 μL, 0.771 mmol), EDCI.HCl (74 mg, 0.386 mmol), HOAt (46 mg, 0.340 mmol) and DMF (0.75 mL) were employed. Flash column chromatography (SiO$_2$, 50% EtOAc/hexanes) provided 56 mg (75) of 16. $^1$H NMR (400 MHz, CDCl$_3$) δ 7.33-7.22 (m, 4H), 7.18 (t, J=7.3 Hz, 2H), 7.10 (m, 4H), 6.64 (s, 1H), 6.43 (s, 1H), 3.84 (m, 1H), 3.68 (m, 1H), 3.62 (m, 1H), 3.43 (m, 1H), 3.26 (dd, J=9.7 Hz, 1H), 3.08 (dd, J=10.0 Hz, 1H), 2.91 (dq, J=7.6, 3.8 Hz, 2H), 2.01 (ddd, J=9.7, 6.3, 3.4 Hz, 2H), 1.46 (s, 9H), 1.26 (ddd, J=9.4, 7.3, 5.0 Hz, 3H), 1.16 (ddd, J=10.1, 5.9, 4.5 Hz, 2H).

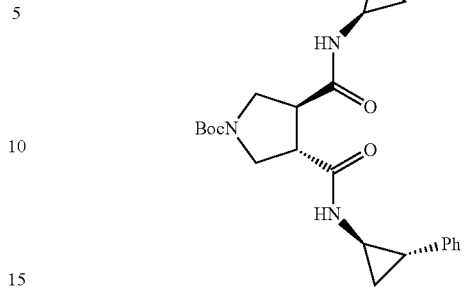

17: (3S,4S)-tert-Butyl 3,4-Bis(((1R,2S)-2-phenyl-cyclopropyl)carbamoyl)pyrrolidine-1-carboxylate The general procedure for the coupling of amines with pyrrolidine diacids was followed: (3S,4S)-1-(tert-butoxycarbonyl)pyrrolidine-3,4-dicarboxylic acid ((S,S)-14, 40 mg, 0.154 mmol), (1R,2S)-trans-2-phenylcyclopropylamine ((1R,2S)-13, 42 mg, 0.316 mmol), 2,6-lutidine (90 μL, 0.771 mmol), EDCI.HCl (74 mg, 0.386 mmol), HOAt (46 mg, 0.340 mmol) and DMF (0.75 mL) were employed. Flash column chromatography (SiO$_2$, 50% EtOAc/hexanes) provided 44 mg (58%) of 17. $^1$H NMR (500 MHz, CDCl$_3$) δ 7.31-7.22 (m, 4H), 7.22-7.16 (m, 2H), 7.11 (m, 4H), 6.68 (s, 1H), 6.49 (s, 1H), 3.85 (t, J=9.7 Hz, 1H), 3.68 (t, J=9.7 Hz, 1H), 3.61 (t, J=10.5 Hz, 1H), 3.43 (t, J=10.4 Hz, 1H), 3.26 (q, J=9.9 Hz, 1H), 3.08 (q, J=9.8 Hz, 1H), 2.96-2.86 (m, 2H), 2.01 (ddd, J=9.7, 6.3, 3.4 Hz, 2H), 1.46 (s, 9H), 1.30-1.21 (m, 2H), 1.15 (ddd, J=9.6, 6.0, 4.5 Hz, 2H).

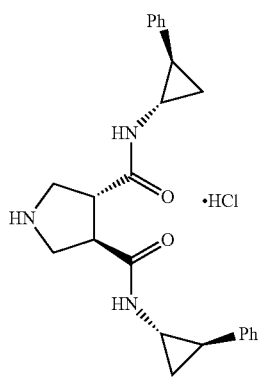 [SMILES: O=C(N[C@H]1C[C@@H]1c1ccccc1)[C@H]1CNC[C@@H]1C(=O)N[C@H]1C[C@@H]1c1ccccc1 ; Cl]

S-12: (3R,4R)—N$^3$,N$^4$-Bis((1S,2R)-2-phenylcyclopropyl)-pyrrolidine-3,4-dicarboxamide Hydrochloride The general procedure for the Boc-pyrrolidine deprotection was employed: N-Boc pyrrolidine 16 (45 mg, 0.0919 mmol), anhydrous THF (1 mL), and 4 N HCl in dioxane (2 mL) were employed. Reconcentration from Et$_2$O (3×3 mL) gave 39 mg (99%) of S-12.

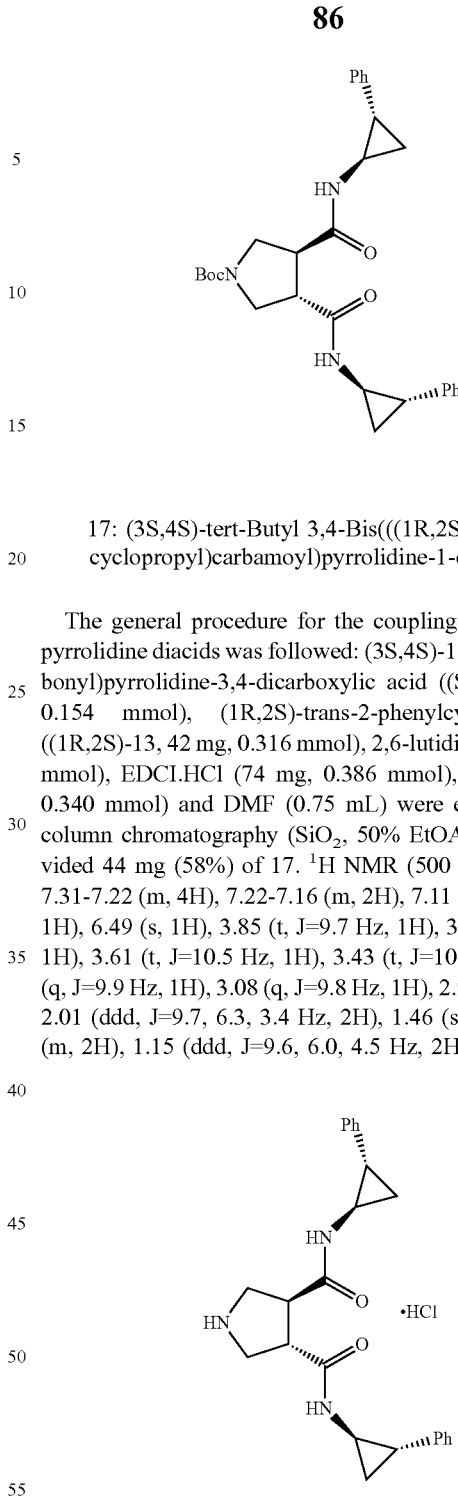

S-13: (3S,4S)—N$^3$,N$^4$-Bis((1R,2S)-2-phenyl-cyclopropyl)-pyrrolidine-3,4-dicarboxamide Hydrochloride The general procedure for the Boc-pyrrolidine deprotection was employed: N-Boc pyrrolidine 17 (44 mg, 0.0899 mmol), anhydrous THF (1 mL), and 4 N HCl in dioxane (3 mL) were employed. Concentration from Et$_2$O (5×3 mL) gave 38 mg (99%) of S-13.

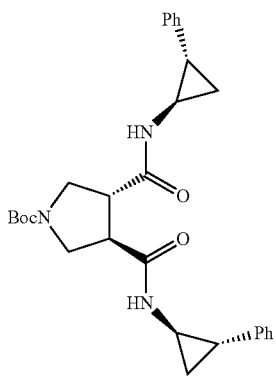 [SMILES: CC(C)(C)OC(=O)N1C[C@H](C(=O)N[C@@H]2C[C@H]2c2ccccc2)[C@@H](C(=O)N[C@@H]2C[C@H]2c2ccccc2)C1]

18: (3R,4R)-tert-Butyl 3,4-Bis(((1R,2S)-2-phenyl-cyclopropyl)carbamoyl)pyrrolidine-1-carboxylate The general procedure for the coupling of amines with pyrrolidine diacids was followed: (3R,4R)-1-(tert-butoxy-carbonyl)pyrrolidine-3,4-dicarboxylic acid ((R,R)-14, 40 mg, 0.154 mmol), (1R,2S)-trans-2-phenylcyclopropylamine ((1R,2S)-13, 42 mg, 0.316 mmol), 2,6-lutidine (90 µL, 0.771 mmol), EDCI.HCl (74 mg, 0.386 mmol), HOAt (46 mg, 0.340 mmol) and DMF (0.75 mL) were employed. Flash column chromatography (SiO$_2$, 50% EtOAc/hexanes) provided 46 mg (60%) of 18. $^1$H NMR (500 MHz, CDCl$_3$) δ 7.27 (m, 4H), 7.23-7.17 (m, 2H), 7.14 (m, 4H), 6.54 (s, 1H), 6.30 (s, 1H), 3.85 (t, J=9.8 Hz, 1H), 3.68 (t, J=9.7 Hz, 1H), 3.60 (t, J=10.3 Hz, 1H), 3.43 (t, J=10.4 Hz, 1H), 3.26 (q, J=10.6 Hz, 1H), 3.11 (q, J=10.3 Hz, 1H), 2.89 (m, 2H), 2.05 (ddt, J=9.4, 6.4, 3.3 Hz, 2H), 1.46 (s, 9H), 1.31-1.21 (m, 2H), 1.14 (dt, J=10.1, 5.5 Hz, 2H).

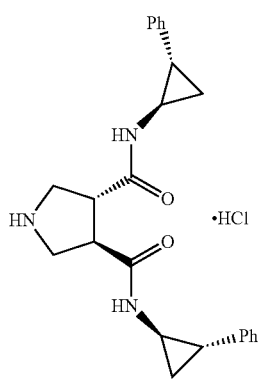 [SMILES: O=C(N[C@@H]1C[C@H]1c1ccccc1)[C@H]1CNC[C@@H]1C(=O)N[C@@H]1C[C@H]1c1ccccc1 ; Cl]

S-14: (3R,4R)—N$^3$,N$^4$-Bis((1R,2S)-2-phenylcyclo-propyl)-pyrrolidine-3,4-dicarboxamide Hydrochloride The general procedure for Boc-pyrrolidine deprotection was employed: N-Boc pyrrolidine 18 (46 mg, 0.0940 mmol), anhydrous THF (1 mL), and 4 N HCl in dioxane (3 mL) were employed. Concentration from Et$_2$O (5×3 mL) gave 40 mg (99%) of S-14.

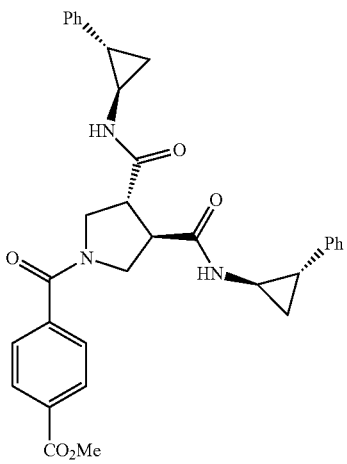 [SMILES: COC(=O)c1ccc(C(=O)N2C[C@H](C(=O)N[C@@H]3C[C@H]3c3ccccc3)[C@@H](C(=O)N[C@@H]3C[C@H]3c3ccccc3)C2)cc1]

S-15: Methyl 4-((3R,4R)-3,4-Bis(((1R,2S)-2-phe-nyl-cyclopropyl)carbamoyl)pyrrolidine-1-carbonyl)-benzoate Pyrrolidine-3,4-dicarboxamide hydrochloride S-14 (11.3 mg, 0.0265 mmol) and monomethyl terephthalate (4.8 mg, 0.0265 mmol) were dissolved in anhydrous DMF (150 µL) at room temperature. i-Pr$_2$NEt (14 µL, 0.0796 mmol) and PyBrOP (12.4 mg, 0.0265 mmol) were added, and the mixture was stirred for 18 hours. The reaction mixture was diluted with EtOAc (20 mL) and washed with aqueous 0.5 N HCl (2×10 mL). The aqueous phase was extracted with EtOAc (1×5 mL). The combined organic phases were washed with saturated aqueous NaHCO$_3$ (10 mL) and saturated aqueous NaCl (5 mL). The organic phase was dried over Na$_2$SO$_4$, decanted and concentrated. Flash column chromatography (SiO$_2$, 75% EtOAc/hexanes) afforded 8.9 mg (61%) of S-15 as a white solid. $^1$H NMR (500 MHz, CDCl$_3$) δ 8.07 (d, J=8.3 Hz, 2H), 7.58 (d, J=8.3 Hz, 2H), 7.32-7.14 (m, 6H), 7.10-7.08 (m, 4H), 6.96 (d, J=3.4 Hz, 1H), 6.86 (d, J=3.4 Hz, 1H), 4.19 (dd, J=12.2, 8.8 Hz, 1H), 3.94 (s, 3H), 3.87 (t, J=10.5 Hz, 1H), 3.75-3.66 (m, 2H), 3.35 (q, J=10.5 Hz, 1H), 3.22 (q, J=9.8 Hz, 1H), 2.92-2.88 (m, 1H), 2.84-2.80 (m, 1H), 2.06-2.00 (m, 1H), 1.97 (ddd, J=9.2, 6.0, 3.3 Hz, 1H), 1.26-1.02 (m, 4H).

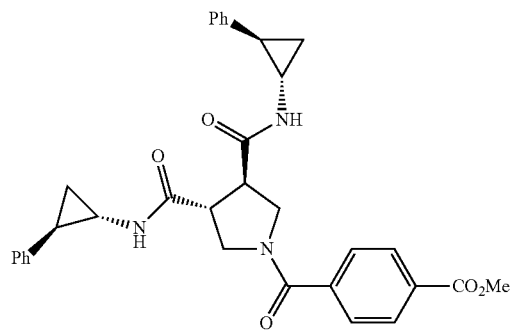 [SMILES: COC(=O)c1ccc(C(=O)N2C[C@H](C(=O)N[C@H]3C[C@@H]3c3ccccc3)[C@@H](C(=O)N[C@H]3C[C@@H]3c3ccccc3)C2)cc1]

S-16: Methyl 4-((3R,4R)-3,4-Bis(((1S,2R)-2-phe-nyl-cyclopropyl)carbamoyl)pyrrolidine-1-carbonyl)-benzoate Pyrrolidine-3,4-dicarboxamide hydrochloride S-12 (3.0 mg, 0.00704 mmol) and monomethyl terephthalate (1.3 mg, 0.00704 mmol) were dissolved in anhydrous DMF (100 µL) at room temperature. i-Pr₂NEt (4 µL, 0.0211 mmol) and PyBrOP (3.3 mg, 0.00704 mmol) were added, and the mixture was stirred for 18 hours. The reaction mixture was diluted with EtOAc (10 mL) and washed with aqueous 0.5 N HCl (2×5 mL). The aqueous phase was extracted with EtOAc (1×2 mL). The combined organic phases were washed with saturated aqueous NaHCO₃ (5 mL) and saturated aqueous NaCl (2 mL). The organic phase was dried over Na₂SO₄, decanted and concentrated. Flash column chromatography (SiO₂, 75% EtOAc/hexanes) afforded 2.3 mg (59%) of S-16 as a white solid. ¹H NMR (400 MHz, CDCl₃) δ 8.08 (d, J=8.0 Hz, 2H), 7.59 (d, J=8.1 Hz, 2H), 7.29-7.15 (m, 6H), 7.13-7.04 (m, 4H), 6.81 (s, 1H), 6.55 (s, 1H), 4.18 (dd, J=15.5, 11.0 Hz, 1H), 3.95 (s, 3H), 3.87 (t, J=10.4 Hz, 1H), 3.81-3.65 (m, 2H), 3.32 (q, J=9.4 Hz, 1H), 3.19 (q, J=9.8 Hz, 1H), 2.98-2.92 (m, 1H), 2.91-2.84 (m, 1H), 2.05-1.94 (m, 2H), 1.25-1.04 (m, 4H).

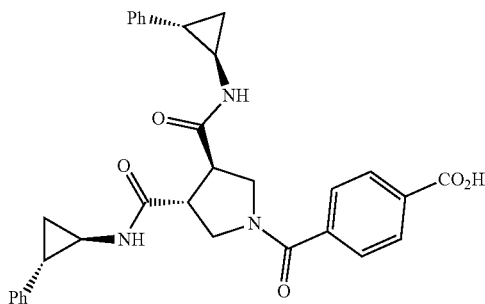 [SMILES: O=C(O)c1ccc(C(=O)N2C[C@H](C(=O)N[C@@H]3C[C@H]3c3ccccc3)[C@@H](C(=O)N[C@@H]3C[C@H]3c3ccccc3)C2)cc1]

S-17: 4-((3R,4R)-3,4-Bis(((1R,2S)-2-phenylcyclopropyl)carbamoyl)pyrrolidine-1-carbonyl)benzoic Acid Methyl benzoate S-15 (8.9 mg, 0.0161 mmol) was dissolved in THF/MeOH/H₂O (80 µL, 20 µL, 20 µL, respectively). LiOH.H₂O (2.7 mg, 0.0645 mmol) was added with vigorous stirring. After 3 hours, the solution was acidified to pH 2 with aqueous 1 N HCl (0.1-0.2 mL) and diluted with H₂O (5 mL). The aqueous phase was extracted with EtOAc (4×4 mL). The organic phase was dried over Na₂SO₄ and concentrated to provide 6.6 mg (77%) of S-17.

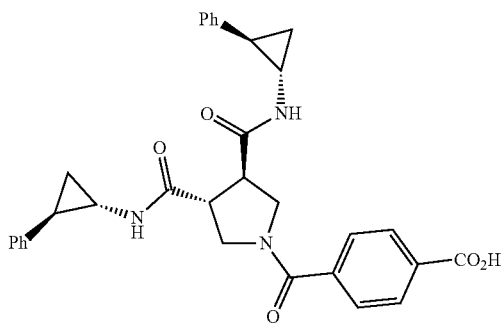 [SMILES: O=C(O)c1ccc(C(=O)N2C[C@H](C(=O)N[C@H]3C[C@@H]3c3ccccc3)[C@@H](C(=O)N[C@H]3C[C@@H]3c3ccccc3)C2)cc1]

S-18: 4-((3R,4R)-3,4-Bis(((1S,2R)-2-phenylcyclopropyl) carbamoyl)pyrrolidine-1-carbonyl)benzoic Acid Methyl benzoate S-16 (2.3 mg, 0.00417 mmol) was dissolved in THF/MeOH/H₂O (80 µL, 20 µL, 20 µL, respectively). LiOH.H₂O (1.0 mg, 0.0208 mmol) was added with vigorous stirring. After 3 hours, the solution was acidified to pH 2 with aqueous 1 N HCl (0.1-0.2 mL) and diluted with H₂O (5 mL). The aqueous phase as extracted with EtOAc (4×4 mL). The organic phase was dried over Na₂SO₄ and concentrated to provide 2.0 mg (91%) of S-18.

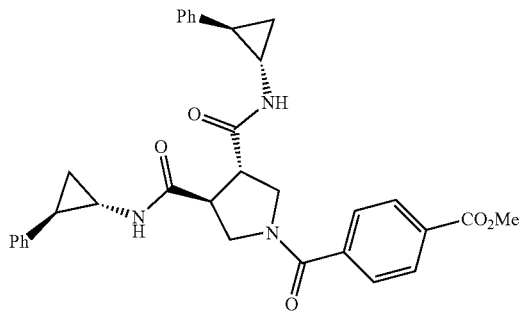 [SMILES: COC(=O)c1ccc(C(=O)N2C[C@@H](C(=O)N[C@H]3C[C@@H]3c3ccccc3)[C@H](C(=O)N[C@H]3C[C@@H]3c3ccccc3)C2)cc1]

S-19: Methyl 4-((3S,4S)-3,4-Bis(((1S,2R)-2-phenylcyclopropyl)carbamoyl)pyrrolidine-1-carbonyl)-benzoate Pyrrolidine-3,4-dicarboxamide hydrochloride S-2 (100 mg, 0.235 mmol) and monomethyl terephthalate (42 mg, 0.235 mmol) were dissolved in anhydrous DMF (1.2 mL) at room temperature. i-Pr₂NEt (125 µL, 0.704 mmol) and PyBrOP (109 mg, 0.235 mmol) were added, and the mixture was stirred for 18 hours. The reaction mixture was diluted with EtOAc (50 mL) and washed with aqueous 0.5 N HCl (2×50 mL). The aqueous phase was extracted with EtOAc (1×25 mL). The combined organic phases were washed with saturated aqueous NaHCO₃ (25 mL) and saturated aqueous NaCl (20 mL). The organic phase was dried over Na₂SO₄, decanted and concentrated. Flash column chromatography (SiO₂, 75% EtOAc/hexanes) afforded 100 mg (77%) of S-19 as a white solid. ¹H NMR (500 MHz, CDCl₃) δ 8.07 (d, J=8.3 Hz, 2H), 7.58 (d, J=8.3 Hz, 2H), 7.31-7.14 (m, 6H), 7.15-7.06 (m, 4H), 6.96 (d, J=3.6 Hz, 1H), 6.86 (d, J=3.7 Hz, 1H), 4.19 (dd, J=12.2, 8.8 Hz, 1H), 3.94 (s, 3H), 3.87 (t, J=10.4 Hz, 1H), 3.75-3.67 (m, 2H), 3.34 (q, J=9.9 Hz, 1H), 3.28-3.16 (m, 1H), 2.90 (dt, J=7.6, 3.8 Hz, 1H), 2.83 (dt, J=7.4, 3.8 Hz, 1H), 2.03 (dq, J=6.4, 3.4, 3.0 Hz, 1H), 1.97 (ddd, J=9.8, 6.4, 3.4 Hz, 1H), 1.25-1.03 (m, 4H). HRMS (ESI-TOF) m/z calcd for $C_{33}H_{34}N_3O_5$ [M+H]⁺ 552.2493, found 552.2497.

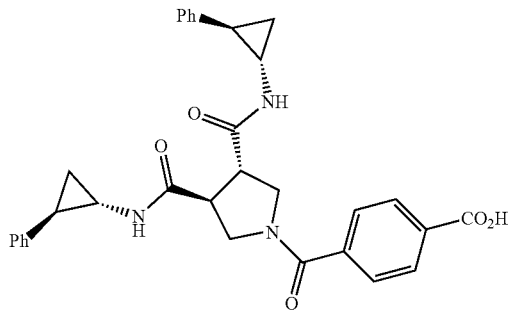 [SMILES: O=C(O)c1ccc(C(=O)N2C[C@@H](C(=O)N[C@H]3C[C@@H]3c3ccccc3)[C@H](C(=O)N[C@H]3C[C@@H]3c3ccccc3)C2)cc1]

S-20: 4-((3S,4S)-3,4-Bis(((1S,2R)-2-phenylcyclopropyl)carbamoyl)pyrrolidine-1-carbonyl)benzoic acid Methyl benzoate S-19 (89 mg, 0.161 mmol) was dissolved in THF/MeOH/H$_2$O (0.8 mL, 0.2 mL, 0.2 mL, respectively). LiOH.H$_2$O (27 mg, 0.645 mmol) was added with vigorous stirring. After 3 hours, the solution was acidified to pH 2 with aqueous 1 N HCl (1-2 mL) and diluted with H$_2$O (20 mL). The aqueous phase as extracted with EtOAc (4×25 mL). The organic phase was dried over Na$_2$SO$_4$ and concentrated to provide 81.7 mg (94%) of S-20. $^1$H NMR (500 MHz, DMSO-d$_6$) δ 8.41 (d, J=4.3 Hz, 1H), 8.26 (d, J=4.3 Hz, 1H), 7.98 (d, J=8.2 Hz, 2H), 7.61 (d, J=8.3 Hz, 2H), 7.25 (dt, J=14.3, 7.4 Hz, 4H), 7.19-7.04 (m, 6H), 3.81 (dd, J=12.0, 8.6 Hz, 1H), 3.62 (dd, J=10.4, 7.8 Hz, 1H), 3.52 (dd, J=12.0, 8.1 Hz, 1H), 3.46 (t, J=9.4 Hz, 1H), 3.19 (q, J=8.3 Hz, 1H), 3.10 (q, J=8.1 Hz, 1H), 2.84 (dq, J=8.3, 4.3 Hz, 1H), 2.77 (dq, J=8.2, 4.3 Hz, 1H), 2.00-1.94 (m, 1H), 1.85 (ddd, J=9.5, 6.4, 3.4 Hz, 1H), 1.21-1.06 (m, 4H). HRMS (ESI-TOF) m/z calcd for C$_{32}$H$_{32}$N$_3$O$_5$ [M+H]$^+$ 538.2336, found 538.2339.

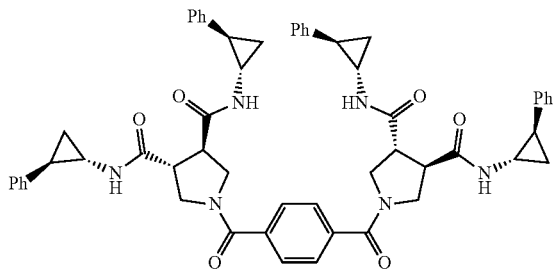 [SMILES: O=C(N[C@H]1C[C@@H]1c1ccccc1)[C@H]1CN(C(=O)c2ccc(C(=O)N3C[C@H](C(=O)N[C@H]4C[C@@H]4c4ccccc4)[C@@H](C(=O)N[C@H]4C[C@@H]4c4ccccc4)C3)cc2)C[C@@H]1C(=O)N[C@H]1C[C@@H]1c1ccccc1]

19: (3R,3'R,4R,4'R)-1,1'-Terephthaloylbis(N$^3$,N$^4$-bis((1S,2R)-2-phenylcyclopropyl)pyrrolidine-3,4-dicarboxamide)

The general procedure for linking diacid coupling was employed: Pyrrolidine-3,4-dicarboxamide hydrochloride S-12 (22.2 mg, 0.0521 mmol), terephthalic acid (benzene-1,4-dicarboxylic acid, 3.9 mg, 0.0236 mmol), i-Pr$_2$NEt (15 μL, 0.0711 mmol), PyBrOP (22.0 mg, 0.0474 mmol) and anhydrous DMF (150 L) were employed. After trituration with cold (0° C.) 1:1 Et$_2$O/EtOAc, 17.0 mg (79%) of 19 was obtained. 1H NMR (500 MHz, DMSO-d$_6$) δ 8.62 (d, J=4.5 Hz, 2H), 8.48 (d, J=4.5 Hz, 2H), 7.56 (s, 4H), 7.24 (q, J=7.6 Hz, 8H), 7.14 (q, J=6.8 Hz, 4H), 7.08 (dd, J=14.6, 7.3 Hz, 8H), 3.77 (dd, J=12.0, 8.4 Hz, 2H), 3.65 (t, J=9.0 Hz, 2H), 3.58-3.47 (m, 4H), 3.20 (q, J=8.0 Hz, 2H), 3.10 (q, J=7.7 Hz, 2H), 2.87 (td, J=8.1, 7.0, 3.3 Hz, 2H), 2.79 (dd, J=8.0, 4.0 Hz, 2H), 1.94 (ddd, J=9.7, 6.3, 3.5 Hz, 2H), 1.89 (ddd, J=9.4, 7.9, 3.7 Hz, 2H), 1.15-1.06 (m, 8H). HRMS (ESI-TOF) m/z calcd for C$_{56}$H$_{57}$N$_6$O$_6$ [M+H]$^+$ 909.4334, found 909.4334.

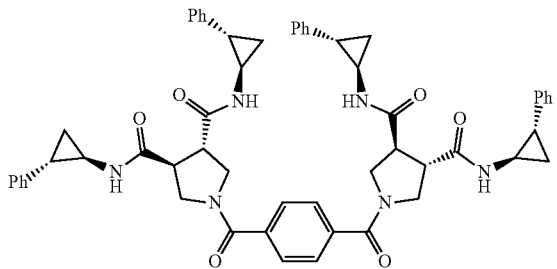 [SMILES: O=C(N[C@@H]1C[C@H]1c1ccccc1)[C@@H]1CN(C(=O)c2ccc(C(=O)N3C[C@@H](C(=O)N[C@@H]4C[C@H]4c4ccccc4)[C@H](C(=O)N[C@@H]4C[C@H]4c4ccccc4)C3)cc2)C[C@H]1C(=O)N[C@@H]1C[C@H]1c1ccccc1]

20: (3S,3'S,4S,4'S)-1,1'-Terephthaloylbis-(N$^3$,N$^4$-bis((1R,2S)-2-phenylcyclopropyl)pyrrolidine-3,4-dicarboxamide)

The general procedure for linking diacid coupling was employed: Pyrrolidine-3,4-dicarboxamide hydrochloride S-13 (22.0 mg, 0.0516 mmol), terephthalic acid (benzene-1,4-dicarboxylic acid, 3.9 mg, 0.0236 mmol), i-Pr$_2$NEt (15 μL, 0.0711 mmol), PyBrOP (22.0 mg, 0.0474 mmol) and anhydrous DMF (150 L) were employed. After trituration with cold (0° C.) 1:1 Et$_2$O/EtOAc, 13.7 mg (64%) of 20 was obtained. 1H NMR (500 MHz, DMSO-d$_6$) δ 8.45 (d, J=4.4 Hz, 2H), 8.32 (d, J=4.6 Hz, 2H), 7.57 (s, 4H), 7.24 (q, J=7.6 Hz, 8H), 7.17-7.04 (m, 12H), 3.85-3.77 (m, 2H), 3.72-3.63 (m, 2H), 3.58-3.45 (m, 4H), 3.17 (dd, J=8.7, 6.5 Hz, 2H), 3.09 (q, J=8.2 Hz, 2H), 2.87 (dt, J=7.8, 5.1 Hz, 2H), 2.78 (d, J=5.8 Hz, 2H), 1.94-1.89 (m, 2H), 1.87 (dt, J=10.5, 6.1 Hz, 2H), 1.21-1.06 (m, 8H). HRMS (ESI-TOF) m/z calcd for C$_{56}$H$_{57}$N$_6$O$_6$ [M+H]$^+$ 909.4334, found 909.4340.

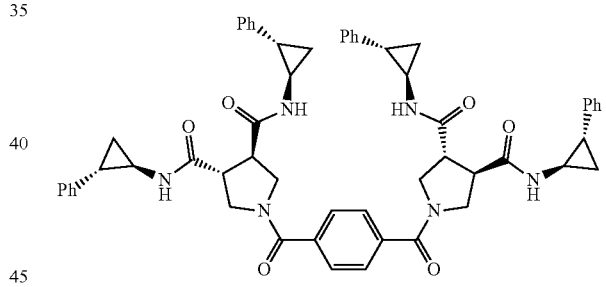

21: (3R,3'R,4R,4'R)-1,1'-Terephthaloylbis-(N$^3$,N$^4$-bis((1R,2S)-2-phenylcyclopropyl)pyrrolidine-3,4-dicarboxamide)

The general procedure for linking diacid coupling was employed: Pyrrolidine-3,4-dicarboxamide hydrochloride S-14 (22.0 mg, 0.0516 mmol), terephthalic acid (benzene-1,4-dicarboxylic acid, 3.9 mg, 0.0236 mmol), i-Pr$_2$NEt (15 μL, 0.0711 mmol), PyBrOP (22.0 mg, 0.0474 mmol) and anhydrous DMF (150 L) were employed. After trituration with cold (0° C.) 1:1 Et$_2$O/EtOAc, 19.9 mg (93%) of 21 was obtained. 1H NMR (500 MHz, DMSO-d$_6$) δ 8.43 (d, J=4.3 Hz, 2H), 8.30 (d, J=4.3 Hz, 2H), 7.56 (s, 4H), 7.24 (dt, J=16.2, 7.6 Hz, 8H), 7.19-7.09 (m, 8H), 7.08-7.04 (m, 4H), 3.80 (dd, J=12.0, 8.5 Hz, 2H), 3.65 (dd, J=10.4, 7.8 Hz, 2H), 3.56-3.46 (m, 4H), 3.24-3.15 (m, 2H), 3.11 (q, J=7.9 Hz, 2H), 2.84 (dd, J=7.8, 3.9 Hz, 2H), 2.77 (dd, J=7.4, 4.0 Hz, 2H), 1.97 (ddd, J=9.6, 6.4, 3.4 Hz, 2H), 1.86 (ddd, J=9.5, 6.8, 3.4 Hz, 2H), 1.22-1.06 (m, 8H). HRMS (ESI-TOF) m/z calcd for C$_{56}$H$_{57}$N$_6$O$_6$ [M+H]$^+$ 909.4334, found 909.4325.

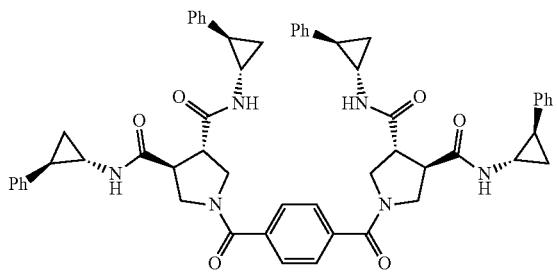 [SMILES: O=C(N[C@H]1C[C@@H]1c1ccccc1)[C@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C[C@@H]1C(=O)N[C@H]1C[C@@H]1c1ccccc1]

22: (3S,4S)-1-(4-((3R,4R)-3,4-Bis(((1S,2R)-2-phenylcyclopropyl)carbamoyl)pyrrolidine-1-carbonyl)benzoyl)—N³,N⁴-bis((1S,2R)-2-phenylcyclopropyl)-pyrrolidine-3,4-dicarboxamide

The general procedure for linking diacid coupling was employed, with equivalents scaled for single acid coupling: Pyrrolidine-3,4-dicarboxamide hydrochloride S-12 (6.9 mg, 0.0162 mmol), benzoic acid S-20 (8.7 mg, 0.0162 mmol), i-Pr₂NEt (8 µL, 0.0485 mmol), PyBrOP (8.0 mg, 0.0170 mmol) and anhydrous DMF (150 µL) were employed. After trituration with cold (0° C.) 1:1 Et₂O/EtOAc, 5.3 mg (36%) of 22 was obtained. ¹H NMR (500 MHz, DMSO-d₆) δ 8.42 (dd, J=12.1, 4.3 Hz, 2H), 8.28 (t, J=5.6 Hz, 2H), 7.56 (s, 4H), 7.29-7.19 (m, 8H), 7.17-7.05 (m, 12H), 3.84-3.78 (m, 2H), 3.66 (q, J=8.9 Hz, 2H), 3.55-3.47 (m, 4H), 3.22-3.14 (m, 2H), 3.09 (q, J=8.2 Hz, 2H), 2.89-2.82 (m, 2H), 2.80-2.76 (m, 2H), 2.00-1.94 (m, 2H), 1.88-1.85 (m, 2H), 1.20-1.04 (m, 8H). HRMS (ESI-TOF) m/z calcd for $C_{56}H_{57}N_6O_6$ [M+H]⁺ 909.4334, found 909.4326.

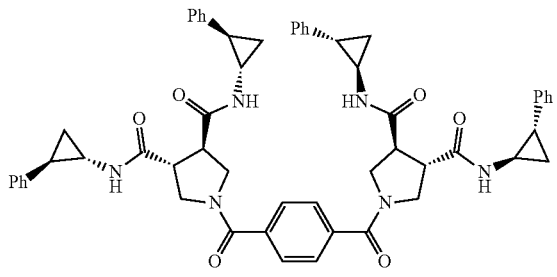 [SMILES: O=C(N[C@H]1C[C@@H]1c1ccccc1)[C@H]1CN(C(=O)c2ccc(C(=O)N3C[C@@H](C(=O)N[C@@H]4C[C@H]4c4ccccc4)[C@H](C(=O)N[C@@H]4C[C@H]4c4ccccc4)C3)cc2)C[C@@H]1C(=O)N[C@H]1C[C@@H]1c1ccccc1]

23: (3R,4R)-1-(4-((3S,4S)-3,4-Bis(((1R,2S)-2-phenyl-cyclopropyl)carbamoyl)-pyrrolidine-1-carbonyl)-benzoyl)—N³,N⁴-bis((1S,2R)-2-phenylcyclopropyl)-pyrrolidine-3,4-dicarboxamide

The general procedure for linking diacid coupling was employed, with equivalents scaled for single acid coupling: Pyrrolidine-3,4-dicarboxamide hydrochloride S-13 (1.6 mg, 0.00372 mmol), benzoic acid S-18 (2.0 mg, 0.00372 mmol), i-Pr₂NEt (2 µL, 0.0112 mmol), PyBrOP (1.8 mg, 0.00390 mmol) and anhydrous DMF (50 µL) were employed. After trituration with cold (0° C.) 1:1 Et₂O/EtOAc, 3.4 mg (99) of 23 was obtained. 1H NMR (500 MHz, DMSO-d₆) δ 8.44 (d, J=4.4 Hz, 2H), 8.29 (d, J=5.4 Hz, 2H), 7.57 (s, 4H), 7.27-7.22 (m, 8H), 7.17-7.14 (m, 4H), 7.11-7.05 (m, 8H), 3.85-3.76 (m, 2H), 3.69-3.63 (m, 2H), 3.55-3.48 (m, 4H), 3.20-3.13 (m, 2H), 3.10-3.05 (m, 2H), 2.88-2.83 (m, 2H), 2.80-2.75 (m, 2H), 1.94-1.85 (m, 4H), 1.17-1.07 (m, 8H). HRMS (ESI-TOF) m/z calcd for $C_{56}H_{57}N_6O_6$ [M+H]⁺ 909.4334, found 909.4344.

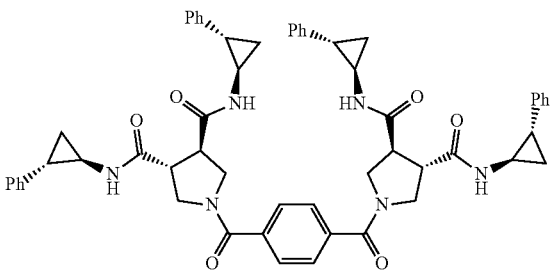 [SMILES: O=C(N[C@@H]1C[C@H]1c1ccccc1)[C@H]1CN(C(=O)c2ccc(C(=O)N3C[C@@H](C(=O)N[C@@H]4C[C@H]4c4ccccc4)[C@H](C(=O)N[C@@H]4C[C@H]4c4ccccc4)C3)cc2)C[C@@H]1C(=O)N[C@@H]1C[C@H]1c1ccccc1]

24: (3S,4S)-1-(4-((3R,4R)-3,4-Bis(((1R,2S)-2-phenyl-cyclopropyl)carbamoyl)-pyrrolidine-1-carbonyl)-benzoyl)—N³,N⁴-bis((1R,2S)-2-phenylcyclopropyl)-pyrrolidine-3,4-dicarboxamide

The general procedure for linking diacid coupling was employed, with equivalents scaled for single acid coupling: Pyrrolidine-3,4-dicarboxamide hydrochloride S-13 (2.6 mg, 0.00645 mmol), benzoic acid S-17 (3.3 mg, 0.00614 mmol), i-Pr₂NEt (3 µL, 0.0184 mmol), PyBrOP (3.0 mg, 0.00645 mmol) and anhydrous DMF (100 µL) were employed. After trituration with cold (0° C.) 1:1 Et₂O/EtOAc, 3.0 mg (54%) of 24 was obtained. ¹H NMR (500 MHz, DMSO-d₆) δ 8.41 (d, J=4.4 Hz, 2H), 8.28 (t, J=5.4 Hz, 2H), 7.56 (s, 4H), 7.29-7.20 (m, 8H), 7.19-7.02 (m, 12H), 3.83-3.77 (m, 2H), 3.69-3.62 (m, 2H), 3.59-3.45 (m, 4H), 3.23-3.14 (m, 2H), 3.12-3.07 (m, 2H), 2.90-2.82 (m, 2H), 2.81-2.74 (m, 2H), 1.99-1.94 (m, 2H), 1.88-1.85 (m, 2H), 1.20-1.06 (m, 8H). HRMS (ESI-TOF) m/z calcd for $C_{56}H_{57}N_6O_6$ [M+H]⁺ 909.4334, found 909.4329.

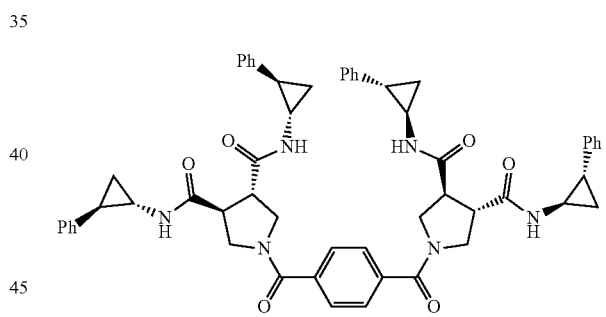

25: (3S,4S)-1-(4-((3S,4S)-3,4-Bis(((1R,2S)-2-phenylcyclopropyl)carbamoyl)-pyrrolidine-1-carbonyl)-benzoyl)—N³,N⁴-bis((1S,2R)-2-phenylcyclopropyl)-pyrrolidine-3,4-dicarboxamide

The general procedure for linking diacid coupling was employed, with equivalents scaled for single acid coupling: Pyrrolidine-3,4-dicarboxamide hydrochloride S-13 (5.3 mg, 0.0125 mmol), benzoic acid S-20 (6.7 mg, 0.0125 mmol), i-Pr₂NEt (7 µL, 0.0347 mmol), PyBrOP (6.1 mg, 0.0131 mmol) and anhydrous DMF (150 µL) were employed. After trituration with cold (0° C.) 1:1 Et₂O/EtOAc, 11.3 mg (99%) of 25 was obtained. ¹H NMR (500 MHz, DMSO-d₆) δ 8.42 (dd, J=11.8, 4.3 Hz, 2H), 8.29 (dd, J=6.5, 4.4 Hz, 2H), 7.56 (s, 4H), 7.24 (ddt, J=12.0, 7.3, 3.6 Hz, 8H), 7.19-7.03 (m, 12H), 3.80 (ddd, J=9.3, 8.7, 4.9 Hz, 2H), 3.66 (dd, J=11.6, 5.5 Hz, 2H), 3.57-3.44 (m, 4H), 3.24-3.14 (m, 2H), 3.18 (dd, J=16.5, 8.5 Hz, 2H), 2.85 (td, J=8.4, 4.0 Hz, 2H), 2.78 (dt, J=8.4, 4.0 Hz, 2H), 2.00-1.91 (m, 2H), 1.87 (dq, J=10.0, 3.1

Hz, 2H), 1.19-1.06 (m, 8H). HRMS (ESI-TOF) m/z calcd for $C_{56}H_{57}N_6O_6$ [M+H]+ 909.4334, found 909.4320.

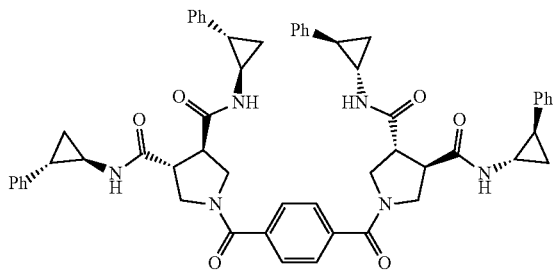 [SMILES: O=C(N[C@H]1C[C@@H]1c1ccccc1)[C@H]1CN(C(=O)c2ccc(C(=O)N3C[C@H](C(=O)N[C@@H]4C[C@H]4c4ccccc4)[C@@H](C(=O)N[C@@H]4C[C@H]4c4ccccc4)C3)cc2)C[C@@H]1C(=O)N[C@H]1C[C@@H]1c1ccccc1]

26: (3R,4R)-1-(4-((3R,4R)-3,4-Bis(((1R,2S)-2-phenylcyclopropyl)carbamoyl)-pyrrolidine-1-carbonyl)-benzoyl)—$N^3,N^4$-bis((1S,2R)-2-phenylcyclopropyl)-pyrrolidine-3,4-dicarboxamide The general procedure for linking diacid coupling was employed, with equivalents scaled for single acid coupling: Pyrrolidine-3,4-dicarboxamide hydrochloride S-12 (2.6 mg, 0.00614 mmol), benzoic acid S-17 (3.3 mg, 0.00614 mmol), i-Pr$_2$NEt (3 µL, 0.0184 mmol), PyBrOP (3.0 mg, 0.00645 mmol) and anhydrous DMF (100 µL) were employed. After trituration with cold (0° C.) 1:1 Et$_2$O/EtOAc, 5.3 mg (95%) of 26 was obtained. $^1$H NMR (500 MHz, DMSO-d$_6$) δ 8.42 (dd, J=11.7, 4.4 Hz, 2H), 8.28 (t, J=5.4 Hz, 2H), 7.56 (s, 4H), 7.30-7.20 (m, 8H), 7.19-7.01 (m, 12H), 3.83-3.78 (m, 2H), 3.69-3.63 (m, 2H), 3.58-3.44 (m, 4H), 3.23-3.14 (m, 2H), 3.10 (q, J=8.8 Hz, 2H), 2.90-2.81 (m, 2H), 2.80-2.75 (m, 2H), 1.99-1.93 (m, 2H), 1.88-1.84 (m, 2H), 1.19-1.06 (m, 8H). HRMS (ESI-TOF) m/z calcd for $C_{56}H_{57}N_6O_6$ [M+H]$^+$ 909.4334, found 909.4338.

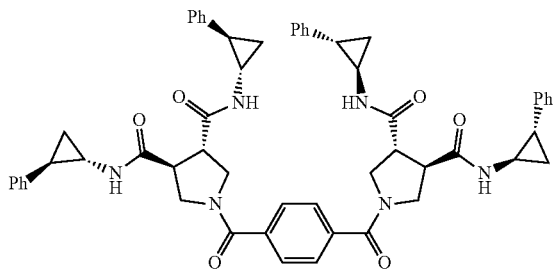 [SMILES: O=C(N[C@@H]1C[C@H]1c1ccccc1)[C@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C[C@@H]1C(=O)N[C@@H]1C[C@H]1c1ccccc1]

27: (3S,4S)-1-(4-((3R,4R)-3,4-Bis(((1R,2S)-2-phenyl-cyclopropyl)carbamoyl)-pyrrolidine-1-carbonyl)-benzoyl)—$N^3,N^4$-bis((1S,2R)-2-phenylcyclopropyl)-pyrrolidine-3,4-dicarboxamide The general procedure for linking diacid coupling was employed, with equivalents scaled for single acid coupling: Pyrrolidine-3,4-dicarboxamide hydrochloride S-14 (5.5 mg, 0.0130 mmol), benzoic acid S-20 (7.0 mg, 0.0130 mmol), i-Pr$_2$NEt (7 µL, 0.0390 mmol), PyBrOP (6.4 mg, 0.0137 mmol) and anhydrous DMF (150 µL) were employed. After trituration with cold (0° C.) 1:1 Et$_2$O/EtOAc, 2.7 mg (23%) of 27 was obtained. $^1$H NMR (500 MHz, DMSO-d$_6$) δ 8.41 (d, J=4.2 Hz, 2H), 8.27 (d, J=4.2 Hz, 2H), 7.56 (s, 4H), 7.25 (dt, J=15.4, 7.9 Hz, 8H), 7.19-7.03 (m, 12H), 3.82-3.78 (m, 2H), 3.68-3.63 (m, 2H), 3.54-3.45 (m, 4H), 3.18 (q, J=8.0 Hz, 2H), 3.11 (q, J=7.5 Hz, 2H), 2.86-2.81 (m, 2H), 2.79-2.75 (m, 2H), 1.99-1.93 (m, 2H), 1.87-1.84 (m, 2H), 1.20-1.05 (m, 8H). HRMS (ESI-TOF) m/z calcd for $C_{56}H_{57}N_6O_6$ [M+H]$^+$ 909.4334, found 909.4334.

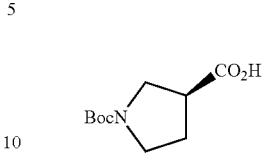

S-21: (S)—N-Boc-β-Proline

[Fuentes et al., *Chem. Sci.* 2011, 2:1997-2005.]

(S)-β-Proline (152 mg, 1.32 mmol) and Boc$_2$O (350 mg, 1.58 mmol) were suspended in deionized H$_2$O (1 mL) and acetone (3 mL). The mixture was cooled to 0° C. and solid Na$_2$CO$_3$ (72 mg, 0.660 mmol) was added. After 3 hours, the acetone was removed in vacuo, and aqueous citric acid (20% w/v) was added dropwise until pH 4 was observed. The mixture was diluted with H$_2$O (15 mL) and EtOAc (15 mL). The aqueous phase was extracted with EtOAc (2×10 mL). The combined organic phases were dried over Na$_2$SO$_4$ and concentrated, upon which the product precipitates as a white solid to afford 284 mg (99%) of S-21. $^1$H NMR (400 µMHz, DMSO-d$_6$) δ 12.45 (s, 1H), 3.49-3.15 (m, 4H), 3.09-2.95 (m, 1H), 2.12-1.87 (m, 2H), 1.39 (s, 9H).

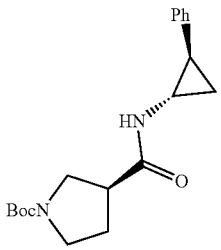 [SMILES: CC(C)(C)OC(=O)N1CC[C@H](C(=O)N[C@H]2C[C@@H]2c2ccccc2)C1]

28: (S)-tert-Butyl 3-((($^1$1,2R)-2-Phenylcyclopropyl)-carbamoyl)pyrrolidine-1-carboxylate (S)—N-Boc-β-Proline (S-21, 164 mg, 0.762 mmol), (1S, 2R)-trans-2-phenylcyclopropylamine ((1S,2R)-13, 107 mg, 0.800 mmol) and HOAt (114 mg, 0.838 mmol) were dissolved in anhydrous DMF (4 mL) at room temperature. 2,6-Lutidine (450 µL, 3.81 mmol) and EDCI.HCl (219 mg, 1.14 mmol) were added. After 24 hours, the reaction mixture was diluted with EtOAc (50 mL) and washed with aqueous 0.5 N HCl (2×50 mL). The organic phase was washed with saturated aqueous NaHCO$_3$ (30 mL) and saturated aqueous NaCl (30 mL), and dried over Na$_2$SO$_4$. Flash column chromatography (SiO$_2$, 50% EtOAc/hexanes) provided 150 mg (60%) of 28. $^1$H NMR (500 MHz, CDCl$_3$) δ 7.32-7.23 (m, 2H), 7.22-7.11 (m, 3H), 6.05 (br s, 1H), 3.69-3.52 (m, 2H), 3.48 (dd, J=11.0, 8.0 Hz, 1H), 3.32 (dt, J=10.5, 7.9 Hz, 1H), 2.94-2.86 (m, 1H), 2.85-2.77 (m, 1H), 2.24-2.10 (m, 1H), 2.10-2.02 (m, 2H), 1.46 (s, 9H), 1.29-1.22 (m, 1H), 1.15 (ddd, J=10.1, 5.9, 4.4 Hz, 1H). HRMS (ESI-TOF) m/z calcd for $C_{19}H_{27}N_2O_3$ [M+H]$^+$ 331.2016, found 331.2017.

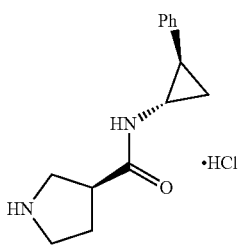 [SMILES: O=C(N[C@H]1C[C@@H]1c1ccccc1)[C@H]1CCNC1 ; Cl]

S-22: (S)—N-((1S,2R)-2-Phenylcyclopropyl)-pyrrolidine-3-carboxamide Hydrochloride Compound 28 (127 mg, 0.384 mmol) was dissolved in anhydrous dioxane (1 mL) at room temperature. 4 N HCl (4.0 mL, 16.0 mmol, 4 M solution in dioxane) was added dropwise down the sides of the reaction vessel. After 4 hours, the dioxane was removed under a stream of $N_2$. The residue was reconcentrated from THF (4×4 mL) and $Et_2O$ (5×4 mL) in vacuo to afford 102 mg (99%) of S-22.

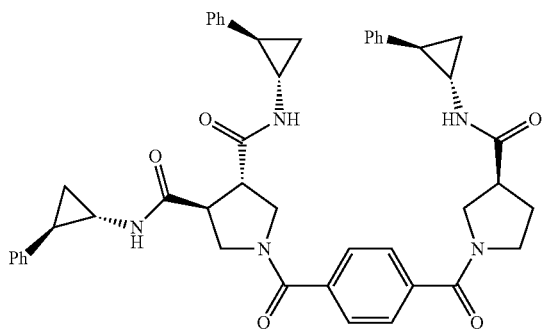 [SMILES: O=C(N[C@H]1C[C@@H]1c1ccccc1)[C@H]1CCN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C1]

29: (3S,4S)—$N^3$,$N^4$-Bis((1S,2R)-2-phenyl-cyclopropyl)-1-(4-((S)-3-(((1S,2R)-2-phenyl-cyclopropyl)-carbamoyl)-pyrrolidine-1-carbonyl)-benzoyl)pyrrolidine-3,4-dicarboxamide Benzoic acid S-20 (13.0 mg, 0.0242 mmol) and hydrochloride salt S-22 (6.5 mg, 0.0242 mmol) were dissolved in anhydrous DMF (120 μL) at room temperature. i-$Pr_2$NEt (13.0 μL, 0.0725 mmol) and PyBrOP (12.0 mg, 0.0254 mmol) were added, and the mixture was stirred for 18 hours. The mixture was diluted with EtOAc (3 mL) and washed with aqueous 1 N HCl (2 mL), saturated aqueous $NaHCO_3$ (2 mL), and saturated aqueous NaCl (1 mL), respectively. The organic phase was filtered through a plug of $Na_2SO_4$ and concentrated to give 16.2 mg (90%) of 29. $^1$H NMR (500 μMHz, DMSO-$d_6$) δ 8.41 (d, J=4.3 Hz, 1H), 8.29 (4.3 Hz, 1H), 8.28 (t, J=4.2 Hz, 1H), 7.55 (s, 4H), 7.28-7.21 (m, 5H), 7.19-7.04 (m, 10H), 3.80 (dd, J=11.9, 8.5 Hz, 1H), 3.65 (q, J=9.2 Hz, 2H), 3.61-3.42 (m, 4H), 3.19 (q, J=8.3 Hz, 1H), 3.11 (q, J=8.1 Hz, 1H), 2.87-2.82 (m, 2H), 2.80-2.75 (m, 2H), 2.15-2.07 (m, 1H), 2.05-1.99 (m, 1H), 1.96 (dq, J=10.2, 3.8 Hz, 2H), 1.89-1.83 (m, 2H), 1.21-1.05 (m, 6H). HRMS (ESI-TOF) m/z calcd for $C_{46}H_{48}N_5O_5$ [M+H]$^+$ 750.3650, found 750.6347.

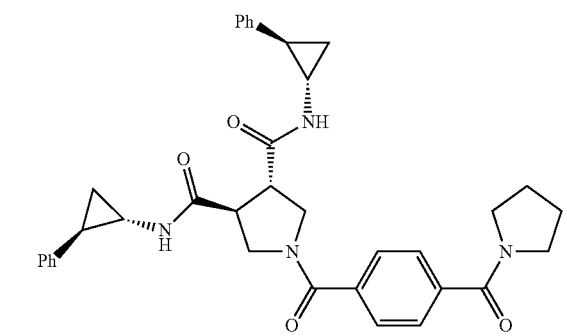 [SMILES: O=C(N[C@H]1C[C@@H]1c1ccccc1)[C@@H]1CN(C(=O)c2ccc(C(=O)N3CCCC3)cc2)C[C@H]1C(=O)N[C@H]1C[C@@H]1c1ccccc1]

30: (3S,4S)—$N^3$,$N^4$-Bis((S, 2R)-2-phenyl-cyclopropyl)-1-(4-(pyrrolidine-1-carbonyl)benzoyl)-pyrrolidine-3,4-dicarboxamide Benzoic acid S-20 (7.7 mg, 0.0143 mmol) and pyrrolidine (1.2 μL, 0.0143 mmol) were dissolved in anhydrous DMF (100 μL) at room temperature. i-$Pr_2$NEt (7.5 μL, 0.0430 mmol) and PyBrOP (7.0 mg, 0.0150 mmol) were added, and the mixture was stirred for 18 hours. The mixture was diluted with EtOAc (3 mL) and washed with aqueous 1 N HCl (2 mL), saturated aqueous $NaHCO_3$ (2 mL), and saturated aqueous NaCl (1 mL), respectively. The organic phase was filtered through a plug of $Na_2SO_4$ and concentrated to give 8.1 mg (95%) of 30. $^1$H NMR (500 MHz, DMSO-$d_6$) δ 8.49 (d, J=4.4 Hz, 1H), 8.36 (d, J=4.3 Hz, 1H), 7.55 (s, 4H), 7.25 (dt, J=13.2, 7.5 Hz, 4H), 7.18-7.04 (m, 6H), 3.79 (dd, J=12.0, 8.5 Hz, 1H), 3.68-3.61 (m, 1H), 3.55-3.43 (m, 4H), 3.36 (t, J=6.5 Hz, 2H), 3.18 (dt, J=6.6, 3.4 Hz, 4H), 3.10 (q, J=7.8 Hz, 1H), 2.85 (dt, J=7.7, 4.1 Hz, 1H), 2.77 (q, J=5.3 Hz, 1H), 1.88-1.83 (m, 4H), 1.22-1.06 (m, 4H). HRMS (ESI-TOF) m/z calcd for $C_{36}H_{39}N_4O_4$ [M+H]$^+$ 591.2966, found 591.2968.

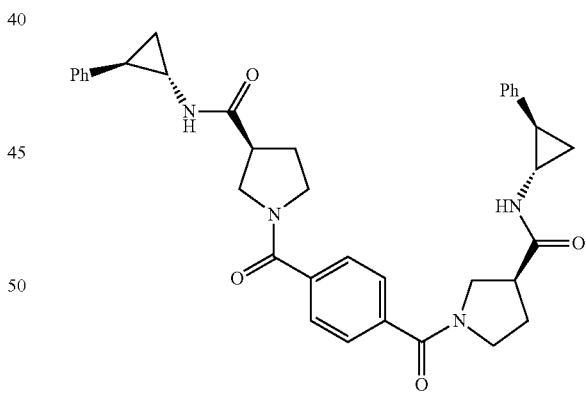

31: (3S,3'S)-1,1'-Terephthaloylbis(N-((1S,2R)-2-phenylcyclopropyl) pyrrolidine-3-carboxamide)

Hydrochloride salt S-22 (17.7 mg, 0.0663 mmol) and terephthalic acid (benzene-1,4-dicarboxylic acid, 5.0 mg, 0.0302 mmol) were dissolved in anhydrous DMF (330 μL) at room temperature. i-$Pr_2$NEt (16.0 μL, 1.60 mmol) was added, followed by PyBrOP (28.0 mg, 0.0603 mmol) after 5 minutes. After 18 hours, the reaction mixture was diluted with EtOAc (2 mL) and washed with aqueous 0.5 N HCl (2×2 mL). The aqueous phase was extracted with EtOAc (1×1 mL). The combined organic phases were washed with saturated aqueous NaHCO₃ (2 mL) and saturated aqueous NaCl (1 mL). The organic phase was dried over Na₂SO₄, decanted and concentrated. The remaining residue was triturated with cold (0° C.) 1:1 Et₂O/EtOAc (3×0.5 mL), decanting the liquid phase to give 11.9 mg (67%) of 31. ¹H NMR (500 MHz, DMSO-$d_6$) δ 8.35 (d, J=4.3 Hz, 1H), 8.26 (s, 1H), 7.54 (s, 4H), 7.30-7.19 (m, 4H), 7.18-7.03 (m, 6H), 3.67 (dd, J=12.2, 8.1 Hz, 1H), 3.63-3.41 (m, 7H), 2.96 (t, J=7.7 Hz, 1H), 2.89 (t, J=7.6 Hz, 1H), 2.87-2.83 (m, 1H), 2.79-2.75 (m, 1H), 2.16-2.06 (m, 1H), 2.05-1.99 (m, 2H), 1.99-1.91 (m, 2H), 1.89-1.84 (m, 1H), 1.21-1.06 (m, 4H). HRMS (ESI-TOF) m/z calcd for $C_{36}H_{39}N_4O_4$ [M+H]⁺ 591.2966, found 591.2963.

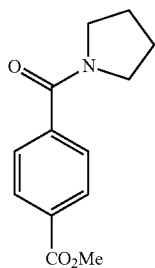 [SMILES: COC(=O)c1ccc(C(=O)N2CCCC2)cc1]

S-23: Methyl 4-(Pyrrolidine-1-carbonyl)benzoate

Pyrrolidine (100 µL, 1.11 mmol) and monomethyl terephthalate (200 mg, 1.11 mmol) were dissolved in anhydrous DMF (5.5 mL) at room temperature. i-Pr₂NEt (0.58 mL, 3.33 mmol) and PyBrOP (518 mg, 1.11 mmol) were added. After 18 hours, the reaction mixture was diluted with EtOAc (75 mL) and washed with aqueous 1 N HCl (2×50 mL), saturated aqueous NaCl (25 mL), saturated aqueous NaHCO₃ (50 mL) and saturated aqueous NaCl (25 mL). The organic phase was dried over Na₂SO₄, filtered and concentrated. Flash column chromatography (50-75% EtOAc/hexanes gradient) gave 205 mg (80%) of S-23. ¹H NMR (500 MHz, acetone-$d_6$) δ 8.04 (d, J=8.3 Hz, 2H), 7.63 (d, J=8.4 Hz, 2H), 3.90 (s, 3H), 3.54 (t, J=6.9 Hz, 2H), 3.41 (t, J=6.5 Hz, 2H), 1.98-1.83 (m, 4H).

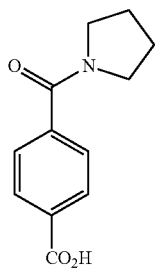 [SMILES: O=C(O)c1ccc(C(=O)N2CCCC2)cc1]

S-24: 4-(Pyrrolidine-1-carbonyl)benzoic Acid

Methyl ester S-23 (113 mg, 0.486 mmol) was dissolved in THF/MeOH/H₂O (2 mL, 0.5 mL, 0.5 mL, respectively). LiOH·H₂O (82 mg, 1.94 mmol) was added, and the reaction mixture was stirred for 3.5 hours. Aqueous 1 N HCl was added until pH 2 was obtained, and the mixture was diluted with EtOAc (50 mL). The aqueous phase was extracted with EtOAc (3×20 mL), and the combined organic phases were dried over Na₂SO₄, filtered and concentrated to give 102 mg (86%) of S-24.

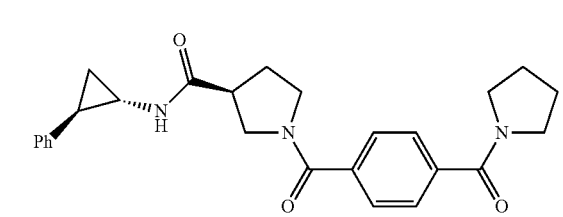 [SMILES: O=C(N[C@H]1C[C@@H]1c1ccccc1)[C@H]1CCN(C(=O)c2ccc(C(=O)N3CCCC3)cc2)C1]

32 (MM-2-434): (S)—N-((1S,2R)-2-Phenylcyclopropyl)-1-(4-(pyrrolidine-1-carbonyl)benzoyl)pyrrolidine-3-carboxamide Compound S-24 (10.8 mg, 0.0493 mmol) and S-22 (13.1 mg, 0.0493 mmol) were dissolved in anhydrous DMF (300 µL) at room temperature. i-Pr₂NEt (26 µL, 0.148 mmol) and PyBrOP (24.0 mg, 0.0567 mmol) were added, and the reaction mixture was stirred 18 hours. The reaction mixture was diluted with EtOAc (2 mL) and washed with aqueous 0.5 N HCl (2×2 mL). The aqueous phase was extracted with EtOAc (1×1 mL). The combined organic phases were washed with saturated aqueous NaHCO₃ (2 mL) and saturated aqueous NaCl (1 mL). The organic phase was dried over Na₂SO₄, decanted and concentrated. The remaining residue was triturated with cold (0° C.) 1:1 Et₂O/EtOAc (3×0.5 mL), decanting the liquid phase to give 11.6 mg (55%) of 32. ¹H NMR (500 MHz, DMSO-$d_6$) δ 8.34 (d, J=4.3 Hz, 1H), 7.54 (s, 4H), 7.28-7.21 (m, 2H), 7.20-7.05 (m, 3H), 3.71-3.64 (m, 1H), 3.63-3.41 (m, 4H), 3.37 (t, J=6.5 Hz, 2H), 2.99-2.94 (m, 1H), 2.89 (t, J=7.7 Hz, 1H), 2.87-2.82 (m, 1H), 2.78 (m, 1H), 2.06-1.91 (m, 2H), 1.90-1.83 (m, 2H), 1.83-1.78 (m, 2H), 1.20-1.08 (m, 2H). HRMS (ESI-TOF) m/z calcd for $C_{26}H_{30}N_3O_3$ [M+H]⁺ 432.2282, found 432.2278.

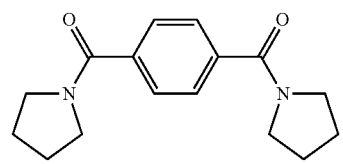 [SMILES: O=C(c1ccc(C(=O)N2CCCC2)cc1)N1CCCC1]

33: 1,4-Phenylenebis(pyrrolidin-1-ylmethanone)

Pyrrolidine (22 µL, 0.265 mmol) and terephthalic acid (benzene-1,4-dicarboxylic acid, 20 mg, 0.120 mmol) were dissolved in anhydrous DMF (600 µL) at room temperature. i-Pr₂NEt (63.0 µL, 0.361 mmol) was added, followed by PyBrOP (112 mg, 0.241 mmol) after 5 minutes. After 18 hours, the reaction mixture was diluted with EtOAc (10 mL) and washed with aqueous 0.5 N HCl (2×10 mL). The aqueous phase was extracted with EtOAc (1×5 mL). The combined organic phases were washed with saturated aqueous NaHCO₃ (10 mL) and saturated aqueous NaCl (5 mL). The organic phase was dried over Na₂SO₄, decanted and concentrated to give 30 mg (92%) of 33, whose spectral data matched those reported previously. [Jones et al., *Zeitschrift für Naturforschung, B* 2002, 57:914-921.]

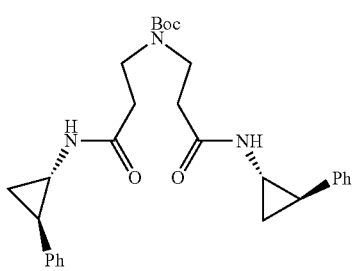 [SMILES: CC(C)(C)OC(=O)N(CCC(=O)N[C@H]1C[C@@H]1c1ccccc1)CCC(=O)N[C@H]1C[C@@H]1c1ccccc1]

S-25: tert-Butyl Bis(3-oxo-3-(((1S,2R)-2-phenylcy-clo-propyl)amino)propyl)carbamate The general procedure for the coupling of amines with diacids was followed: Commercially available N-Boc-iminodipropionic acid (250 mg, 0.957 mmol), (1S,2R)-trans-2-phenylcyclopropylamine ((1S,2R)-13, 261 mg, 1.96 mmol), 2,6-lutidine (560 µL, 4.78 mmol), EDCI.HCl (460 mg, 2.39 mmol), HOAt (287 mg, 2.11 mmol) and DMF (5 mL) were employed. Flash column chromatography (SiO$_2$, 75% EtOAc/hexanes) provided 307 mg (65%) of S-25. $^1$H NMR (500 MHz, CDCl$_3$) δ 7.29-7.23 (m, 4H), 7.20-7.10 (m, 6H), 3.53 (t, J=6.9 Hz, 4H), 2.94-2.85 (m, 2H), 2.52-2.36 (m, 4H), 2.03 (ddd, J=13.1, 6.0, 3.0 Hz, 2H), 1.73 (br s, 2H), 1.47 (s, 9H), 1.22 (dt, J=7.4, 6.0 Hz, 2H), 1.13 (dt, J=10.0, 5.1 Hz, 2H).

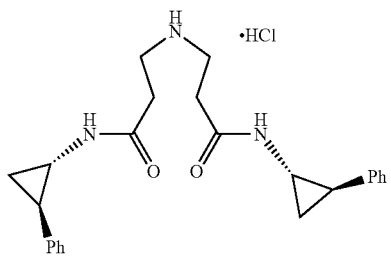 [SMILES: O=C(CCNCCC(=O)N[C@H]1C[C@@H]1c1ccccc1)N[C@H]1C[C@@H]1c1ccccc1 ; Cl]

S-26: 3,3'-Azanediylbis(N-((1S,2R)-2-phenylcyclo-propyl)propanamide) Hydrochloride The general procedure for Boc deprotection was employed: N-Boc amine S-25 (136 mg, 0.277 mmol), anhydrous THF (1 mL), and 4 N HCl in dioxane (5 mL) were employed. Reconcentration from THF (3×5 mL) and Et$_2$O (3×3 mL) gave 119 mg (99%) of S-26.

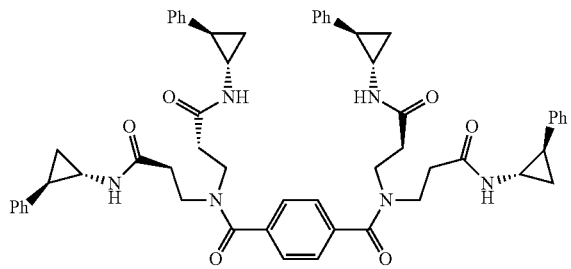

34: N$^1$,N$^1$,N$^4$,N$^4$-Tetrakis(3-oxo-3-(((1S,2R)-2-phenyl-cyclopropyl)amino)propyl)terephthalamide The general procedure for linking diacid coupling was employed: S-26 (21.6 mg, 0.0505 mmol), terephthalic acid (benzene-1,4-dicarboxylic acid, 3.8 mg, 0.0229 mmol), PyBrOP (21.4 mg, 0.0459 mmol), i-Pr$_2$NEt (12 µL, 0.0688 mmol) and DMF (350 µL) gave 20.0 mg (95%) of 34. $^1$H NMR (500 MHz, DMSO-d$_6$) δ 8.30 (s, 2H), 8.22 (s, 2H), 7.37 (s, 4H), 7.23 (t, J=7.2 Hz, 8H), 7.17-7.04 (m, 12H), 3.62-3.55 (m, 4H), 3.44-3.37 (m, 4H), 2.81 (br s, 2H), 2.72 (br s, 2H), 2.46-2.39 (m, 4H), 2.32-2.25 (m, 4H), 1.92 br s, 2H), 1.87 (br s, 2H), 1.18-1.05 (m, 8H). HRMS (ESI-TOF) m/z calcd for C$_{56}$H$_{61}$N$_6$O$_6$ [M+H]$^+$ 913.4647, found 913.4643.

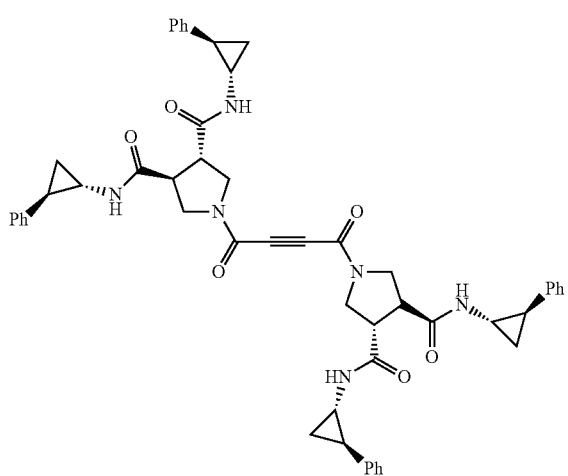

35: (3S,3'S,4S,4'S)-1,1'-(But-2-ynedioyl)-bis(N$^3$,N$^4$-bis((1S,2R)-2-phenylcyclopropyl)-pyrrolidine-3,4-dicarboxamide)

The general procedure for linking diacid coupling was employed: pyrrolidine-3,4-dicarboxamide hydrochloride S-2 (10.8 mg, 0.0254 mmol), acetylene-dicarboxylic acid (1.3 mg, 0.0115 mmol), PyBrOP (10.7 mg, 0.0231 mmol), i-Pr$_2$NEt (6 µL, 0.0346 mmol) and DMF (150 µL) gave 9.4 mg (95%) of 35. $^1$H NMR (500 MHz, DMSO-d$_6$) δ 8.40 (d, J=4.1 Hz, 4H), 7.28-7.21 (m, 8H), 7.19-7.04 (m, 12H), 3.93 (dd, J=10.7, 7.5 Hz, 2H), 3.85-3.61 (m, 4H), 3.39 (dd, J=12.3, 7.1 Hz, 2H), 3.21-3.09 (m, 4H), 2.86-2.79 (m, 4H), 1.99-1.89 (m, 4H), 1.21-1.09 (m, 8H). HRMS (ESI-TOF) m/z calcd for C$_{52}$H$_{53}$N$_6$O$_6$ [M+H]$^+$ 857.4021, found 857.4020.

4H), 1.14 (ddd, J=8.7, 5.8, 2.9 Hz, 8H). HRMS (ESI-TOF) m/z calcd for $C_{54}H_{59}N_6O_6$ [M+H]$^+$ 887.4491, found 887.4490.

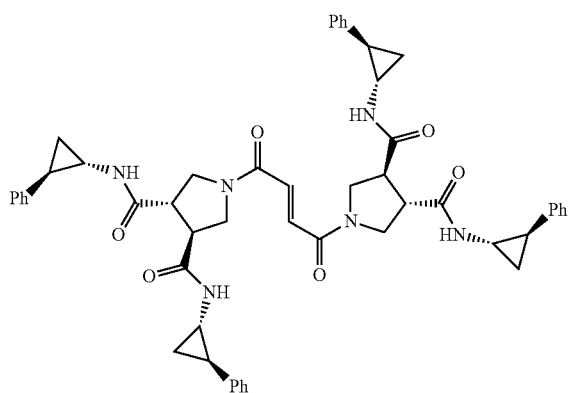 [SMILES: O=C(N[C@H]1C[C@@H]1c1ccccc1)[C@@H]1CN(C(=O)/C=C/C(=O)N2C[C@@H](C(=O)N[C@H]3C[C@@H]3c3ccccc3)[C@H](C(=O)N[C@H]3C[C@@H]3c3ccccc3)C2)C[C@H]1C(=O)N[C@H]1C[C@@H]1c1ccccc1]

36: (3S,3'S,4S,4'S)-1,1'-Fumaroyl-bis(N$^3$,N$^4$-bis((1S,2R)-2-phenylcyclopropyl)pyrrolidine-3,4-dicarboxamide)

The general procedure for linking diacid coupling was employed: pyrrolidine-3,4-dicarboxamide hydrochloride S-2 (10.1 mg, 0.0237 mmol), fumaric acid (1.2 mg, 0.0108 mmol), PyBrOP (10.0 mg, 0.0216 mmol), i-Pr$_2$NEt (6 μL, 0.0346 mmol) and DMF (150 μL) gave 7.1 mg (70%) of 36. $^1$H NMR (500 MHz, DMSO-d$_6$) δ 8.64 (dd, J=8.8, 4.4 Hz, 4H), 7.24 (td, J=7.7, 2.4 Hz, 8H), 7.19-7.06 (m, 12H), 7.03 (s, 2H), 3.88 (dd, J=10.3, 7.7 Hz, 2H), 3.67 (dd, J=12.3, 8.2 Hz, 2H), 3.62 (dd, J=10.1, 7.3 Hz, 2H), 3.40 (dd, J=12.3, 7.2 Hz, 2H), 3.21 (q, J=7.5 Hz, 2H), 3.17-3.10 (m, 2H), 2.82 (dq, J=7.9, 3.7 Hz, 4H), 1.96 (ddt, J=9.7, 6.6, 3.7 Hz, 4H), 1.23-1.08 (m, 8H). HRMS (ESI-TOF) m/z calcd for $C_{52}H_{55}N_6O_6$ [M+H]$^+$ 859.4178, found 859.4173.

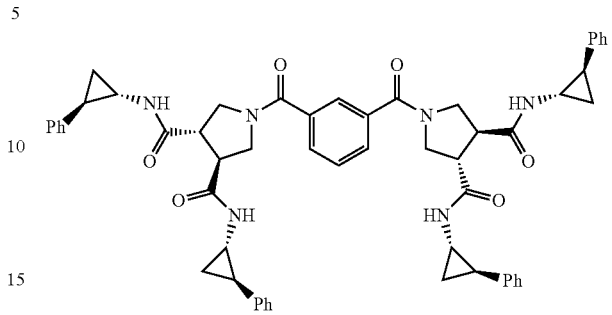

38: (3S,3'S,4S,4'S)-1,1'-Isophthaloyl-bis-(N$^3$,N$^4$-bis((1S,2R)-2-phenylcyclopropyl)-pyrrolidine-3,4-dicarboxamide)

The general procedure for linking diacid coupling was employed: pyrrolidine-3,4-dicarboxamide hydrochloride S-2 (10.2 mg, 0.0239 mmol), isophthalic acid (1.8 mg, 0.0109 mmol), PyBrOP (10.1 mg, 0.0218 mmol), i-Pr$_2$NEt (6 μL, 0.0346 mmol) and DMF (150 μL) gave 9.4 mg (95%) of 38. $^1$H NMR (500 MHz, DMSO-d$_6$) δ 8.40 (d, J=4.3 Hz, 2H), 8.27 (d, J=4.2 Hz, 2H), 7.61 (s, 1H), 7.59 (s, 2H), 7.51 (dd, J=8.6, 6.6 Hz, 1H), 7.30-7.19 (m, 8H), 7.19-7.02 (m, 12H), 3.79 (dd, J=11.9, 8.5 Hz, 2H), 3.67-3.61 (m, 2H), 3.51 (ddd, J=10.3, 9.1, 3.7 Hz, 4H), 3.22-3.14 (m, 2H), 3.12-3.07 (m, 2H), 2.84 (dt, J=8.6, 4.3 Hz, 2H), 2.77 (dd, J=7.8, 4.0 Hz, 2H), 1.96 (ddd, J=9.6, 6.4, 3.5 Hz, 2H), 1.86 (ddd, J=9.6, 6.4, 3.4 Hz, 2H), 1.22-1.04 (m, 8H). HRMS (ESI-TOF) m/z calcd for $C_{56}H_{57}N_6O_6$ [M+H]$^+$ 909.4334, found 909.4339.

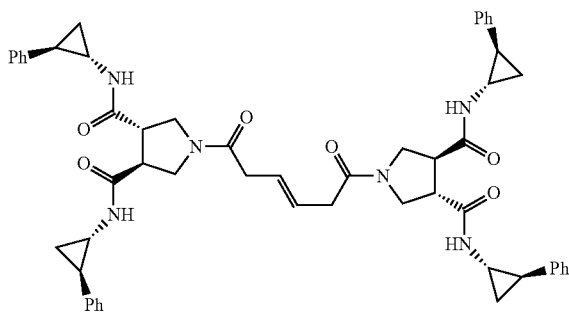 [SMILES: O=C(N[C@H]1C[C@@H]1c1ccccc1)[C@@H]1CN(C(=O)C/C=C/CC(=O)N2C[C@@H](C(=O)N[C@H]3C[C@@H]3c3ccccc3)[C@H](C(=O)N[C@H]3C[C@@H]3c3ccccc3)C2)C[C@H]1C(=O)N[C@H]1C[C@@H]1c1ccccc1]

37: (3S,3'S,4S,4'S)-1,1'-((E)-Hex-3-enedoyl)bis-(N$^3$,N$^4$-bis((1S,2R)-2-phenylcyclopropyl)pyrrolidine-3,4-dicarboxamide)

The general procedure for linking diacid coupling was employed: pyrrolidine-3,4-dicarboxamide hydrochloride S-2 (9.6 mg, 0.0225 mmol), (E)-3-hexenedioic acid (1.5 mg, 0.0102 mmol), PyBrOP (9.6 mg, 0.0205 mmol), i-Pr$_2$NEt (6 μL, 0.0346 mmol) and DMF (150 μL) gave 8.8 mg (96%) of 37. $^1$H NMR (500 MHz, DMSO-d$_6$) δ 8.36 (dd, J=10.3, 4.3 Hz, 4H), 7.25 (t, J=7.5 Hz, 8H), 7.19-7.07 (m, 12H), 5.56 (dd, J=4.4, 2.8 Hz, 2H), 3.76 (dd, J=10.1, 8.2 Hz, 2H), 3.66 (dd, J=11.6, 8.3 Hz, 2H), 3.44 (t, J=9.2 Hz, 2H), 3.22 (dd, J=11.6, 8.5 Hz, 2H), 3.19-3.12 (m, 2H), 3.09-3.02 (m, 6H), 2.82 (dq, J=7.8, 4.2 Hz, 4H), 1.93 (ddt, J=10.1, 7.0, 3.6 Hz,

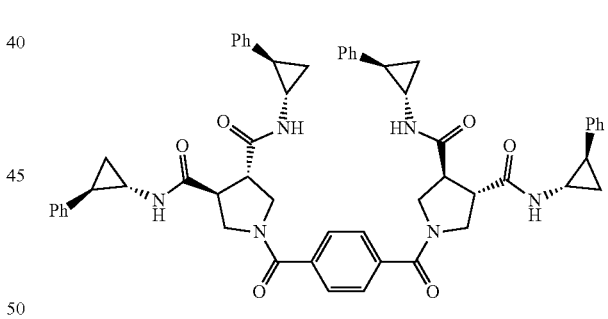

3: (3S,3'S,4S,4'S)-1,1'-Terephthaloyl-bis-(N$^3$,N$^4$-bis((1S,2R)-2-phenylcyclopropyl)pyrrolidine-3,4-dicarboxamide)

The general procedure for linking diacid coupling was employed: pyrrolidine-3,4-dicarboxamide hydrochloride S-2 (10.9 mg, 0.0256 mmol), terephthalic acid (benzene-1,4-dicarboxylic acid, 1.9 mg, 0.0116 mmol), PyBrOP (10.8 mg, 0.0233 mmol), i-Pr$_2$NEt (6 μL, 0.0346 mmol) and DMF (150 μL) gave 10.0 mg (94%) of 3. $^1$H NMR (500 MHz, DMSO-d$_6$) δ 8.51 (d, J=4.2 Hz, 2H), 8.38 (s, 2H), 7.55 (s, 4H), 7.31-7.19 (m, 8H), 7.19-7.03 (m, 12H), 3.78 (dd, J=12.0, 8.4 Hz, 2H), 3.67-3.60 (m, 2H), 3.55-3.48 (m, 4H), 3.20 (q, J=8.0 Hz, 2H), 3.11 (q, J=7.7 Hz, 2H), 2.86-2.82 (m, 2H), 2.80-2.75 (m, 2H), 1.97 (td, J=6.2, 3.1 Hz, 2H), 1.87

(td, J=6.5, 6.1, 3.2 Hz, 2H), 1.21-1.07 (m, 8H). HRMS (ESI-TOF) m/z calcd for $C_{56}H_{57}N_6O_6$ [M+H]$^+$ 909.4334, found 909.4334.

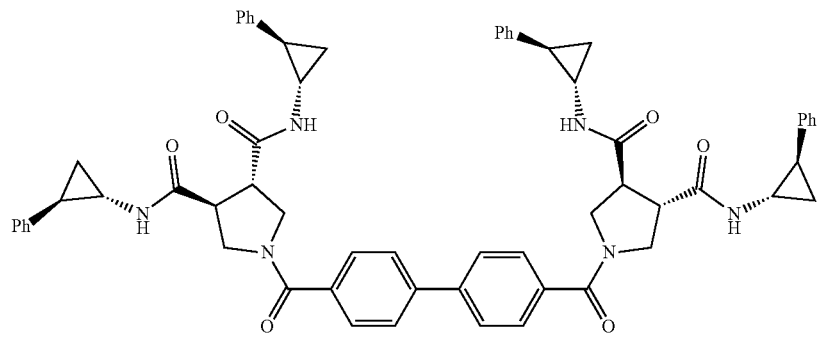 [SMILES: O=C(N[C@H]1C[C@@H]1c1ccccc1)[C@@H]1CN(C(=O)c2ccc(-c3ccc(C(=O)N4C[C@@H](C(=O)N[C@H]5C[C@@H]5c5ccccc5)[C@H](C(=O)N[C@H]5C[C@@H]5c5ccccc5)C4)cc3)cc2)C[C@H]1C(=O)N[C@H]1C[C@@H]1c1ccccc1]

39: (3S,3'S,4S,4'S)-1,1'-(4,4'-Biphenyldicarboxoyl)-bis(N$^3$,N$^4$-bis((1S,2R)-2-phenylcyclopropyl)-pyrrolidine-3,4-dicarboxamide)

The general procedure for linking diacid coupling was employed: pyrrolidine-3,4-dicarboxamide hydrochloride S-2 (10.0 mg, 0.0235 mmol), 4,4'-biphenyldicarboxylic acid (2.6 mg, 0.0107 mmol), PyBrOP (10.0 mg, 0.0213 mmol), i-Pr$_2$NEt (6 µL, 0.0346 mmol) and DMF (150 µL) gave 10.1 mg (96%) of 39. $^1$H NMR (500 µMHz, DMSO-d$_6$) δ 8.53 (s, 2H), 8.40 (s, 2H), 7.77 (d, J=8.4 Hz, 4H), 7.62 (d, J=8.1 Hz, 4H), 7.24 (dt, J=18.3, 7.5 Hz, 8H), 7.19-7.03 (m, 12H), 3.80 (dd, J=12.0, 8.5 Hz, 2H), 3.70 (dd, J=10.4, 7.6 Hz, 2H), 3.59-3.50 (m, 4H), 3.22 (q, J=8.1 Hz, 2H), 3.13 (q, J=7.8 Hz, 2H), 2.88-2.83 (m, 2H), 2.81-2.76 (m, 2H), 1.98 (ddd, J=6.7, 3.7, 3.2 Hz, 2H), 1.87 (ddd, J=9.5, 7.1, 3.5 Hz, 2H), 1.23-1.07 (m, 8H). HRMS (ESI-TOF) m/z calcd for $C_{62}H_{61}N_6O_6$ [M+H]$^+$ 985.4647, found 985.4648.

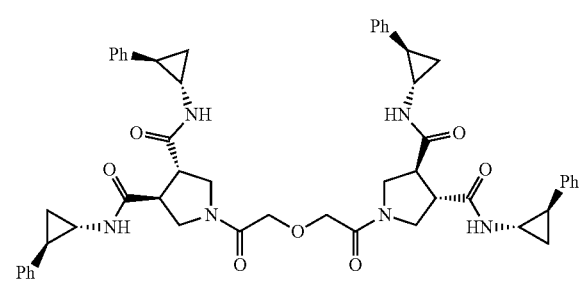 [SMILES: O=C(N[C@H]1C[C@@H]1c1ccccc1)[C@@H]1CN(C(=O)COCC(=O)N2C[C@@H](C(=O)N[C@H]3C[C@@H]3c3ccccc3)[C@H](C(=O)N[C@H]3C[C@@H]3c3ccccc3)C2)C[C@H]1C(=O)N[C@H]1C[C@@H]1c1ccccc1]

40: (3S,3'S,4S,4'S)-1,1'-(2,2'-Oxybis-(acetyl))bis-(N$^3$,N$^4$-bis((1S,2R)-2-phenylcyclopropyl)pyrrolidine-3,4-dicarboxamide)

The general procedure for linking diacid coupling was employed: pyrrolidine-3,4-dicarboxamide hydrochloride S-2 (10.1 mg, 0.0237 mmol), diglycolic acid (1.4 mg, 0.0108 mmol), PyBrOP (10.1 mg, 0.0216 mmol), i-Pr$_2$NEt (6 µL, 0.0346 mmol) and DMF (150 µL) gave 8.9 mg (94%) of 40. $^1$H NMR (500 MHz, DMSO-d$_6$) δ 8.37 (t, J=4.4 Hz, 4H), 7.25 (t, J=7.6 Hz, 8H), 7.19-7.05 (m, 12H), 4.13 (s, 4H), 3.70 (dt, J=11.3, 8.3 Hz, 4H), 3.39 (t, J=9.3 Hz, 2H), 3.26 (dd, J=11.7, 8.2 Hz, 2H), 3.15 (q, J=8.0 Hz, 2H), 3.03 (m, 2H), 2.86-2.78 (m, 4H), 1.93 (ddt, J=8.9, 6.5, 3.1 Hz, 4H), 1.18-1.10 (m, 8H). HRMS (ESI-TOF) m/z calcd for $C_{52}H_{57}N_6O_7$ [M+H]$^+$ 877.4283, found 877.4285.

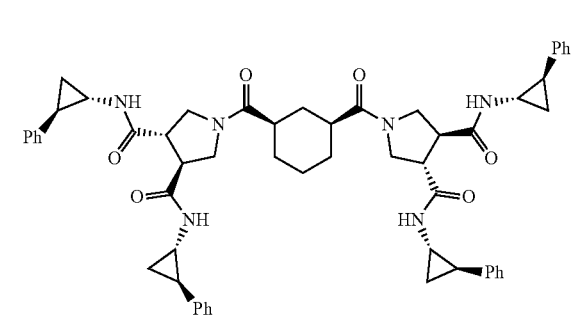 [SMILES: O=C(N[C@H]1C[C@@H]1c1ccccc1)[C@@H]1CN(C(=O)[C@@H]2CCC[C@H](C(=O)N3C[C@@H](C(=O)N[C@H]4C[C@@H]4c4ccccc4)[C@H](C(=O)N[C@H]4C[C@@H]4c4ccccc4)C3)C2)C[C@H]1C(=O)N[C@H]1C[C@@H]1c1ccccc1]

41: (3S,3'S,4S,4'S)-1,1'-(cis-1,3-Cyclohexane-dicarbonyl)bis(N$^3$,N$^4$-bis((1S,2R)-2-phenyl-cyclopropyl) pyrrolidine-3,4-dicarboxamide)

The general procedure for linking diacid coupling was employed: pyrrolidine-3,4-dicarboxamide hydrochloride S-2 (10.5 mg, 0.0247 mmol), cis-1,3-cyclohexanedicarboxylic acid (1.9 mg, 0.0112 mmol), PyBrOP (10.4 mg, 0.0224 mmol), i-Pr$_2$NEt (6 µL, 0.0346 mmol) and DMF (150 µL) gave 9.8 mg (96%) of 41. $^1$H NMR (500 µMHz, DMSO-d$_6$) δ 8.40-8.29 (m, 4H), 7.29-7.20 (m, 8H), 7.19-7.05 (m, 12H), 3.81 (dt, J=17.3, 9.4 Hz, 2H), 3.64 (ddd, J=11.8, 8.3, 5.3 Hz, 2H), 3.47 (ddd, J=10.0, 9.2, 8.7 Hz, 2H), 3.25-3.10 (m, 4H), 3.08-3.02 (m, 2H), 2.85-2.79 (m, 4H), 2.02-1.86 (m, 6H), 1.71-1.57 (m, 4H), 1.28-1.09 (m, 12H). HRMS (ESI-TOF) m/z calcd for $C_{56}H_{63}N_6O_6$ [M+H]$^+$ 915.4804, found 915.4809.

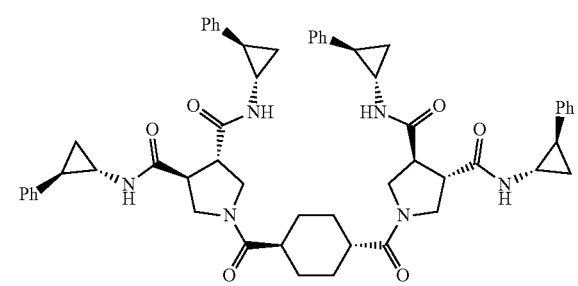 [SMILES: O=C(N[C@H]1C[C@@H]1c1ccccc1)[C@@H]1CN(C(=O)[C@H]2CC[C@H](C(=O)N3C[C@@H](C(=O)N[C@H]4C[C@@H]4c4ccccc4)[C@H](C(=O)N[C@H]4C[C@@H]4c4ccccc4)C3)CC2)C[C@H]1C(=O)N[C@H]1C[C@@H]1c1ccccc1]

42: (3S,3'S,4S,4'S)-1,1'-(trans-1,4-Cyclohexane-dicarbonyl)bis(N³,N⁴-bis((1S,2R)-2-phenyl-cyclopropyl)pyrrolidine-3,4-dicarboxamide)

The general procedure for linking diacid coupling was employed: pyrrolidine-3,4-dicarboxamide hydrochloride S-2 (9.5 mg, 0.0223 mmol), trans-1,4-cyclohexanedicarboxylic acid (1.7 mg, 0.0101 mmol), PyBrOP (9.5 mg, 0.0203 mmol), i-Pr$_2$NEt (6 μL, 0.0346 mmol) and DMF (150 μL) gave 8.7 mg (93%) of 42. $^1$H NMR (500 MHz, DMSO-d$_6$) δ 8.34 (dd, J=9.8, 4.3 Hz, 4H), 7.25 (td, J=7.5, 2.0 Hz, 8H), 7.19-7.08 (m, 12H), 3.82 (t, J=10.5 Hz, 2H), 3.66-3.59 (m, 2H), 3.47 (t, J=9.0 Hz, 2H), 3.21 (dd, J=11.7, 8.2 Hz, 2H), 3.18-3.11 (m, 2H), 3.04 (m, 2H), 2.86-2.79 (m, 4H), 2.42-2.33 (m, 2H), 1.92 (dq, J=9.1, 3.4 Hz, 4H), 1.71 (m, 4H), 1.43-1.33 (m, 3H), 1.15 (q, J=7.5, 6.6 Hz, 10H). HRMS (ESI-TOF) m/z calcd for C$_{56}$H$_{63}$N$_6$O$_6$ [M+H]$^+$ 915.4804, found 915.4800.

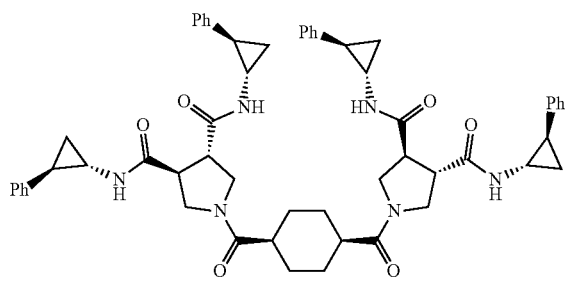 [SMILES: O=C(N[C@H]1C[C@@H]1c1ccccc1)[C@@H]1CN(C(=O)[C@H]2CC[C@@H](C(=O)N3C[C@@H](C(=O)N[C@H]4C[C@@H]4c4ccccc4)[C@H](C(=O)N[C@H]4C[C@@H]4c4ccccc4)C3)CC2)C[C@H]1C(=O)N[C@H]1C[C@@H]1c1ccccc1]

43: (3S,3'S,4S,4'S)-1,1'-(cis-1,4-Cyclohexane-dicarbonyl)bis(N³,N⁴-bis((1S,2R)-2-phenylcyclopropyl)-pyrrolidine-3,4-dicarboxamide)

The general procedure for linking diacid coupling was employed: pyrrolidine-3,4-dicarboxamide hydrochloride S-2 (9.8 mg, 0.0230 mmol), cis-1,4-cyclohexanedicarboxylic acid (1.8 mg, 0.0105 mmol), PyBrOP (9.8 mg, 0.0209 mmol), i-Pr$_2$NEt (6 μL, 0.0346 mmol) and DMF (150 μL) gave 9.0 mg (94%) of 43. $^1$H NMR (500 μMHz, DMSO-d$_6$) δ 8.34 (t, J=4.7 Hz, 4H), 7.25 (td, J=7.5, 1.6 Hz, 8H), 7.20-7.06 (m, 12H), 3.78 (dd, J=10.3, 8.1 Hz, 2H), 3.64 (dd, J=11.7, 8.5 Hz, 2H), 3.45 (t, J=9.2 Hz, 2H), 3.27-3.19 (m, 2H), 3.19-3.12 (m, 2H), 3.07-3.02 (m, 2H), 2.85-2.79 (m, 4H), 1.93 (ddd, J=11.2, 6.8, 3.3 Hz, 4H), 1.87-1.75 (m, 4H), 1.52-1.42 (m, 4H), 1.15 (ddd, J=8.9, 5.9, 3.1 Hz, 10H). HRMS (ESI-TOF) m/z calcd for C$_{56}$H$_{63}$N$_6$O$_6$ [M+H]$^+$ 915.4804, found 915.4803.

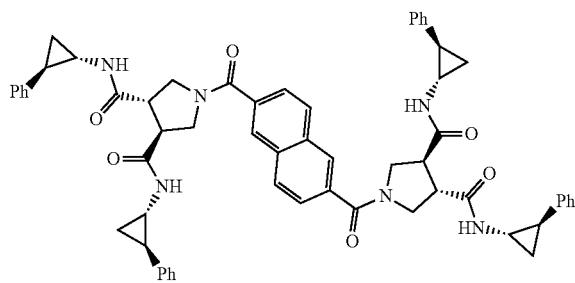 [SMILES: O=C(N[C@H]1C[C@@H]1c1ccccc1)[C@@H]1CN(C(=O)c2ccc3cc(C(=O)N4C[C@@H](C(=O)N[C@H]5C[C@@H]5c5ccccc5)[C@H](C(=O)N[C@H]5C[C@@H]5c5ccccc5)C4)ccc3c2)C[C@H]1C(=O)N[C@H]1C[C@@H]1c1ccccc1]

44: (3S,3'S,4S,4'S)-1,1'-(Naphthalene-2,6-dicarbonyl)bis(N³,N⁴-bis((1S,2R)-2-phenylcyclopropyl)-pyrrolidine-3,4-dicarboxamide)

The general procedure for linking diacid coupling was employed: pyrrolidine-3,4-dicarboxamide hydrochloride S-2 (15.3 mg, 0.0359 mmol), naphthalene-2,6-dicarboxylic acid (3.5 mg, 0.0163 mmol), PyBrOP (15.2 mg, 0.0327 mmol), i-Pr$_2$NEt (9 μL, 0.0522 mmol) and DMF (150 μL) gave 16.7 mg (97%) of 44. $^1$H NMR (500 MHz, DMSO-d$_6$) δ 8.46 (d, J=4.3 Hz, 2H), 8.28 (d, J=4.3 Hz, 2H), 8.15 (d, J=1.7 Hz, 2H), 8.07 (d, J=8.4 Hz, 2H), 7.69-7.63 (m, 2H), 7.27 (t, J=7.5 Hz, 4H), 7.21 (t, J=7.5 Hz, 4H), 7.19-7.08 (m, 8H), 7.04 (d, J=7.6 Hz, 4H), 3.86 (dd, J=12.0, 8.6 Hz, 2H), 3.70 (t, J=8.8 Hz, 2H), 3.57 (dd, J=11.2, 8.2 Hz, 4H), 3.23 (q, J=8.2 Hz, 2H), 3.12 (q, J=8.0 Hz, 2H), 2.87-2.84 (m, 2H), 2.78-2.74 (m, 2H), 2.00-1.97 (m, 2H), 1.86-1.79 (m, 2H), 1.20-1.15 (m, 8H). HRMS (ESI-TOF) m/z calcd for C$_{60}$H$_{59}$N$_6$O$_6$ [M+H]$^+$ 959.4491, found 959.4488.

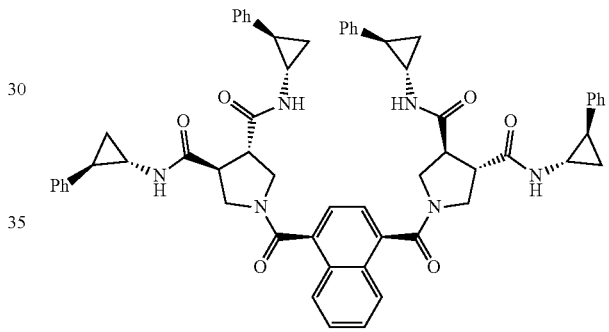

45: (3S,3'S,4S,4'S)-1,1'-(Naphthalene-1,4-dicarbonyl)bis(N³,N⁴-bis((1S,2R)-2-phenylcyclopropyl)-pyrrolidine-3,4-dicarboxamide)

The general procedure for linking diacid coupling was employed: pyrrolidine-3,4-dicarboxamide hydrochloride S-2 (16.3 mg, 0.0383 mmol), naphthalene-1,4-dicarboxylic acid (3.8 mg, 0.0174 mmol), PyBrOP (16.2 mg, 0.0348 mmol), i-Pr$_2$NEt (9 μL, 0.0522 mmol) and DMF (150 μL) gave 14.3 mg (86%) of 45. $^1$H NMR (500 MHz, DMSO-d$_6$) δ 8.42 (d, J=4.2 Hz, 2H), 8.19 (d, J=4.3 Hz, 2H), 7.85 (dd, J=6.4, 3.4 Hz, 2H), 7.59 (dd, J=6.5, 3.4 Hz, 2H), 7.52 (s, 2H), 7.27 (t, J=7.6 Hz, 4H), 7.21 (t, J=7.6 Hz, 4H), 7.19-7.08 (m, 8H), 7.06-7.00 (m, 4H), 3.93 (dd, J=11.5, 9.0 Hz, 2H), 3.68 (dd, J=12.0, 7.5 Hz, 2H), 3.39-3.35 (m, 2H), 3.25 (q, J=7.6 Hz, 2H), 3.22-3.15 (m, 2H), 3.08 (q, J=7.6 Hz, 2H), 2.87-2.84 (m, 2H), 2.76-2.68 (m, 2H), 2.02-1.96 (m, 2H), 1.79-1.74 (m, 2H), 1.21-0.98 (m, 8H). HRMS (ESI-TOF) m/z calcd for C$_{60}$H$_{59}$N$_6$O$_6$ [M+H]$^+$ 959.4491, found 959.4484.

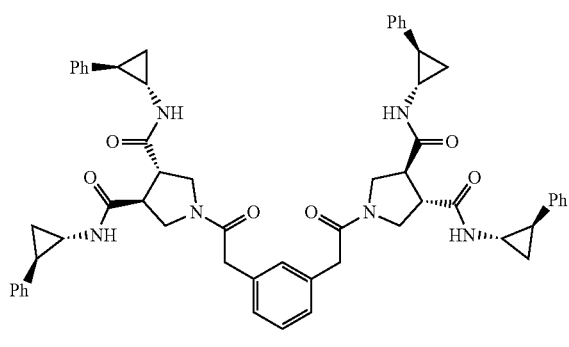 [SMILES: O=C(N[C@H]1C[C@@H]1c1ccccc1)[C@@H]1CN(C(=O)Cc2cccc(CC(=O)N3C[C@@H](C(=O)N[C@H]4C[C@@H]4c4ccccc4)[C@H](C(=O)N[C@H]4C[C@@H]4c4ccccc4)C3)c2)C[C@H]1C(=O)N[C@H]1C[C@@H]1c1ccccc1]

46: (3S,3'S,4S,4'S)-1,1'-((1,3-Phenylene)diacetyl)-bis(N³,N⁴-bis((1S,2R)-2-phenylcyclopropyl)-pyrrolidine-3,4-dicarboxamide)

The general procedure for linking diacid coupling was employed: pyrrolidine-3,4-dicarboxamide hydrochloride S-2 (15.7 mg, 0.0369 mmol), 1,3-phenylene-diacetic acid (3.3 mg, 0.0168 mmol), PyBrOP (15.6 mg, 0.0335 mmol), i-Pr₂NEt (9 µL, 0.0522 mmol) and DMF (150 µL) gave 1.8 mg (11%) of 46. ¹H NMR (500 MHz, DMSO-d₆) δ 8.38 (d, J=4.3 Hz, 2H), 8.35 (d, J=4.3 Hz, 2H), 7.25 (td, J=7.7, 1.5 Hz, 8H), 7.15 (t, J=7.4 Hz, 4H), 7.10-7.06 (m, 12H), 3.81 (dd, J=9.5, 8.0 Hz, 2H), 3.69 (dd, J=12.0, 8.0 Hz, 2H), 3.58 (s, 4H), 3.50 (t, J=9.2 Hz, 2H), 3.29-3.22 (m, 2H), 3.17 (q, J=8.2 Hz, 2H), 3.06 (q, J=8.3 Hz, 2H), 2.84-2.80 (m, 4H), 1.96-1.89 (m, 4H), 1.18-1.10 (m, 8H). HRMS (ESI-TOF) m/z calcd for $C_{58}H_{61}N_6O_6$ [M+H]⁺ 937.4647, found 937.4650.

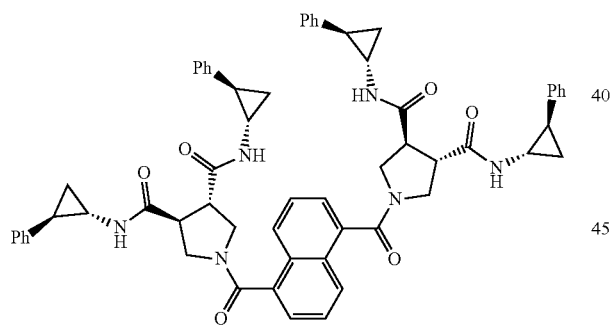

47: (3S,3'S,4S,4'S)-1,1'-(Naphthalene-1,5-dicarbonyl)bis(N³,N⁴-bis((1S,2R)-2-phenylcyclopropyl)-pyrrolidine-3,4-dicarboxamide)

The general procedure for linking diacid coupling was employed: pyrrolidine-3,4-dicarboxamide hydrochloride S-2 (12.8 mg, 0.0300 mmol), naphthalene-1,5-dicarboxylic acid (2.9 mg, 0.0137 mmol), PyBrOP (12.7 mg, 0.0273 mmol), i-Pr₂NEt (9 µL, 0.0522 mmol) and DMF (150 µL) gave 13.0 mg (99%) of 47. ¹H NMR (500 MHz, DMSO-d₆) δ 8.42 (d, J=4.2 Hz, 2H), 8.18 (d, J=4.2 Hz, 2H), 7.85 (d, J=8.3 Hz, 2H), 7.59 (dd, J=8.4, 7.0 Hz, 2H), 7.55-7.50 (m, 2H), 7.31-7.07 (m, 16H), 7.05-6.99 (m, 4H), 3.94 (t, J=10.4 Hz, 2H), 3.67 (dd, J=11.8, 7.3 Hz, 2H), 3.37-3.33 (m, 4H), 3.29-3.14 (m, 4H), 3.07 (q, J=7.6 Hz, 2H), 2.90-2.81 (m, 2H), 2.75-2.68 (m, 2H), 2.02-1.95 (m, 2H), 1.79-1.75 (m, 2H), 1.22-0.99 (m, 8H). HRMS (ESI-TOF) m/z calcd for $C_{60}H_{59}N_6O_6$ [M+H]⁺ 959.4491, found 959.4494.

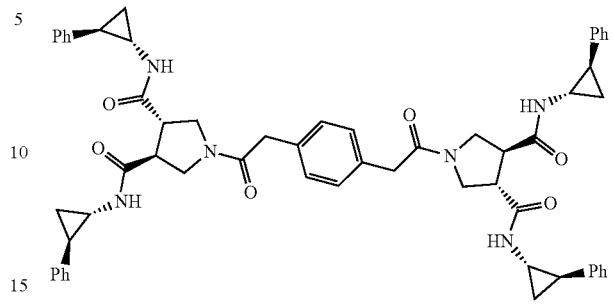

48: (3S,3'S,4S,4'S)-1,1'-((1,4-Phenylene)diacetyl)-bis(N³,N⁴-bis((1S,2R)-2-phenylcyclopropyl)-pyrrolidine-3,4-dicarboxamide)

The general procedure for linking diacid coupling was employed: pyrrolidine-3,4-dicarboxamide hydrochloride S-2 (11.2 mg, 0.0263 mmol), 1,4-phenylene-diacetic acid (2.3 mg, 0.0120 mmol), PyBrOP (11.1 mg, 0.0239 mmol), i-Pr₂NEt (9 µL, 0.0522 mmol) and DMF (150 µL) gave 9.9 mg (89%) of 48. ¹H NMR (500 MHz, DMSO-d₆) δ 8.39 (d, J=4.4 Hz, 2H), 8.34 (d, J=4.3 Hz, 2H), 7.25 (td, J=7.6, 2.8 Hz, 10H), 7.17-7.07 (m, 14H), 3.82 (t, J=9.0 Hz, 2H), 3.69 (dd, J=12.0, 8.5 Hz, 2H), 3.56 (s, 4H), 3.51 (dd, J=10.5, 8.5 Hz, 2H), 3.26 (dd, J=11.0, 8.0 Hz, 2H), 3.21-3.13 (m, 2H), 3.06 (t, J=8.4 Hz, 2H), 2.84-2.80 (m, 4H), 1.92 (dt, J=8.0, 4.0 Hz, 4H), 1.20-1.11 (m, 8H). HRMS (ESI-TOF) m/z calcd for $C_{58}H_{61}N_6O_6$ [M+H]⁺ 937.4647, found 937.4649.

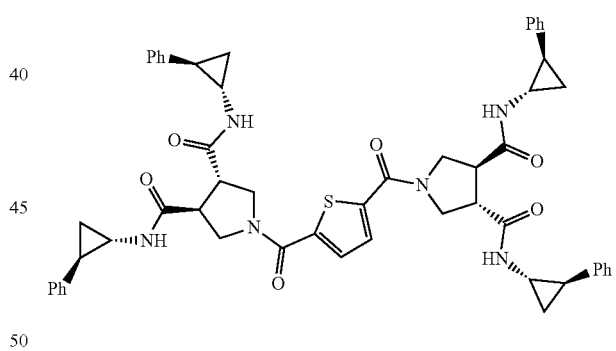

49: (3S,3'S,4S,4'S)-1,1'-(Thiophene-2,5-dicarbonyl)-bis(N³,N⁴-bis((1S,2R)-2-phenylcyclopropyl)-pyrrolidine-3,4-dicarboxamide)

The general procedure for linking diacid coupling was employed: pyrrolidine-3,4-dicarboxamide hydrochloride S-2 (17.8 mg, 0.0418 mmol), thiophene-2,5-dicarboxylic acid (3.3 mg, 0.0190 mmol), PyBrOP (17.7 mg, 0.0380 mmol), i-Pr₂NEt (10 µL, 0.0570 mmol) and DMF (300 µL) gave 9.5 mg (55%) of 49. ¹H NMR (500 MHz, DMSO-d₆) δ 8.42 (d, J=4.2 Hz, 2H), 8.37 (d, J=4.2 Hz, 2H), 7.56 (s, 2H), 7.29-7.20 (m, 8H), 7.20-7.06 (m, 12H), 4.09-4.01 (m, 3H), 3.86-3.74 (m, 3H), 3.57-3.46 (m, 2H), 3.21 (q, J=7.9 Hz, 2H), 3.15 (q, J=8.0 Hz, 2H), 2.84 (m, 4H), 1.95 (m, 4H), 1.21-1.11 (m, 8H). HRMS (ESI-TOF) m/z calcd for $C_{54}H_{55}N_6O_6S$ [M+H]⁺ 915.3898, found 915.3901.

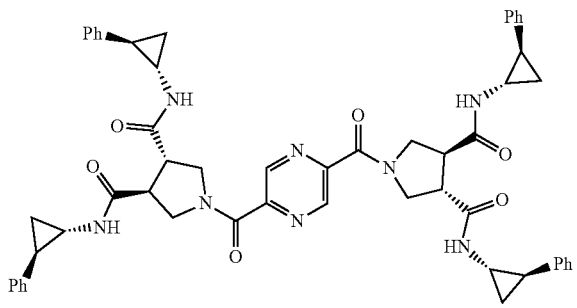 [SMILES: O=C(N[C@H]1C[C@@H]1c1ccccc1)[C@@H]1CN(C(=O)c2cnc(C(=O)N3C[C@@H](C(=O)N[C@H]4C[C@@H]4c4ccccc4)[C@H](C(=O)N[C@H]4C[C@@H]4c4ccccc4)C3)cn2)C[C@H]1C(=O)N[C@H]1C[C@@H]1c1ccccc1]

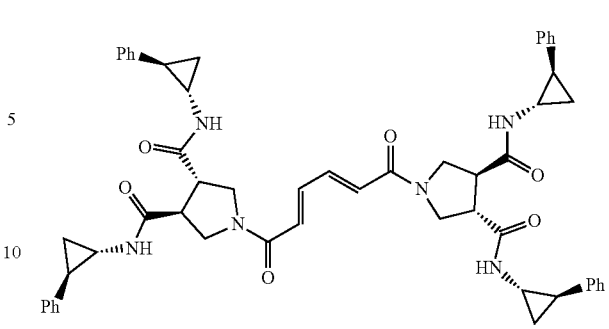

50: (3S,3'S,4S,4'S)-1,1'-(Pyrazine-2,5-dicarbonyl)-bis(N³,N⁴-bis((1S,2R)-2-phenylcyclopropyl)-pyrrolidine-3,4-dicarboxamide)

The general procedure for linking diacid coupling was employed: pyrrolidine-3,4-dicarboxamide hydrochloride S-2 (20.3 mg, 0.0477 mmol), pyrazine-2,5-dicarboxylic acid (3.6 mg, 0.0217 mmol), PyBrOP (20.2 mg, 0.0433 mmol), i-Pr₂NEt (11 µL, 0.0650 mmol) and DMF (300 µL) gave 14.3 mg (73%) of 50. $^1$H NMR (500 µMHz, DMSO-$d_6$) δ 8.96 (s, 2H), 8.46 (d, J=4.3 Hz, 2H), 8.38 (d, J=4.3 Hz, 2H), 7.30-7.20 (m, 8H), 7.19-7.04 (m, 12H), 4.01-3.95 (m, 2H), 3.94-3.85 (m, 2H), 3.75-3.66 (m, 2H), 3.62-3.54 (m, 2H), 3.20-3.12 (m, 4H), 2.85 (dd, J=7.8, 3.9 Hz, 2H), 2.80 (dq, J=6.7, 3.2, 2.5 Hz, 2H), 1.98-1.95 (m, 2H), 1.89 (td, J=7.9, 3.4 Hz, 2H), 1.22-1.09 (m, 8H). HRMS (ESI-TOF) m/z calcd for $C_{54}H_{55}N_8O_6$ [M+H]+ 911.4239, found 911.4239.

52: (3S,3'S,4S,4'S)-1,1'-((2E,4E)-Hexa-2,4-dienedioyl)-bis(N³,N⁴-bis((1S,2R)-2-phenylcyclopropyl)-pyrrolidine-3,4-dicarboxamide)

The general procedure for linking diacid coupling was employed: pyrrolidine-3,4-dicarboxamide hydrochloride S-2 (19.0 mg, 0.0446 mmol), trans,trans-muconic acid (2.9 mg, 0.0203 mmol), PyBrOP (18.9 mg, 0.0406 mmol), i-Pr₂NEt (9 µL, 0.0522 mmol) and DMF (300 µL) gave 17.5 mg (98%) of 52. $^1$H NMR (500 MHz, DMSO-$d_6$) δ 8.45 (dd, J=13.2, 4.1 Hz, 2H), 7.25 (t, J=7.6 Hz, 8H), 7.21 (dd, J=11.0, 3.0 Hz, 2H), 7.17-7.07 (m, 12H), 6.81-6.72 (m, 2H), 3.93-3.84 (m, 2H), 3.73 (dd, J=12.1, 8.2 Hz, 2H), 3.57 (dd, J=10.3, 7.8 Hz, 2H), 3.38-3.34 (m, 4H), 3.19 (q, J=8.0 Hz, 2H), 3.08 (q, J=8.0 Hz, 2H), 2.83 (dq, J=8.1, 4.4 Hz, 4H), 1.96-1.92 (m, 4H), 1.22-1.11 (m, 8H). HRMS (ESI-TOF) m/z calcd for $C_{54}H_{57}N_6O_6$ [M+H]⁺ 885.4334, found 885.4333.

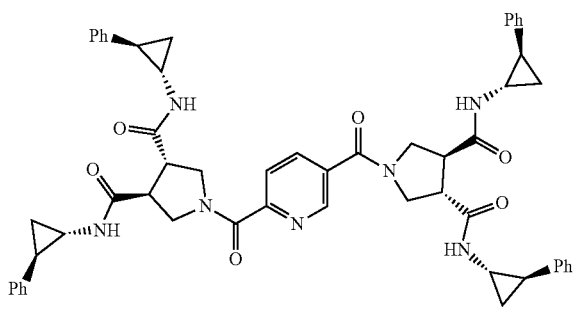 [SMILES: O=C(N[C@H]1C[C@@H]1c1ccccc1)[C@@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)nc2)C[C@H]1C(=O)N[C@H]1C[C@@H]1c1ccccc1]

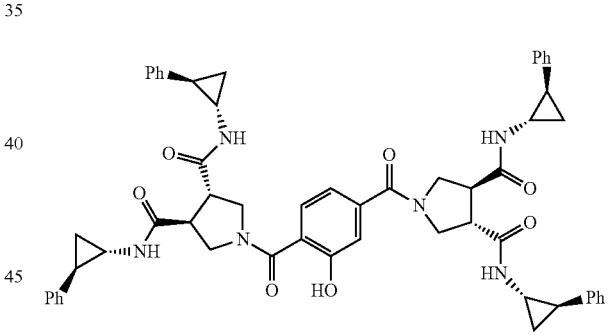

51: (3S,3'S,4S,4'S)-1,1'-(Pyridine-2,5-dicarbonyl)-bis(N³,N⁴-bis((1S,2R)-2-phenylcyclopropyl)-pyrrolidine-3,4-dicarboxamide)

The general procedure for linking diacid coupling was employed: pyrrolidine-3,4-dicarboxamide hydrochloride S-2 (20.1 mg, 0.0472 mmol), pyridine-2,5-dicarboxylic acid (3.6 mg, 0.0214 mmol), PyBrOP (20.0 mg, 0.0429 mmol), i-Pr₂NEt (10 µL, 0.0643 mmol) and DMF (300 µL) gave 19.4 mg (99%) of 51. $^1$H NMR (500 µMHz, DMSO-$d_6$) δ 8.72 (dd, J=2.1, 0.9 Hz, 1H), 8.42 (d, J=4.3 Hz, 2H), 8.34 (d, J=4.2 Hz, 1H), 8.28 (d, J=4.3 Hz, 1H), 8.07 (dd, J=8.1, 2.2 Hz, 1H), 7.81 (dd, J=8.1, 0.8 Hz, 1H), 7.29-7.20 (m, 8H), 7.18-7.04 (m, 12H), 3.99-3.95 (m, 1H), 3.91-3.80 (m, 2H), 3.69 (dd, J=10.4, 7.5 Hz, 2H), 3.54 (dd, J=11.0, 8.1 Hz, 3H), 3.16 (dq, J=21.2, 8.4 Hz, 4H), 2.85 (dq, J=8.2, 4.2 Hz, 2H), 2.78 (ddd, J=11.5, 6.5, 3.1 Hz, 2H), 1.97 (ddd, J=10.0, 7.0, 3.6 Hz, 2H), 1.92-1.83 (m, 2H), 1.21-1.06 (m, 8H). HRMS (ESI-TOF) m/z calcd for $C_{55}H_{56}N_7O_6$ [M+H]⁺910.4287, found 910.4287.

53: (3S,3'S,4S,4'S)-1,1'-(2-Hydroxyterephthaloyl)-bis(N³,N⁴-bis((1S,2R)-2-phenylcyclopropyl)pyrrolidine-3,4-dicarboxamide)

The general procedure for linking diacid coupling was employed: pyrrolidine-3,4-dicarboxamide hydrochloride S-2 (18.5 mg, 0.0434 mmol), 2-hydroxyterephthalic acid (3.6 mg, 0.0197 mmol), PyBrOP (18.4 mg, 0.0395 mmol), i-Pr₂NEt (9 µL, 0.0522 mmol) and DMF (300 µL) gave 18.0 mg (98%) of 53. $^1$H NMR (500 MHz, DMSO-$d_6$) δ 10.21 (s, 1H), 8.39 (d, J=5.2 Hz, 2H), 8.28 (d, J=5.2 Hz, 2H), 7.30-7.18 (m, 10H), 7.18-7.04 (m, 12H), 6.99-6.94 (m, 1H), 3.85-3.62 (m, 4H), 3.54-3.40 (m, 4H), 3.22-3.14 (m, 2H), 3.10 (q, J=8.7 Hz, 2H), 2.87-2.80 (m, 2H), 2.79-2.75 (m, 2H), 2.00-1.93 (m, 2H), 1.89-1.82 (m, 2H), 1.20-1.12 (m, 4H), 1.12-1.05 (m, 4H). HRMS (ESI-TOF) m/z calcd for $C_{56}H_{57}N_6O_7$ [M+H]⁺925.4283, found 925.4286.

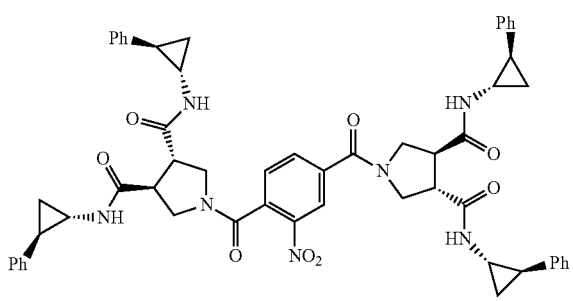 [SMILES: O=C(N[C@H]1C[C@@H]1c1ccccc1)[C@@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)c([N+](=O)[O-])c2)C[C@H]1C(=O)N[C@H]1C[C@@H]1c1ccccc1]

54: (3S,3'S,4S,4'S)-1,1'-(2-Nitroterephthaloyl)-bis(N³,N⁴-bis((1S,2R)-2-phenylcyclopropyl)pyrrolidine-3,4-dicarboxamide)

The general procedure for linking diacid coupling was employed: pyrrolidine-3,4-dicarboxamide hydrochloride S-2 (20.1 mg, 0.0472 mmol), 2-nitroterephthalic acid (4.5 mg, 0.0214 mmol), PyBrOP (20.0 mg, 0.0429 mmol), i-Pr₂NEt (10 μL, 0.0643 mmol) and DMF (300 μL) gave 20.2 mg (98%) of 54. ¹H NMR (500 MHz, DMSO-d₆) δ 8.43 (t, J=4.8 Hz, 2H), 8.30 (t, J=4.2 Hz, 2H), 8.26 (d, J=1.5 Hz, 1H), 7.97 (dd, J=7.8, 1.6 Hz, 1H), 7.67 (d, J=7.8 Hz, 1H), 7.30-7.18 (m, 8H), 7.18-7.03 (m, 12H), 3.89-3.80 (m, 2H), 3.69 (t, J=9.0 Hz, 1H), 3.60-3.45 (m, 4H), 3.29-3.08 (m, 5H), 2.85 (dq, J=8.3, 4.3 Hz, 2H), 2.81-2.73 (m, 2H), 2.01-1.94 (m, 2H), 1.85 (dddd, J=12.9, 9.4, 6.6, 3.3 Hz, 2H), 1.22-1.05 (m, 8H). HRMS (ESI-TOF) m/z calcd for $C_{56}H_{56}N_7O_8$ [M+H]⁺ 954.4185, found 954.4187.

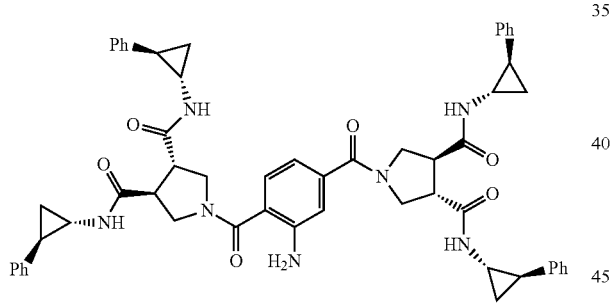

55: (3S,3'S,4S,4'S)-1,1'-(2-Amino-terephthaloyl)-bis(N³,N⁴-bis((1S,2R)-2-phenylcyclopropyl)-pyrrolidine-3,4-dicarboxamide)

Compound 54 (6.2 mg, 0.0065 mmol) was dissolved in anhydrous acetone (300 μL) at room temperature and zinc nanopowder (6.4 mg, 0.0975 mmol, 15 equiv) was added, forming a grey suspension. Saturated aqueous NH₄Cl (200 μL) was added dropwise, upon which the reaction solution becomes clear and salts precipitate. After 15 minutes, the mixture was diluted with EtOAc (5 mL) and aqueous 0.1 N HCl (5 mL). The aqueous phase was extracted with EtOAc (3 mL), and the combined extracts were washed with saturated aqueous NaHCO₃ (3 mL) and saturated aqueous NaCl (2 mL). The organic phase was dried over Na₂SO₄, filtered and concentrated to provide 5.0 mg (83%) of 55. ¹H NMR (500 MHz, DMSO-d₆) δ 8.39 (d, J=4.7 Hz, 2H), 8.29 (d, J=4.2 Hz, 2H), 7.24 (dt, J=15.5, 7.5 Hz, 10H), 7.19-7.03 (m, 13H), 5.53 (s, 2H), 3.74 (t, J=10.2 Hz, 2H), 3.68-3.63 (m, 2H), 3.52-3.39 (m, 4H), 3.17 (q, J=8.4 Hz, 2H), 3.12-3.05 (m, 2H), 2.87-2.81 (m, 2H), 2.80-2.75 (m, 2H), 1.98-1.93 (m, 2H), 1.89-1.84 (m, 2H), 1.20-1.06 (m, 8H). HRMS (ESI-TOF) m/z calcd for $C_{56}H_{58}N_7O_6$ [M+H]+ 924.4443, found 924.4444.

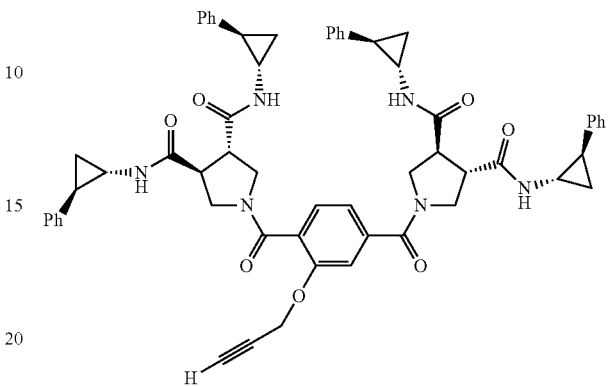

56: (3S,3'S,4S,4'S)-1,1'-(2-(Prop-2-yn-1-yloxy)-terephthaloyl)bis(N³,N⁴-bis((1S,2R)-2-phenylcyclo-propyl) pyrrolidine-3,4-dicarboxamide)

The general procedure for linking diacid coupling was employed: pyrrolidine-3,4-dicarboxamide hydrochloride S-2 (20.5 mg, 0.0481 mmol), 2-(prop-2-yn-1-yloxy)terephthalic acid (4.8 mg, 0.0219 mmol), PyBrOP (20.4 mg, 0.0438 mmol), i-Pr₂NEt (11 μL, 0.0656 mmol) and DMF (300 μL) gave 18.6 mg (89%) of 56. ¹H NMR (500 MHz, DMSO-d₆) δ 8.40 (dd, J=10.1, 4.3 Hz, 2H), 8.30-8.23 (m, 2H), 7.32-7.19 (m, 10H), 7.19-7.02 (m, 13H), 4.94-4.91 (m, 2H), 3.82-3.77 (m, 2H), 3.69-3.62 (m, 1H), 3.57-3.39 (m, 3H), 3.28-3.18 (m, 4H), 3.17 (s, 1H), 3.11 (t, J=7.8 Hz, 2H), 2.84 (dq, J=8.5, 4.3 Hz, 2H), 2.77 (dq, J=8.4, 4.1 Hz, 2H), 2.00-1.94 (m, 2H), 1.90-1.81 (m, 2H), 1.21-1.05 (m, 8H). HRMS (ESI-TOF) m/z calcd for $C_{59}H_{59}N_6O_7$ [M+H]⁺ 963.4440, found 963.4442.

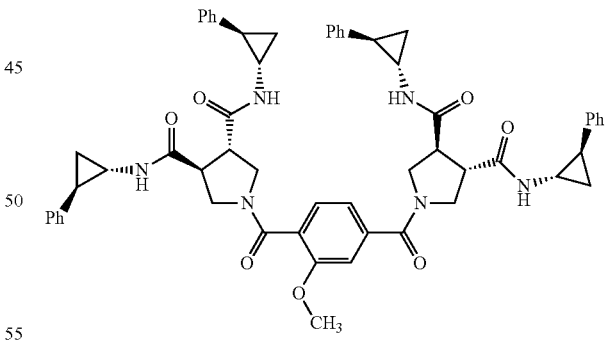

57: (3S,3'S,4S,4'S)-1,1'-(2-Methoxy-terephthaloyl)-bis(N³,N⁴-bis((1S,2R)-2-phenylcyclopropyl)-pyrrolidine-3,4-dicarboxamide)

The general procedure for linking diacid coupling was employed: pyrrolidine-3,4-dicarboxamide hydrochloride S-2 (23.3 mg, 0.0545 mmol), 2-methoxy-terephthalic acid (4.9 mg, 0.0248 mmol), PyBrOP (20.4 mg, 0.0438 mmol), i-Pr₂NEt (11 μL, 0.0656 mmol) and DMF (300 μL) gave 23.0 mg (98%) of 57. ¹H NMR (500 MHz, DMSO-d₆) δ

8.40 (dd, J=11.9, 4.3 Hz, 2H), 8.27 (d, J=4.2 Hz, 2H), 7.31-7.19 (m, 10H), 7.19-7.02 (m, 13H), 3.81 (s, 3H), 3.83-3.77 (m, 2H), 3.66 (t, J=2.5 Hz, 1H), 3.51 (td, J=10.5, 9.2, 3.7 Hz, 2H), 3.42 (t, J=9.8 Hz, 2H), 3.24-3.14 (m, 3H), 3.10 (t, J=8.1 Hz, 2H), 2.88-2.81 (m, 2H), 2.77 (dt, J=8.1, 4.2 Hz, 2H), 1.96 (dq, J=9.4, 3.4 Hz, 2H), 1.89-1.82 (m, 2H), 1.20-1.06 (m, 8H). HRMS (ESI-TOF) m/z calcd for $C_{57}H_{59}N_6O_7$ [M+H]+ 939.4440, found 939.4440.

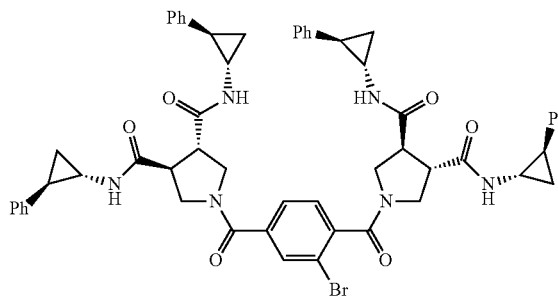

58: (3S,3'S,4S,4'S)-1,1'-(2-Bromoterephthaloyl)-bis(N³,N⁴-bis((1S,2R)-2-phenylcyclopropyl)pyrrolidine-3,4-dicarboxamide)

The general procedure for linking diacid coupling was employed: pyrrolidine-3,4-dicarboxamide hydrochloride S-2 (16.7 mg, 0.0392 mmol), 2-bromoterephthalic acid (4.4 mg, 0.0178 mmol), PyBrOP (16.6 mg, 0.0356 mmol), i-Pr₂NEt (10 µL, 0.0535 mmol) and DMF (250 µL) gave 13.7 mg (78%) of 58. ¹H NMR (500 MHz, DMSO-d₆) δ 8.41 (dd, J=3.5 Hz, 2H), 8.29 (dd, J=13.8, 4.2 Hz, 2H), 7.78 (d, J=1.5 Hz, 1H), 7.57 (dd, J=7.8, 1.5 Hz, 1H), 7.43 (d, J=7.8 Hz, 1H), 7.30-7.19 (m, 8H), 7.19-7.02 (m, 12H), 3.85 (dd, J=12.0, 8.5 Hz, 2H), 3.78 (dd, J=11.9, 8.5 Hz, 2H), 3.65 (dd, J=10.3, 7.8 Hz, 1H), 3.55-3.39 (m, 4H), 3.25-3.06 (m, 6H), 2.84 (dq, J=8.4, 4.2 Hz, 2H), 2.77 (q, J=5.4 Hz, 2H), 1.96 (dq, J=9.2, 3.3 Hz, 2H), 1.86 (td, J=7.5, 3.4 Hz, 2H), 1.22-1.06 (m, 8H). HRMS (ESI-TOF) m/z calcd for $C_{56}H_{56}BrN_6O_6$ [M+H]+ 987.3439, found 987.3441.

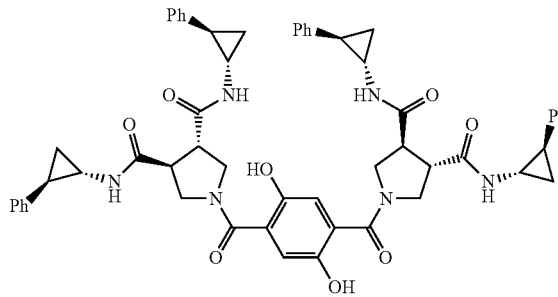

59: (3S,3'S,4S,4'S)-1,1'-(2,5-Dihydroxy-terephthaloyl)bis(N³,N⁴-bis((1S,2R)-2-phenylcyclo-propyl)-pyrrolidine-3,4-dicarboxamide)

The general procedure for linking diacid coupling was employed: pyrrolidine-3,4-dicarboxamide hydrochloride S-2 (21.2 mg, 0.0498 mmol), 2,5-dihydroxyterephthalic acid (4.5 mg, 0.0226 mmol), PyBrOP (21.1 mg, 0.0452 mmol), i-Pr₂NEt (12 µL, 0.0679 mmol) and DMF (250 µL) gave 19.0 mg (89%) of 59. ¹H NMR (600 µMHz, DMSO-d₆) δ 9.47 (s, 1H), 8.86 (s, 1H), 8.39 (d, J=4.2 Hz, 2H), 8.30 (d, J=4.2 Hz, 2H), 7.31-7.19 (m, 8H), 7.19-7.02 (m, 12H), 6.66 (s, 1H), 6.36 (s, 1H), 3.84-3.73 (m, 2H), 3.54 (q, J=9.0 Hz, 2H), 3.45-3.34 (m, 3H), 3.23-3.13 (m, 3H), 3.09 (q, J=8.9 Hz, 2H), 2.83 (dt, J=7.7, 3.9 Hz, 2H), 2.80-2.73 (m, 2H), 1.96 (dq, J=8.5, 4.9, 4.0 Hz, 2H), 1.86 (td, J=8.2, 7.6, 3.2 Hz, 2H), 1.21-1.05 (m, 8H). HRMS (ESI-TOF) m/z calcd for $C_{56}H_{57}N_6O_8$ [M+H]⁺ 941.4232, 941.4231.

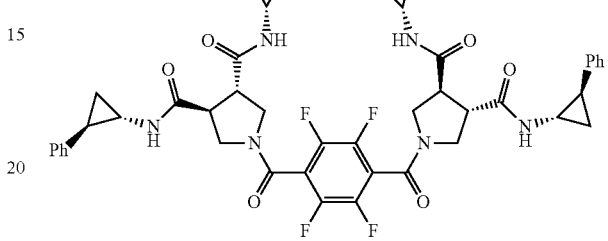

60: (3S,3'S,4S,4'S)-1,1'-(Perfluoroterephthaloyl)-bis(N³,N⁴-bis((1S,2R)-2-phenylcyclopropyl)pyrrolidine-3,4-dicarboxamide)

The general procedure for linking diacid coupling was employed: pyrrolidine-3,4-dicarboxamide hydrochloride S-2 (17.4 mg, 0.0408 mmol), tetrafluoroterephthalic acid (4.4 mg, 0.0186 mmol), PyBrOP (17.3 mg, 0.0371 mmol), i-Pr₂NEt (10 µL, 0.0557 mmol) and DMF (250 µL) gave 13.7 mg (75%) of 60. ¹H NMR (600 MHz, DMSO-d₆) δ 8.44 (d, J=4.2 Hz, 2H), 8.38 (d, J=4.5 Hz, 2H), 7.30-7.20 (m, 8H), 7.19-7.04 (m, 12H), 3.85 (dd, J=12.2, 8.5 Hz, 2H), 3.72 (d, J=7.3 Hz, 2H), 3.55 (d, J=10.2 Hz, 2H), 3.45-3.36 (m, 2H), 3.25-3.10 (m, 4H), 2.84 (ddt, J=7.5, 6.1, 3.7 Hz, 2H), 2.82-2.77 (m, 2H), 1.97 (dt, J=8.4, 3.8 Hz, 2H), 1.91-1.85 (m, 2H), 1.22-1.09 (m, 8H). HRMS (ESI-TOF) m/z calcd for $C_{56}H_{53}F_4N_6O_6$ [M+H]⁺ 981.3957, found 981.3957.

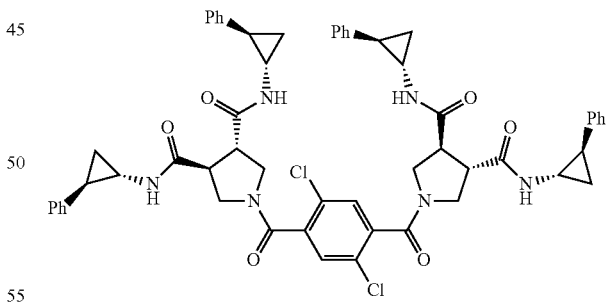

61: (3S,3'S,4S,4'S)-1,1'-(2,5-Dichloroterephthaloyl)-bis(N³,N⁴-bis((1S,2R)-2-phenylcyclopropyl)pyrrolidine-3,4-dicarboxamide)

The general procedure for linking diacid coupling was employed: pyrrolidine-3,4-dicarboxamide hydrochloride S-2 (15.4 mg, 0.0362 mmol), 2,5-dichloroterephthalic acid (3.9 mg, 0.0164 mmol), PyBrOP (15.3 mg, 0.0329 mmol), i-Pr₂NEt (10 µL, 0.0493 mmol) and DMF (250 µL) gave 14.0 mg (87%) of 61. ¹H NMR (500 MHz, DMSO-d₆) δ

8.42 (d, J=4.2 Hz, 2H), 8.35-8.27 (m, 2H), 7.68 (s, 2H), 7.27-7.20 (m, 8H), 7.19-7.03 (m, 12H), 3.83 (dd, J=12.0, 8.4 Hz, 2H), 3.47 (dd, J=11.9, 8.0 Hz, 4H), 3.28-3.12 (m, 6H), 2.84 (dd, J=7.7, 3.9 Hz, 2H), 2.79-2.74 (m, 2H), 1.98-1.93 (m, 2H), 1.88 (td, J=8.0, 3.4 Hz, 2H), 1.22-1.05 (m, 8H). HRMS (ESI-TOF) m/z calcd for $C_{56}H_{55}Cl_2N_6O_6$ [M+H]$^+$ 977.3555, found 977.3557.

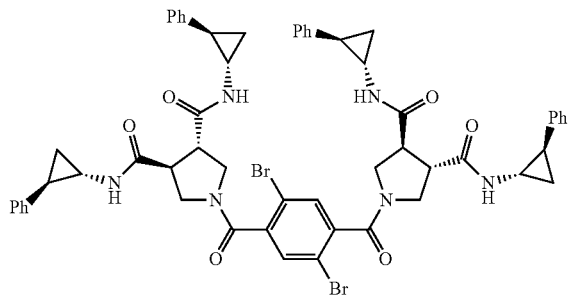 [SMILES: O=C(N[C@H]1C[C@@H]1c1ccccc1)[C@@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)c(Br)c2)C[C@H]1C(=O)N[C@H]1C[C@@H]1c1ccccc1]

62: (3S,3'S,4S,4'S)-1,1'-(2,5-Dibromoterephthaloyl)-bis($N^3,N^4$-bis((1S,2R)-2-phenylcyclopropyl)pyrrolidine-3,4-dicarboxamide)

The general procedure for linking diacid coupling was employed: pyrrolidine-3,4-dicarboxamide hydrochloride S-2 (18.0 mg, 0.0423 mmol), 2,5-dibromoterephthalic acid (6.2 mg, 0.0192 mmol), PyBrOP (18.0 mg, 0.0384 mmol), i-Pr$_2$NEt (10 µL, 0.0576 mmol) and DMF (250 µL) gave 17.4 mg (85%) of 62. $^1$H NMR (500 MHz, DMSO-d$_6$) δ 8.41 (d, J=4.2 Hz, 2H), 8.32 (d, J=4.2 Hz, 2H), 7.76 (s, 2H), 7.27-7.20 (m, 8H), 7.19-7.03 (m, 12H), 3.83 (dd, J=11.9, 8.3 Hz, 2H), 3.46 (t, J=10.1 Hz, 4H), 3.24-3.13 (m, 6H), 2.84 (dd, J=7.6, 4.1 Hz, 2H), 2.76 (t, J=5.5 Hz, 2H), 1.96 (td, J=6.5, 3.4 Hz, 2H), 1.89 (td, J=7.7, 3.2 Hz, 2H), 1.14 (m, 8H). HRMS (ESI-TOF) m/z calcd for $C_{56}H_{55}Br_2N_6O_6$ [M+H]$^+$ 1065.2544, found 1065.2545.

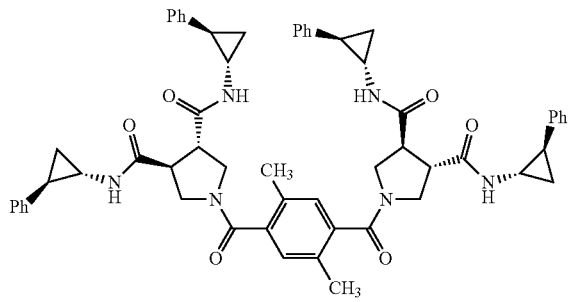 [SMILES: Cc1cc(C(=O)N2C[C@@H](C(=O)N[C@H]3C[C@@H]3c3ccccc3)[C@H](C(=O)N[C@H]3C[C@@H]3c3ccccc3)C2)c(C)cc1C(=O)N1C[C@@H](C(=O)N[C@H]2C[C@@H]2c2ccccc2)[C@H](C(=O)N[C@H]2C[C@@H]2c2ccccc2)C1]

63: (3S,3'S,4S,4'S)-1,1'-(2,5-Dimethylterephthaloyl)-bis($N^3,N^4$-bis((1S,2R)-2-phenylcyclopropyl) pyrrolidine-3,4-dicarboxamide)

The general procedure for linking diacid coupling was employed: pyrrolidine-3,4-dicarboxamide hydrochloride S-2 (20.1 mg, 0.0472 mmol), 2,5-dimethylterephthalic acid (4.2 mg, 0.0214), PyBrOP (20.0 mg, 0.0429 mmol), i-Pr$_2$NEt (11 µL, 0.0643 mmol) and DMF (250 µL) gave 11.0 mg (55%) of 63. $^1$H NMR (600 µMHz, DMSO-d$_6$) δ 8.40 (d, J=4.3 Hz, 2H), 8.27 (d, J=4.3 Hz, 2H), 7.27-7.21 (m, 8H), 7.18-7.03 (m, 14H), 3.79 (dd, J=11.8, 8.4 Hz, 2H), 3.50 (dd, J=11.9, 7.1 Hz, 2H), 3.38 (dd, J=10.5, 7.5 Hz, 2H), 3.20-3.16 (m, 4H), 3.09 (q, J=7.5 Hz, 2H), 2.83 (dq, J=8.6, 4.4 Hz, 2H), 2.79-2.73 (m, 2H), 2.17 (s, 6H), 1.95 (ddd, J=9.7, 6.5, 3.3 Hz, 2H), 1.85 (ddd, J=9.5, 6.6, 3.4 Hz, 2H), 1.23-1.04 (m, 8H). HRMS (ESI-TOF) m/z calcd for $C_{58}H_{61}N_6O_6$ [M+H]$^+$937.4647, found 937.4650.

Diprovocim-2: Side Chain Replacement Analogues

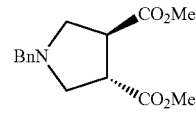

S-27: Dimethyl trans-1-Benzylpyrrolidine-3,4-dicarboxylate

A solution of dimethyl fumarate (2.4 g, 16.7 mmol, 1 equiv) and N-benzyl-1-methoxy-N-((trimethylsilyl)methyl) methanamine (4.8 g, 16.7 mmol, 1 equiv) in 40 mL MeCN was treated with LiF (640 mg, 25 mmol, 1.25 equiv) in one portion. The reaction solution was sonicated for 18 hours. The reaction suspension was poured into EtOAc (100 mL) and H$_2$O (150 mL) and the aqueous layer was extracted with EtOAc (2×100 mL), washed with saturated aqueous NaCl and dried with Na$_2$SO$_4$. The crude product was purified by flash column chromatography (SiO$_2$, 10-20% EtOAc/hexanes) to provide S-27 as a yellow oil (4.3 µg, 83%). $^1$H NMR (400 µMHz, CDCl$_3$) δ 7.40-7.27 (m, 5H), 3.70 (s, 6H), 3.61 (s, 2H), 3.51-3.40 (m, 2H), 2.96-2.85 (m, 2H), 2.84-2.72 (m, 2H).

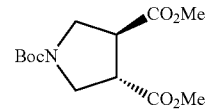

S-28: 1-(tert-Butyl) 3,4-Dimethyl trans-Pyrrolidine-1,3,4-tricarboxylate

A solution of S-27 in MeOH (175 mL) was treated with Pd(OH)$_2$/C (20% weight, 450 mg) and Boc$_2$O (6.65 g, 30.5 mmol, 1.75 equiv), and spatula tip of 4-dimethylaminopyridine (DMAP). The reaction solution was purged with H$_2$ and stirred under 1 atm of H$_2$ for 16 hours. The reaction mixture was filtered through a pad of Celite® and eluted with Et$_2$O. The crude product was purified by flash column chromatography (SiO$_2$, 10-25% EtOAc/hexanes) to provide S-28 as a clear oil (4.0 g, 80%). $^1$H NMR (400 MHz, CDCl$_3$) δ 3.79 (m, 2H), 3.73 (s, 6H), 3.52 (m, 2H), 3.41 (m, 2H).

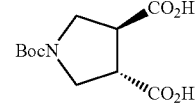

S-29: trans-1-(tert-Butoxycarbonyl)-pyrrolidine-3,4-dicarboxylic Acid

A solution of S-28 in THF/MeOH/H$_2$O (4:1:1, 150 mL) was treated with solid LiOH H$_2$O. The reaction mixture was stirred at 23° C. for 3 hours before being poured into EtOAc (100 mL), washed with aqueous 0.5 M aqueous HCl (100 mL), extracted with EtOAc (2×100 mL), washed with saturated aqueous NH$_4$Cl and dried with Na$_2$SO$_4$. The crude product was isolated as a white solid (S-29, 3.58 g, 99%) and used without additional purification. $^1$H NMR (400 MHz, methanol-d$_4$) δ 3.70-3.63 (m, 2H), 3.57-3.51 (m, 2H), 3.37 (m, 2H), 1.47 (s, 9H)

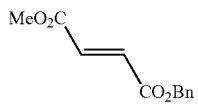

S-30: Benzyl Methyl Fumarate

A solution of methyl fumarate (4.0 g, 30.75 mmol) in 80 mL of DMF at 23° C. was treated with solid K$_2$CO$_3$ (5.1 g, 36.9 mmol, 1.2 equiv) followed by BnBr (3.68 mL, 30.75, 1 equiv). The reaction mixture was stirred at 23° C. for 4 hours after which it was poured into EtOAc (200 mL) and washed with aqueous 0.5 M HCl (200 mL). The product was extracted in EtOAc (3×200 mL), washed with saturated aqueous NaCl and dried with Na$_2$SO$_4$. The crude product was purified by flash column chromatography (SiO$_2$, 10% EtOAc/hexanes) to provide S-30 as a white solid (6.02 g, 89% yield). $^1$H NMR (400 MHz, methanol-d$_4$) δ 7.41-7.28 (m, 5H), 6.84 (s, 2H), 5.22 (s, 2H), 3.77 (s, 3H).

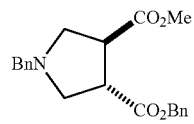

S-31: 3-Benzyl 4-Methyl trans-1-Benzylpyrrolidine-3,4-dicarboxylate

A solution of S-30 (4.4 g, 20 mmol, 1 equiv) and N-benzyl-1-methoxy-N-((trimethylsilyl)-methyl)-methanamine (4.8 g, 20 mmol, 1 equiv) in 40 mL MeCN was treated with LiF (640 mg, 25 mmol, 1.25 equiv) in one portion. The reaction mixture was sonicated 16 hours. The reaction suspension was poured into EtOAc (100 mL) and H$_2$O (150 mL) and the aqueous layer was extracted with EtOAc (2×100 mL), washed with saturated aqueous NaCl and dried with Na$_2$SO$_4$. The crude product was purified by flash column chromatography (SiO$_2$, 10-20% EtOAc/hexanes) to provide S-31 as a yellow oil (16.6 g, 83%). $^1$H NMR (400 μMHz, CDCl$_3$) δ 7.26 (m, 10H), 5.12 (s, 2H), 3.66 (s, 3H), 3.58 (s, 2H), 3.47 (t, J=5.7 Hz, 2H), 2.95-2.71 (m, 4H).

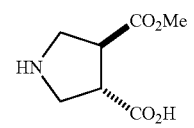

S-32: trans-4-(Methoxycarbonyl)-pyrrolidine-3-carboxylic Acid

A solution of S-31 in 120 mL of MeOH was treated with Pd(OH)$_2$/C (425 mg). The reaction vessel was purged with H$_2$ and the reaction suspension was stirred under H$_2$ (1 atm) for 16 hours. The reaction mixture was filtered through a pad of Celite® and concentrated to provide S-32 as a viscous oil (2.07 g, 99%), which was used without further purification. 1H NMR (400 MHz, methanol-d$_4$) δ 3.78 (s, 3H), 3.66-3.57 (m, 4H), 3.57-3.47 (m, 2H).

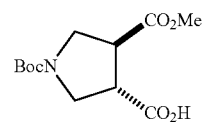

S-33: trans-1-(tert-Butoxycarbonyl)-4-(methoxycarbonyl) pyrrolidine-3-carboxylic Acid A suspension of S-32 (50 mg, 0.27 mmol) in dioxane (0.6 mL) was treated with Boc$_2$O (87 mg, 0.40 mmol, 1.5 equiv) and NEt$_3$ (0.74 mL, 0.53 mmol, 2 equiv). The reaction mixture was stirred at 23° C. for 40 hours before being diluted with EtOAc (5 mL) and washed with aqueous 15% citric acid (5 mL). The aqueous layer was extracted with EtOAc (3×5 mL), washed with saturated aqueous NaCl and dried with Na$_2$SO$_4$. The crude product was purified by flash column chromatography (SiO$_2$, 10% MeOH/CH$_2$Cl$_2$) to provide S-33 as a white solid (50 mg, 68%). $^1$H NMR (400 μMHz, CDCl$_3$) δ 3.72 (s, 3H), 3.68 (m, 2H), 3.54 (m, 2H), 3.39 (m, 2H), 1.43 (s, 9H).

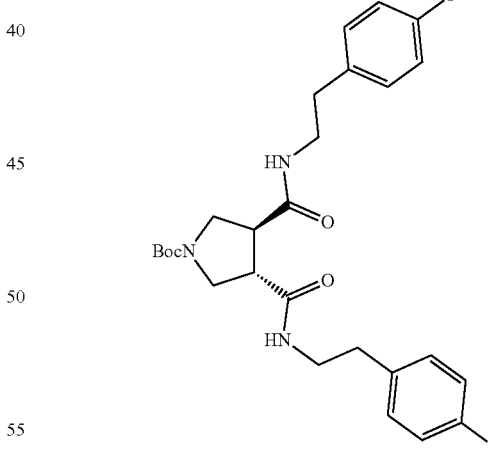

65: tert-Butyl trans-3,4-Bis((4-fluorophenethyl)-carbamoyl)pyrrolidine-1-carboxylate A solution of S-29 (260 mg, 1 mmol, 1 equiv), EDCI.HCl (671 mg, 3.5 mmol, 3.5 equiv), and 2-(4-fluorophenyl)ethan-1-amine hydrochloride (386 mg, 2.2 mmol, 2.2 equiv) in 10 mL DMF was treated with i-Pr$_2$NEt (1.22 mL, 7 mmol, 7 equiv). The reaction mixture was stirred at 23° C. for 24 hours before being poured into EtOAc (20 mL), washed with aqueous 1 M HCl (50 mL), extracted with EtOAc (2×30 mL), washed with saturated aqueous NaCl and dried with $Na_2SO_4$. The crude product was purified by flash column chromatography ($SiO_2$, 75% EtOAc/hexanes) to provide 65 as a white solid (80 mg, 16%). $^1$H NMR (400 MHz, $CDCl_3$) δ 7.10 (d, J=6.5 Hz, 4H), 6.98 (t, J=8.5 Hz, 4H), 6.23 (s, 1H), 6.00 (s, 1H), 3.83-3.67 (m, 1H), 3.60 (t, J=9.9 Hz, 1H), and concentrated. This process was repeated (3×3 mL THF and 3×3 mL $Et_2O$) to provide S-34 as a white solid (78 mg, 98%) that was used without additional purification. $^1$H NMR (500 MHz, methanol-$d_4$) δ 8.24 (b, 1H), 7.22 (dd, J=8.5, 5.4 Hz, 4H), 7.01 (t, J=8.7 Hz, 4H), 3.51 (dd, J=11.6, 7.0 Hz, 2H), 3.48-3.35 (m, 6H), 3.20 (t, J=5.4 Hz, 2H), 2.79 (td, J=7.2, 2.8 Hz, 4H).

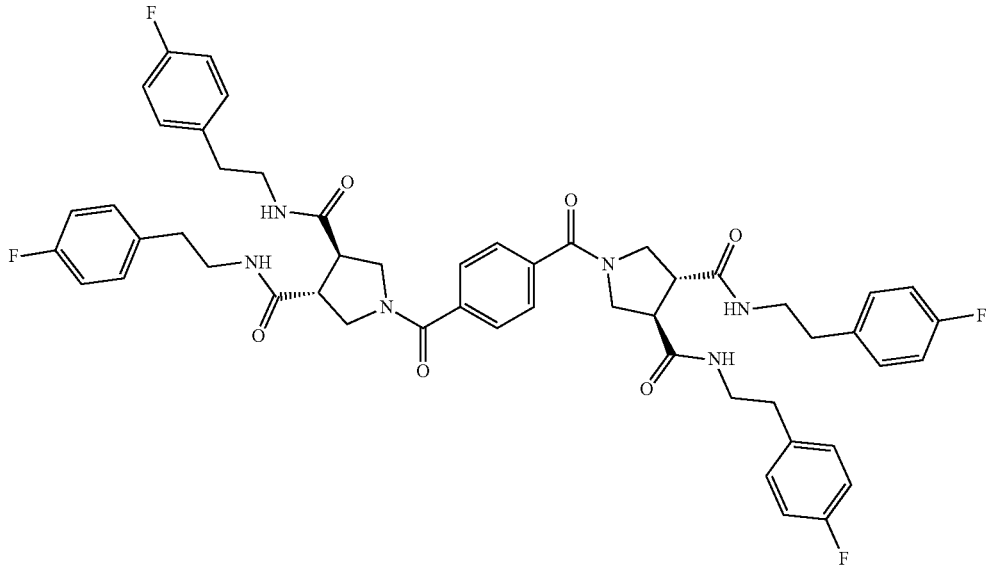

3.55-3.44 (m, 2H), 3.45-3.26 (m, 4H), 3.17 (dd, J=17.7, 7.8 Hz, 1H), 3.01 (t, J=9.9 Hz, 1H), 2.75 (t, J=7.0 Hz, 4H), 1.44 (s, 9H)

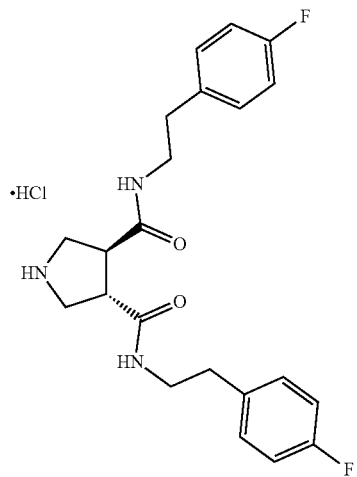 [SMILES: O=C(NCCc1ccc(F)cc1)[C@@H]1CNC[C@H]1C(=O)NCCc1ccc(F)cc1 ; Cl]

S-34: trans-$N^3$,$N^4$-Bis(4-fluorophenethyl)pyrrolidine-3,4-dicarboxamide Hydrochloride A solution of tert-butyl trans-3,4-bis((4-fluorophenethyl)carbamoyl)pyrrolidine-1-carboxylate (65; 80 mg, 0.16 mmol) in 4 M HCl in dioxane (2 mL) was stirred at 23° C. for 3 hours during which time a white solid precipitated out of the reaction mixture. The solvent was removed under a stream of $N_2$ and the crude product taken up in THF (3 mL)

69: 1,1'-Terephthaloylbis($N^3$,$N^4$-bis(4-fluoro-phenethyl)-yrrolidine-trans-3,4-dicarboxamide)

A solution of trans-$N^3$,$N^4$-bis(4-fluorophenethyl)-pyrrolidine-3,4-dicarboxamide hydrochloride (S-34; 78 mg, 0.16 mmol, 2.5 equiv) in DMF (1.6 mL) was treated with terephthalic acid (benzene-1,4-dicarboxylic acid, 10.5 mg, 0.064 mmol, 1 equiv), PyBrOP (75 mg, 0.16 mmol, 2.5 equiv), and i-$Pr_2$NEt (56 μL, 0.32 mmol, 5 equiv). The reaction mixture was placed on a mechanical shaker for 72 hours after which the mixture was diluted with EtOAc (3 mL) and washed with aqueous 0.5 N HCl (2×3 mL). The aqueous phase was extracted with EtOAc (1×3 mL). The combined organic phases were washed with saturated aqueous $NaHCO_3$ (10 mL) and saturated aqueous NaCl (10 mL). The organic phase was dried over $Na_2SO_4$, decanted and concentrated. The product was purified by trituration with cold (0° C.) 1:1 $Et_2O$/EtOAc (3×5 mL), decanting off the liquid phase to provide 113 mg (75%) of 69 as a white solid. $^1$H NMR (600 MHz, HFIP-$d_2$) δ 7.63-7.57 (m, 4H), 7.19 (h, J=5.2, 4.7 Hz, 4H), 7.11 (qd, J=8.2, 5.3, 4.8 Hz, 4H), 7.08-7.01 (m, 4H), 6.95 (dq, J=8.9, 4.7 Hz, 4H), 4.06 (dd, J=12.5, 8.4 Hz, 2H), 3.69 (t, J=11.0 Hz, 4H), 3.64-3.53 (m, 4H), 3.53-3.39 (m, 6H), 3.23 (ddt, J=31.9, 17.9, 7.3 Hz, 4H), 2.82 (dt, J=10.6, 6.8 Hz, 4H), 2.74 (dq, J=10.2, 6.3 Hz, 4H). HRMS (ESI-TOF) m/z calcd for $C_{52}H_{52}F_4N_6O_6[M+H]^+$ 933.3957, found 933.3960.

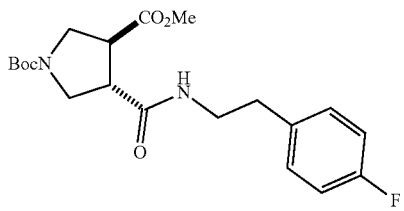 [SMILES: COC(=O)[C@@H]1CN(C(=O)OC(C)(C)C)C[C@H]1C(=O)NCCc1ccc(F)cc1]

S-35: 1-(tert-Butyl) 3-Methyl trans-4-((4-Fluoro-phenethyl)carbamoyl)pyrrolidine-1,3-dicarboxylate A solution of 2-(4-fluorophenyl)ethan-1-amine hydrochloride (263 mg, 1.5 mmol, 1.5 equiv) and PyBOP (780 mg, 1.5 mmol, 1.5 equiv) in DMF (9.5 mL) was treated with trans-1-(tert-butoxycarbonyl)-4-(methoxycarbonyl)pyrrolidine-3-carboxylic acid (S-33; 0.55 mL of a 0.5 M solution in DMF, 1 mmol, 1 equiv) followed by i-Pr$_2$NEt (0.525 mL, 3 mmol, 3 equiv). The reaction mixture was stirred at 23° C. for 48 hours. The reaction mixture was diluted with EtOAc (20 mL) and washed with aqueous 1 M HCl (50 mL). The aqueous layer was extracted with EtOAc (2×50 mL), washed with a saturated aqueous solution of NaHCO$_3$ (150 mL), washed with saturated aqueous NaCl, and dried with Na$_2$SO$_4$. The crude product was purified by flash column chromatography (SiO$_2$, 75% EtOAc/hexanes) to provide S-35 as a tan solid (161 mg, 41%). $^1$H NMR (400 µMHz, CDCl$_3$) δ 7.12 (t, J=6.8 Hz, 2H), 6.97 (t, J=8.4 Hz, 2H), 6.10 (d, J=43.0 Hz, 1H), 3.82 (m, 2H), 3.68 (s, 3H), 3.57-3.42 (m, 2H), 3.35 (m, 2H), 3.31-3.22 (m, 1H), 3.13-3.02 (m, 1H), 2.78 (t, J=7.0 Hz, 2H), 1.50-1.36 (m, 9H).

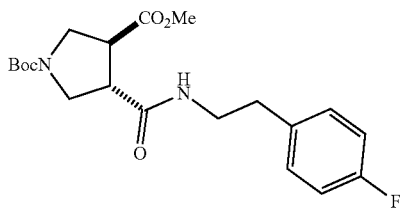 [SMILES: COC(=O)[C@@H]1CN(C(=O)OC(C)(C)C)C[C@H]1C(=O)NCCc1ccc(F)cc1]

S-36: trans-1-(tert-Butoxycarbonyl)-4-((4-fluoro-phenethyl)carbamoyl)pyrrolidine-3-carboxylic Acid solid LiOH.H$_2$O (222 mg, 5.3 mmol, 5 equiv) was added to a solution of 1-(tert-butyl) 3-methyl trans-4-((4-fluoro-phenethyl)carbamoyl)pyrrolidine-1,3-dicarboxylate (S-35; 419 mg, 1.06 mmol) in THF:MeOH:H$_2$O (11 mL, 4:1:1) at 23° C. The reaction mixture was stirred at 23° C. for 2.5 hours. The reaction mixture was poured into 50 mL EtOAc and quenched with the addition of aqueous 1 M HCl (50 mL). The aqueous layer was extracted with EtOAc (2×50 mL), washed with saturated aqueous NaCl, and dried with Na$_2$SO$_4$. The crude product was isolated as a white solid (S-36; 400 mg, 99%) and was advanced without additional purification. $^1$H NMR (400 MHz, methanol-d$_4$) δ 6.99-6.86 (m, 2H), 6.70 (t, J=9.9 Hz, 2H), 3.43 (dd, J=10.8, 8.5 Hz, 1H), 3.31 (t, J=6.9 Hz, 2H), 3.28-3.05 (m, 4H), 2.90 (t, J=8.3 Hz, 1H), 2.57-2.40 (m, 2H), 1.17 (s, 9H).

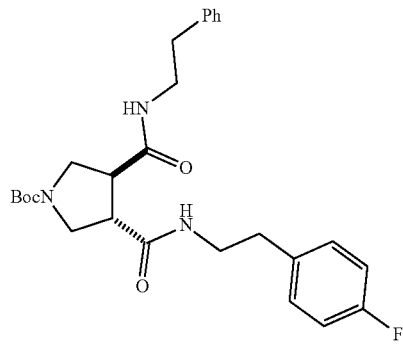 [SMILES: CC(C)(C)OC(=O)N1C[C@@H](C(=O)NCCc2ccccc2)[C@H](C(=O)NCCc2ccc(F)cc2)C1]

64: tert-Butyl trans-3-((4-Fluoro-phenethyl)-carbamoyl)-4-(phenethylcarbamoyl)pyrrolidine-1-carboxylate A solution of trans-1-(tert-butoxy-carbonyl)-4-((4-fluoro-phenethyl)carbamoyl)-pyrrolidine-3-carboxylic acid (S-36; 400 mg, 1.05 mmol, 1 equiv), 2-phenylethan-1-amine (0.20 mL, 1.58 mmol, 1.5 equiv), and i-Pr$_2$NEt (0.55 mL, 3.15 mmol, 3 equiv) in DMF (11 mL) was treated with PyBOP (822 mg, 1.58 mmol, 1.5 equiv). The reaction mixture was stirred at 23° C. for 16 hours. The reaction mixture was poured into EtOAc (25 mL) and washed with aqueous 1 M HCl (25 mL). The aqueous layer was extracted with EtOAc (2×25 mL), washed with a saturated aqueous solution of NaHCO$_3$ (75 mL), saturated aqueous NaCl, and dried with Na$_2$SO$_4$. The crude mixture was purified by flash column chromatography (SiO$_2$, 60-80% EtOAc/hexanes) to provide 64 as a white solid (318 mg, 63%). $^1$H NMR (400 MHz, methanol-d$_4$) δ 8.24 (b, 2H), 7.41 (t, J=7.6 Hz, 2H), 7.38-7.27 (m, 5H), 7.13 (t, J=8.6 Hz, 2H), 3.78 (q, J=9.7, 9.2 Hz, 2H), 3.69-3.48 (m, 2H), 3.44-3.32 (m, 4H), 3.29 (dd, J=15.0, 8.3 Hz, 2H), 2.99-2.84 (m, 4H), 1.60 (s, 9H).

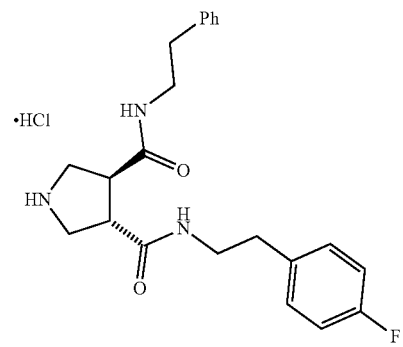 [SMILES: O=C(NCCc1ccccc1)[C@@H]1CNC[C@H]1C(=O)NCCc1ccc(F)cc1 ; Cl]

S-37: trans-N$^3$-(4-Fluorophenethyl)-N$^4$-phenethyl-pyrrolidine-3,4-dicarboxamide Hydrochloride tert-Butyl trans-3-((4-fluorophenethyl)-carbamoyl)-4-(phenethylcarbamoyl)pyrrolidine-1-carboxylate (64; 104 mg, 0.215 mmol) was stirred in a solution of 4 M HCl in dioxane (2 mL) at 23° C. for 3 hours during which time a white solid precipitated out of the reaction mixture. The solvent was removed under a stream of N$_2$ and the crude product taken up in THF (3 mL) and condensed (repeated 3 times) to provide S-37 as a white solid (80 mg, 98%) that was used without additional purification. 1H NMR (400 MHz, methanol-d$_4$) δ 7.27 (t, J=6.6 Hz, 2H), 7.24-7.14 (m, 5H), 6.99 (t, J=8.4 Hz, 2H), 3.72-3.57 (m, 2H), 3.52-3.10 (m, 8H), 2.86-2.67 (m, 4H), 1.46 (s, 9H).

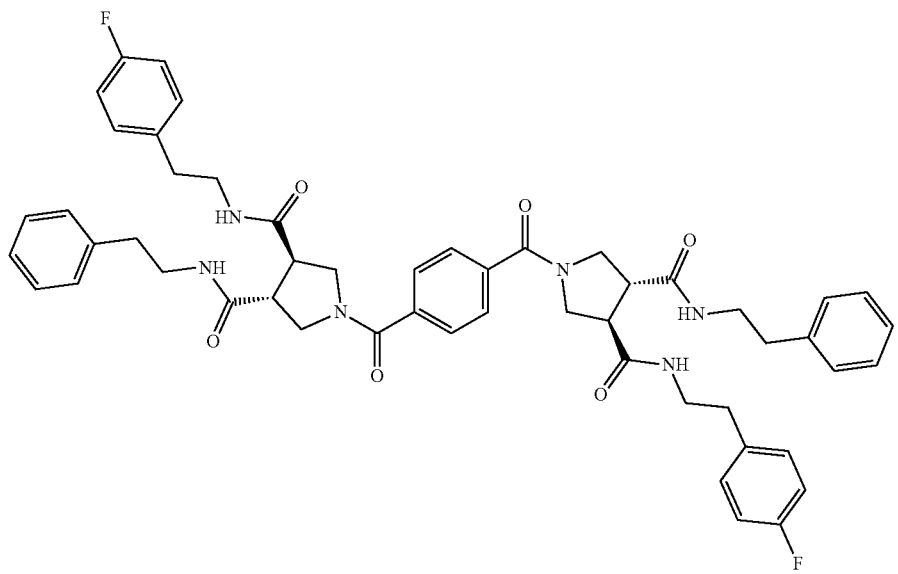 [SMILES: O=C(NCCc1ccccc1)[C@H]1CN(C(=O)c2ccc(C(=O)N3C[C@H](C(=O)NCCc4ccccc4)[C@@H](C(=O)NCCc4ccc(F)cc4)C3)cc2)C[C@@H]1C(=O)NCCc1ccc(F)cc1]

67: 1,1'-Terephthaloylbis(N³-(4-fluorophenethyl)-N⁴-phenethylpyrrolidine-trans-3,4-dicarboxamide The general procedure for linking diacid coupling was employed: trans-N³-(4-fluorophenethyl)-N⁴-phenethylpyrrolidine-3,4-dicarboxamide hydrochloride (S-37; 20 mg, 0.052 mmol, 2.2 equiv), terephthalic acid (benzene-1,4-dicarboxylic acid, 4.0 mg, 0.024 mmol, 1 equiv), PyBrOP (27 mg, 0.058 mmol, 2.4 equiv), and i-Pr₂NEt (21 µL, 0.12 mmol, 5 equiv) in DMF (1 mL) afforded 67 (17 mg, 82%). ¹H NMR (600 MHz, HFIP-d₂) δ 7.60 (d, J=1.3 Hz, 4H), 7.40 (t, J=7.4 Hz, 2H), 7.31 (t, J=7.6 Hz, 3H), 7.26 (d, J=7.8 Hz, 3H), 7.19 (tt, J=6.4, 3.7 Hz, 4H), 7.15-7.09 (m, 2H), 7.05 (t, J=8.7 Hz, 2H), 6.96 (t, J=8.7 Hz, 2H), 4.06 (dd, J=12.6, 8.3 Hz, 2H), 3.69 (s, 6H), 3.66-3.40 (m, 8H), 3.28-3.14 (m, 4H), 2.86 (t, J=6.9 Hz, 2H), 2.82 (t, J=7.0 Hz, 2H), 2.80-2.76 (m, 2H), 2.73 (t, J=7.3 Hz, 2H). HRMS (ESI-TOF) m/z calcd for C₅₂H₅₄F₂N₆O₆[M+H]⁺ 897.4145, found 897.4118.

66: 1-(4-(-3,4-Bis(phenethylcarbamoyl)-pyrrolidine-1-carbonyl)benzoyl)—N³-(4-fluoro-phenethyl)—N⁴-phenethylpyrrolidine-trans-3,4-dicarboxamide A solution of 4-(trans-3,4-bis(phenethyl-carbamoyl)-pyrrolidine-1-carbonyl)benzoic acid (S-8; 16 mg, 0.031 mmol, 1 equiv), trans-N³-(4-fluoro-phenethyl)—N⁴-phenethylpyrrolidine-3,4-dicarboxamide hydrochloride (S-37; 12 mg, 0.031 mmol, 1 equiv), and PyBrOP (16 mg, 0.034 mmol, 1.1 equiv) in DMF (500 µL) was treated with i-Pr₂NEt (16 µL, 0.093 mmol, 3 equiv). The reaction was stirred at 23° C. for 36 hours after which the mixture was diluted with EtOAc (3 mL) and washed with aqueous 0.5 N HCl (2×3 mL). The aqueous phase was extracted with EtOAc (1×3 mL). The combined organic phases were washed with saturated aqueous NaHCO₃ (10 mL) and saturated aqueous NaCl (10 mL). The organic phase was dried over Na₂SO₄, decanted and concentrated. The product was purified by trituration with cold (0° C.) 1:1 Et₂O/EtOAc (3×5 mL), decanting off the liquid phase to provide 14 mg (51%) of 66 as a white solid.

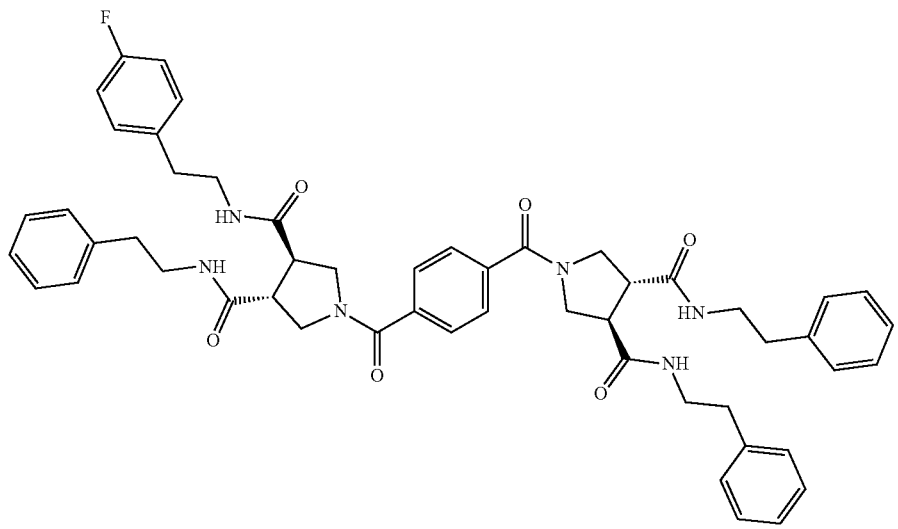 [SMILES: O=C(NCCc1ccccc1)[C@H]1CN(C(=O)c2ccc(C(=O)N3C[C@H](C(=O)NCCc4ccccc4)[C@@H](C(=O)NCCc4ccc(F)cc4)C3)cc2)C[C@@H]1C(=O)NCCc1ccccc1]

¹H NMR (600 μMHz, HFIP-d₂) δ 7.59 (s, 4H), 7.48-7.37 (m, 4H), 7.37-7.29 (m, 4H), 7.26 (d, J=7.4 Hz, 4H), 7.22-7.16 (m, 4H), 7.15-7.10 (m, 1H), 7.09-7.03 (m, 1H), 7.01-6.93 (m, 1H), 4.11-4.00 (m, 2H), 3.75-3.64 (m, 4H), 3.64-3.58 (m, 2H), 3.52-3.40 (m, 8H), 3.21-3.11 (m, 4H), 2.89-2.80 (m, 4H), 2.80-2.71 (m, 4H). HRMS (ESI-TOF) m/z calcd for $C_{52}H_{55}FN_6O_6[M+H]^+$ 879.424, found 879.4222.

J=8.3 Hz, 2H), 6.93 (t, J=8.6 Hz, 2H), 6.23 (s, 1H), 5.86 (s, 1H), 4.05 (t, J=10.7 Hz, 1H), 3.94 (s, 3H), 3.75 (t, J=10.5 Hz, 1H), 3.68 (t, J=11.2 Hz, 1H), 3.65-3.58 (m, 1H), 3.58-3.50 (m, 1H), 3.42 (m, 3H), 3.21 (dd, J=20.0, 10.5 Hz, 1H), 3.08 (q, J=9.9 Hz, 1H), 2.76 (d, J=6.8 Hz, 2H), 2.72 (t, J=7.1 Hz, 2H). HRMS (ESI-TOF) m/z calcd for $C_{31}H_{31}F_2N_3O_5[M+H]^+$ 564.2304, found 564.2304.

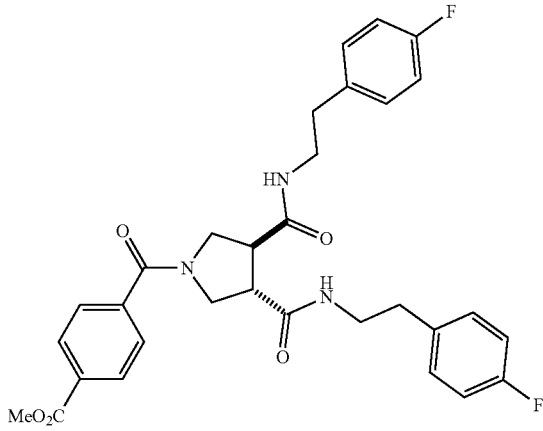 [SMILES: COC(=O)c1ccc(C(=O)N2C[C@@H](C(=O)NCCc3ccc(F)cc3)[C@H](C(=O)NCCc3ccc(F)cc3)C2)cc1]

S-38: Methyl 4-(trans-3,4-Bis((4-fluorophenethyl)-carbamoyl)pyrrolidine-1-carbonyl)benzoate

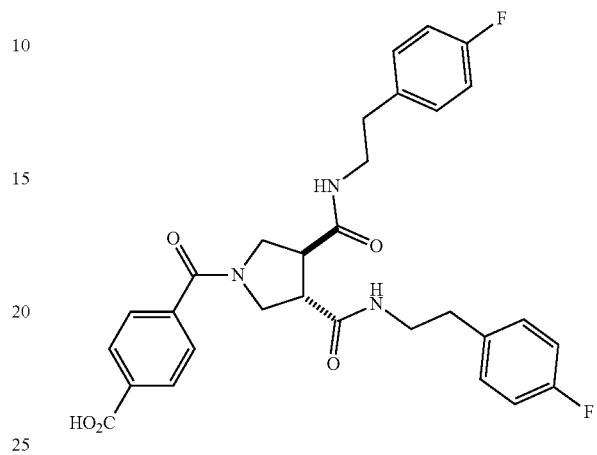

S-39: 4-(trans-3,4-Bis((4-fluorophenethyl)-carbamoyl)pyrrolidine-1-carbonyl)benzoic Acid A solution of 4-(methoxycarbonyl)benzoic acid (26 mg, 0.14 mmol, 1 equiv), trans-$N^3,N^4$-bis(4-fluorophenethyl) pyrrolidine-3,4-dicarboxamide hydrochloride (S-34; 62 mg, 0.14 mmol, 1.0 equiv), and PyBrOP (78 mg, 0.17 mmol, 1.2 equiv) in DMF (1.5 mL) was treated with i-Pr₂NEt (73 μL, 0.42 mmol, 3 equiv). The reaction was stirred at 23° C. for 48 hours before being poured into EtOAc (3 mL) and washed with aqueous 0.5 N HCl (2×3 mL). The aqueous phase was extracted with EtOAc (1×3 mL). The combined organic phases were washed with saturated aqueous NaHCO₃ (10 mL) and saturated aqueous NaCl (10 mL). The organic phase was dried over Na₂SO₄, decanted and concentrated. The crude product (S-38; 79 mg, 99%) was used without additional purification. 1H NMR (600 MHz, CDCl₃) δ 8.08 (d, J=8.4 Hz, 2H), 7.55 (d, J=8.3 Hz, 2H), 7.12 (d, J=6.2 Hz, 2H), 7.07 (td, J=5.6, 1.6 Hz, 2H), 7.01 (t, A solution of methyl 4-(trans-3,4-bis((4-fluorophenethyl) carbamoyl)pyrrolidine-1-carbonyl)-benzoate (S-38; 79 mg, 0.14 mmol) in THF/MeOH/H₂O (1.5 mL, 4:1:1 ratio) was treated with LiOH.H₂O (17 mg, 0.42 mmol, 3 equiv). The suspension was stirred at 23° C. for 5 hours. The reaction mixture was then poured into EtOAc (3 mL), quenched with the addition of aqueous 1 M HCl (5 mL), extracted in EtOAc (2×5 mL), washed with saturated aqueous NaCl, and dried with Na₂SO₄. The crude product (S-39; 73 mg, 95%) was used without additional purification. ¹H NMR (400 MHz, methanol-d₄) δ 8.14 (d, J=8.0 Hz, 2H), 7.62 (d, J=7.9 Hz, 2H), 7.23 (s, 2H), 7.13 (s, 2H), 7.02 (t, J=8.5 Hz, 2H), 6.91 (t, J=8.6 Hz, 2H), 4.03-3.90 (m, 1H), 3.63 (dt, J=19.8, 10.2 Hz, 2H), 3.53-3.38 (m, 4H), 3.18 (d, J=9.4 Hz, 3H), 2.80 (s, 2H), 2.72 (d, J=7.5 Hz, 2H). HRMS (ESI-TOF) m/z calcd for $C_{30}H_{29}F_2N_3O_5[M+H]^+$ 550.2148, found 550.2148.

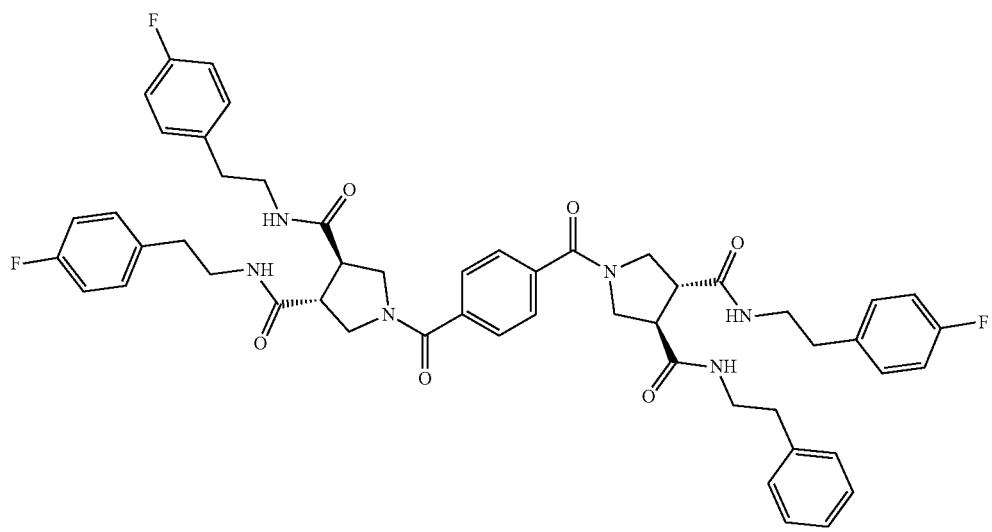 [SMILES: O=C(NCCc1ccccc1)[C@H]1CN(C(=O)c2ccc(C(=O)N3C[C@H](C(=O)NCCc4ccc(F)cc4)[C@@H](C(=O)NCCc4ccc(F)cc4)C3)cc2)C[C@@H]1C(=O)NCCc1ccc(F)cc1]

68: 1-(4-(trans-3,4-Bis((4-fluoro-phenethyl)-carbamoyl)pyrrolidine-1-carbonyl)benzoyl)-$N^3$-(4-fluorophenethyl)-$N^4$-phenethylpyrrolidine-trans-3,4-dicarboxamide A solution of 4-(trans-3,4-bis((4-fluoro-phenethyl)carbamoyl)pyrrolidine-1-carbonyl)benzoic acid (S-39; 60 mg, 0.109 mmol, 1 equiv), trans-$N^3$-(4-fluorophenethyl)-7N-phenethylpyrrolidine-3,4-dicarboxamide hydrochloride (S-37; 42 mg, 0.109 mmol, 1 equiv), and PyBrOP (56 mg, 0.120 mmol, 1.1 equiv) in DMF (1 mL) was treated with i-Pr$_2$NEt (57 μL, 0.327 mmol, 3 equiv). The reaction mixture was stirred at 23° C. for 36 hours after which the mixture was diluted with EtOAc (3 mL) and washed with aqueous 0.5 N HCl (2×3 mL). The aqueous phase was extracted with EtOAc (1×3 mL). The combined organic phases were washed with saturated aqueous NaHCO$_3$ (10 mL) and saturated aqueous NaCl (10 mL). The organic phase was dried over Na$_2$SO$_4$, decanted and concentrated. The product was purified by trituration with cold (0° C.) 1:1 Et$_2$O/EtOAc (3×5 mL), decanting off the liquid phase to provide 81 mg (81%) of 68 as a white solid. 1H NMR (600 MHz, HFIP-d$_2$) δ 7.60 (d, J=4.2 Hz, 4H), 7.40 (t, J=7.1 Hz, 2H), 7.31 (t, J=7.6 Hz, 2H), 7.26 (d, J=7.6 Hz, 2H), 7.24-7.16 (m, 4H), 7.16-7.08 (m, 3H), 7.05 (tt, J=8.7, 2.1 Hz, 3H), 7.01-6.91 (m, 3H), 4.06 (ddd, J=13.0, 7.9, 4.6 Hz, 2H), 3.76-3.64 (m, 4H), 3.58 (dq, J=13.1, 7.8, 6.6 Hz, 4H), 3.54-3.39 (m, 6H), 3.34-3.15 (m, 4H), 2.90-2.81 (m, 4H), 2.75 (q, J=11.5, 7.4 Hz, 4H). HRMS (ESI-TOF) m/z calcd for C$_{52}$H$_{53}$F$_3$N$_6$O$_6$ [M+H]$^+$ 915.4051, found 915.4059.

Aryl Substitution Analogues of Diprovocim-2

70: tert-Butyl trans-3,4-Bis((3-fluorophenethyl)-carbamoyl)pyrrolidine-1-carboxylate The general procedure for the coupling of amines with pyrrolidine diacids was followed: trans-1-(tert-butoxycarbonyl)pyrrolidine-3,4-dicarboxylic acid (S-29; 50 mg) and 2-(3-fluorophenyl)ethan-1-amine hydrochloride (55 μL) provided 87 mg (91%) of 70 without purification.

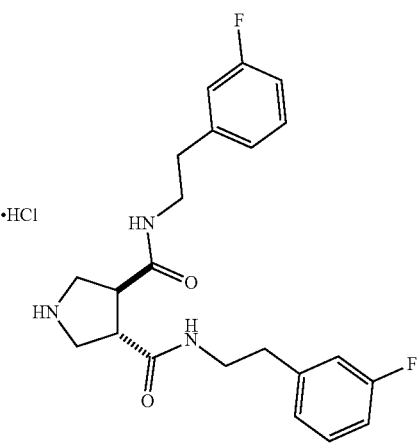

S-40: trans-$N^3$,$N^4$-Bis(3-fluorophenethyl)pyrrolidine-3,4-dicarboxamide Hydrochloride

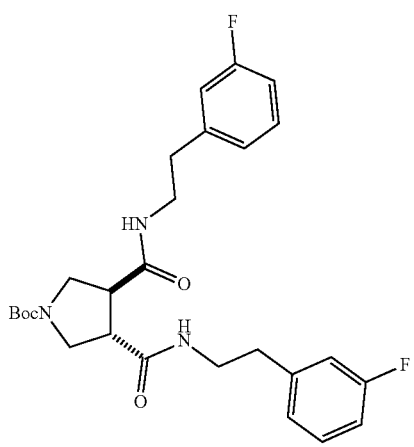 [SMILES: CC(C)(C)OC(=O)N1C[C@@H](C(=O)NCCc2cccc(F)c2)[C@H](C(=O)NCCc2cccc(F)c2)C1]

The general procedure for Boc-pyrrolidine deprotection was employed: tert-butyl trans-3,4-bis((3-fluorophenethyl)carbamoyl)-pyrrolidine-1-carboxylate (70; 87 mg) provided 78 mg (99%) of S-40. $^1$H NMR (600 MHz, methanol-d$_4$) δ 8.28 (s, 1H), 7.31 (td, J=7.9, 6.0 Hz, 2H), 7.08-7.03 (m, 2H), 6.99 (dt, J=10.0, 2.1 Hz, 2H), 6.98-6.93 (m, 2H), 3.57-3.37 (m, 8H), 3.25-3.19 (m, 2H), 2.84 (td, J=7.1, 3.5 Hz, 4H).

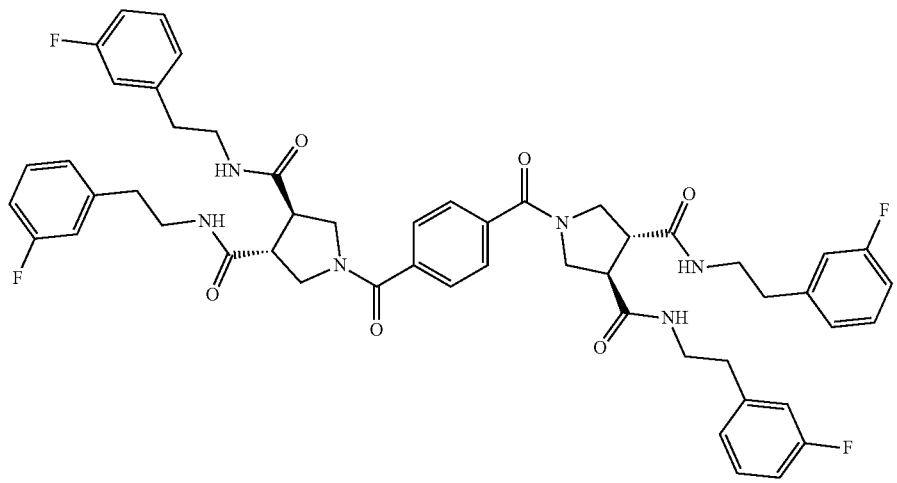 [SMILES: O=C(NCCc1cccc(F)c1)[C@H]1CN(C(=O)c2ccc(C(=O)N3C[C@H](C(=O)NCCc4cccc(F)c4)[C@@H](C(=O)NCCc4cccc(F)c4)C3)cc2)C[C@@H]1C(=O)NCCc1cccc(F)c1]

84: 1,1'-Terephthaloylbis(N³,N⁴-bis(3-fluoro-phenethyl)pyrrolidine-trans-3,4-dicarboxamide)

The general procedure for linking diacid coupling was employed: trans-N³,N⁴-bis(3-fluoro-phenethyl)pyrrolidine-3,4-dicarboxamide hydrochloride (S-40; 44 mg) and terephthalic acid (benzene-1,4-dicarboxylic acid, 7.5 mg) provided 40 mg (97%) of 84. ¹H NMR (400 MHz, HFIP-$d_2$) δ 7.60 (s, 4H), 7.39-7.30 (m, 2H), 7.26 (d, J=7.3 Hz, 2H), 7.02 (d, J=7.7 Hz, 2H), 7.00-6.87 (m, 8H), 6.82 (d, J=10.2 Hz, 2H), 6.55 (bs, 2H), 4.12-4.00 (m, 2H), 3.69 (t, J=10.2 Hz, 4H), 3.57 (q, J=11.2, 10.7 Hz, 6H), 3.46 (m, 4H), 3.32-3.12 (m, 4H), 2.85 (m, 4H), 2.75 (m, 4H). HRMS (ESI-TOF) m/z calcd for $C_{52}H_{52}F_4N_6O_6$ [M+H]⁺ 933.3957, found 933.3955.

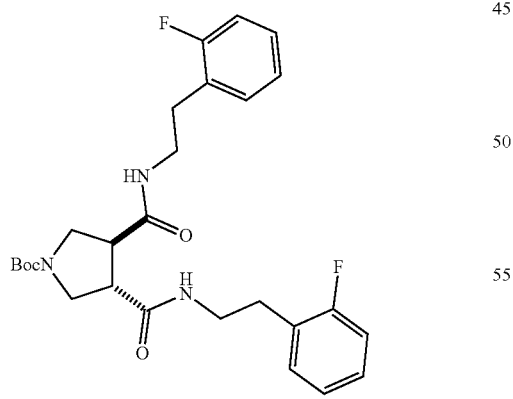

71: tert-Butyl trans-3,4-Bis((2-fluorophenethyl)-carbamoyl)pyrrolidine-1-carboxylate The general procedure for the coupling of amines with pyrrolidine diacids was followed: trans-1-(tert-butoxycarbonyl)pyrrolidine-3,4-dicarboxylic acid (S-29; 50 mg) and 2-(2-fluorophenyl)ethan-1-amine (55 μL) provided 84 mg (88%) of 71 without purification.

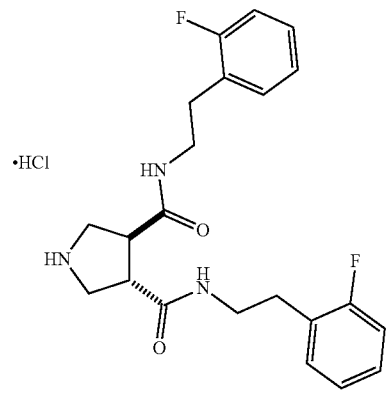 [SMILES: Cl ; O=C(NCCc1ccccc1F)[C@@H]1CNC[C@H]1C(=O)NCCc1ccccc1F]

S-41: trans-N³,N⁴-Bis(2-fluorophenethyl)pyrrolidine-3,4-dicarboxamide Hydrochloride The general procedure for Boc-pyrrolidine deprotection was employed: tert-butyl trans-3,4-bis((2-fluorophenethyl)carbamoyl)pyrrolidine-1-carboxylate (71; 84 mg) provided 75 mg (99%) of S-41. ¹H NMR (600 MHz, methanol-$d_4$) δ 7.25 (qd, J=7.9, 7.4, 1.9 Hz, 4H), 7.11 (td, J=7.5, 1.2 Hz, 2H), 7.05 (ddd, J=10.3, 8.4, 1.2 Hz, 2H), 3.54-3.44 (m, 4H), 3.44-3.34 (m, 4H), 3.19 (ddd, J=5.3, 4.1, 1.8 Hz, 2H), 2.86 (dq, J=18.5, 6.7 Hz, 4H).

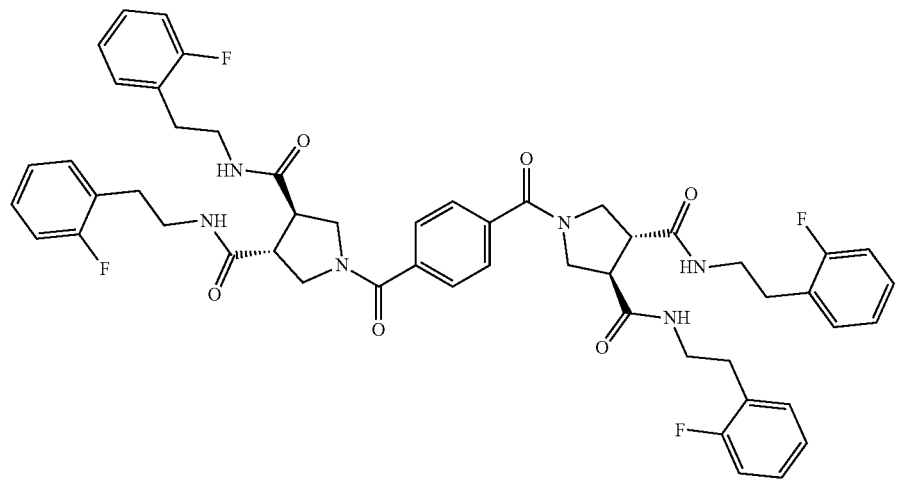 [SMILES: O=C(NCCc1ccccc1F)[C@H]1CN(C(=O)c2ccc(C(=O)N3C[C@H](C(=O)NCCc4ccccc4F)[C@@H](C(=O)NCCc4ccccc4F)C3)cc2)C[C@@H]1C(=O)NCCc1ccccc1F]

85: 1,1'-Terephthaloylbis(N³,N⁴-bis(2-fluoro-phenethyl)pyrrolidine-trans-3,4-dicarboxamide)

The general procedure for linking diacid coupling was employed: trans-N³,N⁴-bis(2-fluoro-phenethyl)pyrrolidine-3,4-dicarboxamide hydrochloride (S-41; 44 mg) and terephthalic acid (benzene-1,4-dicarboxylic acid, 7.5 mg) provided 40 mg (97%) of 85. ¹H NMR (400 μMHz, CDCl$_3$) δ 7.61 (s, 4H), 7.32-7.18 (m, 6H), 7.15 (t, J=6.6 Hz, 4H), 7.07 (d, J=6.1 Hz, 4H), 6.98 (t, J=9.5 Hz, 2H), 6.62 (bs, 2H), 6.56 (bs, 2H), 4.06 (m, 2H), 3.69 (m, 4H), 3.65-3.53 (m, 4H), 3.47 (m, 6H), 3.21 (m, 4H), 2.93 (m, 4H), 2.82 (m, 4H). HRMS (ESI-TOF) m/z calcd for $C_{52}H_{52}F_4N_6O_6[M+H]^+$ 933.3957, found 933.3958.

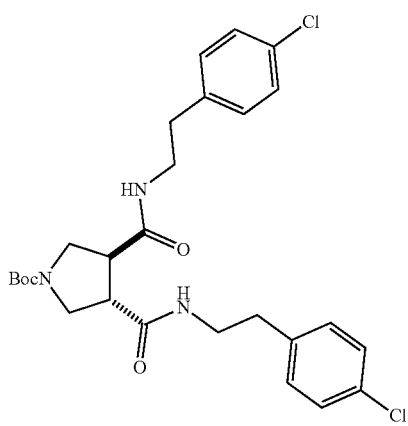 [SMILES: CC(C)(C)OC(=O)N1C[C@@H](C(=O)NCCc2ccc(Cl)cc2)[C@H](C(=O)NCCc2ccc(Cl)cc2)C1]

72: tert-Butyl trans-3,4-Bis((4-chlorophenethyl)-carbamoyl)pyrrolidine-1-carboxylate The general procedure for the coupling of amines with pyrrolidine diacids was followed: trans-1-(tert-butoxycarbonyl)pyrrolidine-3,4-dicarboxylic acid (S-29; 50 mg) and 2-(4-chlorophenyl)ethan-1-amine (59 μL) provided 107 mg (99%) of 72 without purification.

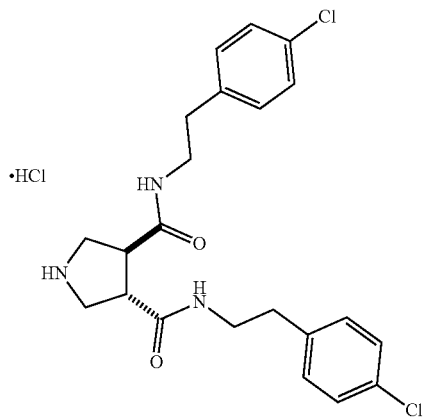 [SMILES: Cl ; O=C(NCCc1ccc(Cl)cc1)[C@@H]1CNC[C@H]1C(=O)NCCc1ccc(Cl)cc1]

S-42: trans-N³,N⁴-Bis(4-chlorophenethyl)pyrrolidine-3,4-dicarboxamide Hydrochloride The general procedure for Boc-pyrrolidine deprotection was employed: tert-butyl trans-3,4-bis((4-chlorophenethyl)carbamoyl)pyrrolidine-1-carboxylate (72; 107 mg) provided 97 mg (99%) of S-42. ¹H NMR (600 MHz, methanol-d$_4$) δ 7.35-7.25 (m, 4H), 7.25-7.15 (m, 4H), 3.56-3.48 (m, 2H), 3.48-3.34 (m, 6H), 3.19 (dd, J=6.2, 4.5 Hz, 2H), 2.79 (td, J=7.1, 3.2 Hz, 4H).

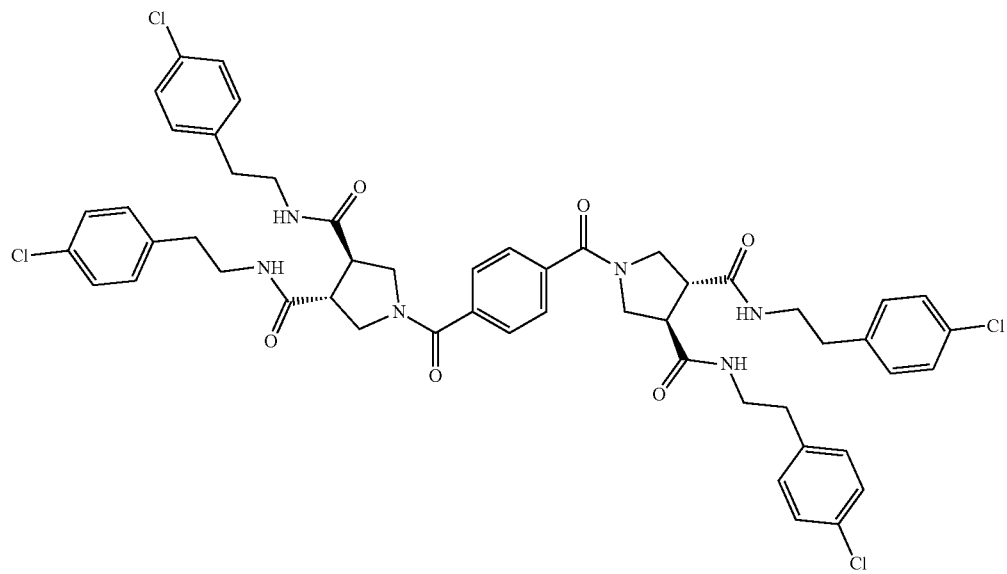 [SMILES: O=C(NCCc1ccc(Cl)cc1)[C@H]1CN(C(=O)c2ccc(C(=O)N3C[C@H](C(=O)NCCc4ccc(Cl)cc4)[C@@H](C(=O)NCCc4ccc(Cl)cc4)C3)cc2)C[C@@H]1C(=O)NCCc1ccc(Cl)cc1]

86 (BJ-1-288): 1,1'-Terephthaloylbis(N³,N⁴-bis(4-chlorophenethyl)pyrrolidine-trans-3,4-dicarboxamide)

The general procedure for linking diacid coupling was employed: trans-N³,N⁴-bis(4-chloro-phenethyl)pyrrolidine-3,4-dicarboxamide hydrochloride (S-42; 47 mg) and terephthalic acid (benzene-1,4-dicarboxylic acid, 7.5 mg) provided 24 mg (53%) of 86. $^1$H NMR (400 MHz, HFIP-d$_2$) δ 7.61 (s, 4H), 7.33 (d, J=7.7 Hz, 4H), 7.24 (d, J=7.9 Hz, 4H), 7.16 (d, J=7.9 Hz, 4H), 7.08 (d, J=7.9 Hz, 4H), 6.54 (bs, 2H), 4.06 (dd, J=12.5, 8.1 Hz, 2H), 3.69 (m, 4H), 3.63-3.48 (m, 6H), 3.44 (m, 4H), 3.34-3.11 (m, 4H), 2.82 (m, 4H), 2.73 (m, 4H). HRMS (ESI-TOF) m/z calcd for C$_{52}$H$_{52}$Cl$_4$N$_6$O$_6$ [M+H]$^+$ 997.2775, found 997.2777.

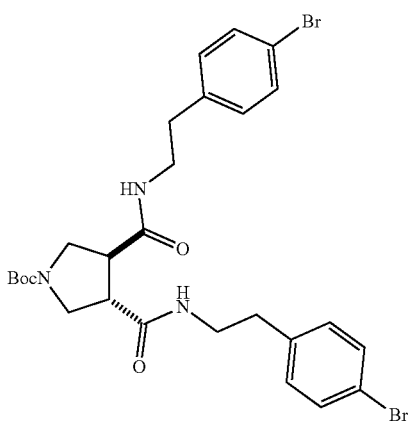

73: tert-Butyl trans-3,4-Bis((4-bromophenethyl)-carbamoyl)pyrrolidine-1-carboxylate The general procedure for the coupling of amines with pyrrolidine diacids was followed: trans-1-(tert-butoxycarbonyl)pyrrolidine-3,4-dicarboxylic acid (S-29; 50 mg) and 2-(4-bromophenyl)ethan-1-amine hydrochloride (99 mg) provided 125 mg (99%) of 73 without purification.

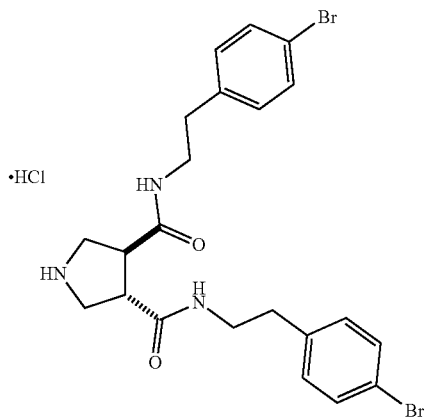

S-43: trans-N³,N⁴-Bis(4-bromophenethyl)pyrrolidine-3,4-dicarboxamide Hydrochloride The general procedure for Boc-pyrrolidine deprotection was employed: tert-butyl trans-3,4-bis((4-bromophenethyl)carbamoyl)pyrrolidine-1-carboxylate (73; 125 mg) provided 119 mg (99%) of S-43. $^1$H NMR (600 MHz, methanol-d$_4$) δ 8.27 (bs, 1H), 7.48-7.43 (m, 4H), 7.19-7.14 (m, 4H), 3.52 (dd, J=11.6, 7.0 Hz, 2H), 3.49-3.40 (m, 4H), 3.40-3.35 (m, 2H), 3.23-3.17 (m, 2H), 2.80 (td, J=7.1, 2.9 Hz, 4H)

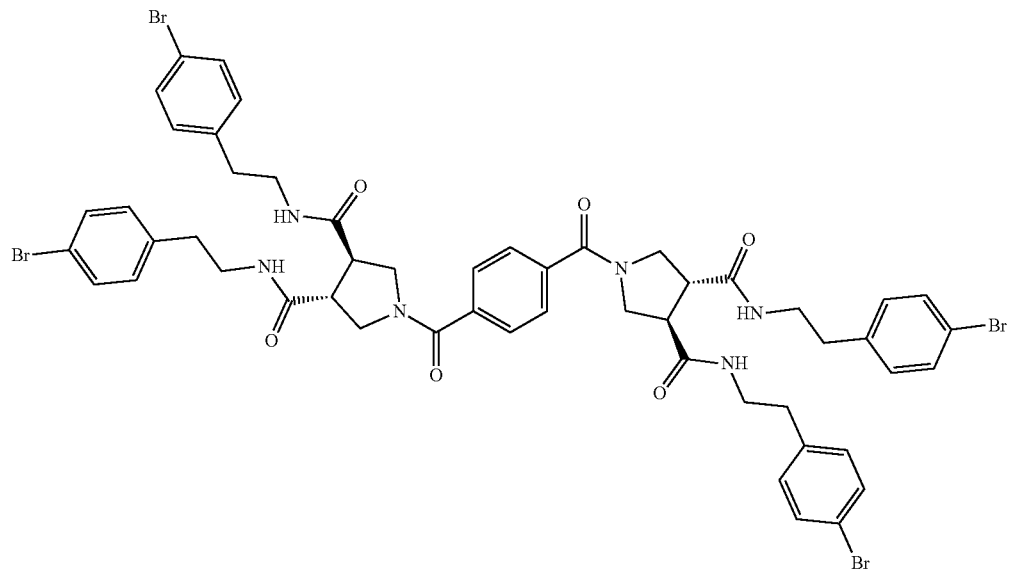 [SMILES: O=C(NCCc1ccc(Br)cc1)[C@H]1CN(C(=O)c2ccc(C(=O)N3C[C@H](C(=O)NCCc4ccc(Br)cc4)[C@@H](C(=O)NCCc4ccc(Br)cc4)C3)cc2)C[C@@H]1C(=O)NCCc1ccc(Br)cc1]

87: 1,1'-Terephthaloylbis(N³,N⁴-bis(4-bromophenethyl)-pyrrolidine-trans-3,4-dicarboxamide)

The general procedure for linking diacid coupling was employed: trans-N³,N⁴-bis(4-bromo-phenethyl)pyrrolidine-3,4-dicarboxamide hydrochloride (S-43; 56 mg) and terephthalic acid (benzene-1,4-dicarboxylic acid, 7.5 mg) provided 36 mg (68%) of 87. ¹H NMR (400 μMHz, HFIP-d₂) δ 7.61 (s, 4H), 7.48 (d, J=7.9 Hz, 4H), 7.39 (d, J=7.9 Hz, 4H), 7.11 (d, J=7.9 Hz, 4H), 7.03 (d, J=8.0 Hz, 4H), 6.61-6.44 (m, 2H), 4.06 (t, J=10.4 Hz, 2H), 3.68 (m, 4H), 3.56 (m, 6H), 3.44 (m, 4H), 3.20 (m, 4H), 2.80 (m, 4H), 2.71 (m, 4H). HRMS (ESI-TOF) m/z calcd for $C_{52}H_{52}Br_4N_6O_6$ [M+H]⁺ 1173.0754, found 1173.0766.

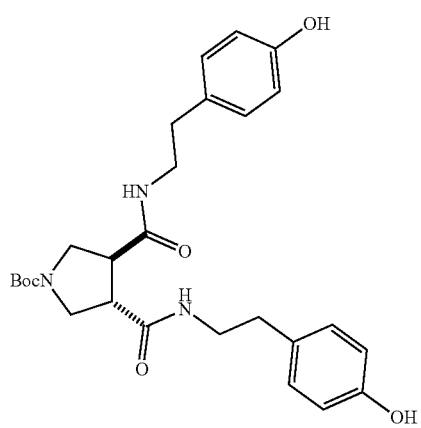

74: tert-Butyl trans-3,4-Bis((4-hydroxyphenethyl)-carbamoyl)pyrrolidine-1-carboxylate The general procedure for the coupling of amines with pyrrolidine diacids was followed: trans-1-(tert-butoxycarbonyl)pyrrolidine-3,4-dicarboxylic acid (S-29; 50 mg), and 4-(2-aminoethyl)phenol (58 mg) provided 103 mg (99%) of 74 after purification by flash column chromatography (SiO₂, 60-85% EtOAc/hexane).

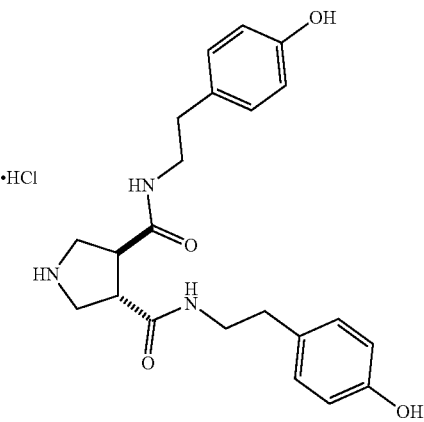 [SMILES: Cl ; O=C(NCCc1ccc(O)cc1)[C@@H]1CNC[C@H]1C(=O)NCCc1ccc(O)cc1]

S-44: trans-N³,N⁴-Bis(4-hydroxyphenethyl)pyrrolidine-3,4-dicarboxamide Hydrochloride The general procedure for Boc-pyrrolidine deprotection was employed: tert-butyl trans-3,4-bis((4-hydroxyphenethyl)carbamoyl)pyrrolidine-1-carboxylate (74; 103 mg) provided 80 mg (98%) of S-44. ¹H NMR (600 MHz, methanol-d₄) δ 7.06-6.97 (m, 4H), 6.76-6.61 (m, 4H), 3.49 (dd, J=11.7, 7.1 Hz, 2H), 3.44-3.33 (m, 6H), 3.18 (q, J=5.2 Hz, 2H), 2.70 (td, J=7.2, 3.0 Hz, 4H).

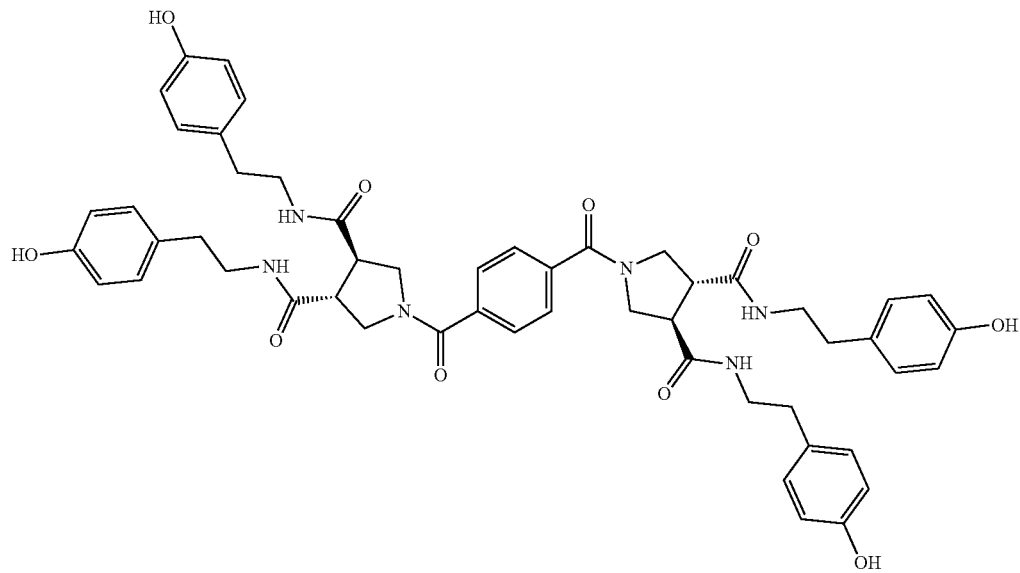 [SMILES: O=C(NCCc1ccc(O)cc1)[C@H]1CN(C(=O)c2ccc(C(=O)N3C[C@H](C(=O)NCCc4ccc(O)cc4)[C@@H](C(=O)NCCc4ccc(O)cc4)C3)cc2)C[C@@H]1C(=O)NCCc1ccc(O)cc1]

88: 1,1'-Terephthaloylbis(N³,N⁴-bis(4-hydroxy-phenethyl)pyrrolidine-trans-3,4-dicarboxamide)

The general procedure for linking diacid coupling was employed: trans-N³,N⁴-bis(4-hydroxy-phenethyl)pyrrolidine-3,4-dicarboxamide hydrochloride (S-44; 43 mg) and terephthalic acid (benzene-1,4-dicarboxylic acid, 7.5 mg) provided 42 mg (99%) of 88. ¹H NMR (600 MHz, HFIP-d₂) δ 7.59 (s, 4H), 7.15 (d, J=8.1 Hz, 4H), 7.01 (d, J=8.1 Hz, 4H), 6.89 (d, J=8.4 Hz, 4H), 6.71 (d, J=8.1 Hz, 4H), 4.06 (dt, J=12.0, 9.0 Hz, 2H), 3.68 (tt, J=12.4, 6.4 Hz, 2H), 3.63-3.50 (m, 4H), 3.51-3.31 (m, 8H), 3.22 (m, 4H), 2.80 (q, J=6.6 Hz, 4H), 2.75 (dt, J=14.0, 6.6 Hz, 2H), 2.69 (p, J=7.7, 7.0 Hz, 2H). HRMS (ESI-TOF) m/z calcd for $C_{52}H_{56}N_6O_{10}[M+H]^+$ 925.413, found 925.4132.

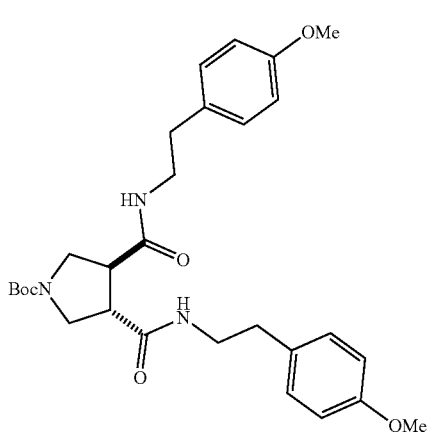 [SMILES: COc1ccc(CCNC(=O)[C@@H]2CN(C(=O)OC(C)(C)C)C[C@H]2C(=O)NCCc2ccc(OC)cc2)cc1]

75: tert-Butyl trans-3,4-Bis((4-methoxyphenethyl)-carbamoyl)pyrrolidine-1-carboxylate The general procedure for the coupling of amines with pyrrolidine diacids was followed: trans-1-(tert-butoxycarbonyl)pyrrolidine-3,4-dicarboxylic acid (S-29; 50 mg), and 2-(4-methoxyphenyl)ethan-1-amine (63 μL) provided 108 mg (99) of 75 without purification.

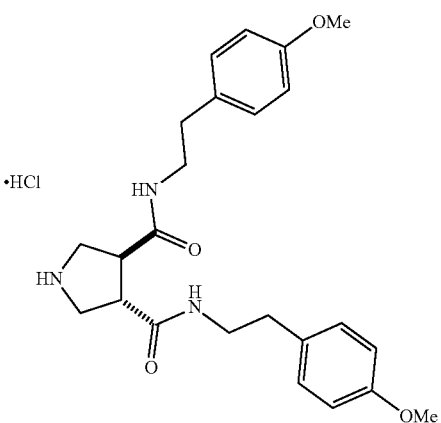 [SMILES: Cl ; COc1ccc(CCNC(=O)[C@@H]2CNC[C@H]2C(=O)NCCc2ccc(OC)cc2)cc1]

S-45: trans-N³,N⁴-Bis(4-methoxyphenethyl)pyrrolidine-3,4-dicarboxamide Hydrochloride The general procedure for Boc-pyrrolidine deprotection was employed: tert-butyl trans-3,4-bis((4-methoxyphenethyl)carbamoyl)pyrrolidine-1-carboxylate (75; 108 mg) provided 96 mg (99%) of S-45. ¹H NMR (600 MHz, methanol-d₄) δ 7.12 (d, J=8.6 Hz, 4H), 6.84 (d, J=8.6 Hz, 4H), 3.75 (s, 6H), 3.54-3.45 (m, 2H), 3.44-3.34 (m, 6H), 3.22-3.15 (m, 2H), 2.73 (td, J=7.2, 2.0 Hz, 4H)

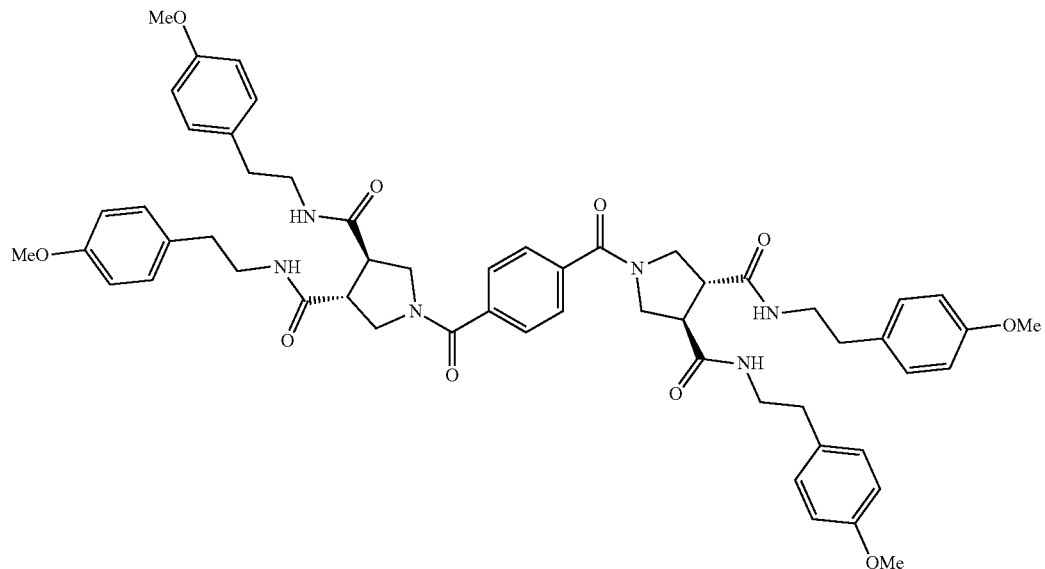 [SMILES: COc1ccc(CCNC(=O)[C@H]2CN(C(=O)c3ccc(C(=O)N4C[C@H](C(=O)NCCc5ccc(OC)cc5)[C@@H](C(=O)NCCc5ccc(OC)cc5)C4)cc3)C[C@@H]2C(=O)NCCc2ccc(OC)cc2)cc1]

89: 1,1'-Terephthaloylbis(N³,N⁴-bis(4-methoxy-phenethyl)pyrrolidine-trans-3,4-dicarboxamide)

The general procedure for linking diacid coupling was employed: trans-N³,N⁴-bis(4-methoxy-phenethyl)pyrrolidine-3,4-dicarboxamide hydrochloride (S-45; 46 mg) and terephthalic acid (benzene-1,4-dicarboxylic acid, 7.5 mg) provided 18 mg (41%) of 89. ¹H NMR (400 μMHz, HFIP-$d_2$) δ 7.61 (s, 4H), 7.21 (d, J=8.1 Hz, 4H), 7.15 (d, J=8.0 Hz, 4H), 7.00 (d, J=7.9 Hz, 4H), 6.94 (d, J=8.0 Hz, 4H), 6.62 (d, J=6.4 Hz, 4H), 4.10 (m, 2H), 3.87 (d, J=9.2 Hz, 12H), 3.71 (m, 6H), 3.64-3.35 (m, 8H), 3.34-3.16 (m, 4H), 2.81 (m, 4H), 2.73 (m, 4H). HRMS (ESI-TOF) m/z calcd for $C_{56}H_{64}N_6O_{10}$ [M+H]⁺ 981.4756, found 981.4754.

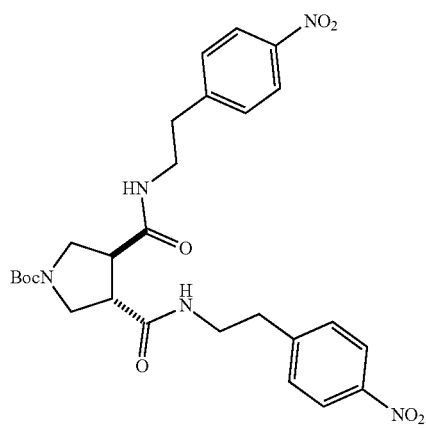 [SMILES: CC(C)(C)OC(=O)N1C[C@@H](C(=O)NCCc2ccc([N+](=O)[O-])cc2)[C@H](C(=O)NCCc2ccc([N+](=O)[O-])cc2)C1]

77: tert-Butyl trans-3,4-Bis((4-nitrophenethyl)-carbamoyl)pyrrolidine-1-carboxylate

The general procedure for the coupling of amines with pyrrolidine diacids was followed: trans-1-(tert-butoxycarbonyl)pyrrolidine-3,4-dicarboxylic acid (S-29; 50 mg) and 2-(4-nitrophenyl)ethan-1-amine hydrochloride (85 mg) provided 100 mg (95%) of 77 without purification.

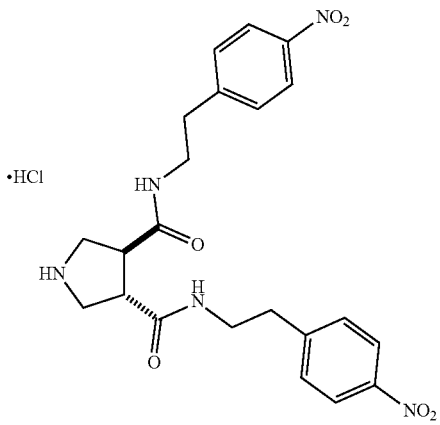 [SMILES: Cl ; O=C(NCCc1ccc([N+](=O)[O-])cc1)[C@@H]1CNC[C@H]1C(=O)NCCc1ccc([N+](=O)[O-])cc1]

S-46: trans-N, 2-Bis(4-nitrophenethyl)pyrrolidine-3,4-dicarboxamide Hydrochloride

The general procedure for Boc-pyrrolidine deprotection was employed: tert-butyl trans-3,4-bis((4-nitrophenethyl)carbamoyl)pyrrolidine-1-carboxylate (77; 100 mg) provided 92 mg (98%) of S-46. ¹H NMR (600 MHz, methanol-$d_4$) δ 8.32 (b, 1H), 8.23-8.11 (m, 4H), 7.47 (d, J=8.6 Hz, 4H), 3.56-3.43 (m, 6H), 3.34 (dd, J=11.6, 5.6 Hz, 2H), 3.24-3.16 (m, 2H), 2.94 (td, J=7.1, 1.9 Hz, 4H).

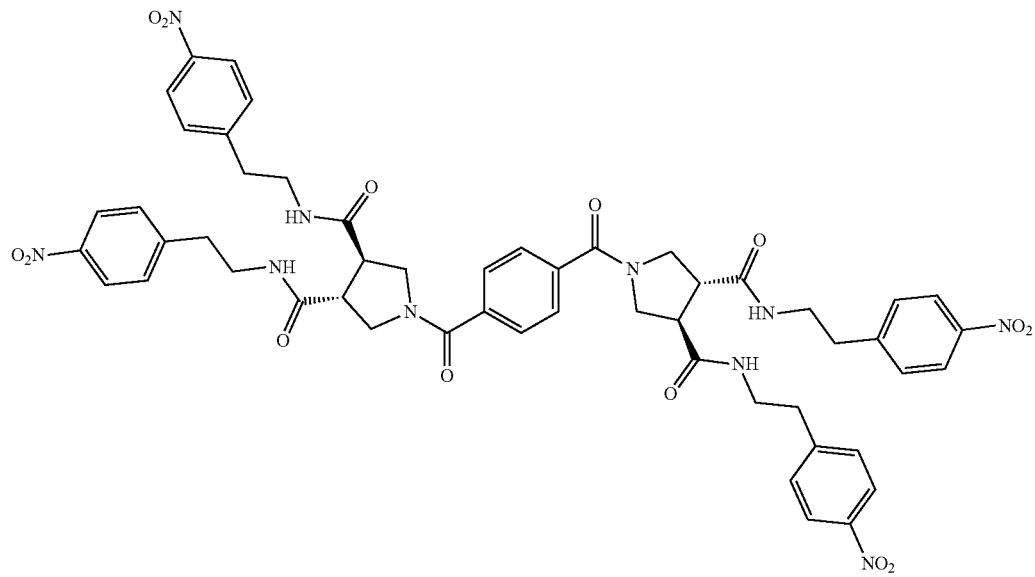 [SMILES: O=C(NCCc1ccc([N+](=O)[O-])cc1)[C@H]1CN(C(=O)c2ccc(C(=O)N3C[C@H](C(=O)NCCc4ccc([N+](=O)[O-])cc4)[C@@H](C(=O)NCCc4ccc([N+](=O)[O-])cc4)C3)cc2)C[C@@H]1C(=O)NCCc1ccc([N+](=O)[O-])cc1]

91: 1,1'-Terephthaloylbis(N³,N⁴-bis(4-nitrophenethyl)-pyrrolidine-trans-3,4-dicarboxamide)

The general procedure for linking diacid coupling was employed: trans-N³,N⁴-bis(4-nitro-phenethyl)pyrrolidine-3,4-dicarboxamide hydrochloride (S-46; 49 mg) and terephthalic acid (benzene-1,4-dicarboxylic acid, 7.5 mg) provided 41 mg (88%) of 91. $^1$H NMR (400 MHz, HFIP-d$_2$) δ 8.25 (d, J=8.3 Hz, 4H), 8.19 (d, J=8.3 Hz, 2H), 8.08 (d, J=8.3 Hz, 2H), 7.65 (s, 2H), 7.60 (s, 2H), 7.42 (d, J=8.3 Hz, 4H), 7.34 (dd, J=14.4, 8.4 Hz, 4H), 4.11 (q, J=9.6 Hz, 2H), 3.88-3.71 (m, 4H), 3.71-3.42 (m, 10H), 3.34 (m, 4H), 3.02-2.95 (m, 4H), 2.95-2.85 (m, 4H). HRMS (ESI-TOF) m/z calcd for C$_{52}$H$_{52}$N$_{10}$O$_{14}$ [M+H]$^+$ 1041.3737, found 1041.3741.

90: 1,1'-Terephthaloylbis(N³,N⁴-bis(4-aminophenethyl)-pyrrolidine-trans-3,4-dicarboxamide)

A solution of 1,1'-terephthaloylbis(N³,N⁴-bis(4-nitrophenethyl)pyrrolidine-trans-3,4-dicarboxamide) (91; 11 mg, 0.01 mmol) in a solution of 50% EtOAc/MeOH was treated with Pd(OH)$_2$/C (3 mg, 20% weight). The suspension was purged with H$_2$ and stirred for 18 hours under 1 atmosphere of H$_2$. The reaction mixture was filtered through Celite® and eluted with 50% MeOH/CH$_2$Cl$_2$ to provide 90 as an amorphous white solid (9 mg, 98%). $^1$H NMR (600 MHz, DMSO-d$_6$) δ 8.08 (t, J=5.6 Hz, 2H), 7.99-7.88 (m, 2H), 7.58 (d, J=1.4 Hz, 4H), 6.84 (d, J=8.3 Hz, 4H), 6.74 (d, J=7.9 Hz, 4H), 6.53-6.43 (m, 4H), 6.39 (d, J=8.0 Hz, 4H), 3.78 (ddd, J=12.4, 8.7, 3.9 Hz, 2H), 3.68-3.58 (m, 2H), 3.52-3.45 (m, 2H), 3.46-3.40 (m, 2H), 3.25-3.15 (m, 8H), 3.15-3.04 (m,

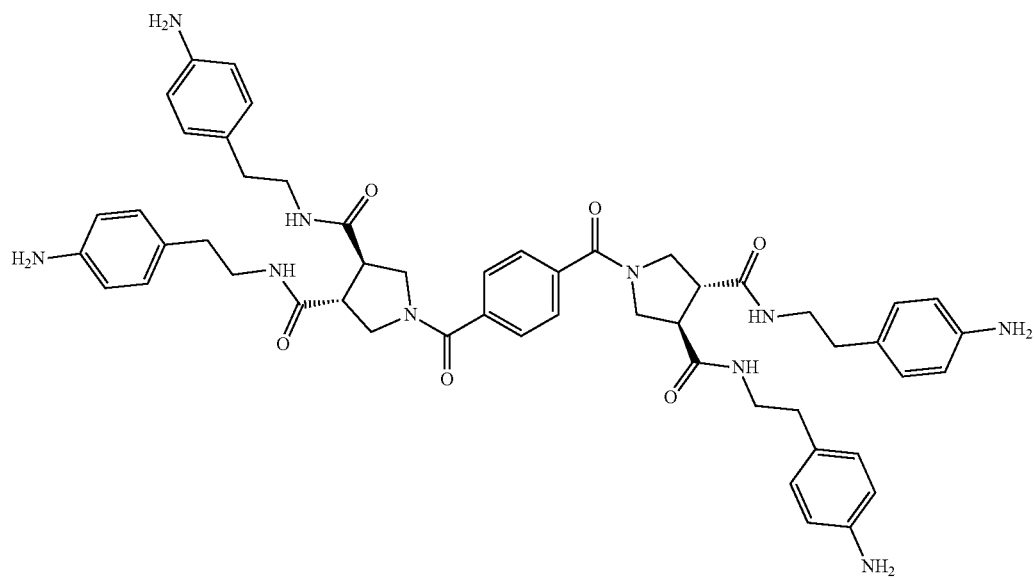

4H), 2.57-2.51 (m, 4H), 2.44 (dq, J=13.6, 6.9 Hz, 4H). HRMS (ESI-TOF) m/z calcd for $C_{52}H_{60}N_{10}O_6[M+H]^+$ 921.477, found 921.4774.

78: tert-Butyl trans-3,4-Bis((4-methylphenethyl)-carbamoyl)pyrrolidine-1-carboxylate

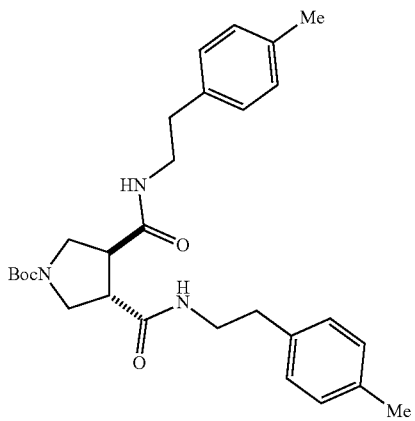 [SMILES: Cc1ccc(CCNC(=O)[C@@H]2CN(C(=O)OC(C)(C)C)C[C@H]2C(=O)NCCc2ccc(C)cc2)cc1]

The general procedure for the coupling of amines with pyrrolidine diacids was followed: trans-1-(tert-butoxycarbonyl)pyrrolidine-3,4-dicarboxylic acid (S-29; 50 mg), and 2-(p-tolyl)ethan-1-amine hydrochloride (72 mg) provided 93 mg (98%) of 78 without purification.

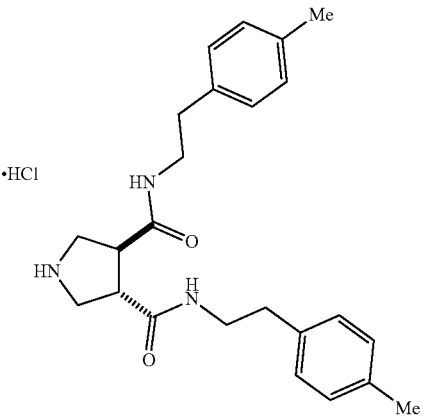 [SMILES: Cl ; Cc1ccc(CCNC(=O)[C@@H]2CNC[C@H]2C(=O)NCCc2ccc(C)cc2)cc1]

S-47: trans-$N^3$,$N^4$-Bis(4-methylphenethyl)pyrrolidine-3,4-dicarboxamide Hydrochloride The general procedure for Boc-pyrrolidine deprotection was employed: tert-butyl trans-3,4-bis((4-methylphenethyl)carbamoyl)pyrrolidine-1-carboxylate (78; 93 mg) provided 77 mg (99%) of S-47. $^1$H NMR (600 MHz, methanol-$d_4$) δ 7.09 (d, J=1.7 Hz, 8H), 3.49 (dd, J=11.6, 7.0 Hz, 2H), 3.45-3.35 (m, 6H), 3.23-3.13 (m, 2H), 2.75 (td, J=7.3, 1.6 Hz, 4H), 2.28 (s, 6H).

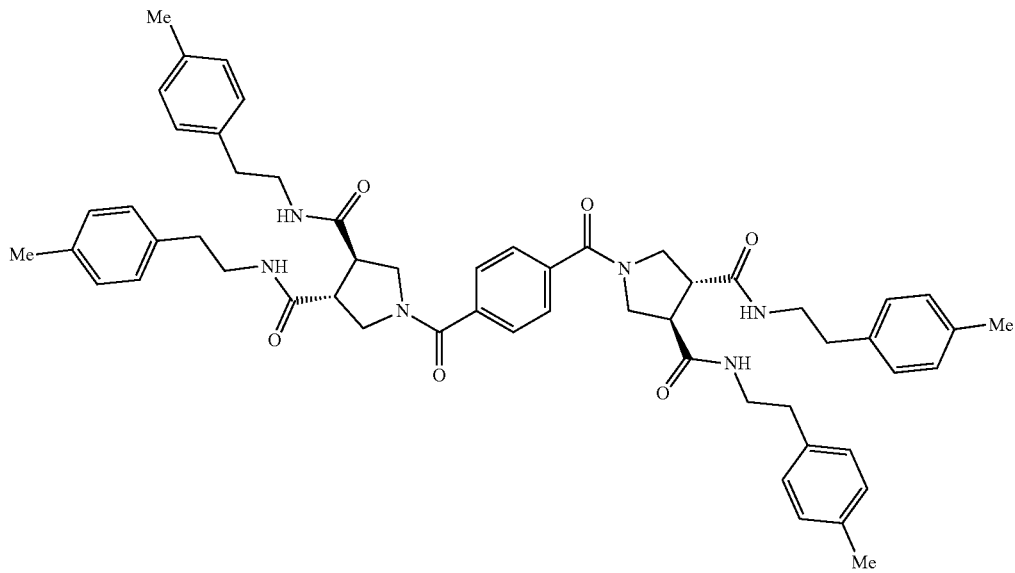 [SMILES: Cc1ccc(CCNC(=O)[C@H]2CN(C(=O)c3ccc(C(=O)N4C[C@H](C(=O)NCCc5ccc(C)cc5)[C@@H](C(=O)NCCc5ccc(C)cc5)C4)cc3)C[C@@H]2C(=O)NCCc2ccc(C)cc2)cc1]

92: 1,1'-Terephthaloylbis(N³,N⁴-bis(4-methyl-phen-ethyl)pyrrolidine-trans-3,4-dicarboxamide)

The general procedure for linking diacid coupling was employed: trans-N³,N⁴-bis(4-methyl-phenethyl)pyrrolidine-3,4-dicarboxamide hydrochloride (S-47; 43 mg) and terephthalic acid (benzene-1,4-dicarboxylic acid, 7.5 mg) provided 29 mg (70) of 92. $^1$H NMR (400 μMHz, HFIP-d$_2$) δ 7.60 (s, 4H), 7.24 (d, J=7.6 Hz, 4H), 7.20 (m, 8H), 7.08 (d, J=7.8 Hz, 4H), 6.52 (m, 4H), 4.05 (dd, J=12.6, 7.8 Hz, 2H), 3.74 (m, 6H), 3.67-3.52 (m, 5H), 3.45 (m, 7H), 2.89-2.77 (m, 4H), 2.74 (m, 4H), 2.32 (d, J=10.9 Hz, 12H). HRMS (ESI-TOF) m/z calcd for $C_{56}H_{64}N_6O_6$ [M+H]$^+$917.496, found 917.4965.

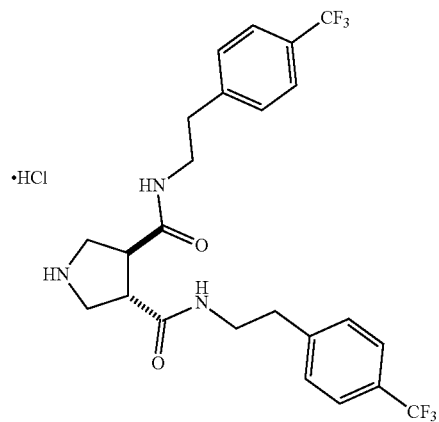 [SMILES: Cl ; O=C(NCCc1ccc(C(F)(F)F)cc1)[C@@H]1CNC[C@H]1C(=O)NCCc1ccc(C(F)(F)F)cc1]

S-48: trans-N³,N⁴-Bis(4-(trifluoromethyl)phen-ethyl)-pyrrolidine-3,4-dicarboxamide Hydrochloride The general procedure for Boc-pyrrolidine deprotection was employed: tert-butyl trans-3,4-bis((4-(trifluoromethyl) phenethyl)carbamoyl)-pyrrolidine-1-carboxylate (79; 121 mg) provided 101 mg (99%) of S-48. $^1$H NMR (600 MHz, methanol-d$_4$) δ 7.59 (d, J=7.9 Hz, 4H), 7.41 (d, J=8.0 Hz, 4H), 3.55-3.48 (m, 4H), 3.48-3.40 (m, 2H), 3.40-3.34 (m, 2H), 3.20 (ddt, J=6.8, 3.2, 1.6 Hz, 2H), 2.90 (dt, J=12.3, 6.8 Hz, 4H).

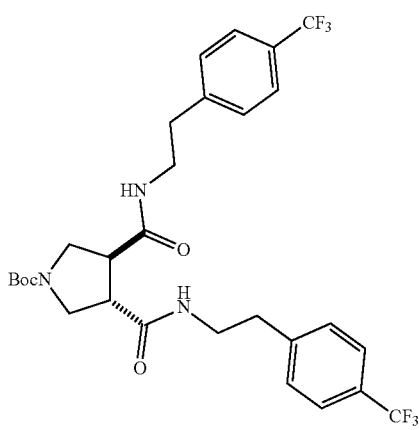

79: tert-Butyl trans-3,4-Bis((4-(trifluoromethyl)-phenethyl)carbamoyl)pyrrolidine-1-carboxylate The general procedure for the coupling of amines with pyrrolidine diacids was followed: trans-1-(tert-butoxycarbonyl)pyrrolidine-3,4-dicarboxylic acid (S-29; 50 mg), and 2-(4-(trifluoromethyl)-phenyl)ethan-1-amine (67 μL) provided 121 mg (99%) of 79 without purification.

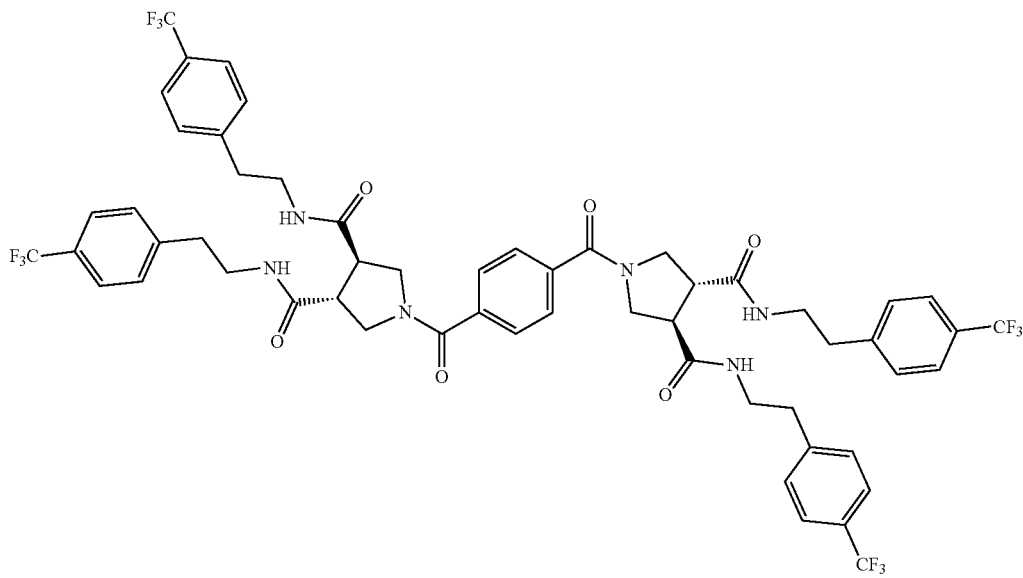 [SMILES: O=C(NCCc1ccc(C(F)(F)F)cc1)[C@H]1CN(C(=O)c2ccc(C(=O)N3C[C@H](C(=O)NCCc4ccc(C(F)(F)F)cc4)[C@@H](C(=O)NCCc4ccc(C(F)(F)F)cc4)C3)cc2)C[C@@H]1C(=O)NCCc1ccc(C(F)(F)F)cc1]

93: 1,1'-Terephthaloylbis(N³,N⁴-bis(4-(trifluoro-methyl)phenethyl)pyrrolidine-trans-3,4-dicarboxamide)

The general procedure for linking diacid coupling was employed: trans-N³,N⁴-bis(4-(trifluoro-methyl)phenethyl) pyrrolidine-3,4-dicarboxamide hydrochloride (S-48; 54 mg) and terephthalic acid (benzene-1,4-dicarboxylic acid, 7.5 mg) provided 50 mg (97) of 93. $^1$H NMR (400 MHz, CDCl$_3$) δ 7.63 (d, J=8.0 Hz, 4H), 7.60 (s, 4H), 7.56 (d, J=8.0 Hz, 4H), 7.33 (d, J=7.9 Hz, 4H), 7.26 (d, J=7.9 Hz, 4H), 6.62 (bs, 2H), 4.16-4.00 (m, 2H), 3.77-3.66 (m, 4H), 3.66-3.55 (m, 4H), 3.55-3.41 (m, 6H), 3.35-3.14 (m, 4H), 2.91 (d, J=7.2 Hz, 4H), 2.83 (d, J=7.3 Hz, 4H). HRMS (ESI-TOF) m/z calcd for C$_{56}$H$_{52}$F$_{12}$N$_6$O$_6$ [M+H]$^+$ 1133.3829, found 1133.3827.

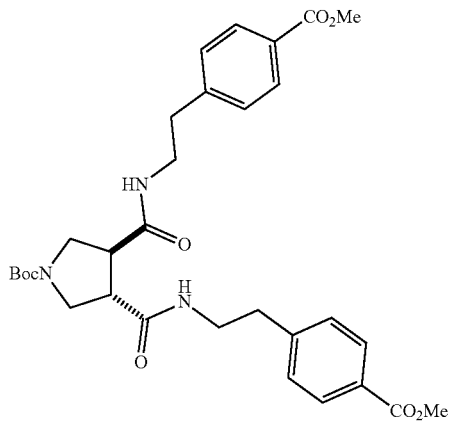 [SMILES: COC(=O)c1ccc(CCNC(=O)[C@@H]2CN(C(=O)OC(C)(C)C)C[C@H]2C(=O)NCCc2ccc(C(=O)OC)cc2)cc1]

80: Dimethyl 4,4'-(((trans-1-(tert-Butoxycarbonyl)-pyrrolidine-3,4-dicarbonyl)bis(azanediyl))-bis(ethane-2,1-diyl))dibenzoate The general procedure for the coupling of amines with pyrrolidine diacids was followed: trans-1-(tert-butoxycarbonyl)pyrrolidine-3,4-dicarboxylic acid (S-29; 50 mg), and methyl 4-(2-aminoethyl)-benzoate hydrochloride (91 mg) provided 121 mg (99%) of 80 without purification. $^1$H NMR (400 MHz, CDCl$_3$) δ 7.97 (d, J=8.0 Hz, 4H), 7.23 (d, J=8.0 Hz, 4H), 6.12 (b, 1H), 5.81 (b, 1H), 3.89 (s, 6H), 3.73 (m, 1H) 3.67-3.40 (m, 6H), 3.36 (m, 1H), 3.14 (m, 1H), 3.00 (m, 1H), 2.83 (t, J=7.1 Hz, 4H), 1.44 (s, 9H).

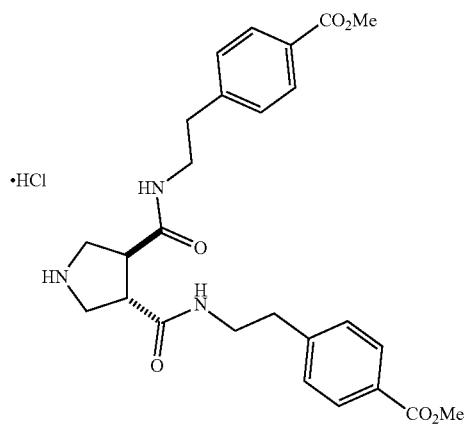 [SMILES: Cl ; COC(=O)c1ccc(CCNC(=O)[C@@H]2CNC[C@H]2C(=O)NCCc2ccc(C(=O)OC)cc2)cc1]

S-49: Dimethyl 4,4'-(((trans-Pyrrolidine-3,4-dicarbonyl)bis(azanediyl))bis(ethane-2,1-diyl))-dibenzoate Hydrochloride The general procedure for Boc-pyrrolidine deprotection was employed: dimethyl 4,4'-(((trans-1-(tert-butoxycarbonyl)pyrrolidine-3,4-dicarbonyl)-bis(azanediyl))bis(ethane-2,1-diyl))dibenzoate (80; 121 mg) provided 98 mg (99%) of S-49. $^1$H NMR (600 MHz, methanol-d$_4$) δ 7.95 (d, J=8.3 Hz, 4H), 7.33 (d, J=8.3 Hz, 4H), 3.88 (s, 6H), 3.55-3.39 (m, 6H), 3.36-3.33 (m, 2H), 3.21-3.16 (m, 2H), 2.87 (t, J=7.3 Hz, 4H).

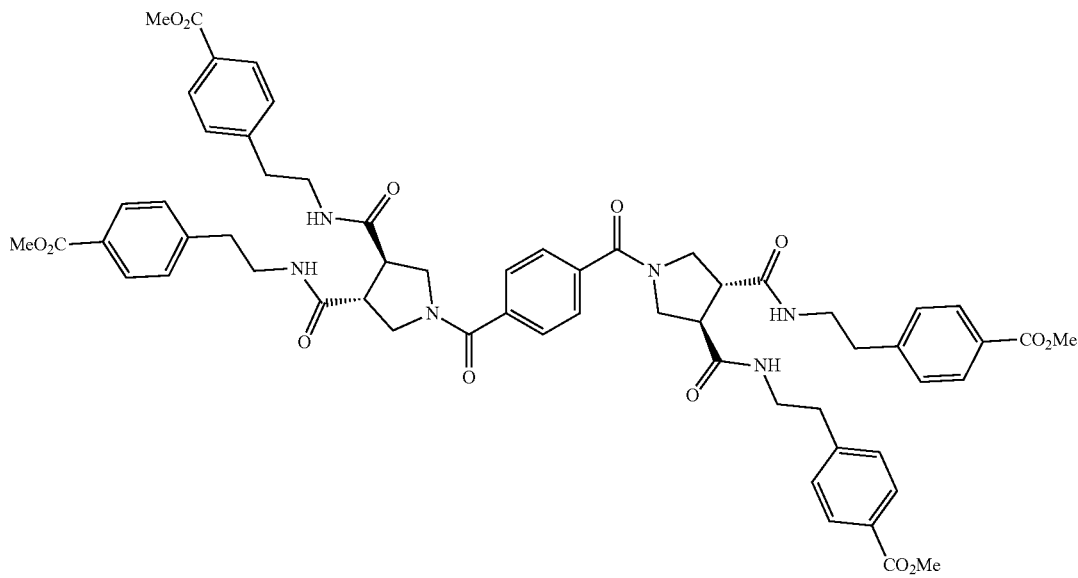 [SMILES: COC(=O)c1ccc(CCNC(=O)[C@H]2CN(C(=O)c3ccc(C(=O)N4C[C@H](C(=O)NCCc5ccc(C(=O)OC)cc5)[C@@H](C(=O)NCCc5ccc(C(=O)OC)cc5)C4)cc3)C[C@@H]2C(=O)NCCc2ccc(C(=O)OC)cc2)cc1]

94: 1,1'-Terephthaloylbis(N$^3$,N$^4$-bis(4-carbomethoxy-phenethyl)pyrrolidine-trans-3,4-dicarboxamide)

The general procedure for linking diacid coupling was employed: dimethyl 4,4'-(((trans-pyrrolidine-3,4-dicarbonyl)bis(azanediyl))bis(ethane-2,1-diyl))dibenzoate hydrochloride (S-49; 58 mg) and terephthalic acid (benzene-1,4- dicarboxylic acid, 7.5 mg) provided 40 mg (83%) of 94. $^1$H NMR (600 MHz, HFIP-d$_2$) δ 8.02 (d, J=8.0 Hz, 4H), 7.97 (d, J=7.9 Hz, 4H), 7.60 (d, 4H), 7.33 (d, J=8.1 Hz, 4H), 7.27 (d, J=8.0 Hz, 4H), 4.16-4.04 (m, 2H), 3.93 (d, J=5.6 Hz, 12H), 3.79-3.68 (m, 4H), 3.70-3.58 (m, 2H), 3.54 (dt, J=14.4, 7.3 Hz, 4H), 3.47-3.35 (m, 4H), 3.35-3.19 (m, 4H), 2.91 (t, J=7.2 Hz, 4H), 2.83 (td, J=13.37, 13.27, 6.53 Hz, 4H). HRMS (ESI-TOF) m/z calcd for C$_{60}$H$_{64}$N$_6$O$_{14}$ [M+H]$^+$ 1093.4553, found 1093.4559.

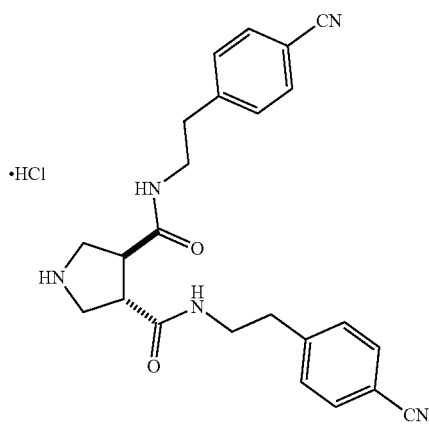

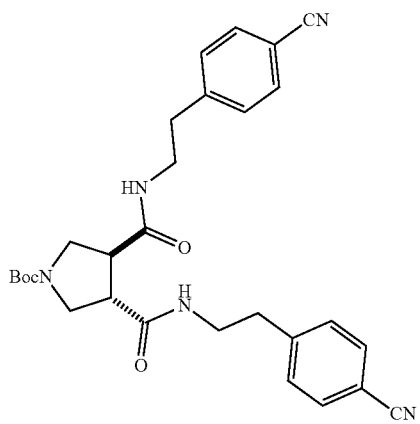 [SMILES: CC(C)(C)OC(=O)N1C[C@@H](C(=O)NCCc2ccc(C#N)cc2)[C@H](C(=O)NCCc2ccc(C#N)cc2)C1]

S-50: trans-N$^3$,N$^4$-Bis(4-cyanophenethyl)pyrrolidine-3,4-dicarboxamide Hydrochloride The general procedure for Boc-pyrrolidine deprotection was employed: tert-butyl trans-3,4-bis((4-cyanophenethyl)carbamoyl)pyrrolidine-1-carboxylate (81; 106 mg) provided 85 mg (99) of S-50. $^1$H NMR (600 MHz, methanol-d$_4$) δ 7.66 (d, J=6.6 Hz, 4H), 7.41 (d, J=8.3 Hz, 4H), 3.54-3.47 (m, 4H), 3.44 (dt, J=13.7, 7.1 Hz, 2H), 3.37-3.33 (m, 2H), 3.23-3.15 (m, 2H), 2.89 (td, J=7.1, 3.7 Hz, 4H).

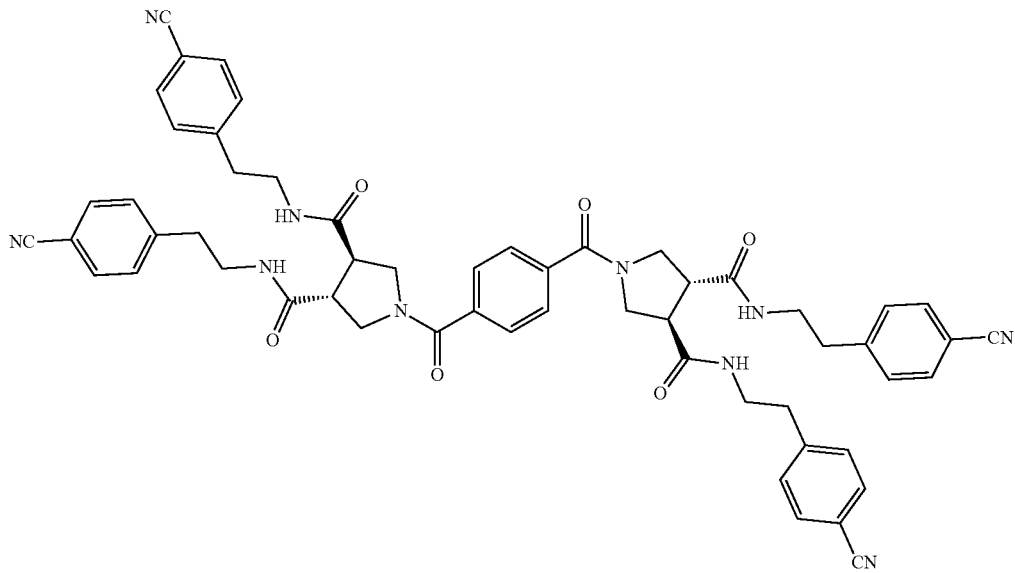 [SMILES: N#Cc1ccc(CCNC(=O)[C@H]2CN(C(=O)c3ccc(C(=O)N4C[C@H](C(=O)NCCc5ccc(C#N)cc5)[C@@H](C(=O)NCCc5ccc(C#N)cc5)C4)cc3)C[C@@H]2C(=O)NCCc2ccc(C#N)cc2)cc1]

81: tert-Butyl trans-3,4-Bis((4-cyanophenethyl)-carbamoyl)pyrrolidine-1-carboxylate The general procedure for the coupling of amines with pyrrolidine diacids was followed: trans-1-(tert-butoxycarbonyl)pyrrolidine-3,4-dicarboxylic acid (S-29; 50 mg), and 4-(2-aminoethyl)benzonitrile hydrochloride (77 mg) provided 106 mg (99) of 81 without purification. $^1$H NMR (400 MHz, CDCl$_3$) δ 7.75 (d, J=7.9 Hz, 4H), 7.43 (d, J=8.1 Hz, 4H), 6.17 (b, 2H), 3.96-3.65 (m, 5H), 3.65-3.46 (m, 4H), 3.11 (s, 1H), 3.01 (t, J=7.1 Hz, 4H), 1.60 (s, 9H).

95: 1,1'-Terephthaloylbis(N$^3$,N$^4$-bis(4-cyanophenethyl)-pyrrolidine-trans-3,4-dicarboxamide)

The general procedure for linking diacid coupling was employed: trans-N$^3$,N$^4$-bis(4-cyano-phenethyl)pyrrolidine-3,4-dicarboxamide hydrochloride (S-50; 52 mg) and terephthalic acid (benzene-1,4-dicarboxylic acid, 7.5 mg) provided 38 mg (89%) of 95. HRMS (ESI-TOF) m/z calcd for C$_{56}$H$_{52}$N$_{10}$O$_6$[M+H]$^+$961.4144, found 961.4159.

153

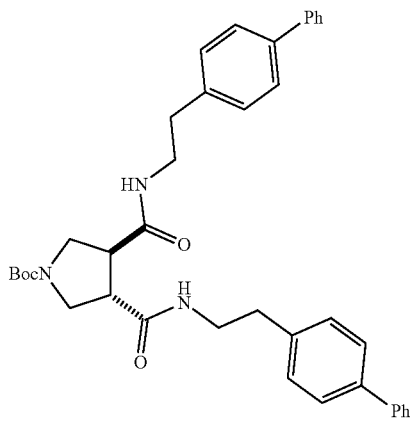 [SMILES: CC(C)(C)OC(=O)N1C[C@@H](C(=O)NCCc2ccc(-c3ccccc3)cc2)[C@H](C(=O)NCCc2ccc(-c3ccccc3)cc2)C1]

82: tert-Butyl trans-3,4-Bis((2-([1,1'-biphenyl]-4-yl)ethyl)carbamoyl)pyrrolidine-1-carboxylate The general procedure for the coupling of amines with pyrrolidine diacids was followed: trans-1-(tert-butoxycarbonyl)pyrrolidine-3,4-dicarboxylic acid (S-29; 50 mg), and 2-([1,1'-biphenyl]-4-yl)-ethan-1-amine hydrochloride (83 mg) provided 124 mg (99%) of 82. $^1$H NMR (400 MHz, CDCl$_3$) δ 7.54 (dd, J=16.3, 7.7 Hz, 8H), 7.43 (t, J=7.6 Hz, 4H), 7.33 (t, J=7.4 Hz, 2H), 7.21 (d, J=7.6 Hz, 4H), 6.12 (b, 1H), 5.79 (b, 1H), 3.85-3.71 (m, 1H), 3.68-3.29 (m, 7H), 3.21-3.12 (m, 1H), 3.07-2.94 (m, 1H), 2.82 (t, J=7.1 Hz, 4H), 1.43 (s, 9H).

154

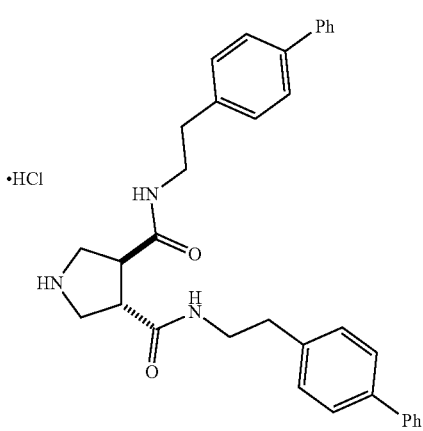 [SMILES: Cl ; O=C(NCCc1ccc(-c2ccccc2)cc1)[C@@H]1CNC[C@H]1C(=O)NCCc1ccc(-c2ccccc2)cc1]

S-51: trans-N$^3$,N$^4$-Bis(2-([1,1'-biphenyl]-4-yl)ethyl)-pyrrolidine-3,4-dicarboxamide Hydrochloride The general procedure for Boc-pyrrolidine deprotection was employed: tert-butyl trans-3,4-bis((2-([1,1'-biphenyl]-4-yl)ethyl) carbamoyl)-pyrrolidine-1-carboxylate (82; 124 mg) provided 105 mg (99%) of S-51. $^1$H NMR (600 MHz, methanol-d$_4$) δ 7.59-7.55 (m, 4H), 7.54 (d, J=8.2 Hz, 4H), 7.41 (dd, J=8.3, 7.2 Hz, 4H), 7.34-7.29 (m, 2H), 7.28 (d, J=8.2 Hz, 4H), 3.52-3.44 (m, 6H), 3.40-3.36 (m, 2H), 3.24-3.17 (m, 2H), 2.84 (t, J=7.2 Hz, 4H).

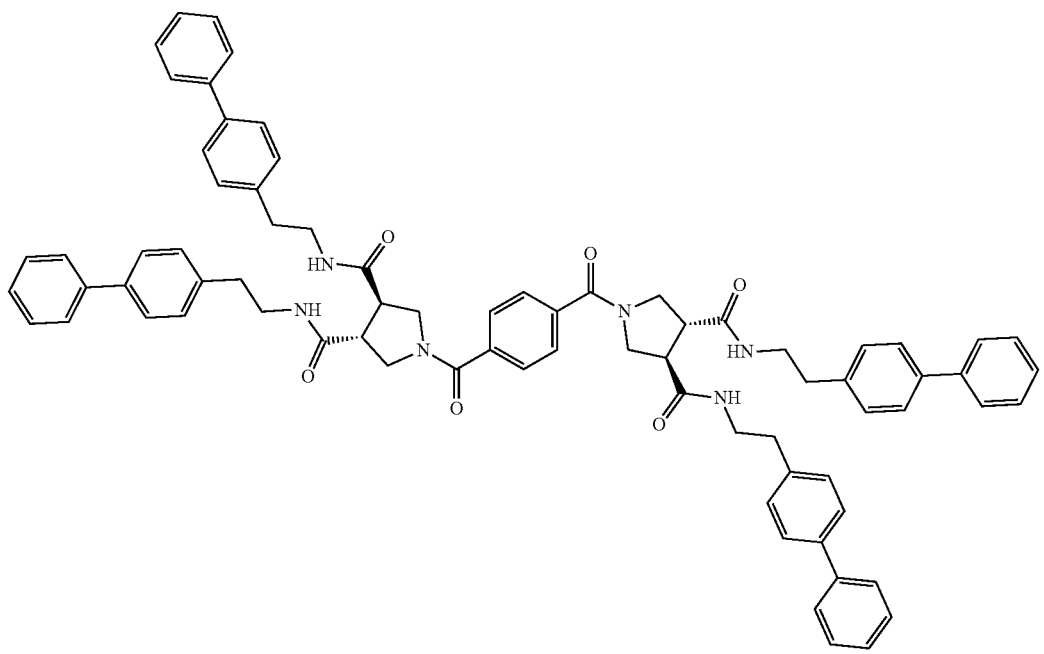 [SMILES: O=C(NCCc1ccc(-c2ccccc2)cc1)[C@H]1CN(C(=O)c2ccc(C(=O)N3C[C@H](C(=O)NCCc4ccc(-c5ccccc5)cc4)[C@@H](C(=O)NCCc4ccc(-c5ccccc5)cc4)C3)cc2)C[C@@H]1C(=O)NCCc1ccc(-c2ccccc2)cc1]

96: 1,1'-Terephthaloylbis(N³,N⁴-bis(4-phenyl-phenethyl)pyrrolidine-trans-3,4-dicarboxamide)

The general procedure for linking diacid coupling was employed: trans-N³,N⁴-bis(2-([1,1'-biphenyl]-4-yl)ethyl) pyrrolidine-3,4-dicarboxamide hydrochloride (S-51; 62 mg) and terephthalic acid (benzene-1,4-dicarboxylic acid, 7.5 mg) provided 22 mg (42%) of 96. $^1$H NMR (600 MHz, HFIP-$d_2$) δ 7.67 (d, J=7.6 Hz, 6H), 7.65-7.61 (m, 8H), 7.56-7.52 (m, 6H), 7.51-7.47 (m, 10H), 7.39 (t, J=7.5 Hz, 4H), 7.27 (dd, J=8.3, 2.9 Hz, 4H), 7.21 (d, J=8.1 Hz, 4H), 6.57 (b, 1H), 6.52 (b, 1H), 4.08 (m, 2H), 3.81-3.71 (m, 2H), 3.71-3.38 (m, 12H), 3.29-3.21 (m, 2H), 3.21-3.14 (m, 2H), 2.91-2.72 (m, 8H). HRMS (ESI-TOF) m/z calcd for $C_{76}H_{72}N_6O_6$ [M+H]$^+$ 1165.5586, found 1165.5586.

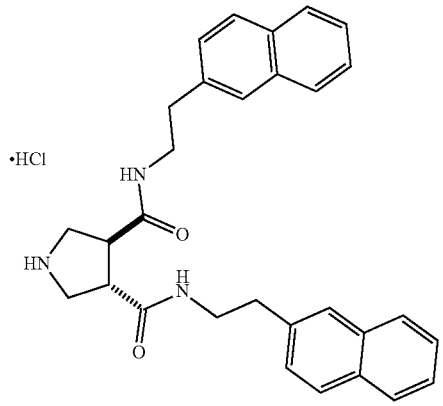

S-52: trans-N³,N⁴-Bis(2-(naphthalen-2-yl)ethyl)-pyrrolidine-3,4-dicarboxamide The general procedure for Boc-pyrrolidine deprotection was employed: tert-butyl trans-3,4-bis((2-(naphthalen-2-yl)ethyl)carbamoyl)pyrrolidine-1-carboxylate (83; 107 mg) provided 95 mg (99%) of S-52. $^1$H NMR (600 MHz, methanol-$d_4$) δ 7.82-7.76 (m, 6H), 7.65 (d, J=1.7 Hz, 2H), 7.42 (dddd, J=17.4, 8.1, 6.9, 1.4 Hz, 4H), 7.35 (dd, J=8.4, 1.8 Hz, 2H), 3.49 (ddp, J=20.6, 13.6, 7.1 Hz, 6H), 3.40 (ddd, J=10.3, 7.9, 4.5 Hz, 2H), 3.15 (td, J=5.1, 1.5 Hz, 2H), 2.95 (d, J=7.2 Hz, 4H).

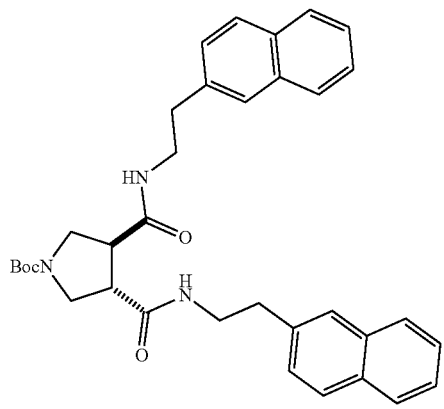 [SMILES: CC(C)(C)OC(=O)N1C[C@@H](C(=O)NCCc2ccc3ccccc3c2)[C@H](C(=O)NCCc2ccc3ccccc3c2)C1]

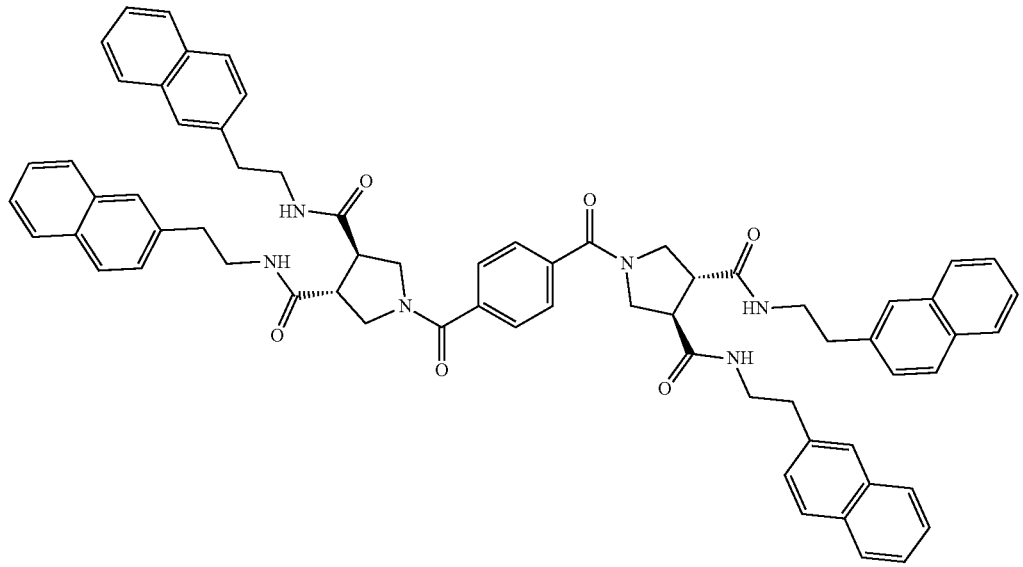 [SMILES: O=C(NCCc1ccc2ccccc2c1)[C@H]1CN(C(=O)c2ccc(C(=O)N3C[C@H](C(=O)NCCc4ccc5ccccc5c4)[C@@H](C(=O)NCCc4ccc5ccccc5c4)C3)cc2)C[C@@H]1C(=O)NCCc1ccc2ccccc2c1]

83: tert-Butyl trans-3,4-Bis((2-(naphthalen-2-yl)ethyl)carbamoyl)pyrrolidine-1-carboxylate The general procedure for the coupling of amines with pyrrolidine diacids was followed: trans-1-(tert-butoxycarbonyl)pyrrolidine-3,4-dicarboxylic acid (S-29; 50 mg), and 2-(naphthalen-2-yl)ethan-1-amine hydrochloride (87 mg) provided 107 mg (99%) of 83 without purification.

97: 1,1'-Terephthaloylbis(N³,N⁴-bis(2-(naphthalen-2-yl)ethyl)pyrrolidine-trans-3,4-dicarboxamide)

The general procedure for linking diacid coupling was employed: trans-N³,N⁴-bis(2-(naphthalen-2-yl)ethyl)pyrrolidine-3,4-dicarboxamide (S-52; 50 mg) and terephthalic acid (benzene-1,4-dicarboxylic acid, 7.5 mg) provided 38 mg (80%) of 97. $^1$H NMR (400 MHz, HFIP-$d_2$) δ 7.89-7.76

(m, 12H), 7.63 (s, 2H), 7.55 (m, 6H), 7.50 (t, J=7.7 Hz, 4H), 7.46 (m, 4H), 7.35 (d, J=8.0 Hz, 2H), 7.30-7.25 (m, 2H), 6.32 (b, 2H), 4.00 (dd, J=12.9, 8.5 Hz, 2H), 3.83-3.74 (m, 2H), 3.71-3.61 (m, 4H), 3.56 (t, J=10.4 Hz, 2H), 3.53-3.45 (m, 2H), 3.45-3.38 (m, 4H), 3.37-3.28 (m, 2H), 3.28-3.17 (m, 2H), 3.13-2.98 (m, 4H), 2.92-2.82 (m, 4H), 2.83-2.71 (m, 2H). HRMS (ESI-TOF) m/z calcd for $C_{68}H_{64}N_6O_6$ [M+H]$^+$ 1061.496, found 1061.4963.

Diprovocim-2 Synthesis

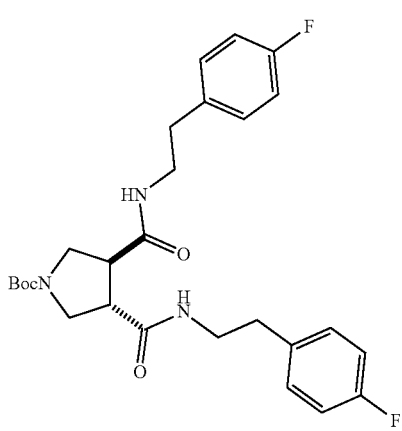 [SMILES: CC(C)(C)OC(=O)N1C[C@@H](C(=O)NCCc2ccc(F)cc2)[C@H](C(=O)NCCc2ccc(F)cc2)C1]

65: tert-Butyl (3S,4S)-3,4-Bis((4-fluorophenethyl)-carbamoyl)pyrrolidine-1-carboxylate A solution of (3S,4S)-1-(tert-butoxy-carbonyl)pyrrolidine-3,4-dicarboxylic acid (S,S-14; 110 mg, 0.43 mmol), HOAt (147 mg, 1.08 mmol, 2.5 equiv), and 2,6-lutidine (322 µL, 3 mmol, 7 equiv) in 4 mL of DMF was treated with 2-(4-fluorophenyl)ethan-1-amine hydrochloride (167 mg, 0.95 mmol, 2.2 equiv) and EDCI.HCl (207 mg, 1.08 mmol, 2.5 equiv). The reaction mixture was stirred at 23° C. for 24 hours. The reaction mixture was then diluted with 50% EtOAc/hexanes (25 mL), washed with aqueous 0.5 M HCl (25 mL), extracted with EtOAc (3×25 mL), washed with H$_2$O (100 mL), saturated aqueous NaHCO$_3$ (100 mL), and saturated aqueous NaCl, dried with Na$_2$SO$_4$, and condensed to provide 65 as a white solid (200 mg, 93%), which was used without additional purification. 1H NMR (400 MHz, CDCl$_3$) δ 7.20-7.05 (m, 4H), 7.02-6.92 (m, 4H), 6.09 (b, 2H), 3.75 (m, 1H), 3.60 (m, 1H), 3.50 (m, 3H), 3.40 (m, 3H), 3.16 (m, 1H), 2.98 (m, 1H), 2.75 (t, J=7.0 Hz, 4H), 1.44 (s, 9H).

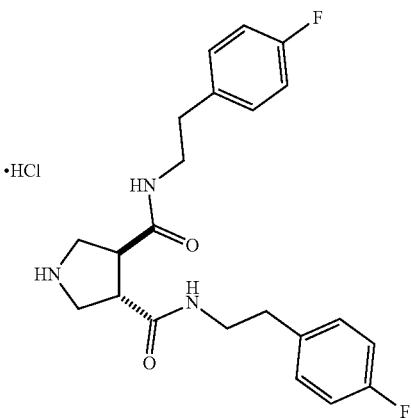 [SMILES: Cl ; O=C(NCCc1ccc(F)cc1)[C@@H]1CNC[C@H]1C(=O)NCCc1ccc(F)cc1]

S-53: (3S,4S)—N$^3$,N$^4$-Bis(4-fluorophenethyl)-pyrrolidine-3,4-dicarboxamide Hydrochloride A solution of tert-butyl (3S,4S)-3,4-bis((4-fluorophenethyl)carbamoyl)pyrrolidine-1-carboxylate (65; 200 mg, 0.40 mmol) was stirred in a solution of 4 M HCl in dioxane at 23° C. for 3 hours. The solvent was removed by a stream of N$_2$ and the crude product was taken up in THF (5 mL) and concentrated. This process was repeated (3×5 mL THF, 3×5 mL Et$_2$O) to provide S-53 as a white solid (170 mg, 99%) which was used without purification. 1H NMR (400 MHz, methanol-d$_4$) δ 7.22 (dd, J=8.2, 5.3 Hz, 4H), 7.01 (t, J=8.6 Hz, 4H), 3.57-3.44 (m, 2H), 3.47-3.31 (m, 6H), 3.25-3.14 (m, 2H), 2.79 (t, J=7.7 Hz, 4H).

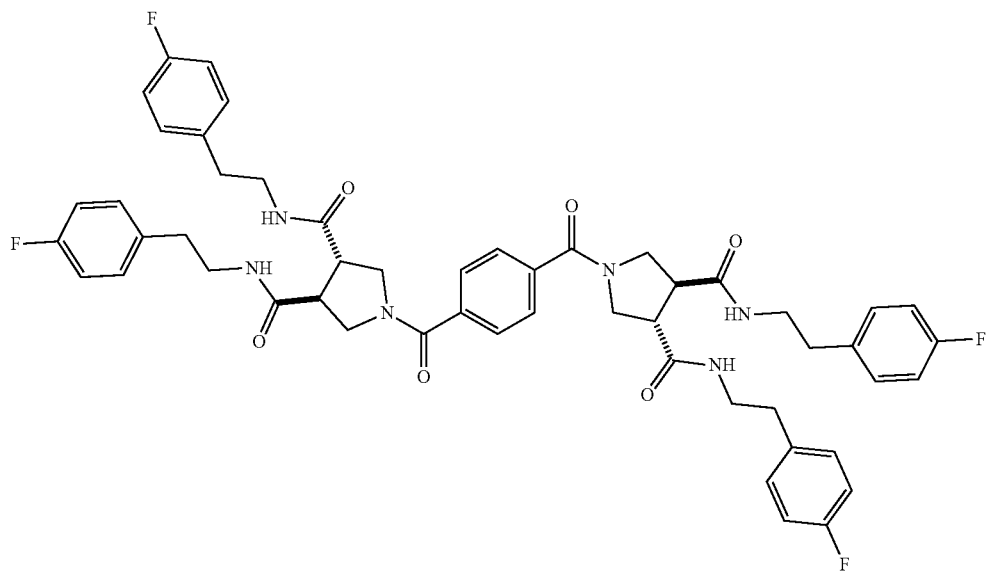 [SMILES: O=C(NCCc1ccc(F)cc1)[C@@H]1CN(C(=O)c2ccc(C(=O)N3C[C@@H](C(=O)NCCc4ccc(F)cc4)[C@H](C(=O)NCCc4ccc(F)cc4)C3)cc2)C[C@H]1C(=O)NCCc1ccc(F)cc1]

4 (Diprovocim-2): (3S,3'S,4S,4'S)-1,1'-Terephtha-loylbis(N³,N⁴-bis(4-fluorophenethyl)-pyrrolidine-3,4-dicarboxamide)

A solution of (3S,4S)—N³,N⁴-bis(4-fluorophenethyl)pyrrolidine-3,4-dicarboxamide hydrochloride (S-53; 44 mg, 0.10 mmol, 2.2 equiv), terephthalic acid (benzene-1,4-dicarboxylic acid, 7.5 mg, 0.045, 1 equiv), and PyBrOP (47 mg, 0.10 mmol, 2.2 equiv) in 500 µL DMF was treated with i-Pr₂NEt (40 µL, 0.23 mmol, 5 equiv). The reaction mixture was stirred at 23° C. for 18 hours after which time the mixture was diluted with EtOAc (3 mL) and washed with aqueous 0.5 N HCl (2×3 mL). The aqueous phase was extracted with EtOAc (1×3 mL). The combined organic phases were washed with saturated aqueous NaHCO₃ (10 mL) and saturated aqueous NaCl (10 mL). The organic phase was dried over Na₂SO₄, decanted and concentrated. The product was purified by trituration with cold (0° C.) 1:1 Et₂O/EtOAc (3×5 mL), decanting off the liquid phase to provide 35 mg (84%) of 4 as a white solid. $^1$H NMR (600 MHz, DMSO-d₆) δ 8.13 (t, J=5.7 Hz, 2H), 7.97 (t, J=5.7 Hz, 2H), 7.56 (s, 4H), 7.23 (ddd, J=9.3, 5.7, 2.9 Hz, 4H), 7.16-7.12 (m, 4H), 7.09 (td, J=9.0, 5.1 Hz, 4H), 7.05-6.98 (m, 4H), 3.76 (dd, J=11.9, 8.5 Hz, 2H), 3.60 (dd, J=10.3, 7.8 Hz, 2H), 3.49-3.37 (m, 4H), 3.29-3.20 (m, 6H), 3.21-3.14 (m, 4H), 3.10 (q, J=8.2 Hz, 2H), 2.70 (td, J=7.1, 2.6 Hz, 4H), 2.66-2.59 (m, 4H). $^{13}$C NMR (151 µMHz, DMSO-d₆) δ 170.6, 169.9, 167.4, 161.60, 161.55, 160.01, 159.96, 137.7, 135.48, 135.46, 135.37, 135.35, 130.44, 130.39, 130.36, 130.31, 127.1, 115.0, 114.9, 114.84, 114.78, 51.7, 48.9, 46.9, 44.9, 40.3, 40.2, 34.1, 34.0. HRMS (ESI-TOF) m/z calcd for C₅₂H₅₂F₄N₆O₆[M+H]⁺ 933.3957, found 933.3986.

Stereoisomers of Diprovocim-2

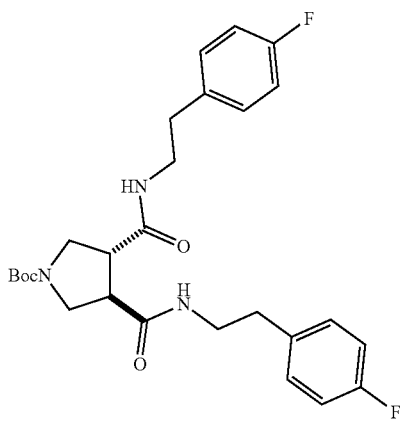 [SMILES: CC(C)(C)OC(=O)N1C[C@H](C(=O)NCCc2ccc(F)cc2)[C@@H](C(=O)NCCc2ccc(F)cc2)C1]

65: tert-Butyl (3R,4R)-3,4-Bis((4-fluorophenethyl)-carbamoyl)pyrrolidine-1-Carboxylate A solution of (3R,4R)-1-(tert-butoxy-carbonyl)pyrrolidine-3,4-dicarboxylic acid (R,R-14; 81 mg, 0.31 mmol), HOAt (149 mg, 0.78 mmol, 2.5 equiv), and 2,6-lutidine (253 µL, 2.17 mmol, 7 equiv) in 4 mL DMF was treated with 2-(4-fluorophenyl)ethan-1-amine hydrochloride (167 mg, 0.95 mmol, 2.2 equiv) and EDCI.HCl (207 mg, 1.08 mmol, 2.5 equiv). The reaction mixture was stirred at 23° C. for 18 hours. The reaction mixture was then diluted with 50% EtOAc/hexanes (25 mL), washed with aqueous 0.5 M HCl (25 mL), extracted with EtOAc (3×25 mL), washed with H₂O (100 mL), saturated aqueous NaHCO₃ (100 mL), saturated aqueous NaCl, dried with Na₂SO₄, and condensed to provide 65 as a white solid (200 mg, 93%), which was used without additional purification. 1H NMR (400 MHz, CDCl₃) δ 7.20-7.05 (m, 4H), 7.02-6.92 (m, 4H), 6.09 (b, 2H), 3.75 (m, 1H), 3.60 (m, 1H), 3.50 (m, 3H), 3.40 (m, 3H), 3.16 (m, 1H), 2.98 (m, 1H), 2.75 (t, J=7.0 Hz, 4H), 1.44 (s, 9H).

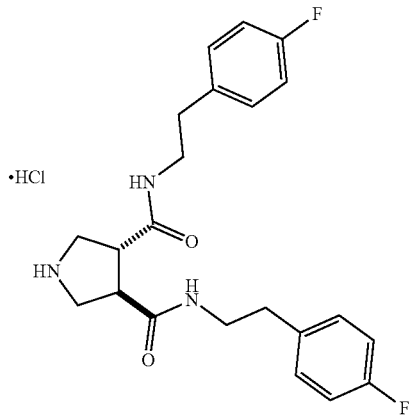 [SMILES: Cl ; O=C(NCCc1ccc(F)cc1)[C@H]1CNC[C@@H]1C(=O)NCCc1ccc(F)cc1]

S-54: (3R,4R)—N³,N⁴-Bis(4-fluorophenethyl)-pyrrolidine-3,4-dicarboxamide Hydrochloride A solution of tert-butyl (3R,4R)-3,4-bis((4-fluorophenethyl)carbamoyl)pyrrolidine-1-carboxylate (65; 152 mg, 0.30 mmol) was stirred in a solution of 4 M HCl in dioxane (2.5 mL) at 23° C. for 3 hours. The solvent was removed by a stream of N₂ and the crude product taken up in THF (5 mL) and condensed. This process was repeated (5×5 mL) to provide S-54 as a white solid (130 mg, 99%) which was used without purification. 1H NMR (400 MHz, methanol-d₄) δ 7.22 (dd, J=8.2, 5.3 Hz, 4H), 7.01 (t, J=8.6 Hz, 4H), 3.57-3.44 (m, 2H), 3.47-3.31 (m, 6H), 3.25-3.14 (m, 2H), 2.79 (t, J=7.7 Hz, 4H).

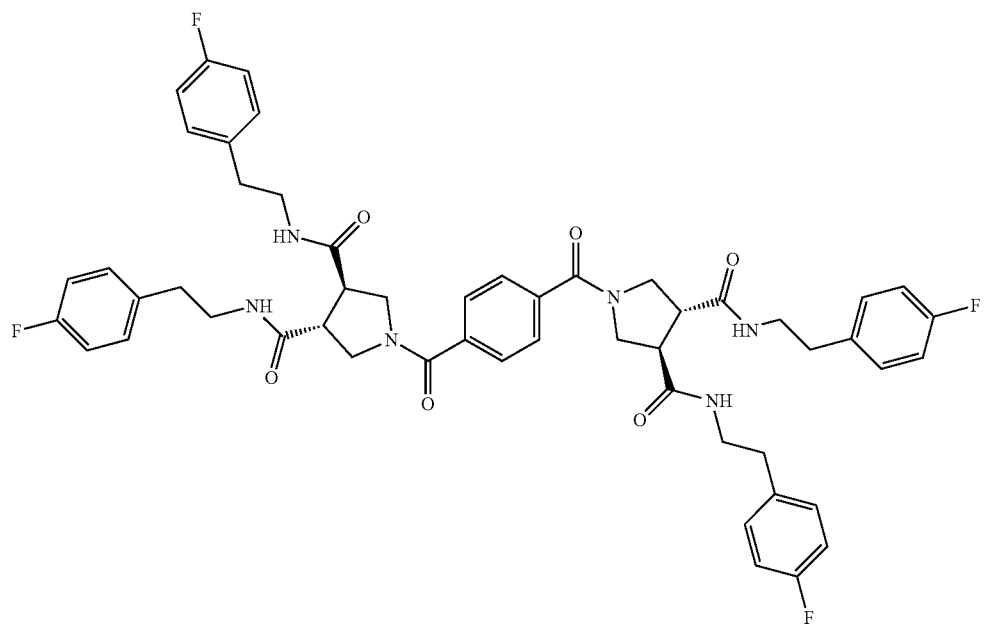 [SMILES: O=C(NCCc1ccc(F)cc1)[C@H]1CN(C(=O)c2ccc(C(=O)N3C[C@H](C(=O)NCCc4ccc(F)cc4)[C@@H](C(=O)NCCc4ccc(F)cc4)C3)cc2)C[C@@H]1C(=O)NCCc1ccc(F)cc1]

98: (3R,3'R,4R,4'R)-1,1'-Terephthaloyl-bis(N³,N⁴-bis-(4-fluorophenethyl)pyrrolidine-3,4-dicarboxamide)

A solution of (3R,4R)—N³,N⁴-bis(4-fluorophenethyl) pyrrolidine-3,4-dicarboxamide hydrochloride (S-54; 44 mg, 0.10 mmol, 2.2 equiv), terephthalic acid (benzene-1,4-dicarboxylic acid, 7.5 mg, 0.045, 1 equiv), and PyBrOP (47 mg, 0.10 mmol, 2.2 equiv) in 500 µL DMF was treated with i-Pr₂NEt (40 µL, 0.23 mmol, 5 equiv). The reaction was stirred at 23° C. for 24 hours after which time the mixture was diluted with EtOAc (3 mL) and washed with aqueous 0.5 N HCl (2×3 mL). The aqueous phase was extracted with EtOAc (1×3 mL). The combined organic phases were washed with saturated aqueous NaHCO₃ (10 mL) and saturated aqueous NaCl (10 mL). The organic phase was dried over Na₂SO₄, decanted and concentrated. The product was purified by trituration with cold (0° C.) 1:1 Et₂O/EtOAc (3×5 mL), decanting off the liquid phase to provide 34 mg (83%) of 98 as a white solid. 1H NMR (600 MHz, HFIP-d₂) δ 7.60 (s, 4H), 7.20 (td, J=5.6, 2.6 Hz, 4H), 7.12 (td, J=5.5, 2.5 Hz, 4H), 7.04 (td, J=8.9, 2.4 Hz, 4H), 6.95 (td, J=8.9, 2.4 Hz, 4H), 4.06 (dd, J=12.5, 8.5 Hz, 2H), 3.74-3.62 (m, 4H), 3.63-3.54 (m, 4H), 3.54-3.39 (m, 6H), 3.33-3.15 (m, 4H), 2.82 (t, J=7.1 Hz, 4H), 2.74 (t, J=6.8 Hz, 4H). HRMS (ESI-TOF) m/z calcd for $C_{52}H_{52}F_4N_6O_6[M+H]^+$ 933.3957, found 933.3952.

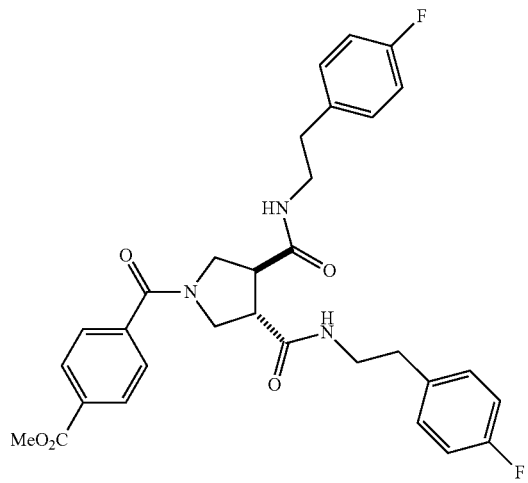 [SMILES: COC(=O)c1ccc(C(=O)N2C[C@@H](C(=O)NCCc3ccc(F)cc3)[C@H](C(=O)NCCc3ccc(F)cc3)C2)cc1]

S-55: Methyl 4-((3S,4S)-3,4-Bis((4-fluorophenethyl)-carbamoyl)pyrrolidine-1-carbonyl)benzoate A solution of 4-(methoxycarbonyl)benzoic acid (20 mg, 0.11 mmol, 1.1 equiv), (3S,4S)—N³,N⁴-bis(4-fluoro-phenethyl)pyrrolidine-3,4-dicarboxamide hydrochloride (44 mg, 0.1 mmol, 1.0 equiv), and PyBrOP (51 mg, 0.11 mmol, 1.1 equiv) in DMF (0.5 mL) was treated with i-Pr₂NEt (53 µL, 0.3 mmol, 3 equiv). The reaction mixture was stirred at 23° C. for 24 hours before being poured into EtOAc (3 mL) and washed with aqueous 0.5 N HCl (2×3 mL). The aqueous phase was extracted with EtOAc (1×3 mL). The combined organic phases were washed with a saturated aqueous solution of NaHCO₃ (10 mL) and saturated aqueous NaCl (10 mL). The organic phase was dried over Na₂SO₄, decanted and concentrated. The crude product (S-55; 61 mg, 99%) was used without additional purification. ¹H NMR (600 MHz, CDCl₃) δ 8.08 (d, J=8.4 Hz, 2H), 7.55 (d, J=8.3 Hz, 2H), 7.12 (d, J=6.2 Hz, 2H), 7.07 (td, J=5.6, 1.6 Hz, 2H), 7.01 (t, J=8.3 Hz, 2H), 6.93 (t, J=8.6 Hz, 2H), 6.23 (s, 1H), 5.86 (s, 1H), 4.05 (t, J=10.7 Hz, 1H), 3.94 (s, 3H), 3.75 (t, J=10.5 Hz, 1H), 3.68 (t, J=11.2 Hz, 1H), 3.65-3.58 (m, 1H), 3.58-3.50 (m, 1H), 3.42 (m, 3H), 3.25-3.18 (m, 1H), 3.08 (q, J=9.9 Hz, 1H), 2.76 (d, J=6.8 Hz, 2H), 2.72 (t, J=7.1 Hz, 2H).

purification. $^1$H NMR (400 MHz, methanol-$d_4$) δ 8.14 (d, J=8.0 Hz, 2H), 7.62 (d, J=7.9 Hz, 2H), 7.23 (s, 2H), 7.13 (s, 2H), 7.02 (t, J=8.5 Hz, 2H), 6.91 (t, J=8.6 Hz, 2H), 4.03-3.90 (m, 1H), 3.63 (dt, J=19.8, 10.2 Hz, 2H), 3.53-3.38 (m, 4H), 3.18 (d, J=9.4 Hz, 3H), 2.80 (s, 2H), 2.72 (d, J=7.5 Hz, 2H).

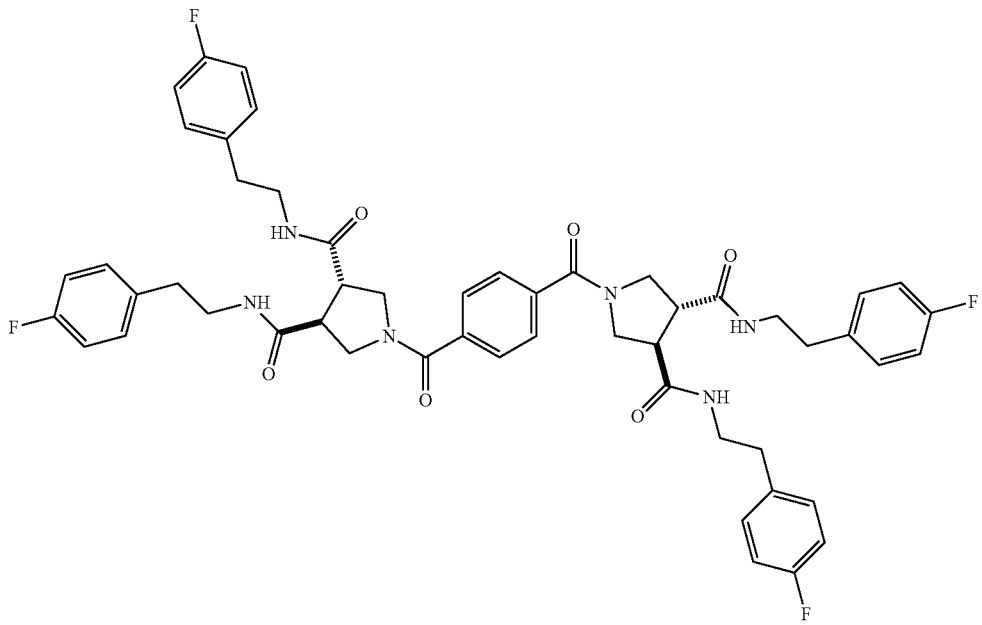

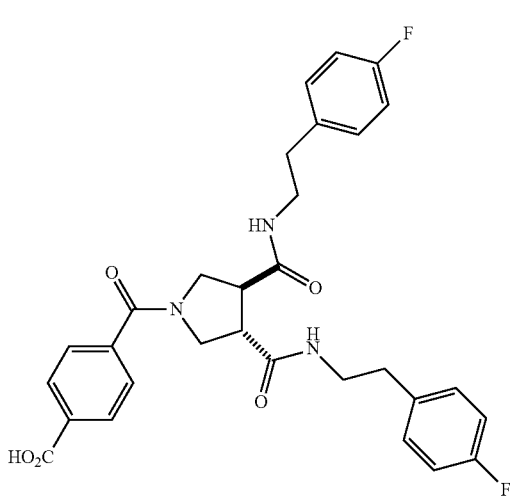 [SMILES: O=C(O)c1ccc(C(=O)N2C[C@@H](C(=O)NCCc3ccc(F)cc3)[C@H](C(=O)NCCc3ccc(F)cc3)C2)cc1]

S-56: 4-((3S,4S)-3,4-Bis((4-fluorophenethyl)-carbamoyl)pyrrolidine-1-carbonyl)benzoic acid A solution of methyl 4-((3S,4S)-3,4-bis((4-fluorophenethyl)carbamoyl)pyrrolidine-1-carbonyl)-benzoate (S-55; 61 mg, 0.1 mmol) in THF/MeOH/H$_2$O (2.5 mL, 4:1:1 ratio) was treated with LiOH.H$_2$O. The suspension was stirred at 23° C. for 2 hours. The reaction mixture was then poured into EtOAc (3 mL), quenched with the addition of aqueous 1 M HCl (5 mL), extracted in EtOAc (2×5 mL), washed with saturated aqueous NaCl, and dried with Na$_2$SO$_4$. The crude product (S-56; 60 mg, 99%) was used without additional 99: (3S,4S)-1-(4-((3R,4R)-3,4-Bis((4-fluorophen-ethyl)carbamoyl)pyrrolidine-1-carbonyl)benzoyl)—N$^3$,N$^4$-bis(4-fluorophenethyl)pyrrolidine-3,4-dicar-boxamide A solution of 4-((3S,4S)-3,4-bis((4-fluorophenethyl)carbamoyl)pyrrolidine-1-carbonyl)-benzoic acid (S-56; 55 mg, 0.10 mmol, 1 equiv), (3R,4R)—N$^3$,N$^4$-bis(4-fluorophenethyl)pyrrolidine-3,4-dicarboxamide hydrochloride (S-54; 44 mg, 0.1, 1 equiv), and PyBrOP (52 mg, 0.11 mmol, 1.1 equiv) in 1 mL DMF was treated with i-Pr$_2$NEt (53 μL, 0.3 mmol, 3 equiv). The reaction mixture was stirred at 23° C. for 40 hours after which time the mixture was diluted with EtOAc (3 mL) and washed with aqueous 0.5 N HCl (2×3 mL). The aqueous phase was extracted with EtOAc (1×3 mL). The combined organic phases were washed with saturated aqueous NaHCO$_3$ (10 mL) and saturated aqueous NaCl (10 mL). The organic phase was dried over Na$_2$SO$_4$, decanted and concentrated. The product was purified by trituration with cold (0° C.) 1:1 Et$_2$O/EtOAc (3×5 mL), decanting off the liquid phase to provide 68 mg (73%) of 99 as a white solid. 1H NMR (400 MHz, HFIP-d$_2$) δ 7.60 (s, 4H), 7.19 (dd, J=8.2, 5.3 Hz, 4H), 7.11 (dd, J=8.3, 5.4 Hz, 4H), 7.04 (t, J=8.7 Hz, 4H), 6.95 (t, J=8.7 Hz, 4H), 4.06 (dd, J=12.5, 8.1 Hz, 2H), 3.84-3.65 (m, 8H), 3.56 (m, 6H), 3.44 (t, J=7.2 Hz, 4H), 2.82 (t, J=7.0 Hz, 4H), 2.74 (t, J=7.2 Hz, 4H). HRMS (ESI-TOF) m/z calcd for C$_{52}$H$_{52}$F$_4$N$_6$O$_6$ [M+H]$^+$ 933.3957, found 933.3950.

Linker Analogues of Diprovocim-2

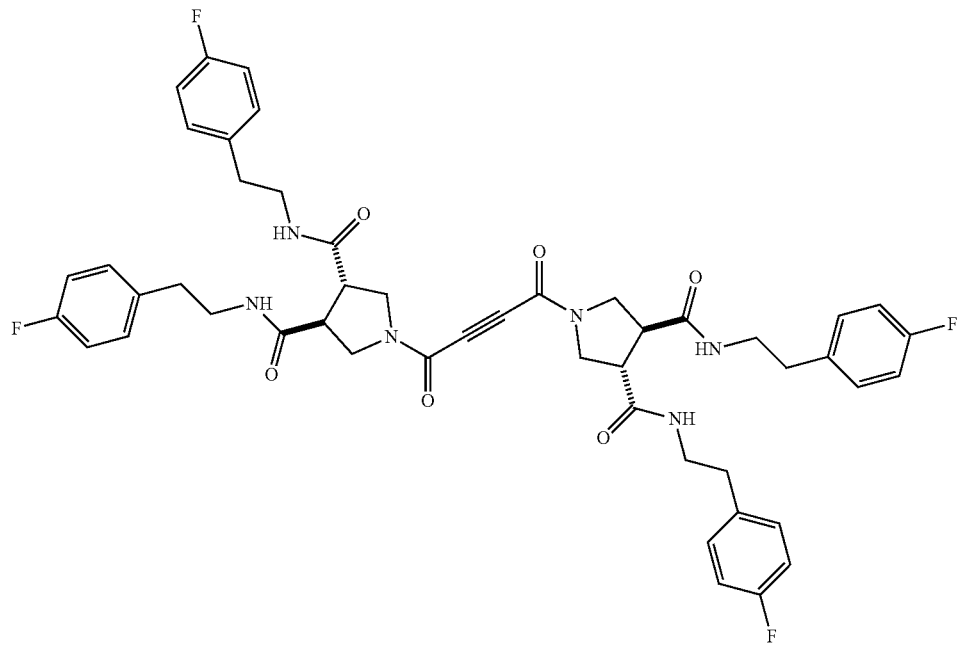 [SMILES: O=C(NCCc1ccc(F)cc1)[C@@H]1CN(C(=O)C#CC(=O)N2C[C@@H](C(=O)NCCc3ccc(F)cc3)[C@H](C(=O)NCCc3ccc(F)cc3)C2)C[C@H]1C(=O)NCCc1ccc(F)cc1]

100: (3S,3'S,4S,4'S)-1,1'-(But-2-ynedi-oyl)bis(N³,N⁴-bis(4-fluorophenethyl)pyrrolidine-3,4-dicarboxamide)

The general procedure for linking diacid coupling was employed: (3S,4S)—N³,N⁴-bis(4-fluoro-phenethyl)pyrrolidine-3,4-dicarboxamide hydrochloride (S-53, 10 mg) and but-2-ynedioic acid (1.3 mg) provided 9.1 mg (73%) of 100. $^1$H NMR (600 MHz, DMSO-$d_6$) δ 8.17-8.06 (m, 4H), 7.23-7.16 (m, 8H), 7.11-7.04 (m, 8H), 3.87 (dd, J=10.6, 7.7 Hz, 1H), 3.73-3.65 (m, 1H), 3.63 (dd, J=12.2, 8.0 Hz, 1H), 3.55 (dd, J=10.6, 7.2 Hz, 1H), 3.31-3.20 (m, 14H), 3.20-3.09 (m, 2H), 2.72-2.63 (m, 8H). HRMS (ESI-TOF) m/z calcd for $C_{48}H_{48}F_4N_6O_6$[M+H]$^+$ 881.3644, found 881.3645.

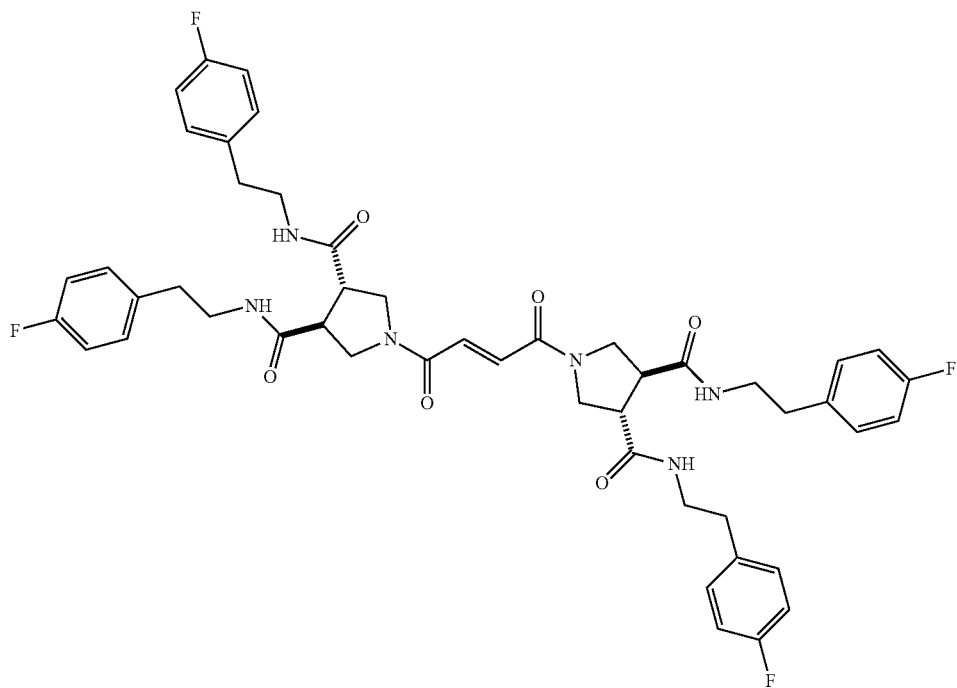 [SMILES: O=C(NCCc1ccc(F)cc1)[C@@H]1CN(C(=O)/C=C/C(=O)N2C[C@@H](C(=O)NCCc3ccc(F)cc3)[C@H](C(=O)NCCc3ccc(F)cc3)C2)C[C@H]1C(=O)NCCc1ccc(F)cc1]

101: (3S,3'S,4S,4'S)-1,1'-Fumaroylbis-(N³,N⁴-bis(4-fluorophnethyl) pyrrolidine-3,4-dicarboxamide)

The general procedure for linking diacid coupling was employed: (3S,4S)—N³,N⁴-bis(⁴-fluoro-phenethyl)pyrrolidine-3,4-dicarboxamide hydrochloride (S-53; 10 mg) and fumaric acid (1.3 mg) provided 9.6 mg (99%) of 101. $^1$H NMR (600 MHz, DMSO-$d_6$) δ 8.17 (t, J=5.6 Hz, 2H), 8.13 (t, J=5.6 Hz, 2H), 7.27-7.18 (m, 8H), 7.13-7.05 (m, 8H), 7.01 (s, 2H), 3.86 (dd, J=10.1, 8.2 Hz, 2H), 3.68 (dd, J=12.2, 8.3 Hz, 2H), 3.50 (dd, J=10.1, 7.7 Hz, 2H), 3.31-3.27 (m, 6H), 3.27-3.16 (m, 6H), 3.10 (q, J=7.9 Hz, 2H), 2.69 (td, J=7.3, 2.6 Hz, 8H). HRMS (ESI-TOF) m/z calcd for $C_{48}H_{50}F_4N_6O_6[M+H]^+$ 883.3801, found 883.3802.

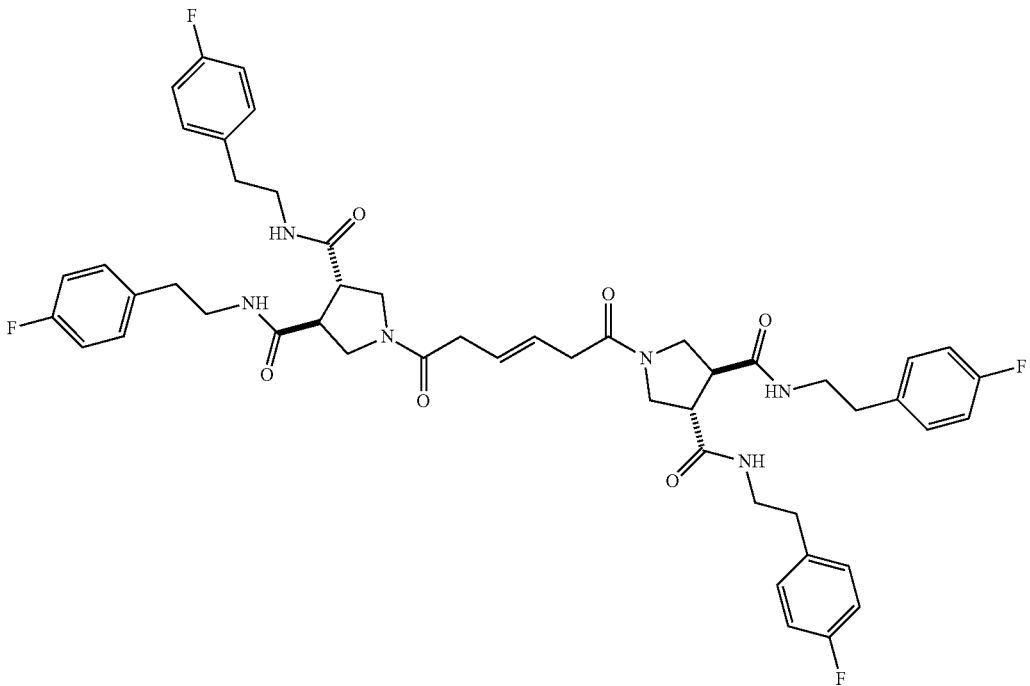 [SMILES: O=C(NCCc1ccc(F)cc1)[C@@H]1CN(C(=O)C/C=C/CC(=O)N2C[C@@H](C(=O)NCCc3ccc(F)cc3)[C@H](C(=O)NCCc3ccc(F)cc3)C2)C[C@H]1C(=O)NCCc1ccc(F)cc1]

102: (3S,3'S,4S,4'S)-1,1'-((E)-Hex-3-enedioyl)bis-(N³,N⁴-bis(4-fluorophenethyl)pyrrolidine-3,4-dicarboxamide)

The general procedure for linking diacid coupling was employed: (3S,4S)—N³,N⁴-bis(4-fluoro-phenethyl)pyrrolidine-3,4-dicarboxamide hydrochloride (S-53, 10 mg) and (E)-hex-3-enedioic acid (1.6 mg) provided 9.9 mg (99%) of 102. $^1$H NMR (600 MHz, DMSO-$d_6$) δ 8.10 (t, J=5.6 Hz, 4H), 7.25-7.19 (m, 8H), 7.12-7.05 (m, 8H), 5.61-5.53 (m, 1H), 3.71 (dd, J=10.0, 8.2 Hz, 2H), 3.62 (dd, J=11.4, 8.3 Hz, 2H), 3.36-3.21 (m, 10H), 3.21-3.12 (m, 4H), 3.08-3.04 (m, 2H), 3.02 (s, 4H), 2.75-2.64 (m, 8H). HRMS (ESI-TOF) m/z calcd for $C_{50}H_{54}F_4N_6O_6[M+H]^+$ 911.4114, found 911.4112.

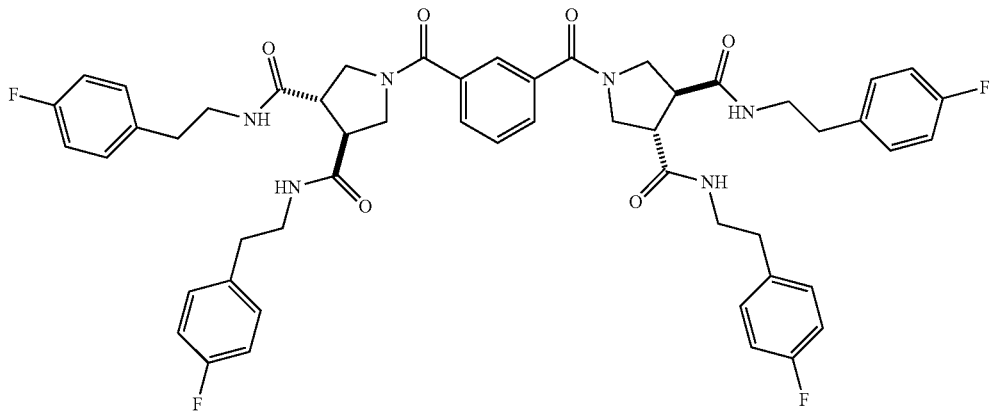 [SMILES: O=C(NCCc1ccc(F)cc1)[C@@H]1CN(C(=O)c2cccc(C(=O)N3C[C@@H](C(=O)NCCc4ccc(F)cc4)[C@H](C(=O)NCCc4ccc(F)cc4)C3)c2)C[C@H]1C(=O)NCCc1ccc(F)cc1]

103: (3S,3'S,4S,4'S)-1,1'-Isophthaloyl-bis-(N³,N⁴-bis(4-fluorophenethyl)pyrrolidine-3,4-dicarboxamide)

The general procedure for linking diacid coupling was employed: (3S,4S)—N³,N⁴-bis(4-fluoro-phenethyl)pyrrolidine-3,4-dicarboxamide hydrochloride (S-53, 10 mg) and isophthalic acid (1.9 mg) provided 7.3 mg (71%) of 103. ¹H NMR (600 MHz, DMSO-$d_6$) δ 8.12 (t, J=5.7 Hz, 2H), 7.96 (t, J=5.6 Hz, 2H), 7.65-7.57 (m, 3H), 7.54 (dd, J=8.2, 6.9 Hz, 1H), 7.22 (td, J=9.8, 9.2, 5.7 Hz, 4H), 7.17-7.11 (m, 4H), 7.11-7.05 (m, 4H), 7.05-6.94 (m, 4H), 3.76 (dd, J=11.9, 8.6 Hz, 2H), 3.59 (dd, J=10.2, 7.8 Hz, 2H), 3.46-3.36 (m, 4H), 3.35-3.14 (m, 10H), 3.14-3.06 (m, 2H), 2.69 (ddd, J=10.9, 8.0, 5.8 Hz, 4H), 2.61 (td, J=6.9, 3.4 Hz, 4H). HRMS (ESI-TOF) m/z calcd for $C_{52}H_{52}F_4N_6O_6[M+H]^+$ 933.3957, found 933.3955.

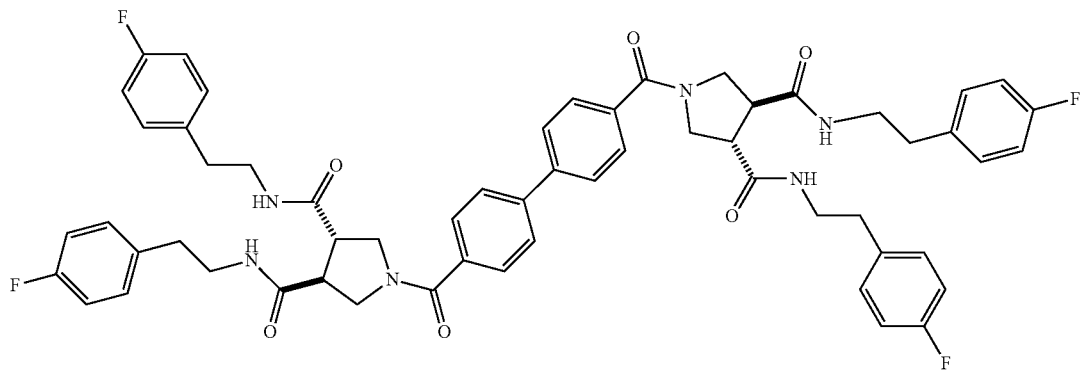 [SMILES: O=C(NCCc1ccc(F)cc1)[C@@H]1CN(C(=O)c2ccc(-c3ccc(C(=O)N4C[C@@H](C(=O)NCCc5ccc(F)cc5)[C@H](C(=O)NCCc5ccc(F)cc5)C4)cc3)cc2)C[C@H]1C(=O)NCCc1ccc(F)cc1]

104: (3S,3'S,4S,4'S)-1,1'-([1,1'-Biphenyl]-4,4'-dicarbonyl)bis(N³,N⁴-bis(4-fluoro-phenethyl)-pyrrolidine-3,4-dicarboxamide)

The general procedure for linking diacid coupling was employed: (3S,4S)—N³,N⁴-bis(4-fluoro-phenethyl)pyrrolidine-3,4-dicarboxamide hydrochloride (S-53, 10 mg) and [1,1'-biphenyl]-4,4'-dicarboxylic acid (2.7 mg) provided 11.0 mg (98%) of 104. ¹H NMR (600 μMHz, DMSO-$d_6$) δ 8.16 (b, 2H), 8.03-7.94 (b, 2H), 7.80 (d, J=8.4 Hz, 4H), 7.62 (d, J=8.2 Hz, 4H), 7.28-7.19 (m, 6H), 7.14 (dd, J=8.3, 5.6 Hz, 4H), 7.13-7.04 (m, 6H), 6.99 (t, J=8.8 Hz, 4H), 3.77 (dd, J=11.9, 8.7 Hz, 2H), 3.65 (dd, J=10.3, 8.0 Hz, 2H), 3.48-3.40 (m, 4H), 3.31-3.19 (m, 8H), 3.19-3.14 (m, 2H), 3.14-3.07 (m, 2H), 2.75-2.58 (m, 8H). HRMS (ESI-TOF) m/z calcd for $C_{58}H_{56}F_4N_6O_6$ $[M+H]^+$ 1009.427, found 1009.4275.

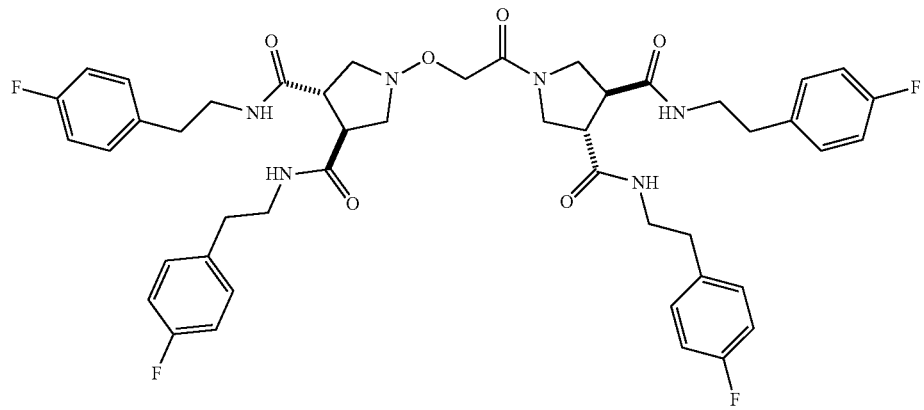 [SMILES: O=C(NCCc1ccc(F)cc1)[C@@H]1CN(OCC(=O)N2C[C@@H](C(=O)NCCc3ccc(F)cc3)[C@H](C(=O)NCCc3ccc(F)cc3)C2)C[C@H]1C(=O)NCCc1ccc(F)cc1]

105: (3S,3'S,4S,4'S)-1,1'-(2,2'-Oxybis(acetyl))bis-(N³,N⁴-bis(4-fluorophenethyl)pyrrolidine-3,4-dicarboxamide)

The general procedure for linking diacid coupling was employed: (3S,4S)—N³,N⁴-bis(4-fluorophenethyl)pyrrolidine-3,4-dicarboxamide hydrochloride (S-53, 10 mg) and 2,2'-oxydiacetic acid (1.5 mg) provided 6.8 mg (69%) of 105. ¹H NMR (600 MHz, DMSO-$d_6$) δ 8.10 (td, J=5.7, 2.3 Hz, 4H), 7.31-7.16 (m, 8H), 7.16-6.99 (m, 8H), 4.12 (d, J=2.8 Hz, 4H), 3.31-3.21 (m, 8H), 3.70-3.62 (m, 4H), 3.21-3.12 (m, 4H), 3.08-2.97 (m, 4H), 2.72-2.64 (m, 8H). HRMS (ESI-TOF) m/z calcd for $C_{48}H_{52}F_4N_6O_7$ [M+H]⁺ 901.3906, found 901.3906.

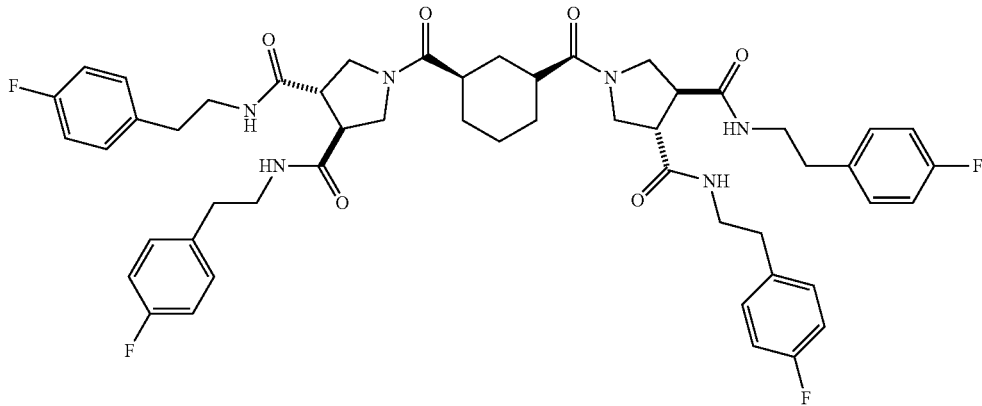

106: (3S,3'S,4S,4'S)-1,1'-((1R,3R)-Cyclohexane-1,3-dicarbonyl)bis(N³,N⁴-bis(4-fluorophenethyl)-pyrrolidine-3,4-dicarboxamide)

The general procedure for linking diacid coupling was employed: (3S,4S)—N³,N⁴-bis(4-fluorophenethyl)pyrrolidine-3,4-dicarboxamide hydrochloride (S-53, 10 mg) and cis-cyclohexane-1,3-dicarboxylic acid (1.9 mg) 9.1 mg (88%) of 106. ¹H NMR (600 MHz, DMSO-$d_6$) δ 8.12-8.02 (m, 4H), 7.26-7.17 (m, 8H), 7.08 (td, J=8.8, 1.6 Hz, 8H), 3.73 (ddd, J=17.7, 9.9, 8.1 Hz, 2H), 3.60 (dt, J=11.6, 8.5 Hz, 2H), 3.41-3.33 (m, 2H), 3.31-3.20 (m, 8H), 3.20-3.09 (m, 4H), 3.06-3.02 (m, 2H), 2.75-2.62 (m, 8H), 2.47-2.39 (m, 2H), 1.83-1.75 (m, 2H), 1.69-1.56 (m, 4H), 1.49-1.31 (m, 2H). HRMS (ESI-TOF) m/z calcd for $C_{52}H_{58}F_4N_6O_6$[M+H]⁺ 939.4426, found 939.4425.

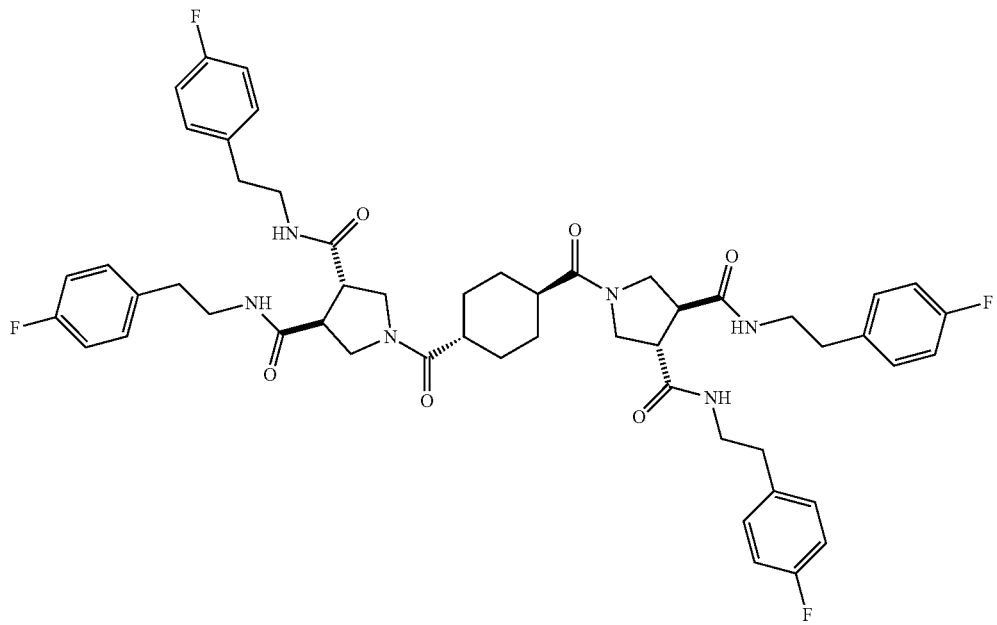 [SMILES: O=C(NCCc1ccc(F)cc1)[C@@H]1CN(C(=O)[C@H]2CC[C@H](C(=O)N3C[C@@H](C(=O)NCCc4ccc(F)cc4)[C@H](C(=O)NCCc4ccc(F)cc4)C3)CC2)C[C@H]1C(=O)NCCc1ccc(F)cc1]

107: (3S,3'S,4S,4'S)-1,1'-((1S,4S)-Cyclohexane-1,4-dicarbonyl)bis(N³,N⁴-bis(4-fluorophenethyl)-pyrrolidine-3,4-dicarboxamide)

The general procedure for linking diacid coupling was employed: (3S,4S)—N³,N⁴-bis(4-fluoro-phenethyl)pyrrolidine-3,4-dicarboxamide hydrochloride (S-53, 10 mg) and trans-cyclohexane-1,4-dicarboxylic acid (1.9 mg) 1.8 mg (17%) of 107. ¹H NMR (600 MHz, DMSO-d₆) δ 3.39-3.34 (m, 2H), 3.07-3.02 (m, 2H), 2.75-2.65 (m, 8H), 2.37-2.28 (m, 2H), 1.71-1.67 (m, 4H), 1.46-1.36 (m, 4H), 3.30-3.19 (m, 8H), 8.18-8.03 (m, 4H), 7.26-7.15 (m, 8H), 7.15-7.02 (m, 8H), 3.75 (dd, J=10.2, 8.3 Hz, 2H), 3.58 (dd, J=11.6, 8.3 Hz, 2H), 3.19-3.10 (m, 4H). HRMS (ESI-TOF) m/z calcd for $C_{52}H_{58}F_4N_6O_6[M+H]^+$ 939.4426, found 939.4427.

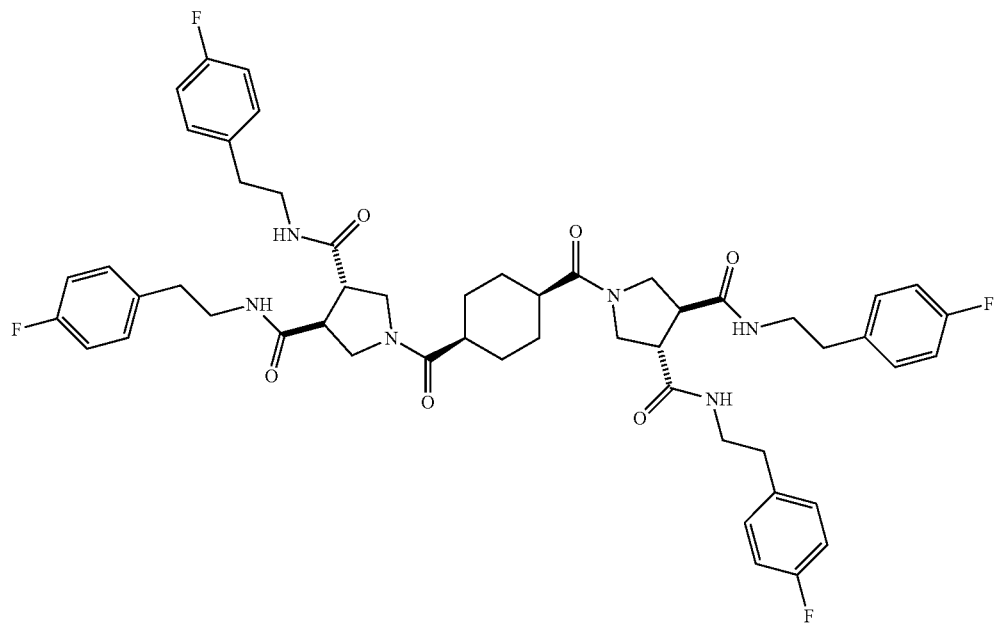 [SMILES: O=C(NCCc1ccc(F)cc1)[C@@H]1CN(C(=O)[C@H]2CC[C@@H](C(=O)N3C[C@@H](C(=O)NCCc4ccc(F)cc4)[C@H](C(=O)NCCc4ccc(F)cc4)C3)CC2)C[C@H]1C(=O)NCCc1ccc(F)cc1]

108: (3S,3'S,4S,4'S)-1,1'-((1R,4R)-Cyclohexane-1,4-dicarbonyl)bis(N³,N⁴-bis(4-fluorophenethyl)-pyrrolidine-3,4-dicarboxamide)

The general procedure for linking diacid coupling was employed: (3S,4S)—N³,N⁴-bis(4-fluoro-phenethyl)pyrrolidine-3,4-dicarboxamide hydrochloride (S-53, 10 mg) and cis-cyclohexane-1,4-dicarboxylic acid (1.9 mg) provided 8.5 mg (82%) of 108. ¹H NMR (600 µMHz, DMSO-d₆) δ 8.08-8.02 (m, 3H), 7.93 (t, J=5.7 Hz, 1H), 7.27-7.16 (m, 8H), 7.13-7.04 (m, 8H), 3.71 (dd, J=10.0, 8.0 Hz, 2H), 3.60 (dd, J=11.6, 8.5 Hz, 2H), 3.33-3.19 (m, 10H), 3.19-3.08 (m, 4H), 3.05-3.02 (m, 2H), 2.73-2.64 (m, 8H), 2.48-2.44 (m, 2H), 1.87-1.77 (m, 4H), 1.52-1.41 (m, 4H). HRMS (ESI-TOF) m/z calcd for $C_{52}H_{58}F_4N_6O_6$ [M+H]⁺ 939.4426, found 939.4427.

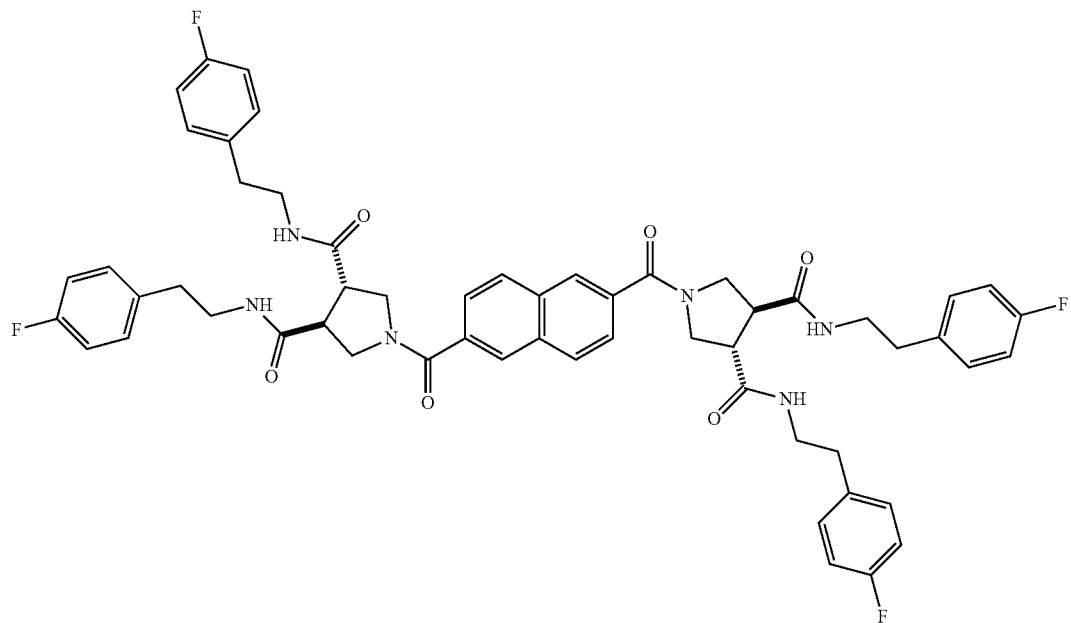 [SMILES: O=C(NCCc1ccc(F)cc1)[C@@H]1CN(C(=O)c2ccc3cc(C(=O)N4C[C@@H](C(=O)NCCc5ccc(F)cc5)[C@H](C(=O)NCCc5ccc(F)cc5)C4)ccc3c2)C[C@H]1C(=O)NCCc1ccc(F)cc1]

109: (3S,3'S,4S,4'S)-1,1'-(Naphthalene-2,6-dicarbonyl)-bis($N^3$,$N^4$-bis(4-fluorophenethyl)-pyrrolidine-3,4-dicarboxamide)

The general procedure for linking diacid coupling was employed: (3S,4S)—$N^3$,$N^4$-bis(4-fluoro-phenethyl)pyrrolidine-3,4-dicarboxamide hydrochloride (S-53; 10 mg) and naphthalene-2,6-dicarboxylic acid (2.4 mg) provided 10.7 mg (99%) of 109. $^1$H NMR (600 MHz, DMSO-$d_6$) δ 8.22-8.17 (m, 4H), 8.12 (d, J=8.5 Hz, 2H), 7.98 (t, J=5.7 Hz, 2H), 7.68 (dd, J=8.4, 1.5 Hz, 2H), 7.27-7.20 (m, 8H), 7.14-7.07 (m, 8H), 6.92 (t, J=8.9 Hz, 2H), 3.83 (dd, J=11.9, 8.6 Hz, 2H), 3.67 (dd, J=10.4, 7.9 Hz, 2H), 3.54-3.43 (m, 4H), 3.31-3.19 (m, 8H), 3.19-3.08 (m, 4H), 2.77-2.65 (m, 4H), 2.65-2.56 (m, 4H). HRMS (ESI-TOF) m/z calcd for $C_{56}H_{54}F_4N_6O_6$[M+H]$^+$ 983.4114, found 983.4117.

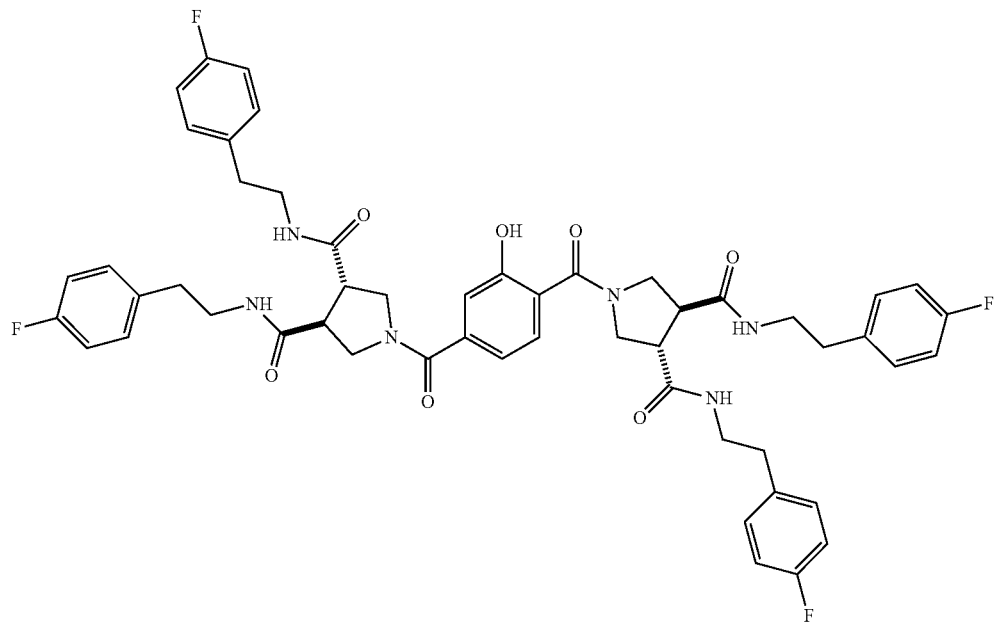 [SMILES: O=C(NCCc1ccc(F)cc1)[C@@H]1CN(C(=O)c2ccc(C(=O)N3C[C@@H](C(=O)NCCc4ccc(F)cc4)[C@H](C(=O)NCCc4ccc(F)cc4)C3)c(O)c2)C[C@H]1C(=O)NCCc1ccc(F)cc1]

110: (3S,3'S,4S,4'S)-1,1'-(2-Hydroxy-terephthaloyl)-bis(N³,N⁴-bis(4-fluorophenethyl)-pyrrolidine-3,4-dicarboxamide)

The general procedure for linking diacid coupling was employed: (3S,4S)—N³,N⁴-bis(4-fluoro-phenethyl)pyrrolidine-3,4-dicarboxamide hydrochloride (S-53, 10 mg) and 2-hydroxyterephthalic acid (2.0 mg) provided 9.1 mg (87%) of 110. $^1$H NMR (600 MHz, DMSO-$d_6$) δ 10.25 (s, 1H), 8.18-8.07 (m, 3H), 7.99 (t, J=5.7 Hz, 1H), 7.25-7.18 (m, 8H), 7.16-7.11 (m, 2H), 7.09 (tt, J=8.9, 2.9 Hz, 6H), 7.05-6.98 (m, 2H), 6.97-6.94 (m, 1H), 3.82-3.68 (m, 2H), 3.67-3.58 (m, 1H), 3.58-3.45 (m, 2H), 3.45-3.34 (m, 3H), 3.29-3.12 (m, 10H), 3.12-3.03 (m, 2H), 2.76-2.65 (m, 6H), 2.65-2.59 (m, 2H). HRMS (ESI-TOF) m/z calcd for $C_{52}H_{52}F_4N_6O_7$[M+H]$^+$ 949.3906, found 949.3908.

Hybrid Analogues of Diprovocim-1 and 2

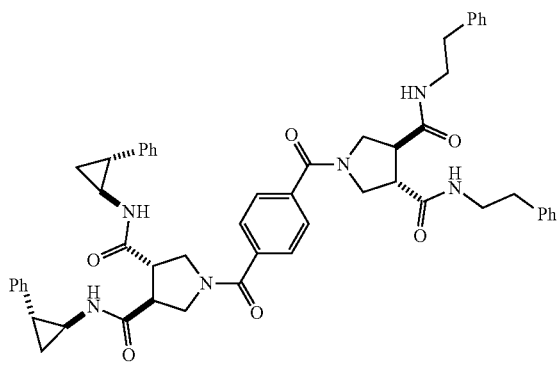

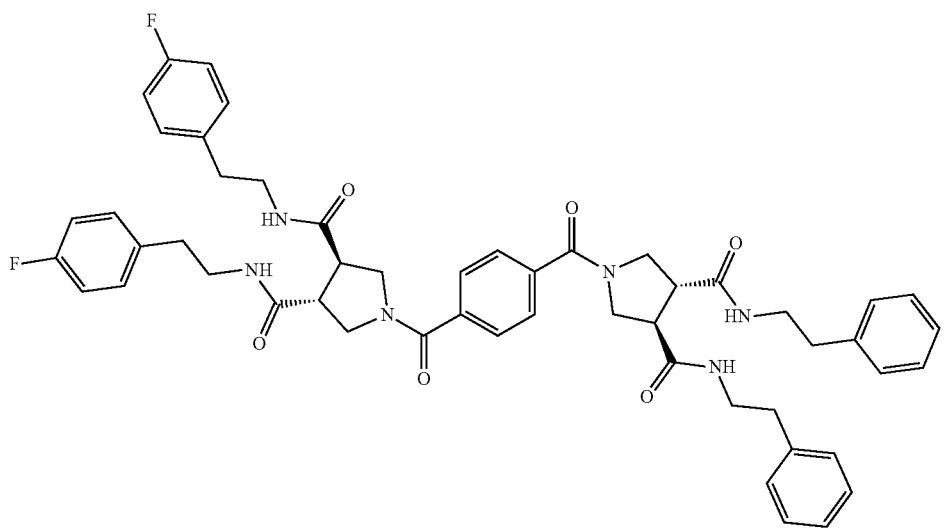 [SMILES: O=C(NCCc1ccccc1)[C@H]1CN(C(=O)c2ccc(C(=O)N3C[C@H](C(=O)NCCc4ccc(F)cc4)[C@@H](C(=O)NCCc4ccc(F)cc4)C3)cc2)C[C@@H]1C(=O)NCCc1ccccc1]

111: 1-(4-(-3,4-bis((4-Fluorophenethyl)-carbamoyl)pyrrolidine-1-carbonyl)benzoyl)-N³,N⁴-diphenethylpyrrolidine-trans-3,4-dicarboxamide A solution of 4-(trans-3,4-bis(phenethyl-carbamoyl)pyrrolidine-1-carbonyl)benzoic acid (S-8; 7.3 mg, 0.014 mmol, 1 equiv), trans-N³-(4-fluoro-phenethyl)-N⁴-phenethylpyrrolidine-3,4-dicarboxamide hydrochloride (S-34; 6.1 mg, 0.014 mmol, 1 equiv), and PyBrOP (7.5 mg, 0.016 mmol, 1.1 equiv) in DMF (250 μL) was treated with i-Pr$_2$NEt (8 μL, 0.042 mmol, 3 equiv). The reaction mixture was stirred at 23° C. for 36 hours after which time the mixture was diluted with EtOAc (3 mL) and washed with aqueous 0.5 N HCl (2×3 mL). The aqueous phase was extracted with EtOAc (1×3 mL). The combined organic phases were washed with saturated aqueous NaHCO$_3$ (10 mL) and saturated aqueous NaCl (10 mL). The organic phase was dried over Na$_2$SO$_4$, decanted and concentrated. The product was purified by trituration with cold (0° C.) 1:1 Et$_2$O/EtOAc (3×5 mL), decanting off the liquid phase to provide 6.3 mg (50%) of 111 as a white solid. HRMS (ESI-TOF) m/z calcd for $C_{52}H_{54}F_2N_6O_6$[M+H]897.4145, found 897.4152.

112: trans-1-(4-(trans-3,4-Bis((trans-2-phenylcyclopropyl)carbamoyl)pyrrolidine-1-carbonyl)-benzoyl)-N³,N⁴-diphenethylpyrrolidine-3,4-dicarboxamide A solution of 4-(trans-3,4-bis(phenethyl-carbamoyl)pyrrolidine-1-carbonyl)benzoic acid (S-8; 7.3 mg, 0.014 mmol, 1 equiv), trans-N³-(trans-2-phenylcyclopropyl)-N⁴-(trans-2-phenylcyclopropyl)-pyrrolidine-3,4-dicarboxamide hydrochloride (S-6; 6 mg, 0.014 mmol, 1 equiv), and PyBrOP (7.5 mg, 0.016 mmol, 1.1 equiv) in DMF (250 μL) was treated with i-Pr$_2$NEt (8 μL, 0.042 mmol, 3 equiv). The reaction mixture was stirred at 23° C. for 36 hours after which time the mixture was diluted with EtOAc (3 mL) and washed with aqueous 0.5 N HCl (2×3 mL). The aqueous phase was extracted with EtOAc (1×3 mL). The combined organic phases were washed with saturated aqueous NaHCO$_3$ (10 mL) and saturated aqueous NaCl (10 mL). The organic phase was dried over Na$_2$SO$_4$, decanted and concentrated. The product was purified by trituration with cold (0° C.) 1:1 Et$_2$O/EtOAc (3×5 mL), decanting off the liquid phase to provide 2.2 mg (18%) of 112 as a white solid. HRMS (ESI-TOF) m/z calcd for $C_{54}H_{56}N_6O_6$ [M+H]$^+$ 885.4334, found 885.4330.

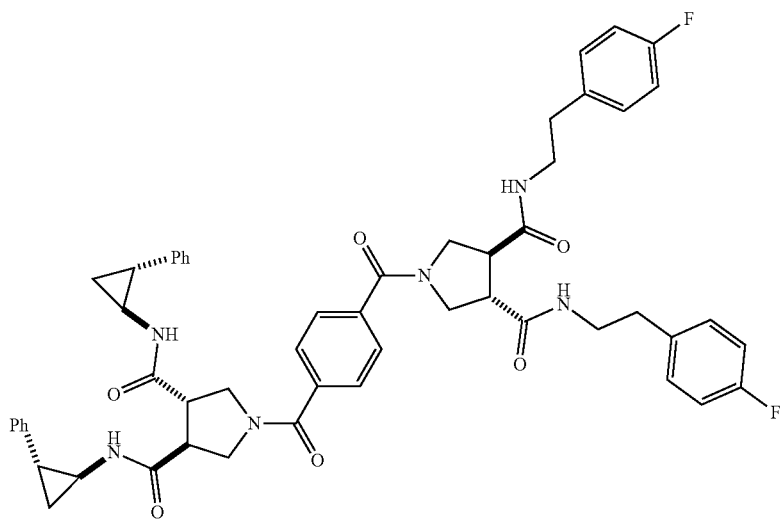

113: trans-1-(4-(trans-3,4-Bis((trans-2-phenylcyclopropyl)carbamoyl)pyrrolidine-1-carbonyl)benzoyl)-$N^3,N^4$-bis(4-fluorophenethyl)pyrrolidine-3,4-dicarboxamide

A solution of 4-(trans-3,4-bis((4-fluoro-phenethyl)carbamoyl)pyrrolidine-1-carbonyl)benzoic acid (S-39; 39 mg, 0.066 mmol, 1 equiv), trans-$N^3$-(trans-2-phenylcyclopropyl)—$N^4$-(trans-2-phenylcyclo-propyl)-pyrrolidine-3,4-dicarboxamide hydrochloride (S-6; 28 mg, 0.066 mmol, 1 equiv), and PyBrOP (34 mg, 0.073 mmol, 1.1 equiv) in DMF (700 µL) was treated with i-Pr$_2$NEt (35 µL, 0.20 mmol, 3 equiv) The reaction mixture was stirred at 23° C. for 36 hours after which the mixture was diluted with EtOAc (3 mL) and washed with aqueous 0.5 N HCl (2×3 mL). The aqueous phase was extracted with EtOAc (1×3 mL). The combined organic phases were washed with saturated aqueous NaHCO$_3$ (10 mL) and saturated aqueous NaCl (10 mL). The organic phase was dried over Na$_2$SO$_4$, decanted and concentrated. The product was purified by trituration with cold (0° C.) 1:1 Et$_2$O/EtOAc (3×5 mL), decanting off the liquid phase to provide 15.6 mg (26%) of 113 as a white solid. HRMS (ESI-TOF) m/z calcd for C$_{54}$H$_{54}$F$_2$N$_6$O$_6$[M+H]+ 921.4145, found 921.4149.

Diprovocim-4 and Diprovocim-5

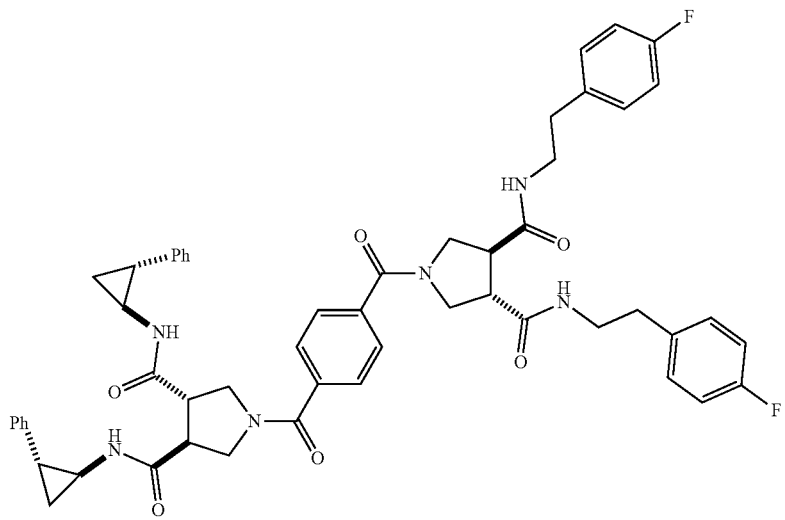

114: (3S,4S)-1-(4-((3S,4S)-3,4-Bis(((1S,2R)-2-phenylcyclopropyl)carbamoyl)-pyrrolidine-1-carbonyl)benzoyl)—N³,N⁴-bis(4-fluorophenethyl)-pyrrolidine-3,4-dicarboxamide A solution of 4-((3S,4S)-3,4-bis(((1S,2R)-2-phenylcyclopropyl)carbamoyl)pyrrolidine-1-carbonyl)benzoic acid (S-20, 4.8 mg, 0.0089 mmol, 1 equiv), (3S,4S)—N³,N-bis(4-fluorophenethyl)-pyrrolidine-3,4-dicarboxamide hydrochloride (S-53, 4.8 mg, 0.011 mmol, 1.2 equiv), and PyBrOP (5.1 mg, 0.011 mmol, 1.2 equiv) in DMF (250 µL) was treated with i-Pr₂NEt (5.0 µL, 0.027 mmol, 3 equiv). The reaction mixture was stirred at 23° C. for 36 hours after which the mixture was diluted with EtOAc (3 mL) and washed with aqueous 0.5 N HCl (2×3 mL). The aqueous phase was extracted with EtOAc (1×3 mL). The combined organic phases were washed with saturated aqueous NaHCO₃ (10 mL) and saturated aqueous NaCl (10 mL). The organic phase was dried over Na₂SO₄, decanted and concentrated. The product was purified by trituration with cold (0° C.) 1:1 Et₂O/EtOAc (3×5 mL), decanting off the liquid phase to provide 7.71 mg (94%) of 114 as a white solid. 1H NMR (600 MHz, HFIP-d₆) δ 7.60 (q, J=8.1 Hz, 4H), 7.38 (t, J=7.5 Hz, 2H), 7.34 (t, J=7.6 Hz, 2H), 7.28 (dt, J=15.5, 7.4 Hz, 2H), 7.18 (t, J=7.7 Hz, 4H), 7.11 (t, J=7.4 Hz, 4H), 7.04 (t, J=8.9 Hz, 2H), 6.95 (t, J=8.7 Hz, 2H), 4.14 (dd, J=12.5, 8.4 Hz, 1H), 4.07 (dd, J=12.6, 8.3 Hz, 1H), 3.85-3.73 (m, 2H), 3.73-3.64 (m, 2H), 3.62-3.52 (m, 2H), 3.52-3.43 (m, 4H), 3.43-3.37 (m, 1H), 3.37-3.30 (m, 1H), 3.30-3.22 (m, 2H), 2.90-2.77 (m, 4H), 2.77-2.70 (m, 2H), 2.16-2.11 (m, 1H), 2.03-1.96 (m, 1H), 1.43-1.38 (m, 2H), 1.37-1.27 (m, 2H), 1.22 (dt, J=10.6, 5.5 Hz, 1H).

115: (3R,4R)-1-(4-((3S,4S)-3,4-Bis(((1S,2R)-2-phenylcyclopropyl)carbamoyl)-pyrrolidine-1-carbonyl)benzoyl)-N³,N⁴-bis(4-fluorophnethyl pyrrolidine-3,4-dicarboxamide A solution of 4-((3S,4S)-3,4-bis(((1S,2R)-2-phenylcyclopropyl)carbamoyl) pyrrolidine-1-carbonyl)benzoic acid (S-20, 4.9 mg, 0.0091 mmol, 1 equiv), (3R,4R)—N³,N⁴-bis(4-fluorophenethyl)-pyrrolidine-3,4-dicarboxamide hydrochloride (S-54, 4.8 mg, 0.011 mmol, 1.2 equiv), and PyBrOP (5.1 mg, 0.011 mmol, 1.2 equiv) in DMF (250 µL) was treated with i-Pr₂NEt (5.0 µL, 0.027 mmol, 3 equiv). The reaction mixture was stirred at 23° C. for 36 hours after which the mixture was diluted with EtOAc (3 mL) and washed with aqueous 0.5 N HCl (2×3 mL). The aqueous phase was extracted with EtOAc (1×3 mL). The combined organic phases were washed with saturated aqueous NaHCO₃ (10 mL) and saturated aqueous NaCl (10 mL). The organic phase was dried over Na₂SO₄, decanted and concentrated. The product was purified by trituration with cold (0° C.) 1:1 Et₂O/EtOAc (3×5 mL), decanting off the liquid phase to provide 8.05 mg (96%) of 115 as a white solid. 1H NMR (600 MHz, HFIP-d₆) δ 7.61 (q, J=8.2 Hz, 4H), 7.38 (t, J=7.6 Hz, 2H), 7.34 (t, J=7.5 Hz, 2H), 7.28 (dt, J=18.5, 7.4 Hz, 2H), 7.23-7.15 (m, 4H), 7.14-7.07 (m, 4H), 7.04 (t, J=8.9 Hz, 2H), 6.95 (t, J=8.8 Hz, 2H), 4.13 (dd, J=12.5, 8.4 Hz, 1H), 4.06 (dd, J=12.6, 8.4 Hz, 1H), 3.87-3.74 (m, 3H), 3.74-3.64 (m, 3H), 3.62-3.54 (m, 2H), 3.52-3.38 (m, 4H), 3.37-3.29 (m, 1H), 3.29-3.22 (m, 1H), 2.91-2.80 (m, 4H), 2.80-2.71 (m, 2H), 2.16-2.10 (m, 1H), 2.03-1.96 (m, 1H), 1.42-1.36 (m, 2H), 1.34-1.27 (m, 2H), 1.22 (dt, J=10.5, 5.8 Hz, 1H).

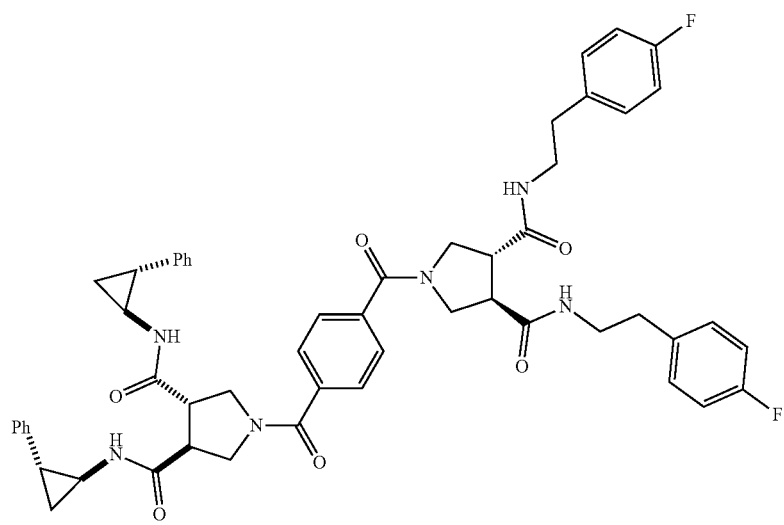

Synthesis of Diprovocim-3

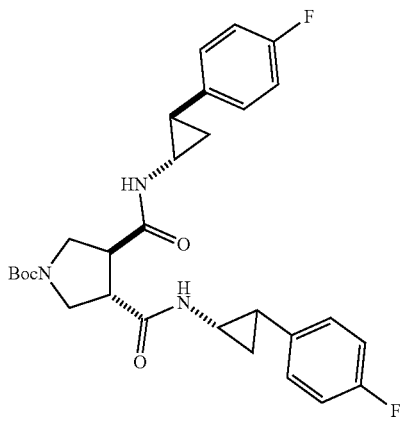

117: tert-butyl (3S,4S)-3,4-Bis(((1S,2R)-2-(4-fluoro-phenyl)cyclopropyl)carbamoyl)pyrrolidine-1-carboxylate The general procedure for the coupling of amines with pyrrolidine diacids was followed: (3S,4S)-1-(tert-butoxycarbonyl)pyrrolidine-3,4-dicarboxylic acid (S,S-14, 34.5 mg), and (1S,2R)-2-(4-fluorophenyl)cyclopropan-1-amine hydrochloride (116; 52 mg) provided 29 mg (42%) of 117 after flash column chromatography (SiO$_2$, 20% EtOAc/hexanes). 1H NMR (400 MHz, CDCl$_3$) δ 7.12 (m, 4H), 6.95 (t, J=8.6 Hz, 4H), 6.63 (b, 1H), 6.45 (b, 1H), 3.84 (t, J=9.9 Hz, 1H), 3.67 (t, J=9.4 Hz, 1H), 3.59 (t, J=10.5 Hz, 1H), 3.46-3.33 (m, 1H), 3.26 (m, J=9.6 Hz, 1H), 3.12 (t, J=9.4 Hz, 1H), 2.79 (m, 2H), 2.01 (m, 2H), 1.45 (s, 9H), 1.18 (q, J=6.6 Hz, 2H), 1.11 (dt, J=10.2, 5.3 Hz, 2H).

S-57: (3S,4S)—N$^3$,N$^4$-Bis((1S,2R)-2-(4-fluorophenyl)-cyclopropyl)pyrrolidine-3,4-dicarboxamide Hydrochloride The general procedure for Boc-pyrrolidine deprotection was employed: tert-butyl (3S,4S)-3,4-bis(((1S,2R)-2-(4-fluorophenyl)cyclopropyl)-carbamoyl)-pyrrolidine-1-carboxylate (117; 29 mg) provided 26 mg (99%) of S-57. $^1$H NMR (400 MHz, CDCl$_3$) 7.18 (b, 4H), 7.01 (t, J=8.7 Hz, 4H), 3.69-3.47 (m, 4H), 3.26 (b, 2H), 2.86 (s, 2H), 2.07 (b, 2H), 1.23 (m, 4H).

118: (3S,3'S,4S,4'S)-1,1'-Terephthaloyl-bis(N³,N⁴-bis-((1S,2R)-2-(4-fluorophenyl)cyclopropyl)pyrrolidine-3,4-dicarboxamide)

The general procedure for linking diacid coupling was employed: (3S,4S)—N³,N⁴-bis((1S,2R)-2-(4-fluorophenyl)cyclopropyl)pyrrolidine-3,4-dicarboxamide hydrochloride (S-57; 26 mg) and terephthalic acid (benzene-1,4-dicarboxylic acid, 4.2 mg) provided 16 mg (65%) of 118. $^1$H NMR (600 MHz, DMSO-$d_6$) δ 8.42 (d, J=4.2 Hz, 2H), 8.29 (d, J=4.2 Hz, 2H), 7.56 (d, J=4.1 Hz, 4H), 7.17 (dd, J=8.5, 5.5 Hz, 4H), 7.15-7.02 (m, 11H), 3.80 (dd, J=11.9, 8.6 Hz, 2H), 3.70-3.61 (m, 2H), 3.55-3.44 (m, 4H), 3.23-3.15 (m, 2H), 3.10 (q, J=8.0 Hz, 2H), 2.79 (tt, J=8.2, 4.1 Hz, 2H), 2.72 (dq, J=8.0, 4.4, 3.9 Hz, 2H), 2.00-1.95 (m, 2H), 1.89-1.82 (m, 2H), 1.19-1.11 (m, 5H), 1.11-1.02 (m, 4H). $^{13}$C NMR (151 μMHz, DMSO-$d_6$) δ 171.7, 171.0, 167.5, 161.4, 159.7, 137.7, 137.4, 137.3, 130.3, 127.78, 127.74, 127.73, 127.69, 127.1, 114.95, 114.91, 114.80, 114.77, 51.5, 48.7, 46.9, 45.1, 39.5, 32.4, 32.3, 23.3, 23.2, 15.1, 15.0. HRMS (ESI-TOF) m/z calcd for $C_{56}H_{52}F_4N_6O_6[M+H]^+$ 981.3957, found 981.3960.

General Procedure for Coupling of Amines with Benzoic Acid 4-((3S,4S)-3,4-Bis(((S, 2R)-2-phenyl-cyclopropyl)carbamoyl)pyrrolidine-1-carbonyl)benzoic acid (120, 0.0034-0.015 mmol), primary amine or pyrrolidine-3,4-dicarboxamide hydrochloride (0.0040-0.018 mmol, 1.2 equiv), HOAt (0.0037-0.016 mmol, 1.1 equiv), and 2,6-lutidine (0.010-0.045 mmol, 3.0 equiv) were dissolved in anhydrous DMF/$CH_2Cl_2$ (1/0-0/1, 0.1-0.2 mL). Upon dissolution of the reagents (ca. 5 minutes), EDCI.HCl (0.0050-0.022 mmol, 1.5 equiv) was added in one portion, and the reaction mixture was stirred at room temperature for 3-4 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous $NaHCO_3$ (2 mL), and saturated aqueous NaCl (2 mL), sequentially. The organic phase was dried over $Na_2SO_4$, filtered and concentrated. Preparative thin-layer chromatography (SiO$_2$, 10% MeOH/CH$_2$Cl$_2$) was employed to purify the product.

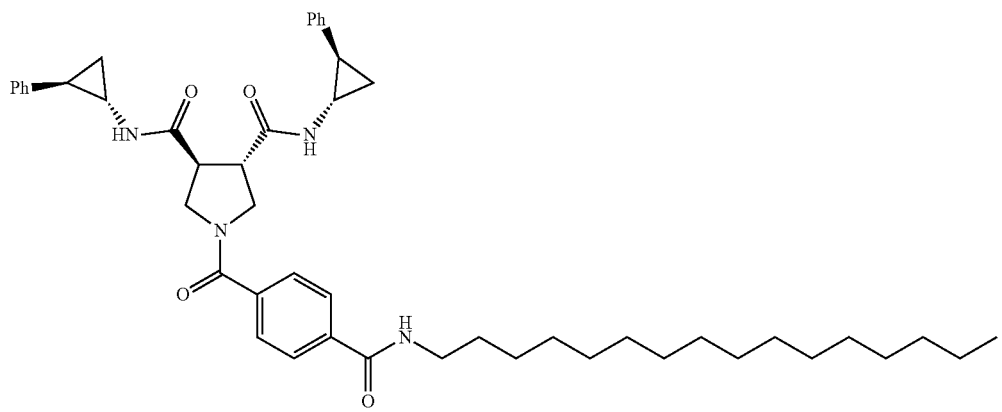 [SMILES: CCCCCCCCCCCCCCCCNC(=O)c1ccc(C(=O)N2C[C@@H](C(=O)N[C@H]3C[C@@H]3c3ccccc3)[C@H](C(=O)N[C@H]3C[C@@H]3c3ccccc3)C2)cc1]

121 (3S,4S)-1-(4-(Hexadecylcarbamoyl)benzoyl)-N³,N⁴-bis((1S,2R)-2-phenylcyclopropyl)pyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 8.0 mg) and hexadecylamine (4.3 mg) provided 9.4 mg (83%) of 121. $^1$H NMR (500 MHz, CDCl$_3$) δ 7.75 (d, J=8.0 Hz, 2H), 7.49 (d, J=8.0 Hz, 2H), 7.29-7.23 (m, 4H), 7.20-7.15 (m, 2H), 7.10 (t, J=8.0 Hz, 4H), 7.04 (d, J=3.5 Hz, 1H), 7.00 (d, J=3.5 Hz, 1H), 6.60, (t, J=5.5 Hz, 1H), 3.83 (dd, J=9.5, 12.0 Hz, 1H), 3.68 (t, J=11.0 Hz, 2H), 3.59 (dd, J=8.5, 10.5 Hz, 1H), 3.45-3.28 (m, 2H), 3.18 (q, J=10.0 Hz, 1H), 2.95 (q, J=9.5 Hz, 1H), 2.92-2.87 (m, 1H), 2.85-2.79 (m, 1H), 2.07-2.01 (m, 1H), 2.00-1.95 (m, 1H), 1.61-1.54 (m, 2H), 1.38-1.06 (m, 30H), 0.88 (t, J=7.0 Hz, 3H). HRMS (ESI-TOF) m/z calcd for $C_{48}H_{65}N_4O_4 [M+H]^+$ 761.5000, found 761.5001.

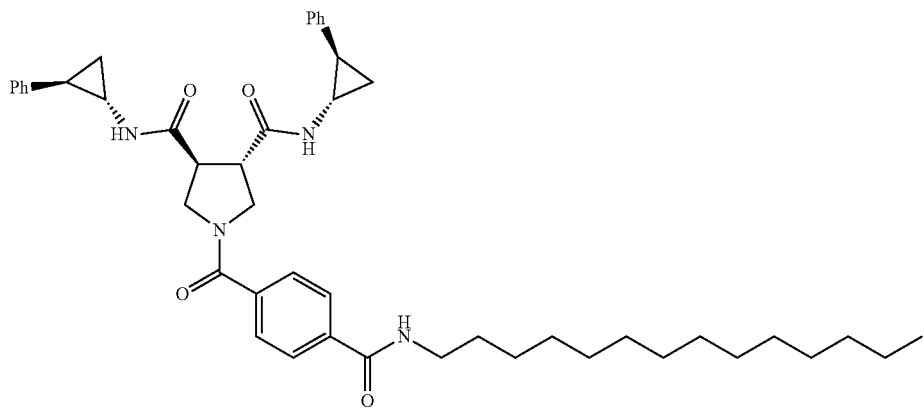 [SMILES: CCCCCCCCCCCCCCNC(=O)c1ccc(C(=O)N2C[C@@H](C(=O)N[C@H]3C[C@@H]3c3ccccc3)[C@H](C(=O)N[C@H]3C[C@@H]3c3ccccc3)C2)cc1]

122: (3S,4S)—$N^3$,$N^4$-Bis((1S,2R)-2-phenylcyclopropyl)-1-(4-(tetradecylcarbamoyl)-benzoyl)pyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 8.0 mg) and tetradecylamine (3.8 mg) provided 8.7 mg (80%) of 122. $^1$H NMR (500 MHz, CDCl$_3$) δ 7.75 (d, J=8.0 Hz, 2H), 7.49 (d, J=8.0 Hz, 2H), 7.29-7.22 (m, 4H), 7.21-7.14 (m, 2H), 7.10 (t, J=8.5 Hz, 4H), 7.05 (d, J=3.5 Hz, 1H), 7.01 (d, J=3.5 Hz, 1H), 6.61 (t, J=5.5 Hz, 1H), 3.83 (dd, J=12.0, 9.5 Hz, 1H), 3.68 (t, J=11.0 Hz, 2H), 3.59 (dd, J=10.0, 9.0 Hz, 1H), 3.45-3.28 (m, 2H), 3.18 (q, J=10.0 Hz, 1H), 2.96 (q, J=10.0 Hz, 1H), 2.92-2.87 (m, 1H), 2.85-2.80 (m, 1H), 2.07-2.02 (m, 1H), 2.00-1.95 (m, 1H), 1.62-1.54 (m, 2H), 1.37-1.06 (m, 26H), 0.88 (t, J=7.0 Hz, 3H). HRMS (ESI-TOF) m/z calcd for $C_{46}H_{61}N_4O_4$ [M+H]$^+$ 733.4687, found 733.4682.

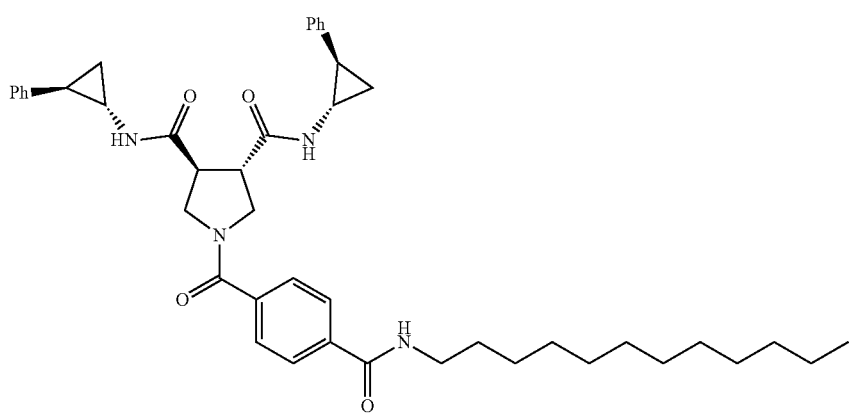 [SMILES: CCCCCCCCCCCCNC(=O)c1ccc(C(=O)N2C[C@@H](C(=O)N[C@H]3C[C@@H]3c3ccccc3)[C@H](C(=O)N[C@H]3C[C@@H]3c3ccccc3)C2)cc1]

123: (3S,4S)-1-(4-(Dodecylcarbamoyl)benzoyl)-$N^3$, $N^4$-bis((1S,2R)-2-phenylcyclopropyl)pyrrolidine-3, 4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 8.0 mg) and dodecylamine (3.3 mg) provided 8.4 mg (80%) of 123. $^1$H NMR (500 MHz, CDCl$_3$) δ 7.75 (d, J=8.0 Hz, 2H), 7.49 (d, J=8.0 Hz, 2H), 7.29-7.22 (m, 4H), 7.21-7.14 (m, 2H), 7.10 (t, J=8.5 Hz, 4H), 7.03 (br, 1H), 6.98 (br, 1H), 6.59 (t, J=5.5 Hz, 1H), 3.84 (dd, J=12.0, 8.5 Hz, 1H), 3.69 (t, J=10.5 Hz, 2H), 3.59 (dd, J=10.0, 9.0 Hz, 1H), 3.45-3.29 (m, 2H), 3.18 (q, J=10.0 Hz, 1H), 2.97 (q, J=10.0 Hz, 1H), 2.92-2.87 (m, 1H), 2.85-2.80 (m, 1H), 2.07-2.02 (m, 1H), 2.00-1.95 (m, 1H), 1.62-1.54 (m, 2H), 1.38-1.07 (m, 22H), 0.88 (t, J=7.0 Hz, 3H). HRMS (ESI-TOF) m/z calcd for $C_{44}H_{57}N_4O_4$ [M+H]$^+$ 705.4374, found 705.4372.

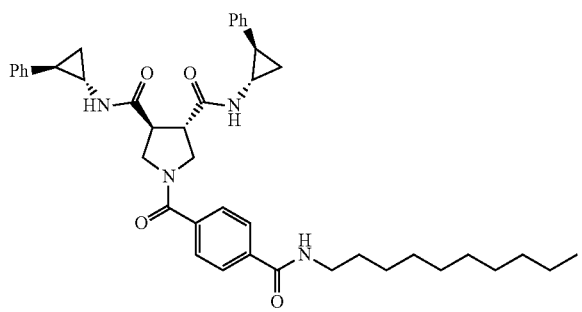 [SMILES: CCCCCCCCCCNC(=O)c1ccc(C(=O)N2C[C@@H](C(=O)N[C@H]3C[C@@H]3c3ccccc3)[C@H](C(=O)N[C@H]3C[C@@H]3c3ccccc3)C2)cc1]

124: (3S,4S)-1-(4-(Decylcarbamoyl)benzoyl)-N³, N⁴-bis((1S,2R)-2-phenylcyclopropyl)pyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 8.0 mg) and decylamine (2.8 mg) provided 7.9 mg (78%) of 124. $^1$H NMR (500 MHz, CDCl$_3$) δ 7.74 (d, J=8.0 Hz, 2H), 7.49 (d, J=7.5 Hz, 2H), 7.29-7.22 (m, 4H), 7.21-7.14 (m, 2H), 7.12-7.06 (m, 5H), 7.05 (br, 1H), 6.64 (t, J=5.5 Hz, 1H), 3.82 (dd, J=12.0, 9.0 Hz, 1H), 3.67 (t, J=11.0 Hz, 2H), 3.59 (dd, J=10.0, 9.0 Hz, 1H), 3.45-3.28 (m, 2H), 3.18 (q, J=10.0 Hz, 1H), 2.95 (q, J=9.5 Hz, 1H), 2.93-2.87 (m, 1H), 2.85-2.80 (m, 1H), 2.08-2.01 (m, 1H), 2.00-1.94 (m, 1H), 1.61-1.54 (m, 2H), 1.38-1.07 (m, 18H), 0.88 (t, J=7.0 Hz, 3H). HRMS (ESI-TOF) m/z calcd for C$_{42}$H$_{54}$N$_4$O$_4$ [M+H]$^+$ 677.4061, found 607.4062.

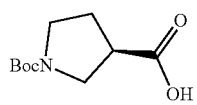 [SMILES: CC(C)(C)OC(=O)N1CC[C@@H](C(=O)O)C1]

S-55: (R)—N-Boc-β-Proline (R)-β-Proline (115 mg, 0.999 mmol) and Boc$_2$O (262 mg, 1.20 mmol) were suspended in deionized H$_2$O (1 mL) and acetone (3 mL). The mixture was cooled to 0° C. and solid Na$_2$CO$_3$ (53 mg, 0.500 mmol) was added. After 4 hours, the acetone was removed in vacuo, and aqueous citric acid (20% w/v) was added dropwise until pH 4 was observed. The mixture was diluted with H$_2$O (15 mL) and EtOAc (15 mL). The aqueous phase was extracted with EtOAc (2×10 mL). The combined organic phases were dried over Na$_2$SO$_4$ and concentrated. The product was washed with hexane to afford 91 mg (42%) of S-55. $^1$H NMR (400 MHz, DMSO-d$_6$) 12.45 (s, 1H), 3.49-3.15 (m, 4H), 3.09-2.95 (m, 1H), 2.12-1.87 (m, 2H), 1.39 (s, 9H).

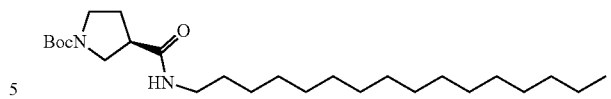

S-56: tert-Butyl (R)-3-(Hexadecylcarbamoyl)-pyrrolidine-1-carboxylate (R)—N-Boc-β-Proline (S-55, 10 mg, 0.047 mmol, 1.0 equiv), hexadecylamine (13.5 mg, 0.056 mmol, 1.2 equiv), HOAt (7.0 mg, 0.051 mmol, 1.1 equiv), and 2,6-lutidine (15.0 mg, 0.140 mmol, 3.00 equiv) were dissolved in CH$_2$Cl$_2$ (0.2 mL). Upon dissolution of the reagents (ca. 5 minutes), EDCI.HCl (13.4 mg, 0.070 mmol, 1.5 equiv) was added in one portion, and the reaction mixture was stirred at room temperature for 3.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous NaHCO$_3$ (2 mL), and saturated aqueous NaCl (2 mL), sequentially. The organic phase was dried over Na$_2$SO$_4$, filtered and concentrated. Short path column chromatography (SiO$_2$, 5% MeOH/CH$_2$Cl$_2$) provided 21.9 mg (quant.) of S-56.

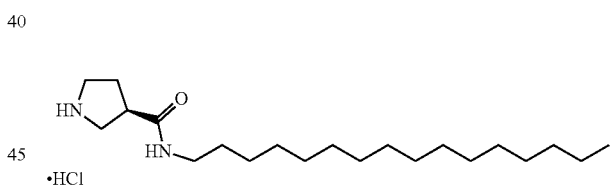

S-57: (R)—N-Hexadecylpyrrolidine-3-carboxamide Hydrochloride tert-Butyl (R)-3-(hexadecylcarbamoyl)-pyrrolidine-1-carboxylate (S-56, 17.5 mg, 0.040 mmol) was stirred in a solution of 4 M HCl in dioxane (0.2 mL) at room temperature for 1 hour. The solvent was removed by N$_2$ stream. The residual solids were suspended in THF and condensed (repeat twice) to ensure complete removal of the dioxane. This process was repeated with Et$_2$O to provide 17.5 mg (quant.) of S-57.

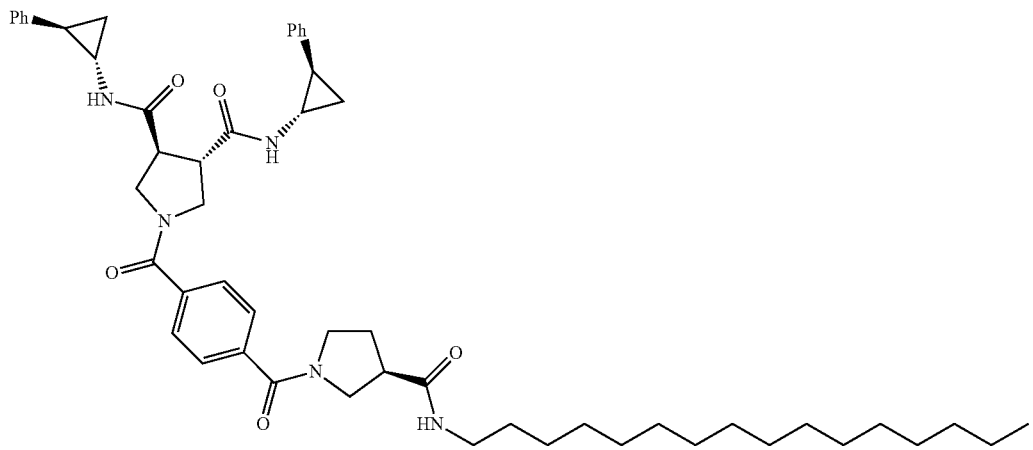 [SMILES: CCCCCCCCCCCCCCCCNC(=O)[C@@H]1CCN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C1]

125: (3S,4S)-1-(4-((R)-3-(Hexadecylcarbamoyl)-pyrrolidine-1-carbonyl)benzoyl)-N³,N⁴-bis((1S,2R)-2-phenylcyclopropyl)pyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 2.2 mg) and (R)—N-hexadecylpyrrolidine-3-carboxamide hydrochloride (S-57, 1.8 mg) provided 2.9 mg (83%) of 125. ¹H NMR (500 MHz, CDCl₃, mixture of rotamers) δ 7.57-7.51 (m, 4H), 7.30-7.22 (m, 4H), 7.21-7.09 (m, 6H), 7.00-6.67 (m, 2H), 5.64-5.57 (m, 1H), 4.04-3.38 (m, 8H), 3.28-3.12 (m, 4H), 2.93-2.76 (m, 3H), 2.24-2.14 (m, 2H), 2.10-1.96 (m, 2H), 1.54-1.41 (m, 2H), 1.34-1.06 (m, 30H), 0.88 (t, J=7.0 Hz, 3H). HRMS (ESI-TOF) m/z calcd for $C_{53}H_{72}N_5O_5$ [M+H]+ 858.5528, found 858.5528.

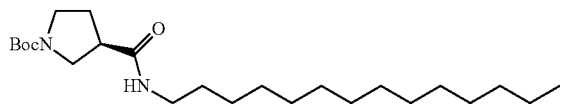 [SMILES: CCCCCCCCCCCCCCNC(=O)[C@@H]1CCN(C(=O)OC(C)(C)C)C1]

S-58: tert-Butyl (R)-3-(Tetradecylcarbamoyl)-pyrrolidine-1-carboxylate (R)—N-Boc-β-Proline (S-55, 10 mg, 0.047 mmol, 1.0 equiv), tetradecylamine (11.9 mg, 0.056 mmol, 1.2 equiv), HOAt (7.0 mg, 0.051 mmol, 1.1 equiv), and 2,6-lutidine (15.0 mg, 0.140 mmol, 3.00 equiv) were dissolved in CH₂Cl₂ (0.2 mL). Upon dissolution of the reagents (about 5 minutes), EDCI.HCl (13.4 mg, 0.070 mmol, 1.5 equiv) was added in one portion, and the reaction mixture was stirred at room temperature for 3.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous NaHCO₃ (2 mL), and saturated aqueous NaCl (2 mL), sequentially. The organic phase was dried over Na₂SO₄, filtered and concentrated. Short path column chromatography (SiO₂, 5% MeOH/CH₂Cl₂) provided 18.6 mg (97%) of S-58.

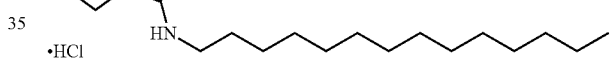

S-59: (R)—N-Tetradecylpyrrolidine-3-carboxamide Hydrochloride tert-Butyl (R)-3-(tetradecylcarbamoyl)-pyrrolidine-1-carboxylate (S-58, 18.2 mg, 0.044 mmol) was stirred in a solution of 4 M HCl in dioxane (0.2 mL) at room temperature for 1 hour. The solvent was removed by N₂ stream. The residual solids were suspended in THF and condensed (repeat twice) to ensure complete removal of the dioxane. This process was repeated with Et₂O to provide 15.9 mg (quant.) of S-59.

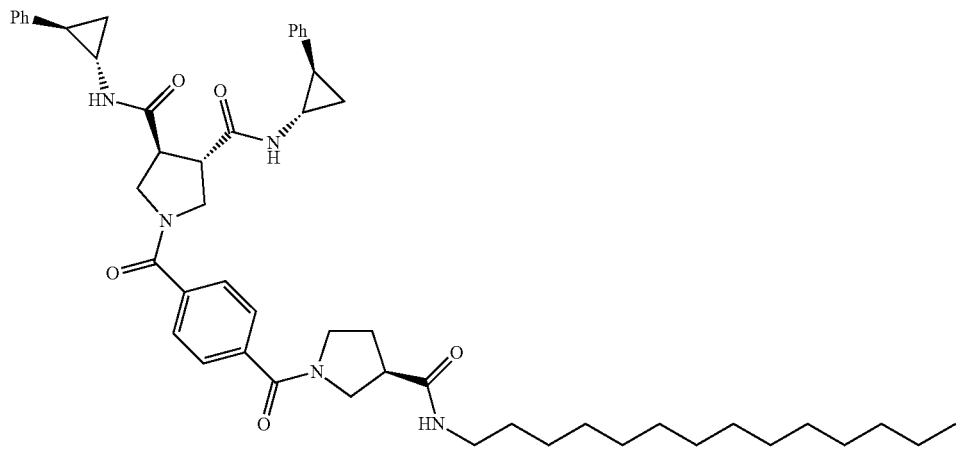 [SMILES: CCCCCCCCCCCCCCNC(=O)[C@@H]1CCN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C1]

126: (3S,4S)—N³,N⁴-Bis((1S,2R)-2-phenylcyclopropyl)-1-(4-((R)-3-(tetradecylcarbamoyl)pyrrolidine-1-carbonyl)benzoyl)pyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 2.2 mg) and (R)—N-tetradecylpyrrolidine-3-carboxamide hydrochloride (S-59, 1.7 mg) provided 2.8 mg (82%) of 126. $^1$H NMR (500 MHz, CDCl$_3$, mixture of rotamers) δ 7.56-7.50 (m, 4H), 7.30-7.22 (m, 4H), 7.21-7.08 (m, 6H), 7.01-6.70 (m, 2H), 5.65-5.59 (m, 1H), 4.04-3.38 (m, 8H), 3.28-3.12 (m, 4H), 2.93-2.75 (m, 3H), 2.25-2.14 (m, 2H), 2.10-1.96 (m, 2H), 1.53-1.41 (m, 2H), 1.34-1.06 (m, 26H), 0.88 (t, J=7.0 Hz, 3H). HRMS (ESI-TOF) m/z calcd for $C_{51}H_{68}N_5O_5$ [M+H]$^+$ 830.5215, found 830.5216.

was dried over Na$_2$SO$_4$, filtered and concentrated. Short path column chromatography (SiO$_2$, 5% MeOH/CH$_2$Cl$_2$) provided 17.9 mg (quant.) of S-60.

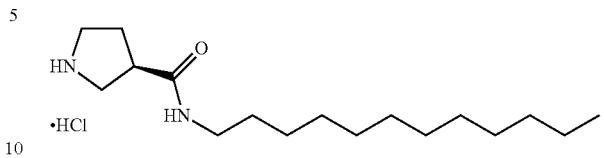

S-61: (R)—N-Dodecylpyrrolidine-3-carboxamide Hydrochloride tert-Butyl (R)-3-(dodecylcarbamoyl)-pyrrolidine-1-carboxylate (S-60, 14.2 mg, 0.037 mmol) was stirred in a solution of 4 M HCl in dioxane (0.2 mL) at room temperature for 1 hour. The solvent was removed by N$_2$ stream. The residual solids were suspended in THF and condensed (repeat twice) to ensure complete removal of the dioxane. This process was repeated with Et$_2$O to provide 14.6 mg (quant.) of S-61.

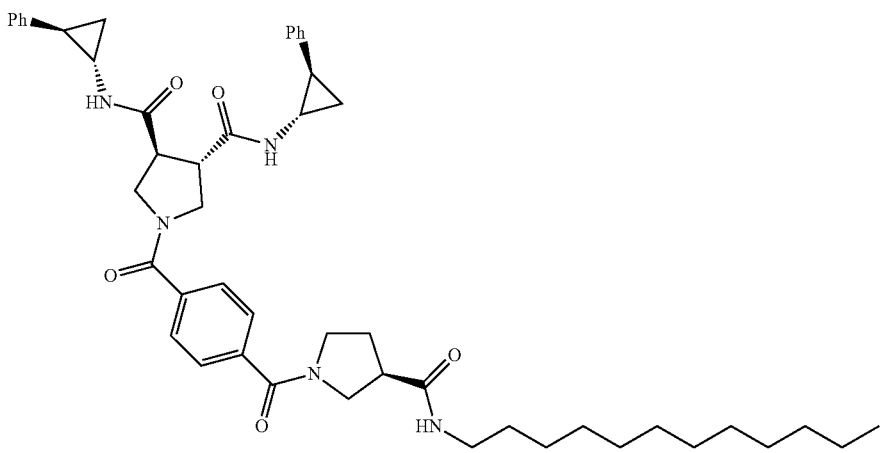

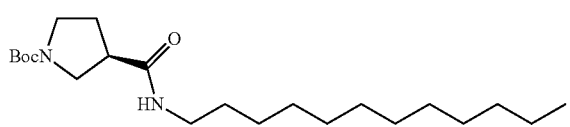 [SMILES: CCCCCCCCCCCCNC(=O)[C@@H]1CCN(C(=O)OC(C)(C)C)C1]

S-60: tert-Butyl (R)-3-(Dodecylcarbamoyl)pyrrolidine-1-carboxylate (R)—N-Boc-β-Proline (S-55, 10 mg, 0.047 mmol, 1.0 equiv), dodecylamine (10.3 mg, 0.056 mmol, 1.2 equiv), HOAt (7.0 mg, 0.051 mmol, 1.1 equiv), and 2,6-lutidine (15.0 mg, 0.140 mmol, 3.00 equiv) were dissolved in DMF (0.2 mL). Upon dissolution of the reagents (about 5 minutes), EDCI.HCl (13.4 mg, 0.070 mmol, 1.5 equiv) was added in one portion, and the reaction mixture was stirred at room temperature for 3.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous NaHCO$_3$ (2 mL), and saturated aqueous NaCl (2 mL), sequentially. The organic phase

127: (3S,4S)-1-(4-((R)-3-(Dodecylcarbamoyl)-pyrrolidine-1-carbonyl)benzoyl)—N³,N⁴-bis((1S,2R)-2-phenylcyclopropyl)pyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 2.2 mg) and (R)—N-dodecylpyrrolidine-3-carboxamide hydrochloride (S-61, 1.6 mg) provided 2.9 mg (88%) of 127. $^1$H NMR (500 MHz, CDCl$_3$, mixture of rotamers) δ 7.57-7.50 (m, 4H), 7.30-7.22 (m, 4H), 7.21-7.08 (m, 6H), 7.01-6.69 (m, 2H), 5.65-5.59 (m, 1H), 4.05-3.38 (m, 8H), 3.28-3.12 (m, 4H), 2.93-2.75 (m, 3H), 2.25-2.14 (m, 2H), 2.10-1.96 (m, 2H), 1.54-1.41 (m, 2H), 1.34-1.06 (m, 22H), 0.88 (t, J=7.0 Hz, 3H). HRMS (ESI-TOF) m/z calcd for $C_{49}H_{64}N_5O_5$ [M+H]$^+$ 802.4902, found 802.4899.

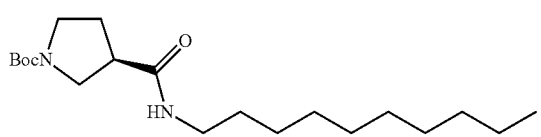 [SMILES: CCCCCCCCCCNC(=O)[C@@H]1CCN(C(=O)OC(C)(C)C)C1]

S-62: tert-Butyl (R)-3-(Decylcarbamoyl)pyrrolidine-1-carboxylate (R)—N-Boc-β-Proline (S-55, 10 mg, 0.047 mmol, 1.0 equiv), decylamine (8.8 mg, 0.056 mmol, 1.2 equiv), HOAt (7.0 mg, 0.051 mmol, 1.1 equiv), and 2,6-lutidine (15.0 mg, 0.140 mmol, 3.00 equiv) were dissolved in DMF (0.2 mL). Upon dissolution of the reagents (about 5 minutes), EDCI.HCl (13.4 mg, 0.070 mmol, 1.5 equiv) was added in one portion, and the reaction mixture was stirred at room temperature for 3.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous NaHCO$_3$ (2 mL), and saturated aqueous NaCl (2 mL), sequentially. The organic phase was dried over Na$_2$SO$_4$, filtered and concentrated. Short path column chromatography (SiO$_2$, 5% MeOH/CH$_2$Cl$_2$) provided 18.3 mg (quant.) of S-62. $^1$H NMR (400 MHz, CDCl$_3$) δ 5.67 (br, 1H), 3.63-3.48 (m, 2H), 3.44 (dd, J=13.5, 10.0 Hz, 1H), 3.34-3.20 (m, 3H), 2.84-2.75 (m, 1H), 2.18-2.00 (m, 2H), 1.54-1.40 (m, 11H), 1.33-1.19 (m, 14H), 0.86 (t, J=8.5 Hz, 3H).

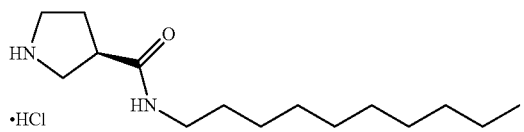 [SMILES: Cl ; CCCCCCCCCCNC(=O)[C@@H]1CCNC1]

S-63: (R)—N-Decylpyrrolidine-3-carboxamide Hydrochloride tert-Butyl (R)-3-(decylcarbamoyl)-pyrrolidine-1-carboxylate (S-62, 14.7 mg, 0.042 mmol) was stirred in a solution of 4 M HCl in dioxane (0.2 mL) at room temperature for 1 hour. The solvent was removed by N$_2$ stream. The residual solids were suspended in THF and condensed (repeat twice) to ensure complete removal of the dioxane. This process was repeated with Et$_2$O to provide 14.5 mg (quant.) of S-63.

128: (3S,4S)-1-(4-((R)-3-(Decylcarbamoyl)pyrrolidine-1-carbonyl)benzoyl)—N$^3$,N$^4$-bis((1S,2R)-2-phenyl-cyclopropyl)pyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 2.2 mg) and (R)—N-decylpyrrolidine-3-carboxamide hydrochloride (S-63, 1.4 mg) provided 2.6 mg (81%) of 128. $^1$H NMR (500 MHz, CDCl$_3$, mixture of rotamers) δ 7.57-7.51 (m, 4H), 7.30-7.22 (m, 4H), 7.21-7.09 (m, 6H), 7.01-6.69 (m, 2H), 5.66-5.59 (m, 1H), 4.04-3.38 (m, 8H), 3.28-3.12 (m, 4H), 2.93-2.76 (m, 3H), 2.25-2.14 (m, 2H), 2.10-1.97 (m, 2H), 1.54-1.41 (m, 2H), 1.34-1.06 (m, 18H), 0.91-0.85 (m, 3H). HRMS (ESI-TOF) m/z calcd for C$_{47}$H$_{60}$N$_5$O$_5$ [M+H]$^+$ 774.4589, found 774.4589.

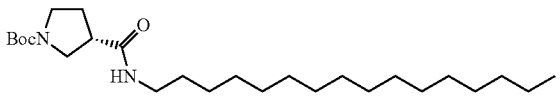

S-64: tert-Butyl (S)-3-(Hexadecylcarbamoyl)-pyrrolidine-1-carboxylate (S)—N-Boc-β-Proline (S-18, 10 mg, 0.047 mmol, 1.0 equiv), hexadecylamine (13.5 mg, 0.056 mmol, 1.2 equiv), HOAt (7.0 mg, 0.051 mmol, 1.1 equiv), and 2,6-lutidine (15.0 mg, 0.140 mmol, 3.00 equiv) were dissolved in CH$_2$Cl$_2$ (0.2 mL). Upon dissolution of the reagents (about 5 minutes), EDCI.HCl (13.4 mg, 0.070 mmol, 1.5 equiv) was added in one portion, and the reaction mixture was stirred at room temperature for 3.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous NaHCO$_3$ (2 mL), and saturated aqueous NaCl (2 mL), sequentially. The organic phase was dried over Na$_2$SO$_4$, filtered and concentrated. Short path column chromatography (SiO$_2$, 5% MeOH/CH$_2$Cl$_2$) provided 17.5 mg (86%) of S-64.

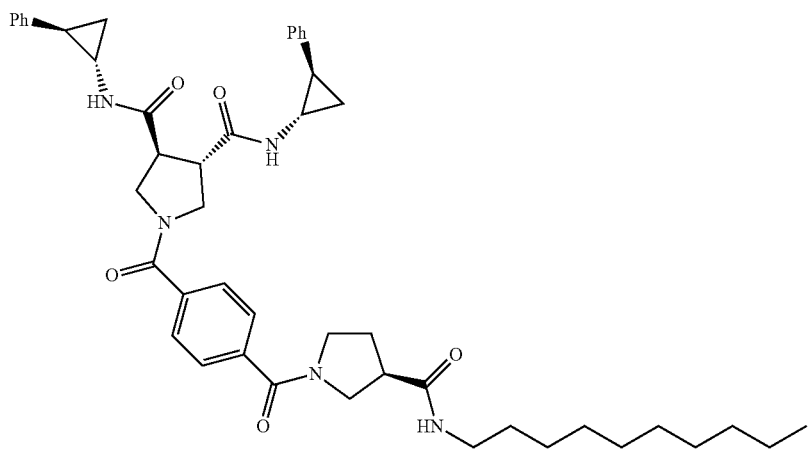 [SMILES: CCCCCCCCCCNC(=O)[C@@H]1CCN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C1]

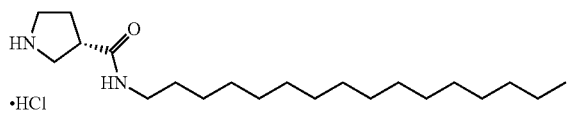 [SMILES: CCCCCCCCCCCCCCCCNC(=O)[C@H]1CCNC1 ; Cl]

S-65: (S)—N-Hexadecylpyrrolidine-3-carboxamide Hydrochloride tert-Butyl (S)-3-(hexadecylcarbamoyl)-pyrrolidine-1-carboxylate (S-64, 17.5 mg, 0.040 mmol) was stirred in a solution of 4 M HCl in dioxane (0.2 mL) at room temperature for 1 hour. The solvent was removed by $N_2$ stream. The residual solids were suspended in THF and condensed (repeat twice) to ensure complete removal of the dioxane. This process was repeated with $Et_2O$ to provide 17.0 mg (quant.) of S-65.

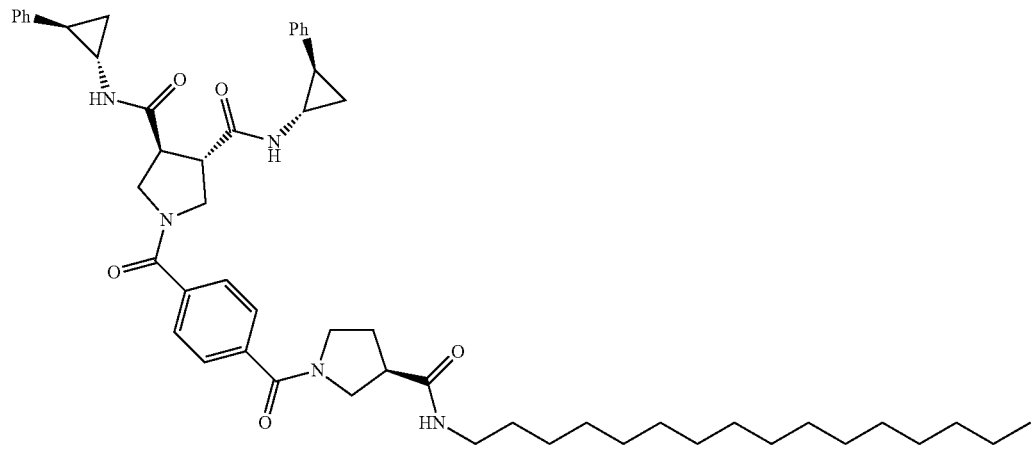 [SMILES: CCCCCCCCCCCCCCCCNC(=O)[C@@H]1CCN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C1]

129: (3S,4S)-1-(4-((S)-3-(Hexadecylcarbamoyl)-pyrrolidine-1-carbonyl)benzoyl)—$N^3$,$N^4$-bis((1S,2R)-2-phenylcyclopropyl)pyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 2.2 mg) and (S)—N-hexadecylpyrrolidine-3-carboxamide hydrochloride (S-65, 1.8 mg) provided 2.4 mg (69%) of 129. $^1$H NMR (500 MHz, CDCl$_3$, mixture of rotamers) δ 7.59-7.48 (m, 4H), 7.30-7.22 (m, 4H), 7.21-7.08 (m, 6H), 7.03 (br, 1H), 6.76 (br, 1H), 5.88-5.78 (m, 1H), 3.99-3.35 (m, 8H), 3.29-3.11 (m, 3H), 3.08-2.95 (m, 1H), 2.92-2.67 (m, 3H), 2.26-1.95 (m, 4H), 1.55-1.41 (m, 2H), 1.35-1.05 (m, 30H), 0.88 (t, J=7.0 Hz, 3H). HRMS (ESI-TOF) m/z calcd for $C_{53}H_{72}N_5O_5$ [M+H]$^+$ 858.5528, found 858.5528.

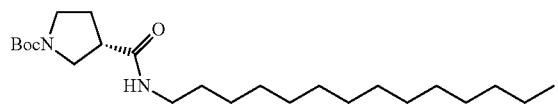 [SMILES: CCCCCCCCCCCCCCNC(=O)[C@H]1CCN(C(=O)OC(C)(C)C)C1]

S-66: tert-Butyl (S)-3-(Tetradecylcarbamoyl)-pyrrolidine-1-carboxylate (S)—N-Boc-β-Proline (S-18, 10 mg, 0.047 mmol, 1.0 equiv), tetradecylamine (11.9 mg, 0.056 mmol, 1.2 equiv), HOAt (7.0 mg, 0.051 mmol, 1.1 equiv), and 2,6-lutidine (15.0 mg, 0.140 mmol, 3.00 equiv) were dissolved in $CH_2Cl_2$ (0.2 mL). Upon dissolution of the reagents (about 5 minutes), EDCI.HCl (13.4 mg, 0.070 mmol, 1.5 equiv) was added in one portion, and the reaction mixture was stirred at room temperature for 3.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous NaHCO$_3$ (2 mL), and saturated aqueous NaCl (2 mL), sequentially. The organic phase was dried over Na$_2$SO$_4$, filtered and concentrated. Short path column chromatography (SiO$_2$, 5% MeOH/CH$_2$Cl$_2$) provided 18.2 mg (95%) of S-66.

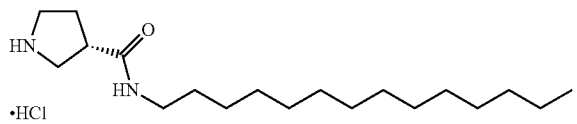 [SMILES: CCCCCCCCCCCCCCNC(=O)[C@H]1CCNC1 ; Cl]

S-67: (S)—N-Tetradecylpyrrolidine-3-carboxamide Hydrochloride tert-Butyl (S)-3-(tetradecylcarbamoyl)-pyrrolidine-1-carboxylate (S-66, 18.2 mg, 0.044 mmol) was stirred in a solution of 4 M HCl in dioxane (0.2 mL) at room temperature for 1 hour. The solvent was removed by $N_2$ stream. The residual solids were suspended in THF and condensed (repeat twice) to ensure complete removal of the dioxane. This process was repeated with $Et_2O$ to provide 16.2 mg (quant.) of S-67.

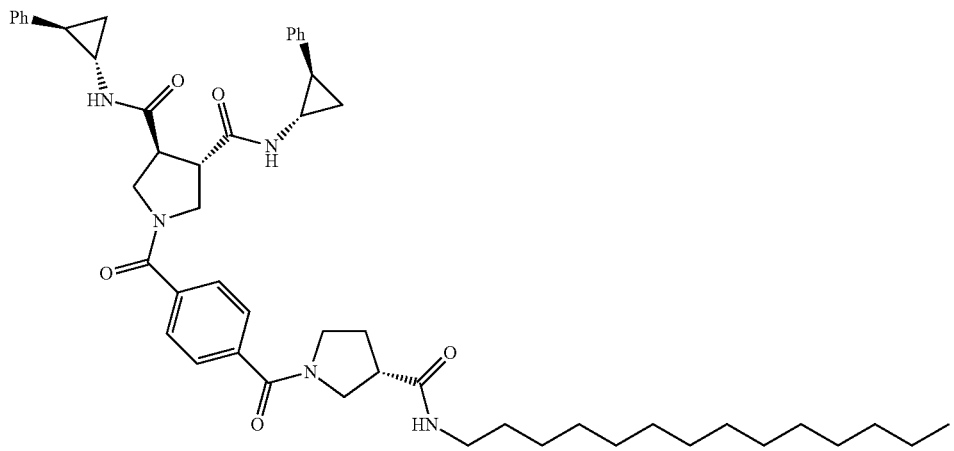 [SMILES: CCCCCCCCCCCCCCNC(=O)[C@H]1CCN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C1]

130: (3S,4S)—N³,N⁴-Bis((1S,2R)-2-phenylcyclopropyl)-1-(4-((S)-3-(tetradecylcarbamoyl)pyrrolidine-1-carbonyl)benzoyl)pyrrolidine-3,4-dicarboxamide

The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 2.2 mg) and (S)—N-tetradecylpyrrolidine-3-carboxamide hydrochloride (S-67, 1.7 mg) provided 2.8 mg (76%) of 130. ¹H NMR (500 MHz, CDCl₃, mixture of rotamers) δ 7.58-7.49 (m, 4H), 7.30-7.22 (m, 4H), 7.21-7.08 (m, 6H), 7.00 (br, 1H), 6.74 (br, 1H), 5.87-5.76 (m, 1H), 3.99-3.35 (m, 8H), 3.30-3.11 (m, 3H), 3.09-2.96 (m, 1H), 2.92-2.67 (m, 3H), 2.28-1.96 (m, 4H), 1.55-1.41 (m, 2H), 1.35-1.06 (m, 26H), 0.88 (t, J=7.0 Hz, 3H). HRMS (ESI-TOF) m/z calcd for C₅₁H₆₈N₅O₅ [M+H]⁺ 830.5215, found 830.5213.

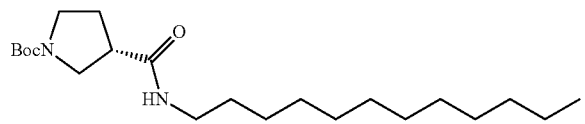 [SMILES: CCCCCCCCCCCCNC(=O)[C@H]1CCN(C(=O)OC(C)(C)C)C1]

S-68: tert-Butyl (S)-3-(Dodecylcarbamoyl)pyrrolidine-1-carboxylate

(S)—N-Boc-β-Proline (S-18, 10 mg, 0.047 mmol, 1.0 equiv), dodecylamine (10.3 mg, 0.056 mmol, 1.2 equiv), HOAt (7.0 mg, 0.051 mmol, 1.1 equiv), and 2,6-lutidine (15.0 mg, 0.140 mmol, 3.00 equiv) were dissolved in anhydrous DMF (0.2 mL). Upon dissolution of the reagents (about 5 minutes), EDCI.HCl (13.4 mg, 0.070 mmol, 1.5 equiv) was added in one portion, and the reaction mixture was stirred at room temperature for 3.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous NaHCO₃ (2 mL), and saturated aqueous NaCl (2 mL), sequentially. The organic phase was dried over Na₂SO₄, filtered and concentrated. Short path column chromatography (SiO₂, 5% MeOH/CH₂Cl₂) provided 14.2 mg (80%) of S-68.

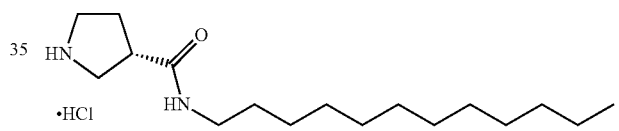

S-69: (S)—N-Dodecylpyrrolidine-3-carboxamide Hydrochloride tert-Butyl (S)-3-(dodecylcarbamoyl)-pyrrolidine-1-carboxylate (S-69, 14.2 mg, 0.037 mmol) was stirred in a solution of 4 M HCl in dioxane (0.2 mL) at room temperature for 1 hour. The solvent was removed by N₂ stream. The residual solids were suspended in THF and condensed (repeat twice) to ensure complete removal of the dioxane. This process was repeated with Et₂O to provide 13.4 mg (quant.) of S-69.

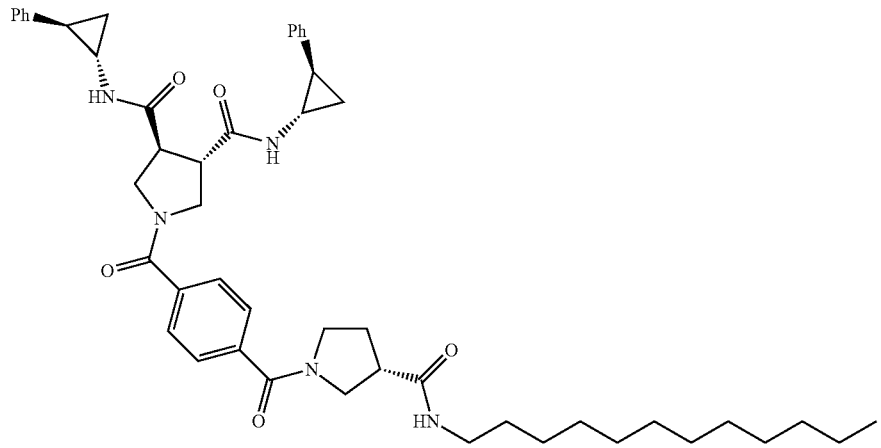 [SMILES: CCCCCCCCCCCCNC(=O)[C@H]1CCN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C1]

131: (3S,4S)-1-(4-((S)-3-(Dodecylcarbamoyl)-pyrrolidine-1-carbonyl)benzoyl)—N³,N⁴-bis((1S,2R)-2-phenylcyclopropyl)pyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 2.2 mg) and (S)—N-dodecylpyrrolidine-3-carboxamide hydrochloride (S-69, 1.6 mg) provided 2.1 mg (64%) of 131. ¹H NMR (500 MHz, CDCl₃, mixture of rotamers) δ 7.59-7.49 (m, 4H), 7.30-7.22 (m, 4H), 7.21-7.08 (m, 6H), 7.04 (br, 1H), 6.76 (br, 1H), 5.89-5.78 (m, 1H), 3.99-3.35 (m, 8H), 3.30-3.11 (m, 3H), 3.08-2.95 (m, 1H), 2.92-2.67 (m, 3H), 2.27-1.96 (m, 4H), 1.55-1.41 (m, 2H), 1.35-1.06 (m, 22H), 0.90-0.85 (m, 3H). HRMS (ESI-TOF) m/z calcd for $C_{49}H_{64}N_5O_5$ [M+H]⁺ 802.4902, found 802.4903.

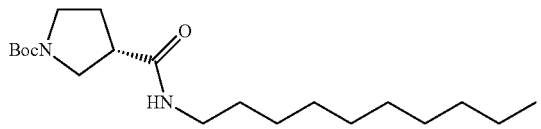 [SMILES: CCCCCCCCCCNC(=O)[C@H]1CCN(C(=O)OC(C)(C)C)C1]

S-70: tert-Butyl (S)-3-(Decylcarbamoyl)pyrrolidine-1-carboxylate (S)—N-Boc-β-Proline (S-18, 10 mg, 0.047 mmol, 1.0 equiv), decylamine (8.8 mg, 0.056 mmol, 1.2 equiv), HOAt (7.0 mg, 0.051 mmol, 1.1 equiv), and 2,6-lutidine (15.0 mg, 0.140 mmol, 3.00 equiv) were dissolved in anhydrous DMF (0.2 mL). Upon dissolution of the reagents (about 5 minutes), EDCI.HCl (13.4 mg, 0.070 mmol, 1.5 equiv) was added in one portion, and the reaction mixture was stirred at room temperature for 3.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous NaHCO₃ (2 mL), and saturated aqueous NaCl (2 mL), sequentially. The organic phase was dried over Na₂SO₄, filtered and concentrated. Short path column chromatography (SiO₂, 5% MeOH/CH₂Cl₂) provided 14.7 mg (89%) of S-70. H NMR (400 μMHz, CDCl₃) δ 5.61 (br, 1H), 3.65-3.48 (m, 2H), 3.45 (dd, J=13.5, 10.0 Hz, 1H), 3.34-3.20 (m, 3H), 2.85-2.75 (m, 1H), 2.18-2.00 (m, 2H), 1.54-1.40 (m, 11H), 1.33-1.19 (m, 14H), 0.86 (t, J=8.5 Hz, 3H).

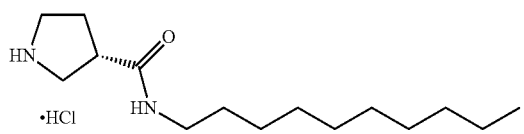 [SMILES: CCCCCCCCCCNC(=O)[C@H]1CCNC1 ; Cl]

S-71: (S)—N-Decylpyrrolidine-3-carboxamide Hydrochloride tert-Butyl (S)-3-(decylcarbamoyl)-pyrrolidine-1-carboxylate (S-70, 14.7 mg, 0.042 mmol) was stirred in a solution of 4 M HCl in dioxane (0.2 mL) at room temperature for 1 hour. The solvent was removed by N₂ stream. The residual solids were suspended in THF and condensed (repeat twice) to ensure complete removal of the dioxane. This process was repeated with Et₂O to provide 12.5 mg (quant.) of S-71.

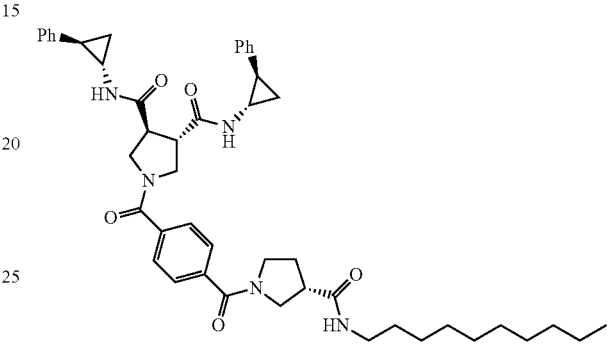

132: (3S,4S)-1-(4-((S)-3-(Decylcarbamoyl)pyrrolidine-1-carbonyl)benzoyl)—N³,N⁴-bis((1S,2R)-2-phenyl-cyclopropyl)pyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 2.2 mg) and (S)—N-decylpyrrolidine-3-carboxamide hydrochloride (S-71, 1.4 mg) provided 2.3 mg (72%) of 132. ¹H NMR (500 MHz, CDCl₃, mixture of rotamers) δ 7.59-7.48 (m, 4H), 7.30-7.22 (m, 4H), 7.21-7.07 (m, 7H), 6.80 (br, 1H), 5.92-5.80 (m, 1H), 3.97-3.35 (m, 8H), 3.30-3.11 (m, 3H), 3.06-2.94 (m, 1H), 2.91-2.66 (m, 3H), 2.28-1.96 (m, 4H), 1.55-1.41 (m, 2H), 1.35-1.06 (m, 18H), 0.90-0.85 (m, 3H). HRMS (ESI-TOF) m/z calcd for $C_{47}H_{60}N_5O_5$ [M+H]⁺ 774.4589, found 774.4588.

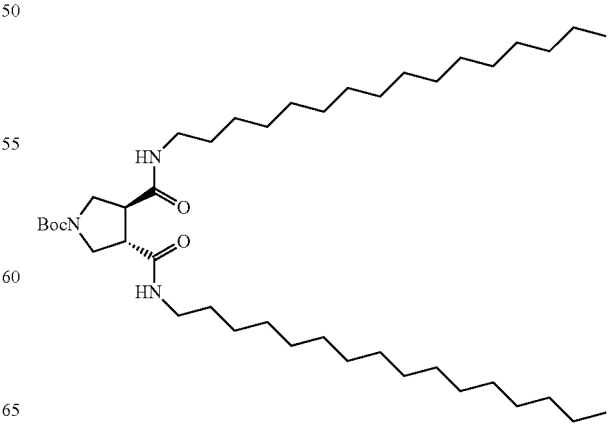

S-72: tert-Butyl (3S,4S)-3,4-Bis(hexadecylcarbamoyl)-pyrrolidine-1-carboxylate (3S,4S)-1-(tert-Butoxycarbonyl) pyrrolidine-3,4-dicarboxylic acid ((S,S)-14, 8.0 mg, 0.031 mmol, 1.0 equiv), hexadecylamine (16.4 mg, 0.068 mmol, 2.2 equiv), HOAt (9.3 mg, 0.068 mmol, 2.2 equiv), and 2,6-lutidine (16.6 mg, 0.155 mmol, 5.00 equiv) were dissolved in anhydrous DMF/CH$_2$Cl$_2$ (1/1, 0.3 mL). Upon dissolution of the reagents (about 5 minutes), EDCI.HCl (17.8 mg, 0.093 mmol, 3.0 equiv) was added in one portion, and the reaction mixture was stirred at room temperature for 3.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous NaHCO$_3$ (2 mL), and saturated aqueous NaCl (2 mL), sequentially. The organic phase was dried over Na$_2$SO$_4$, filtered and concentrated. Short path column chromatography (SiO$_2$, 5% MeOH/CH$_2$Cl$_2$) provided 19.8 mg (91%) of S-72.

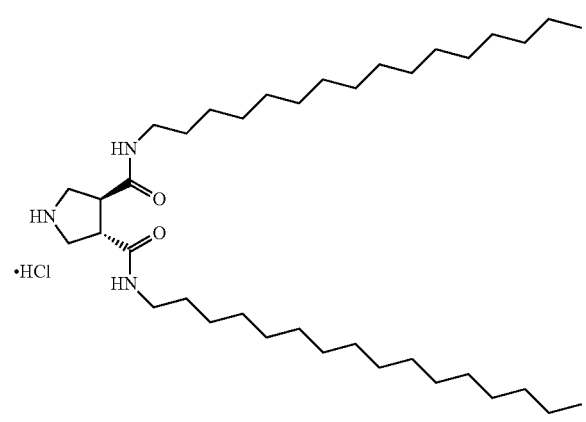 [SMILES: Cl ; CCCCCCCCCCCCCCCCNC(=O)[C@@H]1CNC[C@H]1C(=O)NCCCCCCCCCCCCCCCC]

S-73: (3S,4S)—N$^3$,N$^4$-Dihexadecylpyrrolidine-3,4-dicarboxamide Hydrochloride tert-Butyl (3S,4S)-3,4-bis(hexadecyl-carbamoyl)pyrrolidine-1-carboxylate (S-72, 19.8 mg, 0.028 mmol) was stirred in a solution of 4 M HCl in dioxane (0.2 mL) at room temperature for 1 hour. The solvent was removed by N$_2$ stream. The residual solids were suspended in THF and condensed (repeat twice) to ensure complete removal of the dioxane. This process was repeated with Et$_2$O to provide 18.9 mg (quant.) of S-73.

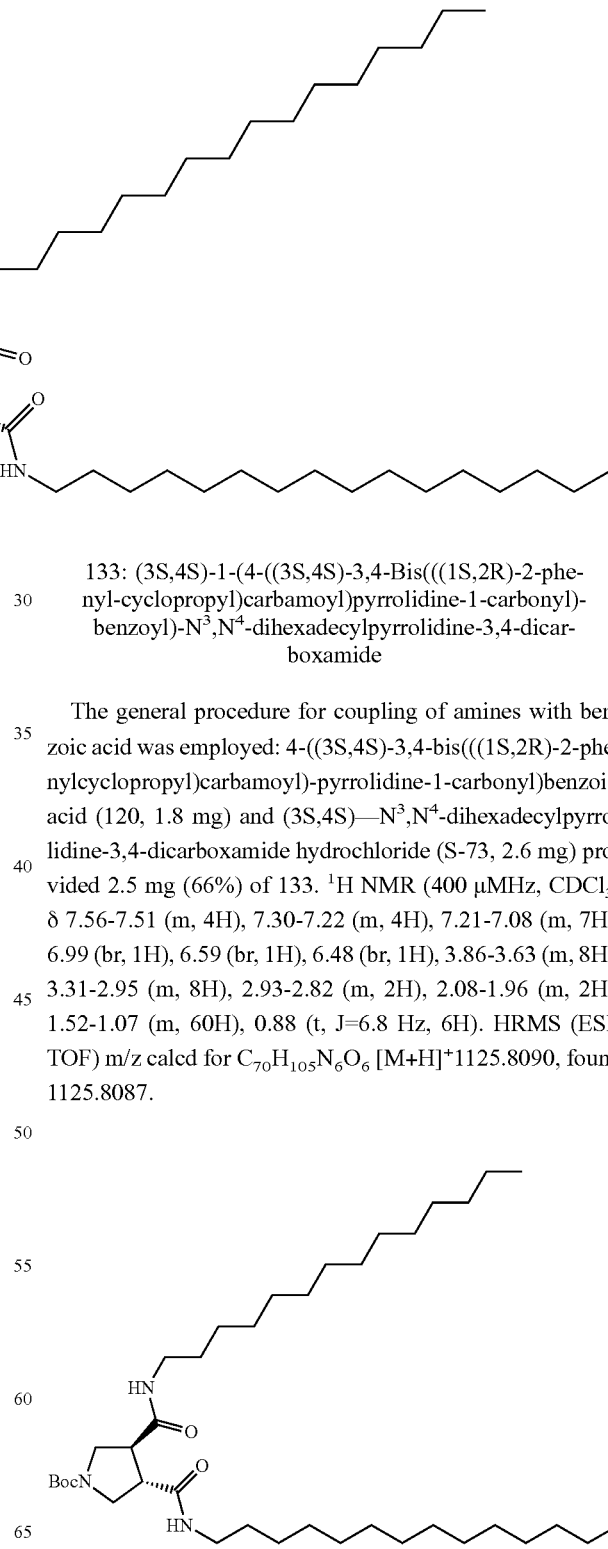

133: (3S,4S)-1-(4-((3S,4S)-3,4-Bis(((1S,2R)-2-phenyl-cyclopropyl)carbamoyl)pyrrolidine-1-carbonyl)-benzoyl)-N$^3$,N$^4$-dihexadecylpyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 1.8 mg) and (3S,4S)—N$^3$,N$^4$-dihexadecylpyrrolidine-3,4-dicarboxamide hydrochloride (S-73, 2.6 mg) provided 2.5 mg (66%) of 133. $^1$H NMR (400 µMHz, CDCl$_3$) δ 7.56-7.51 (m, 4H), 7.30-7.22 (m, 4H), 7.21-7.08 (m, 7H), 6.99 (br, 1H), 6.59 (br, 1H), 6.48 (br, 1H), 3.86-3.63 (m, 8H), 3.31-2.95 (m, 8H), 2.93-2.82 (m, 2H), 2.08-1.96 (m, 2H), 1.52-1.07 (m, 60H), 0.88 (t, J=6.8 Hz, 6H). HRMS (ESI-TOF) m/z calcd for C$_{70}$H$_{105}$N$_6$O$_6$ [M+H]$^+$1125.8090, found 1125.8087.

S-74: tert-Butyl (3S,4S)-3,4-Bis(tetradecyl-carbamoyl)pyrrolidine-1-carboxylate (3S,4S)-1-(tert-Butoxycarbonyl) pyrrolidine-3,4-dicarboxylic acid ((S,S)-14, 8.0 mg, 0.031 mmol, 1.0 equiv), tetradecylamine (14.5 mg, 0.068 mmol, 2.2 equiv), HOAt (9.3 mg, 0.068 mmol, 2.2 equiv), and 2,6-lutidine (16.6 mg, 0.155 mmol, 5.00 equiv) were dissolved in anhydrous DMF/CH$_2$Cl$_2$ (1/1, 0.3 mL). Upon dissolution of the reagents (about 5 minutes), EDCI.HCl (17.8 mg, 0.093 mmol, 3.0 equiv) was added in one portion, and the reaction mixture was stirred at room temperature for 3.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous NaHCO$_3$ (2 mL), and saturated aqueous NaCl (2 mL), sequentially. The organic phase was dried over Na$_2$SO$_4$, filtered and concentrated. Short path column chromatography (SiO$_2$, 5% MeOH/CH$_2$Cl$_2$) provided 20.1 mg (quant.) of S-74.

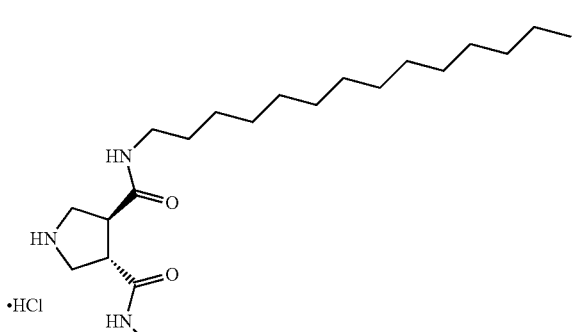

S-75: (3S,4S)—N$^3$,N$^4$-Ditetradecylpyrrolidine-3,4-dicarboxamide Hydrochloride tert-Butyl (3S,4S)-3,4-bis(tetradecyl-carbamoyl)pyrrolidine-1-carboxylate (S-74, 20.1 mg, 0.031 mmol) was stirred in a solution of 4 M HCl in dioxane (0.2 mL) at room temperature for 1 hour. The solvent was removed by N$_2$ stream. The residual solids were suspended in THF and condensed (repeat twice) to ensure complete removal of the dioxane. This process was repeated with Et$_2$O to provide 20.7 mg (quant.) of S-75.

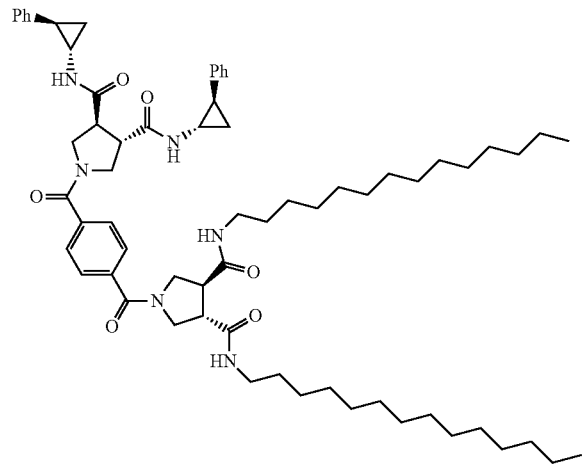 [SMILES: CCCCCCCCCCCCCCNC(=O)[C@@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C[C@H]1C(=O)NCCCCCCCCCCCCCC]

134: (3S,4S)-1-(4-((3S,4S)-3,4-Bis(((1S,2R)-2-phenylcyclopropyl)carbamoyl)pyrrolidine-1-carbonyl)benzoyl)-N$^3$,N$^4$-ditetradecylpyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 1.8 mg) and (3S,4S)—N$^3$,N$^4$-ditetradecylpyrrolidine-3,4-dicarboxamide hydrochloride (S-75, 2.4 mg) provided 2.9 mg (81%) of 134. $^1$H NMR (400 MHz, CDCl$_3$) δ 7.56-7.51 (m, 4H), 7.30-7.08 (m, 11H), 7.05 (br, 1H), 6.63 (br, 1H), 6.53 (br, 1H), 3.86-3.62 (m, 8H), 3.32-2.94 (m, 8H), 2.93-2.82 (m, 2H), 2.08-1.96 (m, 2H), 1.52-1.07 (m, 52H), 0.88 (t, J=6.8 Hz, 6H). HRMS (ESI-TOF) m/z calcd for C$_{66}$H$_{97}$N$_6$O$_6$ [M+H]$^+$1069.7464, found 1069.7464.

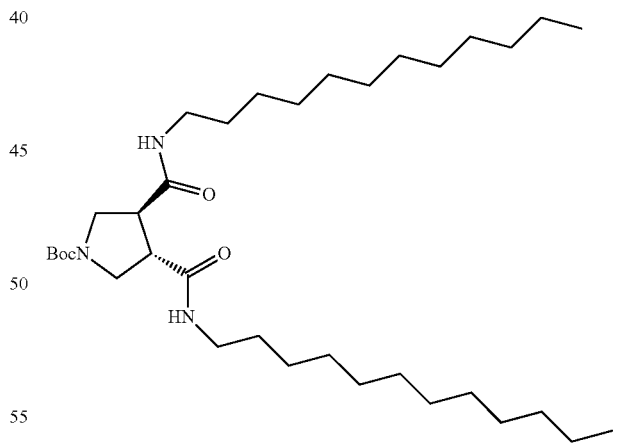

S-76: tert-Butyl (3S,4S)-3,4-Bis(dodecyl-carbamoyl)pyrrolidine-1-carboxylate (3S,4S)-1-(tert-Butoxycarbonyl) pyrrolidine-3,4-dicarboxylic acid ((S,S)-14, 8.0 mg, 0.031 mmol, 1.0 equiv), dodecylamine (12.6 mg, 0.068 mmol, 2.2 equiv), HOAt (9.3 mg, 0.068 mmol, 2.2 equiv), and 2,6-lutidine (16.6 mg, 0.155 mmol, 5.00 equiv) were dissolved in anhydrous DMF (0.15 mL). Upon dissolution of the reagents (about 5 minutes), EDCI.HCl (17.8 mg, 0.093 mmol, 3.0 equiv) was added in one portion, and the reaction mixture was stirred at room temperature for 3.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous NaHCO$_3$ (2 mL), and saturated aqueous NaCl (2 mL), sequentially. The organic phase was dried over Na$_2$SO$_4$, filtered and concentrated. Short path column chromatography (SiO$_2$, 5% MeOH/CH$_2$Cl$_2$) provided 17.6 mg (96%) of S-76.

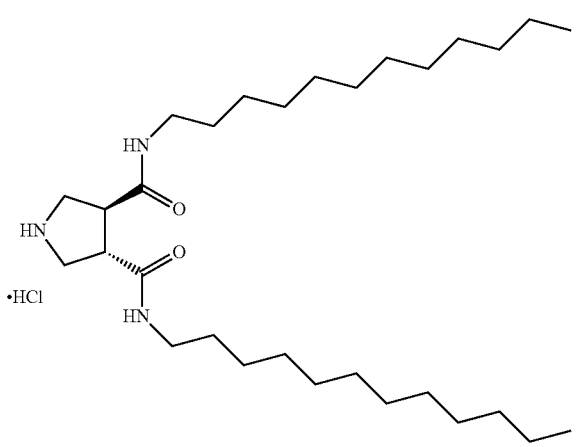 [SMILES: Cl ; CCCCCCCCCCCCNC(=O)[C@@H]1CNC[C@H]1C(=O)NCCCCCCCCCCCC]

S-77: (3S,4S)—N$^3$,N$^4$-Didodecylpyrrolidine-3,4-dicarboxamide Hydrochloride tert-Butyl (3S,4S)-3,4-bis(dodecyl-carbamoyl)pyrrolidine-1-carboxylate (S-76, 17.6 mg, 0.030 mmol) was stirred in a solution of 4 M HCl in dioxane (0.2 mL) at room temperature for 1 hour. The solvent was removed by N$_2$ stream. The residual solids were suspended in THF and condensed (repeat twice) to ensure complete removal of the dioxane. This process was repeated with Et$_2$O to provide 16.8 mg (quant.) of S-77.

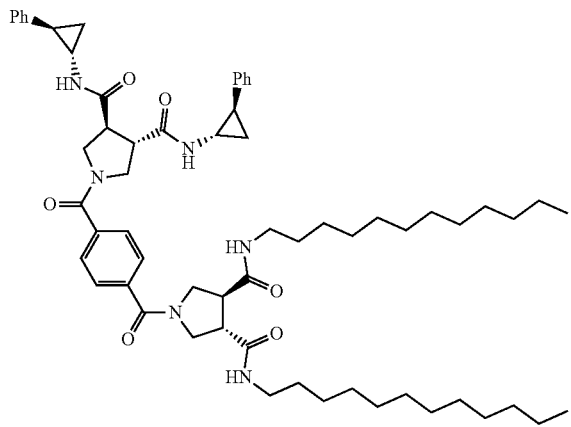 [SMILES: CCCCCCCCCCCCNC(=O)[C@@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C[C@H]1C(=O)NCCCCCCCCCCCC]

135: (3S,4S)-1-(4-((3S,4S)-3,4-Bis(((1S,2R)-2-phenylcyclopropyl)carbamoyl)pyrrolidine-1-carbonyl)benzoyl)-N$^3$,N$^4$-didodecylpyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 1.8 mg) and (3S,4S)—N$^3$,N$^4$-didodecylpyrrolidine-3,4-dicarboxamide hydrochloride (S-77, 2.1 mg) provided 2.6 mg (76%) of 135. $^1$H NMR (400 µMHz, CDCl$_3$) δ 7.56-7.51 (m, 4H), 7.30-7.08 (m, 11H), 7.00 (br, 1H), 6.60 (br, 1H), 6.49 (br, 1H), 3.86-3.63 (m, 8H), 3.31-2.95 (m, 8H), 2.93-2.82 (m, 2H), 2.08-1.96 (m, 2H), 1.52-1.07 (m, 44H), 0.88 (t, J=6.8 Hz, 3H), 0.87 (t, J=6.8 Hz, 3H). HRMS (ESI-TOF) m/z calcd for C$_{62}$H$_{89}$N$_6$O$_6$ [M+H]$^+$ 1013.6838, found 1013.6834.

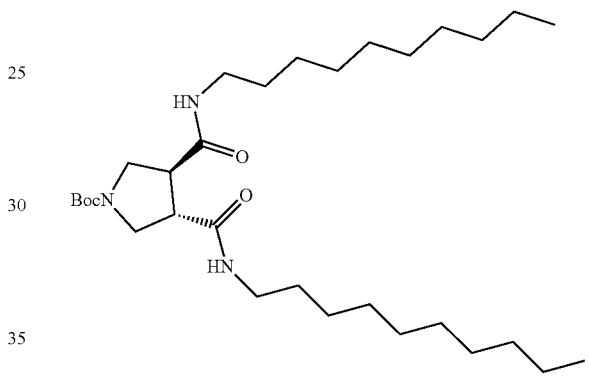

S-78: tert-Butyl (3S,4S)-3,4-Bis(decylcarbamoyl)-pyrrolidine-1-carboxylate (3S,4S)-1-(tert-Butoxycarbonyl) pyrrolidine-3,4-dicarboxylic acid ((S,S)-14, 8.0 mg, 0.031 mmol, 1.0 equiv), decylamine (10.7 mg, 0.068 mmol, 2.2 equiv), HOAt (9.3 mg, 0.068 mmol, 2.2 equiv), and 2,6-lutidine (16.6 mg, 0.155 mmol, 5.00 equiv) were dissolved in anhydrous DMF (0.15 mL). Upon dissolution of the reagents (about 5 minutes), EDCI.HCl (17.8 mg, 0.093 mmol, 3.0 equiv) was added in one portion, and the reaction mixture was stirred at room temperature for 3.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous NaHCO$_3$ (2 mL), and saturated aqueous NaCl (2 mL), sequentially. The organic phase was dried over Na$_2$SO$_4$, filtered and concentrated. Short path column chromatography (SiO$_2$, 5% MeOH/CH$_2$Cl$_2$) provided 19.0 mg (quant.) of S-78. $^1$H NMR (400 µMHz, CDCl$_3$) δ 6.32 (br, 1H), 6.15 (br, 1H), 3.88-3.76 (m, 1H), 3.70-3.50 (m, 2H), 3.44-3.33 (m, 1H), 3.27-3.15 (m, 5H), 3.12-3.01 (m, 1H), 1.51-1.37 (m, 13H), 1.34-1.19 (m, 28H), 0.87 (t, J=7.6 Hz, 6H).

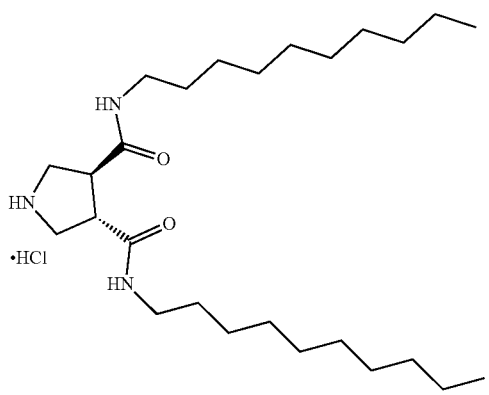 [SMILES: Cl ; CCCCCCCCCCNC(=O)[C@@H]1CNC[C@H]1C(=O)NCCCCCCCCCC]

S-79: (3S,4S)—N³,N⁴-Didecylpyrrolidine-3,4-dicarboxamide Hydrochloride tert-Butyl (3S,4S)-3,4-bis(decylcarbamoyl)-pyrrolidine-1-carboxylate (S-78, 6.6 mg, 0.031 mmol) was stirred in a solution of 4 M HCl in dioxane (0.2 mL) at room temperature for 1 hour. The solvent was removed by $N_2$ stream. The residual solids were suspended in THF and condensed (repeat twice) to ensure complete removal of the dioxane. This process was repeated with $Et_2O$ to provide 16.5 mg (quant.) of S-79.

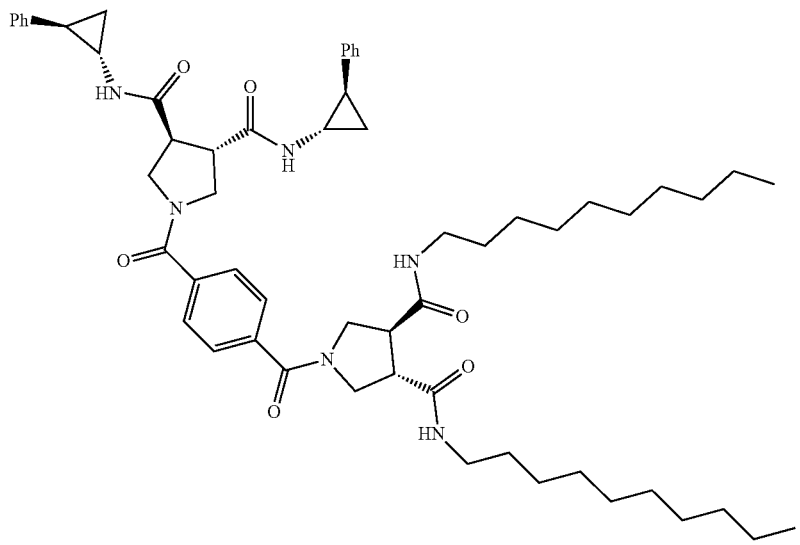 [SMILES: CCCCCCCCCCNC(=O)[C@@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C[C@H]1C(=O)NCCCCCCCCCC]

136: (3S,4S)-1-(4-((3S,4S)-3,4-Bis(((1S,2R)-2-phenylcyclopropyl)carbamoyl)pyrrolidine-1-carbonyl)benzoyl)-N³,N⁴-didecylpyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 1.8 mg) and (3S,4S)—N³,N⁴-didecylpyrrolidine-3,4-dicarboxamide hydrochloride (S-79, 1.9 mg) provided 2.5 mg (78%) of 136. ¹H NMR (400 μMHz, CDCl₃) δ 7.57-7.51 (m, 4H), 7.30-7.08 (m, 11H), 7.03 (br, 1H), 6.62 (br, 1H), 6.51 (br, 1H), 3.85-3.63 (m, 8H), 3.32-2.95 (m, 8H), 2.93-2.82 (m, 2H), 2.08-1.96 (m, 2H), 1.52-1.07 (m, 36H), 0.88 (t, J=6.4 Hz, 3H), 0.87 (t, J=6.8 Hz, 3H). HRMS (ESI-TOF) m/z calcd for $C_{58}H_{81}N_6O_6$ [M+H]⁺ 957.6212, found 957.6216.

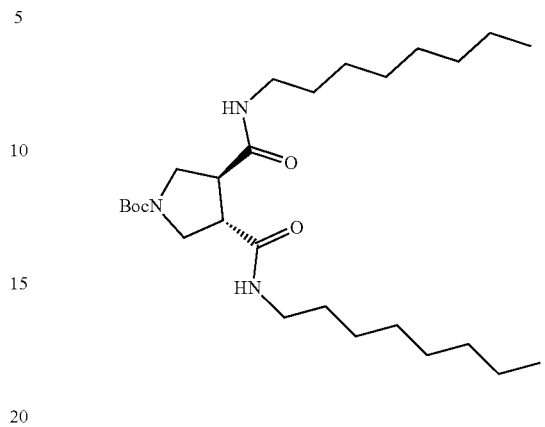

S-80: tert-Butyl (3S,4S)-3,4-Bis(octylcarbamoyl)-pyrrolidine-1-carboxylate (3S,4S)-1-(tert-Butoxycarbonyl) pyrrolidine-3,4-dicarboxylic acid ((S,S)-14, 8.0 mg, 0.031 mmol, 1.0 equiv), octylamine (8.8 mg, 0.068 mmol, 2.2 equiv), HOAt (9.3 mg, 0.068 mmol, 2.2 equiv), and 2,6-lutidine (16.6 mg, 0.155 mmol, 5.00 equiv) were dissolved in $CH_2Cl_2$ (0.15 mL). Upon dissolution of the reagents (about 5 minutes), EDCI.HCl (17.8 mg, 0.093 mmol, 3.0 equiv) was added in one portion, and the reaction mixture was stirred at room temperature for 3.5 h, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous $NaHCO_3$ (2 mL), and saturated aqueous NaCl (2 mL), sequentially. The organic phase was dried over $Na_2SO_4$, filtered and concentrated. Short path column chromatography ($SiO_2$, 5% MeOH/$CH_2Cl_2$) provided 15.2 mg (quant.) of S-80.

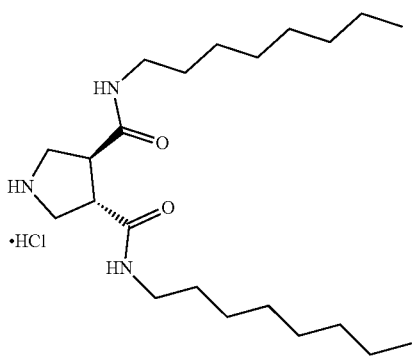 [SMILES: Cl ; CCCCCCCCNC(=O)[C@@H]1CNC[C@H]1C(=O)NCCCCCCCC]

S-81: (3S,4S)—N³,N⁴-Dioctylpyrrolidine-3,4-dicarboxamide Hydrochloride tert-Butyl (3S,4S)-3,4-bis(octylcarbamoyl)-pyrrolidine-1-carboxylate (S-80, 14.9 mg, 0.031 mmol) was stirred in a solution of 4 M HCl in dioxane (0.2 mL) at room temperature for 1 hour. The solvent was removed by $N_2$ stream. The residual solids were suspended in THF and condensed (repeat twice) to ensure complete removal of the dioxane. This process was repeated with $Et_2O$ to provide 13.8 mg (quant.) of S-81.

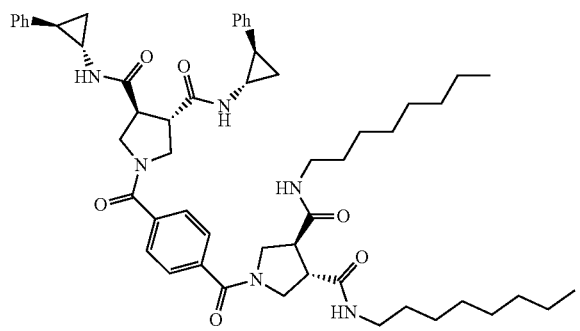 [SMILES: CCCCCCCCNC(=O)[C@@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C[C@H]1C(=O)NCCCCCCCC]

137: (3S,4S)-1-(4-((3S,4S)-3,4-Bis(((1S,2R)-2-phenylcyclopropyl)carbamoyl)pyrrolidine-1-carbonyl)benzoyl)-N³,N⁴-dioctylpyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 2.5 mg) and (3S,4S)—N³,N⁴-dioctylpyrrolidine-3,4-dicarboxamide hydrochloride (S-81, 2.3 mg) provided 3.9 mg (93%) of 137. ¹H NMR (500 MHz, DMSO-d₆) δ 8.41 (d, J=4.0 Hz, 1H), 8.28 (d, J=4.5 Hz, 1H), 8.01 (d, J=5.5 Hz, 1H), 7.87 (t, J=5.5 Hz, 1H), 7.55 (s, 4H), 7.29-7.21 (m, 4H), 7.18-7.10 (m, 4H), 7.09-7.04 (m, 2H), 3.79 (dt, J=7.0, 7.5 Hz, 2H), 3.64 (q, J=9.0 Hz, 2H), 3.55-3.43 (m, 4H), 3.19 (q, J=8.5 Hz, 2H), 3.14-2.97 (m, 5H), 2.95-2.81 (m, 2H), 2.80-2.75 (m, 1H), 1.99-1.94 (m, 1H), 1.88-1.83 (m, 1H), 1.42-1.06 (m, 28H), 0.86 (t, J=6.5 Hz, 3H), 0.84 (t, J=7.0 Hz, 3H). HRMS (ESI-TOF) m/z calcd for $C_{54}H_{73}N_6O_6$ [M+H]⁺ 901.5586, found 901.5586.

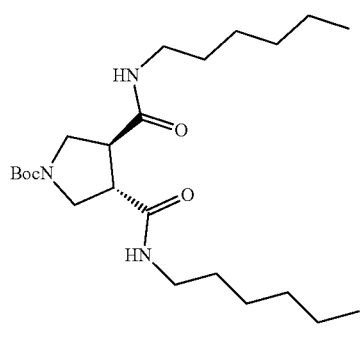 [SMILES: CCCCCCNC(=O)[C@@H]1CN(C(=O)OC(C)(C)C)C[C@H]1C(=O)NCCCCCC]

S-82: tert-Butyl (3S,4S)-3,4-Bis(hexylcarbamoyl)-pyrrolidine-1-carboxylate (3S,4S)-1-(tert-Butoxycarbonyl) pyrrolidine-3,4-dicarboxylic acid ((S,S)-14, 8.0 mg, 0.031 mmol, 1.0 equiv), hexylamine (6.9 mg, 0.068 mmol, 2.2 equiv), HOAt (9.3 mg, 0.068 mmol, 2.2 equiv), and 2,6-lutidine (16.6 mg, 0.155 mmol, 5.00 equiv) were dissolved in $CH_2Cl_2$ (0.15 mL). Upon dissolution of the reagents (about 5 minutes), EDCI.HCl (17.8 mg, 0.093 mmol, 3.0 equiv) was added in one portion, and the reaction mixture was stirred at room temperature for 3.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous $NaHCO_3$ (2 mL), and saturated aqueous NaCl (2 mL), sequentially. The organic phase was dried over $Na_2SO_4$, filtered and concentrated. Short path column chromatography ($SiO_2$, 5% $MeOH/CH_2Cl_2$) provided 12.4 mg (94%) of S-82.

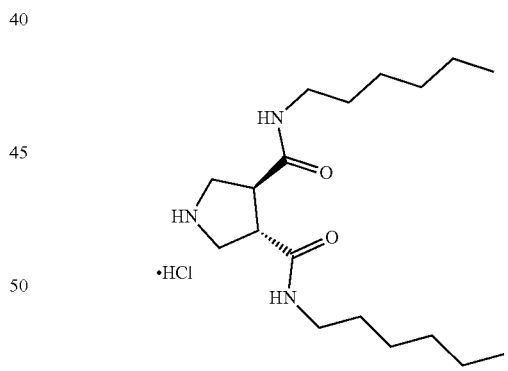

S-83: (3S,4S)—N³,N⁴-Dihexylpyrrolidine-3,4-dicarboxamide Hydrochloride tert-Butyl (3S,4S)-3,4-bis(hexylcarbamoyl)pyrrolidine-1-carboxylate (S-82, 12.4 mg, 0.029 mmol) was stirred in a solution of 4 M HCl in dioxane (0.2 mL) at room temperature for 1 hour. The solvent was removed by $N_2$ stream. The residual solids were suspended in THF and condensed (repeat twice) to ensure complete removal of the dioxane. This process was repeated with $Et_2O$ to provide 12.7 mg (quant.) of S-83.

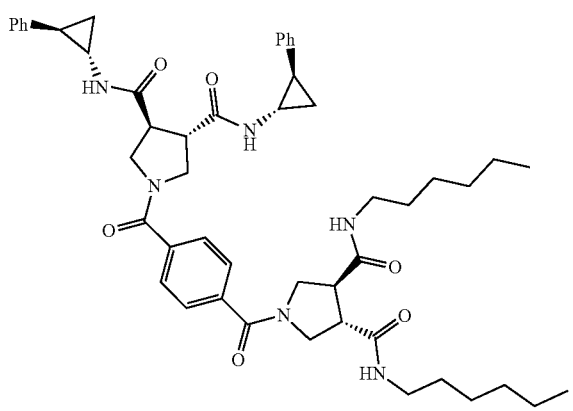 [SMILES: CCCCCCNC(=O)[C@@H]1CN(C(=O)c2ccc(C(=O)N3C[C@@H](C(=O)N[C@H]4C[C@@H]4c4ccccc4)[C@H](C(=O)N[C@H]4C[C@@H]4c4ccccc4)C3)cc2)C[C@H]1C(=O)NCCCCCC]

138 (Diprovocim-6): (3S,4S)-1-(4-((3S,4S)-3,4-Bis (((1S,2R)-2-phenylcyclopropyl) carbamoyl)-pyrrolidine-1-carbonyl)benzoyl)-$N^3,N^4$-dihexylpyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 2.5 mg) and (3S,4S)—$N^3,N^4$-dihexylpyrrolidine-3,4-dicarboxamide hydrochloride (S-83, 2.0 mg) provided 3.5 mg (90%) of 138. $[\alpha]^{23}_D$ 23.13 (c=0.66, MeOH), IR (neat) $v_{max}$ 3280, 2928, 1645, 1620, 1550, 1434, 1395, 697 cm$^{-1}$. $^1$H NMR (500 MHz, DMSO-d$_6$) δ 8.41 (d, J=4.5 Hz, 1H), 8.28 (d, J=4.0 Hz, 1H), 8.01 (d, J=5.5 Hz, 1H), 7.87 (t, J=5.5 Hz, 1H), 7.55 (s, 4H), 7.29-7.21 (m, 4H), 7.18-7.10 (m, 4H), 7.09-7.04 (m, 2H), 3.83-3.76 (m, 2H), 3.68-3.61 (m, 2H), 3.55-3.43 (m, 4H), 3.23-3.16 (m, 2H), 3.14-2.97 (m, 5H), 2.96-2.90 (m, 1H), 2.87-2.82 (m, 1H), 2.80-2.75 (m, 1H), 1.99-1.94 (m, 1H), 1.88-1.83 (m, 1H), 1.42-1.06 (m, 20H), 0.86 (t, J=7.0 Hz, 3H), 0.82 (t, J=7.0 Hz, 3H). $^{13}$C NMR (151 MHz, DMSO-d$_6$) δ 171.65, 170.93, 170.42, 169.69, 167.47, 167.42, 141.29, 141.20, 137.71, 128.18, 128.14, 127.08, 125.84, 125.79, 125.61, 125.59, 51.81, 51.49, 48.95, 48.74, 47.22, 46.96, 45.24, 45.08, 38.64, 38.59, 32.55, 32.46, 30.98, 30.90, 28.99, 28.87, 25.98, 25.93, 23.91, 23.81, 22.05, 22.00, 15.34, 15.25, 13.91, 13.87. HRMS (ESI-TOF) m/z calcd for $C_{50}H_{65}N_6O_6$ [M+H]$^+$ 845.4960, found 845.4959.

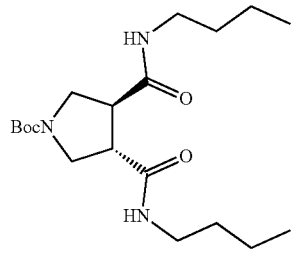 [SMILES: CCCCNC(=O)[C@@H]1CN(C(=O)OC(C)(C)C)C[C@H]1C(=O)NCCCC]

S-84: tert-Butyl (3S,4S)-3,4-Bis(butylcarbamoyl)-pyrrolidine-1-carboxylate (3S,4S)-1-(tert-Butoxycarbonyl)pyrrolidine-3,4-dicarboxylic acid ((S,S)-14, 8.0 mg, 0.031 mmol, 1.0 equiv), butylamine (5.0 mg, 0.068 mmol, 2.2 equiv), HOAt (9.3 mg, 0.068 mmol, 2.2 equiv), and 2,6-lutidine (16.6 mg, 0.155 mmol, 5.00 equiv) were dissolved in CH$_2$Cl$_2$ (0.15 mL). Upon dissolution of the reagents (about 5 minutes), EDCI.HCl (17.8 mg, 0.093 mmol, 3.0 equiv) was added in one portion, and the reaction mixture was stirred at room temperature for 3.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous NaHCO$_3$ (2 mL), and saturated aqueous NaCl (2 mL), sequentially. The organic phase was dried over Na$_2$SO$_4$, filtered and concentrated. Short path column chromatography (SiO$_2$, 5% MeOH/CH$_2$Cl$_2$) provided 10.8 mg (95%) of S-84.

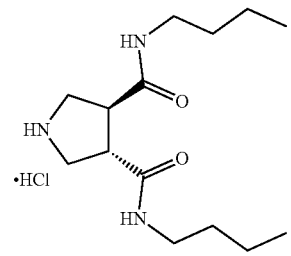 [SMILES: Cl ; CCCCNC(=O)[C@@H]1CNC[C@H]1C(=O)NCCCC]

S-85: (3S,4S)—$N^3,N^4$-Dibutylpyrrolidine-3,4-dicarboxamide Hydrochloride tert-Butyl (3S,4S)-3,4-bis(butylcarbamoyl)-pyrrolidine-1-carboxylate (S-84, 10.8 mg, 0.029 mmol) was stirred in a solution of 4 M HCl in dioxane (0.2 mL) at room temperature for 1 hour. The solvent was removed by N$_2$ stream. The residual solids were suspended in THF and condensed (repeat twice) to ensure complete removal of the dioxane. This process was repeated with Et$_2$O to provide 11.5 mg (quant.) of S-85.

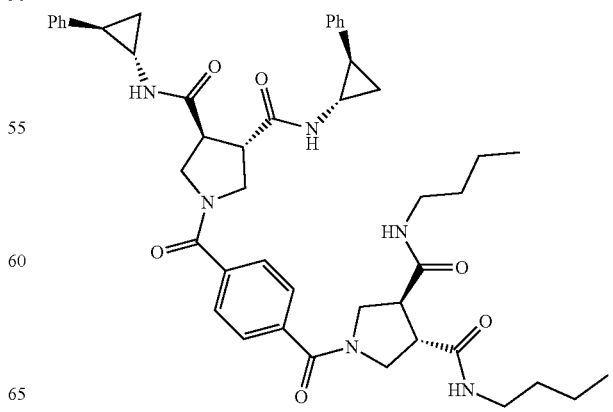

139: (3S,4S)-1-(4-((3S,4S)-3,4-Bis(((1S,2R)-2-phenylcyclopropyl)carbamoyl)pyrrolidine-1-carbonyl)benzoyl)-$N^3$,$N^4$-dibutylpyrrolidine-3,4-dicarboxamide The general procedure for coupling of amines with benzoic acid was employed: 4-((3S,4S)-3,4-bis(((1S,2R)-2-phenylcyclopropyl)carbamoyl)-pyrrolidine-1-carbonyl)benzoic acid (120, 2.5 mg) and (3S,4S)—$N^3$,$N^4$-dibutylpyrrolidine-3,4-dicarboxamide hydrochloride (S-85, 1.7 mg) provided 2.0 mg (54%) of 139. $^1$H NMR (500 MHz, DMSO-$d_6$) δ 8.41 (d, J=4.5 Hz, 1H), 8.27 (d, J=4.5 Hz, 1H), 8.01 (d, J=5.5 Hz, 1H), 7.87 (t, J=5.5 Hz, 1H), 7.56 (s, 4H), 7.29-7.21 (m, 4H), 7.18-7.10 (m, 4H), 7.09-7.04 (m, 2H), 3.83-3.74 (m, 2H), 3.68-3.61 (m, 2H), 3.55-3.43 (m, 4H), 3.23-3.16 (m, 2H), 3.14-2.99 (m, 5H), 2.97-2.91 (m, 1H), 2.87-2.82 (m, 1H), 2.80-2.75 (m, 1H), 1.99-1.94 (m, 1H), 1.88-1.83 (m, 1H), 1.41-1.06 (m, 12H), 0.87 (t, J=7.0 Hz, 3H), 0.81 (t, J=7.0 Hz, 3H). HRMS (ESI-TOF) m/z calcd for $C_{46}H_{57}N_6O_6$ [M+H]$^+$ 789.4334, found 789.4334.

140): (3S,3'S,4S,4'S)-1,1'-Terephthaloylbis($N^3$,$N^4$-dihexadecylpyrrolidine-3,4-dicarboxamide)

Terephthalic acid (benzene-1,4-dicarboxylic acid, 0.6 mg, 0.0037 mmol, 1.0 equiv), (3S,4S)—$N^3$,$N^4$-dihexadecylpyrrolidine-3,4-dicarboxamide hydrochloride (S-73, 5.3 mg, 0.0082 mmol, 2.2 equiv), HOAt (1.1 mg, 0.0082 mmol, 2.2 equiv), and 2,6-lutidine (2.0 mg, 0.019 mmol, 5.0 equiv) were dissolved in anhydrous DMF/$CH_2Cl_2$ (1/1, 0.2 mL). Upon dissolution of the reagents (about 5 minutes) at 0° C., EDCI*HCl (1.8 mg, 0.0093 mmol, 2.5 equiv) was added in one portion at 0° C., and the reaction mixture was stirred at room temperature for 4 hours, after which it was poured into aqueous 1 N HCl (2 mL) and $CH_2Cl_2$ (3 mL). The aqueous phase was extracted with $CH_2Cl_2$ (3 mL), and the combined organic phases were washed with aqueous 1 N HCl (2 mL), saturated aqueous $NaHCO_3$ (2 mL), and saturated aqueous NaCl (2 mL), sequentially. The organic phase was dried over $Na_2SO_4$, filtered and concentrated. Preparative thin-layer chromatography ($SiO_2$, 10% MeOH/$CH_2Cl_2$) provided 4.2 mg (84%) of 140. $^1$H NMR (500 MHz, $CDCl_3$/$CD_3OD$=4/1) δ 7.51 (s, 4H), 3.97-3.93 (m, 2H), 3.69-3.60 (m, 6H), 3.20-3.00 (m, 12H), 1.48-1.34 (m, 8H), 1.29-1.16 (m, 104H), 0.83 (t, J=7.0 Hz, 12H). HRMS (ESI-TOF) m/z calcd for $C_{84}H_{153}N_6O_6$ [M+H]+ 1342.1845, found 1342.1834.

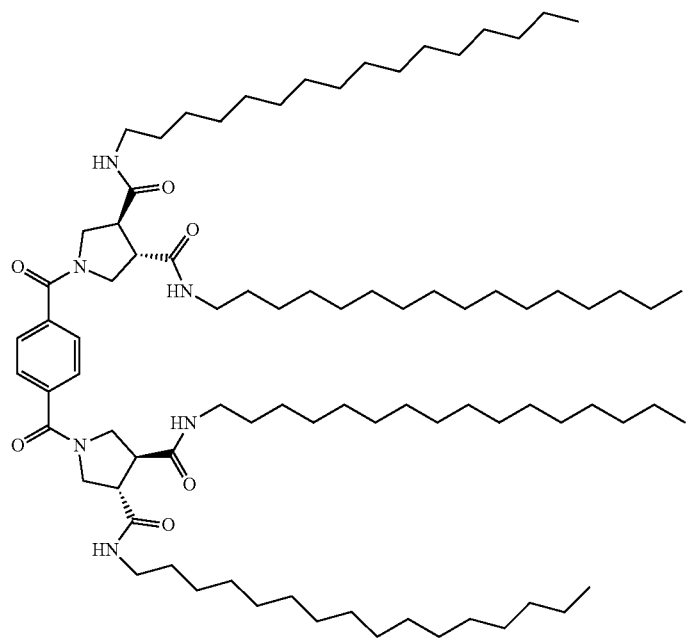 [SMILES: CCCCCCCCCCCCCCCCNC(=O)[C@@H]1CN(C(=O)c2ccc(C(=O)N3C[C@@H](C(=O)NCCCCCCCCCCCCCCCC)[C@H](C(=O)NCCCCCCCCCCCCCCCC)C3)cc2)C[C@H]1C(=O)NCCCCCCCCCCCCCCCC]

217

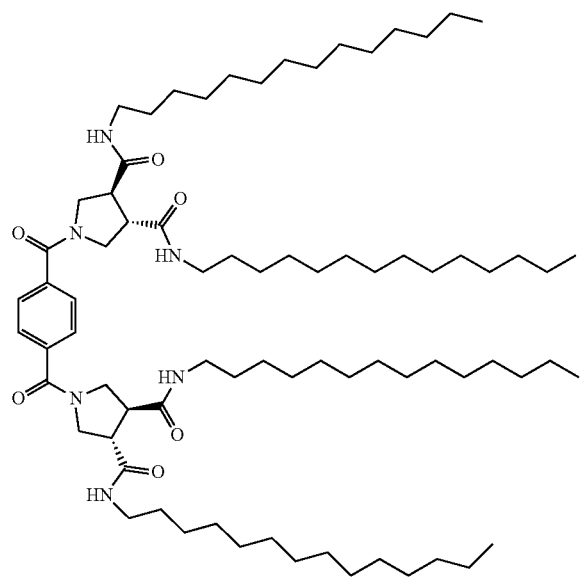 [SMILES: CCCCCCCCCCCCCCNC(=O)[C@@H]1CN(C(=O)c2ccc(C(=O)N3C[C@@H](C(=O)NCCCCCCCCCCCCCC)[C@H](C(=O)NCCCCCCCCCCCCCC)C3)cc2)C[C@H]1C(=O)NCCCCCCCCCCCCCC]

141: (3S,3'S,4S,4'S)-1,1'-Terephthaloylbis(N³,N⁴-ditetradecylpyrrolidine-3,4-dicarboxamide)

Terephthalic acid (benzene-1,4-dicarboxylic acid, 0.7 mg, 0.0041 mmol, 1.0 equiv), (3S,4S)—N³,N⁴-ditetradecylpyrrolidine-3,4-dicarboxamide hydrochloride (S-75, 5.2 mg, 0.0090 mmol, 2.2 equiv), HOAt (1.2 mg, 0.0090 mmol, 2.2 equiv), and 2,6-lutidine (2.2 mg, 0.020 mmol, 5.0 equiv) were dissolved in anhydrous DMF/CH$_2$Cl$_2$ (1/1, 0.2 mL). Upon dissolution of the reagents (about 5 minutes) at 0° C., EDCI*HCl (2.0 mg, 0.010 mmol, 2.5 equiv) was added in one portion at 0° C., and the reaction mixture was stirred at room temperature for 4 hours, after which it was poured into aqueous 1 N HCl (2 mL) and CH$_2$Cl$_2$ (3 mL). The aqueous phase was extracted with CH$_2$Cl$_2$ (3 mL), and the combined organic phases were washed with aqueous 1 N HCl (2 mL), saturated aqueous NaHCO$_3$ (2 mL), and saturated aqueous NaCl (2 mL), sequentially. The organic phase was dried over Na$_2$SO$_4$, filtered and concentrated. Preparative thin-layer chromatography (SiO$_2$, 10% MeOH/CH$_2$Cl$_2$) provided 4.5 mg (90%) of 141. $^1$H NMR (500 MHz, CDCl$_3$/CD$_3$OD=4/1) δ 7.52 (s, 4H), 4.00-3.93 (m, 2H), 3.72-3.60 (m, 6H), 3.22-3.01 (m, 12H), 1.49-1.35 (m, 8H), 1.30-1.17 (m, 88H), 0.84 (t, J=7.0 Hz, 12H). HRMS (ESI-TOF) m/z calcd for C$_{76}$H$_{137}$N$_6$O$_6$ [M+H]+ 1230.0594, found 1230.0590.

218

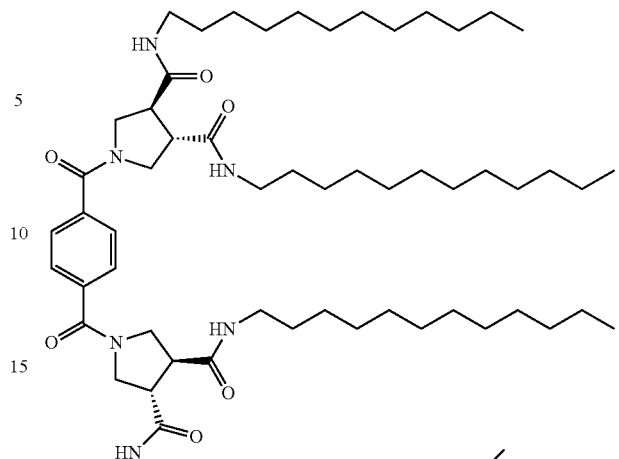

142: (3S,3'S,4S,4'S)-1,1'-Terephthaloylbis(N³,N⁴-didodecylpyrrolidine-3,4-dicarboxamide)

Terephthalic acid (benzene-1,4-dicarboxylic acid, 0.7 mg, 0.0045 mmol, 1.0 equiv), (3S,4S)—N³,N⁴-didodecylpyrrolidine-3,4-dicarboxamide hydrochloride (S-77, 5.2 mg, 0.0098 mmol, 2.2 equiv), HOAt (1.3 mg, 0.0098 mmol, 2.2 equiv), and 2,6-lutidine (2.4 mg, 0.022 mmol, 5.0 equiv) were dissolved in anhydrous DMF/CH$_2$Cl$_2$ (1/1, 0.2 mL). Upon dissolution of the reagents (about 5 minutes) at 0° C., EDCI.HCl (2.1 mg, 0.011 mmol, 2.5 equiv) was added in one portion at 0° C., and the reaction mixture was stirred at room temperature for 4 hours, after which it was poured into aqueous 1 N HCl (2 mL) and CH$_2$Cl$_2$ (3 mL). The aqueous phase was extracted with CH$_2$Cl$_2$ (3 mL), and the combined organic phases were washed with aqueous 1 N HCl (2 mL), saturated aqueous NaHCO$_3$ (2 mL), and saturated aqueous NaCl (2 mL), sequentially. The organic phase was dried over Na$_2$SO$_4$, filtered and concentrated. Preparative thin-layer chromatography (SiO$_2$, 10% MeOH/CH$_2$Cl$_2$) provided 3.9 mg (78%) of 142. $^1$H NMR (500 MHz, CDCl$_3$/CD$_3$OD=4/1) δ 7.51 (s, 4H), 3.99-3.93 (m, 2H), 3.70-3.60 (m, 6H), 3.20-3.01 (m, 12H), 1.48-1.35 (m, 8H), 1.29-1.16 (m, 72H), 0.832 (t, J=7.0 Hz, 6H), 0.827 (t, J=7.0 Hz, 6H). HRMS (ESI-TOF) m/z calcd for C$_{68}$H$_{121}$N$_6$O$_6$ [M+H]+ 1117.9342, found 1117.9342.

219

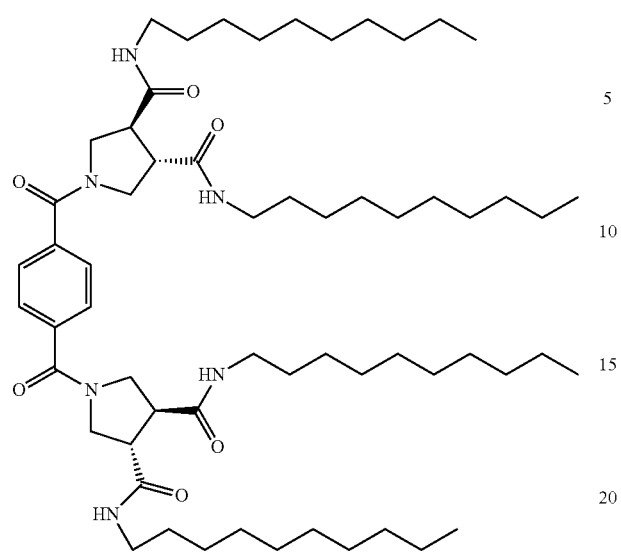

143: (3S,3'S,4S,4'S)-1,1'-Terephthaloylbis($N^3,N^4$-didecylpyrrolidine-3,4-dicarboxamide)

Terephthalic acid (benzene-1,4-dicarboxylic acid, 0.7 mg, 0.0040 mmol, 1.0 equiv), (3S,4S)—$N^3,N^4$-didecylpyrrolidine-3,4-dicarboxamide hydrochloride (S-79, 4.2 mg, 0.0088 mmol, 2.2 equiv), HOAt (1.2 mg, 0.0088 mmol, 2.2 equiv), and 2,6-lutidine (2.1 mg, 0.020 mmol, 5.0 equiv) were dissolved in anhydrous DMF/$CH_2Cl_2$ (1/2, 0.3 mL). Upon dissolution of the reagents (about 5 minutes) at 0° C., EDCI.HCl (1.9 mg, 0.010 mmol, 2.5 equiv) was added in one portion at 0° C., and the reaction mixture was stirred at room temperature for 4.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous $NaHCO_3$ (2 mL), and saturated aqueous NaCl (2 mL), sequentially. The organic phase was dried over $Na_2SO_4$, filtered and concentrated. Preparative thin-layer chromatography ($SiO_2$, 10% MeOH/$CH_2Cl_2$) provided 1.9 mg (48%) of 143. $^1$H NMR (500 μMHz, $CDCl_3$) δ 7.54 (s, 4H), 6.44 (br, 2H), 6.20 (br, 2H), 3.93 (dd, J=12.0, 8.5 Hz, 2H), 3.81-3.65 (m, 6H), 3.28-3.10 (m, 12H), 1.52-1.40 (m, 8H), 1.34-1.20 (m, 56H), 0.88 (t, J=7.0 Hz, 6H), 0.87 (t, J=7.0 Hz, 6H). HRMS (ESI-TOF) m/z calcd for $C_{60}H_{105}N_6O_6$ [M+H]$^+$ 1005.8090, found 1005.8107.

220

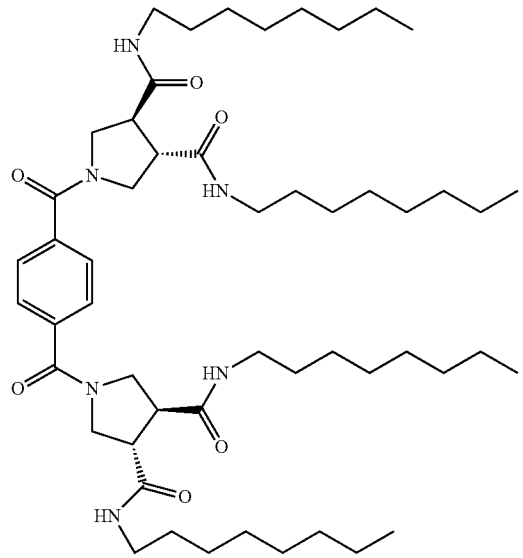 [SMILES: CCCCCCCCNC(=O)[C@@H]1CN(C(=O)c2ccc(C(=O)N3C[C@@H](C(=O)NCCCCCCCC)[C@H](C(=O)NCCCCCCCC)C3)cc2)C[C@H]1C(=O)NCCCCCCCC]

144: (3S,3'S,4S,4'S)-1,1'-Terephthaloylbis($N^3,N^4$-dioctylpyrrolidine-3,4-dicarboxamide)

Terephthalic acid (benzene-1,4-dicarboxylic acid, 0.8 mg, 0.0048 mmol, 1.0 equiv), (3S,4S)—$N^3,N^4$-dioctylpyrrolidine-3,4-dicarboxamide hydrochloride (S-81, 4.4 mg, 0.011 mmol, 2.2 equiv), HOAt (1.4 mg, 0.011 mmol, 2.2 equiv), and 2,6-lutidine (2.6 mg, 0.024 mmol, 5.0 equiv) were dissolved in anhydrous DMF/$CH_2Cl_2$ (1/2, 0.3 mL). Upon dissolution of the reagents (about 5 minutes) at 0° C., EDCI.HCl (2.3 mg, 0.012 mmol, 2.5 equiv) was added in one portion at 0° C., and the reaction mixture was stirred at room temperature for 4.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous $NaHCO_3$ (2 mL), and saturated aqueous NaCl (2 mL), sequentially. The organic phase was dried over $Na_2SO_4$, filtered and concentrated. Preparative thin-layer chromatography ($SiO_2$, 10% MeOH/$CH_2Cl_2$) provided 3.7 mg (93%) of 144. $^1$H NMR (500 μMHz, $CDCl_3$) δ 7.54 (s, 4H), 6.61 (br, 2H), 6.44 (br, 2H), 3.85 (dd, J=12.5, 9.0 Hz, 2H), 3.77 (t, J=11.0, 2H), 3.70 (d, J=9.0 Hz, 4H), 3.28-3.04 (m, 12H), 1.52-1.39 (m, 8H), 1.34-1.19 (m, 40H), 0.88 (t, J=7.0 Hz, 6H), 0.87 (t, J=7.0 Hz, 6H). HRMS (ESI-TOF) m/z calcd for $C_{52}H_{89}N_6O_6$ [M+H]$^+$ 893.6838, found 893.6826.

221

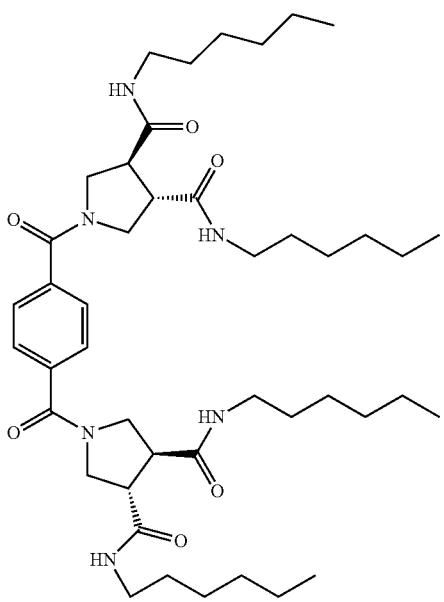 [SMILES: CCCCCCNC(=O)[C@@H]1CN(C(=O)c2ccc(C(=O)N3C[C@@H](C(=O)NCCCCCC)[C@H](C(=O)NCCCCCC)C3)cc2)C[C@H]1C(=O)NCCCCCC]

145: (3S,3'S,4S,4'S)-1,1'-Terephthaloylbis(N$^3$,N$^4$-dihexylpyrrolidine-3,4-dicarboxamide)

Terephthalic acid (benzene-1,4-dicarboxylic acid, 0.9 mg, 0.0051 mmol, 1.0 equiv), (3S,4S)—N$^3$,N$^4$-dihexylpyrrolidine-3,4-dicarboxamide hydrochloride (S-83, 4.1 mg, 0.011 mmol, 2.2 equiv), HOAt (1.5 mg, 0.011 mmol, 2.2 equiv), and 2,6-lutidine (2.7 mg, 0.026 mmol, 5.0 equiv) were dissolved in anhydrous DMF/CH$_2$Cl$_2$ (1/2, 0.3 mL). Upon dissolution of the reagents (about 5 minutes) at 0° C., EDCI.HCl (2.5 mg, 0.013 mmol, 2.5 equiv) was added in one portion at 0° C., and the reaction mixture was stirred at room temperature for 4.5 hours, after which it was poured into aqueous 1 N HCl (2 mL) and EtOAc (3 mL). The aqueous phase was extracted with EtOAc (3 mL), and the combined organic phases were washed with aqueous 1 N HCl (2 mL), saturated aqueous NaHCO$_3$ (2 mL), and saturated aqueous NaCl (2 mL), sequentially. The organic phase was dried over Na$_2$SO$_4$, filtered and concentrated. Preparative thin-layer chromatography (SiO$_2$, 10% MeOH/CH$_2$Cl$_2$) provided 4.0 mg (quant.) of 145. $^1$H NMR (500 µMHz, CDCl$_3$) δ 7.56 (br, 2H), 7.50 (br, 2H), 6.64 (br, 2H), 6.49 (br, 2H), 3.90-3.81 (m, 2H), 3.80-3.63 (m, 6H), 3.32-3.02 (m, 12H), 1.53-1.38 (m, 8H), 1.35-1.21 (m, 24H), 0.92-0.83 (m, 12H). HRMS (ESI-TOF) m/z calcd for C$_{44}$H$_{73}$N$_6$O$_6$ [M+H]$^+$ 781.5586, found 781.5588.

222

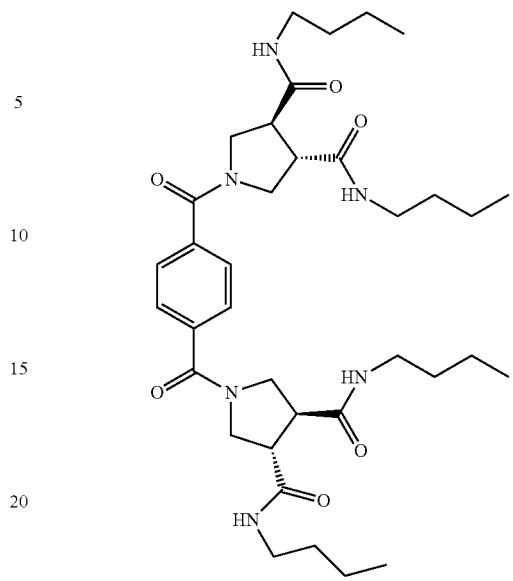

146: (3S,3'S,4S,4'S)-1,1'-Terephthaloylbis(N$^3$,N$^4$-dibutylpyrrolidine-3,4-dicarboxamide)

Terephthalic acid (benzene-1,4-dicarboxylic acid, 1.2 mg, 0.0075 mmol, 1.0 equiv), (3S,4S)—N$^3$,N$^4$-dibutylpyrrolidine-3,4-dicarboxamide hydrochloride (S-85, 5.0 mg, 0.017 mmol, 2.2 equiv), HOAt (2.2 mg, 0.017 mmol, 2.2 equiv), and 2,6-lutidine (4.0 mg, 0.037 mmol, 5.0 equiv) were dissolved in anhydrous DMF/CH$_2$Cl$_2$ (1/1, 0.2 mL). Upon dissolution of the reagents (about 5 minutes) at 0° C., EDCI.HCl (3.6 mg, 0.019 mmol, 2.5 equiv) was added in one portion at 0° C., and the reaction mixture was stirred at room temperature for 4 hours, after which it was poured into aqueous 1 N HCl (2 mL) and CH$_2$Cl$_2$ (3 mL). The aqueous phase was extracted with CH$_2$Cl$_2$ (3 mL), and the combined organic phases were washed with aqueous 1 N HCl (2 mL), saturated aqueous NaHCO$_3$ (2 mL), and saturated aqueous NaCl (2 mL), sequentially. The organic phase was dried over Na$_2$SO$_4$, filtered and concentrated. Preparative thin-layer chromatography (SiO$_2$, 10% MeOH/CH$_2$Cl$_2$) provided 2.6 mg (52%) of 146. $^1$H NMR (400 µMHz, CDCl$_3$) δ 7.54 (br, 4H), 6.64 (br, 2H), 6.49 (br, 2H), 3.88-3.64 (m, 8H), 3.33-3.01 (m, 12H), 1.52-1.39 (m, 8H), 1.38-1.23 (m, 16H), 0.92 (t, J=7.6 Hz, 6H), 0.89 (t, J=7.2 Hz, 6H). HRMS (ESI-TOF) m/z calcd for C$_{36}$H$_{57}$N$_6$O$_6$ [M+H]$^+$ 669.4334, found 669.4333.

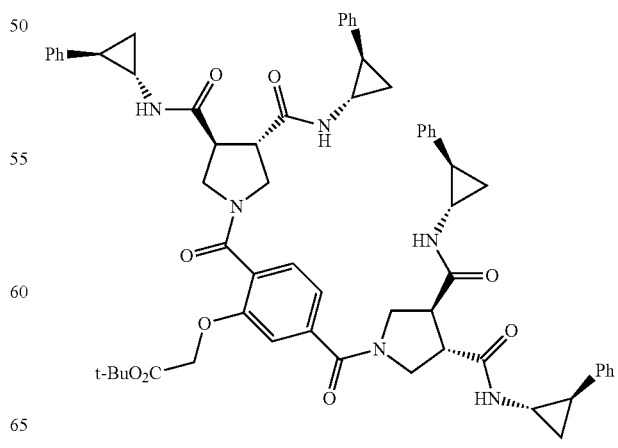

147: tert-Butyl 2-(2,5-Bis((3S,4S)-3,4-bis(((1S,2R)-2-phenylcyclopropyl) carbamoyl)-pyrrolidine-1-carbonyl)phenoxy)acetate (3S,3'S,4S,4'S)-1,1'-(2-hydroxy-terephthaloyl)bis($N^3,N^4$-bis((1S,2R)-2-phenylcyclopropyl)pyrrolidine-3,4-dicarboxamide) (53, 140 mg, 0.151 mmol) and $K_2CO_3$ (62.6 mg, 0.453 mmol) were dissolved in anhydrous DMF (1.5 mL) at room temperature. A solution of tert-butyl bromoacetate (3.7 mg, 0.0178 mmol) in anhydrous DMF (0.8 mL) was added dropwise, and the mixture was stirred for 3.5 hours. The mixture was poured into aqueous 1 N HCl (10 mL) and EtOAc (30 mL) at 0° C. The aqueous phase was extracted twice with EtOAc (10 mL), and the combined organic phases were washed with aqueous 1 N HCl (5 mL), saturated aqueous $NaHCO_3$ (5 mL) and saturated aqueous NaCl (5 mL). The organic phase was dried over $Na_2SO_4$, filtered and concentrated. Flash column chromatography ($SiO_2$, 5% $MeOH/CH_2Cl_2$) provided 152 mg (97%) of 147. $^1$H NMR (400 MHz, DMSO-$d_6$) δ 8.42 (d, J=5.6 Hz, 1H), 8.41 (d, J=5.6 Hz, 1H), 8.30 (d, J=4.4 Hz, 2H), 7.30-7.19 (m, 10H), 7.19-7.00 (m, 13H), 4.82 (d, J=16.8 Hz, 1H), 4.76 (d, J=16.4 Hz, 1H), 3.88-3.73 (m, 3H), 3.64 (t, J=9.2 Hz, 1H), 3.55-3.40 (m, 4H), 3.23-3.14 (m, 2H), 3.13-3.04 (m, 2H), 2.88-2.72 (m, 4H), 2.00-1.92 (m, 2H), 1.90-1.79 (m, 2H), 1.33 (s, 9H), 1.20-1.05 (m, 8H). HRMS (ESI-TOF) m/z calcd for $C_{63}H_{67}N_8O_{12}$ [M+H]$^+$ 1039.4964, found 1039.4964.

148: tert-Butyl 3-(2-(2-(2-(2,5-Bis((3S,4S)-3,4-bis(((1S,2R)-2-phenyl-cyclopropyl)carbamoyl)-pyrrolidine-1-carbonyl)-phenoxy)ethoxy)ethoxy)-ethoxy) propanoate (3S,3'S,4S,4'S)-1,1'-(2-hydroxy-terephthaloyl)bis($N^3,N^4$-bis((1S,2R)-2-phenyl-cyclopropyl)pyrrolidine-3,4-dicarboxamide) (53, 8.0 mg, 0.00865 mmol) and $K_2CO_3$ (3.6 mg, 0.0260 mmol) were dissolved in anhydrous DMF (100 μL) at room temperature. A solution of bromo-PEG3-tert-butyl ester (Broadpharm, 9380 Waples St., Suite 101, San Diego, Calif. 92121; 3.5 mg, 0.0104 mmol) in anhydrous DMF (100 L) was added. The mixture was warmed at 60° C. and stirred for 4 hours. After cooling to room temperature, the mixture was poured into aqueous 1 N HCl (3 mL) and EtOAc (5 mL). The aqueous phase was extracted with EtOAc (3 mL), and the combined organic phases were washed with aqueous 1 N HCl (3 mL), saturated aqueous $NaHCO_3$ (3 mL) and saturated aqueous NaCl (3 mL). The organic phase was dried over $Na_2SO_4$, filtered and concentrated. Preparative thin-layer chromatography ($SiO_2$, 8% $MeOH/CH_2Cl_2$) gave 6.0 mg (58%) of 148. $^1$H NMR (400 MHz, DMSO-$d_6$) δ 8.40 (d, J=11.6 Hz, 2H), 8.26 (d, J=11.6 Hz, 2H), 7.32-7.01 (m, 23H), 4.17 (br, 2H), 3.85-3.62 (m, 6H), 3.58-3.39 (m, 14H), 3.24-3.04 (m, 4H), 2.90-2.72 (m, 4H), 2.38 (br, 2H), 2.01-1.92 (m, 2H), 1.90-1.80 (m, 2H), 1.38 (s, 9H), 1.22-1.04 (m, 8H). HRMS (ESI-TOF) m/z calcd for $C_{69}H_{81}N_6O_{12}$ [M+H]$^+$ 1185.5907, found 1185.5908.

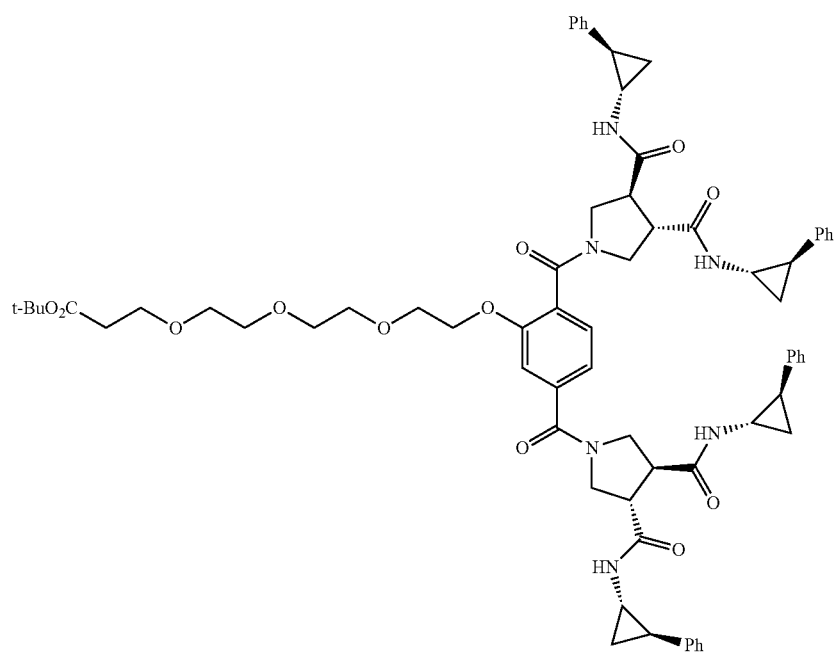

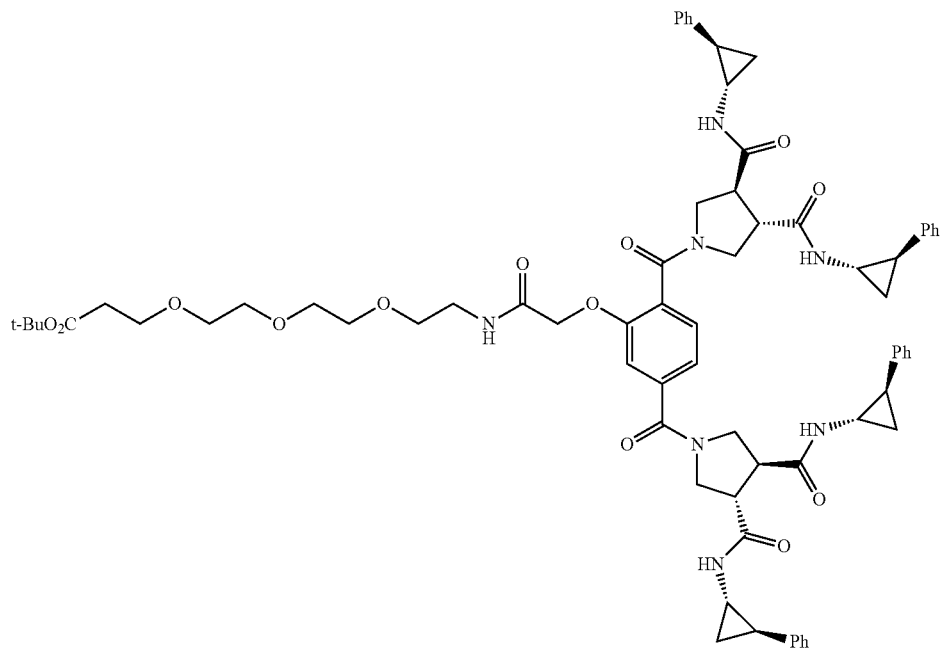

149: tert-Butyl 1-(2,5-Bis((3S,4S)-3,4-bis(((1S,2R)-2-phenylcyclopropyl)carbamoyl)pyrrolidine-1-carbonyl)phenoxy)-2-oxo-6,9,12-trioxa-3-azapentadecan-15-oate

(3S,3'S,4S,4'S)-1,1'-(2-hydroxy-terephthaloyl)bis(N³,N⁴-bis((1S,2R)-2-phenyl-cyclopropyl)pyrrolidine-3,4-dicarboxamide) (53, 8.8 mg, 0.0095 mmol) and bromoacetamido-PEG3-tert-butyl ester (Broadpharm, above; 4.5 mg, 0.0114 mmol) were dissolved in anhydrous DMF (150 μL) and the mixture was warmed at 60° C. K₂CO₃ (4.0 mg, 0.0285 mmol) was added, and the mixture was stirred for 16 hours. After cooling to room temperature, the mixture was diluted with EtOAc (5 mL) and washed with aqueous 0.5 N HCl (2×3.5 mL) and saturated aqueous NaCl (4 mL). The organic phase was dried over Na₂SO₄, decanted and concentrated. Preparative thin-layer chromatography (SiO₂, 10% MeOH/CH₂Cl₂) gave 7.3 mg (62%) of 149. ¹H NMR (400 MHz, DMSO-d₆) δ 8.41 (d, J=4.4 Hz, 2H), 8.28 (d, J=3.6 Hz, 1H), 8.25 (d, J=4.0 Hz, 1H), 8.06 (t, J=5.2 Hz, 1H), 7.35-7.02 (m, 23H), 4.66 (s, 2H), 3.79 (q, J=10.0 Hz, 2H), 3.68-3.40 (m, 16H), 3.39-3.28 (m, 2H), 3.27-3.14 (m, 4H), 3.13-3.04 (m, 2H), 2.89-2.73 (m, 4H), 2.39 (t, J=6.0 Hz, 2H), 2.00-1.93 (m, 2H), 1.91-1.82 (m, 2H), 1.38 (s, 9H), 1.21-1.05 (m, 8H). HRMS (ESI-TOF) m/z calcd for C₇₁H₈₄N₇O₁₃ [M+H]⁺ 1242.6121, found 1242.6125.

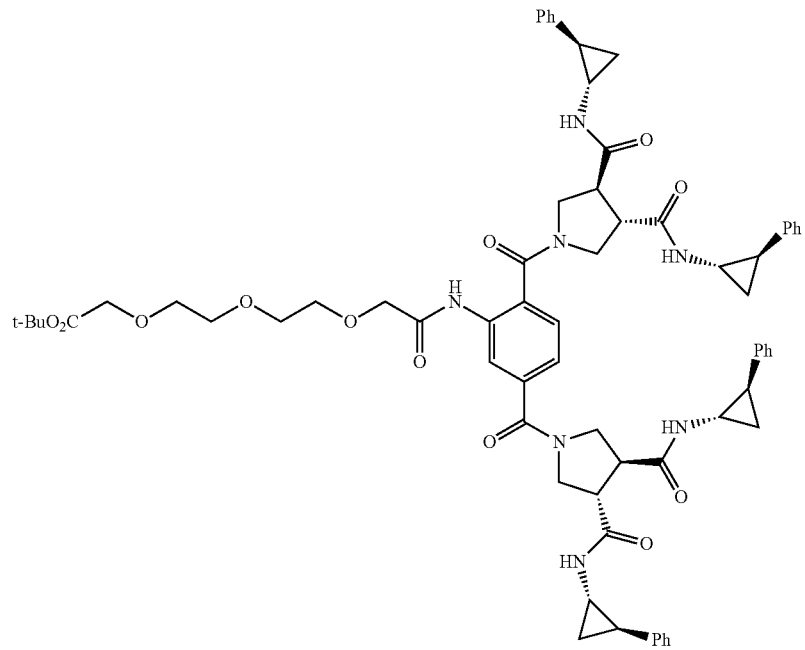

150: tert-Butyl 2-(2-(2-(2-((2,5-Bis((3S,4S)-3,4-bis(((1S,2R)-2-phenylcyclopropyl) carbamoyl)-pyrrolidine-1-carbonyl)phenyl)amino)-2-oxoethoxy)ethoxy)ethoxy)acetate (3S,3'S, 4S, 4'S)-1,1'-(2-Amino-terephthaloyl)bis($N^3,N^4$-bis((1S,2R)-2-phenyl-cyclopropyl)pyrrolidine-3,4-dicarboxamide) (55, 5.3 mg, 0.0057 mmol), and 13,13-dimethyl-11-oxo-3,6,9,12-tetraoxatetradecan-1-oic acid (1.6 mg, 0.0057 mmol) were dissolved in anhydrous DMF (100 µL) at room temperature. DEPBT (1.9 mg, 0.0063 mmol) and $Et_3N$ (1.6 µL, 0.0115 mmol) were added, and the mixture was stirred 16 hours. The mixture was diluted with EtOAc (10 mL) and washed with aqueous citric acid (5 mL, 10% w/v) and saturated aqueous $NaHCO_3$ (3 mL). The organic phase was dried over $Na_2SO_4$, decanted and concentrated. Preparative thin-layer chromatography ($SiO_2$, 10% MeOH/$CH_2Cl_2$) gave 2.9 mg (43%) of 150. $^1$H NMR (400 MHz, DMSO-$d_6$) δ 8.43 (d, J=3.6 Hz, 1H), 8.42 (d, J=4.0 Hz, 1H), 8.30 (d, J=4.8 Hz, 1H), 8.29 (d, J=4.8 Hz, 1H), 8.22 (s, 1H), 7.54 (d, J=8.0 Hz, 1H), 7.31-7.20 (m, 9H), 7.18-7.01 (m, 12H), 4.05 (br, 2H), 3.94 (s, 2H), 3.79 (t, J=10.4 Hz, 2H), 3.70-3.44 (m, 12H), 3.27-3.14 (m, 4H), 3.13-3.05 (m, 2H), 2.87-2.81 (m, 2H), 2.80-2.72 (m, 2H), 2.00-1.93 (m, 2H), 1.89-1.82 (m, 2H), 1.39 (s, 9H), 1.19-1.06 (m, 8H). HRMS (ESI-TOF) m/z calcd for $C_{68}H_{78}N_7O_{12}$ [M+H]$^+$ 1184.5703, found 1184.5722.

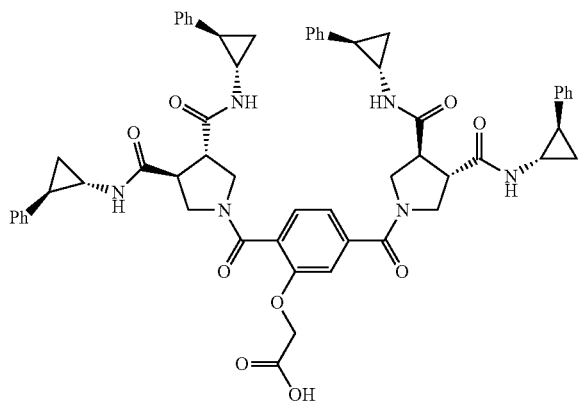 [SMILES: O=C(O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1]

S-86: 2-(2,5-Bis((3S,4S)-3,4-bis(((1S,2R)-2-phenylcyclopropyl)carbamoyl)pyrrolidine-1-carbonyl)phenoxy) acetic Acid tert-Butyl 2-(2,5-bis((3S,4S)-3,4-bis(((1S,2R)-2-phenylcyclopropyl)carbamoyl)-pyrrolidine-1-carbonyl)phenoxy) acetate (147, 142 mg, 0.137 mmol) was dissolved in $CH_2Cl_2$ (0.4 mL) at room temperature. TFA (0.4 mL) was added, and the mixture was stirred for 2 hours. The solvent was removed by $N_2$ stream. The residual solids were suspended in MeCN and condensed (repeat twice) to ensure complete removal of the TFA. This process was repeated with $CH_2Cl_2$. Flash column chromatography ($SiO_2$, 0.1% formic acid/10% MeOH/$CH_2Cl_2$) provided 146 mg (quant.) of S-86. $^1$H NMR (500 MHz, DMSO-$d_6$) δ 8.43 (d, J=4.5 Hz, 1H), 8.41 (d, J=4.0 Hz, 1H), 8.30 (d, J=4.5 Hz, 1H), 8.27 (d, J=4.0 Hz, 1H), 7.31-7.02 (m, 23H), 4.84 (d, J=17.0 Hz, 1H), 4.80 (d, J=16.5 Hz, 1H), 3.87-3.73 (m, 2H), 3.65 (dd, J=10.5, 7.5 Hz, 1H), 3.60-3.41 (m, 5H), 3.24-3.16 (m, 2H), 3.14-3.07 (m, 2H), 2.88-2.82 (m, 2H), 2.81-2.73 (m, 2H), 2.00-1.94 (m, 2H), 1.92-1.83 (m, 2H), 1.21-1.06 (m, 8H). $^{13}$C NMR (125 MHz, DMSO-$d_6$) δ 171.69, 171.53, 170.91, 169.86, 167.30, 165.41, 153.32, 141.35, 141.30, 141.29, 138.31, 128.22, 128.18, 127.98, 127.87, 125.87, 125.84, 125.65, 125.62, 119.74, 111.07, 64.67, 51.43, 50.02, 48.78, 48.26, 47.02, 46.63, 45.28, 45.11, 32.62, 32.60, 32.53, 32.51, 23.96, 23.95, 23.86, 15.41, 15.39, 15.30. HRMS (ESI-TOF) m/z calcd for $C_{58}H_{59}N_6O_9$ [M+H]$^+$ 983.4338, found 983.4339.

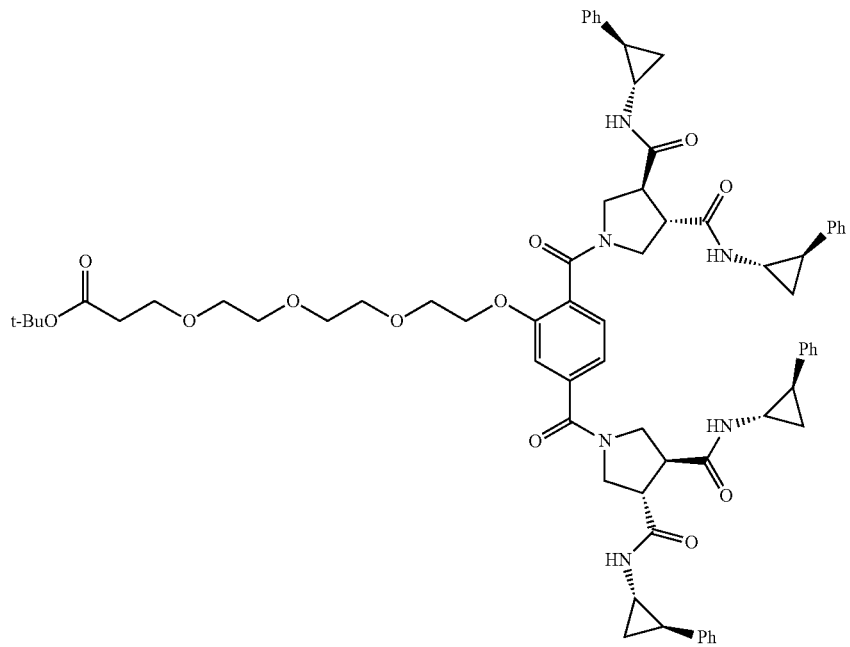 [SMILES: CC(C)(C)OC(=O)CCOCCOCCOCCOc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1]

148: tert-Butyl 3-(2-(2-(2-(2-(2,5-Bis((3S,4S)-3,4-bis(((1S,2R)-2-phenylcyclopropyl) carbamoyl)-yrrolidine-1-carbonyl)phenoxy)ethoxy)ethoxy)-thoxy)propanoate 3S,3'S, 4S, 4'S)-1,1'-(2-hydroxy-erephthaloyl)bis($N^3,N^4$-bis((1S,2R)-2-phenyl-yclopropyl)pyrrolidine-3,4-dicarboxamide) (53, 8.0 mg, 0.00865 mmol) and $K_2CO_3$ (3.6 mg, 0.0260 mmol) were dissolved in anhydrous DMF (100 µL) at room temperature. A solution of bromo-PEG3-tert-butyl ester (Broadpharm; 3.5 mg, 0.0104 mmol) in anhydrous DMF (100 µL) was added. The mixture was warmed at 60° C. and stirred for 4 hours. After cooling to room temperature, the mixture was poured into aqueous 1 N HCl (3 mL) and EtOAc (5 mL). The aqueous phase was extracted with EtOAc (3 mL), and the combined organic phases were washed with aqueous 1 N HCl (3 mL), saturated aqueous $NaHCO_3$ (3 mL) and saturated aqueous NaCl (3 mL). The organic phase was dried over $Na_2SO_4$, filtered and concentrated. Preparative thin-layer chromatography ($SiO_2$, 8% MeOH/$CH_2Cl_2$) gave 6.0 mg (58%) of 148. $^1$H NMR (400 MHz, DMSO-$d_6$) δ 8.40 (d, J=11.6 Hz, 2H), 8.26 (d, J=11.6 Hz, 2H), 7.32-7.01 (m, 23H), 4.17 (br, 2H), 3.85-3.62 (m, 6H), 3.58-3.39 (m, 14H), 3.24-3.04 (m, 4H), 2.90-2.72 (m, 4H), 2.38 (br, 2H), 2.01-1.92 (m, 2H), 1.90-1.80 (m, 2H), 1.38 (s, 9H), 1.22-1.04 (m, 8H). HRMS (ESI-TOF) m/z calcd for $C_{69}H_{81}N_6O_{12}$ [M+H]$^+$ 1185.5907, found 1185.5908.

149: tert-Butyl 1-(2,5-Bis((3S,4S)-3,4-bis(((1S,2R)-2-phenylcyclopropyl)carbamoyl)pyrrolidine-1-carbonyl)phenoxy)-2-oxo-6,9,12-trioxa-3-azapentadecan-15-oate (3S,3'S,4S,4'S)-1,1'-(2-Hydroxy-terephthaloyl)bis($N^3$,$N^4$-bis((1S,2R)-2-phenyl-cyclopropyl)pyrrolidine-3,4-dicarboxamide) (53, 8.8 mg, 0.0095 mmol) and bromoacetamido-PEG3-tert-butyl ester (Broadpharm; 4.5 mg, 0.0114 mmol) were dissolved in anhydrous DMF (150 µL) and the mixture was warmed at 60° C. $K_2CO_3$ (4.0 mg, 0.0285 mmol) was added, and the mixture was stirred for 16 hours. After cooling to room temperature, the mixture was diluted with EtOAc (5 mL) and washed with aqueous 0.5 N HCl (2×3.5 mL) and saturated aqueous NaCl (4 mL). The organic phase was dried over $Na_2SO_4$, decanted and concentrated. Preparative thin-layer chromatography ($SiO_2$, 10% MeOH/$CH_2Cl_2$) gave 7.3 mg (62%) of 149. $^1$H NMR (400 MHz, DMSO-$d_6$) δ 8.41 (d, J=4.4 Hz, 2H), 8.28 (d, J=3.6 Hz, 1H), 8.25 (d, J=4.0 Hz, 1H), 8.06 (t, J=5.2 Hz, 1H), 7.35-7.02 (m, 23H), 4.66 (s, 2H), 3.79 (q, J=10.0 Hz, 2H), 3.68-3.40 (m, 16H), 3.39-3.28 (m, 2H), 3.27-3.14 (m, 4H), 3.13-3.04 (m, 2H), 2.89-2.73 (m, 4H), 2.39 (t, J=6.0 Hz, 2H), 2.00-1.93 (m, 2H), 1.91-1.82 (m, 2H), 1.38 (s, 9H), 1.21-1.05 (m, 8H). HRMS (ESI-TOF) m/z calcd for $C_{71}H_{84}N_7O_{13}$ [M+H]$^+$ 1242.6121, found 1242.6125.

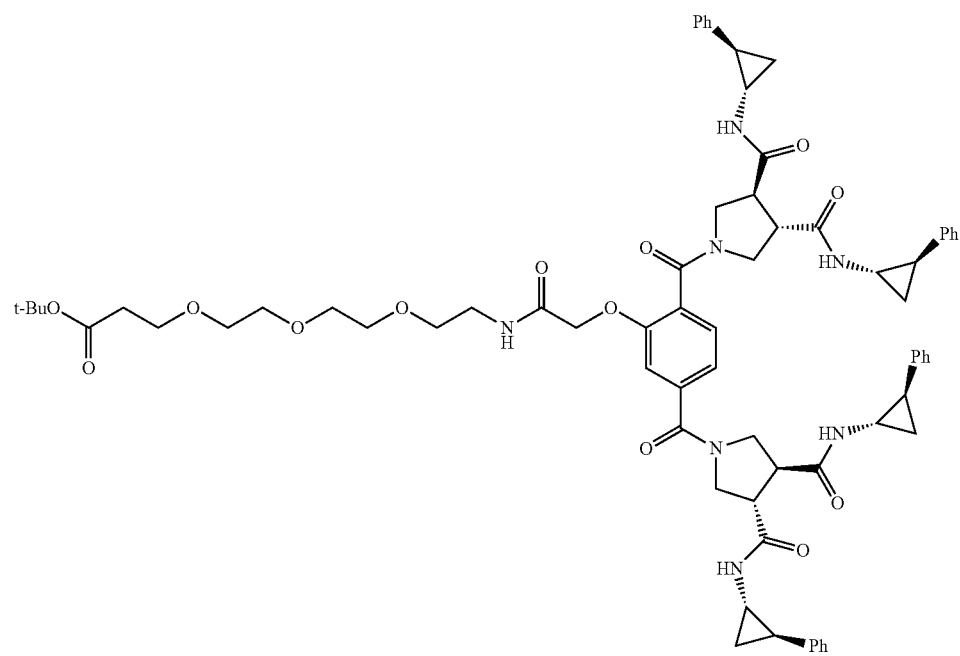 [SMILES: CC(C)(C)OC(=O)CCOCCOCCOCCNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1]

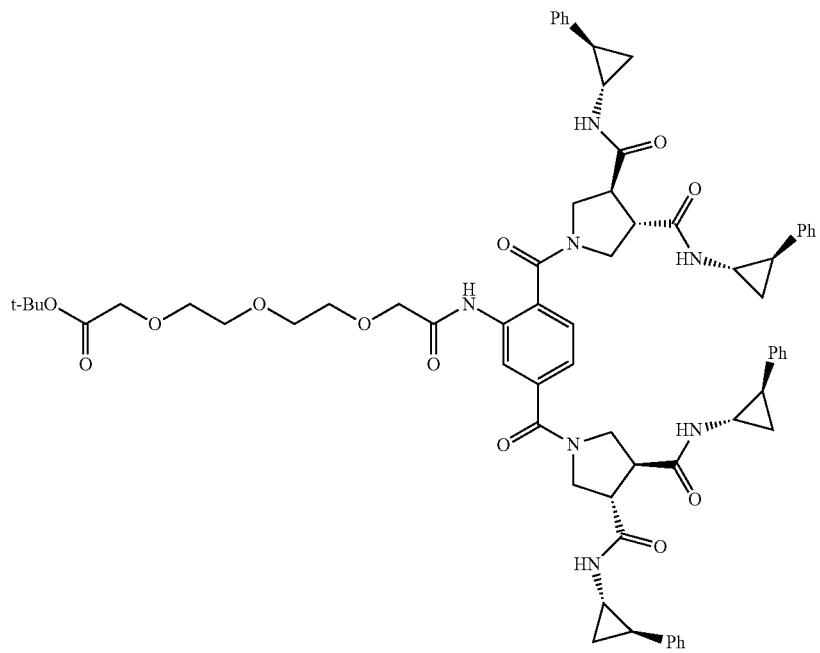 [SMILES: CC(C)(C)OC(=O)COCCOCCOCC(=O)Nc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1]

150: tert-Butyl 2-(2-(2-(2-((2,5-Bis((3S,4S)-3,4-bis(((1S,2R)-2-phenylcyclopropyl) carbamoyl)-pyrrolidine-1-carbonyl)phenyl)amino)-2-oxoethoxy)-ethoxy)ethoxy)acetate.

(3S,3'S, 4S, 4'S)-1,1'-(2-Amino-terephthaloyl)bis($N^3,N^4$-bis((1S,2R)-2-phenyl-cyclopropyl)pyrrolidine-3,4-dicarboxamide) (55, 5.3 mg, 0.0057 mmol), and 13,13-dimethyl-11-oxo-3,6,9,12-tetraoxatetradecan-1-oic acid (1.6 mg, 0.0057 mmol) were dissolved in anhydrous DMF (100 µL) at room temperature. DEPBT (1.9 mg, 0.0063 mmol) and Et$_3$N (1.6 µL, 0.0115 mmol) were added, and the mixture was stirred 16 hours. The mixture was diluted with EtOAc (10 mL) and washed with aqueous citric acid (5 mL, 10% w/v) and saturated aqueous NaHCO$_3$ (3 mL). The organic phase was dried over Na$_2$SO$_4$, decanted and concentrated. Preparative thin-layer chromatography (SiO$_2$, 10% MeOH/CH$_2$Cl$_2$) gave 2.9 mg (43%) of 150. $^1$H NMR (400 MHz, DMSO-d$_6$) δ 8.43 (d, J=3.6 Hz, 1H), 8.42 (d, J=4.0 Hz, 1H), 8.30 (d, J=4.8 Hz, 1H), 8.29 (d, J=4.8 Hz, 1H), 8.22 (s, 1H), 7.54 (d, J=8.0 Hz, 1H), 7.31-7.20 (m, 9H), 7.18-7.01 (m, 12H), 4.05 (br, 2H), 3.94 (s, 2H), 3.79 (t, J=10.4 Hz, 2H), 3.70-3.44 (m, 12H), 3.27-3.14 (m, 4H), 3.13-3.05 (m, 2H), 2.87-2.81 (m, 2H), 2.80-2.72 (m, 2H), 2.00-1.93 (m, 2H), 1.89-1.82 (m, 2H), 1.39 (s, 9H), 1.19-1.06 (m, 8H). HRMS (ESI-TOF) m/z calcd for C$_{68}$H$_{78}$N$_7$O$_{12}$ [M+H]$^+$ 1184.5703, found 1184.5722.

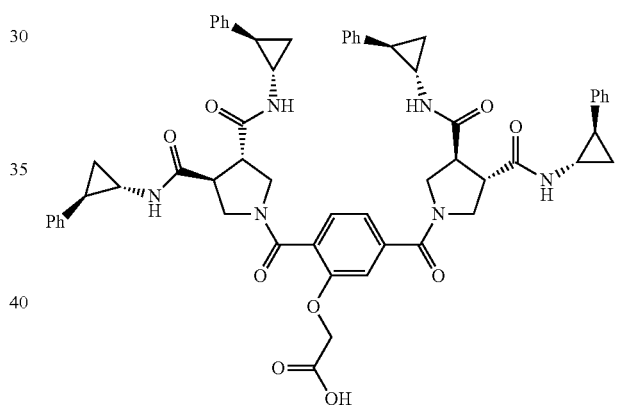

S-86:2-(2,5-Bis((3S,4S)-3,4-bis(((1S,2R)-2-phenyl-cyclopropyl)carbamoyl)pyrrolidine-1-carbonyl)phenoxy) acetic Acid tert-Butyl 2-(2,5-bis((3S,4S)-3,4-bis(((1S,2R)-2-phenyl-cyclopropyl)carbamoyl)-pyrrolidine-1-carbonyl)phenoxy) acetate (147, 142 mg, 0.137 mmol) was dissolved in CH$_2$Cl$_2$ (0.4 mL) at room temperature. TFA (0.4 mL) was added, and the mixture was stirred for 2 hours. The solvent was removed by N$_2$ stream. The residual solids were suspended in MeCN and condensed (repeat twice) to ensure complete removal of the TFA. This process was repeated with CH$_2$Cl$_2$. Flash column chromatography (SiO$_2$, 0.1% formic acid/10% MeOH/CH$_2$Cl$_2$) provided 146 mg (quant.) of S-86. $^1$H NMR (500 MHz, DMSO-d$_6$) δ 8.43 (d, J=4.5 Hz, 1H), 8.41 (d, J=4.0 Hz, 1H), 8.30 (d, J=4.5 Hz, 1H), 8.27 (d, J=4.0 Hz, 1H), 7.31-7.02 (m, 23H), 4.84 (d, J=17.0 Hz, 1H), 4.80 (d, J=16.5 Hz, 1H), 3.87-3.73 (m, 2H), 3.65 (dd, J=10.5, 7.5 Hz, 1H), 3.60-3.41 (m, 5H), 3.24-3.16 (m, 2H), 3.14-3.07 (m, 2H), 2.88-2.82 (m, 2H), 2.81-2.73 (m, 2H), 2.00-1.94 (m, 2H), 1.92-1.83 (m, 2H), 1.21-1.06 (m, 8H). $^{13}$C NMR (125 MHz, DMSO-d$_6$) δ 171.69, 171.53, 170.91, 169.86, 167.30, 165.41, 153.32, 141.35, 141.30, 141.29, 138.31, 128.22, 128.18, 127.98, 127.87, 125.87, 125.84, 125.65, 125.62, 119.74, 111.07, 64.67, 51.43, 50.02, 48.78, 48.26, 47.02, 46.63, 45.28, 45.11, 32.62, 32.60, 32.53, 32.51, 23.96, 23.95, 23.86, 15.41, 15.39, 15.30. HRMS (ESI-TOF) m/z calcd for C$_{58}$H$_{59}$N$_6$O$_9$ [M+H]$^+$ 983.4338, found 983.4339.

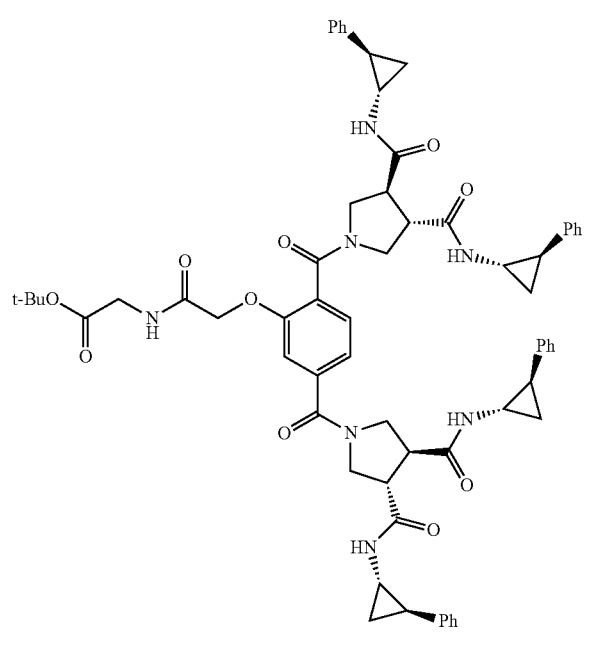 [SMILES: CC(C)(C)OC(=O)CNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1]

S-87: tert-Butyl (2-(2,5-Bis((3S,4S)-3,4-bis(((1S,2R)-2-phenylcyclopropyl) carbamoyl)-pyrrolidine-1-carbonyl)phenoxy)acetyl)glycinate 2-(2,5-Bis((3S,4S)-3,4-bis(((1S,2R)-2-phenylcyclopropyl)carbamoyl)pyrrolidine-1-carbonyl)-phenoxy)acetic acid (S-86, 150 mg, 0.153 mmol, 1.00 equiv), tert-butyl glycinate hydrochloride (51 mg, 0.306 mmol, 2.00 equiv), HOAt (31 mg, 0.320 mmol, 1.50 equiv), and 2,6-lutidine (89 μL, 0.765 mmol, 5.00 equiv) were dissolved in anhydrous DMF (0.8 mL). Upon dissolution of the reagents (about 5 minutes) at 0° C., EDCI.HCl (88 mg, 0.459 mmol, 3.00 equiv) was added in one portion at 0° C., and the reaction mixture was stirred at the same temperature for 30 minutes. The reaction mixture was warmed to room temperature, and stirred for 4 hours, after which it was poured into aqueous 1 N HCl (5 mL) and EtOAc (20 mL) at 0° C. The aqueous phase was extracted twice with EtOAc (8 mL), and the combined organic phases were washed with aqueous 1 N HCl (5 mL), saturated aqueous NaHCO$_3$ (5 mL), and saturated aqueous NaCl (5 mL), sequentially. The organic phase was dried over Na$_2$SO$_4$, filtered and concentrated. Flash column chromatography (SiO$_2$, 5% MeOH/CH$_2$Cl$_2$) provided 134 mg (80%) of S-87. $^1$H NMR (500 MHz, DMSO-d$_6$) δ 8.41 (d, J=4.0 Hz, 2H), 8.32 (t, J=6.0 Hz, 1H), 8.29 (d, J=4.5 Hz, 1H), 8.26 (d, J=4.5 Hz, 1H), 7.33 (d, J=7.5 Hz, 1H), 7.29-7.04 (m, 22H), 4.73 (d, J=15.5 Hz, 1H), 4.70 (d, J=15.0 Hz, 1H), 3.85-3.73 (m, 4H), 3.66 (dd, J=10.5, 7.5 Hz, 1H), 3.60-3.47 (m, 5H), 3.23-3.15 (m, 2H), 3.14-3.07 (m, 2H), 2.88-2.82 (m, 2H), 2.81-2.75 (m, 2H), 2.00-1.94 (m, 2H), 1.92-1.84 (m, 2H), 1.35 (s, 9H), 1.21-1.07 (m, 8H). $^{13}$C NMR (125 μMHz, DMSO-d$_6$) δ 171.81, 171.57, 171.16, 170.81, 168.51, 167.89, 167.12, 165.46, 153.39, 141.30, 141.25, 141.20, 138.58, 128.19, 128.14, 128.00, 127.82, 125.83, 125.78, 125.63, 125.62, 125.60, 120.26, 112.13, 80.74, 67.28, 51.43, 50.11, 48.77, 48.14, 47.00, 46.57, 45.20, 45.09, 41.14, 32.56, 32.51, 32.46, 27.66, 23.91, 23.88, 23.80, 15.37, 15.27. HRMS (ESI-TOF) m/z calcd for C$_{64}$H$_{70}$N$_7$O$_{10}$ [M+H]$^+$ 1096.5178, found 1096.5183.

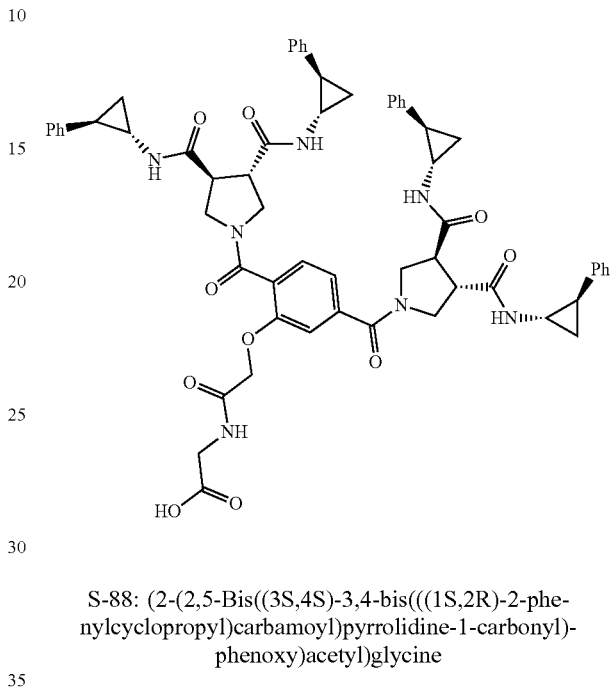

S-88: (2-(2,5-Bis((3S,4S)-3,4-bis(((1S,2R)-2-phenylcyclopropyl)carbamoyl)pyrrolidine-1-carbonyl)-phenoxy)acetyl)glycine tert-Butyl (2-(2,5-bis((3S,4S)-3,4-bis(((1S,2R)-2-phenylcyclopropyl)carbamoyl)-pyrrolidine-1-carbonyl)phenoxy)acetyl)glycinate (S-87, 134 mg, 0.122 mmol) was dissolved in CH$_2$Cl$_2$ (0.6 mL) at room temperature. TFA (0.6 mL) was added at 0° C., and the mixture was stirred for 2 hours at room temperature. The solvent was removed by N$_2$ stream. The residual solids were suspended in MeCN and condensed (repeat twice) to ensure complete removal of the TFA. This process was repeated with CH$_2$Cl$_2$. Flash column chromatography (SiO$_2$, 0.1% formic acid/10% MeOH/CH$_2$Cl$_2$) provided 125 mg (98%) of S-88. $^1$H NMR (500 MHz, DMSO-d$_6$) δ 8.42 (br, 2H), 8.30 (d, J=6.0 Hz, 1H), 8.29 (d, J=5.0 Hz, 1H), 8.26 (t, J=3.0 Hz, 1H), 7.32 (d, J=7.5 Hz, 1H), 7.28-7.03 (m, 22H), 4.72 (d, J=15.5 Hz, 1H), 4.69 (d, J=15.0 Hz, 1H), 3.88-3.75 (m, 4H), 3.65 (dd, J=10.5, 8.0 Hz, 1H), 3.59-3.46 (m, 4H), 3.32 (t, J=9.5 Hz, 1H), 3.23-3.15 (m, 2H), 3.13-3.06 (m, 2H), 2.87-2.81 (m, 2H), 2.80-2.74 (m, 2H), 2.00-1.93 (m, 2H), 1.91-1.84 (m, 2H), 1.21-1.06 (m, 8H). $^{13}$C NMR (125 μMHz, DMSO-d$_6$) δ 171.84, 171.62, 171.16, 170.87, 170.84, 167.84, 167.16, 165.46, 153.41, 141.33, 141.30, 141.25, 138.60, 128.21, 128.17, 128.00, 127.85, 125.84, 125.80, 125.64, 125.60, 120.23, 117.68, 117.68, 115.72, 112.11, 67.29, 51.45, 50.11, 48.76, 48.12, 47.03, 46.64, 45.22, 45.11, 40.48, 32.59, 32.54, 32.48, 23.92, 23.87, 23.81, 15.46, 15.38, 15.31. HRMS (ESI-TOF) m/z calcd for C$_{60}$H$_{62}$N$_7$O$_{10}$ [M+H]$^+$ 1040.4552 found 1040.4550.

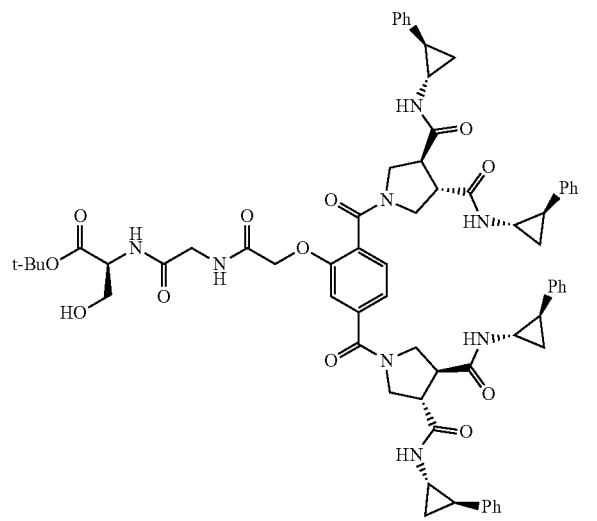 [SMILES: CC(C)(C)OC(=O)[C@H](CO)NC(=O)CNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1]
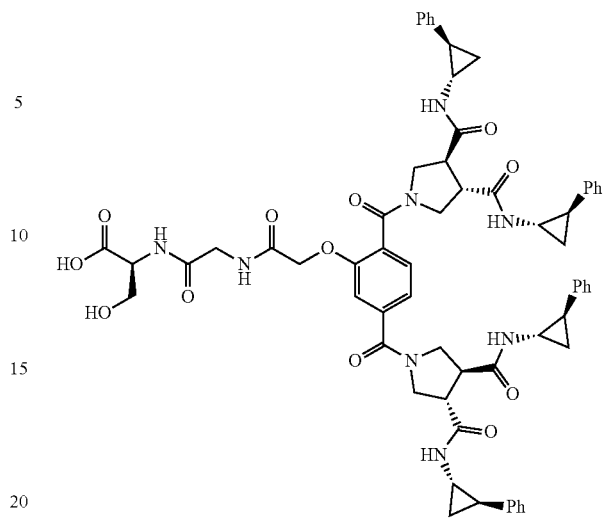

S-89 (YM1-98-1): tert-Butyl (2-(2,5-Bis((3S,4S)-3,4-bis(((1S,2R)-2-phenylcyclopropyl) carbamoyl)-pyrrolidine-1-carbonyl)phenoxy)acetyl)glycyl-L-serinate (2-(2,5-Bis((3S,4S)-3,4-bis(((1S,2R)-2-phenylcyclopropyl)carbamoyl)pyrrolidine-1-carbonyl)phenoxy)acetyl)glycine (S-88, 15.1 mg, 0.0145 mmol, 1.00 equiv), tert-butyl L-serinate hydrochloride (3.4 mg, 0.0174 mmol, 1.20 equiv), HOAt (2.2 mg, 0.0160 mmol, 1.10 equiv), and 2,6-lutidine (4.7 mg, 0.0435 mmol, 3.00 equiv) were dissolved in anhydrous DMF (0.1 mL). Upon dissolution of the reagents (about 5 minutes) at room temperature, EDCI.HCl (4.2 mg, 0.0218 mmol, 1.50 equiv) was added in one portion, and the reaction mixture was for 2.5 hours, after which it was poured into aqueous 1 N HCl (2 mL) and EtOAc (5 mL) at 0° C. The aqueous phase was extracted with EtOAc (2 mL), and the combined organic phases were washed with aqueous 1 N HCl (1 mL), saturated aqueous NaHCO$_3$ (1 mL), and saturated aqueous NaCl (1 mL), sequentially. The organic phase was dried over Na$_2$SO$_4$, filtered and concentrated. Preparative thin-layer chromatography (SiO$_2$, 10% MeOH/CH$_2$Cl$_2$) gave 13.6 mg (79%) of S-89. $^1$H NMR (400 MHz, DMSO-d$_6$) δ 8.41 (br, 1H), 8.37 (br, 1H), 8.28 (br, 1H), 8.25 (br, 1H), 8.18 (br, 1H), 8.14 (d, J=8.0 Hz, 1H), 7.34-7.01 (m, 23H), 4.99 (br, 1H), 4.70 (s, 2H), 4.25 (br, 1H), 3.92-3.74 (m, 4H), 3.70-3.45 (m, 8H), 3.23-3.14 (m, 2H), 3.13-3.05 (m, 2H), 2.88-2.74 (m, 4H), 2.00-1.92 (m, 2H), 1.91-1.82 (m, 2H), 1.38 (s, 9H), 1.20-1.05 (m, 8H). HRMS (ESI-TOF) m/z calcd for C$_{67}$H$_{75}$N$_8$O$_{12}$ [M+H]$^+$ 1183.5499, found 1183.5478.

151: (2-(2,5-Bis((3S,4S)-3,4-bis(((1S,2R)-2-phenylcyclopropyl)carbamoyl)pyrrolidine-1-carbonyl)phenoxy)acetyl)glycyl-L-serine tert-Butyl (2-(2,5-bis((3S,4S)-3,4-bis(((1S,2R)-2-phenylcyclopropyl)carbamoyl)-pyrrolidine-1-carbonyl)phenoxy)acetyl)glycyl-L-serinate (S-89, 11.0 mg, 0.00930 mmol) was dissolved in CH$_2$Cl$_2$ (0.1 mL) at room temperature. TFA (0.1 mL) was added, and the mixture was stirred for 2 hours. The solvent was removed by N$_2$ stream. The residual solids were suspended in MeCN and condensed (repeat twice) to ensure complete removal of the TFA. This process was repeated with CH$_2$Cl$_2$. Preparative thin-layer chromatography (SiO$_2$, 10% MeOH/CH$_2$Cl$_2$) gave 11.8 mg (quant.) of 151. [α]$^{22}_D$ 48.21 (c=0.92, MeOH). IR (neat) v$_{max}$ 3282, 1650, 1551, 1442, 1197, 1137, 696 cm$^{-1}$. $^1$H NMR (500 MHz, DMSO-d$_6$) δ 8.44 (d, J=4.5 Hz, 1H), 8.41 (d, J=4.5 Hz, 1H), 8.31 (d, J=4.5 Hz, 1H), 8.29 (d, J=4.0 Hz, 1H), 8.21-8.15 (m, 2H), 8.09 (d, J=6.0 Hz, 1H), 7.31 (d, J=7.5 Hz, 1H), 7.28-7.03 (m, 22H), 4.70 (s, 2H), 4.28 (dt, J=7.5, 5.0 Hz, 1H), 3.88-3.74 (m, 4H), 3.73-3.26 (m, 8H), 3.23-3.15 (m, 2H), 3.14-3.06 (m, 2H), 2.88-2.81 (m, 2H), 2.80-2.74 (m, 2H), 2.00-1.94 (m, 2H), 1.91-1.84 (m, 2H), 1.21-1.06 (m, 8H). $^{13}$C NMR (125 MHz, DMSO-d$_6$) δ 172.05 171.70, 171.65, 171.01, 171.89, 168.34, 167.63, 167.20, 165.47, 153.50, 141.35, 141.28, 138.60, 128.22, 128.18, 127.99, 127.82, 125.87, 125.84, 125.81, 125.65, 125.61, 120.15, 118.25, 116.26, 112.07, 67.32, 61.45, 54.68, 51.45, 50.16, 48.75, 48.17, 47.05, 46.69, 45.30, 45.10, 41.61, 32.62, 32.56, 32.52, 23.93, 23.91, 23.83, 23.80, 15.44, 15.39, 15.33. HRMS (ESI-TOF) m/z calcd for C$_{63}$H$_{67}$N$_8$O$_{12}$ [M+H]$^+$ 1127.4873, found 1127.4871.

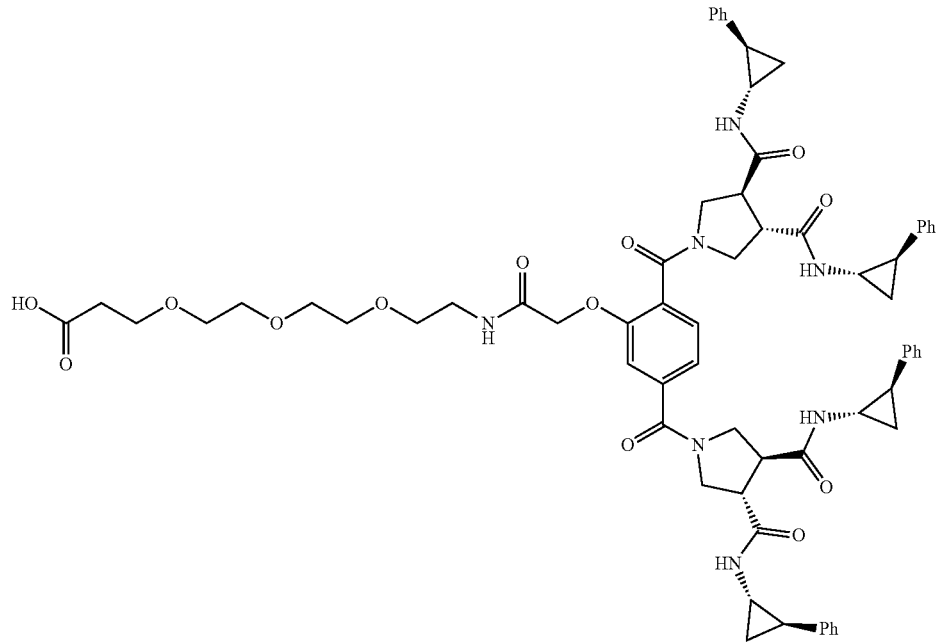 [SMILES: O=C(O)CCOCCOCCOCCNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1]

152: 1-(2,5-Bis((3S,4S)-3,4-bis(((1S,2R)-2-phenyl-cyclopropyl)carbamoyl)pyrrolidine-1-carbonyl)-phenoxy)-2-oxo-6,9,12-trioxa-3-azapentadecan-15-oic Acid tert-Butyl 1-(2,5-bis((3S,4S)-3,4-bis(((1S,2R)-2-phenyl-cyclopropyl)carbamoyl)-pyrrolidine-1-carbonyl)phenoxy)-2-oxo-6,9,12-trioxa-3-azapentadecan-15-oate (149, 13.3 mg, 0.0107 mmol) was dissolved in $CH_2Cl_2$ (0.2 mL) at room temperature. TFA (0.2 mL) was added, and the mixture was stirred for 1 hour at room temperature. The solvent was removed by $N_2$ stream. The residual solids were suspended in MeCN and condensed (repeat twice) to ensure complete removal of the TFA. This process was repeated with $CH_2Cl_2$. Flash column chromatography ($SiO_2$, 0.1% formic acid/10% MeOH/$CH_2Cl_2$) provided 12.5 mg (98%) of 152. $^1$H NMR (500 MHz, DMSO-$d_6$) δ 8.50 (br, 1H), 8.46 (br, 1H), 8.36 (br, 2H), 8.09 (t, J=5.5 Hz, 1H), 7.31 (d, J=8.0 Hz, 1H), 7.28-7.04 (m, 22H), 4.66 (s, 2H), 3.81-3.74 (m, 2H), 3.64 (dd, J=10.5, 8.0 Hz, 1H), 3.60-3.55 (m, 3H), 3.54-3.40 (m, 10H), 3.38-3.28 (m, 4H), 3.26-3.16 (m, 4H), 3.13-3.06 (m, 2H), 2.87-2.82 (m, 2H), 2.81-2.75 (m, 2H), 2.38 (t, J=6.5 Hz, 2H), 1.97 (ddd, J=9.5, 6.0, 3.5 Hz, 2H), 1.90-1.85 (m, 2H), 1.21-1.07 (m, 8H). HRMS (ESI-TOF) m/z calcd for $C_{67}H_{76}N_7O_{13}$ [M+H]$^+$ 1186.5495, found 1186.5497.

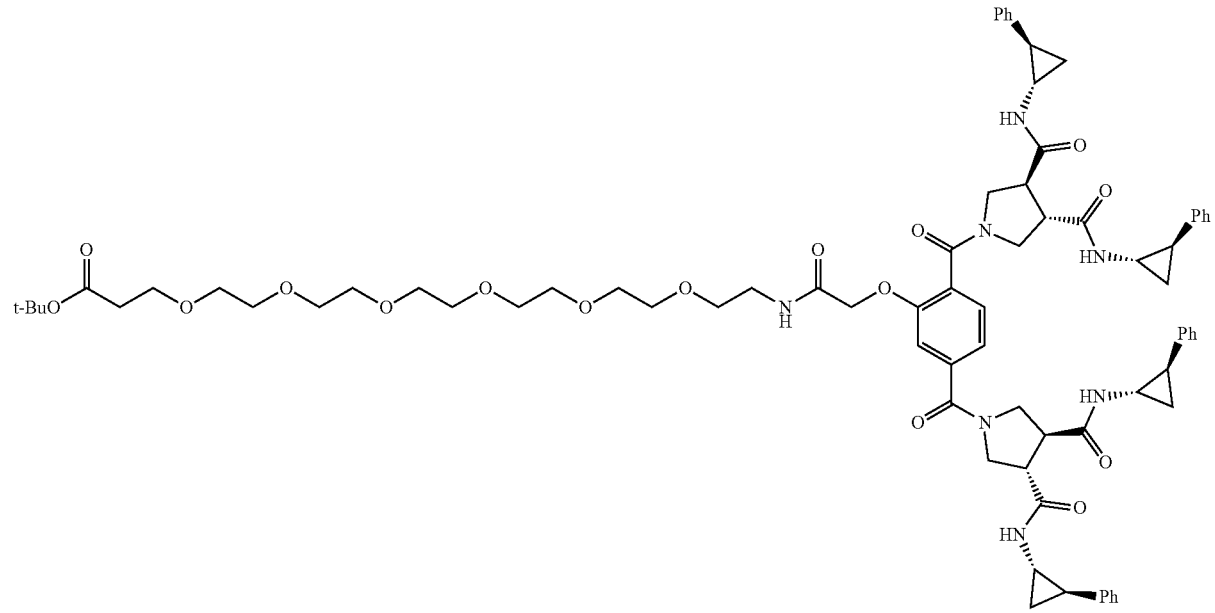 [SMILES: CC(C)(C)OC(=O)CCOCCOCCOCCOCCOCCOCCNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1]

153: tert-Butyl 1-(2,5-Bis((3S,4S)-3,4-bis(((1S,2R)-2-phenylcyclopropyl)carbamoyl)-pyrrolidine-1-carbonyl)phenoxy)-2-oxo-6,9,12,15,18,21-hexaoxa-3-azatetracosan-24-oate 2-(2,5-Bis((3S,4S)-3,4-bis(((1S,2R)-2-phenylcyclopropyl)carbamoyl)pyrrolidine-1-carbonyl)-phenoxy)acetic acid (S-86, 15 mg, 0.0153 mmol, 1.00 equiv), tert-butyl 1-amino-3,6,9,12,15,18-hexaoxahenicosan-21-oate (9.4 mg, 0.0230 mmol, 1.50 equiv), DMAP (trace amount), and i-Pr$_3$NEt (4.0 mg, 0.0306 mmol, 2.00 equiv) were dissolved in anhydrous DMF (0.1 mL). Upon dissolution of the reagents (ca. 5 min), EDCI.HCl (5.9 mg, 0.0306 mmol, 2.00 equiv) was added in one portion at room temperature, and the reaction mixture was stirred for 20 hours. HOAt (2.3 mg, 0.0168 mmol, 1.10 equiv), 2,6-lutidine (1 drop) and EDCI.HCl (5.9 mg, 0.0306 mmol, 2.00 equiv) was added. The reaction mixture was stirred for 4 hours, after which it was poured into aqueous 1 N HCl (1 mL) and EtOAc (4 mL). The aqueous phase was extracted twice with EtOAc (2 mL), and the combined organic phases were washed with aqueous 1 N HCl (1 mL), saturated aqueous NaHCO$_3$ (1 mL), and saturated aqueous NaCl (1 mL), sequentially. The organic phase was dried over Na$_2$SO$_4$, filtered and concentrated. Flash column chromatography (SiO$_2$, 6% MeOH/CH$_2$Cl$_2$) provided 9.3 mg (44%) of 153. $^1$H NMR (500 MHz, DMSO-d$_6$) δ 8.40 (d, J=4.5 Hz, 2H), 8.28 (d, J=4.5 Hz, 1H), 8.25 (d, J=4.5 Hz, 1H), 8.05 (t, J=5.5 Hz, 1H), 7.32 (d, J=8.0 Hz, 1H), 7.28-7.20 (m, 9H), 7.18-7.04 (m, 13H), 4.66 (s, 2H), 3.79 (td, J=12.0, 9.0 Hz, 2H), 3.66-3.55 (m, 5H), 3.54-3.41 (m, 23H), 3.39-3.28 (m, 2H), 3.27-3.15 (m, 4H), 3.13-3.05 (m, 2H), 2.87-2.81 (m, 2H), 2.80-2.74 (m, 2H), 2.40 (t, J=6.0 Hz, 2H), 1.99-1.94 (m, 2H), 1.90-1.84 (m, 2H), 1.38 (s, 9H), 1.20-1.07 (m, 8H). HRMS (ESI-TOF) m/z calcd for C$_{77}$H$_{96}$N$_7$O$_{16}$ [M+H]$^+$ 1374.6908, found 1374.6936.

154: 1-(2,5-Bis((3S,4S)-3,4-bis(((1S,2R)-2-phenylcyclopropyl)carbamoyl)pyrrolidine-1-carbonyl)-phenoxy)-2-oxo-6,9,12,15,18,21-hexaoxa-3-azatetracosan-24-oic Acid tert-Butyl 1-(2,5-bis((3S,4S)-3,4-bis(((1S,2R)-2-phenylcyclopropyl)carbamoyl)-pyrrolidine-1-carbonyl)phenoxy)-2-oxo-6,9,12,15,18,21-hexaoxa-3-azatetracosan-24-oate (153, 7.5 mg, 0.00546 mmol) was dissolved in CH$_2$Cl$_2$ (0.1 mL) at room temperature. TFA (0.1 mL) was added, and the mixture was stirred for 1 hour at room temperature. The solvent was removed by N$_2$ stream. The residual solids were suspended in MeCN and condensed (repeat twice) to ensure complete removal of the TFA. This process was repeated with CH$_2$Cl$_2$. Preparative thin-layer chromatography (SiO$_2$, 10% MeOH/CH$_2$Cl$_2$) provided 6.7 mg (93%) of 154. $^1$H NMR (500 MHz, DMSO-d$_6$) δ 8.47 (br, 1H), 8.44 (br, 1H), 8.32 (br, 2H), 8.07 (t, J=6.0 Hz, 1H), 7.31 (d, J=8.0 Hz, 1H), 7.28-7.04 (m, 22H), 4.65 (s, 2H), 3.81-3.74 (m, 2H), 3.66-3.55 (m, 4H), 3.54-3.41 (m, 24H), 3.38-3.35 (m, 2H), 3.26-3.16 (m, 4H), 3.13-3.06 (m, 2H), 2.87-2.82 (m, 2H), 2.80-2.75 (m, 2H), 2.41 (t, J=6.5 Hz, 2H), 1.99-1.94 (m, 2H), 1.90-1.85 (m, 2H), 1.20-1.07 (m, 8H). HRMS (ESI-TOF) m/z calcd for C$_{73}$H$_{88}$N$_7$O$_{16}$ [M+H]$^+$ 1318.6282, found 1318.6287.

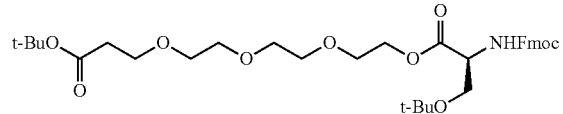

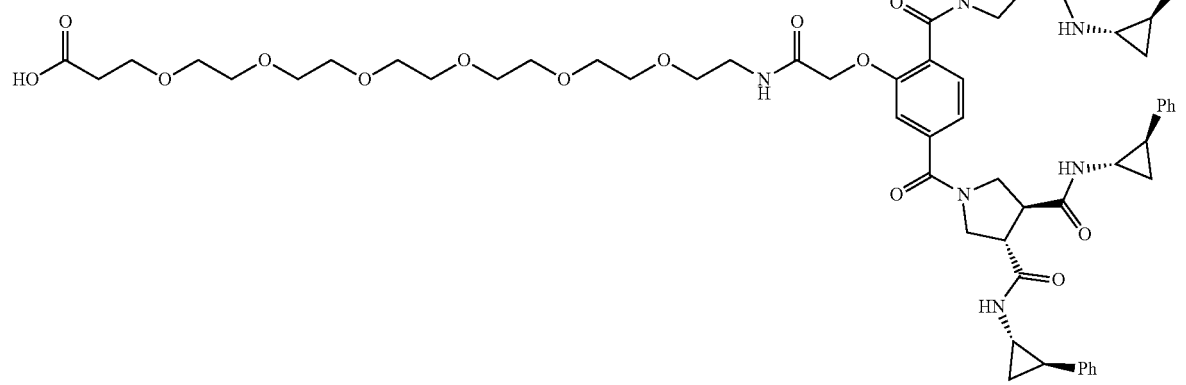

14,14-Dimethyl-12-oxo-3,6,9,13-tetraoxapentadecyl N-(((9H-Fluoren-9-yl)methoxy) carbonyl)-O-(tert-butyl)-L-serinate tert-Butyl 3-(2-(2-(2-hydroxyethoxy)-ethoxy)ethoxy)propanoate [Broadpharm, 9380 Waples St., Suite 101, San Diego, Calif. 92121] (50 mg, 0.180 mmol, 1.00 equiv), N-(((9H-fluoren-9-yl)methoxy)-carbonyl)-O-(tert-butyl)-L-serine (69 mg, 0.180 mmol, 1.00 equiv) and DMAP (22 mg, 0.180 mmol, 1.00 equiv) were dissolved in $CH_2Cl_2$ (0.9 mL). Upon dissolution of the reagents (about 5 minutes), EDCI.HCl (52 mg, 0.270 mmol, 1.50 equiv) was added in one portion at room temperature, and the reaction mixture was stirred for 17.5 hours, after which it was poured into aqueous 1 N HCl (3 mL) and EtOAc (15 mL). The aqueous phase was extracted twice with EtOAc (5 mL), and the combined organic phases were washed with aqueous 1 N HCl (2 mL), saturated aqueous $NaHCO_3$ (2 mL), and saturated aqueous NaCl (2 mL), sequentially. The organic phase was dried over $Na_2SO_4$, filtered and concentrated. Flash column chromatography ($SiO_2$, 5% $MeOH/CH_2Cl_2$) provided 95.7 mg (83%) of the title compound as a colorless oil. $^1H$ NMR (500 MHz, DMSO-$d_6$) δ 7.76 (d, J=7.5 Hz, 2H), 7.63 (d, J=7.5 Hz, 1H), 7.62 (d, J=7.5 Hz, 1H), 7.40 (t, J=7.5 Hz, 2H), 7.32 (t, J=7.5 Hz, 2H), 5.68 (d, J=8.5 Hz, 1H), 4.54-4.49 (m, 1H), 4.43-4.21 (m, 5H), 3.85 (br, 1H), 3.74-3.57 (m, 13H), 2.49 (t, J=6.5 Hz, 2H), 1.44 (s, 9H), 1.16 (s, 9H)

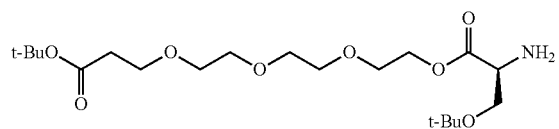 [SMILES: CC(C)(C)OC[C@H](N)C(=O)OCCOCCOCCOCCC(=O)OC(C)(C)C]

14,14-Dimethyl-12-oxo-3,6,9,13-tetraoxapentadecyl O-(tert-Butyl)-L-serinate 14,14-Dimethyl-12-oxo-3,6,9,13-tetraoxa-pentadecyl N-(((9H-fluoren-9-yl)methoxy)-carbonyl)-O-(tert-butyl)-L-serinate (40.7 mg, 0.0632 mmol) was dissolved in $CH_2Cl_2$ (0.3 mL) at room temperature. $Et_2NH$ (0.3 mL) was added, and the mixture was stirred for 3 hours at room temperature. The solvent was removed by $N_2$ stream. The residual solids were suspended in $CH_2Cl_2$ and condensed (repeat twice) to ensure complete removal of the $Et_2NH$. Flash column chromatography ($SiO_2$, 4% $MeOH/CH_2Cl_2$) provided 14.7 mg (55%) of the title compound as a colorless amorphous. $^1H$ NMR (500 MHz, DMSO-$d_6$) δ 4.31-4.23 (m, 2H), 3.74-3.56 (m, 15H), 2.49 (t, J=6.5 Hz, 2H), 1.43 (s, 9H), 1.15 (s, 9H).

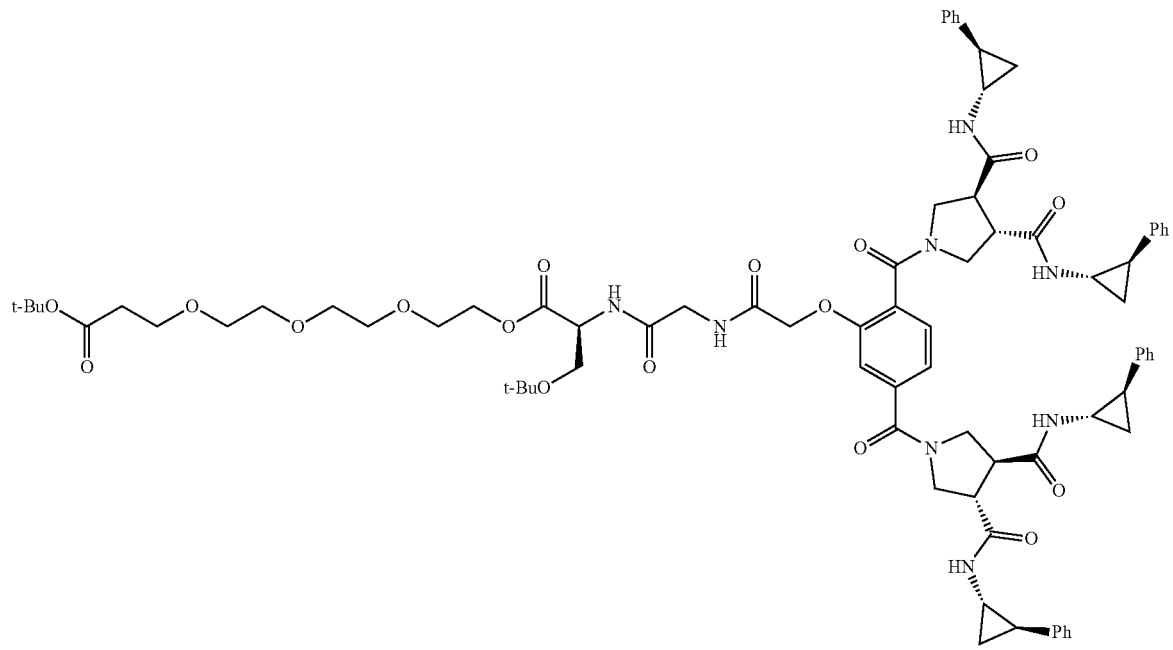 [SMILES: CC(C)(C)OC[C@H](NC(=O)CNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1)C(=O)OCCOCCOCCOCCC(=O)OC(C)(C)C]

155: 14,14-Dimethyl-12-oxo-3,6,9,13-tetraoxapentadecyl N-((2-(2,5-Bis((3S,4S)-3,4-bis(((1S,2R)-2-phenylcyclopropyl)carbamoyl)pyrrolidine-1-carbonyl)-phenoxy)acetyl)glycyl)-O-(tert-butyl)-L-serinate (2-(2,5-Bis((3S,4S)-3,4-bis(((1S,2R)-2-phenylcyclopropyl)carbamoyl)pyrrolidine-1-carbonyl)-phenoxy)acetyl) glycine (S-88, 8.0 mg, 0.00769 mmol, 1.00 equiv), 14,14-dimethyl-12-oxo-3,6,9,13-tetraoxa-pentadecyl O-(tert-butyl)-L-serinate (4.8 mg, 0.0115 mmol, 1.50 equiv), HOAt (1.3 mg, 0.00923 mmol, 1.20 equiv), and 2,6-lutidine (2.5 mg, 0.0231 mmol, 3.00 equiv) were dissolved in anhydrous DMF (0.1 mL). Upon dissolution of the reagents (about 5 minutes) at 0° C., EDCI.HCl (3.0 mg, 0.0154 mmol, 2.00 equiv) was added in one portion, and the reaction mixture was stirred for 3.5 hours at room temperature, after which it was poured into aqueous 1 N HCl (1 mL) and EtOAc (3 mL) at 0° C. The aqueous phase was extracted twice with EtOAc (2 mL), and the combined organic phases were washed with aqueous 1 N HCl (1 mL), saturated aqueous NaHCO$_3$ (1 mL), and saturated aqueous NaCl (1 mL), sequentially. The organic phase was dried over Na$_2$SO$_4$, filtered and concentrated. Preparative thin-layer chromatography (SiO$_2$, 10% MeOH/CH$_2$Cl$_2$) gave 6.1 mg (55%) of 155 as a colorless solid. $^1$H NMR (500 MHz, DMSO-d$_6$) δ 8.40 (d, J=4.5 Hz, 1H), 8.37 (d, J=4.5 Hz, 1H), 8.24 (d, J=8.0 Hz, 1H), 8.23 (d, J=4.5 Hz, 1H), 8.18 (t, J=6.0 Hz, 1H), 7.32 (d, J=7.5 Hz, 1H), 7.28-7.20 (m, 8H), 7.19-7.10 (m, 10H), 7.08-7.04 (m, 4H), 4.69 (s, 2H), 4.47 (dt, J=8.0, 4.5 Hz, 1H), 4.20-4.07 (m, 2H), 3.88 (d, J=6.0 Hz, 2H), 3.87-3.75 (m, 2H), 3.68-3.54 (m, 7H), 3.53-3.45 (m, 12H), 3.22-3.15 (m, 3H), 3.13-3.06 (m, 2H), 2.87-2.81 (m, 2H), 2.80-2.74 (m, 2H), 2.40 (t, J=6.5 Hz, 2H), 1.96 (ddd, J=9.5, 7.0, 3.5 Hz, 2H), 1.90-1.83 (m, 2H), 1.38 (s, 9H), 1.19-1.13 (m, 4H), 1.12-1.05 (m, 4H), 1.08 (s, 9H). HRMS (ESI-TOF) m/z calcd for C$_{80}$H$_{99}$N$_8$O$_{17}$ [M+H]$^+$ 1443.7122, found 1443.7099.

156: (S)-1-(2,5-Bis((3S,4S)-3,4-bis(((1S,2R)-2-phenylcyclopropyl)carbamoyl)pyrrolidine-1-carbonyl)-phenoxy)-7-(hydroxymethyl)-2,5,8-trioxo-9,12,15,18-tetraoxa-3,6-diazahenicosan-21-oic Acid 14,14-Dimethyl-12-oxo-3,6,9,13-tetraoxapentadecyl N-((2-(2,5-bis((3S,4S)-3,4-bis(((1S,2R)-2-phenylcyclopropyl)carbamoyl)-pyrrolidine-1-carbonyl)phenoxy)acetyl) glycyl)-O-(tert-butyl)-L-serinate (155, 3.1 mg, 0.00215 mmol) was dissolved in CH$_2$Cl$_2$ (0.1 mL) at room temperature. TFA (0.1 mL) was added at 0° C., and the mixture was stirred for 2 hours at room temperature. The solvent was removed by N$_2$ stream. The residual solids were suspended in MeCN and condensed (repeat twice) to ensure complete removal of the TFA. This process was repeated with CH$_2$Cl$_2$. Preparative thin-layer chromatography (SiO$_2$, 15% MeOH/CH$_2$Cl$_2$) gave 2.4 mg (83%) of 156 as a colorless solid. 1H NMR (500 MHz, DMSO-d$_6$) δ 8.42 (d, J=4.5 Hz, 1H), 8.40 (d, J=4.0 Hz, 1H), 8.38 (br, 1H), 8.29 (d, J=4.5 Hz, 1H), 8.27 (d, J=4.0 Hz, 1H), 8.26 (br, 1H), 7.31 (d, J=7.5 Hz, 1H), 7.28-7.20 (m, 8H), 7.18-7.10 (m, 10H), 7.08-7.04 (m, 4H), 4.70 (s, 2H), 4.37 (dt, J=7.0, 5.0 Hz, 1H), 4.18-4.10 (m, 2H), 3.86 (d, J=5.5 Hz, 2H), 3.85-3.75 (m, 2H), 3.72-3.45 (m, 19H), 3.23-3.15 (m, 3H), 3.13-3.06 (q, J=8.5 Hz, 2H), 2.87-2.81 (m, 2H), 2.80-2.74 (m, 2H), 2.40 (t, J=7.0 Hz, 2H), 1.97 (ddd, J=9.5, 6.5, 3.5 Hz, 2H), 1.90-1.84 (m, 2H), 1.20-1.06 (m, 8H). HRMS (ESI-TOF) m/z calcd for C$_{72}$H$_{83}$N$_8$O$_{17}$[M+H]+ 1331.5870, found 1331.5871.

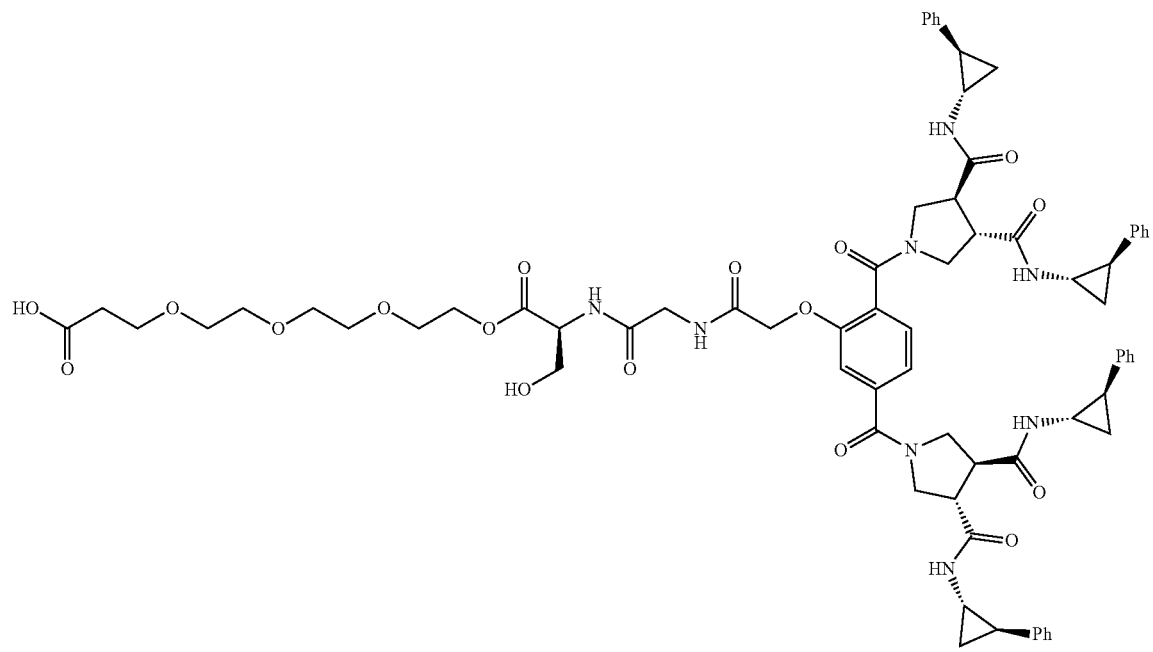 [SMILES: O=C(O)CCOCCOCCOCCOC(=O)[C@H](CO)NC(=O)CNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1]

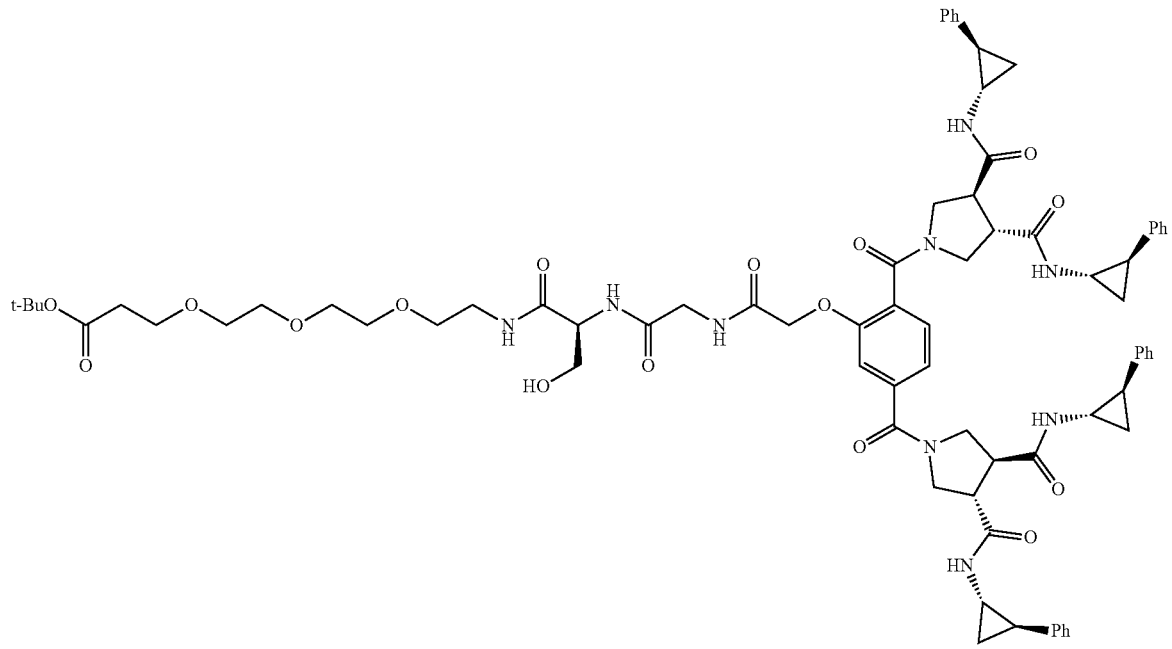 [SMILES: CC(C)(C)OC(=O)CCOCCOCCOCCNC(=O)[C@H](CO)NC(=O)CNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1]

157: tert-Butyl (S)-1-(2,5-Bis((3S,4S)-3,4-bis-(((1S, 2R)-2-phenylcyclopropyl)carbamoyl)pyrrolidine-1-carbonyl)phenoxy)-7-(hydroxymethyl)-2,5,8-trioxo-12,15,18-trioxa-3,6,9-triazahenicosan-21-oate (2-(2,5-Bis((3S,4S)-3,4-bis(((1S,2R)-2-phenylcyclopropyl)carbamoyl)pyrrolidine-1-carbonyl)-phenoxy)acetyl)glycyl-L-serine (151, 8.0 mg, 0.00710 mmol, 1.00 equiv), tert-butyl 3-(2-(2-(2-aminoethoxy)ethoxy)ethoxy)propanoate [Broadpharm, 9380 Waples St., Suite 101, San Diego, Calif. 92121] (2.4 mg, 0.00852 mmol, 1.20 equiv), HOAt (1.1 mg, 0.00781 mmol, 1.10 equiv), and 2,6-lutidine (2.3 mg, 0.0213 mmol, 3.00 equiv) were dissolved in anhydrous DMF (0.1 mL). Upon dissolution of the reagents (about 5 minutes) at 0° C., EDCI.HCl (2.1 mg, 0.0107 mmol, 1.50 equiv) was added in one portion, and the reaction mixture was stirred for 4.5 hours at room temperature, after which it was poured into aqueous 1 N HCl (1 mL) and $CH_2Cl_2$ (3 mL) at 0° C. The aqueous phase was extracted twice with $CH_2Cl_2$ (2 mL), and the combined organic phases were washed with aqueous 1 N HCl (1 mL), saturated aqueous $NaHCO_3$ (1 mL), and saturated aqueous NaCl (1 mL), sequentially. The organic phase was dried over $Na_2SO_4$, filtered and concentrated. Preparative thin-layer chromatography ($SiO_2$, 10% $MeOH/CH_2Cl_2$) gave 4.4 mg (45%) of 157 as a colorless solid. $^1H$ NMR (400 MHz, DMSO-$d_6$) δ 8.41 (d, J=4.4 Hz, 1H), 8.37 (d, J=4.4 Hz, 1H), 8.28 (d, J=4.4 Hz, 1H), 8.25 (d, J=4.4 Hz, 1H), 8.17 (t, J=5.2 Hz, 1H), 8.04 (d, J=8.0 Hz, 1H), 7.90 (t, J=6.0 Hz, 1H), 7.32 (d, J=7.6 Hz, 1H), 7.29-7.03 (m, 22H), 4.87 (t, J=5.6 Hz, 1H), 4.70 (s, 2H), 4.28 (dt, J=7.6, 5.6 Hz, 1H), 3.92-3.75 (m, 4H), 3.68-3.44 (m, 17H), 3.41-3.34 (m, 3H), 3.23-3.14 (m, 4H), 3.13-3.05 (m, 2H), 2.88-2.81 (m, 2H), 2.81-2.73 (m, 2H), 2.40 (t, J=6.4 Hz, 2H), 2.00-1.93 (m, 2H), 1.91-1.83 (m, 2H), 1.38 (s, 9H), 1.21-1.06 (m, 8H). HRMS (ESI-TOF) m/z calcd for $C_{76}H_{92}N_9O_{16}$ $[M+H]^+$ 1386.6656, found 1386.6654.

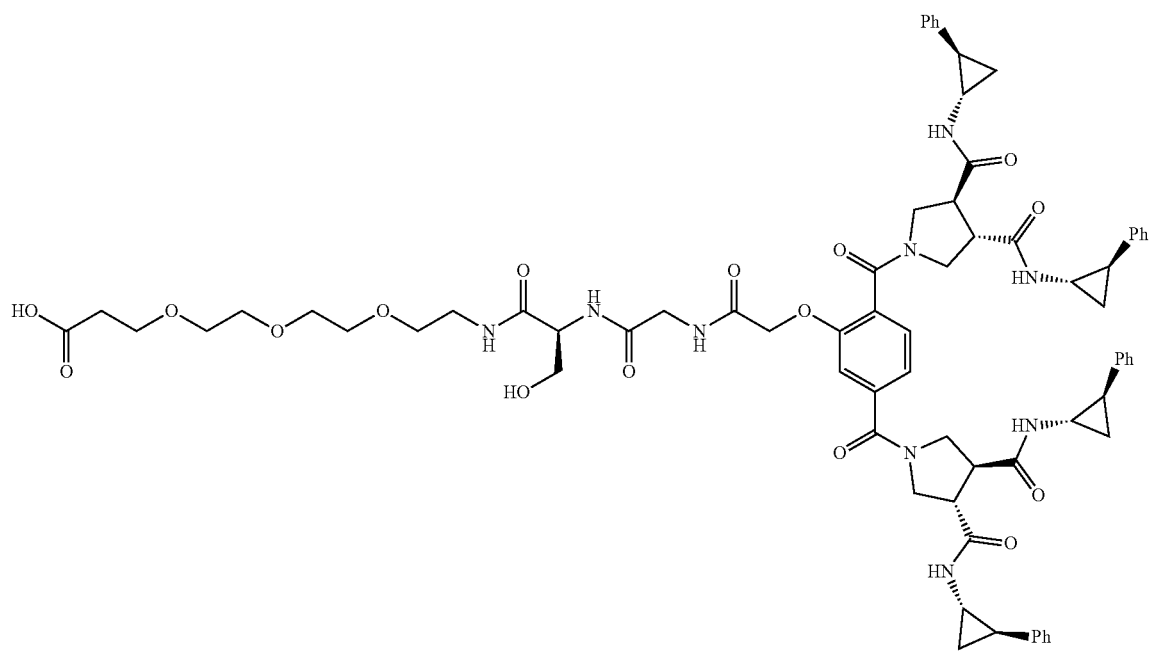 [SMILES: O=C(O)CCOCCOCCOCCNC(=O)[C@H](CO)NC(=O)CNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1]

158: (S)-1-(2,5-Bis((3S,4S)-3,4-bis(((1S,2R)-2-phenylcyclopropyl)carbamoyl)pyrrolidine-1-carbonyl)-phenoxy)-7-(hydroxymethyl)-2,5,8-trioxo-12,15,18-trioxa-3,6,9-triazahenicosan-21-oic Acid tert-Butyl (S)-1-(2,5-bis((3S,4S)-3,4-bis(((1S,2R)-2-phenylcyclopropyl)carbamoyl)-pyrrolidine-1-carbonyl)phenoxy)-7-(hydroxymethyl)-2,5,8-trioxo-12,15,18-trioxa-3,6,9-triazahenicosan-21-oate (157, 2.2 mg, 0.00158 mmol) was dissolved in CH$_2$Cl$_2$ (0.1 mL) at room temperature. TFA (0.1 mL) was added at 0° C., and the mixture was stirred for 2 hours at room temperature. The solvent was removed by N$_2$ stream. The residual solids were suspended in MeCN and condensed (repeat twice) to ensure complete removal of the TFA. This process was repeated with CH$_2$Cl$_2$. Preparative thin-layer chromatography (SiO$_2$, 12% MeOH/CH$_2$Cl$_2$) gave 1.7 mg (81%) of 158 as a colorless solid. $^1$H NMR (500 MHz, DMSO-d$_6$) δ 8.43 (d, J=4.0 Hz, 1H), 8.42 (d, J=5.0 Hz, 1H), 8.34-8.27 (m, 4H), 7.91 (t, J=6.0 Hz, 1H), 7.31 (d, J=7.5 Hz, 1H), 7.28-7.03 (m, 22H), 4.70 (s, 2H), 4.26 (dt, J=7.5, 5.5 Hz, 1H), 3.91-3.75 (m, 4H), 3.67-3.44 (m, 17H), 3.41-3.36 (m, 3H), 3.24-3.15 (m, 4H), 3.13-3.07 (m, 2H), 2.87-2.82 (m, 2H), 2.80-2.74 (m, 2H), 2.37 (t, J=6.5 Hz, 2H), 2.00-1.94 (m, 2H), 1.91-1.84 (m, 2H), 1.21-1.07 (m, 8H)

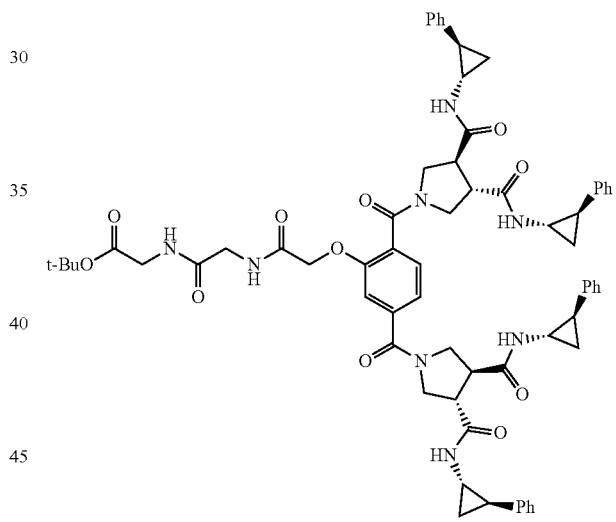

tert-Butyl (2-(2,5-Bis((3S,4S)-3,4-bis(((1S,2R)-2-phenylcyclopropyl)carbamoyl)pyrrolidine-1-carbonyl)-phenoxy)acetyl)glycylglycinate (2,5-Bis((3S,4S)-3,4-bis(((1S,2R)-2-phenylcyclopropyl)carbamoyl)pyrrolidine-1-carbonyl)-phenoxy)acetyl)glycine (S-88, 23.0 mg, 0.0221 mmol, 1.00 equiv), tert-butyl glycinate hydrochloride (5.6 mg, 0.0332 mmol, 1.50 equiv), HOAt (3.6 mg, 0.0265 mmol, 1.20 equiv), and 2,6-lutidine (9.5 mg, 0.0884 mmol, 4.00 equiv) were dissolved in anhydrous DMF (0.11 mL). Upon dissolution of the reagents (about 5 minutes) at 0° C., EDCI.HCl (8.5 mg, 0.0442 mmol, 2.00 equiv) was added in one portion, and the reaction mixture was stirred for 3 hours at room temperature, after which it was poured into aqueous 1 N HCl (2 mL) and CH$_2$Cl$_2$ (5 mL). The aqueous phase was extracted with CH$_2$Cl$_2$ (2 mL), and the combined organic phases were washed with aqueous 1 N HCl (1 mL), saturated aqueous NaHCO$_3$ (1 mL), and saturated aqueous NaCl (1 mL), sequentially. The organic phase was dried over Na$_2$SO$_4$, filtered and concentrated. Preparative thin-layer chromatography (SiO$_2$, 10% MeOH/CH$_2$Cl$_2$) gave 19.3 mg (76%) of the title compound as a colorless solid.

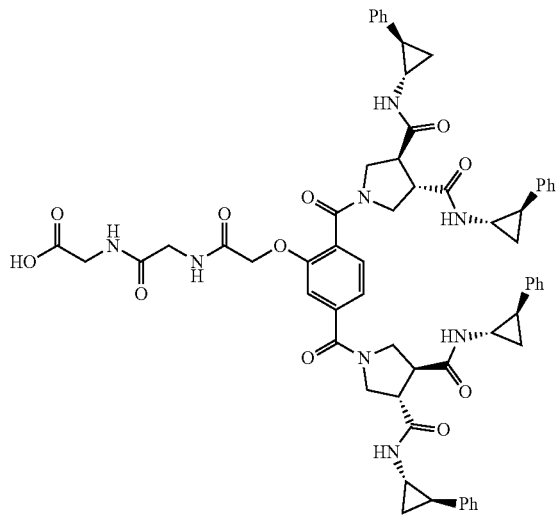 [SMILES: O=C(O)CNC(=O)CNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1]

159: (2-(2,5-Bis((3S,4S)-3,4-bis(((1S,2R)-2-phenylcyclopropyl)carbamoyl)pyrrolidine-1-carbonyl)phenoxy)acetyl)glycylglycine tert-Butyl (2-(2,5-bis((3S,4S)-3,4-bis(((1S,2R)-2-phenylcyclopropyl)carbamoyl)-pyrrolidine-1-carbonyl)phenoxy) acetyl)glycylglycinate (19.3 mg, 0.00167 mmol) was dissolved in CH$_2$Cl$_2$ (0.1 mL) at room temperature. TFA (0.1 mL) was added at 0° C., and the mixture was stirred for 2 hours at room temperature. The solvent was removed by N$_2$ stream. The residual solids were suspended in MeCN and condensed (repeat twice) to ensure complete removal of the TFA. This process was repeated with CH$_2$Cl$_2$. Preparative thin-layer chromatography (SiO$_2$, 0.05% formic acid/20% MeOH/CH$_2$Cl$_2$) gave 22.5 mg (quant.) of 159 as a colorless solid. $^1$H NMR (500 MHz, DMSO-d$_6$) δ 8.49 (d, J=4.5 Hz, 1H), 8.47 (d, J=4.0 Hz, 1H), 8.36 (d, J=4.5 Hz, 1H), 8.33 (d, J=4.0 Hz, 1H), 8.28 (t, J=6.0 Hz, 1H), 8.21 (t, J=6.0 Hz, 1H), 7.31 (d, J=7.5 Hz, 1H), 7.28-7.20 (m, 8H), 7.18-7.04 (m, 14H), 4.71 (s, 2H), 3.83-3.74 (m, 6H), 3.64 (dd, J=7.5, 10.5 Hz, 1H), 3.59-3.47 (m, 4H), 3.23-3.16 (m, 3H), 3.10 (q, J=8.0 Hz, 2H), 2.87-2.81 (m, 2H), 2.80-2.74 (m, 2H), 1.97 (ddd, J=9.5, 6.0, 3.0 Hz, 2H), 1.91-1.85 (m, 2H), 1.22-1.06 (m, 8H). HRMS (ESI-TOF) m/z calcd for C$_{62}$H$_{65}$NO$_{11}$ [M+H]$^+$ 1097.4767, found 1097.4765.

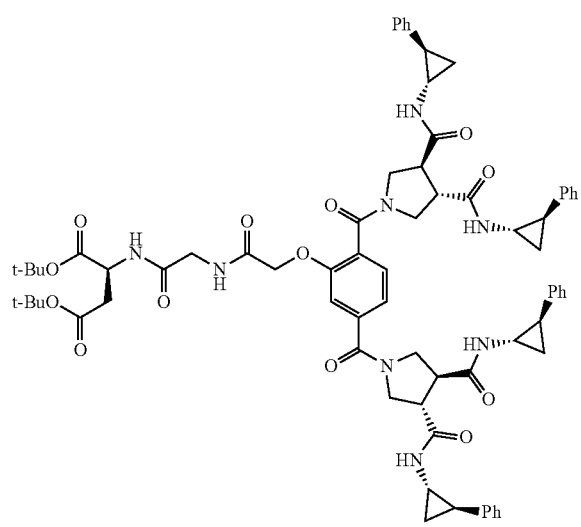 [SMILES: CC(C)(C)OC(=O)C[C@H](NC(=O)CNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1)C(=O)OC(C)(C)C]

160: Di-tert-butyl (2-(2,5-Bis((3S,4S)-3,4-bis(((1S,2R)-2-phenylcyclopropyl) carbamoyl)-pyrrolidine-1-carbonyl)phenoxy)acetyl)glycyl-L-aspartate (2-(2,5-Bis((3S,4S)-3,4-bis(((1S,2R)-2-phenylcyclopropyl)carbamoyl)pyrrolidine-1-carbonyl)-phenoxy)acetyl) glycine (S-88, 8.0 mg, 0.00769 mmol, 1.00 equiv), di-tert-butyl L-aspartate hydrochloride (2.6 mg, 0.00923 mmol, 1.20 equiv), HOAt (1.2 mg, 0.00846 mmol, 1.10 equiv), and 2,6-lutidine (2.5 mg, 0.0231 mmol, 3.00 equiv) were dissolved in anhydrous DMF (0.1 mL). Upon dissolution of the reagents (about 5 minutes) at 0° C., EDCI.HCl (2.2 mg, 0.0115 mmol, 1.50 equiv) was added in one portion, and the reaction mixture was stirred for 3.5 hours at room temperature, after which it was poured into aqueous 1 N HCl (1 mL) and EtOAc (3 mL) at 0° C. The aqueous phase was extracted twice with EtOAc (2 mL), and the combined organic phases were washed with aqueous 1 N HCl (1 mL), saturated aqueous NaHCO$_3$ (1 mL), and saturated aqueous NaCl (1 mL), sequentially. The organic phase was dried over Na$_2$SO$_4$, filtered and concentrated. Flash column chromatography (SiO$_2$, 5% MeOH/CH$_2$Cl$_2$) gave 7.1 mg (73%) of 160 as a colorless solid. $^1$H NMR (500 MHz, DMSO-d$_6$) δ 8.40 (br, 1H), 8.38 (br, 1H), 8.29-8.20 (m, 4H), 7.32 (d, J=7.5 Hz, 1H), 7.29-7.04 (m, 22H), 4.69 (s, 2H), 4.51 (dt, J=7.5, 6.5 Hz, 1H), 3.87-3.75 (m, 4H), 3.65 (t, J=9.0 Hz, 1H), 3.59-3.47 (m, 4H), 3.22-3.15 (m, 3H), 3.13-3.06 (m, 2H), 2.87-2.81 (m, 2H), 2.80-2.74 (m, 2H), 2.64 (dd, J=16.0, 6.5 Hz, 1H), 2.53 (dd, J=16.0, 6.5 Hz, 1H), 2.00-1.94 (m, 2H), 1.91-1.84 (m, 2H), 1.37 (s, 9H), 1.36 (s, 9H), 1.20-1.07 (m, 8H). HRMS (ESI-TOF) m/z calcd for C$_{72}$H$_{83}$N$_8$O$_{13}$ [M+H]$^+$ 1267.6074, found 1267.6052.

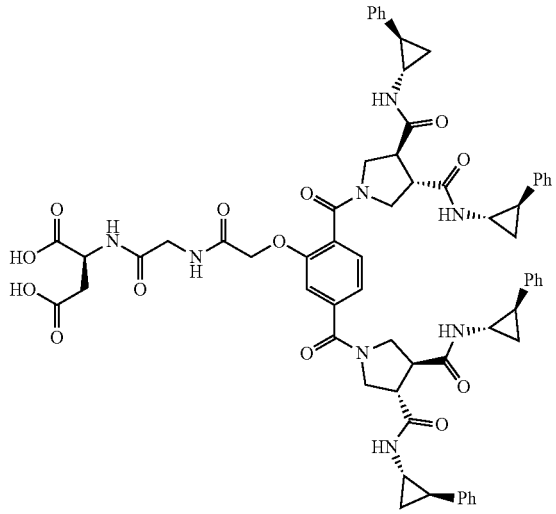 [SMILES: O=C(O)C[C@H](NC(=O)CNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1)C(=O)O]

161: (2-(2,5-Bis((3S,4S)-3,4-bis(((1S,2R)-2-phenylcyclopropyl)carbamoyl)pyrrolidine-1-carbonyl)-phenoxy) acetyl)glycyl-L-aspartic Acid Di-tert-butyl (2-(2,5-bis((3S,4S)-3,4-bis(((1S,2R)-2-phenylcyclopropyl)carbamoyl)-pyrrolidine-1-carbonyl)phenoxy)acetyl)glycyl-L-aspartate (160, 3.6 mg, 0.00284 mmol) was dissolved in CH$_2$Cl$_2$ (0.1 mL) at room temperature. TFA (0.1 mL) was added at 0° C., and the mixture was stirred for 2 hours at room temperature. The solvent was removed by N$_2$ stream. The residual solids were suspended in MeCN and condensed (repeat twice) to ensure complete removal of the TFA. This process was repeated with CH₂Cl₂. Preparative thin-layer chromatography (SiO₂, 15% MeOH/CH₂Cl₂) gave 3.7 mg (quant.) of 161 as a colorless solid. ¹H NMR (400 MHz, DMSO-d₆) δ 8.45 (d, J=4.8 Hz, 1H), 8.43 (d, J=4.0 Hz, 1H), 8.31 (d, J=4.4 Hz, 2H), 8.21 (t, J=5.2 Hz, 1H), 7.88 (br, 1H), 7.33-7.06 (m, 23H), 4.69 (s, 2H), 4.21 (br, 1H), 3.87-3.73 (m, 4H), 3.66 (t, J=8.8 Hz, 1H), 3.58-3.06 (m, 9H), 2.88-2.81 (m, 2H), 2.81-2.74 (m, 2H), 2.58-2.48 (m, 1H), 2.43-2.31 (m, 1H), 2.01-1.94 (m, 2H), 1.91-1.84 (m, 2H), 1.22-1.06 (m, 8H). HRMS (ESI-TOF) m/z calcd for C₆₄H₆₇N₈O₁₃ [M+H]⁺ 1155.4822, found 1155.4824.

chromatography (SiO₂, 10% MeOH/CH₂Cl₂) gave 7.8 mg (76%) of 162 as a colorless solid. ¹H NMR (400 MHz, DMSO-d₆) δ 8.40 (d, J=4.0 Hz, 1H), 8.37 (d, J=4.4 Hz, 1H), 8.27 (d, J=4.4 Hz, 1H), 8.24 (d, J=4.4 Hz, 1H), 8.18 (br, 1H), 8.17 (d, J=6.8 Hz, 1H), 7.32 (d, J=7.6 Hz, 1H), 7.29-7.19 (m, 8H), 7.18-7.04 (m, 14H), 7.74 (t, J=5.6 Hz, 1H), 4.69 (s, 2H), 4.14-4.06 (m, 1H), 3.89-3.74 (m, 4H), 3.69-3.62 (m, 1H), 3.59-3.46 (m, 4H), 3.23-3.14 (m, 3H), 3.13-3.15 (m, 2H), 2.91-2.81 (m, 4H), 2.80-2.74 (m, 2H), 1.96 (ddd, J=9.6, 6.8, 3.2 Hz, 2H), 1.91-1.83 (m, 2H), 1.68-1.49 (m, 2H), 1.37

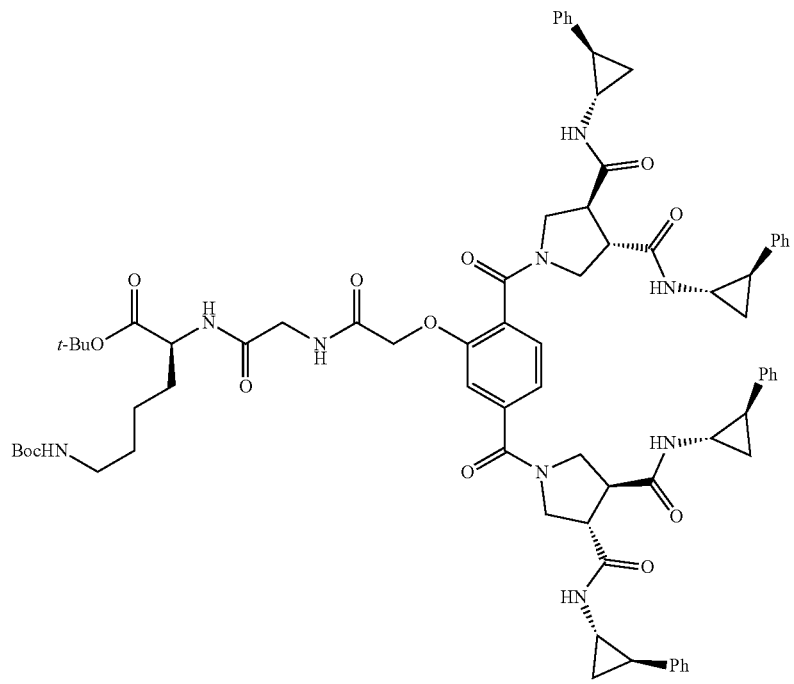 [SMILES: CC(C)(C)OC(=O)NCCCC[C@H](NC(=O)CNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1)C(=O)OC(C)(C)C]

162: tert-Butyl N²-((2-(2,5-Bis((3S,4S)-3,4-bis(((1S,2R)-2-phenylcyclopropyl) carbamoyl)-pyrrolidine-1-carbonyl)phenoxy)acetyl)glycyl)-N⁶-(tert-butoxycarbonyl)-L-lysinate (s, 9H), 1.36 (s, 9H), 1.42-1.30 (m, 2H), 1.29-1.21 (m, 2H), 1.19-1.06 (m, 8H). HRMS (ESI-TOF) m/z calcd for C₇₅H₉₀N₉O₁₃ [M+H]⁺ 1324.6652, found 1324.6657.

(2-(2,5-Bis((3S,4S)-3,4-bis(((1S,2R)-2-phenylcyclopropyl)carbamoyl)pyrrolidine-1-carbonyl)-phenoxy)acetyl)glycine (S-88, 8.0 mg, 0.00769 mmol, 1.00 equiv), tert-butyl N⁶-(tert-butoxycarbonyl)-L-lysinate hydrochloride (3.9 mg, 0.0115 mmol, 1.50 equiv), HOAt (1.3 mg, 0.00923 mmol, 1.20 equiv), and 2,6-lutidine (3.3 mg, 0.0308 mmol, 4.00 equiv) were dissolved in anhydrous DMF (0.1 mL). Upon dissolution of the reagents (about 5 minutes) at 0° C., EDCI*HCl (3.0 mg, 0.0154 mmol, 2.00 equiv) was added in one portion, and the reaction mixture was stirred for 3 hours at room temperature, after which it was poured into aqueous 1 N HCl (1 mL) and CH₂Cl₂ (3 mL) at 0° C. The aqueous phase was extracted with CH₂Cl₂ (2 mL), and the combined organic phases were washed with aqueous 1 N HCl (1 mL), saturated aqueous NaHCO₃ (1 mL), and saturated aqueous NaCl (1 mL), sequentially. The organic phase was dried over Na₂SO₄, filtered and concentrated. Preparative thin-layer

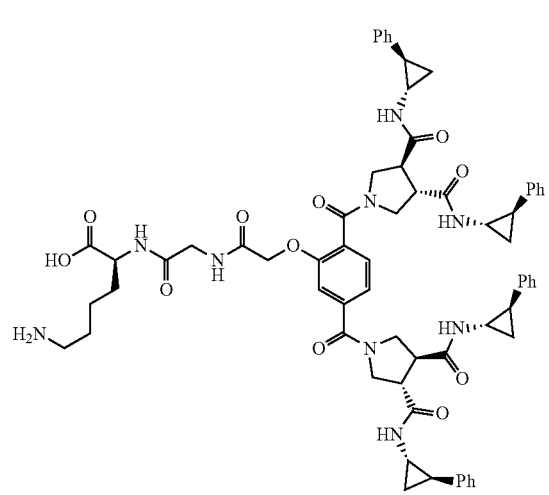 [SMILES: NCCCC[C@H](NC(=O)CNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1)C(=O)O]

163: (2-(2,5-Bis((3S,4S)-3,4-bis(((1S,2R)-2-phenyl-cyclopropyl)carbamoyl)pyrrolidine-1-carbonyl)-phenoxy)acetyl)glycyl-L-lysine tert-Butyl N$^2$-((2-(2,5-bis((3S,4S)-3,4-bis(((1S,2R)-2-phenylcyclopropyl)carbamoyl)-pyrrolidine-1-carbonyl)phenoxy)acetyl)glycyl)-N$^6$-(tert-butoxycarbonyl)-L-lysinate (162, 3.8 mg, 0.00287 mmol) was dissolved in CH$_2$Cl$_2$ (0.1 mL) at room temperature. TFA (0.1 mL) was added at 0° C., and the mixture was stirred for 2 hours at room temperature. The solvent was removed by N$_2$ stream. The residual solids were suspended in MeCN and condensed (repeat twice) to ensure complete removal of the TFA. This process was repeated with CH$_2$Cl$_2$. Preparative thin-layer chromatography (SiO$_2$, 0.05% formic acid/20% MeOH/CH$_2$Cl$_2$) gave 5.2 mg (quant.) of 163 as a colorless solid. $^1$H NMR (500 MHz, DMSO-d$_6$) δ 8.58 (br, 1H), 8.55 (br, 1H), 8.50 (br, 1H), 8.48 (d, J=4.5 Hz, 1H), 8.31 (t, J=6.0 Hz, 1H), 8.25 (br, 3H), 7.79 (br, 1H), 7.31 (d, J=8.0 Hz, 1H), 7.28-7.03 (m, 22H), 4.70 (s, 2H), 4.01 (br, 1H), 3.85-3.74 (m, 4H), 3.70 (t, J=9.0 Hz, 1H), 3.56-3.45 (m, 2H), 3.32 (t, J=10.0 Hz, 1H), 3.25-3.18 (m, 2H), 3.16-3.09 (m, 2H), 2.88-2.82 (m, 2H), 2.80-2.75 (m, 2H), 2.72 (t, J=7.5 Hz, 2H), 2.01-1.94 (m, 2H), 1.91-1.85 (m, 2H), 1.74-1.64 (m, 1H), 1.60-1.44 (m, 3H), 1.32-1.23 (m, 2H), 1.22-1.05 (m, 8H). HRMS (ESI-TOF) m/z calcd for C$_{66}$H$_{74}$N$_9$O$_{11}$ [M+H]+ 1168.5502, found 1168.5503.

164: tert-Butyl N$^2$-(2-(2,5-Bis((3S,4S)-3,4-bis(((1S,2R)-2-phenylcyclopropyl) carbamoyl)-pyrrolidine-1-carbonyl)phenoxy)acetyl)glycyl-L-seryl-N$^6$-(tert-butoxycarbonyl)-L-lysinate (2-(2,5-Bis((3S,4S)-3,4-bis(((1S,2R)-2-phenylcyclopropyl)carbamoyl)pyrrolidine-1-carbonyl)-phenoxy)acetyl)glycyl-L-serine (151, 9.3 mg, 0.00825 mmol, 1.00 equiv), tert-butyl N$^6$-(tert-butoxy-carbonyl)-L-lysinate hydrochloride (3.3 mg, 0.00990 mmol, 1.20 equiv), HOAt (1.2 mg, 0.00908 mmol, 1.10 equiv), and 2,6-lutidine (2.7 mg, 0.0248 mmol, 3.00 equiv) were dissolved in anhydrous DMF (0.1 mL). Upon dissolution of the reagents (about 5 minutes) at room temperature, EDCI.HCl (2.4 mg, 0.0124 mmol, 1.50 equiv) was added in one portion, and the reaction mixture was stirred for 4 hours at room temperature, after which it was poured into aqueous 1 N HCl (1 mL) and CH$_2$Cl$_2$ (2 mL). The aqueous phase was extracted with CH$_2$Cl$_2$ (1 mL), and the combined organic phases were washed with aqueous 1 N HCl (1 mL), saturated aqueous NaHCO$_3$ (1 mL), and saturated aqueous NaCl (1 mL), sequentially. The organic phase was dried over Na$_2$SO$_4$, filtered and concentrated. Preparative thin-layer chromatography (SiO$_2$, 10% MeOH/CH$_2$Cl$_2$) gave 8.6 mg (74%) of 164 as a colorless solid. $^1$H NMR (500 MHz, DMSO-d$_6$) δ 8.40 (d, J=4.0 Hz, 1H), 8.37 (d, J=4.0 Hz, 1H), 8.27 (d, J=4.0 Hz, 1H), 8.24 (d, J=4.5 Hz, 1H), 8.18 (br, 1H), 8.07 (d, J=7.5 Hz, 1H), 8.04 (d, J=8.0 Hz, 1H), 7.32 (d, J=7.5 Hz, 1H), 7.28-7.04 (m, 22H), 6.73 (t, J=6.0 Hz, 1H), 4.83 (t, J=5.5 Hz, 1H), 4.70 (s, 2H), 4.41 (dt, J=6.5, 6.0 Hz, 1H), 4.06 (dt, J=7.0, 7.0 Hz, 1H), 3.88-3.75 (m, 4H), 3.68-3.46 (m, 6H), 3.22-3.15 (m, 2H), 3.13-3.06 (m, 2H), 2.90-2.81 (m, 4H), 2.80-2.74 (m, 2H), 1.99-1.94 (m, 2H), 1.90-1.83 (m, 2H), 1.68-1.51 (m, 2H), 1.37 (s, 9H), 1.35 (s, 9H), 1.38-1.31 (m, 1H), 1.29-1.21 (m, 3H), 1.20-1.06 (m, 8H). HRMS (ESI-TOF) m/z calcd for C$_{78}$H$_{95}$N$_{10}$O$_{15}$ [M+H]$^+$ 1411.6973, found 1411.6969.

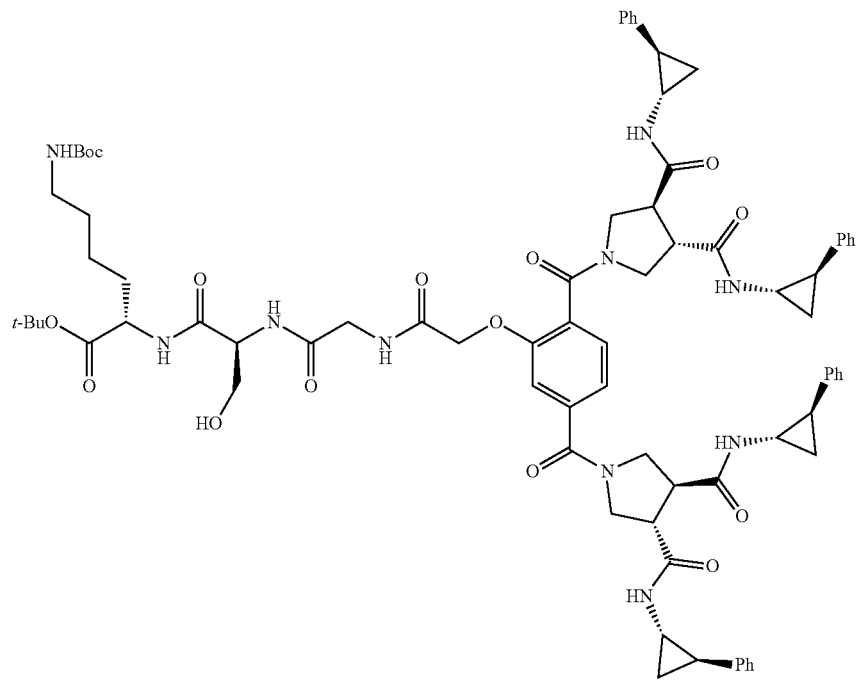 [SMILES: CC(C)(C)OC(=O)NCCCC[C@H](NC(=O)[C@H](CO)NC(=O)CNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1)C(=O)OC(C)(C)C]

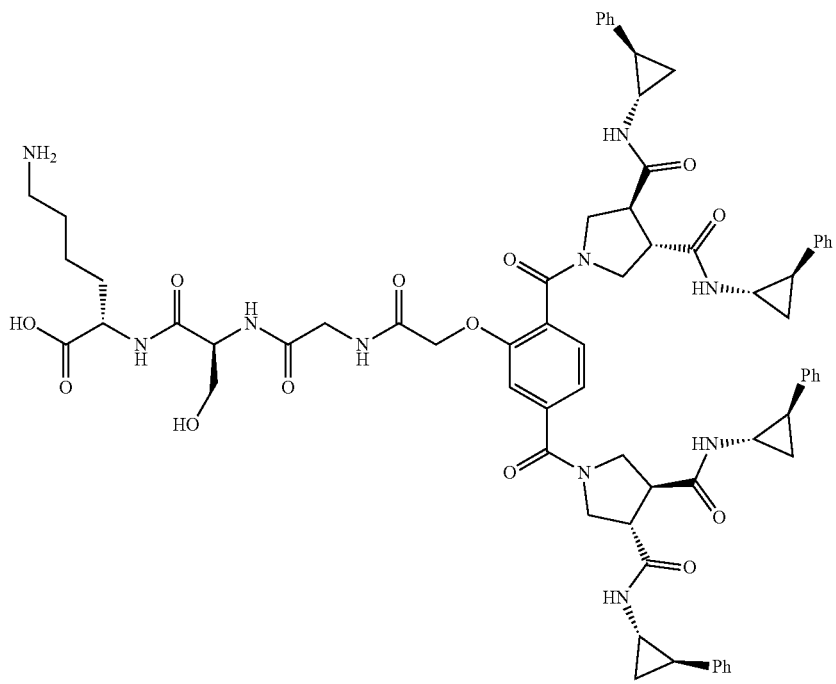 [SMILES: NCCCC[C@H](NC(=O)[C@H](CO)NC(=O)CNC(=O)COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1)C(=O)O]

165: (2-(2,5-Bis((3S,4S)-3,4-bis(((1S,2R)-2-phenyl-cyclopropyl)carbamoyl)pyrrolidine-1-carbonyl)-phenoxy)acetyl)glycyl-L-seryl-L-lysine tert-Butyl $N^2$-(2-(2,5-bis((3S,4S)-3,4-bis(((1S,2R)-2-phenylcyclopropyl)carbamoyl)-pyrrolidine-1-carbonyl)phenoxy)acetyl)glycyl-L-seryl-$N^6$-(tert-butoxycarbonyl)-L-lysinate (164, 4.8 mg, 0.00340 mmol) was dissolved in $CH_2Cl_2$ (0.1 mL) at room temperature. TFA (0.1 mL) was added, and the mixture was stirred for 3 hours at room temperature. The solvent was removed by $N_2$ stream. The residual solids were suspended in MeCN and condensed (repeat twice) to ensure complete removal of the TFA. This process was repeated with $CH_2Cl_2$. Preparative thin-layer chromatography ($SiO_2$, 15% $MeOH/CH_2Cl_2$) gave 6.3 mg (quant.) of 165 as a colorless solid. $^1$H NMR (500 MHz, DMSO-$d_6$) δ 8.58 (br, 1H), 8.53 (br, 1H), 8.40 (d, J=4.5 Hz, 1H), 8.36 (d, J=4.0 Hz, 1H), 8.24 (br, 1H), 7.99 (d, J=8.0 Hz, 1H), 7.68 (br, 1H), 7.31 (d, J=7.5 Hz, 1H), 7.28-7.03 (m, 22H), 4.70 (s, 2H), 4.32 (dt, J=5.5, 7.0 Hz, 1H), 3.93 (br, 1H), 3.87-3.75 (m, 4H), 3.66-3.45 (m, 6H), 3.24-3.17 (m, 2H), 3.15-3.08 (m, 2H), 2.88-2.82 (m, 2H), 2.80-2.74 (m, 2H), 2.73 (t, J=8.0 Hz, 2H), 2.00-1.95 (m, 2H), 1.91-1.84 (m, 2H), 1.77-1.68 (m, 1H), 1.61-1.43 (m, 3H), 1.37-1.27 (m, 2H), 1.22-1.05 (m, 8H). HRMS (ESI-TOF) m/z calcd for $C_{69}H_{79}N_{10}O_{13}$ [M+H]$^+$ 1255.5822, found 1255.5820.

General Procedure for Solid-Phase Peptide Synthesis

Peptides were synthesized on Wang resin (1.00 equiv) by Fmoc-based solid-phase peptide synthesis. The C-terminal amino acid was installed using $N^2$-(((9H-fluoren-9-yl)methoxy) carbonyl)—$N^6$-(tert-butoxycarbonyl)-L-lysine or N-(((9H-fluoren-9-yl)methoxy)carbonyl)-O-(tert-butyl)-L-serine (5.00 equiv), DCC (5.00 equiv) and DMAP (0.500 equiv) in DMF (1.0-1.5 mL) for 1 hour. The capping step was performed using benzoic anhydride (5.00 equiv) in pyridine/DMF (1/4, 1.0-2.0 mL) for 1 hour. The Fmoc group was removed using piperidine/DMF (1/4, 1.0-2.0 mL) for 1 minute and 10 minute respectively. The coupling of amino acid was performed using $N^2$-(((9H-fluoren-9-yl)methoxy) carbonyl)—$N^6$-(tert-butoxycarbonyl)-L-lysine or N-(((9H-fluoren-9-yl)methoxy)carbonyl)-O-(tert-butyl)-L-serine (3.00-5.00 equiv), HBTU (3.00-5.00 equiv), HOBt (3.00-5.00 equiv) and DIEA (6.00-10.0 equiv) in DMF/NMP (1/1, 0.3-1.1 mL) for 15 minutes. The coupling was monitored by standard Kaiser test.

General Procedure for Coupling of Diprovocim-1 Fragment with Peptide Resin and Cleavage of the Functionalized Derivatives The coupling of Diprovocim-1 fragment was performed using (2-(2,5-bis((3S,4S)-3,4-bis(((1S,2R)-2-phenylcyclopropyl)carbamoyl)pyrrolidine-1-carbonyl)phenoxy)acetyl) glycine (S-88, 3.3-8.0 mg, 0.00315-0.00769 mmol, 1.00 equiv), peptide resin (0.00378-0.00923 mmol, 1.20 equiv), EDCI.HCl (1.8-4.4 mg, 0.00945-0.0231 mmol, 3.00 equiv), HOAt (0.6-6.3 mg, 0.00473-0.0461 mmol, 1.50-6.00 equiv) and 2,6-lutidine (1.4-4.9 mg, 0.0126-0.0461 mmol, 4.00-6.00 equiv) in DMF (0.8-1.5 mL) for 2.5-5 hours. All derivatives were cleaved from resin using TFA/i-$Pr_3$SiH/ $H_2O$ (95/2.5/2.5, 0.4 mL) for 1.5 hours at room temperature, participated from $Et_2O$, and purified by reverse phase column chromatography (C18, 0.05% TFA/40-60% MeCN/ $H_2O$) to give the desired product (12-74%).

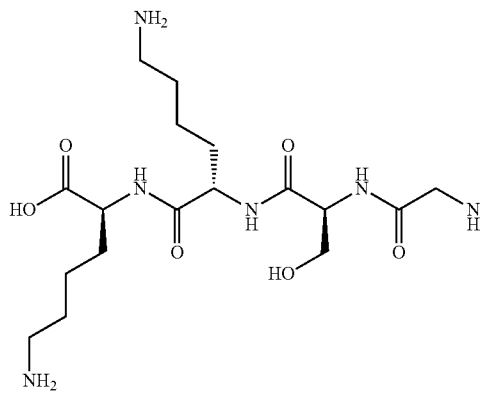
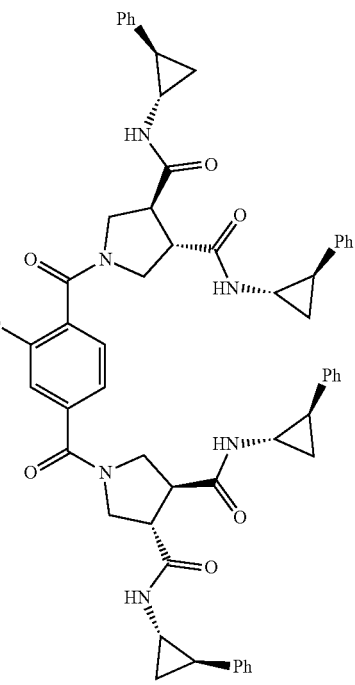

166: (2-(2,5-Bis((3S,4S)-3,4-bis(((1S,2R)-2-phenyl-cyclopropyl)carbamoyl)pyrrolidine-1-carbonyl)-phenoxy)acetyl)glycyl-L-seryl-L-lysyl-L-lysine The general procedure for solid-phase peptide synthesis was employed to synthesize the L-seryl-L-lysyl-L-lysine immobilized resin. The general procedure for coupling of diprovocim-1 fragment with peptide resin and cleavage of the functionalized derivatives was employed: (2-(2,5-bis ((3S,4S)-3,4-bis(((1S,2R)-2-phenylcyclopropyl)-carbamoyl)pyrrolidine-1-carbonyl)phenoxy)acetyl)-glycine (S-88, 4.9 mg, 0.00467 mmol) and the L-seryl-L-lysyl-L-lysine immobilized resin (0.00560 mmol) provided 5.2 mg (74%) of 166 (TFA salt) as a colorless solid. $^1$H NMR (600 MHz, DMSO-$d_6$) δ 8.43 (d, J=4.8 Hz, 1H), 8.41 (d, J=4.2 Hz, 1H), 8.30 (d, J=4.2 Hz, 1H), 8.28 (d, J=4.2 Hz, 1H), 8.22 (t, J=5.4 Hz, 1H), 8.08 (d, J=7.8 Hz, 1H), 8.07 (d, J=7.8 Hz, 1H), 8.04 (d, J=8.4 Hz, 1H), 7.67 (br, 6H), 7.33 (d, J=7.8 Hz, 1H), 7.28-7.10 (m, 18H), 7.08-7.04 (m, 4H), 5.07 (t, J=6.0 Hz, 1H), 4.70 (s, 2H), 4.36 (dt, J=7.8, 6.0 Hz, 1H), 4.28 (td, J=8.4, 4.2 Hz, 1H), 4.14 (td, J=8.4, 4.8 Hz, 1H), 3.90-3.75 (m, 4H), 3.65 (dd, J=10.8, 7.8 Hz, 1H), 3.60 (q, J=5.4 Hz, 1H), 3.57-3.48 (m, 5H), 3.36-3.30 (m, 1H), 3.21-3.15 (m, 2H), 3.11-3.06 (m, 2H), 2.87-2.82 (m, 2H), 2.80-2.70 (m, 6H), 1.99-1.94 (m, 2H), 1.90-1.84 (m, 2H), 1.76-1.68 (m, 2H), 1.61-1.45 (m, 6H), 1.38-1.28 (m, 4H), 1.20-1.07 (m, 8H). HRMS (ESI-TOF) m/z calcd for $C_{75}H_{91}N_{12}O_{14}$ [M+H]$^+$ 1383.6772, found 1383.6786.

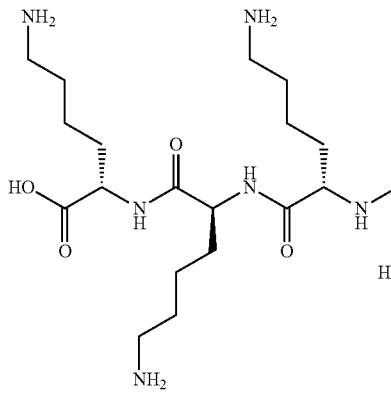
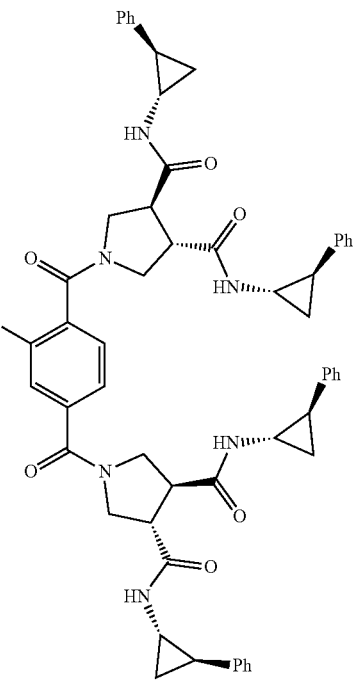

167: (2-(2,5-Bis((3S,4S)-3,4-bis(((1S,2R)-2-phenyl-cyclopropyl)carbamoyl)pyrrolidine-1-carbonyl)-phenoxy)acetyl)glycyl-L-seryl-L-lysyl-L-lysyl-L-lysine The general procedure for solid-phase peptide synthesis was employed to synthesize the L-seryl-L-lysyl-L-lysyl-L-lysine immobilized resin. The general procedure for coupling of diprovocim-1 fragment with peptide resin and cleavage of the functionalized derivatives was employed: (2-(2,5-bis((3S,4S)-3,4-bis(((1S,2R)-2-phenylcyclopropyl)-carbamoyl)pyrrolidine-1-carbonyl)phenoxy)acetyl)-glycine (S-88, 4.2 mg, 0.00402 mmol) and the L-seryl-L-lysyl-L-lysyl-L-lysine immobilized resin (0.00482 mmol) provided 5.2 mg (74%) of 167 (TFA salt) as a colorless solid. H NMR (600 MHz, DMSO-$d_6$) δ 8.44 (d, J=4.2 Hz, 1H), 8.42 (d, J=4.2 Hz, 1H), 8.31 (d, J=4.8 Hz, 1H), 8.29 (d, J=4.8 Hz, 1H), 8.24 (t, J=5.4 Hz, 1H), 8.13 (d, J=7.8 Hz, 1H), 8.10 (d, J=8.4 Hz, 1H), 8.08 (d, J=8.4 Hz, 1H), 7.89 (d, J=7.8 Hz, 1H), 7.73 (br, 9H), 7.33 (d, J=7.8 Hz, 1H), 7.28-7.10 (m, 18H), 7.08-7.04 (m, 4H), 5.07 (t, J=6.0 Hz, 1H), 4.70 (s, 2H), 4.36 (q, J=6.6 Hz, 1H), 4.27-4.20 (m, 2H), 4.13 (td, J=8.4, 4.8 Hz, 1H), 3.90-3.75 (m, 4H), 3.65 (dd, J=10.2, 7.8 Hz, 1H), 3.60 (q, J=5.4 Hz, 1H), 3.58-3.48 (m, 5H), 3.36-3.30 (m, 1H), 3.21-3.15 (m, 2H), 3.11-3.06 (m, 2H), 2.87-2.82 (m, 2H), 2.80-2.70 (m, 8H), 1.99-1.94 (m, 2H), 1.90-1.84 (m, 2H), 1.76-1.63 (m, 3H), 1.62-1.45 (m, 9H), 1.39-1.26 (m, 6H), 1.20-1.07 (m, 8H). HRMS (ESI-TOF) m/z calcd for $C_{81}H_{103}N_{14}O_{15}$ [M+H]$^+$ 1511.7721, found 1511.7708.

168: (2-(2,5-Bis((3S,4S)-3,4-bis(((1S,2R)-2-phenyl-cyclopropyl)carbamoyl)pyrrolidine-1-carbonyl)-phenoxy)acetyl)glycyl-L-seryl-L-lysyl-L-lysyl-L-lysyl-L-lysine The general procedure for solid-phase peptide synthesis was employed to synthesize the L-seryl-L-lysyl-L-lysyl-L-lysyl-L-lysine immobilized resin. The general procedure for coupling of diprovocim-1 fragment with peptide resin and cleavage of the functionalized derivatives was employed: (2-(2,5-bis((3S,4S)-3,4-bis(((1S,2R)-2-phenylcyclo-propyl)carbamoyl)pyrrolidine-1-carbonyl)phenoxy)-acetyl)glycine (S-88, 8.0 mg, 0.00769 mmol) and the L-seryl-L-lysyl-L-lysyl-L-lysyl-L-lysine immobilized resin (0.00923 mmol) provided 4.6 mg (30%) of 168 (TFA salt) as a colorless solid. $^1$H NMR (600 MHz, DMSO-$d_6$) δ 8.44 (d, J=4.2 Hz, 1H), 8.42 (d, J=4.2 Hz, 1H), 8.31 (d, J=4.2 Hz, 1H), 8.29 (d, J=4.2 Hz, 1H), 8.25 (br, 1H), 8.17-8.07 (m, 3H), 7.92-7.87 (m, 2H), 7.75 (br, 12H), 7.33 (d, J=7.8 Hz, 1H), 7.28-7.04 (m, 22H), 5.18 (br, 1H), 4.70 (s, 2H), 4.36 (q, J=6.6 Hz, 1H), 4.27-4.18 (m, 3H), 4.12 (q, J=7.2 Hz, 1H), 3.90-3.75 (m, 4H), 3.67-3.59 (m, 2H), 3.58-3.48 (m, 5H), 3.36-3.30 (m, 1H), 3.21-3.15 (m, 2H), 3.11-3.06 (m, 2H), 2.87-2.82 (m, 2H), 2.80-2.70 (m, 10H), 1.99-1.94 (m, 2H), 1.90-1.84 (m, 2H), 1.75-1.62 (m, 4H), 1.61-1.45 (m, 12H), 1.39-1.26 (m, 8H), 1.20-1.07 (m, 8H). $^{13}$C NMR (151 MHz, DMSO-$d_6$) δ 173.36, 171.71, 171.63, 171.50, 171.46, 171.28, 170.99, 170.90, 170.29, 168.55, 167.97, 167.12, 165.52, 153.59, 141.27, 141.26, 141.19, 141.18, 138.63, 128.20, 128.16, 127.86, 125.83, 125.80, 125.78, 125.64, 125.61, 120.17, 118.32, 116.31, 112.26, 109.52, 67.40, 61.74, 54.88, 52.58, 52.27, 52.03, 51.76, 51.43, 50.23, 48.75, 48.13, 47.06, 46.76, 45.32, 45.17, 41.78, 38.73, 38.70, 38.63, 38.59, 32.56, 32.53, 32.45, 31.49, 31.20, 30.75, 30.37, 26.67, 26.59, 26.57, 26.55, 23.88, 23.85, 23.80, 23.77, 22.38, 22.36, 22.21, 22.11, 15.44, 15.37, 15.31. HRMS (ESI-TOF) m/z calcd for $C_{43.5}H_{58}N_8O_8$ [M+2H]$^{2+}$ 820.4372, found 820.4373.

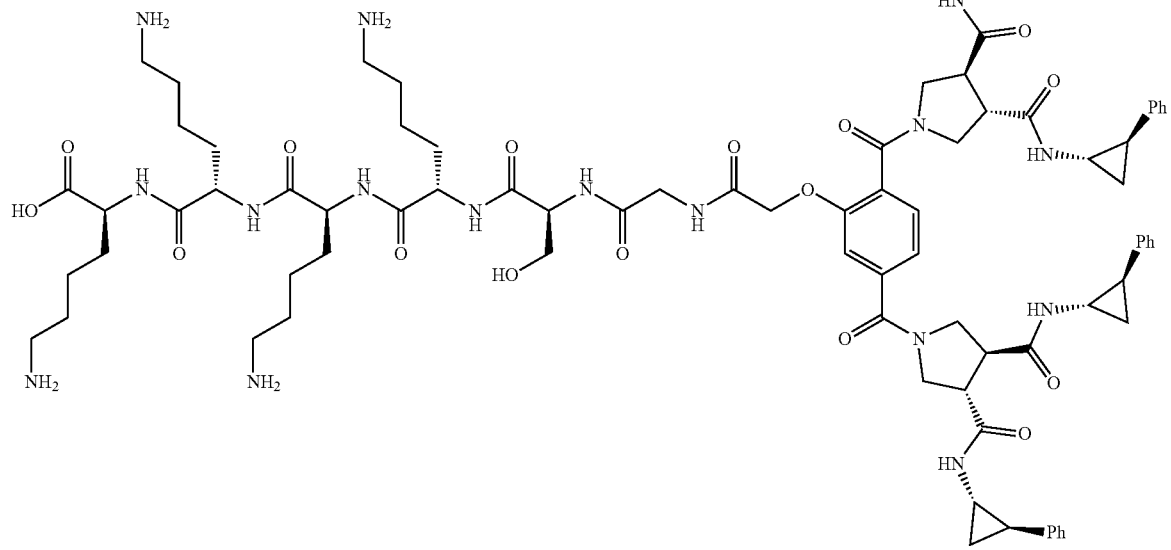

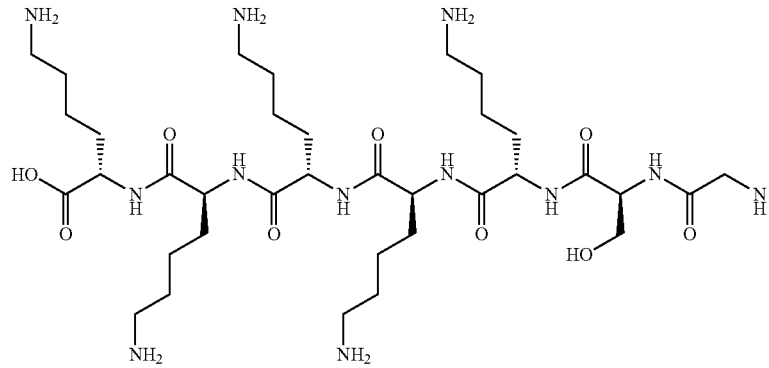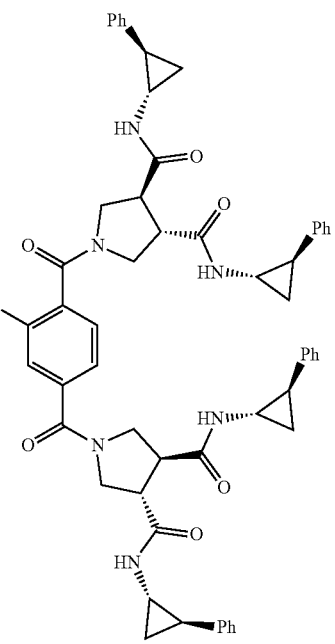

169: (2-(2,5-Bis((3S,4S)-3,4-bis(((1S,2R)-2-phenyl-cyclopropyl)carbamoyl)pyrrolidine-1-carbonyl)phenoxy)acetyl)glycyl-L-seryl-L-lysyl-L-lysyl-L-lysyl-L-lysyl-L-lysyl-L-lysine The general procedure for solid-phase peptide synthesis was employed to synthesize the L-seryl-L-lysyl-L-lysyl-L-lysyl-L-lysyl-L-lysine immobilized resin. The general procedure for coupling of diprovocim-1 fragment with peptide resin and cleavage of the functionalized derivatives was employed: (2-(2,5-bis((3S,4S)-3,4-bis(((1S,2R)-2-phenyl-cyclopropyl)carbamoyl)pyrrolidine-1-carbonyl)phenoxy)acetyl)glycine (S-88, 3.3 mg, 0.00315 mmol) and the L-seryl-L-lysyl-L-lysyl-L-lysyl-L-lysyl-L-lysine immobilized resin (0.00378 mmol) provided 5.1 mg (73%) of 169 (TFA salt) as a colorless solid. $^1$H NMR (600 MHz, DMSO-d$_6$) δ 8.44 (d, J=4.2 Hz, 1H), 8.42 (d, J=4.2 Hz, 1H), 8.31 (d, J=4.2 Hz, 1H), 8.29 (d, J=4.8 Hz, 1H), 8.26 (t, J=5.4 Hz, 1H), 8.16 (d, J=7.2 Hz, 2H), 8.10 (d, J=7.8 Hz, 1H), 7.94 (d, J=7.8 Hz, 1H), 7.90 (d, J=6.6 Hz, 1H), 7.88 (d, J=7.2 Hz, 1H), 7.78 (br, 15H), 7.33 (d, J=7.8 Hz, 1H), 7.28-7.10 (m, 18H), 7.08-7.04 (m, 4H), 5.20 (br, 1H), 4.70 (s, 2H), 4.36 (q, J=6.6 Hz, 1H), 4.27-4.18 (m, 4H), 4.15-4.08 (m, 1H), 3.90-3.75 (m, 4H), 3.68-3.59 (m, 2H), 3.58-3.49 (m, 5H), 3.36-3.30 (m, 1H), 3.21-3.15 (m, 2H), 3.11-3.06 (m, 2H), 2.87-2.82 (m, 2H), 2.80-2.70 (m, 12H), 1.99-1.94 (m, 2H), 1.90-1.84 (m, 2H), 1.74-1.44 (m, 20H), 1.38-1.23 (m, 10H), 1.20-1.07 (m, 8H). HRMS (ESI-TOF) m/z calcd for $C_{46.5}H_{64}N_9O_{8.5}[M+2H]^{2+}$ 884.4847, found 884.4847.

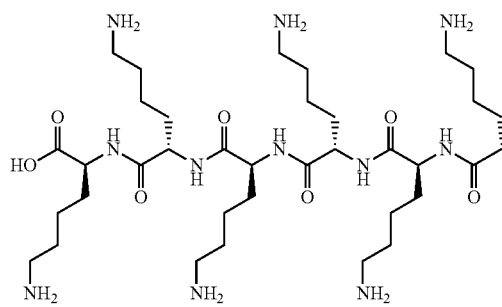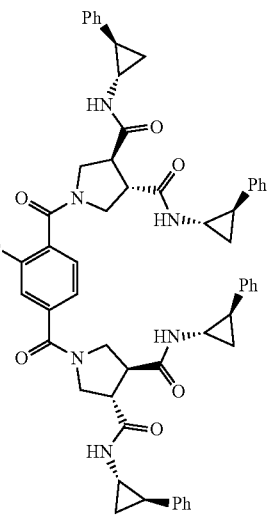

170: (2-(2,5-Bis((3S,4S)-3,4-bis(((1S,2R)-2-phenyl-cyclopropyl)carbamoyl)pyrrolidine-1-carbonyl)-phenoxy)acetyl)glycyl-L-lysyl-L-lysyl-L-lysyl-L-lysyl-L-lysine The general procedure for solid-phase peptide synthesis was employed to synthesize the L-lysyl-L-lysyl-L-lysyl-L-lysyl-L-lysine immobilized resin. The general procedure for coupling of diprovocim-1 fragment with peptide resin and cleavage of the functionalized derivatives was employed: (2-(2,5-bis((3S,4S)-3,4-bis(((1S,2R)-2-phenylcyclo-propyl)carbamoyl)pyrrolidine-1-carbonyl)phenoxy)-acetyl)glycine (S-88, 3.4 mg, 0.00328 mmol) and the L-lysyl-L-lysyl-L-lysyl-L-lysyl-L-lysine immobilized resin (0.00394 mmol) provided 3.8 mg (54%) of 170 (TFA salt) as a colorless solid. $^1$H NMR (600 MHz, DMSO-$d_6$) δ 8.47-8.42 (m, 2H), 8.32 (d, J=4.2 Hz, 1H), 8.30 (d, J=4.8 Hz, 1H), 8.27 (t, J=6.0 Hz, 1H), 8.16 (d, J=7.2 Hz, 1H), 8.11 (d, J=8.4 Hz, 1H), 8.02 (d, J=7.8 Hz, 1H), 7.97 (d, J=7.8 Hz, 1H), 7.92 (d, J=8.4 Hz, 1H), 7.78 (br, 15H), 7.33 (d, J=7.2 Hz, 1H), 7.28-7.10 (m, 18H), 7.08-7.04 (m, 4H), 4.71 (s, 2H), 4.30-4.19 (m, 4H), 4.13 (td, J=8.4, 4.8 Hz, 1H), 3.84-3.75 (m, 4H), 3.65 (dd, J=10.2, 7.8 Hz, 1H), 3.56-3.49 (m, 4H), 3.36-3.30 (m, 1H), 3.21-3.15 (m, 2H), 3.11-3.05 (m, 2H), 2.87-2.82 (m, 2H), 2.80-2.70 (m, 12H), 1.99-1.94 (m, 2H), 1.90-1.84 (m, 2H), 1.74-1.45 (m, 20H), 1.37-1.23 (m, 10H), 1.20-1.07 (m, 8H). HRMS (ESI-TOF) m/z calcd for $C_{45}H_{61.5}N_{8.5}O_{7.5}[M+2H]^2+$ 840.9687, found 840.9687.

171: (2-(2,5-Bis((3S,4S)-3,4-bis(((1S,2R)-2-phenyl-cyclopropyl)carbamoyl)pyrrolidine-1-carbonyl)-phenoxy)acetyl)glycyl-L-seryl-L-seryl-L-seryl-L-seryl-L-serine The general procedure for solid-phase peptide synthesis was employed to synthesize the L-seryl-L-seryl-L-seryl-L-seryl-L-serine immobilized resin. The general procedure for coupling of diprovocim-1 fragment with peptide resin and cleavage of the functionalized derivatives was employed: (2-(2,5-bis((3S,4S)-3,4-bis(((1S,2R)-2-phenylcyclo-propyl)carbamoyl)pyrrolidine-1-carbonyl)phenoxy)-acetyl)glycine (S-88, 8.0 mg, 0.00769 mmol) and the L-seryl-L-seryl-L-seryl-L-seryl-L-serine immobilized resin (0.00923 mmol) provided 1.3 mg (12%) of 171 as a colorless solid. $^1$H NMR (600 MHz, DMSO-$d_6$) δ 8.41 (d, J=4.8 Hz, 1H), 8.38 (d, J=4.2 Hz, 1H), 8.28 (d, J=4.2 Hz, 1H), 8.25 (d, J=4.2 Hz, 1H), 8.20 (t, J=6.0 Hz, 1H), 8.08 (d, J=7.8 Hz, 2H), 7.97 (d, J=7.8 Hz, 1H), 7.95 (d, J=7.8 Hz, 1H), 7.92 (d, J=8.4 Hz, 1H), 7.32 (d, J=7.8 Hz, 1H), 7.28-7.10 (m, 18H), 7.08-7.04 (m, 4H), 5.06-4.94 (m, 4H), 4.86 (br, 1H), 4.70 (s, 2H), 4.44 (dt, J=7.2, 6.0 Hz, 1H), 4.40-4.33 (m, 3H), 4.26 (dt, J=7.8, 4.8 Hz, 1H), 3.88-3.75 (m, 4H), 3.71-3.47 (m, 13H), 3.36-3.30 (m, 1H), 3.22-3.15 (m, 2H), 3.12-3.06 (m, 2H), 2.87-2.82 (m, 2H), 2.80-2.74 (m, 2H), 1.99-1.94 (m, 2H), 1.90-1.84 (m, 2H), 1.20-1.07 (m, 8H).

The articles "a" and "an" are used herein to refer to one or to more than one (i.e., to at least one) of the grammatical object of the article. Each of the patents, patent applications and articles cited herein is incorporated by reference.

The foregoing description and the examples are intended as illustrative and are not to be taken as limiting. Still other variations within the spirit and scope of this invention are possible and will readily present themselves to those skilled in the art.

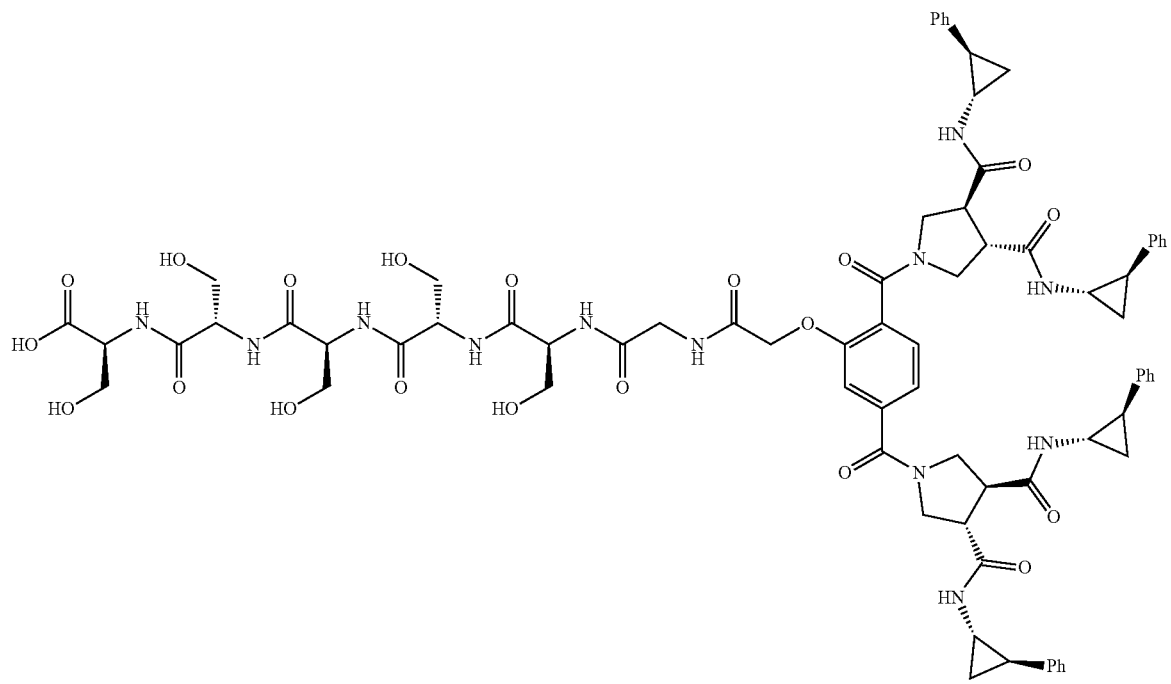 [SMILES: O=C(COc1cc(C(=O)N2C[C@@H](C(=O)N[C@H]3C[C@@H]3c3ccccc3)[C@H](C(=O)N[C@H]3C[C@@H]3c3ccccc3)C2)ccc1C(=O)N1C[C@@H](C(=O)N[C@H]2C[C@@H]2c2ccccc2)[C@H](C(=O)N[C@H]2C[C@@H]2c2ccccc2)C1)NCC(=O)N[C@@H](CO)C(=O)N[C@@H](CO)C(=O)N[C@@H](CO)C(=O)N[C@@H](CO)C(=O)N[C@@H](CO)C(=O)O]

The invention claimed is:

1. A compound of Formula V,

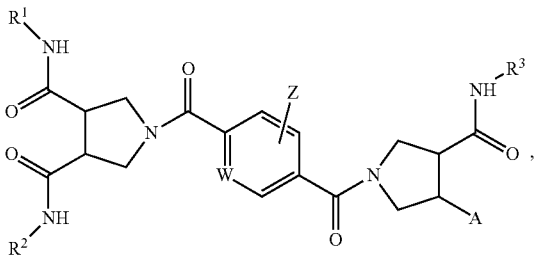

V wherein

-A is —H (hydrido) or —C(O)NH-R$^4$;

R$^1$, R$^2$, R$^3$ and R$^4$ are the same or different and are a 2-(4-fluorophenyl)ethyl, a trans-2-phenylcyclopropyl, a trans-2-(4-fluorophenyl)-cyclopropyl or a C$_3$-C$_{18}$ hydrocarbyl group with the provisos that:

1) at least two of R$^1$, R$^2$, R$^3$ and R$^4$ (R$^{1-4}$) or at least two of R$^1$, R$^2$, and R$^3$ (R$^{1-3}$) are a trans-2-phenylcyclopropyl, a trans-2-(4-fluorophenyl)-cyclopropyl group or a mixture thereof, or each of R$^{1-4}$ is a 2-(4-fluorophenyl) ethyl group, 2) at least one depicted pyrrolidinyldi-carboxamido group has the (S,S) configuration, and each depicted R substituent other than a C$_3$-C$_{18}$ hydrocarbyl group is a trans-2-phenylcyclopropyl, a trans-2-(4-fluorophenyl) cyclopropyl group or a mixture thereof when each of R$^{1-4}$ is other than 2-(4-fluorophenyl)-ethyl, 3) no more than two of R$^{1-4}$ are C$_8$-C$_{18}$ hydrocarbyl groups when -A is —C(O)NH-R$^4$, and 4) when A is hydrido, one of R$^{1-3}$ can be a C$_8$-C$_{18}$ hydrocarbyl group and the depicted R$^3$-containing pyrrolidinylcarboxamido group can have either the R or S configurations, or a mixture of both configurations;

—Z is one or more of halogen —H, —NH$_2$, —OH, —OCH$_3$, —NO$_2$, —OCH$_2$CO$_2$H, —O(CH$_2$CH$_2$O)$_n$CH$_2$CH$_2$CO$_2$H, —OCH$_2$CONH(CH$_2$CH$_2$O)$_n$CH$_2$CH$_2$CO$_2$H, —NHCOCH$_2$O—(CH$_2$CH$_2$O)$_n$CH$_2$CO$_2$H, —OCH$_2$CONHCH$_2$CONHCH(CHOH)CO$_2$H, —OCH$_2$CONHCH$_2$CONHCHCO$_2$H(CH$_2$CO$_2$H), —OCH$_2$CONHCH$_2$CONHCH(CHOH) (CH$_2$CH$_2$O)$_n$ CH$_2$CH$_2$CO$_2$H, —OCH$_2$CONHCH$_2$CONHCH[(CH$_2$)$_4$NH$_2$]CO$_2$H, —OCH$_2$CONHCH$_2$CONHCH(CH$_2$OH)CO{NHCH[(CH$_2$)$_4$NH$_2$]CO}$_m$NHCH—[(CH$_2$)$_4$NH$_2$]CO$_2$H (SEQ ID NOs: 3-8), —OCH$_2$CONHCH$_2$CO{NHCH[(CH$_2$)$_4$NH$_2$]CO}$_p$NHCH[(CH$_2$)$_4$NH$_2$]CO$_2$H (SEQ ID NOs: 9-13) and —OCH$_2$CONHCH$_2$CO{NHCH(CH$_2$OH)CO}$_q$NHCH(CH$_2$OH)CO$_2$H (SEQ ID NOs: 14-18);

W is nitrogen (N) or CH;

"n" is a number whose average value is one to about eight;

"m" is a number whose value is 1 to about 6; "p" is a number whose value is 1 to about 6; and "q" is a number whose value is 1 to about 6.

2. The compound according to claim 1, wherein A is hydrido and said compound has the structural Formula Va, wherein R$^{1-3}$, W and Z moieties:

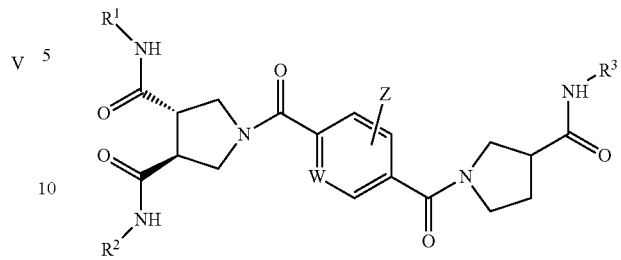

Va are as described above.

3. The compound according to claim 2, wherein one of R$^{1-3}$ is a C$_8$-C$_{18}$ hydrocarbyl group.

4. The compound according to claim 2, wherein each of R$^{1-3}$ is a is a trans-2-phenyl-cyclopropyl group, a trans-2-(4-fluorophenyl)-cyclopropyl group or a mixture thereof.

5. The compound according to claim 1, wherein W is nitrogen CH.

6. The compound according to claim 5, wherein -A is —C(O)NH-R$^4$ and said compound has the structural Formula I, and wherein the R$^{1-4}$, W and Z

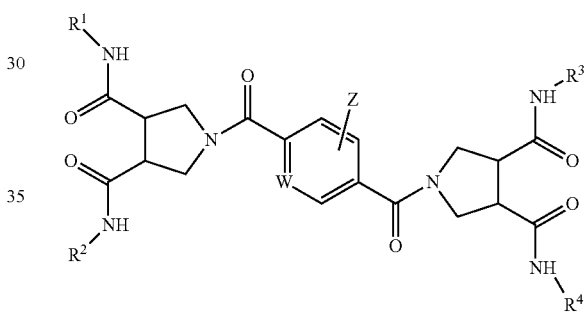

I moieties are as described above.

7. The compound according to claim 5, wherein each depicted pyrrolidinyldicarboxamido group has the (S, S) configuration.

8. The compound according to claim 7, wherein W is CH, and said compound has the structural Formula Ia, and wherein the R$^{1-4}$ and Z moieties are as

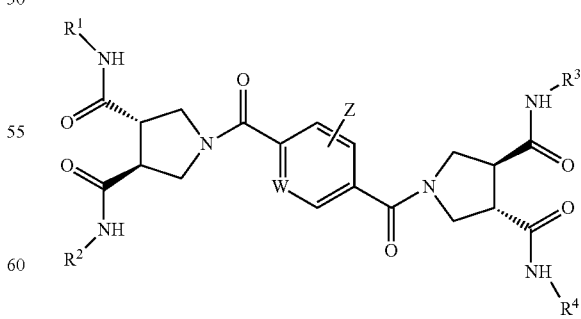

Ia described above.

9. The compound according to claim 8, wherein —Z is selected from the group consisting of one or more of halogen —H, —NH$_2$, —OH, —OCH$_3$ and —NO$_2$.

10. The compound according to claim 8, wherein —Z is selected from the group consisting of one or more of —OCH$_2$CO$_2$H, —O(CH$_2$CH$_2$O)$_n$CH$_2$CH$_2$CO$_2$H, —OCH$_2$CONH(CH$_2$CH$_2$O)$_n$CH$_2$CH$_2$CO$_2$H, —NHCOCH$_2$O—(CH$_2$CH$_2$O)$_n$CH$_2$CO$_2$H, —OCH$_2$CONHCH$_2$CONHCH(CHOH)CO$_2$H, —OCH$_2$CONHCH$_2$CONHCHCO$_2$H(CH$_2$CO$_2$H), —OCH$_2$CONHCH$_2$CONHCH(CHOH)(CH$_2$O)$_n$CH$_2$CH$_2$CO$_2$H, —OCH$_2$CONHCH$_2$CONHCH[(CH$_2$)$_4$NH$_2$]CO$_2$H, —OCH$_2$CONHCH$_2$CONHCH(CH$_2$OH)CO{NHCH[(CH$_2$)$_4$NH$_2$]CO}$_m$NHCH—[(CH$_2$)$_4$NH$_2$]CO$_2$H (SEQ ID NOs: 3-8), —OCH$_2$CONHCH$_2$CO{NHCH[(CH$_2$)$_4$NH$_2$]CO}$_p$NHCH[(CH$_2$)$_4$NH$_2$]CO$_2$H (SEQ ID NOs: 9-13) and —OCH$_2$CONHCH$_2$CO{NHCH(CH$_2$OH)CO}$_q$NHCH(CH$_2$OH)CO$_2$H (SEQ ID NOs: 14-18);

"n" is a number whose average value is one to about eight; "m" is a number whose value is 1 to about 6; "p" is a number whose value is 1 to about 6; and "q" is a number whose value is 1 to about 6.

11. The compound according to claim 8, wherein at least two of R$^{1-4}$ are a trans-2-phenyl-cyclopropyl group or a trans-2-(4-fluorophenyl)-cyclopropyl group having the (1S, 2R) configuration, and at least one of the remaining two of R$^{1-4}$ is a C$_3$-C$_{18}$ hydrocarbyl group.

12. The compound according to claim 8, wherein each of R$^{1-4}$ is a trans-2-phenylcyclopropyl group or a trans-2-(4-fluorophenyl)cyclopropyl group having the (1S,2R) configuration.

13. The compound according to claim 8 that is a single enantiomer.

14. The compound according to claim 8, having a structural selected from the group consisting of one or more of Formulas A, B, C, D, E, F, G and H

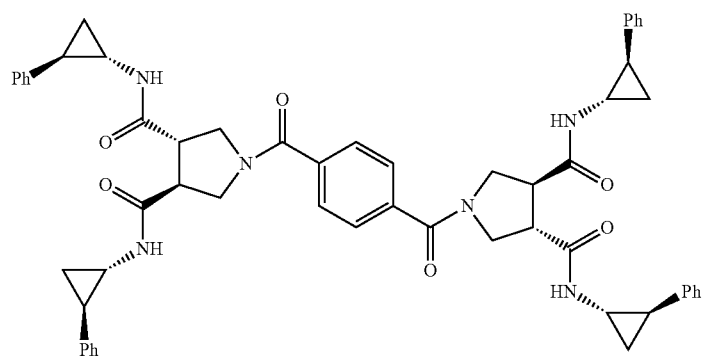

A

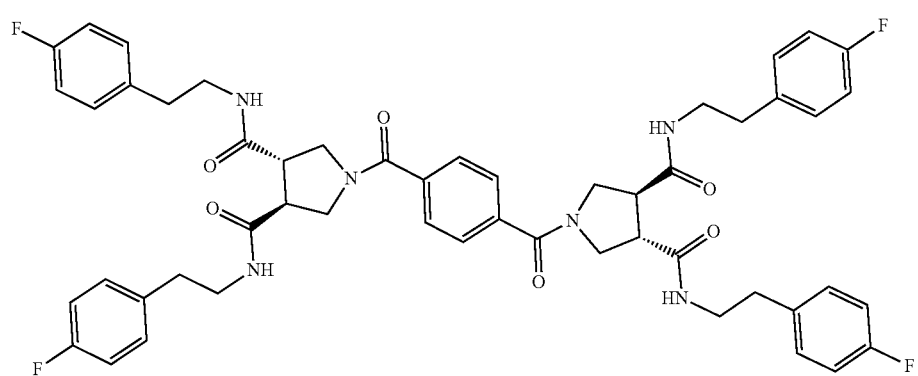

B

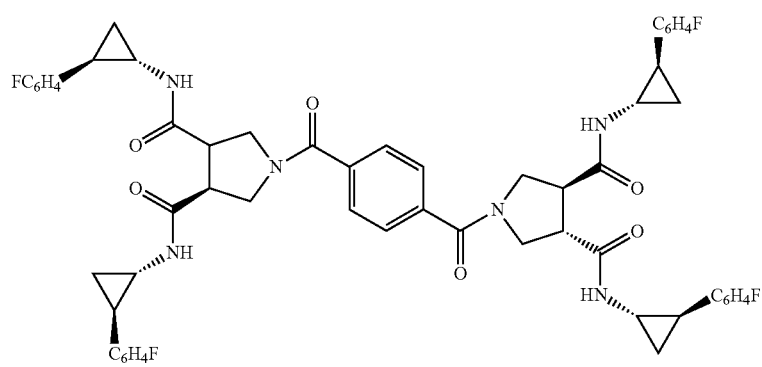

C

-continued
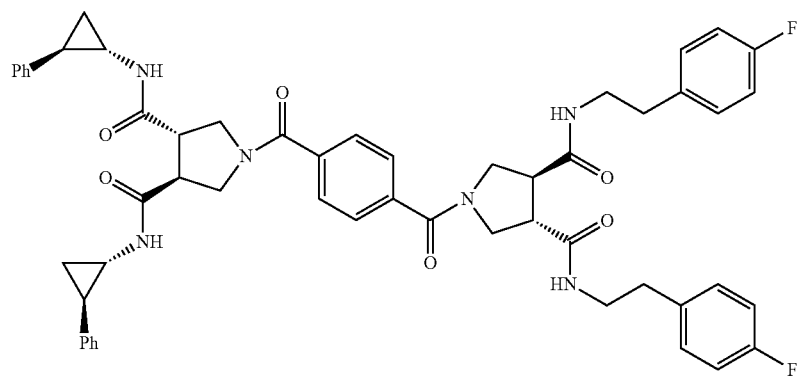
D
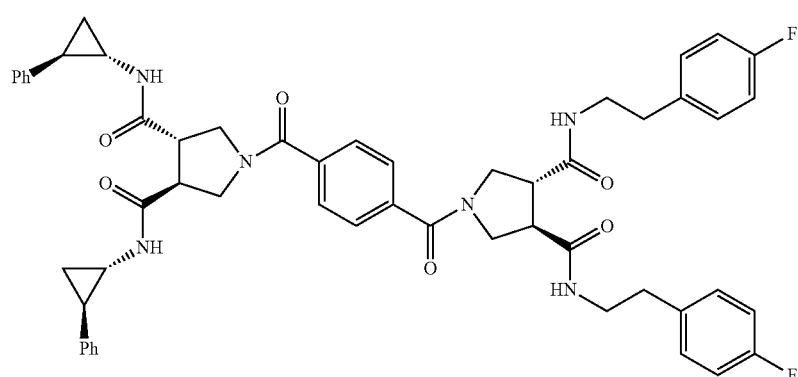
E
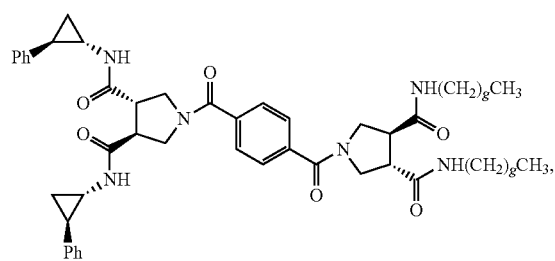
g = 2-17
F
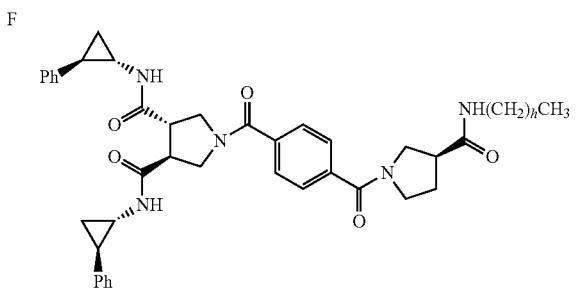
h = 7-17
G
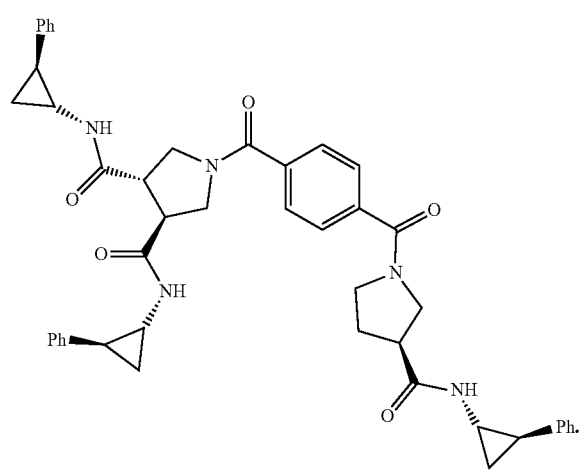
H 15. A pharmaceutical composition comprising a concentration of a compound of claim 1 effective to induce release of TNF-α from one or both of in vitro cultured human PMA differentiated THP-1 cells and or mouse macrophages, said compound being dissolved or dispersed in a physiologically tolerable diluent.

16. The pharmaceutical composition according to claim 15, wherein said compound is a single enantiomer.

* * * * *

SEQUENCE LISTING

```
<160> NUMBER OF SEQ ID NOS: 18

<210> SEQ ID NO 1
<211> LENGTH: 5
<212> TYPE: PRT
<213> ORGANISM: Artificial Sequence
<220> FEATURE:
<223> OTHER INFORMATION: SYNTHETIC CONSTRUCT

<400> SEQUENCE: 1

Ser Lys Lys Lys Lys
1               5

<210> SEQ ID NO 2
<211> LENGTH: 13
<212> TYPE: PRT
<213> ORGANISM: Artificial Sequence
<220> FEATURE:
<223> OTHER INFORMATION: SYNTHETIC CONSTRUCT

<400> SEQUENCE: 2

Gly Asn Asn Asp Glu Ser Asn Ile Ser Phe Lys Glu Lys
1               5                   10

<210> SEQ ID NO 3
<211> LENGTH: 4
<212> TYPE: PRT
<213> ORGANISM: Artificial Sequence
<220> FEATURE:
<223> OTHER INFORMATION: SYNTHETIC CONSTRUCT

<400> SEQUENCE: 3

Gly Ser Lys Lys
1

<210> SEQ ID NO 4
<211> LENGTH: 5
<212> TYPE: PRT
<213> ORGANISM: Artificial Sequence
<220> FEATURE:
<223> OTHER INFORMATION: SYNTHETIC CONSTRUCT

<400> SEQUENCE: 4

Gly Ser Lys Lys Lys
1               5

<210> SEQ ID NO 5
<211> LENGTH: 6
<212> TYPE: PRT
<213> ORGANISM: Artificial Sequence
<220> FEATURE:
<223> OTHER INFORMATION: SYNTHETIC CONSTRUCT

<400> SEQUENCE: 5

Gly Ser Lys Lys Lys Lys
1               5

<210> SEQ ID NO 6
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 6

Gly Ser Lys Lys Lys Lys Lys
1               5
```

```
<210> SEQ ID NO 7
<211> LENGTH: 8
<212> TYPE: PRT
<213> ORGANISM: Artificial Sequence
<220> FEATURE:
<223> OTHER INFORMATION: SYNTHETIC CONSTRUCT

<400> SEQUENCE: 7

Gly Ser Lys Lys Lys Lys Lys Lys
1               5

<210> SEQ ID NO 8
<211> LENGTH: 9
<212> TYPE: PRT
<213> ORGANISM: Artificial Sequence
<220> FEATURE:
<223> OTHER INFORMATION: SYNTHETIC CONSTRUCT

<400> SEQUENCE: 8

Gly Ser Lys Lys Lys Lys Lys Lys Lys
1               5

<210> SEQ ID NO 9
<211> LENGTH: 4
<212> TYPE: PRT
<213> ORGANISM: Artificial Sequence
<220> FEATURE:
<223> OTHER INFORMATION: SYNTHETIC CONSTRUCT

<400> SEQUENCE: 9

Gly Lys Lys Lys
1

<210> SEQ ID NO 10
<211> LENGTH: 5
<212> TYPE: PRT
<213> ORGANISM: Artificial Sequence
<220> FEATURE:
<223> OTHER INFORMATION: SYNTHETIC CONSTRUCT

<400> SEQUENCE: 10

Gly Lys Lys Lys Lys
1               5

<210> SEQ ID NO 11
<211> LENGTH: 6
<212> TYPE: PRT
<213> ORGANISM: Artificial Sequence
<220> FEATURE:
<223> OTHER INFORMATION: SYNTHETIC CONSTRUCT

<400> SEQUENCE: 11

Gly Lys Lys Lys Lys Lys
1               5

<210> SEQ ID NO 12
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 12

Gly Lys Lys Lys Lys Lys Lys
1               5
```

```
<210> SEQ ID NO 13
<211> LENGTH: 8
<212> TYPE: PRT
<213> ORGANISM: Artificial Sequence
<220> FEATURE:
<223> OTHER INFORMATION: SYNTHETIC CONSTRUCT

<400> SEQUENCE: 13

Gly Lys Lys Lys Lys Lys Lys Lys
1               5

<210> SEQ ID NO 14
<211> LENGTH: 4
<212> TYPE: PRT
<213> ORGANISM: Artificial Sequence
<220> FEATURE:
<223> OTHER INFORMATION: SYNTHETIC CONSTRUCT

<400> SEQUENCE: 14

Gly Ser Ser Ser
1

<210> SEQ ID NO 15
<211> LENGTH: 5
<212> TYPE: PRT
<213> ORGANISM: Artificial Sequence
<220> FEATURE:
<223> OTHER INFORMATION: SYNTHETIC CONSTRUCT

<400> SEQUENCE: 15

Gly Ser Ser Ser Ser
1               5

<210> SEQ ID NO 16
<211> LENGTH: 6
<212> TYPE: PRT
<213> ORGANISM: Artificial Sequence
<220> FEATURE:
<223> OTHER INFORMATION: SYNTHETIC CONSTRUCT

<400> SEQUENCE: 16

Gly Ser Ser Ser Ser Ser
1               5

<210> SEQ ID NO 17
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 17

Gly Ser Ser Ser Ser Ser Ser
1               5

<210> SEQ ID NO 18
<211> LENGTH: 8
<212> TYPE: PRT
<213> ORGANISM: Artificial Sequence
<220> FEATURE:
<223> OTHER INFORMATION: SYNTHETIC CONSTRUCT

<400> SEQUENCE: 18

Gly Ser Ser Ser Ser Ser Ser Ser
1               5
```